US006455571B1

(12) United States Patent
Maring et al.

(10) Patent No.: US 6,455,571 B1
(45) Date of Patent: Sep. 24, 2002

(54) INHIBITORS OF NEURAMINIDASES

(75) Inventors: Clarence J. Maring, Palatine; Yu Gui Gu; Hui-Ju Chen, both of Grayslake, all of IL (US); Yuanwei Chen, North Haven, CT (US); David A. Degoey, Kenosha, WI (US); William J. Flosi, Des Plaines, IL (US); Vincent L. Giranda, Gurnee, IL (US); David J. Grampovnik, Waukegan, IL (US); Warren M. Kati, Gurnee, IL (US); Dale J. Kempf, Libertyville, IL (US); April Kennedy, Grayslake, IL (US); Larry L. Klein, Lake Forest, IL (US); Allan C. Krueger; Zhen Lin, both of Gurnee, IL (US); Darold L. Madigan, Elk Grove Village, IL (US); Keith F. McDaniel, Grayslake, IL (US); Steven W. Muchmore, Libertyville, IL (US); Hing L. Sham, Mundelein, IL (US); Kent D. Stewart, Gurnee, IL (US); Vincent S. Stoll; Minghua Sun, both of Libertyville, IL (US); Noah P. Tu; Frank L. Wagenaar, both of Gurnee, IL (US); Gary T. Wang, Niles, IL (US); Sheldon Wang, Grayslake, IL (US); Paul E. Wiedeman, Deerfield, IL (US); Yibo Xu, Ridgefield, CT (US); Ming C. Yeung, Grayslake, IL (US); Chen Zhao, Libertyville, IL (US); Stephen Hanessian, Beaconsfield (CA); Malken Bayrakdarian, Verdun (CA); Xuehong Luo, Montreal (CA)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/421,787

(22) Filed: Oct. 19, 1999

Related U.S. Application Data

(63) Continuation-in-part of application No. 09/282,139, filed on Mar. 31, 1999, now abandoned.
(60) Provisional application No. 60/082,828, filed on Apr. 23, 1998.

(51) Int. Cl.[7] .................. A61K 31/40; A61K 31/415; C07D 207/00; C07D 403/02; C07D 277/28
(52) U.S. Cl. .................. 514/423; 514/422; 514/397; 514/365; 514/374; 548/532; 548/533; 548/518; 548/314.7; 548/205; 548/236; 548/237
(58) Field of Search .................. 514/423, 422, 514/397, 365, 375; 548/532, 533, 518, 314.7, 237, 236, 205

(56) References Cited

U.S. PATENT DOCUMENTS 5,360,817 A    11/1994   von Itzstein et al.
5,453,533 A    9/1995    Luo et al.
5,512,596 A    4/1996    Kim et al.
5,541,343 A    7/1996    Himmelsbach et al.
5,591,769 A    1/1997    Himmelsbach et al.
5,602,277 A    2/1997    Babu et al.
5,648,379 A    7/1997    von Itzstein et al.
5,763,483 A    6/1998    Bischofberger et al.
5,919,819 A    7/1999    Andrews et al.
6,239,150 B1 * 5/2001    Oshima et al. ............. 514/330
6,242,476 B1 * 6/2001    Mita et al. ..................... 514/23
6,245,801 B1 * 6/2001    Bryans et al. ............... 514/423
6,258,833 B1 * 7/2001    Martins et al. ............. 514/395

FOREIGN PATENT DOCUMENTS

EP    0483667    5/1992
EP    0539204    4/1993
EP    0823428    2/1998
EP    0882721    12/1998
GB    2292081    2/1996

(List continued on next page.)

OTHER PUBLICATIONS

Aoyama, et al., *Tetrahedron Letters*, vol. 32, No. 46, 1991, pp. 6731–6734.
Bernardi, et al., *Tetrahedron*, vol. 46, No. 6, 1990, pp. 1987–1998.
Bonner, et al., *J. of the Amer. Chem. Society*, vol. 73, No. 7, 1951, pp. 3126–3131.
Brouillette, et al., *Bioorganic & Medicinal Chemistry Letters*, vol. 9, 1999, pp. 1901–1906.
Coates, et al., *J. of Organic Chemistry*, vol. 51, No. 9, 1996, pp. 1383–1389.
Dyong, et al., *Chem. Ber.*, vol. 106, 1973, pp. 2654–2662.
Fehrentz, et al., *Synthesis*, No. 8, Aug. 1, 1983, pp. 676–678.
Itaya, et al., *Chem. Pharm. Bull.*, vol. 37, No. 5, 1989, pp. 1221–1225.
Keck, et al., *J. Org. Chem.*, vol. 56, 1991, pp. 417–420.
Larcheveque, et al., *J. Chem. Soc., Chem. Commun.*, No. 1, 1989, pp. 31–33.

(List continued on next page.)

*Primary Examiner*—Deborah C. Lambkin
(74) *Attorney, Agent, or Firm*—B. Gregory Donner

(57) ABSTRACT

Disclosed are compounds of the formula:

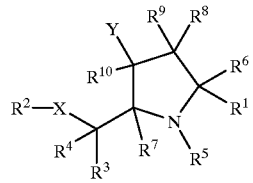

which are useful for inhibiting neuraminidases from disease-causing microorganisms, especially, influenza neuraminidase. Also disclosed are compositions and methods for preventing and treating diseases caused by microorganisms having a neuraminidase, processes for preparing the compounds and synthetic intermediates used in these processes.

115 Claims, No Drawings

FOREIGN PATENT DOCUMENTS

| | | |
|---|---|---|
| WO | 9116320 | 10/1991 |
| WO | 9206691 | 4/1992 |
| WO | 9518800 | 7/1995 |
| WO | 9520583 | 8/1995 |
| WO | 9626933 | 9/1996 |
| WO | 9630329 | 10/1996 |
| WO | 9636628 | 11/1996 |
| WO | 9706157 | 2/1997 |
| WO | 9732214 | 9/1997 |
| WO | 9747194 | 12/1997 |
| WO | 9893487 | 1/1998 |
| WO | 9806721 | 2/1998 |
| WO | 9807685 | 2/1998 |
| WO | 9811083 | 3/1998 |
| WO | 9817647 | 4/1998 |
| WO | 9821243 | 5/1998 |
| WO | 9906369 | 2/1999 |
| WO | 9914185 | 3/1999 |
| WO | 9914191 | 3/1999 |
| WO | 9931047 | 6/1999 |
| WO | 9933781 | 7/1999 |
| WO | 99/54290 | 10/1999 |
| WO | 99/54299 | 10/1999 |

OTHER PUBLICATIONS

Merino, et al., *J. Org. Chem.*, vol. 63, No. 16, 1998, pp. 5627–5630.

Y. Nishimura, et al., Natural Product Letters 1 33–38 (1992).

G. Kok, et al., J. Chem. Soc. Perkin Trans. I 905–908 (1998).

Petersen, et al., J. Am. Chem. Soc. 106 4539–4547 (1984).

Skibic, et al., J. Pharm Sci. 82 (10) 1010–1017 (1993).

Atigadda, et al., J. Med. Chem. 42 2332–2343 (1999).

\* cited by examiner

INHIBITORS OF NEURAMINIDASES

This application claims the benefit of U.S. Provisional Application for Patent No. 60/082,828, filed Apr. 23, 1998 and a CIP of U.S. patent application Ser. No. 09/282,139, filed Mar. 31, 1999, abandoned both of which are incorporated herein by reference.

TECHNICAL FIELD

The present invention relates to novel compounds, compositions and methods for inhibiting neuraminidase, especially influenza neuraminidase. The invention also contemplates a composition and methods for preventing and treating an influenza infection and processes for making such compounds and synthetic intermediates employed in these processes.

BACKGROUND OF THE INVENTION

Many disease-causing microorganisms possess a neuraminidase (also known as sialidase) which is involved in the replication process of the microorganism. In particular, viruses of the orthomyxovirus and paramyxovirus groups possess a neuraminidase. Diseases associated with paramyxoviruses include RSV (respiratory syncytial virus-related diseases), pneumonia and bronchiolitis (associated with paramyxovirus type 3) and laryngotracheobronchitis (associated with paramyxovirus type 1). Some of the more important disease-causing microorganisms in man and/or animals which possess a neuraminidase include Vibrio cholerae, Clostridium perfringens, Streptococcus pneumoniae, Arthrobacter sialophilus, influenza virus, parainfluenza virus, mumps virus, Newcastle diseane virus, fowl plague virus, equine influenza virus and Sendai virus.

Morality due to influenza is a serious problem throughout the world. The disease is devastating to man, lower mammals and some birds. Although vaccines containing attenuated influenza virus are available, those vaccines only provide immunological protection toward a few influenza strains and are less effective in otherwise immunologically compromised populations such as the elderly, young children, and in those who suffer from chronic respiratory illness. The productivity loss from absence due to sickness from influenza virus infection has been estimated to be more than $1 billion per year.

There are two major strains of influenza virus (designated A and B). Currently, there are only a few pharmaceutical products approved for treating influenza. These include amantadine and rimantadine, which are active only against the A strain of influenza viruses, and ribavirin, which suffers from dose-limiting toxicity. Mutant virus which is resistant to amantadine and rimantadine emerges quickly during treatment with these agents.

Very recently the first influenza neuraminidase inhibitor, zanamivir, was approved. However, it can only be administered by inhalation. Therefore, there is a continuing need for improved agents for treatment and/or prevention of influenza infection.

Neuraminidase is one of two major viral proteins which protrude from the envelope of influenza virus. During the release of progeny virus from infected cells, neuraminidase cleaves terminal sialic acid residues from glycoproteins, glycolipids and oligosaccharides on the cell surface. Inhibition of neuraminidase enzymatic activity leads to aggregation of progeny virus at the surface. Such virus is incapable of infecting new cells, and viral replication is therefore retarded or blocked. X-ray crystallographic studies and sequence alignments have shown that the residues which directly contact the sialic acid portion of the substrate are strictly conserved in the neuraminidase from all A and B influenza strains. Thus, a compound which binds to the sialic acid binding region of the neuraminidase active site will block the replication of both the A and B strains of influenza virus. Compounds which are influenza neuraminidase inhibitors will be useful for the prevention of influenza infection and will be useful for the treatment of influenza infection.

The following references disclose neuraminic acid derivatives with the disclosed utility listed after each reference:

L. Von ltzstein, et al., European Patent Application No. EP539204, published Apr. 28, 1993 (antiviral agent);

T. Honda, et al., European Patent Application No. EP823428, published Feb. 11, 1998 (sialidase inhibitor; influenza treatment);

T. Honda, et al., International Patent Application No. WO98/06712, published Feb. 19, 1998 (sialidase inhibitor; influenza remedy);

L. Von Itzstein, et al., International Patent Application No. WO95/20583, published Aug. 3, 1995 (viral neuraminidase inhibitor; influenza treatment);

P. Smith, International Patent Application No. WO95/18800, published Jul. 13, 1995 (viral neuraminidase inhibitor);

P. Colman, et al., International Patent Application No. WO92/06691, published Apr. 30, 1992 (viral neuraminidase inhibitor);

L. Von Itzstein, et al., U.S. Pat. No. 5,648,379, issued Jul. 15, 1997 (influenza treatment);

P. Reece, et al., International Patent Application No. WO97/32214, published Sep.4, 1997 (bind to influenza virus neuraminidase active site); and P. Reece, et al., International Patent Application No. WO98/21243, published May 23, 1998 (anti-influenza agent).

The following references disclose sialic acid derivatives with the disclosed utility listed after each reference:

Y. Ohira, et al., International Patent Application No. WO98/11083, published Mar. 19, 1998 (antiviral agent);

Y. Ohira, European Patent Application No. EP882721, published Dec. 9, 1998 (antiviral agent); and B. Glanzer, et al., Helvetica Chimica Acta 74 343–369 (1991) (Vibrio cholerae neuraminidase inhibitor).

The following references disclose benzene derivatives, cyclohexane derivatives or cyclohexene derivatives with the disclosed utility listed after each reference:

Y. Babu, et al., U.S. Pat. No. 5,602,277, issued Feb. 11, 1997 (neuraminidase inhibitors);

M. Luo, et al., U.S. Pat. No. 5,453,533, issued Sep. 26, 1995 (influenza neuraminidase inhibitor; influenza treatment);

Y. Babu, et al., International Patent Application No. WO96/30329, published Oct. 3,1996 (neuraminidase inhibitor; viral infection treatment);

N. Bischofberger, et al., U.S. Pat. No. 5,763,483, issued Jun. 9, 1998 (neuraminidase inhibitor);

C. Kim, et al., International Patent Application No. WO99/31047, published Jun. 24, 1999 (neuraminidase inhibitor, influenza treatment);

V. Atigadda, et al., J. Med. Chem. 42 2332–2343 (1999) (influenza neuraminidase inhibitor); and K. Kent, et al., International Patent Application No. 98/07685, published Feb. 26, 1998 (intermediates for the preparation of neuraminidase inhibitors).

C. Kim, et al., International Patent Application No. WO98/17647, published Apr. 30, 1998 discloses piperidine derivatives that are useful as neuraminidase inhibitors.

N. Bischofberger, et al., International Patent Application No. WO96/26933, published Sep. 6, 1996 and N.

Bischofberger, et al., International Patent Application No. WO99/141 85, published Mar. 25, 1999 disclose various substituted 6-membered ring compounds that are useful as neuraminidase inhibitors.

The following references disclose dihydropyran derivatives that are useful as viral neuraminidase inhibitors:

D. Andrews, et al., International Patent Application No. WO97/06157, published Feb. 20, 1997 and U.S. Pat. No. 5,919,819, issued Jul. 6, 1999; and P. Cherry, et al., International Patent Application No. WO96/36628, published Nov. 21, 1996.

C. Kim, et al., U.S. Pat. No. 5,512,596, issued Apr. 30, 1996 discloses 6-membered aromatic ring derivatives that are useful as neuraminidase inhibitors.

G. Diana, et al., International Patent Application No. WO98/03487, published Jan. 29, 1998 discloses substituted pyridazines that are useful for treatment of influenza.

B. Horenstein, et al., International Patent Application No. WO99/06369, published Feb. 11, 1999 discloses piperazine derivatives that are useful as neuraminidase inhibitors.

The following references disclose substituted cyclopentanes that are useful as neuraminidase inhibitors and treatments for influenza:

Y. Babu, et al., International Patent Application No. WO97/47194, published Dec. 18, 1997; and Y. Babu, et al., International Patent Application No. WO99/33781, published Jul. 8, 1999.

L. Czollner, et al., Helvetica Chimica Acta 73 1338–1358 (1990) discloses pyrrolidine analogs of neuraminic acid that are useful as Vibrio cholerae sialidase inhibitors.

W. Brouillette, et al., International Patent Application No. WO99/14191, published Mar. 25, 1999, discloses substituted pyrrolidin-2-one compounds that are useful as neuraminidase inhibitors and treatments for influenza.

The following references disclose siastatin B analogs that are useful as neuraminidase inhibitors:

Y. Niphimura, et al., Natural Product Letters 1 39–44 (1992); and

Y. Nishimura, et al., Natural Product Letters 1 33–38 (1992).

C. Penn, UK Patent Application No. GB2292081, published Feb. 14, 1996 discloses the use of a neuraminidase inhibitor in combination with an influenza vaccine.

An object of the invention is to provide compounds that inhibit neuraminidase of disease-causing microorganisms; especially, viral neuraminidase; and, most especially, influenza neuraminidase.

An object of the invention is also to provide compounds that inhibit neuraminidase from both A and B strains of influenza.

Another object of the invention is to provide prophylaxis of influenza infection in humans and other mammals.

Another object of the invention is to provide treatment of influenza infection in humans and other mammals.

Another object of the invention is to provide compounds that exhibit activity against influenza A virus and and influenza B virus by virtue of inhibiting influenza neuraminidase when such compounds are administered orally.

Another object of the invention is to provide a compound that can be effectively transported from the plasma into the lung bronchoaveolar fluid of humans and other mammals in order to block the replication of influenza virus in that tissue.

DISCLOSURE OF THE INVENTION

The present invention discloses compounds having Formula I:

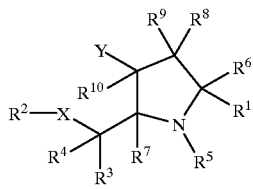

or a pharmaceutically acceptable salt, ester or prodrug thereof, wherein $R^1$ is selected from the group consisting of
(a) $-CO_2H$, (b) $-CH_2CO_2H$, (c) $-SO_3H$, (d) $-CH_2SO_3H$, (e) $-SO_2H$,
(f) $-CH_2SO_2H$, (g) $-PO_3H_2$, (h) $-CH_2PO_3H_2$, (i) $-PO_2H$, (j) $-CH_2PO_2H$,
(k) tetrazolyl, (l) $-CH_2$-tetrazolyl, (m) $-C(=O)-NH-S(O)_2-R^{11}$,
(n) $-CH_2C(=O)-NH-S(O)_2-R^{11}$, (o) $-SO_2N(T-R^{11})R^{12}$ and
(p) $-CH_2SO_2N(T-R^{11})R^{12}$ wherein T is selected from the group consisting of
(i) a bond, (ii) $-C(=O)-$, (iii) $-C(=O)O-$, (iv) $-C(=O)S-$, (v) $-C(=O)NR^{36}-$, (vi) $-C(=S)O-$, (vii) $-C(=S)S-$, and (viii) $-C(=S)NR^{36}-$, $R^{11}$ is selected from the group consisting of
(i) $C_1-C_{12}$ alkyl, (ii) $C_2-C_{12}$ alkenyl, (iii) cycloalkyl, (iv) (cycloalkyl)alkyl,
(v) (cycloalkyl)alkenyl, (vi) cycloalkenyl, (vii) (cycloalkenyl)alkyl, (viii) (cycloalkenyl)alkenyl,
(ix) aryl, (x) (aryl)alkyl, (xi) (aryl)alkenyl,
(xii) heterocyclic, (xiii) (heterocyclic)alkyl and (xiii) (xiv) (heterocyclic)alkenyl; and $R^{12}$ and $R^{36}$ are independently selected from the group consisting of
(i) hydrogen, (ii) $C_1-C_{12}$ alkyl, (iii) $C_2-C_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl)alkenyl, (x) aryl, (xi) (aryl)alkyl, (xii) (aryl)alkenyl, (xiii) heterocyclic, (xiv) (heterocyclic)alkyl and (xv) (heterocyclic)alkenyl;

X is selected from the group consisting of
(a) $-C(=O)-N(R^*)-$, (b) $-N(R^*)-C(=O)-$, (c) $-C(=S)-N(R^*)-$, (d) $-N(R^*)-C(=S)-$, (e) $-N(R^*)-SO_2-$, and (f) $-SO_2-N(R^*)-$ wherein $R^*$ is hydrogen, $C_1-C_3$ loweralkyl or cyclopropyl;

$R^2$ is selected from the group consisting of
(a) hydrogen, (b) $C_1-C_6$ alkyl, (c) $C_2-C_6$ alkenyl, (d) $C_3-C_6$ cycloalkyl, (e) $C_5-C_6$ cycloalkenyl, (f) halo $C_1-C_6$ alkyl and (g) halo $C_2-C_6$ alkenyl;

or $R^2-X-$ is

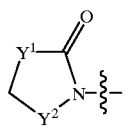

wherein $Y^1$ is $-CH_2-$, $-O-$, $-S-$ or $-NH-$ and $Y^2$ is $-C(=O)-$ or $-C(R^{aa})(R^{bb})-$ wherein $R^{aa}$ and $R^{bb}$ are indepedently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R^3$ and $R^4$ are independently selected from the group consisting of (a) hydrogen, (b) cycloalkyl, (c) cycloalkenyl, (d) heterocyclic, (e) aryl and (f) —Z—$R^{14}$ wherein Z is (i) —C($R^{37a}$)($R^{37b}$)—, (ii) —C($R^{47}$)=C($R^{48}$)—, (iii) —C≡C—, (iv) —C(=O)—, (v) —C(=S)—, (vi) —C(=N$R^{15}$)—, (vii) —C($R^{37a}$)(O$R^{37c}$)—, (viii) —C($R^{37a}$)(S$R^{37c}$)—, (ix) —C($R^{37a}$)(N($R^{37b}$)($R^{37c}$))—, (x) —C($R^{37a}$)($R^{37b}$)—O—, (xi) —C($R^{37a}$)($R^{37b}$)—N($R^{37c}$)—, (xii) —C($R^{37a}$)($R^{37b}$)—N(O)($R^{37c}$)—, (xiii) —C($R^{37a}$)($R^{37b}$)—N(OH)—, (xiv) —C($R^{37a}$)($R^{37b}$)—S—, (xv) —C($R^{37a}$)($R^{37b}$)—S(O)—, (xvi) —C($R^{37a}$)($R^{37b}$)—S(O)$_2$—, (xvii) —C($R^{37a}$)($R^{37b}$)—C(=O), (xviii) —C($R^{37a}$)($R^{37b}$)—C(=S)—, (xix) —C($R^{37a}$)($R^{37b}$)—C(=N$R^{15}$)—, (xx) —C($R^{37a}$)(O$R^{37c}$)—C(=O)—, (xxi) —C($R^{37a}$)(S$R^{37c}$)—C(=O)—, (xxii) —C($R^{37a}$)(O$R^{37c}$)—C(=S)—, (xxiii) —C($R^{37a}$)(S$R^{37c}$)—C(=S)—, (xxiv) —C(=O)—C($R^{37a}$)(O$R^{37c}$)—, (xxv) —C(=O)—C($R^{37a}$)(S$R^{37c}$)—, (xxvi) —C(=S)—C($R^{37a}$)(O$R^{37c}$)—, (xxvii) —C(=S)—C($R^{37a}$)(S$R^{37c}$)—, (xxviii) —C($R^{37a}$)(O$R^{37c}$)—C($R^{37a}$)(O$R^{37c}$)—, (xxix) —C($R^{37a}$)(S$R^{37c}$)—C($R^{37a}$)(O$R^{37c}$)—, (xxx) —C($R^{37a}$)(O$R^{37c}$)—C($R^{37a}$)(S$R^{37c}$)—, (xxxi) —C($R^{37a}$)(S$R^{37c}$)—C($R^{37a}$)(S$R^{37c}$)—, (xxxii) —C(=O)—C(=O)—, (xxxiii) —C(=S)—C(=S)—, (xxxiv) —C(=O)—O—, (xxxv) —C(=O)—S—, (xxxvi) —C(=S)—O—, (xxxvii) —C(=S)—S—, (xxxviii) —C(=O)—N($R^{37a}$)—, (xxxix) —C(=S)—N($R^{37a}$)—, (xl) —C($R^{37a}$)($R^{37b}$)—C(=O)—N($R^{37a}$)—, (xli) —C($R^{37a}$)($R^{37b}$)—C(=S)—N $R^{37a}$—, (xlii) —C($R^{37a}$)($R^{37b}$)—C(=O)—O—, (xliii) —C($R^{37a}$)($R^{37b}$)—C(=O)—S—, (xliv) —C($R^{37a}$)($R^{37b}$)—C(=S)—O—, (xlv) —C($R^{37a}$)($R^{37b}$)—C(=S)—S—, (xivi) —C($R^{37a}$)($R^{37b}$)—N($R^{37b}$)—C(=O)—, (xlvii) —C($R^{37a}$)($R^{37b}$)—N($R^{37b}$)—C(=S)—, (xlviii) —C($R^{37a}$)($R^{37b}$)—O—C(=O)—, (xlix) —C($R^{37a}$)($R^{37b}$)—S—C(=O)—, (l) —C($R^{37a}$)($R^{37b}$)—O—C(=S)—, (li) —C($R^{37a}$)($R^{37b}$)—S—C(=S)—, (lii) —C($R^{37a}$)($R^{37b}$)—N N($R^{37b}$)—C(=O)—N($R^{37a}$)—, (liii) —C($R^{37a}$)($R^{37b}$)—N($R^{37b}$)—C(=S)—N($R^{37a}$)—, (liv) —C($R^{37a}$)($R^{37b}$)—N($R^{37b}$)—C(=O)—O—, (lv) —C($R^{37a}$)($R^{37b}$)—N($R^{37b}$)—C(=O)—S—, (lvi) —C($R^{37a}$)($R^{37b}$)—N($R^{37b}$)—C(=S)—O—, (lvii) —C($R^{37a}$)($R^{37b}$)—N($R^{37b}$)—C(=S)—S—, (lviii) —C($R^{37a}$)($R^{37b}$)—O—C(=O)—N($R^{37a}$)—, (lix) —C($R^{37a}$)($R^{37b}$)—S—C(=O)—N($R^{37a}$)—, (lx) —C($R^{37a}$)($R^{37b}$)—O—C(=S)—N($R^{37a}$)—, (lxi) —C($R^{37a}$)($R^{37b}$)—S—C(=S)—N($R^{37a}$)—, (lxii) —C($R^{37a}$)($R^{37b}$)—O—C(=O)—O—, (lxiii) —C($R^{37a}$)($R^{37b}$)—S—C(=O)—O—, (lxiv) —C($R^{37a}$)($R^{37b}$)—O—C(=O)—S—, (lxv) —C($R^{37a}$)($R^{37b}$)—S—C(=O)—S—, (lxvi) —C($R^{37a}$)($R^{37b}$)—O—C(=S)—O—, (lxvii) —C($R^{37a}$)($R^{37b}$)—S—C(=S)—O—, (lxviii) —C($R^{37a}$)($R^{37b}$)—O—C(=S)—S—, (lxix) —C($R^{37a}$)($R^{37b}$)—S—C(=S)—O—, or (lxx) —C($R^{37a}$)($R^{37b}$)—C($R^{37a}$)(O$R^{37c}$)—;

$R^{14}$ is (i) hydrogen, (ii) $C_1$–$C_{12}$ alkyl, (iii) haloalkyl, (iv) hydroxyalkyl, (v) thiol-substituted alkyl, (vi) $R^{37c}$O-substituted alkyl, (vii) $R^{37c}$S-substituted alkyl, (viii) aminoalkyl, (ix) ($R^{37c}$)NH-substituted alkyl, (x) ($R^{37a}$)($R^{37c}$)N-susbstituted alkyl, (xi) $R^{37a}$O—(O=)C-substituted alkyl, (xii) $R^{37a}$S—(O=)C-substituted alkyl, (xiii) $R^{37a}$O-(S=)C-substituted alkyl, (xiv) $R^{37a}$S—(S=)C-substituted alkyl, (xv) ($R^{37a}$O)$_2$—P(=O)-substituted alkyl, (xvi) cyanoalkyl, (xvi) $C_2$–$C_{12}$ alkenyl, (xviii) haloalkenyl, (xix) $C_2$–$G_{12}$ alkynyl, (xx) cycloalkyl, (xxi) (cycloalkyl)alkyl, (xxii) (cycloalkyl)alkenyl, (xxiii) (cycloalkyl)alkynyl, (xxiv) cycloalkenyl, (xxv) (cycloalkenyl)alkyl, (xxvi) (cycloalkenyl)alkenyl, (xxvii) (cycloalkenyl)alkynyl, (xxviii) aryl, (xxix) (aryl)alkyl, (xxx) (aryl)alkenyl, (xxxi) (aryl)alkynyl, (xxxii) heterocyclic, (xxxiii) (heterocyclic)alkyl, (xxxiv) (heterocyclic)alkenyl or (xxxv) (heterocyclic)alkynyl, with the proviso that $R^{14}$ is other than hydrogen when Z is —C($R^{37a}$)($R^{37b}$)—N($R^{37b}$)—C(=O)—O—, —C($R^{37a}$)($R^{37b}$)—N($R^{37b}$)—C(=S)—O—, —C($R^{37a}$)($R^{37b}$)—N($R^{37b}$)—C(=O)—S—, —C($R^{37a}$)($R^{37b}$)—N($R^{37b}$)—C(=S)—S—, —C($R^{37a}$)($R^{37b}$)—O—C(=O)—O—, —C($R^{37a}$)($R^{37b}$)—O—C(=S)—O—, —C($R^{37a}$)($R^{37b}$)—S—C(=O)—O—, —C($R^{37a}$)($R^{37b}$)—S—C(=S)—O—, —C($R^{37a}$)($R^{37b}$)—O—C(=O)—S—, —C($R^{37a}$)($R^{37b}$)—O—C(=S)—S—, —C($R^{37a}$)($R^{37b}$)—S—C(=O)—S—, or —C($R^{37a}$)($R^{37b}$)—S—C(=S)—S—;

$R^{37a}$, $R^{37b}$, $R^{47}$, and $R^{48}$ at each occurrence are independently selected from the group consisting of (i) hydrogen, (ii) $C_1$–$C_{12}$ alkyl, (iii) haloalkyl, (iv) hydroxyalkyl, (v) alkoxyalkyl, (vi) $C_2$–$C_{12}$ alkenyl, (vii) haloalkenyl, (viii) $C_2$–$C_{12}$ alkynyl, (ix) cycloalkyl, (x) (cycloalkyl)alkyl, (xi) (cycloalkyl)alkenyl, (xii) (cycloalkyl)alkynyl, (xiii) cycloalkenyl, (xiv) (cycloalkenyl)alkyl, (xv) (cycloalkenyl)alkenyl, (xvi) (cycloalkenyl) alkynyl, (xvii) aryl, (xviii) (aryl)alkyl, (xix) (aryl) alkenyl, (xx) (aryl)alkynyl, (xxi) heterocyclic, (xxii) (heterocyclic)alkyl, (xxiii) (heterocyclic) alkenyl and (xxiv) (heterocyclic)alkynyl;

$R^{37c}$ at each occurrence is independently selected from the group consisting of (i) hydrogen, (ii) $C_1$–$G_{12}$ alkyl, (iii) haloalkyl, (iv) $C_2$–$C_{12}$ alkenyl, (v) haloalkenyl, (vi) $C_2$–$C_{12}$ alkynyl, (vii) cycloalkyl, (viii) (cycloalkyl)alkyl, (ix) (cycloalkyl)alkenyl, (x) (cycloalkyl)alkynyl, (xi) cycloalkenyl, (xii) (cycloalkenyl)alkyl, (xiii) (cycloalkenyl)alkenyl, (xiv) (cycloalkenyl) alkynyl, (xv) aryl, (xvi) (aryl)alkyl, (xvii) (aryl) alkenyl, (xviii) (aryl)alkynyl, (xix) heterocyclic, (xx) (heterocyclic)alkyl, (xxi) (heterocyclic) alkenyl, (xxii) (heterocyclic)alkynyl, (xxiii) —C(=O)—$R^{14}$, (xxiv) —C(=S)—$R^{14}$, (xxv) —S(O)$_2$—$R^{14}$ and (xxvi) hydroxyalkyl;

or when Z is —C($R^{37a}$)($R^{37b}$)—N($R^{37c}$)—, then N($R^{37c}$) and $R^{14}$ when taken together are an azido group;

or when Z is —C($R^{37a}$)($R^{37b}$)—N(O)($R^{37c}$)—, then N(O)($R^{37c}$) and $R^{14}$ when taken together are an N-oxidized 3–7 membered heterocyclic ring having at least one N-oxidized ring nitrogen atom;

or when Z is —C($R^{37a}$)($R^{37b}$)—, —C($R^{37a}$)(O$R^{37c}$)—, —C($R^{37a}$)(S$R^{37c}$)— or —C($R^{37a}$)(N($R^{37b}$)($R^{37c}$))—, then $R^{37a}$, $R^{14}$ and the carbon atom to which they are bonded when taken together form a cyclopentyl, cyclopentenyl, cyclohexyl or cyclohexenyl ring or then O$R^{37c}$ or S$R^{37c}$ or N($R^{37c}$) and $R^{14}$ and the carbon atom to which they are bonded when taken together form a heterocyclic ring containing an O, S or N atom, respectively, and having from 4 to 8 ring atoms;

$R^{15}$ is selected from the group consisting of
(i) hydrogen, (ii) hydroxy, (iii) amino, (iv) $C_1$–$C_{12}$ alkyl, (v) haloalkyl, (vi) $C_2$—$C_{12}$ alkenyl, (vii) haloalkenyl, (viii) cycloalkyl, (ix) (cycloalkyl) alkyl, (x) (cycloalkyl)alkenyl, (xi) cycloalkenyl, (xii) (cycloalkenyl)alkyl, (xiii) (cycloalkenyl) alkenyl, (xiv) aryl, (xv) (aryl)alkyl, (xvi) (aryl) alkenyl, (xvii) heterocyclic, (xviii) (heterocyclic) alkyl and (xix) (heterocyclic)alkenyl;

or $R^3$ and $R^4$ taken together, with the atom to which they are attached, form a carbocyclic or heterocyclic ring having from 3 to 8 ring atoms;

$R^5$ is selected from the group consisting of
(a) hydrogen, (b) —CH($R^{38}$)$_2$, (c) —O—$R^{40}$, (d) $C_2C_4$ alkynlyl, (e) cyclopropyl, (f)cyclobutyl, (g) —C(=$Q^1$)—$R^{17}$, and (h) —N($R^{19}$)$_2$
wherein $Q^1$ is O, S, or N($R^{18}$);
$R^{17}$ and $R^{18}$ are independently selected, at each occurrence, from the group consisting of hydrogen, methyl, and ethyl,
$R^{19}$, $R^{38}$, and $R^{40}$ are independently selected, at each occurrence, from the group consisting of
(i) hydrogen, (ii) $C_1$–$C_{12}$ alkyl, (iii) haloalkyl, (iv) $C_2$—$C_{12}$ alkenyl, (v) haloalkenyl, (vi) cycloalkyl, (vii) (cycloalkyl)alkyl, (viii) (cycloalkyl)alkenyl, (ix) cycloalkenyl, (x) (cycloalkenyl)alkyl, (xi) (cycloalkenyl)alkenyl, (xii) aryl, (xiii) (aryl)alkyl, (xiv) (aryl)alkenyl, (xv) heterocyclic, (xvi) (heterocyclic)alkyl and (xvii) (heterocyclic) alkenyl;

Y is selected from the group consisting of
(a) hydrogen, (b) $C_1$–$C_5$ alkyl, (C) $C_1$–$C_5$ haloalkyl, (d) $C_2$—$C_5$ alkenyl, (e) $C_2$—$C_5$ haloalkenyl, (f) $C_2$–$C_5$ alkynyl, (g) $C_3$–$C_5$ cycloalkyl, (h) $C_3$–$C_5$ cycloalkyl-$C_1$-to-$C_3$-alkyl, (i) $C_5$ cycloalkenyl, (j) $C_5$ cycloalkenyl-$C_1$-to-$C_3$-alkyl, (k) $C_5$ cycloalkenyl-$C_2$-to-$C_3$-alkenyl, (l) —(CH$R^{39}$)$_n$O$R^{20}$, (m) —CH(O$R^{20}$)—CH$_2$(O$R^{20}$), (n) —(CH$R^{39}$)$_n$S$R^{21}$ (o) —(CH$R^{39}$)$_n$CN, (p) —(CH$R^{39}$)$_n$N$_3$, (q) phenyl, (r) halo-substituted phenyl, (s) —(CH$R^{39}$)$_n$C(=$Q^2$)$R^{22}$, (t) —(CH$R^{39}$)$_n$N(=$Q^3$), (u) —N(O)=CHCH$_3$, (v) —(CH$R^{39}$)$_n$N$R^{23}R^{24}$, (w) halo and (x) a heterocyclic ring having from 3 to 6 ring atoms;
wherein n is 0, 1, or 2; $Q^2$ is O, S, N$R^{25}$, or CH$R^{26}$; and $Q^3$ is N$R^{41}$, or CH$R^{42}$;

$R^{20}$ at each occurrence is independently
(i) hydrogen, (ii) methyl, (iii) ethyl, (iv) n-propyl, (v) isopropyl, (vi) $C_1$–$C_3$ haloalkyl, (vii) vinyl, (viii) propenyl, (ix) isopropenyl, (x) allyl, (xi) $C_2$–$C_3$ haloalkenyl, (xii) amino, (xiii) —NHCH$_3$, (xiv) —N(CH$_3$)$_2$, (xv) —NHCH$_2$CH$_3$, (xvi) —N(CH$_3$)(CH$_2$CH$_3$), (xvii) —N(CH$_2$CH$_3$)$_2$ or (xviii) —N(=CH$_2$);

$R^{21}$ is
hydrogen, (ii) methyl, (iii) ethyl, (iv) n-propyl, (v) isopropyl, (vi) $C_1$–$C_3$ haloalkyl, (vii) vinyl, (viii) propenyl, (ix) isopropenyl, (x) allyl or (xi) $C_2$–$C_3$ haloalkenyl;

$R^{22}$ is
(i) hydrogen, (ii) methyl, (iii) ethyl, (iv) n-propyl, (v) isopropyl, (vi) hydroxy, (vii) thiol, (viii) methoxy, (ix) ethoxy, (x) n-propoxy, (xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —N($R^{28a}$)($R^{28b}$), (xxiii) —CH$_2R^{29}$, (xxiv) aminomethyl, (xxv) hydroxymethyl, (xxvi) thiolmethyl, (xxvii) —NHNH$_2$, (xxviii) —N(CH$_3$)NH$_2$ or (xxix) —NHNH(CH$_3$);

$R^{23}$ and $R^{39}$ are independently hydrogen or methyl;
$R^{41}$ and $R^{42}$ are independently hydrogen, methyl, or ethyl;
$R^{24}$ is selected from the group consisting of
(i) hydrogen, (ii) $C_1$–$C_4$ alkyl, (iii) $C_2$–$C_4$ alkenyl, (iv) $C_2$–$C_4$ alkynyl, (v) cyclopropyl, (vi) —C(=$Q^4$)—$R^{30}$, (v) —O$R^{31}$, and (vi) —N($R^{32}$)$_2$, wherein $Q^4$ is O, S, or N($R^{33}$);

$R^{25}$ is hydrogen, hydroxy, methyl, ethyl, amino, —CN, or —NO$_2$,
$R^{26}$ group is hydrogen, methyl or ethyl;
$R^{28a}$ hydrogen, hydroxy, methyl, ethyl, amino, —NHCH$_3$, —N(CH$_3$)$_2$, methoxy, ethoxy, or —CN;
$R^{28b}$ is hydrogen, methyl or ethyl;
or $R^{28a}$, $R^{28b}$ and the nitrogen to which they are bonded taken together represent azetidinyl;
$R^{29}$ group is hydrogen, hydroxy, thiol, methyl, ethyl, amino, methoxy, ethoxy, methylthio, ethylthio, methylamino or ethylamino;
$R^{30}$ group is hydrogen, methyl, ethyl, —O$R^{34}$, —S$R^{34}$, —N($R^{35}$)$_2$, —NHOH, —NHNH$_2$, —N(CH$_3$)NH$_2$, or —N(CH$_2$CH$_3$)NH$_2$;
$R^{31}$ and $R^{32}$ substituents, at each occurrence, are independently hydrogen, methyl or ethyl;
$R^{33}$ group is hydrogen, hydroxy, methyl, ethyl, amino, —CN, or —NO$_2$;
$R^{34}$ group is methyl or ethyl;
$R^{35}$ group is independently hydrogen, methyl or ethyl; with the proviso that when $Q^2$ is CH$R^{26}$ then $R^{22}$ is selected from the group consisting of hydrogen, —CH$_3$, —C$_2H_5$, —C$_3H_7$, —OCH$_3$, —SCH$_3$, —C$_2H_5$, and —S—$C_2H_5$, and with the proviso that when $R^3$ and $R^4$ are each hydrogen, then Y is other than hydrogen;

$R^6$ and $R^7$ are independently selected from the group consisting of
(a) hydrogen, (b) $C_1$–$C_{12}$ alkyl, (c) $C_2$–$C_{12}$ alkenyl, (d) cycloalkyl, (e) (cycloalkyl)alkyl, (f) (cycloalkyl) alkenyl, (g) cycloalkenyl, (h) (cycloalkenyl)alkyl, (i) (cycloalkenyl),alkenyl, (j) aryl, (k) (aryl)alkyl, (l) (aryl) alkenyl, (m) heterocyclic, (n) (heterocyclic)alkyl and (o) (heterocyclic)alkenyl; and $R^8$, $R^9$, and $R^{10}$ are independently selected from the group consisting of
(a) hydrogen, (b) $C_1$–$C_6$ alkyl, (c) $C_2$–$C_6$ alkenyl, (d) $C_3$—$C_6$ cycloalkyl, (e) $C_3$–$C_6$ cycloalkenyl, and (f) fluorine, with the proviso that the total number of atoms, other than hydrogen, in each of $R^8$, $R^9$, and $R^{10}$, is 6 atoms or less.

Preferred compounds of the invention are compounds having the relative sterochemistry depicted by Formula IIA:

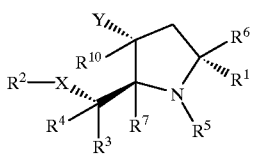

IIA or a pharmaceutically acceptable salt, ester or prodrug thereof, wherein $R^1$, $R^2$, $R^3$, $R^4$, $R^5$, $R^6$, $R^7$, $R^8$, $R^9$, $R^{10}$, X and Y are as defined above and wherein $R^3$ and $R^4$ are not both the same.

More preferred compounds of the invention are enantiomerically enriched compounds having the absolute sterochemistry depicted by Formula IIB:

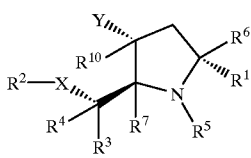

IIB or a pharmaceutically acceptable salt, ester or prodrug thereof, wherein $R^1$, $R^2$, $R^3$, $R^4$, $R^5$, $R^6$, $R^7$, $R^8$, $R^9$, $R^{10}$, X and Y are as defined above and wherein $R^3$ and $R^4$ are not both the same.

Other preferred compounds of the invention are compounds having the relative sterochemistry depicted by Formula IIIA:

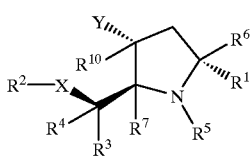

IIIA or a pharmaceutically acceptable salt, ester or prodrug thereof, wherein $R^1$, $R^2$, $R^3$, $R^4$, $R^5$, $R^6$, $R^7$, $R^8$, $R^9$, $R^{10}$, X and Y are as defined above and wherein $R^3$ and $R^4$ are not both the same.

Other more preferred compounds of the invention are enantiomerically enriched compounds having the absolute sterochemistry depicted by Formula

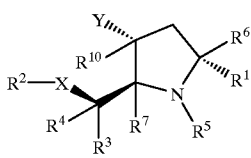

IIIB or a pharmaceutically acceptable salt, ester or prodrug thereof, wherein $R^1$, $R^2$, $R^3$, $R^4$, $R^5$, $R^6$, $R^7$, $R^8$, $R^9$, $R^{10}$, X and Y are as defined above and wherein $R^3$ and $R^4$ are not both the same.

Other preferred compounds of the invention are compounds having Formula I, IIA, IIB, IIIA or IIIB or a salt, ester or prodrug thereof wherein $R^1$ is defined as above; —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

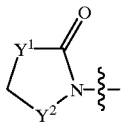

wherein
$Y^1$ is —CH$_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen,
$C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;
$R^3$ and $R^4$ are independently selected from hydrogen, heterocyclic and —Z—$R^{14}$ wherein Z and $R^{14}$ are defined as above and wherein one of $R^3$ and $R^4$ is other than hydrogen;
$R^5$ is hydrogen or loweralkyl;
$R^6$ and $R^7$ are independently hydrogen or loweralkyl;
$R^8$ and $R^9$ are independently hydrogen, fluoro or loweralkyl;
$R^{10}$ is hydrogen, fluoro or loweralkyl; and
Y is $C_2$–$C_5$ alkenyl, $C_2$–$C_5$ haloalkenyl, —C(=$Q^2$)$R^{22}$, —N(=$Q^3$), —N(O)=CHCH$_3$, —NR$^{23}$R$^{24}$ or a heterocyclic ring having from 3 to 6 ring atoms, wherein $R^{22}$, $R^{23}$, $R^{24}$, $Q^2$ and $Q^3$ are defined as above.

More preferred compounds of the invention are compounds having Formula I, IIA, IIB, IIIA or IIIB or a salt, ester or prodrug thereof wherein $R^1$ is defined as above; —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

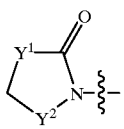

wherein
$Y^1$ is —CH$_2$— and $Y^2$ is —C(=O)— or —C($R^{aa}$)($R^{bb}$) wherein $R^{aa}$ and $R^{bb}$ are independently selected from the group consisting of hydrogen,
$C_1$–$C_3$ loweralkyl, hydroxymethyl, 1-hydroxyethyl and 2-hydroxyethyl;
$R^3$ and $R^4$ are independently selected from hydrogen, heterocyclic and —Z—$R^{14}$ wherein Z and $R^{14}$ are defined as above and wherein one of $R^3$ and $R^4$ is other than hydrogen;
$R^5$ is hydrogen or loweralkyl;
$R^6$ and $R^7$ are independently hydrogen or loweralkyl:
$R^8$ and $R^9$ are independently hydrogen or loweralkyl;
$R^{10}$ is hydrogen or loweralkyl; and
Y is $C_2$–$C_5$ alkenyl, $C_2$–$C_5$ haloalkenyl, —C(=$Q^2$)$R^{22}$, —N(=$Q^3$), —N(O)=CHCH$_3$, —NR$^{23}$R$^{24}$ or a heterocyclic ring having 5 ring atoms and also containing one or two double bonds, wherein $R^{22}$, $R^{23}$, $R^{24}$, $Q^2$ and $Q^3$ are defined as above.

Even more preferred compounds of the invention are compounds having Formula I, IIA, IIB, IIIA or IIIB or a salt, ester or prodrug thereof wherein $R^1$ is defined as above;

—X—R² is R²—C(=O)—NH—, R²—NH—C(=O)—, R²—NH—SO₂— or R²—SO₂—NH— wherein R² is C₁–C₃ loweralkyl, halo C₁–C₃ loweralkyl, C₂–C₃ alkenyl or halo C₁–C₃ alkenyl or —X—R² is

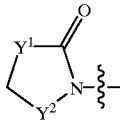

wherein

Y¹ is —CH₂— and Y² is —C(=O)— or —C(R$^{aa}$)(R$^{bb}$) wherein R$^{aa}$ and R$^{bb}$ are independently selected from the group consisting of hydrogen, C₁–C₃ loweralkyl, hydroxymethyl, 1-hydroxyethyl and 2-hydroxyethyl;

R³ and R⁴ are independently selected from hydrogen, heterocyclic and —Z—R¹⁴ wherein Z and R¹⁴ are defined as above and wherein one of R³ and R⁴ is other than hydrogen;

R⁵ is hydrogen or loweralkyl;

R⁶ and R⁷ are independently hydrogen or loweralkyl;

R⁸ and R⁹ are independently hydrogen or loweralkyl;

R¹⁰ is hydrogen or loweralkyl; and

Y is C₂–C₅ alkenyl, C₂–C₅ haloalkenyl, NH₂, —NHC(=NH)NH₂ or a heterocyclic ring having 5 ring atoms and also containing one or two double bonds.

More highly preferred compounds of the invention are compounds having Formula I, IIA, IIB, IIIA or IIIB or a salt, ester or prodrug thereof wherein R¹ is —CO₂H; —X—R² is R²—C(=O)—NH—, R²—NH—C(=O)—, R²—NH—SO₂— or R²—SO₂—NH— wherein R² is C₁–C₃ loweralkyl or halo- C₁–C₃ loweralkyl;

R³ and R⁴ are independently selected from hydrogen, heterocyclic and —Z—R¹⁴ wherein Z and R¹⁴ are defined as above and wherein one of R³ and R⁴ is other than hydrogen;

R⁵ is hydrogen or loweralkyl;

R⁶ and R⁷ are hydrogen independently hydrogen or loweralkyl;

R⁸ and R⁹ are hydrogen independently hydrogen or loweralkyl;

R¹⁰ is hydrogen or loweralkyl; and

Y is C₂–C₅ alkenyl, C₂–C₅ haloalkenyl, NH₂, —NHC(=NH)NH₂ or a heterocyclic ring having 5 ring atoms and also containing one or two double bonds.

Even more highly preferred compounds of the invention are compounds having Formula I, IIA, IIB, IIIA or IIIB or a salt, ester or prodrug thereof wherein R¹ is —CO₂H; —X—R² is R²—O(=O)—NH—, R²—NH—C(=O)—, R²—NH—SO₂— or R²—SO₂—NH— wherein R² is C₁–C₃ loweralkyl or halo- C₁–C₃ loweralkyl;

R⁴ is hydrogen or loweralkyl and R³ is heterocyclic or —Z—R¹⁴ wherein Z and R¹⁴ are defined as above;

R⁵ is hydrogen,

R⁶ and R⁷ are hydrogen;

R⁸ and R⁹ are hydrogen;

R¹⁰ is hydrogen; and

Y is C₂–C₅ alkenyl, C₂–C₅ haloalkenyl, NH₂, —NHC(=NH)NH₂ or a heterocyclic ring having 5 ring atoms and also containing one or two double bonds.

Other even more highly preferred compounds of the invention are compounds having Formula I, IIA, IIB, IIIA or IIIB or a salt, ester or prodrug thereof wherein R¹ is —CO₂H;

—X—R² is R²—C(=O)—NH—, R²—NH—C(=O)—, R²—NH—SO₂— or R²—SO₂—NH— wherein R² is C₁–C₃ loweralkyl or halo C₁–C₃ loweralkyl;

R⁴ is hydrogen or loweralkyl and R³ is (a) heterocyclic, (b) alkyl, (b) cycloalkyl, (d) cycloalkylalkyl, (e) alkenyl, (f alkynyl, (g) —C(=O)—R¹⁴, (h) —C(R$^{37a}$)(OR$^{37c}$)—R or (i) —C(R$^{37a}$)(R$^{37b}$)—N(O)(R$^{37c}$)R¹⁴ wherein R¹⁴ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$O)₂—P(=O)-substituted alkyl;

R$^{37a}$ and R$^{37b}$ are independently selected from the group consisting of (i) hydrogen, (ii) loweralkyl and (iii) loweralkenyl; and R$^{37c}$ is hydrogen, (ii) loweralkyl or (iii) loweralkenyl;

R⁵ is hydrogen;

R⁶ and R⁷ are hydrogen;

R⁸ and R⁹ are hydrogen;

R¹⁰ is hydrogen; and

Y is C₂–C₅ alkenyl, C₂–C₅ haloalkenyl, NH₂, —NHC(=NH)NH₂ or a heterocyclic ring having 5 ring atoms and also containing one or two double bonds.

Most highly preferred compounds of the invention are compounds having Formula I, IIA, IIB, IIIA or IIIB or a salt, ester or prodrug thereof wherein R¹ is —CO₂H;

—X—R² is R²—C(=O)—NH—, R²—NH—C(=O)—, R²—NH—SO₂— or R²—SO₂—NH— wherein R² is C₁–C₃ loweralkyl or halo C₁–C₃ loweralkyl;

R⁴ is hydrogen and R³ is (a) heterocyclic, (b) alkyl or (c) —C(R$^{37a}$)(OR$^{37c}$)—R¹⁴ wherein R¹⁴ is (i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$O)₂—P(=O)-substituted alkyl;

R$^{37a}$ and R$^{37b}$ are independently selected from the group consisting of (i) hydrogen, (ii) loweralkyl and (iii) loweralkenyl; and R$^{37c}$ is hydrogen, (ii) C₁–C₃ loweralkyl or (iii) allyl;

R⁵ is hydrogen,

R⁶ and R⁷ are hydrogen;

R⁸ and R⁹ are hydrogen;

R¹⁰ is hydrogen; and

Y is C₂–C₅ alkenyl, C₂–C₅ haloalkenyl, NH₂, —NHC(=NH)NH₂ or a heterocyclic ring having 5 ring atoms and also containing one or two double bonds.

Other most highly preferred compounds of the invention are compounds having Formula I, IIA, IIB, IIIA or IIIB or a salt, ester or prodrug thereof wherein R¹ is —CO₂H;

—X—R² is R²—C(=O)—NH— or R²—SO₂—NH— wherein R² is C₁–C₃ loweralkyl or halo C₁–C₃ loweralkyl;

R⁴ is hydrogen and R³ is (a) heterocyclic, (b) alkyl or (c) —C(R$^{37a}$)(OR$^{37c}$)—R¹⁴ wherein R¹⁴ is (i) loweralkyl, (ii) loweralkenyl, (iii) hydroxy-substituted loweralkyl or (iv) alkoxy-substituted loweralkyl;

$R^{37a}$ is
  (i) hydrogen, (ii) loweralkyl or (iii) loweralkenyl; and
$R^{37c}$ is
  (i) hydrogen, (ii) $C_1$–$C_3$ loweralkyl or (iii) allyl;
$R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl, $NH_2$, —NHC(=NH)$NH_2$ or a heterocyclic ring having 5 ring atoms and also containing one or two double bonds.

Other most highly preferred compounds of the invention are compounds having Formula I, IIA, IIB, IIIA or IIIB or a salt, ester or prodrug thereof wherein $R^1$ is —$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is —C($R^{37a}$)(O$R^{37c}$)—$R^{14}$ wherein $R^{14}$ is
  loweralkyl, loweralkenyl or alkoxy-substituted loweralkyl;
$R^{37a}$ is
  loweralkyl or loweralkenyl; and
$R^{37c}$ is
  hydrogen, $C_1$–$C_3$ loweralkyl or allyl;
$R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl, $C_2$–$C_5$ haloalkenyl, $NH_2$, —NHC(=NH)$NH_2$ or a heterocyclic ring having 5 ring atoms and also containing one or two double bonds.

Other most highly preferred compounds of the invention are compounds having Formula I, IIA, IIB, IIIA or IIIB or a salt, ester or prodrug thereof wherein $R^1$ is —$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is —C($R^{37a}$)(O$R^{37c}$)—$R^{14}$ wherein $R^{14}$ is
  loweralkyl, loweralkenyl or alkoxy-substituted loweralkyl;
$R^{37a}$ is
  loweralkyl or loweralkenyl; and
$R^{37c}$ is
  hydrogen, $C_1$–$C_3$ loweralkyl or allyl;
$R^5$ is hydrogen;
$R^6$ and $R^7$ are hydrogen;
$R^8$ and $R^9$ are hydrogen;
$R^{10}$ is hydrogen; and
Y is $C_2$–$C_5$ alkenyl.

Preferred substituents $R^1$ include —$CO_2H$ or esters or prodrugs thereof. Preferred esters include $C_1$–$C_6$ loweralkyl esters, cycloalkyl esters (for example, cyclopropyl ester, cyclohexyl ester and the like), cycloalkylalkyl esters, aryl esters (for example, phenyl ester, 2-methylphenyl ester and the like), arylalkyl esters (for example, benzyl ester, phenylethyl ester and the like), haloalkyl esters (for example, 2,2,2-trichloroethyl ester and the like), heterocyclic esters (for example, N-methylpiperazin-4-yl ester and the like), (heterocyclic)alkyl esters (for example, pyridyl methyl ester, pyridylethyl ester, N-methylpiperazin-4-ylmethyl ester, piperidin-1-ylmethyl ester, morpholin-4-ylmethyl ester, 2-(piperidin-1-yl)ethyl ester, 2-(morpholin-4-yl)ethyl ester, 2(-N-methylpiperazin-4-yl)ethyl ester, 1,1-dimethyl-2-(piperidin-1-yl)ethyl ester, 1,1-dimethyl-2-(morpholin-4-yl) ethyl ester, 1,1-dimethyl-2-(N-methylpiperazin-4-yl)ethyl ester, phthalidylmethyl ester and the like), di-loweralkylaminoalkyl esters (for example, 2-N,N-dimethylaminoethyl ester, 2-N,N-diethylaminoethyl ester and the like), acyloxyalkyl esters (for example, t-butylcarbonyloxymethyl ester and the like), alkoxycarbonyloxyalkyl esters (for example, t-butyloxycarbonyloxymethyl ester and the like), di-loweralkylaminocarbonylalkyl esters (for example, N,N-dimethylaminocarbonylmethyl ester, N,N-diethylaminocarbonylmothyl ester and the like), acylalkyl esters (for example, t-butylcarbonylmethyl ester and the like), (heterocyclic)carbonylalkyl esters (for example, piperidin-1-ylcarbonylmethyl ester, morpholin-4-ylcarbonylmethyl ester, N-methylpiperazin-4-ylcarbonylmethyl ester and the like), di-loweralkylaminocarbonyloxyalkyl esters (for example, N,N-dimthylaminocarbonyloxymethyl ester, N,N-diethylaminocarbonyloxymethyl ester, N-t-butyl-N-methyl-aminocarbonyloxymethyl ester and the like), alkoxycarbonylalkyl esters (for example, ethoxycarbonylmethyl ester, isopropoxycarbonylmethyl ester and the like), (heterocyclic)carbonyloxyalkyl esters (for example, pyridylcarbonyloxymethyl ester and the like) and the like. Preferred substituents $R^1$ also include —S(O)$_2$NHC(=O)$R^{11}$ wherein $R^{11}$ is defined as above.

Most highly preferred substituents $R^1$ include —$CO_2H$ or esters or prodrugs thereof. Most highly preferred esters include $C_1$–$C_6$ loweralkyl esters, cycloalkyl esters, cycloalkylalkyl esters or substituted or unsubstituted benzyl esters.

Preferred substituents —X—$R^2$ include $R^2$—C(=O)—NH—, $R^2$—NH—C(=O)—, $R^2$—NH—$SO_2$— or $R^2$—$SO_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

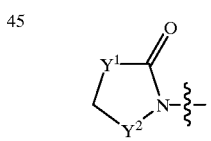

wherein $Y^1$ is —$CH_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl.

More preferred substituents —X—$R^2$ include $R^2$—C(=O)—NH—, $R^2$—NH—C(=O)—, $R^2$—$SO_2$— or $R^2$—$SO_2$— wherein $R^2$ is $C_1$–$C_3$ loweralkyl, halo $C_1$–$C_3$ loweralky wherein
Y$^1$ is —CH$_2$— and Y$^2$ is —C(=O)— or —C(R$^{aa}$)(R$^{bb}$)— wherein R$^{aa}$ and R$^{bb}$ are independently selected from the group consisting of hydrogen, C$_1$–C$_3$ loweralkyl, hydroxymethyl, 1-hydroxyethyl and 2-hydroxyethyl.

Even more preferred substituents —X—R$^2$ include R$^2$—C(=O)—NH—, R$^2$—NH—C(=O)—, R$^2$—NH—SO$_2$— or R$^2$—SO$_2$—NH— wherein R$^2$ is C$_1$–C$_3$ loweralkyl, halo C$_1$–C$_3$ loweralkyl, C$_2$–C$_3$ alkenyl or halo C$_2$–C$_3$ alkenyl.

More highly preferred substituents —X—R$^2$ include R$^2$—C(=O)—NH—, R$^2$—NH—C(=O)—, R$^2$—NH—SO$_2$— or R$^2$—SO$_2$—NH— wherein R$^2$ is C$_1$–C$_3$ loweralkyl or halo-C$_1$–C$_3$ loweralkyl.

Even more highly preferred substituents —X—R$^2$ include R$^2$—C(=O)—NH—, R$^2$—NH—C(=O)—, R$^2$—NH—SO$_2$— or R$^2$—SO$_2$—NH— wherein R$^2$ is C$_1$–C$_2$ loweralkyl or halo C$_1$–C$_2$ loweralkyl, and especially, CH$_3$—C(=O)—NH—, CF$_3$—C(=O)—NH—, CH$_3$—SO$_2$—NH— or CF$_3$—SO$_2$—NH—.

Preferred substituents R$^3$ and R$^4$ are independently selected from the group consisting of hydrogen, heterocyclic and —Z—R$^{14}$ wherein Z and R$^{14}$ are defined as most broadly defined previously herein and wherein one of R$^3$ and R$^4$ is other than hydrogen.

More highly preferred, substituent R$^4$ is hydrogen or loweralkyl and R$^3$ includes heterocyclic or —Z—R$^{14}$ wherein Z and R$^{14}$ are defined as most broadly defined previously herein.

Even more highly preferred, substituent R$^4$ is hydrogen or loweralkyl and R$^3$ includes
(a) heterocyclic, (b) alkyl, (c) cycloalkyl, (d) cycloalkylalkyl, (e) alkenyl, (f) alkynyl, (g) —C(=O)—R$^{14}$, (h) —C(R$^{37a}$)(OR$^{37c}$)—R$^{14}$ or (i) —C(R$^{37a}$)(R$^{37b}$)—N(O)(R$^{37c}$)R$^{14}$ wherein R$^{14}$ is
(i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$)$_2$ P(=O)-substituted alkyl;
R$^{37a}$ and R$^{37b}$ are independently selected from the group consisting of
(i) hydrogen, (ii) loweralkyl and (iii) loweralkenyl; and
R$^{37c}$ is (i) hydrogen, (ii) loweralkyl or (iii) loworalkenyl.

Most highly preferred, substituent R$^4$ is hydrogen and R$^3$ includes
(a) heterocyclic, (b) alkyl or (c) —C(R$^{37a}$)(OR$^{37c}$)—R$^{14}$ wherein R$^{14}$ is
(i) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$O)$_2$—P(=O)-substituted alkyl;
R$^{37a}$ and R$^{37b}$ are independently selected from the group consisting of
(i) hydrogen, (ii) loweralkyl and (iii) loweralkenyl; and
R$^{37c}$ is (i) hydrogen, (ii) C$_1$–C$_3$ loweralkyl or (iii) allyl.

Also most highly preferred, substituent R$^4$ is hydrogen and R$^3$ includes
(a) heterocyclic, (b) alkyl or (c) —C(R$^{37a}$)(OR$^{37c}$)—R$^{14}$ wherein R$^{14}$
(i) loweralkyl, (ii) loweralkenyl, (iii) hydroxy-substituted loweralkyl or (iv) alkoxy-substituted loweralkyl;
R$^{37a}$ is (i) hydrogen, (ii) loweralkyl or (iii) loweralkenyl; and
R$^{37c}$ is (i) hydrogen, (ii) C$_1$–C$_3$ loweralkyl or (iii) allyl.

Also most highly preferred, substituent R$^4$ is hydrogen and R$^3$ includes —C(R$^{37a}$)(OR$^{37c}$)—R$^{14}$ wherein R$^{14}$ is loweralkyl, loweralkenyl or alkoxy-substituted loweralkyl;
R$^{37a}$ is loweralkyl or loweralkenyl; and
R$^{37c}$ is hydrogen, C$_1$–C$_3$ loweralkyl or allyl, and especially, wherein R$^{37c}$ is hydrogen or methyl.

Preferred substituents R$^5$ include hydrogen or loweralkyl. Most highly preferred, R$^5$ is hydrogen.

Preferred substituents R$^6$ and R$^7$ include independently hydrogen and loweralkyl. Most highly preferred, R$^6$ and R$^7$ are hydrogen.

Preferred substituents R$^8$, R$^9$ and R$^{10}$ include independently hydrogen, fluoro and loweralkyl. Most highly preferred, R$^8$, R$^9$ and R$^{10}$ are hydrogen.

Preferred substituent Y includes C$_2$–C$_5$ alkenyl, C$_2$C$_5$ haloalkenyl, —C(=Q$^2$)R$^{22}$, —N(=Q$^3$), —N(O)=CHCH$_3$, —NR$^{23}$R$^{24}$ or a heterocyclic ring having from 3 to 6 ring atoms, wherein R$^{22}$, R$^{23}$, R$^{24}$, Q$^2$ and Q$^3$ are defined as above.

More preferred substituent Y includes C$_2$–C$_5$ alkenyl, C$_2$–C$_5$ haloalkenyl, —C(=Q$^2$)R$^{22}$, —N(=Q$^3$), —N(O)=CHCH$_5$, —NR$^{23}$R$^{24}$ or a heterocyclic ring having 5 ring atoms and also containing one or two double bonds, wherein R$^{22}$, R$^{23}$, R$^{24}$, Q$^2$ and Q$^3$ are defined as above.

Even more preferred substituent Y includes C$_2$–C$_5$ alkenyl, C$_2$–C$_5$ haloalkenyl, NH$_2$, —NHC(=NH)NH$_2$ or a heterocyclic ring having 5 ring atoms and also containing one or two double bonds. Representative alkenyl and haloalkenyl substituents Y include:
—CH=CH$_2$, —CH=CHF, —CH=CH—CH$_3$, —CH=CH—CF$_3$, —CH=CHCl, —CH=CHBr, —CH=CF$_2$, —CH=CF(CH$_3$), —CH=CF(CF$_3$), —CH=CFCl, —CH=CFBr, —CH=C(CH$_3$)$_2$, —CH=C(CH$_3$)(CF$_3$), —CH=CCl(CH$_3$), —CH=CBr(CH$_3$), —CH=C(CF$_3$)$_2$, —CH=CCl(CF$_3$), —CH=CBr(CF$_3$), —CH=CCl$_2$, —CH=CClBr, —CF=CH$_2$, —CF=CHF, —CF=CH—CH$_3$, —CF=CH—CF$_3$, —CF=CHCl, —CF=CHBr, —CF=CF$_2$, —CF=CF(CH$_3$), —CF=CF(CF$_3$), —CF=CFCl, —CF=CFBr, —CF=C(CH$_3$)$_2$, —CF=C(CH$_3$)(CF$_3$), —CF=CCl(CH$_3$), —CF=CBr(CH$_3$), —CF=C(CF$_3$)$_2$, —CF=CCl(CF$_3$), —CF=CBr(CF$_3$), —CF=CCl$_2$, —CF=CClBr, —C(CH$_3$)=CH$_2$, —C(CH$_3$)=CHF, —C(CH$_3$)=CH—CH$_3$, —C(CH$_3$)=CH—CF$_3$, —C(CH$_3$)=CHCl, —C(CH$_3$)=CHBr, —C(CH$_3$)=CF$_2$, —C(CH$_3$)=CF(CH$_3$), —C(CH$_3$)=CF(CF$_3$), —C(CH$_3$)=CFCl, —C(CH$_3$)=CFBr, —C(CH$_3$)=C(CH$_3$)$_2$, —C(CH$_3$)=C(CH$_3$)(CF$_3$), —C(CH$_3$)=CCl(CH$_3$), —C(CH$_3$)=CBr(CH$_3$), —C(CH$_3$)=C(CF$_3$)$_2$, —C(CH$_3$)=CCl(CF$_3$), —C(CH$_3$)=CBr(CF$_3$), —C(CH$_3$)=CCl$_2$, —C(CH$_3$)=CClBr, —C(CF$_3$)=CH$_2$, —C(CF$_3$)=CHF, —C(CF$_3$)=CH—CH$_3$, —C(CF$_3$)=CH—CF$_3$, —C(CF$_3$)=CHCl, —C(CF$_3$)=CHBr, —C(CF$_3$)=CF$_2$, —C(CF$_3$)=CF(CH$_3$), —C(CF$_3$)=CF(CF$_3$), —C(CF$_3$)=CFCl, —C(CF$_3$)=CFBr, —C(CF$_3$)=(CH$_3$)$_2$, —C(CF$_3$)=C (CH$_3$)(CF$_3$), —C(CF$_3$)=CCl(CH$_3$), —C(CF$_3$)=CBr(CH$_3$), —C(CF$_3$)=C(CF$_3$)$_2$, —C(CF$_3$)=CCl(CF$_3$), —C(CF$_3$)=CBr(CF$_3$), —C(CF$_3$)=CCl$_2$, —C(CF$_3$)=CClBr, —CCl=CH$_2$, —CCl=CHF, —CCl=CH—CH$_3$, —CCl=CH—CF$_3$, —CCl=CHCl, —CCl=CHBr, —CCl=CF$_2$, —CCl=CF(CH$_3$), —CCl=CF(CF$_3$), —CCl=CFCl, —CCl=CFBr, —CCl=C(CH$_3$)$_2$, —CCl=C(CH$_3$)(CF$_3$), —CCl=CCl(CH$_3$), —CCl=CBr(CH$_3$), —CCl=C(CF$_3$)$_2$, —CCl=CCl(CF$_3$), —CCl=CBr(CF$_3$), —CCl=CCl$_2$, —CCl=CClBr, —CH=CH—CH$_2$CH$_3$, —CH=CF—CH$_2$CH$_3$, —CF=CH—CH$_2$CH$_3$, —CF=CF—CH$_2$CH$_3$, —CH=C(CH$_3$)(CH$_2$CH$_3$), —CF=C(CH$_3$)(CH$_2$CH$_3$), —CH=CCl(CH$_2$CH$_3$), —CF=CCl(CH$_2$CH$_3$), —C(CH$_3$)=CH—CH$_2$CH$_3$, —C(CH$_3$)=CF—CH$_2$CH$_3$, —CCl=CH—CH$_2$CH$_3$, —CCl=CF—CH$_2$CH$_3$, —C(CH$_2$CH$_3$)=CH$_2$, —C(CH$_2$CH$_3$)=CHF, —C(CH$_2$CH$_3$)=CF$_2$, —C(CH$_2$CH$_3$)=CH—CH$_3$, —C(CH$_2$CH$_3$)=CF—CH$_3$, —C(CH$_2$CH$_3$)=CH—Cl, —C(CH$_2$CH$_3$)=CFCl.

Representative Y substituents which are heterocyclic rings having 5 ring atoms and also containing one or two double bonds include: furanyl, dihydrofuranyl, didehydrodioxolanyl, dithiolyl, imidazolyl, imidazolinyl, isothiazolyl, isothiazolinyl, isoxazolyl, isoxazolinyl, oxadiazolyl, oxadiazolinyl, oxathiolyl, oxazolyl, oxazolinyl, pyrazolyl, pyrazolinyl, pyrrolyl, dihydropyrrolyl, tetrazolyl, tetrazolinyl, thiadiazolyl, thiadiazolinyl, thiazolyl, thiazolinyl, thienyl, dihydrothienyl, triazolyl, triazolinyl.

More highly preferred substituents Y include cis-propenyl, trans-propenyl, isobutenyl, cis-2-chlorovinyl, vinyl, 2,2-difluorovinyl, imidazolyl, pyrazolyl, oxazolyl, igomazolyl, thiazolyl, isoxazolyl, NH$_2$, —NHC(=NH)NH$_2$.

Most highly preferred substituents Y include cis-propenyl, cis-2-chlorovinyl, vinyl, imidazolyl, pyrazolyl, oxazolyl, isoxazolyl, thiazolyl, isoxazolyl, NH$_2$, —NHC(=NH)NH$_2$, especially, cis-propenyl.

Preferred definitions for the substituents in the compounds of the invention also apply to the intermediates disclosed herein that are useful in the preparation of the compounds of the invention.

Preferred compounds of the invention include compounds having the indicated relative stereochemistry selected from the group consisting of:

(±)-(2R,3S,5R,1'R)-2-(1-Acetamido-2-ethyl-2-hydroxy)butyl-3-(cis-propen-1-yl)-pyrrolidine-5-carboxylic Acid;

(±)-(2R,3S,5R,1'R,2'S)-2-(1-Acetamido-2-hydroxy-2-methyl)pentyl-3-(cis-propen-1-yl)-pyrrolidine-5-carboxylic Acid;

(±)-(2R,3S,5R,1'R,2'S)-2-(1-Acetamido-2-ethyl-2-hydroxy)pentyl-3-(cis-propen-1yl)-pyrrolidine-5-carboxylic Acid;

(±)-(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;

(±)-(2R,3S,5R,1'R,2'R)-2-(1-Acetamido-2,3-dihydroxy)propyl-3-(cis-propen-1-yl)-pyrrolidine-5-carboxylic Acid;

(±)-(2R,3S,5R,1'R,2'S)-2-(1-Acetamido-2-hydroxy-4-vinyl)butyl-3-(cis-propen-1-yl)-pyrrolidine-5-carboxylic Acid;

(−)-(2R,3S,5R,1'S)-2-(1-Acetamido-2-hydroxy)butyl-3-(cis-propen-1-yl)-pyrrolidine-5-carboxylate Ammonium Salt;

(±)-(2R,3S,5R,1'R,2'R)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-methoxy-2-vinyl)ethyl-3-(cis-propen-1-yl)-pyrrolidine-5-carboxylic Acid;

(±)-(2R,3S,5R,1'S,)-2-(1-Acetamido-2-ethyl)butyl-3-(cis-propen-1-yl)-pyrrolidine-5-carboxylic Acid;

(±)-(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;

(±)-(2R,3S,5R,1'R,2'S)-2-(1-Acetamido-2-methoxy)butyl-3-(cis-propen-1-yl)-pyrrolidine-5-carboxylic Acid;

(±)-(2R,3S,5R,1'R,2'S)-2-(1-Acetamido-2-methoxy)pentyl-3-(cis-propen-1-yl)-pyrrolidine-5-carboxylic Acid;

(±)-(2R,3S,5R,1'R,2'S)-2-(1-Acetamido-2-hydroxy)butyl-3-(pyrazol-3-yl)-pyrrolidine-5-carboxylic Acid;

(±)-(2R,3S,5R,1'R,2'S)-2-(1-Acetamido-2-hydroxy)butyl-3-(cis-propen-1-yl)-pyrrolidine-5-carboxylic Acid;

(±)-(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;

(±)-(2R,3S,5R,1'R,2'S)-2-(1-Acetamido-2-methoxy-2-allyl)ethyl-3-(cis-propen-1-yl)-pyrrolidine-5-carboxylic Acid;

(±)-(2R,3S,5R,1'R,2'S,3'S)-2-(1-Acetamido-2-hydroxy-3-methyl)pentyl-3-(cis-propen-1-yl)-pyrrolidine-5-carboxylic Acid;

(±)-(2R,3S,5R,1'R,2'S)-2-(1-Acetamido-2-methoxy-4-vinyl)butyl-3-(cis-propen-1-yl)-pyrrolidine-5-carboxylic Acid;

(±)-(2R,3S,5R,1'R,2'S)2-(1-Acetamido-2-hydroxy-3-cyano)propyl-3-(cis-propen-1-yl)-pyrrolidine-5-carboxylic Acid;

(±)-(2R,3S,5R,1'R2'S)-2-(1-Acetamido-1-(3,6-dihydro-2-H-pyran-2-yl))methyl-3-(cis-propen-1-yl)-pyrrolidine-5-carboxylic Acid;

(±)-(2R,3S,5R,1'R,2'S)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid;

(±)-(2R,3S,5R,1'R,2'S)-2-(1-Acetamido-2-ethoxy)pentyl-3-(cis-propen-1yl)-pyrrolidine-5-carboxylic Acid;

(±)-(2R,3S,5R, 1'R,2'S)-2-(1-Acetamido-2-hydroxy-3-dimethyl)butyl-3-(cis-propen-1-yl)-pyrrolidine-5-carboxylic Acid;

(±)-(2R,3S,5R, 1'R,2'S)-2-(1-Acetamido-2-ethoxy-3-vinyl)propyl-3-(cis-propen-1-yl)-pyrrolidine-5-carboxylic Acid;

(±)-(2R,3S,5R, 1'R,2'S)-2-(1-Acetamido-2-hydroxy-2-(propeny-2-yl))ethyl-3-(cis-propen-1-yl)-pyrrolidine-carboxylic Acid;

(±)-(2R,3S,5R,1'R,2'S)-2-(1-Acetamido-2-hydroxy)hexyl-3-(cis-propen-1-yl)-pyrrolidine-5-carboxylic Acid;

(±)-(2R,3S, 5R,1'S)-2-(1-acetamido-3-methyl)butyl-3-(cis-propen-1-yl)-pyrrolidine-5-carboxylic Acid;

(±)-(2R,3S,5R,1'R,2'S)-2-(1-Acetamido-2-hydroxy)butyl-3-vinyl-pyrrolidine-5-carboxylic Acid;

(±)-(2R,3S,5R,1'R,2'S)-2-(1-Acetamido-2-hydroxy)pentyl-3-vinyl-pyrrolidine-5-carboxylic Acid;

(±)-(2R,3S,5R,1'R,2'R)-2-(1-Acetamido-2-hydroxyethyl-2-hydroxy)pentyl-3-(cis-propen-1-yl)-pyrrolidine-5-carboxylic Acid;

(±)-(2R,3S,5R,1'R,2'R)-2-(1-Acetamido-2-hydroxy)butyl-3-vinyl-pyrrolidine-5-carboxylic Acid;

(±)-(2R,3S,5R,1'R,2'R)-2-(1-Acetamido-2-methoxy)pentyl-3-(cis-propen-1-yl)-pyrrolidine-5-carboxylic Acid;

(±)-(2R,3S,5R,1'R,2'R)-2-(1-Acetamido-2-hydroxy)pentyl-3-vinyl-pyrrolidine-5-carboxylic Acid;

(±)-(2R,3S, 5R,1'R)-2-(1-Acetamido-2-hydroxy)ethyl-3-(cis-propen-1-yl)-pyrrolidine-5-carboxylic Acid;
(±)-(2R,3S,5R,1'S)-2-(1-acetamido-3-methyl)butyl-3-(cis-2-chloro-vin-1-yl)-pyrrolidine-5-carboxylic Acid;
(±)-(2R,3R,5R,1'S)-2-(1-acetamido-3-methyl)butyl-3-(pyrazol-3-yl)-pyrrolidine-5-carboxylic Acid;
(±)-(2R,3S,5R,1'S,3'R)-2-(1-Acetamido-3-hydroxy)pentyl-3-(cis-propen-1-yl)-pyrrolidine-5-carboxylic Acid;
(±)-(2R,3R,5R,1'S)-2-(1-Acetamido-3-methyl)butyl-3-(thiazol-4-yl)-pyrrolidine-5-carboxylic Acid;
(±)-(2R,3R,5R,1'S)-1-t-Butoxycarbonyl-2-(1-acetamido-3-methyl)butyl-3-(thiazol-2-yl)-pyrrolidine-5-carboxylic Acid;
(±)-(2R,3S,5R,1'S)-2-(1-Acetamido-3-methyl)butyl-3-vinyl-pyrrolidine-5-carboxylic Acid;
(±)-(2R,3S,5R,1'S)-2-(1-acetamido-3-methyl)butyl-3-(2,2-difluoro-vin-1-yl)-pyrrolidine-5-carboxylic Acid;
(±)-(2R, 3R, 5R,1'S)-2-(1-acetamido-3-methyl)butyl-3-(pyrazol-3-yl)-pyrrolidine-5-carboxylic Acid;
(±)-(2R,3R,5R,1'S)-2-(1-acetamido-3-methyl)butyl-3-(isoxazol-3-yl)-pyrrolidine-5-carboxylic Acid;
(±)-(2R,3R,5R,1'S)-2-(1-acetamido-3-methyl)butyl-3-(isoxazol-5-yl)-pyrrolidine-5-carboxylic Acid;
(±)-(2R,3R,5R,1'S)-2-(1-Acetamido-3-methyl)butyl-3-(imidazol-2-yl)-pyrrolidine-5-Carboxylic Acid;
(±)-(2R,3R,5R,1'S)-2-(1-Acetamido-3-methyl)butyl-3-(imidazol-4-yl)-pyrrolidine-5-carboxylic Acid;
(±)-(2S,3R,5R,1'S)-2-(1-acetamido-3-methyl)butyl-3-amino-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carbomylic Acid Ethyl Ester;
(±)-(2R,3S,5R,1'R,2'S)-2-(1-Acetamido-2-vinyl-2-methoxy)pentyl-3-(cis-propen-1-yl)-pyrrolidine-5-carboxylic Acid;
(±)-(2R,3S,5R,1'R)-2-(1-Acetamido-2-ethyl-2-methoxy)butyl-3-(cis-propen-1-yl)-pyrrolidine-5-carboxylic Acid;
(±)-(2R,3S,5R,1'R,2'S)-2-(1-Acetamido-2-methyl-2,3-dimethoxy)propyl-3-(cis-propen-1-yl)-pyrrolidine-5-carboxylic Acid; and
(±)-(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

Other preferred compounds of the invention include enantiomerically enriched compounds having the indicated absolute stereochemistry selected from the group consisting of:
(2R,3S,5R,1'R)-2-(1-Acetamido-2-ethyl-2-hydroxy)butyl-3-(cis-propen-1-yl)-pyrrolidine-5-carboxylic Acid;
(2R,3S,5R,1'R,2'S)-2-(1-Acetamido-2-hydroxy-2-methyl)pentyl-3-(cis-propen-1-yl)-pyrrolidine-5-carboxylic Acid;
(2R,3S,5R,1'R,2'S)-2-(1-Acetamido-2-ethyl-2-hydroxy)pentyl-3-(cis-propen-1-pyrrolidine-5-carboxylic Acid;
(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;
(2R,3R,5R,1'R,2'R)-2-(1-Acetamido-2,3-dihydroxy)propyl-3-(cis-propen-1-yl)-pyrrolidine-5-carboxylic Acid;
(2R,3S,5R,1'R,2'S)-2-(1-Acetamido-2-hydroxy-4-vinyl)butyl-3-(cis-propen-1-yl)-pyrrolidine-5-carboxylic Acid;
(2R,3S,5R,1'S)-2-(1-Acetamido-2-hydroxy)butyl-3-(cis-propen-1-yl)-pyrrolidine-5-carboxylate Ammonium Salt;
(2R,3S,5R,1'R,2'R)-2-(1-Acetamido-2,3-dimethoxy)propyl-3-(cis-propen-1-yl)-pyrrolidine-5-carboxylic Acid;
(2R,3S,5R,1'R,2'S)-2-(1-Acetamido-2-methoxy-2-vinyl)ethyl-3-(cis-propen-1-yl)-pyrrolidine-5-carboxylic Acid;
(2R,3S,5R,1'S)-2-(1-Acetamido-2-ethyl)butyl-3-(cis-propen-1-yl)-pyrrolidine-5-carboxylic Acid;
(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;
(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;
(2R,3S,5R,1'R,2'R)-2-(1-Acetamido-2-methoxy)butyl-3-(cis-propen-1-yl)-pyrrolidine-5-carboxylic Acid;
(2R,3S,5R,1'R,2'S)-2-(1-Acetamido-2-methoxy)pentyl-3-(cis-propen-1-yl)-pyrrolidine-5-carboxylic Acid;
(2R,3R,5R,1'R,2'S)-2-(1-Acetamido-2-hydroxy)butyl-3-(pyrazol-3-yl)-pyrrolidine-5-carboxylic Acid;
(2R,3S,5R,1'R,2'S)-2-(1-Acetamido-2-hydroxy)butyl-3-(cis-propen-1-yl)-pyrrolidine-5-carboxylic Acid;
(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;
(2R,3S5R,1'R,2'S)-2-(1-Acetamido-2-methoxy-2-allyl)ethyl-3-(cis-propen-1-yl)-pyrrolidine-5-carboxylic Acid;
(2R,3S,5R,1'R,2'S,3'S)-2-(1-Acetamido-2-hydroxy-3-methyl)pentyl-3-(cis-propen-1-yl)-pyrrolidine-5-carboxylic Acid;
(2R,3S,5R,1'R,2'S)-2-(1-Acetamido-2-methoxy-4-vinyl)butyl-3-(cis-propen-1-yl)-pyrrolidine-5-carboxylic Acid;
(2R,3S,5R,1'R,2'S)-2-(1-Acetamido-2-hydroxy-3-cyano)propyl-3-(cis-propen-1-yl)-pyrrolidine-5-carboxylic Acid;
(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;
(2R,3S,5R,1'R,2'S)-2-(1-Acetamido-2,3-dimethoxy)propyl-3-(cis-propen-1-yl)-pyrrolidine-5-carboxylic Acid;
(2R,3S,5R,1'R,2'S)-2-(1-Acetamido-2-hydroxymethyl-2-hydroxy)pentyl-3-(cis-propen-1-yl)-pyrrolidine-5-carboxylic Acid;
(2R,3S,5R,1'R,2'S)-2-(1-Acetamido-2-ethoxy)pentyl-3-(cis-propen-1-yl)-pyrrolidine-5-carboxylic Acid;
(2R,3S,5R,1'R,2'S)-2-(1-Acetamido-2-hydroxy-3-dimethyl)butyl-3-(cis-propen-1-yl)-pyrrolidine-5-carboxylic Acid;
(2R,3S,5R,1'R,2'S)-2-(1-Acetamido-2-ethoxy-3-vinyl)propyl-3-(cis-propen-1-yl)-pyrrolidine-5-carboxylic Acid;
(2R,3S,5R,1'R,2'S)-2-(1-Acetamido-2-hydroxy-2-(propeny-2-yl))ethyl-3-(cis-propen-1-yl)-pyrrolidine-5-carboxylic Acid;
(2R,3S,5R,1'R,2'S)-2-(1-Acetamido-2-hydroxy)hexyl-3-(cis-propen-1-yl)-pyrrolidine-5-carboxylic Acid;
(2R,3S,5R,1'S)-2-(1-acetamido-3-methyl)butyl-3-(cis-propen-1-yl)-pyrrolidine-5-carboxylic Acid;
(2R,3S,5R,1'R,2'S)-2-(1-Acetamido-2-hydroxy)butyl-3-vinyl-pyrrolidine-5-carboxylic Acid;
(2R,3S,5R,1'R,2'S)-2-(1-Acetamido-2-hydroxy)pentyl-3-vinyl-pyrrolidine-5-carboxylic Acid;
(2R,3S,5R,1'R,2'R)-2-(1-Acetamido-2-hydroxyethyl-2-hydroxy)pentyl-3-(cis-propen-1-yl)-pyrrolidine-5-carboxylic Acid;
(2R,3S,5R,1'R,2'R)-2-(1-Acetamido-2-hydroxy)butyl-3vinyl-pyrrolidine-5-carboxylic Acid;
(2R,3S,5R,1'R,2'R)-2-(1-Acetamido-2-methoxy)pentyl-3-(cis-propen-1-yl)-pyrrolidine-5-carboxylic Acid;
(2R,3S,5R,1'R,2'R)-2-(1-Acetamido-2-hydroxy)pentyl-3-vinyl-pyrrolidine-5-carboxylic Acid;

(2R,3S,5R,1'R)-2-(1-Acetamido-2-hydroxy)ethyl-3-(cis-propen-1-yl)-pyrrolidine-5-carboxylic Acid;

(2R,3S,5R,1'S)-2-(1-acetamido-3-methyl)butyl-3-(cis-2-chloro-vin-1-yl)-pyrrolidine-5-carboxylic Acid;

(2R,3R,5R,1'S)-2-(1-acetamido-3-methyl)butyl-3-(pyrazol-3-yl)-pyrrolidine-5-carboxylic Acid;

(2R,3S,5R,1'S,3'R)-2-(1-Acetamido-3-hydroxy)pentyl-3-(cis-propen-1-yl)-pyrrolidine-5-carboxylic Acid;

(2 R,3 R,5R,1'S)-2-(1-Acetamido-3-methyl)butyl-3-(thiazol-4-yl)-pyrrolidine-5-carboxylic Acid;

(2R,3R,5R,1'S)-1-t-Butoxycarbonyl-2-(1-acetamido-3-methyl)butyl-3-(thiazol-2-yl)-pyrrolidine-5-carboxylic Acid;

(2R,3S,5R,1'S)-2-(1-Acetamido-3-methyl)butyl-3-vinyl-pyrrolidine-5-carboxylic Acid;

(2R,3R,5R,1'S)-2-(1-acetamido-3-methyl)butyl-3-(2,2-difluoro-vin-1-yl)-pyrrolidine-5-carboxylic Acid;

(2R,3R,5R,1'S)-2-(1-acetamido-3-methyl)butyl-3-(pyrazol-3-yl)-pyrrolidine-5-carboxylic Acid;

(2R,3R,5R,1'S)-2-(1-acetamido-3-methyl)butyl-3-(isoxazol-3-yl)-pyrrolidine-5-carboxylic Acid;

(2R,3R,5R,1'S)-2-(1-acetamido-3-methyl)butyl-3-(isoxazol-5-yl)-pyrrolidine-5-carboxylic Acid;

(2R,3R,5R,1'S)-2-(1-Acetamido-3-methyl)butyl-3-(imidazol-2-yl)-pyrrolidine-5-Carboxylic Acid;

(2R,3R,5R,1'S)-2-(1-Acetamido-3-methyl)butyl-3-(imidazol-4-yl)-pyrrolidine-5-carboxylic Acid;

(2S,3R,5R,1'S)-2-(1-acetamido-3-methyl)butyl-3-amino-pyrrolidine-5-carboxylic Acid; (2R,3S,5R,1'R,2'S)-2-(1-Acetamido-2-methyl-2-methoxy)pentyl-3-(cis-propen-1-yl)-pyrrolidine-5-carboxylic Acid;

(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;

(2R,3S,5R,1'R,2'S)-2-(1-Acetamido-2-vinyl-2-methoxy)pentyl-3-(cis-propen-1-yl)-pyrrolidine-5-carboxylic Acid;

(2R,3S,5R,1'R)-2-(1-Acetamido-2-ethyl-2-methoxy)butyl-3-(cis-propen-1-yl)-pyrrolidine-5-carboxylic Acid;

(2R,3S,5R,1'R,2'S)-2-(1-Acetamido-2-methyl-2,3-dimethoxy)propyl-3-(cis-propen-1-yl)-pyrrolidine-5-carboxylic Acid; and (2R,3S,5R,1'R,2'S)-2-(1-Acetamido-2-methyl-2-methoxy)butyl-3-(cis-propen-1-yl)-pyrrolidine-5-carboxylic Acid;

or a pharmaceutically acceptable salt, ester or prodrug thereof.

More preferred compounds of the invention include compounds having the indicated relative stereochemistry selected from the group consisting of:

(±)-(2R,3S,5R,1'R)-2-(1-Acetamido-2-ethyl-2-hydroxy)butyl-3-(cis-propen-1-yl)-pyrrolidine-5-carboxylic Acid;

(±)-(2R,3S,5R,1'R,2'S)-2-(1-Acetamido-2-hydroxy-2-methyl)pentyl-3-(cis-propen-1-yl)-pyrrolidine-5-carboxylic Acid;

(±)-(2R,3S,5R,1'R,2'S)-2-(1-Acetamido-2-ethyl-2-hydroxy)pentyl-3-(cis-propen-1-yl)-pyrrolidine-5-carboxylic Acid;

(±)-(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;

(±)-(2R,3R,5R,1'R,2'R)-2-(1-Acetamido-2,3-dihydroxy)propyl-3-(cis-propen-1-yl)-pyrrolidine-5-carboxylic Acid;

(±)-(2R,3S,5R,1'R,2'S)-2-(1-Acetamido-2-hydroxy-4-vinyl)butyl-3-(cis-propen-1-yl)-pyrrolidine-5-carboxylic Acid;

(−)-(2R,3S,5R,1'S)-2-(1-Acetamido-2-ethyl)butyl-3-(cis-propen-1-yl)-pyrrolidine-5-carboxylate Ammonium Salt;

(±)-(2R,3S,5R,1'R,2'R)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-methoxy-2-vinyl)ethyl-3-(cis-propen-1-yl)-pyrrolidine-5-carboxylic Acid;

(±)-(2R,3S,5R,1'S)-2-(1-Acetamido-2-ethyl)butyl-3-(cis-propen-1-yl)-pyrrolidino-5-carboxylic Acid;

(±)-(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;

(±)-(2R,3S,5R,1'R,2'S)-2-(1-Acetamido-2-methoxy)butyl-3-(cis-propen-1-yl)-pyrrolidino-5-carboxylic Acid;

(±)-(2R,3S,5R,1'R,2'S)-2-(1-Acetamido-2-methoxy)pentyl-3-(cis-propen-1-yl)-pyrrolidine-5-carboxylic Acid;

(±)-(2R,3R,5R,1'R,2'S)-2-(1-Acetamido-2-hydroxy)butyl-3-(pyrazol-3-yl)-pyrrolidine-5-carboxylic Acid;

(±)-(2R,3S,5R,1'R,2'S)-2-(1-Acetamido-2-hydroxy)butyl-3-(cis-propen-1-yl)-pyrrolidine-5-carboxylic Acid;

(±)-(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;

(±)-(2R,3S,5R,1'R,2'S)-2-(1-Acetamido-2-methoxy-2-allyl)ethyl-3-(cis-propen-1-yl)-pyrrolidine-5-carboxylic Acid;

(±)-(2R,3S,5R,1'R,2'S,3'S)-2-(1-Acetamido-2-hydroxy-3-methyl)pentyl-3-(cis-propen-1-yl)-pyrrolidine-5-carboxylic Acid;

(±)-(2R,3S,5R,1'R,2'S)-2-(1-Acetamido-2-methoxy-4-vinyl)butyl-3-(cis-propen-1-yl)-pyrrolidine-5-carboxylic Acid;

(±)-(2R,3S,5R,1'R,2'S)-2-(1-Acetamido-2-hydroxy-3-cyano)propyl-3-(cis-propen-1-yl)-pyrrolidine-5-carboxylic Acid;

(±)-(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;

(±)-(2R,3S,5R,1'R,2'S)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid;

(±)-(2R,3S,5R,1'R,2'S)-2-(1-Acetamido-2-ethoxy)pentyl-3-(cis-propen-1-yl)-pyrrolidine-5-carboxylic Acid;

(±)-(2R,3S,5R,1'R,2'S)-2-(1-Acetamido-2-hydroxy-3-dimethyl)butyl-3-(cis-propen-1-yl)-pyrrolidine-5-carboxylic Acid;

(±)-(2R,3S,5R,1'R,2'S)-2-(1-Acetamido-2-ethoxy-3-vinyl)propyl-3-(cis-propen-1-yl)-pyrrolidine-5-carboxylic Acid;

(±)-(2R,3S ,5R,1'R,2'S)-2-(1-Acetamido-2-hydroxy-2-(propeny-2-yl))ethyl-3-(cis-propen-1-yl)-pyrrolidine-5-carboxylic Acid;

(±)-(2R,3S,5R,1'R,2'S)-2-(1-Acetamido-2-hydroxy)hexyl-3-(cis-propen-1-yl)-pyrrolidine-5-carboxylic Acid;

(±)-(2R,3S,5R,1'R,2'S)-2-(1-Acetamido-2-methyl-2-methoxy)pentyl-3-(cis-propen-1-yl)-pyrrolidine-5-carboxylic Acid;

(±)-(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;

(±)-(2R,3S,5R,1'R,2'S)-2-(1-Acetamido-2-vinyl-2-methoxy)pentyl-3-(cis-propen-1-yl)-pyrrolidine-5-carboxylic Acid;

(±)-(2R,3S,5R,1'R)-2-(1-Acetamido-2-ethyl-2-methoxy)
butyl-3-(cis-propen-1-yl)-pyrrolidine-5-carboxylic Acid;

(±)-(2R,3S,5R,1'R,2'S)-2-(1-Acetamido-2-methyl-2,3-
dimethoxy)propyl-3-(cis-propen-1-yl)-pyrrolidine-5-
carboxylic Acid; and (±)-(2R,3S,5R, 1'R,2'S)-2-(1-Acetamido-2-methyl-2-
methoxy)butyl-3-(cis-propen-1-yl)-pyrrolidine-5-
carboxylic Acid;

or a pharmaceutically acceptable salt, ester or prodrug thereof.

Other more preferred compounds of the invention include enantiomerically enriched compounds having the indicated absolute stereochemistry selected from the group consisting of:

(2R,3S,5R,1'R)-2-(1-Acetamido-2-ethyl-2-hydroxy)butyl-
3-(cis-propen-1-yl)-pyrrolidine-5-carboxylic Acid;

(2R,3S,5R,1'R,2'S)-2-(1-Acetamido-2-hydroxy-2-methyl)
pentyl-3-(cis-propen-1-yl)-pyrrolidine-5-carboxylic
Acid;

(2R,3S,5R,1'R,2'S)-2-(1-Acetamido-2-ethyl-2-hydroxy)
pentyl-3-(cis-propen-1-yl)-pyrrolidine-5-carboxylic
Acid;

(2R,3S,5R,1'R,2'S)-2-(1-Acetamido-2-hydroxy)pentyl-3-
(cis-propen-1-yl)-pyrrolidine-5-carboxylic Acid Trifluoroacetic Acid Salt;

(2R,3R,5R,1'R,2'R)-2-(1-Acetamido-2,3-dihydroxy)propyl-
3-(cis-propen-1-yl)-pyrrolidine-5-carboxylic Acid;

(2R,3S,5R,1'R,2'S)-2-(1-Acetamido-2-hydroxy-4-vinyl)
butyl-3-(cis-propen-1-yl)-pyrrolidine-5-carboxylic Acid;

(−)-(2R,3S,5R,1'S)-2-(1-Acetamido-2-ethyl)butyl-3-(cis-
propen-1-yl)-pyrrolidine-5-carboxylate Ammonium Salt;

(2R,3S,5R,1'R,2'R)-2-(1-Acetamido-2,3-dimethoxy)propyl-
3-(cis-propen-1-yl)-pyrrolidine-5-carboxylic Acid;

(2R,3S,5R,1'R,2'S)-2-(1-Acetamido-2-methoxy-2-vinyl)
ethyl-3-(cis-propen-1-yl)-pyrrolidine-5-carboxylic Acid;

(2R,3S,5R,1'S)-2-(1-Acetamido-2-ethyl)butyl-3-(cis-
propen-1-yl)-pyrrolidine-5-carboxylic Acid;

(2R,3S,5R,1'S,3'S)-2-(1-Acetamido-2-(N-isopropyl-N-
methylamino-N-oxide))ethyl-3-(cis-propen-1-yl)-
pyrrolidine-5-carboxylic Acid;

(2R,3S,5R,1'S,3'S)-2-(1-Acetamido-2-(N-ethyl-N-
methylamino-N-oxide))ethyl-3-(cis-propen-1-yl)-
pyrrolidine-5-carboxylic Acid;

(2R,3S,5R,1'R,2'S)-2-(1-Acetamido-2-methoxy)butyl-3-
(cis-propen-1-yl)-pyrrolidine-5-carboxylic Acid;

(2R,3S,5R,1'R,2'S)-2-(1-Acetamido-2-methoxy)pentyl-3-
(cis-propen-1-yl)-pyrrolidine-5-carboxylic Acid;

(2R,3R,5R,1'R,2'S)-2-(1-Acetamido-2-hydroxy)butyl-3-
(pyrazol-3-yl)-pyrrolidine-5-carboxylic Acid;

(2R,3S,5R,1'R,2'S)-2-(1-Acetamido-2-hydroxy)butyl-3-
(cis-propen-1-yl)-pyrrolidine-5-carboxylic Acid;

(2R,3S,5R,1'R,2'R)-2-(1-Acetamido-1-(3,6-dihydro-2-H-
pyran-2-yl))propyl-3-(cis-propen-1-yl)-pyrrolidine-5-
carboxylic Acid;

(2R,3S,5R,1'R,2'S)-2-(1-Acetamido-2-methoxy-2-allyl)
ethyl-3-(cis-propen-1pyrrolidine-5-carboxylic Acid;

(2R,3S,5R,1'R,2'S,3'S)-2-(1-Acetamido-2-hydroxy-3-
methyl)pentyl-3-(cis-propen-1-yl)-pyrrolidine-5-
carboxylic Acid;

(2R,3S,5R,1'R,2'S)-2-(1-Acetamido-2-methoxy-4-vinyl)
butyl-3-(cis-propen-1-yl)-pyrrolidine-5-carboxylic Acid;

(2R,3S,5R,1'R,2'S)-2-(1-Acetamido-2-hydroxy-3-cyano)
propyl-3-(cis-propen-1yl)-pyrrolidine-5-carboxylic Acid;

(2R,3S,5R,1'R,2'S)-2-(1-Acetamido-1-(3,6-dihydro-2-H-
pyran-2-yl))methyl-3-(cis-propen-1-yl)-pyrrolidine-5-
carboxylic Acid;

(2R,3S,5R,1'R,2'S)-2-(1-Acetamido-2,3-dimethoxy)propyl-
3-(cis-propen-1-yl)-pyrrolidine-5-carboxylic Acid;

(2R,3S,5R,1'R,2'S)-2-(1-Acetamido-2-hydroxymethyl-2-
hydroxy)pentyl-3-(cis-propen-1-yl)-pyrrolidine-5-
carboxylic Acid;

(2R,3S,5R,1'R,2'S)-2-(1-Acetamido-2-ethoxy)pentyl-3-
(cis-propen-1-yl)-pyrrolidine-5-carboxylic Acid;

(2R,3S,5R,1'R,2'S)-2-(1-Acetamido-2-hydroxy-3-dimethyl)
butyl-3-(cis-propen-1-yl)-pyrrolidine-5-carboxylic Acid;

(2R,3S,5R,1'R,2'S)-2-(1-Acetamido-2-ethoxy-3-vinyl)
propyl-3-(cis-propen-1-yl)-pyrrolidine-5-carboxylic Acid;

(2R,3S,5R,1'R,2'S)-2-(1-Acetamido-2-hydroxy-2-(propeny-
2-yl))ethyl-3-(cis-propen-1-yl)-pyrrolidine-5-carboxylic Acid;

(2R,3S,5R,1'R,2'S)-2-(1-Acetamido-2-hydroxy)hexyl-3-
(cis-propen-1-yl)-pyrrolidine-5-carboxylic Acid;

(2R,3S,5R,1'R,2'S)-2-(1-Acetamido-2-methyl-2-methoxy)
pentyl-3-(cis-propen-1-yl)-pyrrolidine-5-carboxylic
Acid;

(2R,3S,5R,1'R,2'S)-2-(1-Acetamido-2-methyl-2-methoxy)
pentyl-3-(cis-propen-1-yl)-pyrrolidine-5-carbomylic
Acid Ethyl Ester;

(2R,3S,5R,1'R,2'S)-2-(1-Acetamido-2-vinyl-2-methoxy)
pentyl-3-(cis-propen-1pyrrolidino-5-carboxylic Acid;

(2R,3S,5R,1'R)-2-(1-Acetamido-2-ethyl-2-methoxy)butyl-
3-(cis-propen-1-yl)-pyrrolidine-5-carboxylic Acid;

(2R,3S,5R,1'R,2'S)-2-(1-Acetamido-2-methyl-2,3-
dimethoxy)propyl-3-(cis-propen-1-yl)-pyrrolidine-5-
carboxylic Acid; and (2R,3S,5R,1'R,2'S)-2-(1-Acetamido-2-methyl-2-methoxy)
butyl-3-(cis-propen-1-yl)-pyrrolidine-5-carboxylic Acid;

or a pharmaceutically acceptable salt, ester or prodrug thereof.

Even more preferred compounds of the invention include compounds having the indicated relative stereochemistry selected from the group consisting of:

(±)-(2R,3S,5R,1'R,2'S)-2-(1-Acetamido-2-methyl-2-
methoxy)pentyl-3-(cis-propen-1-yl)-pyrrolidine-5-
carboxylic Acid;

(±)-(2R,3S,5R,1'R,2'S)-2-(1-Acetamido-2-methyl-2-
methoxy)pentyl-3-(cis-propen-1-yl)-pyrrolidine-5-
carboxylic Acid Ethyl Ester;

(±)-(2R,3S,5R,1'R,2'S)-2-(1-Acetamido-2-vinyl-2-
methoxy)pentyl-3-(cis-propen-1-yl)-pyrrolidine-5-
carboxylic Acid;

(±)-(2R,3S,5R,1'R)-2-(1-Acetamido-2-ethyl-2-methoxy)
butyl-3-(cis-propen-1-yl)-pyrrolidine-5-carboxylic Acid;

(±)-(2R,3S,5R,1'R,2'S)-2-(1-Acetamido-2-methyl-2,3-
dimethoxy)propyl-3-(cis-propen-1-yl)-pyrrolidine-5-
carboxylic Acid; and (±)-(2R,3S,5R,1'R,2'S)-2-(1-Acetamido-2-methyl-2-
methoxy)butyl-3-(cis-propen-1-yl)-pyrrolidine-5-
carboxylic Acid;

or a pharmaceutically acceptable salt, ester or prodrug thereof.

Other even more preferred compounds of the invention include enantiomerically enriched compounds having the indicated absolute stereochemistry selected from the group consisting of:

(−)-(2R,3S,5R,1'R,2'S)-2-(1-Acetamido-2-methyl-2-
methoxy)pentyl-3-(cis-propen-1-yl)-pyrrolidine-5-
carboxylic Acid;

(−)-(2R,3S,5R,1'R,2'S)-2-(1-Acetamido-2-methyl-2-
methoxy)pentyl-3-(cis-propen-1-yl)-pyrrolidine-5-
carboxylic Acid Ethyl Ester;

(2R,3S,5R, 1'R,2'S)-2-(1-Acetamido-2-vinyl-2-methoxy)
pentyl-3-(cis-propen-1-yl)-pyrrolidine-5-carboxylic
Acid;

(2R,3S,5R,1'R)-2-(1-Acetamido-2-ethyl-2-methoxy)butyl-3-(cis-propen-1-yl)-pyrrolidine-5-carboxylic Acid;

(2R,3S,5R,1'R,2'S)-2-(1-Acetamido-2-methyl-2,3-dimethoxy)propyl-3-(cis-propen-1-yl)-pyrrolidine-5-carboxylic Acid; and (2R,3S,5R,1'R,2'S)-2-(1-Acetamido-2-methyl-2-methoxy)butyl-3-(cis-propen-1-yl)-pyrrolidine-5-carboxylic Acid;

or a pharmaceutically acceptable salt, ester or prodrug thereof.

Most highly preferred compounds of the invention include enantiomerically enriched esters or prodrugs of compounds having the indicated absolute stereochemistry selected from the group consisting of:

(−)-(2R,3S,5R,1'R,2'S)-2-(1-Acetamido-2-methyl-2-methoxy)pentyl-3-(cis-propen-1-yl)-pyrrolidine-5-carboxylic Acid;

(2R,3S,5R,1'R,2'S)-2-(1-Acetamido-2-vinyl-2-methoxy)pentyl-3-(cis-propen-1-yl)-pyrrolidine-5-carboxylic Acid;

(2R,3S,5R,1'R)-2-(1-Acetamido-2-ethyl-2-methoxy)butyl-3-(cis-propen-1-yl)-pyrrolidine-5-carboxylic Acid;

(2R,3S,5R,1'R,2'S)-2-(1-Acetamido-2-methyl-2,3-dimethoxy)propyl-3-(cis-propen-1-yl)-pyrrolidine-5-carboxylic Acid; and (2R,3S,5R,1'R,2'S)-2-(1-Acetamido-2-methyl-2-methoxy)butyl-3-(cis-propen-1-yl)-pyrrolidine-5-carboxylic Acid;

or a pharmaceutically acceptable salt thereof.

Most highly preferred compounds of the invention also include enantiomerically enriched esters or prodrugs of the compound having the indicated absolute stereochemistry:

(−)-(2R,3S,5R,1'R,2'S)-2-(1-Acetamido-2-methyl-2-methoxy)pentyl-3-(cis-propen-1-yl)-pyrrolidine-5-carboxylic Acid;

or a pharmaceutically acceptable salt thereof.

The term "acid protecting group" as used herein refers to groups used to protect acid groups (for example, —$CO_2H$, —$SO_3H$, —$SO_2H$, —$PO_3H_2$, —$PO_2H$ groups and the like) against undesirable reactions during synthetic procedures. Commonly used acid protecting groups are disclosed in T.H. Greene and P.G.M. Wuts, *Protective Groups in Organic Synthesis,* 2nd edition, John Wiley & Sons, New York (1991) which is incorporated herein by reference. Most frequently, such acid protecting groups are esters.

Such esters include:

alkyl esters, especially loweralkyl esters, including, but not limited to, ethyl, n-propyl, isopropyl, n-butyl, sec-butyl, isobutyl, t-butyl, n-pentyl esters and the like;

arylalkyl esters including, but not limited to, benzyl, phenethyl, 3-phenylpropyl, naphthylmethyl esters and the like, wherein the aryl part of the arylalkyl group is unsubstituted or substituted as previously defined herein;

silylesters, especially, (tri-loweralkyl)silyl esters, (di-loweralkyl)(aryl)silyl esters and (loweralkyl)(di-aryl) silyl esters, including, but not limited to, trimethylsilyl, triethylsilyl, isopropyldimethylsilyl, t-butyldimethylsilyl, methyldiisopropylsilyl, methyldi-t-butylsilyl, trfisopropylsilyl, methyldiphenylsilyl, isopropyidiphenylsilyl, butyldiphenylsilyl, phenyidiisopropylsilyl esters and the like; and the like.

Preferred acid protecting groups are loweralkyl esters.

The term "activated carboxylic acid group" as used herein refers to acid halides such as acid chlorides and also refers to activated ester derivatives including, but not limited to, formic and acetic acid derived anhydrides, anhydrides derived from alkoxycarbonyl halides such as isobutyloxycarbonylchloride and the like, anhydrides derived from reaction of the carboxylic acid with N,N'-carbonyidiimidazole and the like, N-hydroxysuccinimide derived esters, N-hydroxyphthalimide derived esters, N-hydroxybenzotriazole derived esters, N-hydroxy-5-norbornene-2,3-dicarboximide derived esters, 2,4,5-trichlorophenol derived esters, p-nitrophenol derived esters, phenol derived esters, pentachlorophenol derived esters, 8-hydroxyquinoline derived esters and the like.

The term "acyl" as used herein, refers to groups having the formula —C(=O)—$R^{95}$ wherein $R^{95}$ is hydrogen or an alkyl group. Preferred alkyl groups as $R^{95}$ are loweralkyl groups. Representative examples of acyl groups include groups such as, for example, formyl, acetyl, propionyl, and the like.

The term "acylalkyl" as used herein refers to an acyl group appended to an alkyl radical. Representative examples of acylalkyl groups include acetylmethyl, acetylethyl, propionylmethyl, propionylethyl and the like.

The term "acylamino" as used herein, refers to groups having the formula —NH$R^{89}$ wherein $R^{89}$ is an acyl group. Representative examples of acylamino include acetylamino, propionylamino, and the like.

The term "acyloxyalkyl" as used herein refers to an acyloxy group (i.e., $R^{95}$—C(O)—O— wherein $R^{95}$ is hydrogen or an alkyl group) which is appended to an alkyl radical. Representative examples of acyloxyalkyl include acetyloxymethyl, acetyloxyethyl, propioyloxymethyl, propionyloxyethyl and the like.

The term "alkenyl" as used herein, refers to a straight or branched chain hydrocarbon radical containing from 2 to 15 carbon atoms and also containing at least one carbon-carbon double bond. The term "lower alkenyl" refers to straight or branched chain alkenyl radicals containing from 2 to 6 carbon atoms. Representative examples of alkenyl groups include groups such as, for example, vinyl, 2-propenyl, 2-methyl-1-propenyl, 3-butenyl, 4-pentenyl, 5-hexenyl and the like.

The term "alkenylene" as used herein, refers to a divalent group derived from a straight or branched chain hydrocarbon containing from 2 to 15 carbon atoms and also containing at least one carbon-carbon double bond. The term "lower alkenylene" refers to a divalent group derived from a straight or branched chain alkene group having from 2 to 6 carbon atoms. Representative examples of alkenylene groups include groups such as, for example, —CH=CH—, —$CH_2$CH=CH—, —C($CH_3$)=CH—, —$CH_2$CH=CHCH$_2$—, and the like.

The term "alkenyloxy" as used herein, refers to groups having the formula —O$R^{81}$ where $R^{81}$ is an alkenyl group.

The term "alkoxy" as used herein, refers to groups having the formula —O$R^{99}$ wherein $R^{99}$ is an alkyl group. Preferred $R^{99}$ groups are loweralkyl groups. Representative examples of alkoxy groups include groups such at for example, methoxy, ethoxy, tert-butoxy, and the like.

The term "alkoxyalkoxy" as used herein, refers to groups having the formula —O—$R^{96}$—$R^{97}$ wherein $R^{97}$ is loweralkyl, as defined herein, and $R^{96}$ is a lower alkylene group. Representative examples of alkoxyalkoxy groups include groups such as, for example, methoxymethoxy, ethoxymethoxy, t-butoxymethoxy and the like.

The term "alkoxyalkyl" as used herein refers to an alkyl radical to which is appended an alkoxy group, for example, methoxymethyl, methoxylpropyl and the like.

The term "alkoxycarbonyl" as used herein, refers to groups having the formula, —C(=O)—$R^{80}$, where $R^{80}$ is an alkoxy group.

The term "alkoxycarbonylalkyl" as used herein, refers to groups having the formula, —C(=O)—$R^{79}$, appended to the parent molecular moiety through an alkylene linkage, where $R^{79}$ is an alkoxy group.

The term "alkoxycarbonyloxyalkyl" as used herein refers to an alkoxycarbonyloxy group (i.e., $R^{80}$—C(O)—O wherein $R^{80}$ is an alkoxy group) appended to an alkyl radical. Representative examples of alkoxycarbonyloxyalkyl include methoxycarbonyloxymethyl, ethoxycarbonyloxymethyl, methoxycarbonyloxyethyl and the like.

As used herein, the term "alkyl" refers to straight or branched chain hydrocarbon radicals containing from 1 to 12 carbon atoms. The term "loweralkyl" refers to straight or branched chain alkyl radicals containing from 1 to 6 carbon atoms. Representative examples of alkyl groups include groups such as, for example, methyl, ethyl, n-propyl, iso-propyl, n-butyl, iso-butyl, sec-butyl, t-butyl n-pentyl, 1-methylbutyl, 2,2-dimethylbutyl, 2-methylpentyl, 2,2-dimethyl-propyl, n-hexyl, and the like. The hydrocarbon chains in alkyl groups or the alkyl portion of an alkyl-containing substituent can be optionally interrupted by one or two heteroatoms or heterogroups independently selected from the group consisting of oxygen, —N($R^{27}$)— and sulfur wherein $R^{27}$ at each occurrence is independently hydrogen, loweralkyl, cylcoalkyl, cycloalkylalkyl or arylalkyl and wherein two such heteroatoms or heterogroups are separated by at least one carbon atom.

The term "alkylamino" as used herein, refers to groups having the formula —NH$R^{91}$ wherein $R^{91}$ is an alkyl group. Preferred $R^{91}$ groups are loweralkyl groups. Representative examples of alkylamino include methylamino, ethylamino, and the like.

The term "alkylene" as used herein, refers to a divalent group derived from a straight or branched chain saturated hydrocarbon group having from 1 to 15 carbon. The term "lower alkylene" refers to a divalent group derived from a straight or branched chain saturated hydrocarbon group having from 1 to 6 carbon atoms. Representative examples of alkylene groups include groups such as, for example, methylene (—CH$_2$—), 1,2-ethylene (—CH$_2$CH$_2$—), 1,1-ethylene (—CH(CH$_3$)—), 1,3-propylene (—CH$_2$CH$_2$CH$_2$—), 2,2-dimethylpropylene (—CH$_2$C(CH$_3$)$_2$CH$_2$—), and the like. The hydrocarbon chains in alkylene groups or the alkylene portion of an alkylene-containing substituent can be optionally interrupted by one or two heteroatoms or heterogroups independently selected from the group consisting of oxygen, —N($R^{27}$)— and sulfur wherein $R^{27}$ at each occurrence is independently hydrogen, loweralkyl, cylcoalkyl, cycloalkylalkyl or arylalkyl and wherein two such heteroatoms or heterogroups are separated by at least one carbon atom.

The term "alkylsulfonyl" as used herein refers to the group having the formula, —SO$_2$—$R^{78}$ where $R^{78}$ is an alkyl group. Preferred groups $R^{78}$ are loweralkyl groups.

The term "alkylsulfonylamino" as used herein refers to the group having the formula, —SO$_2$—$R^{77}$, appended to the parent molecular moiety through an amino linkage (—NH—), where $R^{77}$ is an alkyl group. Preferred groups $R^{77}$ are loweralkyl groups.

The term "alkynyl" as used herein refers to a straight or branched chain hydrocarbon radical containing from 2 to 15 carbon atoms and also containing at least one carbon-carbon triple bond. The term "lower alkynyl" refers to straight or branched chain alkynyl radicals containing from 2 to 6 carbon atoms. Representative examples of alkynyl groups include groups such as, for example, acetylenyl, 1-propynyl, 2-propynyl, 3-butynyl, 2-pentynyl, 1-butynyl and the like.

The term "alkynylene" as used herein, refers to a divalent group derived from a straight or branched chain hydrocarbon containing from 2 to 15 carbon atoms and also containing at least one carbon-carbon triple bond. The term "lower alkynylene" refers to a divalent group derived from a straight or branched chain alkynylene group from 2 to 6 carbon atoms. Representative examples of alkynylene groups include groups such as, for example, —C≡C—, —CH$_2$—C≡C—, —C≡C—CH$_2$—, —CH(CH$_3$)—C≡C—, and the like.

The term "aminoalkyl" as used herein refers to an alkyl radical to which is appended an amino (—NH$_2$) group.

The term "aryl" as used herein refers to a carbocyclic ring system having 6–10 ring atoms and one or two aromatic rings. Representative examples of aryl groups include groups such as, for example, phenyl, naphthyl, tetrahydronaphthyl, indanyl, indenyl and the like.

The aryl groups can be unsubstituted or substituted with one, two or three substituents, each independently selected from loweralkyl, halo, haloalkyl, haloalkoxy, hydroxy, oxo (=O), hydroxyalkyl, alkenyloxy, alkoxy, alkoxyalkoxy, alkoxycarbonyl, alkoxycarbonylalkyl, thioalkoxy, amino, alkylamino, alkylsulfonyl, dialkylamino, acylamino, unsubstituted aryl, unsubstituted arylalkyl, unsubstituted arylalkoxy, unsubstituted aryloxy, mercapto, cyano, nitro, carboxy, carboxaldehyde, NH$_2$C(=O)—, cycloalkyl, carboxyalkyl, alkylsulfonylamino, unsubstituted heterocyclic, unsubstituted (heterocyclic)alkyl, unsubstituted (heterocyclic)alkoxy, unsubstituted (heterocyclic)oxy and —SO$_3$H. Preferred aryl substituents are each independently selected from the group consisting of loweralkyl, halo, haloalkyl, hydroxy, hydroxyalkyl, alkenyloxy, alkoxy, alkoxyalkoxy, thioalkoxy, amino, alkylamino, dialkylamino, alkylsulfonyl, acylamino, cyano and nitro. Examples of substituted aryl include 3-chlorophenyl, 3-fluorophenyl, 4-chlorophenyl, 4-fluorophenyl, 3,4-dichlorophenyl, 3-chloro-4-fluoro-phenyl, 4-methylsulfonylphenyl, and the like.

The term "(aryl)alkenyl" refers to a lower alkenyl group having appended thereto an aryl group. Representative examples of (aryl)alkenyl groups include groups such as, for example phenylethylenyl, phenylpropenyl, and the like.

The term "(aryl)alkyl" refers to a loweralkyl group having appended thereto. an aryl group. Representative examples of (aryl)alkyl groups include groups such as, for example benzyl and phenylethyl.

The term "arylalkoxy" as used herein refers to the group having the formula, —O—$R^{76}$ where $R^{76}$ is an arylalkyl group.

The term "(aryl)alkynyl" refers to an alkynylene group having appended thereto an aryl group. Representative examples of (aryl)alkynyl groups include groups such as, for example phenylacetylenyl, phenylpropynyl, and the like.

The term "aryloxy" as used herein refers to the group having the formula, —O—$R^{72}$, where $R^{72}$ is an aryl group.

The term "carbamoyl" as used herein refers to the group having the formula, —C(=O)—NH$_2$.

The term "carboxyalkyl" as used herein, refers to the group having the formula, —$R^{64}$—COOH, where $R^{64}$ is a lower alkylene group.

The term "cyanoalkyl" as used herein refers to an alkyl radical to which is appended a cyano group (—CN).

The term "cycloalkenyl" as used herein refers to an aliphatic ring system having 5 to 10 carbon atoms and 1 or 2 rings containing at least one double bond in the ring structure. Representative examples of cycloalkenyl groups include groups such as, for example, cyclohexene, cyclopentene, norbornene and the like.

Cycloalkenyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkenyl)alkenyl" as used herein refers to a cycloalkenyl group appended to a lower alkenyl radical. Representative examples of (cycloalkenyl)alkenyl groups include groups such as, for example, cyclohexenylethylene, cyclopentenylethylene, and the like.

The term "(cycloalkenyl)alkyl" as used herein refers to a cycloalkenyl group appended to a lower alkyl radical. Representative examples of (cycloalkenyl)alkyl groups include groups such as, for example, cyclohexenylmethyl, cyclopentenylmethyl, cyclohexenylethyl, cyclopentenylethyl, and the like.

The term "(cycloalkenyl)alkynyl" as used herein refers to a cycloalkenyl group appended to a lower alkynyl radical. Representative examples of (cycloalkenyl)alkynyl groups include groups such as, for example, cyclohexenylacetylenyl, cyclopentenylpropynyl, and the like.

The term "cycloalkyl" as used herein refers to an aliphatic ring system having 3 to 10 carbon atoms and 1 or 2 rings. Representative cylcoalkyl groups include, for example, cyclopropyl, cyclobutyl, cyclopentyl, cyclohexyl, cycloheptyl, norbornane, bicyclo[2.2.2]octane and the like.

Cycloalkyl groups can be unsubstituted or substituted with one, two or three substituents independently selected hydroxy, halo, amino, alkylamino, dialkylamino, alkoxy, alkoxyalkoxy, thioalkoxy, haloalkyl, mercapto, loweralkenyl and loweralkyl. Preferred substitutents are independently selected from loweralkyl, loweralkenyl, haloalkyl, halo, hydroxy and alkoxy.

The term "(cycloalkyl)alkyl" as used herein refers to a cycloalkyl group appended to a loweralkyl radical. Representative examples of (cycloalkyl)alkyl groups include groups such as, for example, cyclohexylmethyl, cyclopentylmethyl, cyclohexylethyl, cyclopentylethyl, and the like.

The term "(cycloalkyl)alkenyl" as used herein refers to a cycloalkyl group appended to a lower alkenyl radical. Representative examples of (cycloalkyl)alkenyl groups include groups such as, for example, cyclohexylethylene, cyclopentylethylene, and the like.

The term "(cycloalkyl)alkynyl" as used herein refers to a cycloalkyl group appended to a lower alkynyl radical. Representative examples of (cycloalkyl)alkynyl groups include groups such as, for example, cyclohexylacetylenyl, cyclopentylpropynyl, and the like.

The term "dialkylamino" as used herein, refers to groups having the formula —N($R^{90}$)$_2$ wherein each $R^{90}$ is independently a lower alkyl group. Representative examples of dialkylamino include dimethylamino, diethylamino, N-methyl-N-isopropylamino and the like.

The term "dialkylaminoalkyl" as used herein refers to a dialkylamino group appended to an alkyl radical. Representative examples of dialkylaminoalkyl include dimethylaminomethyl, dimethylaminoethyl, N-methyl-N-ethylaminoethyl and the like.

The term "dialkylaminocarbonylalkyl" as used herein refers to a —C(O)—N($R^{90}$)$_2$ group (wherein each $R^{90}$ is independently a lower alkyl group) appended to an alkyl radical. Representative examples of dialkylaminocarbonylalkyl include dimethylaminocarbonylmethyl, diethylaminocarbonylmethyl, N-methyl-N-ethylaminocarbonylethyl and the like.

The term "dialkylaminocarbonyloxyalkyl" as used herein refers to a —O—C(O)—N($R^{90}$)$_2$ group (wherein each $R^{90}$ is independently a lower alkyl group) appended to an alkyl radical. Representative examples of dialkylaminocarbonyloxyalkyl include dimethylaminocarbonyloxymethyl, diethylaminocarbonyloxymethyl, N-methyl-N-ethylaminocarbonyloxyethyl and the like.

The term "enantiomerically enriched" as used herein refers to a compound which comprises unequal amounts of the enantiomers of an enantiomeric pair. In other words, an enantiomerically enriched compound comprises more than 50% of one enantiomer of an enantiomeric pair and less than 50% of the other enantiomer of the enantiomeric pair. Preferably, a compound that is enantiomerically enriched comprises predominantly one enantiomer of an enantiomeric pair. Preferably, an enantiomerically enriched compound comprises greater than 80% of one enantiomer of an enantiomeric pair and less than 20% of the other enantiomer of the enantiomeric pair. More preferably, an enantiomerically enriched compound comprises greater than 90% of one enantiomer of an enantiomeric pair and less than 10% of the other enantiomer of the enantiomeric pair. Even more preferably, an enantiomerically enriched compound comprises greater than 95% of one enantiomer of an enantiomeric pair and less than 5% of the other enantiomer of the enantiomeric pair. Even more highly preferably, an enantiomerically enriched compound comprises greater than 97% of one enantiomer of an enantiomeric pair and less than 3% of the other enantiomer of the enantiomeric pair. Yet even more highly preferably, an enantiomerically enriched compound comprises greater than 98% of one enantiomer of an enantiomeric pair and less than 2% of the other enantiomer of the enantiomeric pair. Most preferably, an enantiomerically enriched compound comprises greater than 99% of one enantiomer of an enantiomeric pair and less than 1% of the other enantiomer of the enantiomeric pair.

The term "halo" or "halide" as used herein refers to F, Cl, Br or I.

The term "haloalkenyl" as used herein refers to a loweralkenyl group in which one or more hydrogen atoms is replaced with a halogen. Examples of haloalkenyl groups include 2-fluoroethylene, 1-chloroethylene, 1,2-difluoroethylene, trifluoroethylene, 1,1,1-trifluoro-2-propylene and the like.

The term "haloalkoxy" as used herein refers to the group having the formula, —OR$^{69}$, where R$^{69}$ is a haloalkyl group as defined herein. Examples of haloalkoxy include chloromethoxy, fluoromethoxy, dichloromethoxy, trifluoromethoxy and the like.

The term "haloalkyl" as used herein, refers to a loweralkyl group in which one or more hydrogen atoms has been replaced with a halogen including, but not limited to, trifluoromethyl, trichloromethyl, difluoromethyl, dichloromethyl, fluoromethyl, chloromethyl, chloroethyl, 2,2-dichloroethyl, 2,2,2-trichloroethyl, pentafluoroethyl and the like.

The term "heterocyclic ring" or "heterocyclic" or "heterocycle" as used herein, refers to any 3- or 4-membered ring containing a heteroatom selected from oxygen, nitrogen and sulfur; or a 5-, 6- or 7-membered ring containing one, two, three, or four nitrogen atoms; one oxygen atom; one sulfur atom; one nitrogen atom and one sulfur atom; two nitrogen atoms and one sulfur atom; one nitrogen atom and one oxygen atom; two nitrogen atoms and one oxygen atom; two oxygen atoms in non-adjacent positions; one oxygen atom and one sulfur atom in non-adjacent positions; or two sulfur atoms in non-adjacent positions. The 5-membered ring has 0–2 double bonds and the 6- and 7-membered rings have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring, such as, for example, indolyl, dihydroindolyl, quinolyl, isoquinolyl, tetrahydroquinolyl, tetrahydroisoquinolyl, decahydroquinolyl, decahydroisoquinolyl, benzofuryl, dihydrobenzofuryl or benzothienyl and the like.

Heterocyclic groups include, but are not limited to groups such as, for example, aziridinyl, azetidinyl, epoxide, oxetanyl, thietanyl, pyrrolyl, pyrrolinyl, pyrrolidinyl, pyrazolyl, pyrazolinyl, pyrazolidinyl, imidazolyl, imidazolinyl, imidazolidinyl, pyridyl, tetrahydropyridyl, piperidinyl, homopiperidinyl, pyrazinyl, piperazinyl, pyrimidinyl, pyridazinyl, oxazolyl, oxazolinyl, oxazolidinyl, isoxazolyl, isoxazolidinyl, morpholinyl, thiomorpholinyl, thiazolyl, thiazolinyl, thiazolidinyl, isothiazolyl, isothiazolidinyl, indolyl, quinolinyl, isoquinolinyl, benzimidazolyl, benzothiazolyl, benzoxazolyl, oxetanyl, dihydrofuranyl, tetrahydrofuranyl, dihydropyranyl, tetrahydropyranyl, thienyl, dihydrothienyl, tetrahydrothienyl, triazolyl, triazolinyl, tetrazolyl, tetrazolinyl, isoxazolyl, 1,2,3-oxadiazolyl, 1,2,4oxadiazolyl, 1,3,4-oxadiazolyl, 1,2,5-oxadiazoyly, oxadiazolinyl, 1,2,3-thiadiazoyly, 1,2,4-thiadiazolyl, 1,3,4-thiadiazolyl, 1,2,5-thiadiazolyl, thiadiazolinyl, 1,3-dithiolinyl, 1,2-dithiolyl, 1,3-dithiolyl, 1,3-dioxolinyl, didehydrodioxolanyl, 1,3-oxathiolinyl, oxathiolyl, pyrimidyl, benzothienyl and the like. Heterocyclic groups also include compounds of the formula

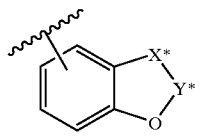

where X* is —CH$_2$ or —O— and Y* is —C(O)— or [—C(R$^{92}$)$_2$—]$_v$ where R$^{92}$ is hydrogen or C$_1$–C$_4$ alkyl where v is 1, 2, or 3 such as 1,3-benzodioxolyl, 1,4-benzodioxanyl and the like. Heterocyclic groups also include bicyclic rings such as quinuclidinyl and the like.

Heterocyclic groups can be unsubstituted or substituted with from one to three substituents, each independently selected from loweralkyl, hydroxy, alkoxy, thioalkoxy, amino, alKylamino, dialkylamino and halogen. In addition, nitrogen containing heterocyclic rings can be N-protected.

The term "(heterocyclic)alkenyl" as used herein refers to a heterocyclic group appended to a lower alkenyl radical including, but not limited to, pyrrolidinylethenyl, morpholinylethenyl and the like.

The term "(heterocyclic)alkoxy" as used herein refers to the group having the formula, —OR$^{68}$, where R$^{68}$ is a (heterocyclic)alkyl group.

The term "(heterocyclic)alkyl" as used herein refers to a heterocyclic group appended to a loweralkyl radical including, but not limited to, pyrrolidinylmethyl, morpholinylmethyl and the like.

The term "(heterocyclic)alkynyl" as used herein refers to a heterocyclic group appended to a lower alkynyl radical including, but not limited to, pyrrolidinylacetylenyl, morpholinylpropynyl and the like.

The term "(heterocyclic)carbonylalkyl" as used herein refers to a heterocyclic group appended to an alkyl radical via a carbonyl group. Representative examples of (heterocyclic)carbonylalkyl include pyridylcarbonylmethyl, morpholinocarbonylethyl, piperazinylcarbonylmethyl and the like.

The term "(heterocyclic)carbonyloxyalkyl" as used herein refers to a heterocyclic group appended to an alkyl radical via a carbonyloxy group (i.e., —C(O)—O—). Representative examples of (heterocyclic)carbonylalkyl include pyridylcarbonylmethyl, morpholinocarbonylethyl, piperazinylcarbonylmethyl and the like.

The term "(heterocyclic)oxy" as used herein refers to a heterocyclic group appended to the parent molecular moiety through an oxygen atom (—O—).

The term "hydroxy protecting group", "hydroxyl protecting group" or "—OH protecting group" as used herein refers to refers to groups used to hydroxy groups against undesirable reactions during synthetic procedures. Commonly used hydroxy protecting groups are disclosed in T. H. Greene and P. G. M. Wuts, *Protective Groups in Organic Synthesis,* 2nd edition, John Wiley & Sons, New York (1991) which is incorporated by reference herein. Such hydroxy protecting groups include:

methyl ether;
substituted methyl ethers, including, but not limited to, methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, t-butoxymethyl, 2-methoxyethoxymethyl, 2,2,2-trichloroethoxymethyl, 2-(trimethylsilyl)ethoxymethyl, tetrahydropyranyl, tetrahydrothiopyranyl, tetrahydrofuranyl, tetrahydrothiofuranyl ether and the like;
substituted ethyl ethers, including, but not limited to, 1-ethoxyethyl, 1-methyl-1-methoxyethyl, 1-methyl-1-benzyloxyethyl, 2,2,2-trichloroethyl, trimethylsilylethyl, t-butyl ether and the like;
benzyl ether;
substituted benzyl ethers, including, but not limited to, p-methoxybenzyl, 3,4-dimethoxybenzyl, o-nitorbenzyl, p-halobenzyl, p-cyanobenzyl, diphenylmethyl, triphenylmethyl ether and the like;
silyl ethers, including, but not limited to, trimethylsilyl, triethylsilyl, triisopropylsilyl, dimethylisopropylsilyl, diethylisopropylsilyl, dimethylthexylsilyl, t-butyidimethylsilyl, t-butyldiphenylsilyl, tribenzylsilyl, triphenylsilyl, diphenylmethylsilyl ether and the like;
esters, including, but not limited to, formate, acetate, chloroacetate, dichloroacetate, trichloroacetate, trifluoroacetate, methoxyacetate, phenoxyacetate, pivaloate, benzoate ester and the like; and the like.

Preferred hydroxy protecting groups include substituted methyl ethers, benzyl ether, substituted benzyl ethers, silyl ethers and esters.

The term "hydroxyalkyl" as used herein refers to the group having the formula, —R$^{65}$—OH, where R$^{65}$ is an alkylene group.

The term "leaving group" as used herein refers to a group which is easily displaced from the compound by a nucleophile. Examples of leaving groups include a halide (for example, Cl, Br or I) or a sulfonate (for example, mesylate, tosylate, triflate and the like) and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in T. H. Greene and P. G. M. Wuts, *Protective Groups in Organic Synthesis,* 2nd edition, John Wiley & Sons, New York (1991). N-protecting groups comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; sulfenyl groups such as phenylsulfenyl (phenyl-S—), triphenylmethylsulfenyl (trityl-S—) and the like; sulfinyl groups such as p-methylphenylsulfinyl (p-methylphenyl-S(O)—), t-butylsulfinyl (t-Bu—S(O)—) and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoyybenzyloxycarbonyl, 3,4,6-trimethoxybenzyloxycarbonyl, 1-(p-biphenylyl)-1-methylethoxycarbonyl, α,α-dimethyl-3,5-dimethoxybenzyloxy-carbonyl, benzhydryloxycarbonyl, t-butyloxycarbonyl, diisopropylmethoxy-carbonyl, isopropyloxycarbonyl, ethoxycarbonyl, methoxycarbonyl, allyloxycarbonyl, 2,2,2-trichloroethoxycarbonyl, phenoxycarbonyl, 4-nitro-phenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, p-methoxybenzyl, triphenylmethyl, benzyloxymethyl and the like; p-methoxyphenyl and the like; and silyl groups such as trimethylsilyl and the like. Preferred N-protecting groups include formyl, acetyl, benzoyl, pivaloyl, t-butylacetyl, phenylsulfonyl, benzyl, t-butyloxycarbonyl (Boc) and benzyloxycarbonyl (Cbz).

The term "thioalkoxy" as used herein refers to groups having the formula —SR$^{98}$ wherein R$^{98}$ is an alkyl group. Preferred groups R$^{98}$ are loweralkyl groups.

The term "thio-substituted alkyl" as used herein refers to an alkyl radical to which is appended a thiol group (—SH).

As used herein, the terms "S" and "R" configuration are as defined by the IUPAC 1974 Recommendations for Section E, Fundamental Stereochemistry, Pure Appl. Chem. (1976) 45, 13–30.

The compounds of the invention can comprise asymmetrically substituted carbon atoms. As a result, all stereoisomers of the compounds of the invention are meant to be included in the invention, including racemic mixtures, mixtures of diastereomers, as well as individual optical isomers, including, enantiomers and single diastereomers of the compounds of the invention substantially free from their enantiomers or other diastereomers. By "substantially free" is meant greater than about 80% free of other enantiomers or diastereomers of the compound, more preferably greater than about 90% free of other enantiomers or diastereomers of the compound, even more preferably greater than about 95% free of other enantiomers or diastereomers of the compound, even more highly preferably greater than about 98% free of other enantiomers or diastereomers of the compound and most preferably greater than about 99% free of other enantiomers or diastereomers of the compound.

In addition, compounds comprising the possible geometric isomers of carbon-carbon double bonds and carbon-nitrogen double are also meant to be included in this invention.

Individual stereoisomers of the compounds of this invention can be prepared by any one of a number of methods which are within the knowledge of one of ordinary skill in the art. These methods include stereospecific synthesis, chromatographic separation of diastereomers, chromatographic resolution of enantiomers, conversion of enantiomers in an enantiomeric mixture to diastereomers and then chromatographically separating the diastereomers and regeneration of the individual enantiomers, enzymatic resolution and the like.

Stereospecific synthesis involves the use of appropriate chiral starting materials and synthetic reactions which do not cause racemization or inversion of stereochemistry at the chiral centers.

Diastereomeric mixtures of compounds resulting from a synthetic reaction can often be separated by chromatographic techniques which are well-known to those of ordinary skill in the art.

Chromatographic resolution of enantiomers can be accomplished on chiral chromatography resins. Chromatography columns containing chiral resins are commercially available. In practice, the racemate is placed in solution and loaded onto the column containing the chiral stationary phase. The enantiomers are then separated by HPLC.

Resolution of enantiomers can also be accomplished by converting the enantiomers in the mixture to diastereomers by reaction with chiral auxiliaries. The resulting diastereomers can then be separated by column chromatography. This technique is especially useful when the compounds to be separated contain a carboxyl, amino or hydroxyl group that will form a salt or covalent bond with the chiral auxiliary. Chirally pure amino acids, organic carboxylic acids or organosulfonic acids are especially useful as chiral auxiliaries. Once the diastereomers have been separated by chromatography, the individual enantiomers can be regenerated. Frequently, the chiral auxiliary can be recovered and used again.

Enzymes, such as esterases, phosphatases and lipases, can be useful for resolution of derivatives of the enantiomers in an enantiomeric mixture. For example, an ester derivative of a carboxyl group in the compounds to be separated can be prepared. Certain enzymes will selectively hydrolyze only one of the enantiomers in the mixture. Then the resulting enantiomerically pure acid can be separated from the unhydrolyzed ester.

In addition, solvates and hydrates of the compounds of Formula I, IIA, IIB, IIIA or IIIB are meant to be included in this invention.

When any variable (for example R$^1$, R$^2$, R$^3$, m, n, etc.) occurs more than one time in any substituent or in the compound of Formula I, IIA, IIB, IIIA or IIIB or any other formula herein, its definition on each occurrence is independent of its definition at every other occurrence. In addition, combinations of substituents are permissible only if such combinations result in stable compounds. Stable compounds are compounds which can be isolated in a useful degree of purity from a reaction mixture.

This invention is intended to encompass compounds having Formula I, IIA, IIB, IIIA or IIIB when prepared by synthetic processes or by metabolic processes. Preparation of the compounds of the invention by metabolic processes include those occurring in the human or animal body (in vivo) or processes occurring in vitro.

Compounds of the invention can be prepared according to the methods described in Schemes 1–10 as shown below.

Throughout the schemes, methods will be illustrated wherein R$^1$ is a carboxylic acid or carboxylic acid ester substituent. It will be understood by those skilled in the art that other $R^1$ substituents can (a) be obtained either from the carboxylic acid or carboxylic acid ester group, (b) can be introduced by similar methods to those used to introduce the carboxylic acid or carboxylic acid ester group or (c) can be introduced by other methods generally known in the art.

In addition, throughout the schemes, methods will be illustrated wherein $R^4$, $R^6$, $R^7$, $R^8$, $R^9$ and $R^{10}$ are hydrogen. It will be understood by those skilled in the art that compounds wherein one or more of these substituents is other than hydrogen can be prepared by methods analogous to those disclosed in the schemes or by other methods generally known in the art.

In addition, unless otherwise noted, methods will be illustrated for obtaining compounds of the invention having the preferred relative stereochemistry. It will be understood by those skilled in the art that compounds of the invention having other relative stereochemistry can be prepared by methods analogous to those disclosed in the schemes or by other methods generally known in the art.

In addition, throughout the schemes, methods will be illustrated wherein X is —C(=O)—NH—. It will be understood by those skilled in the art that other X groups can be prepared by methods analogous to those disclosed in the schemes or by other methods generally known in the art.

As shown in Scheme 1, reaction of acrolein with an N-protected α-amino acid ester 1 ($P^1$ is an N-protecting group, preferably a benzyl group or the like and $P^2$ is a carboxylic acid protecting group, preferably a t-butyl group or the like) in an inert solvent (for example, toluene and the like) in the presence of an acid catalyst (for example, acetic acid and the like), followed by equilibration with a base (for example, with triethylamine or the like) and separation of the isomers by chromatography, provides substituted pyrrolidine 2. Reduction of the aldehyde group to an alcohol with an aldehyde to alcohol reducing agent (for example, sodium borohydride or the like) in an inert solvent (for example, methanol or the like), followed by chromatographic separation of the isomers provides alcohol 3.2 Alcohol 3 can be protected with an hydroxy protecting group $P^3$ (preferably with a silyl protecting group, for example, t-butyidimethylsilyl or the like) using standard alcohol protection methods to provide 4. Oxidation of the vinyl group of compound 4 to an aldehyde is accomplished by reacting compound 4 with $OsO_4$ and N-methylmorpholine N-oxide to give the corresponding diol. The diol is then treated with sodium periodate to provide aldehyde 5. Substituents $R^3$ can be introduced via reaction of aldehyde 5 with a Grignard reagent (for example, $R^3MgBr$ or the like) to give alcohol 6. Oxidation of alcohol 6 (for example, Swern oxidation or the like) provides ketone 7. Reductive amination of ketone 7 (for example, by reaction with ammonium acetate and sodium cyanoborohydride in methanol or the like) gives amine 8. Amine 8 can be further functionalized to complete the introduction of the $R^2$-X-substituent (for example, by reaction of the amine with an acylating agent such as acetic anhydride or the like or by other acylation methods), followed by chromatographic separation of the diastereomers to give 9a. The other diastereomeric amine (9b) can also be isolated and further transformed according to Scheme 1.

Removal of hydroxy protecting group $P^3$ (for example, by reaction with a fluoride ion source, such as tetrabutylammonium fluoride or the like, when $P^3$ is a silyl protecting group) provides alcohol 10. Transformation of the hydroxy group of alcohol 10 allows introduction of various substituents Y.

For example, alkylation of the hydroxy group provides ethers 11. N-deprotection (for example, where $P^1$ is a benzyl group, by hydrogenation) gives 12', followed by ester hydrolysis (for example, with acid such at HCl), provides compound 12" of the invention.

Oxidation of the hydroxy group of 10 (for example, Swern oxidation or the like) provides aldehyde 13. Oxidation of aldehyde 13 (for example, with $NaClO_2$ or the like) provides carboxylic acid 14. The carboxylic acid substituent of 14 can be used to introduce a variety of other functional groups in substituent Y. For example, the carboxylic acid can be esterified (for example, by reaction with diazomethane or with ethanol and DCC or the like) or the carboxylic acid or an activated derivative thereof can be reacted with amines to provide 15 (wherein —C(=O)—$R^{22}$ represents an ester or an amide). N-deprotection (for example, where $P^1$ is a benzyl group, by hydrogenation) gives 16', followed by ester hydrolysis (for example, with acid such as HCl), provides compound 16" of the invention.

Derivatives of the aldehyde group of 13 or the carboxylic acid group of 14 can be used to introduce substituents Y which are —CN or various heterocycles, according to methods known to those skilled in the art and according to the specific methods exemplified herein.

Reaction of aldehyde 13 with loweralkyl- or loweralkenyl-Grignard reagents, followed by oxidation (for example, Swern oxidation or the like), provides ketones 17 wherein $R^{22}$ is loweralkyl or loweralkenyl. N-deprotection (for example, where $P^1$ is a benzyl group, by hydrogenation) gives 18', followed by ester hydrolysis (for example, with acid such as HCl), provides compound 18" of the invention.

Compounds wherein substituent Y is an amino group or a derivative of an amino group can be prepared as shown in Scheme 2. Oxidation of aldehyde 2 (for example, with AgO or $NaClO_2$ or the like) provides carboxylic acid 19. Curtius rearrangement of carboxylic acid 19 (for example, reaction with DPPA, $Et_3N$ and benzyl alcohol or the like), followed by chromatographic separation of the diastereomers, provides amide 20 wherein $P^4$ is an N-protecting group (for example, benzyloxycarbonyl or the like). Transformations analogous to those which converted compound 4 to compound 9a and 9b in Scheme 1, enable the conversion of 20 to 21a and 21b, which can be separated by chromatography. Removal of protecting group $P^4$ (for example, by selective hydrogenation) provides 22. Further derivatization of the amino group allows for introduction of substituents Y which are amine derivatives. N-deprotection (for example, where $P^1$ is a benzyl group, by hydrogenation), followed by ester hydrolysis (for example, with acid such as HCl), provides compounds of the invention wherein Y is amino or an amine derivative.

Olefination of aldehyde 13 (for example, with $Ph_3PCH_2$ or the like), followed by hydrogenation (causing N-deprotection (for example, where $P^1$ is a benzyl group) and olefin saturation, followed by ester hydrolysis (for example, with acid such as HCl), provides compounds of the invention wherein Y is loweralkyl.

As shown in Scheme 3, oxidation of the vinyl group of compound 4 to a diol (for example, with $OsO_4$ and N-methylmorpholine N-oxide or the like) gives diol 23. Removal of N-protecting group $P^1$ (for example, where $P^1$ is a benzyl group, by hydrogenation) provides pyrrolidine 24. Reprotection with an acidlabile N-protecting group $P^5$ (for example, t-butoxycarbonyl or the like) provides 25. Transformation of compound 25 to aldehyde 26a and 26b can be accomplished in a manner analogous to conversion of compound 4a to compound 10 and compound 10 to compound 13 as shown in Scheme 1. 26a and 26b can be separated by chromatography.

Olefination of 26a (for example, with $Ph_3PCH_2$, or triphenylphosine/methylene chloride/n-BuLi, or $I^-Ph_3P^+CH_2CH_3$/KOtBu, or the like) provides 27 wherein Y is an olefinic substituent. N-deprotection of the $P^5$ protecting group and ester hydrolysis, under acidic conditions, provides compounds of the invention 28 wherein Y is an olefinic substituent.

In yet another alternative method shown in Scheme 4, the hydroxy group of alcohol 3 is protected with a base-labile hydroxy protecting group $P^6$ (for example, acetyl or the like) to give compound 29. Oxidation of the vinyl group of 29 with $OsO_4$ and N-methylmorpholine N-oxide provides diol 30. Removal of the $P^1$ protecting group (for example, by hydrogenation or the like) provides pyrrolidine 31. Reprotection with an acid-labile N-protecting group $P^5$ (for example, t-butoxycarbonyl or the like) provides 32. Selective protection of the primary alcohol of 32 with a hydroxy protecting group $P^7$ (for example, a silyl protecting group such as triisopropylsilyl or the like) provides compound 33. Oxidation of 33 (for example, Swern oxidation or the like) provides ketone 34. Reductive amination of ketone 34 (for example, by reaction with ammonium acetate and sodium cyanoborohydride in methanol or the like) gives amine 35. Amine 35 can be further functionalized to complete the introduction of the $R^2$-X-substituent (for example, by reaction of the amine with an acylating agent such as acetic anhydride or the like or by other acylation methods), followed by chromatographic separation of the diastereomers to give 36a. The other diastereomeric amine (36b) can also be isolated and further transformed according this scheme.

Selective removal of the $P^6$ hydroxy protecting group in 36a (for example, with $K_2CO_3$ in methanol or the like) provides alcohol 37. Oxidation of the alcohol to an aldehyde (for example, Swern oxidation or the like) provides 38. The aldehyde, can serve as a precursor for various substituents Y in the compounds of the invention. For example, olefination of 38 (for example, with $Ph_3PCH_2$, or triphenylphosine/methylene chloride/n-BuLi, or $I^-Ph_3P^+CH_2CH_3$/KOtBu, or the like) provides 39 wherein Y is an olefinic substituent. Removal of the $P^7$ hydroxy protecting group (for example, with a fluoride ion source such as tetrabutylammonium fluoride or the like) gives alcohol 40.

The alcohol can serve as a precursor for a variety of $R^3$ substituents in the compounds of the invention. For example, the alcohol of 40 can be oxidized to an aldehyde (for example, by Dess-Martin oxidation or the like) to give 41. Aldehyde 41 can be reacted with Grignard reagents ($R^{14}MgBr$ or the like) or other organometallic reagents (for example, organolithium reagents such as $R^{14}Li$ or the like) to provide 42 as a mixture of alcohol diastereomers which can be separated chromatographically to provide the major isomer 42a and the other isomer 42b. Isomer 42a or the mixture of isomers 42 can be oxidized (for example, by Dess-Martin oxidation or the like) to give ketone 43. Reduction of ketone 43 (for example, with sodium borohydride in ethanol or the like) provides alcohol 42b as the major isomer, which can be isolated by chromatography. N-deprotection of the $P^5$ protecting group and ester hydrolysis, under acidic conditions, provides compounds of the invention 44a or 44b, respectively, wherein Y is an olefinic substituent.

Alkylation of alcohol 42a or 42b provides ethers 45a or 45b, respectively. N-deprotection of the $P^5$ protecting group and ester hydrolysis, under acidic conditions, provides compounds of the invention 48a or 48b, respectively, wherein Y is an olefinic substituent.

As shown in Scheme 5, reaction of ketone 43 with with Grignard reagents ($R^{37a}MgBr$ or the like) or other organometallic reagents (for example, organolithium reagents such as $R^{37a}Li$ or the like) provides alcohols 46a and 46b as a mixture of alcohol diastereomers which can be separated chromatographically. N-deprotection of the $P^5$ protecting group and ester hydrolysis, under acidic conditions, provides compounds of the invention 47a or 47b, respectively, wherein Y is an olefinic substituent.

Alkylation of alcohol 46a or 46b provides ethers 49a or 49b, respectively. N-deprotection of the $P^5$ protecting group and ester hydrolysis, under acidic conditions, provides compounds of the invention 50a or 50b, respectively, wherein Y is an olefinic substituent.

Esters or prodrugs of the compounds of the invention can be prepared by methods known in the art.

Scheme 6 illustrates a method for preparing enantiomerically enriched compounds of the invention having the preferred absolute stereochemistry. Protected pyrrole 51 (wherein $P^8$ is an N-protecting group, for example, t-butyloxycarbonyl or the like, and $P^9$ is a hydroxy protecting group, for example, t-butyldimethylsilyl or the like; J. Org. Chem. 57 3760–3763 (1992)) is reacted with imine 52 (wherein $P^{10}$ is an N-protecting group, for example, p-toluenesulfinyl (—S(O)Tol), t-butylsulfinyl (—S(O)-t-Bu), tritylsulfenyl ((Ph)$_3$C—S—), phenylsulfenyl (Ph—S—), p-methoxyphenyl, p-methoxybenzyl or the like and wherein any functional groups within group $R^3$ that require protection are appropriately protected) in the presence of a Lewis acid, for example, trimethylsilyltriflate, borontrifluoride etherate or the like, in an inert solvent, for example, dichloromethane or the like, to provide unsaturated lactam 53 Preferably, N-protecting groups $P^8$ and $P^{10}$ can be selectively deprotected/removed in the presence of each other. Reaction of 53 with an organometallic reagent Y-M (wherein M is a metal), for example, a cuprate reagent or the like, in an inert solvent, for example, THF or the like, provides substituted lactam 54. Lactam 54 is converted to cyano-substituted pyrrolidine 55, for example, by (i) reduction with a lactam reducing agent, for example, diisobutylaluminum hydride or the like, in an inert solvent, for example, THF or the like, followed by (ii) treatment with methanol and a catalytic amount of an acid, for example, pyridinium p-toluenesulfonic acid or the like, followed by (iii) reaction with a cyanide source, for example, trimethylsilylcyanide or the like, in an inert solvent, for example, dichloromethane or the like. Alternatively, lactam 54 is converted to cyano-substituted pyrrolidine 55, for example, by (i) reduction with a lactam reducing agent, for example, diisobutylaluminum hydride or the like, in an inert solvent, for example, THF or the like, followed by (ii) reaction with a cyanide source, for example, trimethylsilylcyanide or the like, in an inert solvent, for example, dichloromethane or the like in the presence of a Lewis acid such as trimethylsilyl triflate or the like. Removal of protecting group $P^{10}$ (for example, with an acid such as trifluoroacetic acid, pyridinium p-toluenesulfonic acid or the like in a suitable solvent), followed by reaction of the amine with an acylating agent such as acetic anhydride or the like or by other acylation methods gives 56. Hydrolysis of the nitrile of 56 and removal of protecting group $P^8$, for example, with hydrochloric acid or the like, and deprotection of any protected functional groups within group $R^3$ provides carboxylic acid 57. Esters or prodrugs of 57 can be prepared by methods known in the art.

Among the preferred compounds of the invention are compounds such as 58 or esters or prodrugs thereof wherein $R^{37a}$, $R^{37c}$ and $R^{14}$ are as defined most broadly herein. Especially preferred are compounds 58 or esters or prodrugs thereof wherein $R^{37a}$ is loweralkyl or loweralkenyl, $R^{37c}$ is hydrogen, $C_1$–$C_3$ loweralkyl or allyl and $R^{14}$ is loweralkyl, loweralkenyl or alkoxy-substituted loweralkyl. In those cases where $R^{37c}$ is hydrogen, the hydroxy group will be protected throughout the process of Scheme 6. Compound 58 can be prepared according to the process described in Scheme 6 by first reacting 51 with imine 59.

The N-protected imine 52 is prepared by reaction of the corresponding aldehyde with $P^{10}NH_2$.

Scheme 7 illustrates a method for preparing preferred imines 59. Allylic alcohol 60 (wherein $R^{14a}$ and the carbon to which it is bonded, when taken together, will become substituent $R^{14}$) is asymmetrically epoxidized, for example, by Sharpless epoxidation with t-butyl hydroperoxide, (−)-dimethyl D-tartrate and titanium tetraisopropoxide or the like in an inert solvent such as dichloromethane and the like and the alcohol is protected (for example, $P^{11}$ is benzoate or the like) to give 61. Epoxide 61 is reduced, for example, with lithium aluminum hydride or the like in an inert solvent such as THF or the like, followed by protection of the primary alcohol of 62 (for example, $P^{12}$ is benzyl or the like) to give 63. Where $R^{37c}$ is other than hydrogen, 63 is reacted with a non-nucleophilic strong base, for example, sodium bis(trimethylsilyl)amide or the like, and $R^{37c}$—X wherein X is a halide or other leaving group in an inert solvent such as THF or the like to provide 64. Where $R^{37c}$ is hydrogen, the hydroxy group is protected. Protecting group $P^{12}$ is removed, preferably, selectively if any other hydroxy protecting groups are present in the compound, for example, by hydrogenation when it is a benzyl group, and the resulting alcohol is oxidized to an aldehyde, for example, with pyridinium chlorochromate or the like to give aldehyde 65. Reaction of 65 with $P^{10}NH_2$ gives 59.

An alternative method for preparation of enantiomerically enriched compounds of the invention having the preferred absolute stereochemistry is shown in Scheme 8. Unsaturated lactam 66 (Tetrahedron Asymmetry 1167–1180 (1996)) wherein $P^{13}$ is an N-protecting group, for example, t-butyloxycarbonyl or the like, and $P^{14}$ is a hydroxy protecting group, for example, t-butyldimethylsilyl or the like, is reacted with an organometallic reagent Y-M (wherein M is a metal), for example, a cuprate reagent or the like, in an inert solvent, for example, THF or the like, to provide 67. Lactam 67 is converted to cyano-substituted pyrrolidine 68, for example, by (i) reduction with a lactam reducing agent, for example, diisobutylaluminum hydride or the like, in an inert solvent, for example, THF or the like, followed by (ii) treatment with methanol and a catalytic amount of an acid, for example, pyridinium p-toluenesulfonic acid or the like, followed by (iii) reaction with a cyanide source, for example, trimethylsilylcyanide or the like, in an inert solvent, for example, dichloromethane or the like. Deprotection of the alcohol (for example, with a fluoride ion source such as tetrabutylammonium fluoride or the like when $P^{14}$ is a silyl based hydroxy protecting group), followed by conversion of the alcohol to an azide group (for example, by reaction with triphenylphosphine, diethyl diazodicarboxylate and diphenylphosphory azide or the like in an inert solvent such as THF or the like) provides 69. The azide is reduced (for example, with triphenylphosphine in THF/water or the like), the resulting amine is acylated (for example, with an acylating agent such as acetic anhydride or the like or by other acylation methods) and the diol is deprotected (for example, with acetic acid or the like) to give 70. Diol 70 is oxidized to the aldehyde 71, for example, with sodium metaperiodate or the like. The aldehyde 71 can be converted to 72 by methods described in Schemes 4 and 5.

Compound 72 can be converted to 57 according to the method described in Scheme 6 for converting 56 to 57.

More particularly, compounds 58 wherein $R^{37a}$ is loweralkyl or loweralkenyl, $R^{37c}$ is hydrogen, $C_1$–$C_3$ loweralkyl or allyl and $R^{14}$ is loweralkyl, loweralkenyl or alkoxy-substituted loweralkyl are prepared from 71 according to the methods outlined in Schemes 4 and 5 to give 73, which is converted to 58. In those cases where $R^{37c}$ is hydrogen, the hydroxy group will be protected throughout the process of Scheme 8.

Another alternative method for preparation of enantiomerically enriched compounds of the invention having the preferred absolute stereochemistry is shown in Scheme 9. Aldehyde 74 (wherein $P^{15}$ is an N-protecting group, for example, t-butyloxycarbonyl or the like and, preferably, wherein $R^{37a}$ is loweralkyl or loweralkenyl, $R^{37c}$ is hydrogen, $C_1$–$C_3$ loweralkyl or allyl and $R^{14}$ is loweralkyl, loweralkenyl or alkoxy-substituted loweralkyl) is reacted with N-protected hydroxylamine $P^{16}$—NHOH wherein $P^{16}$ is an N-protecting group, for example, p-methoxybenzyl or the like, to provide nitrone 75. Preferably, N-protecting groups $P^{15}$ and $P^{16}$ can be selectively deprotected/removed in the presence of each other. The carbanion of a carboxy protected propiolate is prepared by reacting the carboxy protected propiolate ($P^{17}$ is an acid protecting group, for example, methyl or t-butyl or the like) with a non-nucleophilic strong base, for example, n-BuLi or the like in an inert solvent, for example, THF or the like. The propiolate carbanion is then reacted with nitrone 75 to give 76. Reaction of 76 with zinc dust in acetic acid/methanol provides unsaturated lactam 77. Unsaturated lactam 77 is reacted with an organometallic reagent Y-M (wherein M is a metal), for example, a cuprate reagent or the like, in an inert solvent, for example, THF or the like, to provide 78. Removal of protecting group $P^{15}$ (for example, with an acid such as trifluoroacetic acid, pyridinium p-toluenesulfonic acid or the like in a suitable solvent), followed by reaction of the amine with an acylating agent such as acetic anhydride or the like or by other acylation methods gives 79. Optionally, N-protecting group $P^{16}$ can be replaced by another N-protecting group before completing the process (for example, where $P^{16}$ is p-methoxybenzyl or the like it can be removed and replaced with t-butyloxycarbonyl or the like). Lactam 79 is converted to cyano-substituted pyrrolidine 80, for example, by (i) reduction with a lactam reducing agent, for example, diisobutylaluminum hydride or the like, in an inert solvent, for example, THF or the like, followed by (ii) treatment with methanol and a catalytic amount of an acid, for example, pyridinium p-toluenesulfonic acid or the like, followed by (iii) reaction with a cyanide source, for example, trimethylsilylcyanide or the like, in an inert solvent, for example, dichloromethane or the like. Hydrolysis of the nitrile of 80 and removal of protecting group $P^{16}$, for example, with hydrochloric acid or the like, provides carboxylic acid 58. In those cases where $R^{37c}$ is hydrogen, the hydroxy group will be protected throughout the process of Scheme 9. Esters or prodrugs of 58 can be prepared by methods known in the art.

Compound 74 can be prepared according to the process shown in Scheme 10. In Scheme 10, $P^{15}$ is exemplified by t-butyloxycarbonyl (Boc), but can be other N-protecting groups. Compound 81 is prepared from D-serine according to Campbell, et al., Synthesis 1707 (1998). Reaction of 81 with an organometallic reagent $R^{14}$—M wherein M is a metal (for example, a Grignard reagent ($R^{14}$—MgCl or $R^{14}$—MgBr or the like) in an inert solvent, for example, THF or the like, provides 82. Ketone 82 is reacted with an organometallic reagent $R^{37a}$—M wherein M is a metal (for example, a Grignard reagent, $R^{37a}$—MgCl or $R^{37a}$—MgBr or the like) in an inert solvent, for example, THF or the like, to provide 83. Where $R^{37c}$ is other than hydrogen, 83 is reacted with a non-nucleophilic strong base (for example, sodium hydride or the like) in an inert solvent such as THF or the like, followed by reaction with $R^{37c}$—X where X is a leaving group such as a halide or the like to provide 84. Where $R^{37c}$ is hydrogen, the hydroxy group is suitably protected. Deprotection of 84, for example, with p-toluenesulfonic acid in methanol or the like, provides 85. Oxidation of 85, for example, with pyridine sulfur trioxide complex, DMSO and pyridine or the like, gives aldehyde 86 which corresponds to 74 wherein $P^{15}$ is t-butyloxycarbonyl.

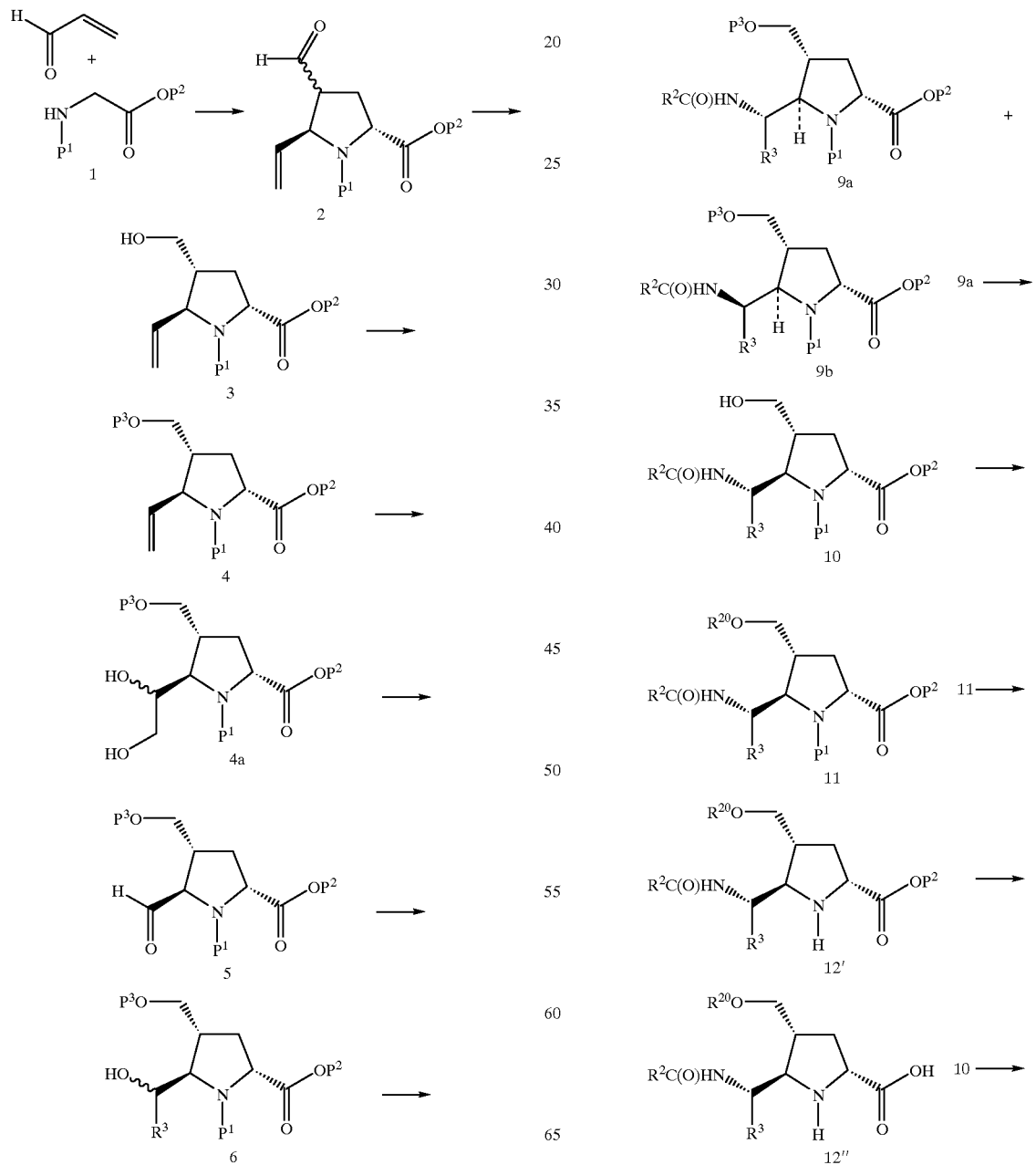

SCHEME 1

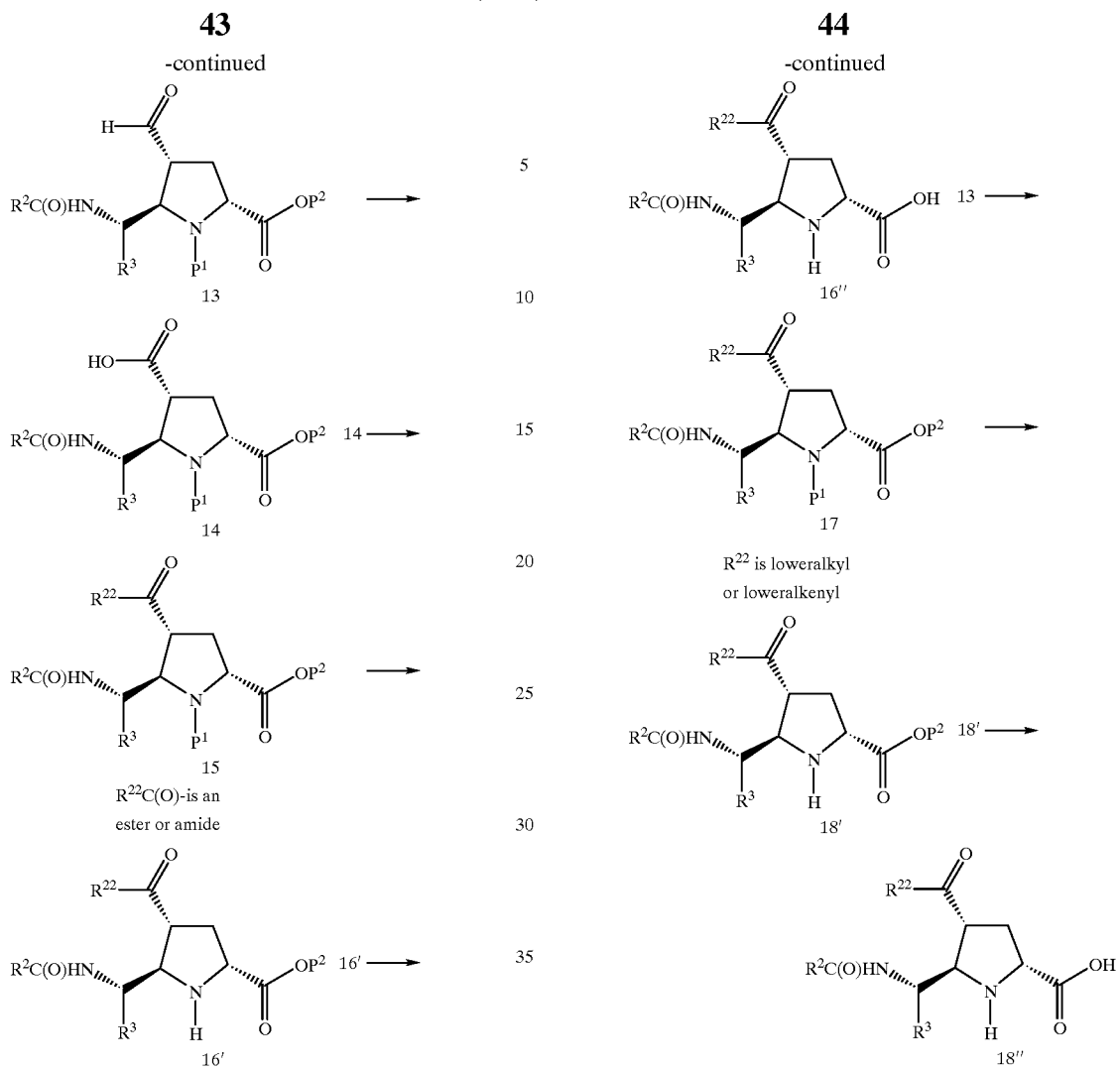
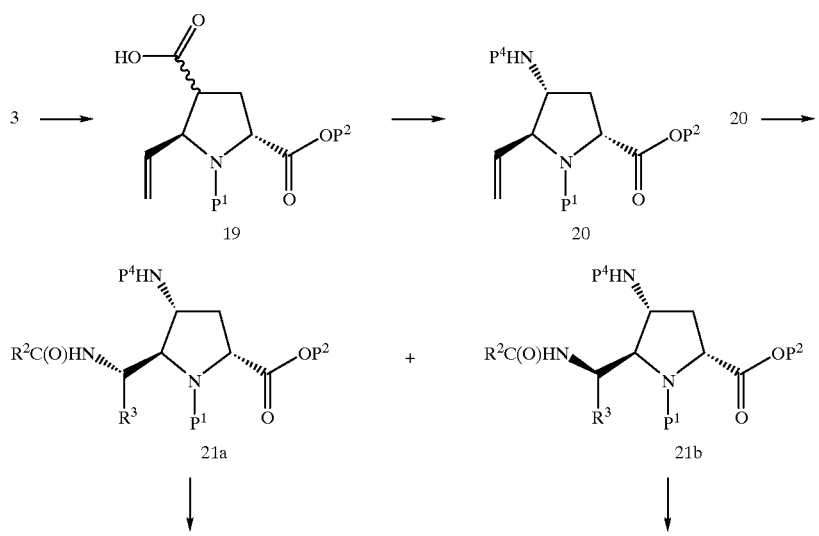
SCHEME 2

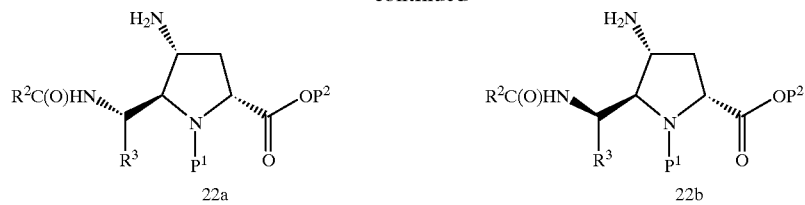
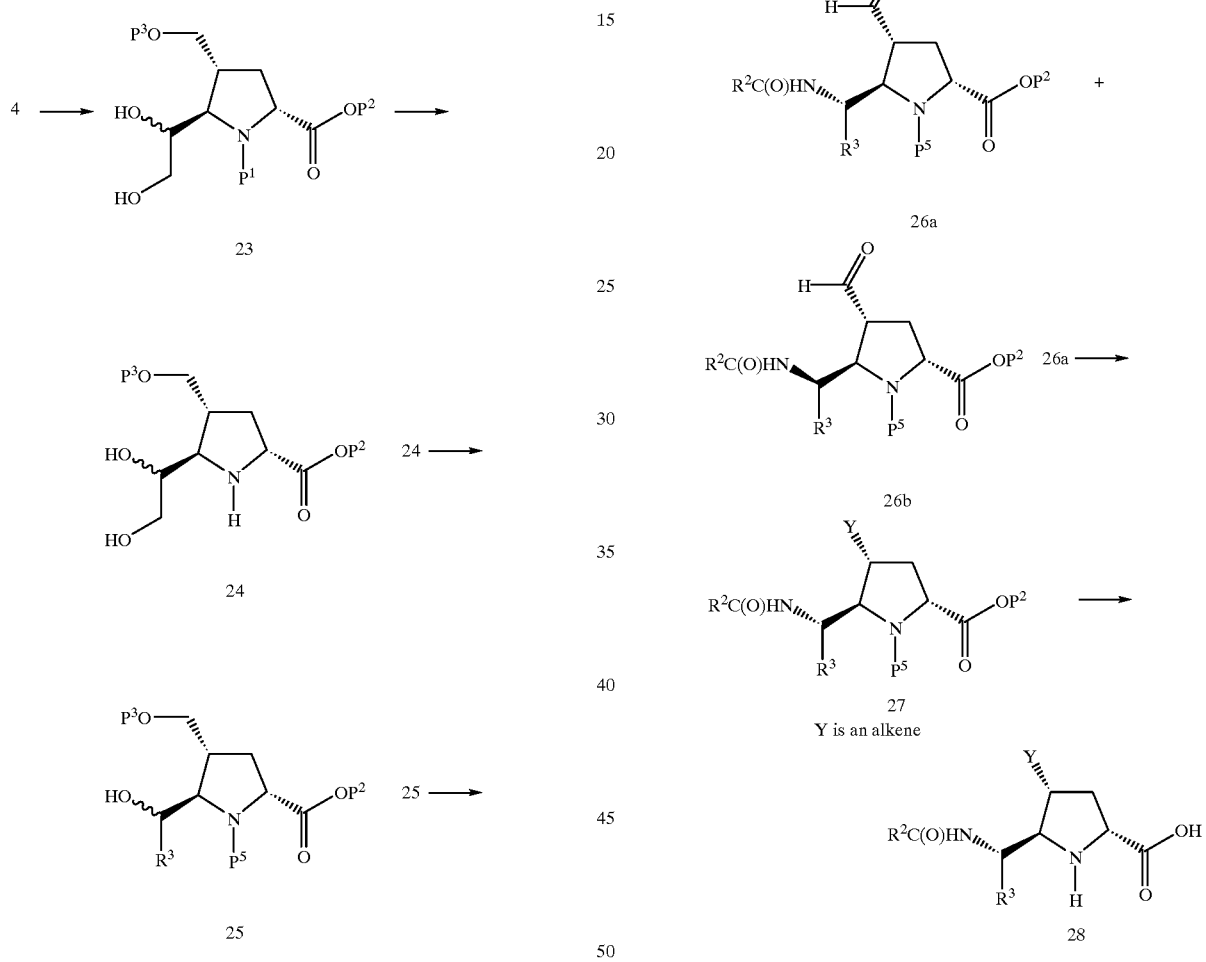
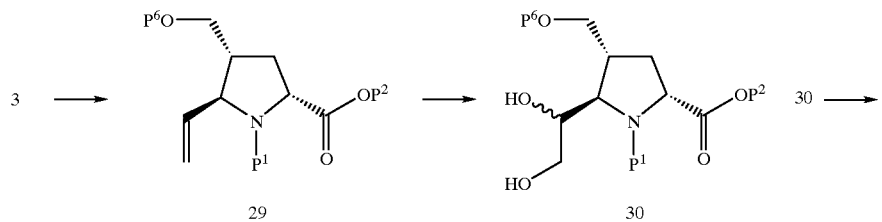

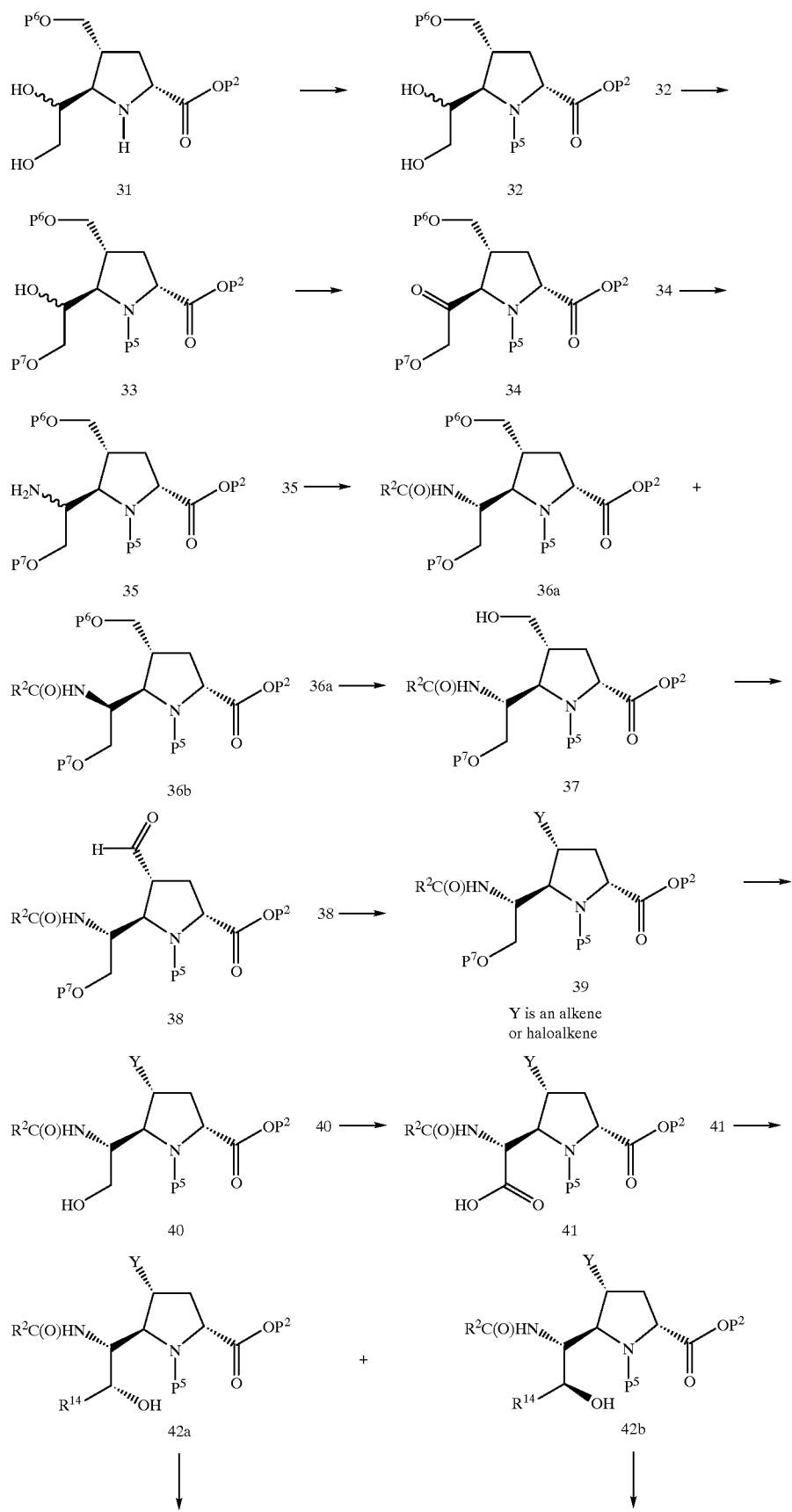

-continued
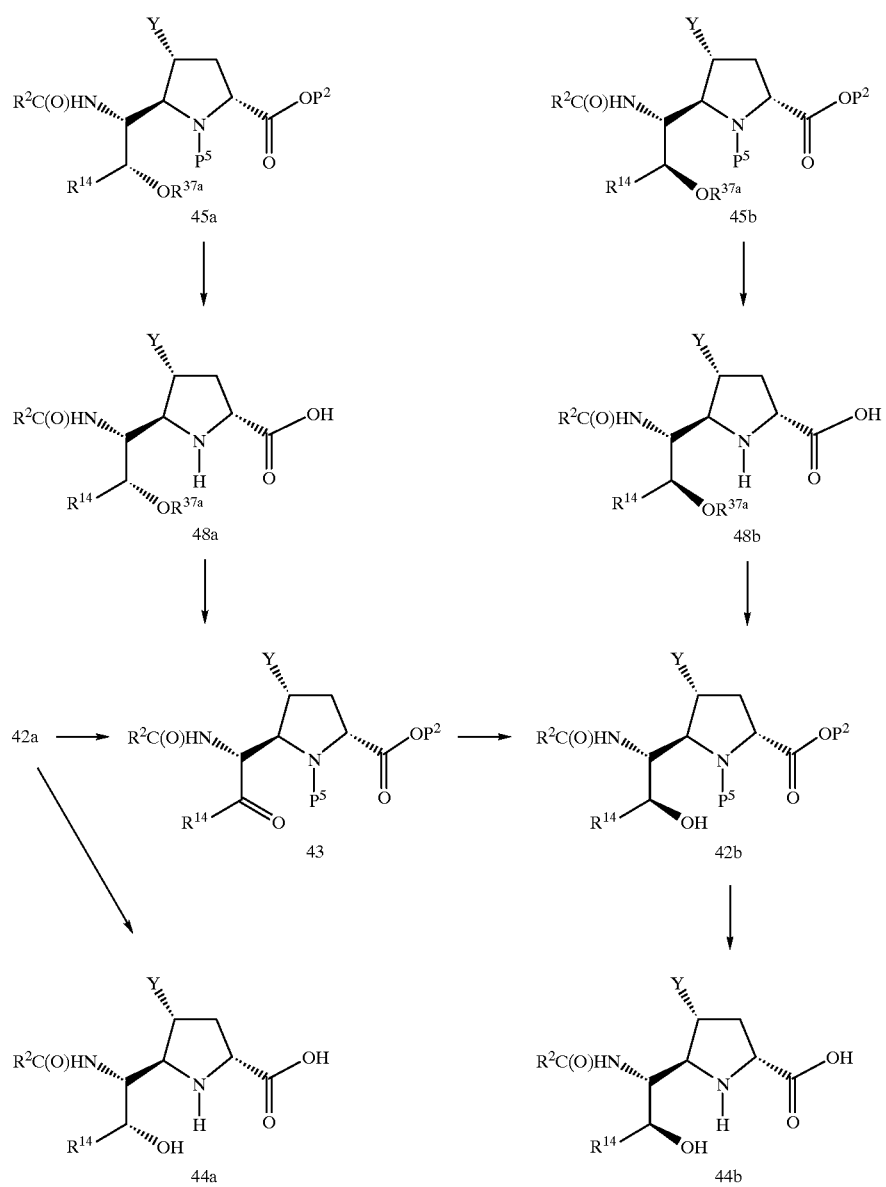
SCHEME 5
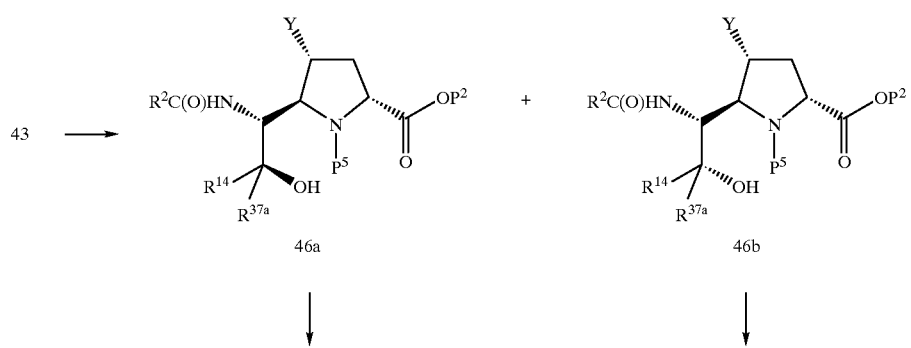

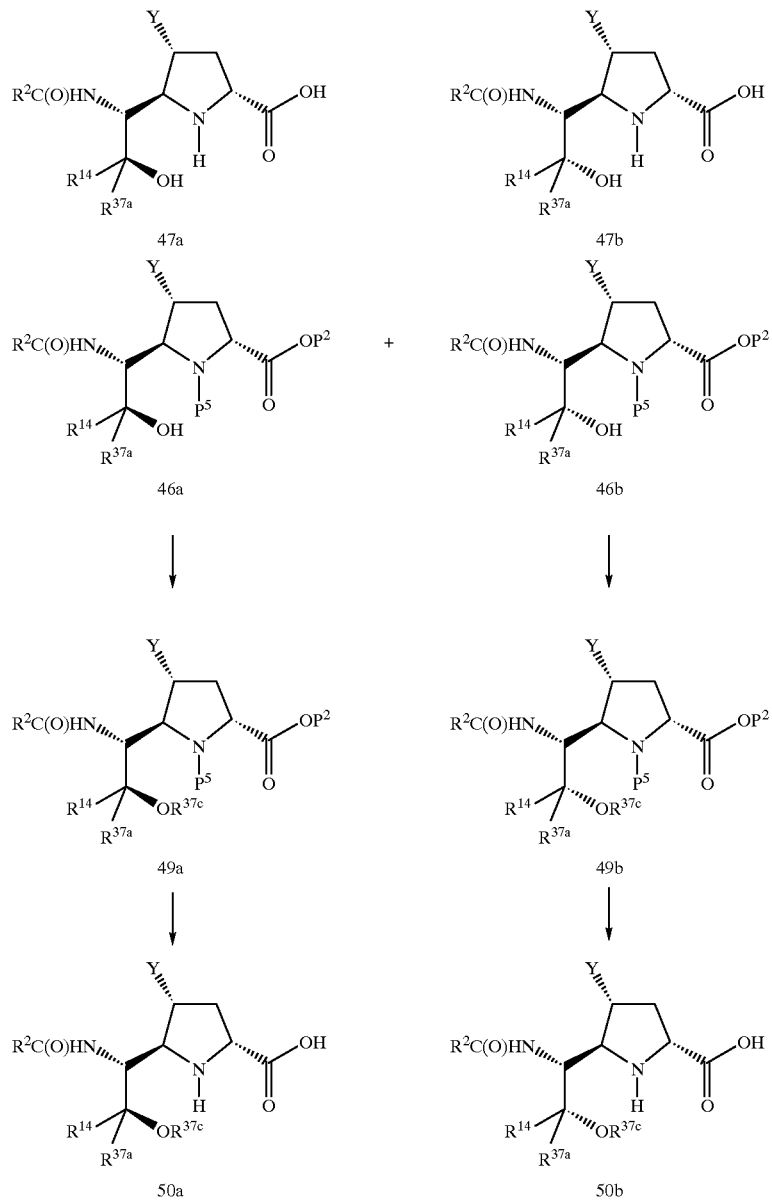
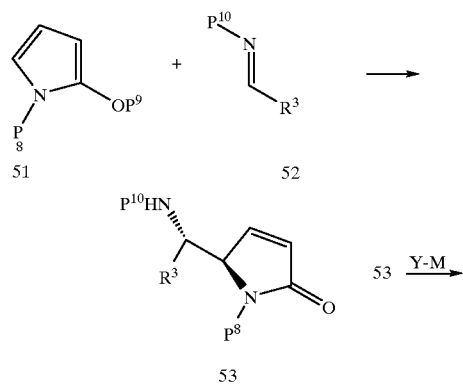
SCHEME 6
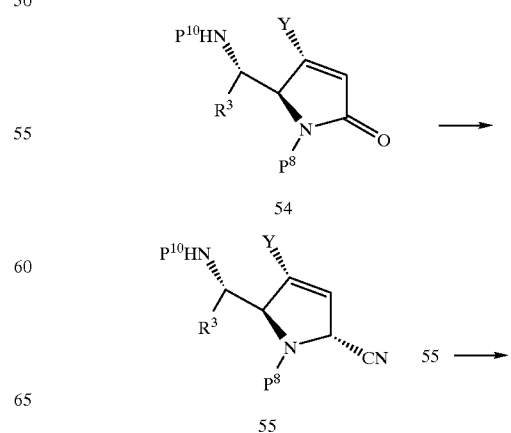

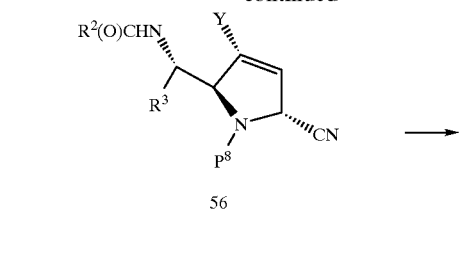
56
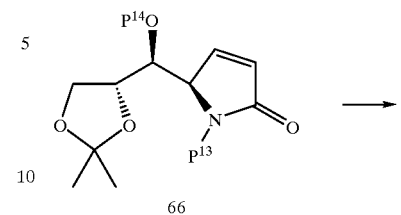
SCHEME 8
66
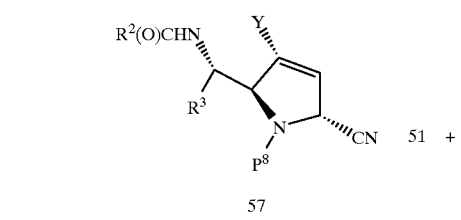
57 +
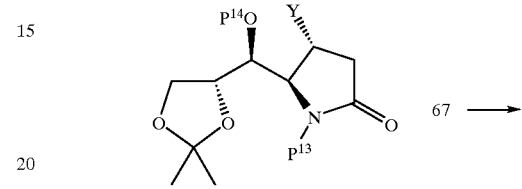
67
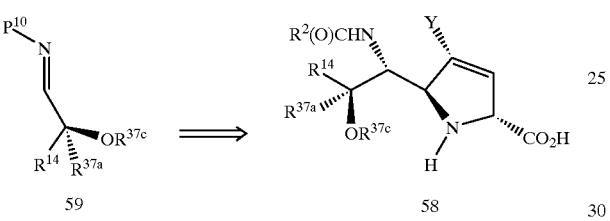
59     58
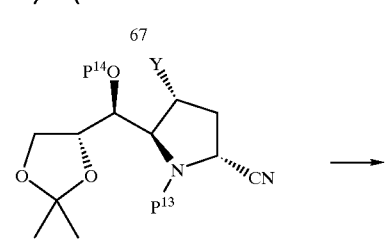
68
SCHEME 7
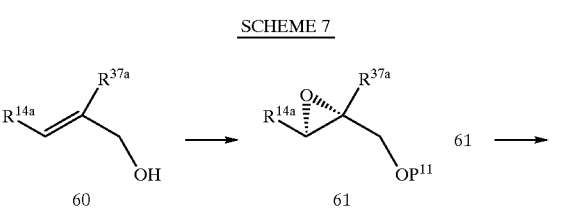
60     61
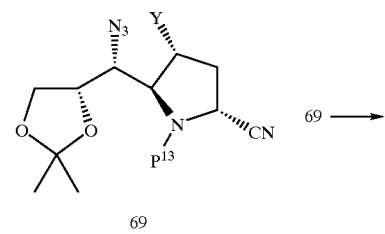
69
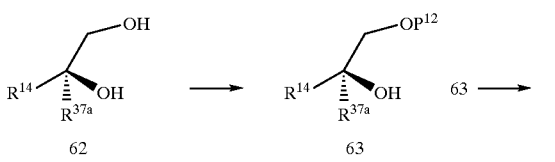
62     63
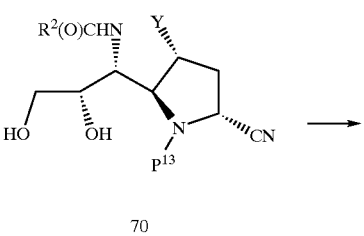
70
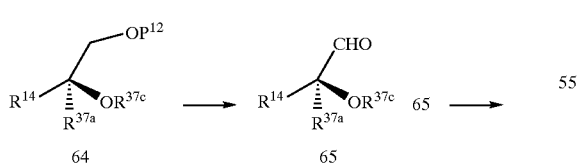
64     65
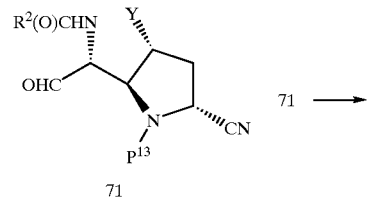
71
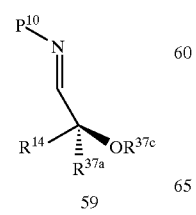
59
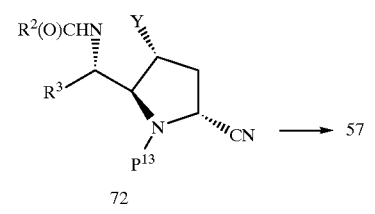
72

-continued

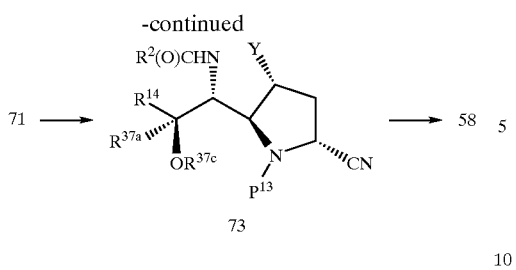

73

→ 58

-continued

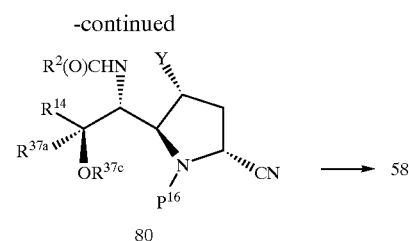

80

→ 58

SCHEME 9

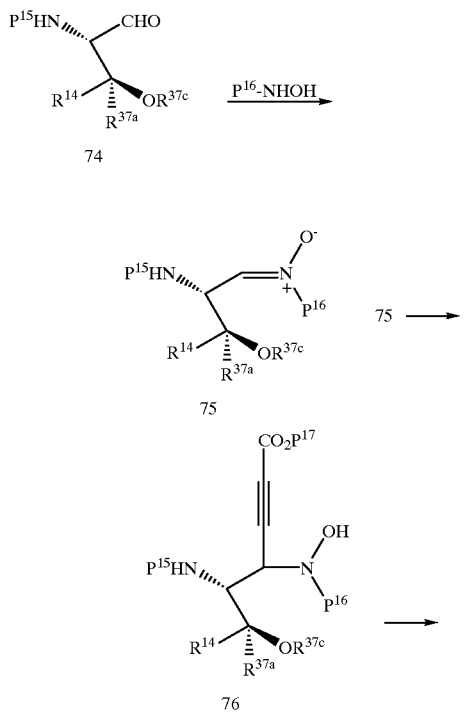

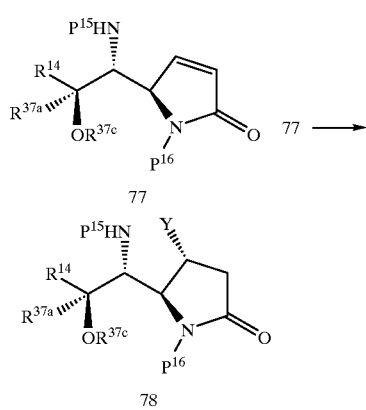

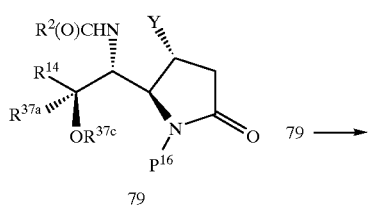

SCHEME 10

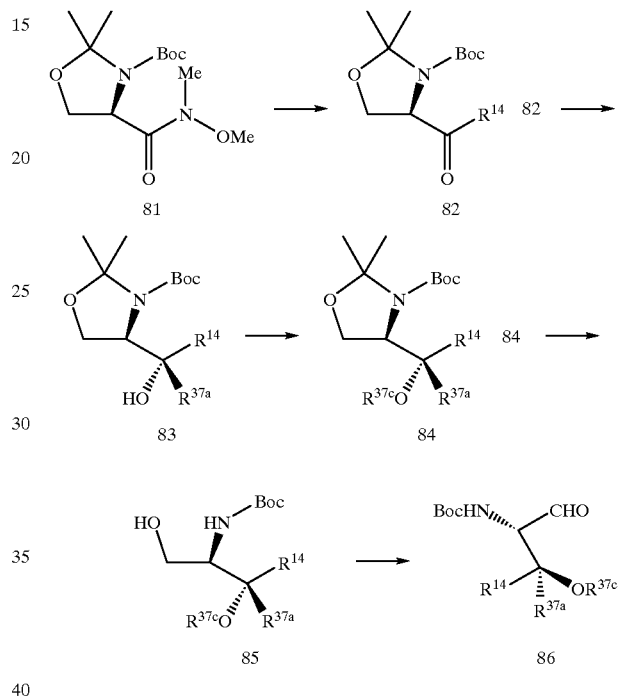

The other compounds of the invention can be readily prepared from the compounds described herein using techniques known in the chemical literature. The methods required are known and can be readily practiced by those having ordinary skill in the art.

Key intermediates for the preparation of compounds of the invention include the following:

(1)

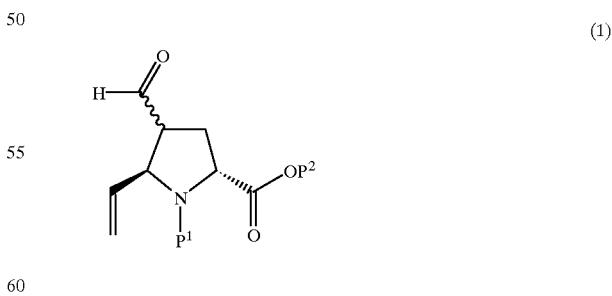

wherein $P^1$ is an N-protecting group (preferably, a benzyl group or a substituted benzyl group) and $P^2$ is a carboxylic acid protecting group (preferably, a loweralkyl group, especially t-butyl); preferably, $P^1$ and $P^2$ can be selectively deprotected/removed; or a salt thereof;

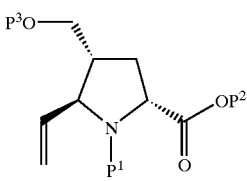

(2)

wherein $P^1$ is an N-protecting group (preferably, a benzyl group or a substituted benzyl group) and $P^2$ is a carboxylic acid protecting group (preferably, a loweralkyl group, especially t-butyl); and $P^3$ is hydrogen or a hydroxy protecting group (preferably, an acyl protecting group, for example, acetyl and the like, or a silyl protecting group, for example, t-butyldimethylsilyl and the like); preferrably, $P^1$, $P^2$ and $P^3$ can be selectively deprotected/removed; or a salt thereof;

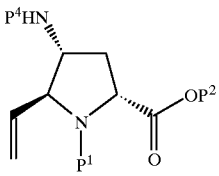

(3)

wherein $P^1$ is an N-protecting group (preferably, a benzyl group or a substituted benzyl group) and $P^2$ is a carboxylic acid protecting group (preferably, a loweralkyl group, especially t-butyl); and $P^4$ is hydrogen or an N-protecting group (preferably, a carbamate N-protecting group, for example, benzyloxycarbonyl and the like); preferrably, $P^1$, $P^2$ and $P^4$ can be selectively deprotected/removed; or a salt thereof;

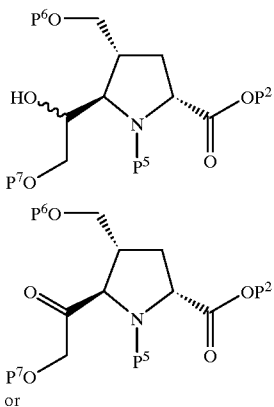

(4)

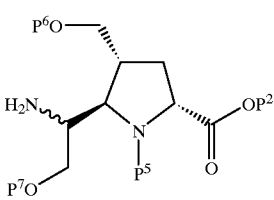

wherein $P^5$ is an N-protecting group (preferably, an acid labile N-protecting group, such as t-butyloxycarbonyl and the like) and $P^2$ is a carboxylic acid protecting group (preferably, a loweralkyl group, especially t-butyl); and $P^6$ is hydrogen or a hydroxy protecting group (preferably, a base labile hydroxy protecting group, such as acetyl and the like); and $P^7$ is hydroxy protecting group (preferably, a silyl protecting group, such as triisopropylsilyl and the like); preferrably, $P^2$, $P^5$, $P^6$ and $P^7$ can be selectively deprotected/removed; or a salt thereof; and

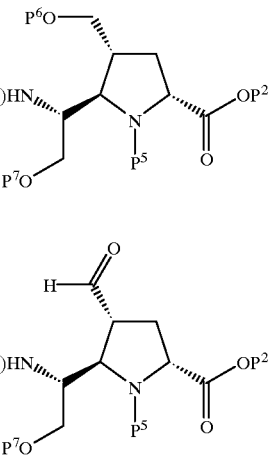

(5)

or wherein $P^5$ is an N-protecting group (preferably, an acid labile N-protecting group, such as t-butyloxycarbonyl and the like) and $P^2$ is a carboxylic acid protecting group (preferably, a loweralkyl group, especially t-butyl); and $P^6$ is hydrogen or a hydroxy protecting group (preferably, a base labile hydroxy protecting group, such as acetyl and the like); and $P^7$ is hydroxy protecting group (preferably, a silyl protecting group, such as triisopropylsilyl and the like); and $R^2$ is defined as herein (preferably, loweralkyl or haloloweralkyl; most preferably, methyl or trifluoromethyl); preferrably, $P^2$, $P^5$, $P^6$ and $P^7$ can be selectively deprotected/removed; or a salt thereof.

Other key intermediates for the preparation of compounds of the invention include compounds, including mixtures of compounds having the indicated relative stereochemistry or enantiomerically enriched compounds having the indicated absolute stereochemistry, of the formula (6)–(17).

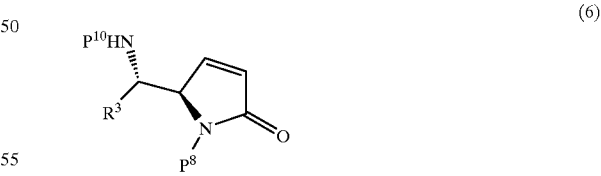

(6)

wherein $P^8$ is an N-protecting group (including, t-butyloxycarbonyl or the like), $P^{10}$ is an N-protecting group (including, p-toluenesulfinyl (—S(O)Tol), t-butylsulfinyl (—S(O)-t-Bu), tritylsulfenyl ((Ph)$_3$C—S—), phenylsulfenyl (Ph—S—), p-methoxyphenyl, p-methoxybenzyl or the like) and $R^3$ is defined as above (both in terms of its broadest definition and in terms of each of the preferred embodiments); or a salt thereof. In addition, any functional groups in substituent $R^3$ can be suitably protected. Most highly preferred is substituent $R^3$ of the formula:

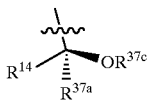

wherein $R^{37a}$, $R^{37c}$ and $R^{14}$ are as defined above (both in terms of their broadest definitions and in terms of each of their preferred embodiments). Especially preferred are compounds wherein $R^{37a}$ is loweralkyl or loweralkenyl, $R^{37c}$ is hydrogen, $C_1$–$C_3$ loweralkyl or allyl and $R^{14}$ is loweralkyl, loweralkenyl or alkoxy-substituted loweralkyl. In those cases where $R^{37c}$ is hydrogen, the hydroxy group can be protected with a hydroxy protecting group. Preferably, $P^8$ and $P^{10}$ can be selectively deprotected/removed.

(7)

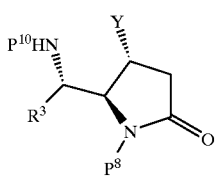

wherein $P^8$, $P^{10}$ and $R^3$ are defined as in (6) above and wherein Y is defined as above (both in terms of its broadest definition and in terms of each of the preferred embodiments); or a salt thereof.

(8)

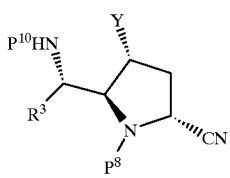

wherein $P^8$, $P^{10}$, $R^3$ and Y are defined as in (7) above; or a salt thereof.

(9)

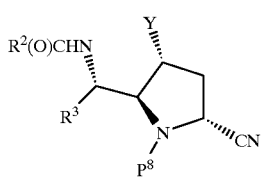

wherein $P^8$, $R^3$ and Y are defined as in (7) above and $R^2$ is defined as above (both in terms of its broadest definition and in terms of each of the preferred embodiments); or a salt thereof.

(10)

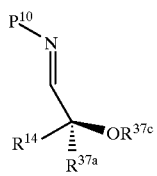

wherein $P^{10}$, $R^{14}$, $R^{37a}$ and $R^{37c}$ are as defined in (6) above; or a salt thereof.

(11)

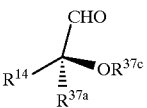

wherein $R^{14}$, $R^{37a}$ and $R^{37c}$ are as defined in (6) above; or a salt thereof.

(12)

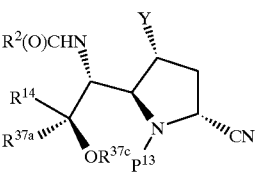

wherein $R^{14}$, $R^{37a}$ and $R^{37c}$ are as defined in (6) above, $R^2$ is as defined in (9) above and $P^{13}$ is an N-protecting group (including, t-butyloxycarbonyl or the like); or a salt thereof.

(13)

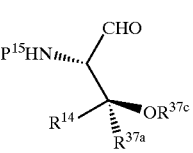

wherein $R^{14}$, $R^{37a}$ and $R^{37c}$ are as defined in (6) above and $P^{15}$ is an N-protecting group (including, t-butyloxycarbonyl or the like); or a salt thereof.

(14)

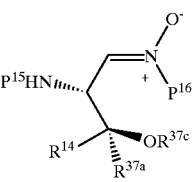

wherein $R^{14}$, $R^{37a}$, $R^{37c}$ and $P^{15}$ are as defined in (13) above and $P^{16}$ is an N-protecting group (including, p-methoxybenzyl or the like); or a salt thereof. Preferably, $P^{15}$ and $P^{16}$ can be selectively deprotected/removed.

(15)

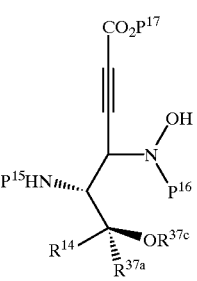

wherein $R^{14}$, $R^{37a}$, $R^{37c}$, $P^{15}$ and $P^{16}$ are as defined in (14) above and $P^{17}$ is an acid protecting group (including, methyl or t-butyl or the like); or a salt thereof.

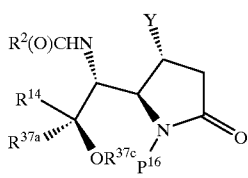

(16)

wherein $R^{14}$, $R^{37a}$, $R^{37c}$ and $P^{16}$ are as defined in (14) above and $R^2$ is as defined in (9) above; or a salt thereof.

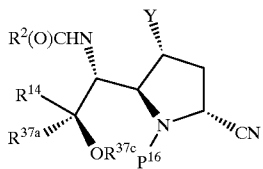

(17)

wherein $R^{14}$, $R^{37a}$, $R^{37c}$, $P^{16}$ and $R^2$ are as defined in (16) above; or a salt thereof.

The reagents required for the synthesis of the compounds of the invention are readily available from a number of commercial sources such as Aldrich Chemical Co. (Milwaukee, Wis., USA); Sigma Chemical Co. (St. Louis, Mo., USA); and Fluka Chemical Corp. (Ronkonkoma, N.Y., USA); Alfa Aesar (Ward Hill, Mass. 01835-9953); Eastman Chemical Company (Rochester, N.Y. 14652-3512); Lancaster Synthesis Inc. (Windham, N.H. 03087-9977); Spectrum Chemical Manufacturing Corp. (Janssen Chemical) (New Brunswick, N.J. 08901); Pfaltz and Bauer (Waterbury, Conn. 06708). Compounds which are not commercially available can be prepared by employing known methods from the chemical literature.

The following examples will serve to further illustrate the preparation of the compounds of the invention, without limitation.

EXAMPLE 1

(±)-(2R,3R,5R,1'S)-2-(1-Acetamido-3-ethyl)pentyl-3-(methoxymethyl)-pyrrolidine-5-carboxylic Acid Hydrochloride

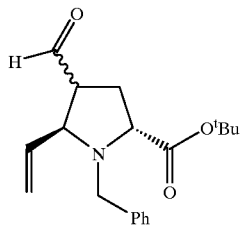

1A. (±)-(2S,3R,5R)- and (±)-(2S,3S,5R)-1-Benzyl-2-vinyl-3-formyl-pyrrolidine-5-carboxylic Acid t-Butyl Ester (8:1 ratio)

Acrolein (8 mL, 120 mmole) was added to a solution of t-butyl N-benzyl-glycinate (4.34 g, 19.6 mmole) and acetic acid (5 drops) in toluene (100 mL). The solution was heated at reflux. After 1 hour, the reaction was cooled to about 50° C. and an additional 3 mL of acrolein were added. The reaction was heated at reflux for an additional 2 hours and concentrated in vacuo. The residue was purified by chromatography on silica gel using 5% ethyl acetate/hexanes to provide a mixture of (±)-(2S,3R,5R)- and (±)-(2S,3S,5R)-1-benzyl-2-vinyl-3-formyl-pyrrolidine-5-carboxylic acid t-butyl esters as an oil (yield: 2.78 g, 45%). The mixture of aldehydes was equilibrated to an 8:1 ratio by stirring the crude product with triethylamine (0.5 mL) in ethyl acetate at room temperature followed by evaporation of the solvents.

$^1$H NMR (CDCl$_3$)(major isomer only): δ1.45 (s, 9H), 2.26 (m, 1H), 2.69 (m, 1H), 3.49 (dd, J=7.8, 3.0 Hz, 1H), 3.61 (d, J=13.5 Hz, 1H), 3.93 (m, 1H), 3.94 (d, J=13.5 Hz, 1H), 5.22–5.33 (two dd, 2H), 5.7 (ddd, J=17.7, 10.2, 7.8 Hz, 1H), 7.21–7.35 (m, 5H), 9.71 (d, J=1.2 Hz, 1H).

MS (M+H)$^+$=316.

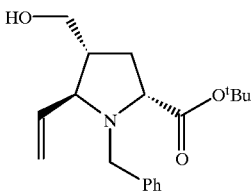

1B. (±)-(2S,3R,5R)-1-Benzyl-2-vinyl-3-(hydroxymethyl)-pyrrolidine-5-carboxylic Acid t-Butyl Ester A solution of the 8:1 mixture of (±)-(2S,3R,5R)- and (±)-(2S,3S,5R)-1-benzyl-2-vinyl-3-formylpyrrolidine-5-carboxylic acid t-butyl ester (6.0 g, 19.0 mmole), prepared according to the method described in Example 1A, in 100 mL of methanol was cooled to 0° C. and treated with sodium borohydride (0.72 g, 19.0 mmole). The mixture was stirred for 0.5 hour, warmed to room temperature, and stirred for an additional 1 hour. The reaction was quenched with aqueous ammonium chloride, and the solvent was evaporated. The residue was partiationed between ethyl acetate and water. The organic layer was dried over MgSO$_4$, filtered and concentrated in vacuo. The residual oil was purified by chromatography on silica gel using a gradient of 20–30% ethyl acetate/hexanes to furnish the title compound as a colorless oil (yield; 4.0 g, 66%).

$^1$H NMR (CDCl$_3$): δ1.46 (s, 9H), 1.80 (m, 1H), 2.16 (m, 1H), 2.39 (m, 1H), 2.54 (m, 1H), 3.48–3.53 (m, 2H), 3.08 (d, 2H), 3.91 (d, 2H), 5.17–5.22 (m, 2H), 5.70 (m, 1H), 7.23–7.34 (m, 5H).

MS (M+H)$^+$=318.

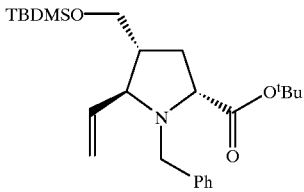

1C. (±)-(2S,3R,5R)-1-Benzyl-2-vinyl-3-(t-butyldimethylsilyloxymethyl)-pyrrolidine-5-carboxylic Acid t-Butyl Ester A solution of (±)-(2S,3R,5R)-1-benzyl-2-vinyl-3-(hydroxymethyl)-pyrrolidine-5-carboxylic acid t-butyl ester (3.6 g, 11.4 mmole), tert-butyldimethylsilyl chloride (3.7 g, 24.5 mmole) and imidazole (2.8 g, 41.2 mmole) in 60 mL of DMF was stirred at room temperature for 1.5 hours. The reaction was diluted with ethyl acetate, washed with water and brine, dried over MgSO₄, and concentrated in vacuo. The residue was purified by chromatography on silica gel using 5% ethyl acetate/hexanes to provide the title compound, as a colorless oil (yield: 3.5 g, 71%).

¹H NMR (CDCl₃): δ0.02 (d, 6H), 0.86 (s, 9H), 1.43 (s, 9H), 1.67(ddd, 1H), 2.11 (m, 1H), 2.28 (m, 1H), 3.40–3.70 (m, 6H), 3.90 (d, 2H), 5.11–5.19 (m, 2H), 5.69 (ddd, 1H), 7.20–7.30 (m, 5H).

MS (M+H)⁺=432.

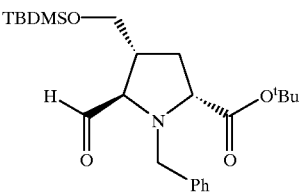

1D. (±)-(2R,3R,5R)-1-Benzyl-2-formyl-3-(t-butyldimethylsilyloxymethyl)-pyrrolidine-5-carboxylic Acid t-Butyl Ester Osmium tetroxide (20 mg) was added to a room temperature solution of (±)-(2S,3R,5R)-1-benzyl-2-vinyl-3-(t-butyldimethylsilyloxymethyl)-pyrrolidine-5 -carboxylic acid t-butyl ester (3.5 g, 8.12 mmole) in 60 mL of 8:1 acetone/water and N-methylmorpholine N-oxide (3.0 g, 25.6 mmole). The reaction mixture was stirred at room temperature for 6 hours and quenched with saturated aqueous Na₂S₂O₃. The mixture was stirred for an additional 10 minutes and the solvent removed. The brownish residue was partitioned between dichloromethane and water. The organic layer was dried over MgSO₄ and concentrated in vacuo to provide the intermediate diol as an oil (~3.8 g ) which was used without additional purification.

MS (crude): (M+H)⁺=466

The crude diol was dissolved in 6:1 tetrahydrofuran (THF)/water (50 mL) and treated with sodium periodate (3.0 g, 14.0 mmole). The mixture was stirred at room temperature for 1 hour and diluted with ethyl acetate, washed with water, dried over MgSO₄, filtered, and concentrated in vacuo. The crude aldehyde was purified by chromatography on silica gel using 3% ethyl acetate/hexanes to provide the title compound as a colorless oil (yield: 1.6 g, 46%).

¹H NMR (CDCl₃): δ0.03 (d, 6H), 0.86 (s, 9H), 1.46 (s, 9H), 1.72 (m, 1H), 2.26–2.45 (m, 2H), 3.53–3.71 (m, 5H), 3.84 (d, 1H), 3.93 (d, 1H), 7.27–7.3 (m, 5H), 9.32 (d, 1H).

MS (M+H)⁺=434.

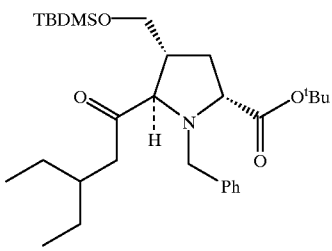

1E. (±)-(2R,3R,5R)-1-Benzyl-2-(1-oxo-3-ethyl)pentyl-3-(t-butyldimethylsilyloxy-methyl)-pyrrolidine-5-carboxylic Acid t-Butyl Ester A dry flask containing magnesium (0.14 g, 5.83 mmole), under argon, was charged with 10 mL of dry THF and 3 drops of dibromoethane. This was followed by addition of 1-bromo-2-ethylbutane (0.95 g, 5.83 mmole). The reaction mixture was heated at reflux for 45 minutes, until most of the magnesium had reacted. The reaction mixture was cooled to −30° C. and (±)-(2R,3R,5R)-1-benzyl-2-formyl-3-(t-butyldimethylsilyloxymethyl)-pyrrolidine-5-carboxylic acid t-butyl ester (0.5 g, 1.15 mmole) in of THF (6 mL) was added, dropwise. The reaction was slowly warmed to −10° C., over a period of about 2 hours, and quenched with aqueous ammonium chloride. The resultant slurry was diluted with ethyl acetate and washed with water, brine, and dried over MgSO₄ and concentrated. The crude alcohol product, an oil (~0.85 g), was used without further purification.

MS (M+H)⁺=520.

A solution of oxalyl chloride (2.5 mL, 2M in CH₂Cl₂) in 10 mL of anhydrous dichloromethane was prepared and maintained under a nitrogen atmosphere, at −78° C. DMSO (0.77 mL, 9.83 mmole) was added slowly to the solution. The mixture was stirred for 15 minutes and treated with the crude alcohol prepared above, about 0.85 g, in 5 mL of anhydrous dichloromethane. The solution was stirred for 1 hour and triethylamine (2.3 mL, 16.4 mmole) was added slowly to the reaction mixture. The solution was then allowed to slowly warmed to room temperature and diluted with dichloromethane. The organic layer was washed with water, dried over MgSO₄, and concentrated. The residue was purified by chromatography on silica gel using 3% ethyl acetate/hexanes to provide the title compound, as an oil (yield: 0.35 g, 66%).

MS (M+H)⁺=518.

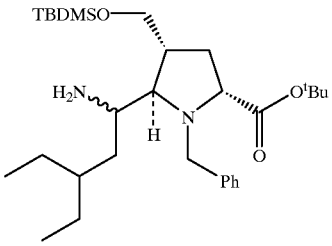

1F. (±)-(2R,3R,5R,1'R)- and (+)-(2R,3R,5R,1'S)-1-Benzyl-2-(1-amino-3-ethyl)-pentyl-3-(t-butyldimethylsilyloxymethyl)-pyrrolidine-5-carboxylic Acid t-Butyl Ester A solution of (±)-(2R,3R,5R)-1-benzyl-2-(1-oxo-3-ethyl)pentyl-3-(t-butyl-dimethylsilyloxymethyl)-pyrrolidine-5-carboxylic acid t-butyl ester (0.20 g, 0.39 mmole), ammonium acetate (30 equiv.) and sodium cyanoborohydride (10 equiv.) in 5 mL of methanol was heated at reflux for 24 hours with occasional addition of an additional 60 equivalents of ammonium acetate and 20 equivalents of sodium cyanoborohydride. The solvent was evaporated. The resultant residue was partitioned between dichloromethane and water. The organic layer was dried over MgSO₄, filtered, and concentrated. The product was purified by chromatography on silica gel using 30–50% ethyl acetate/hexanes to provide the title compound as a colorless oil (yield: 130 mg, 64%).

¹H NMR (CDCl₃) δ7.30 (m, 5H), 4.91 (s, 1H), 3.53(m, 2H), 3.08 (m, 1H), 2.88 (m, 1H), 2.35 (m, 1H), 1.85 (m, 1H), 1.44 (s, 9H), 1.20–1.40 (m, 7H), 0.88 (s, 9H), 0.85 (m, 6H), 0.03 (s, 6H)

MS (M+H)⁺=519.

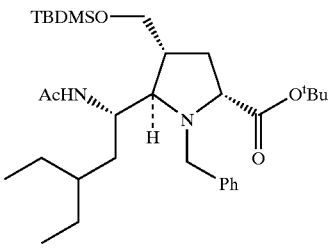

1G. (±)-(2R,3R,5R,1'S)-1-Benzyl-2-(1-acetamido-3-ethyl)pentyl-3-(t-butyl-dimethylsilyloxymethyl)-pyrrolidine-5-carboxylic Acid t-Butyl Ester A solution of (±)-(2R,3R,5R,1'R)- and (±)-(2R,3R,5R,1'S)-1-benzyl-2-(1-amino-3-ethyl)pentyl-3-(t-butyldimethylsilyloxymethyl)-pyrrolidine-5-carboxylic acid t-butyl ester (110 mg, 0.21 mmole) and acetic anhydride (214 mg, 2.1 mmole) in 10 mL of dichloromethane was stirred for 1 hour. The solvent and excess acetic anhydride were removed in vacuo. The residue was purified by chromatography on silica gel using 30% ethyl acetate/hexanes to provide the title compound as a white solid (yield: 85 mg, 72%).

$^1$H NMR (CDCl$_3$) δ7.28 (m, 5H), 5.14 (d, J=14 Hz, 1H), 4.36 (m, 1H), 3.95 (m, 2H), 3.62 (m, 1H), 3.52 (m, 1H), 3.45 (m, 1H), 2.98 (m, 1H), 1.98 (s, 3H), 1.60 (m, 2H), 1.43 (s, 9H), 1.20–1.40 (m, 7H), 0.88 (s, 9H), 0.80 (m, 6H), 0.04 (s, 6H)

MS (M+H)$^+$=561.

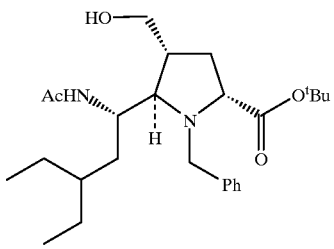

1H. (±)-(2R,3R,5R,1'S)-1-Benzyl-2-(1-acetamido-3-ethyl)pentyl-3-(hydroxy-methyl)-pyrrolidine-5-carboxylic Acid t-Butyl Ester A solution of (±)-(2R,3R,5R,1'S)-1-benzyl-2-(1-amino-3-ethyl)pentyl-3-(t-butyldimethylsilyloxymethyl)-pyrrolidine-5-carboxylic acid t-butyl ester (85 mg, 0.15 mmole) in dry THF (5 mL) was prepared and maintained at room temperature under a nitrogen atmosphere. Tetrabutylammonium fluoride (1M in THF, 0.23 mL) was added slowly to the solution. The reaction mixture was stirred for 1 hour. The solvent was removed in vacuo and the residue purified by chromatography on silica gel using 30–50% ethyl acetate/hexanes to provide the title compound as a white foam (yield: 41 mg, 61%).

$^1$H NMR (CDCl$_3$) δ7.20–7.35 (m, 5H), 5.20 (d, J=14 Hz, 1H), 4.28 (m 1H), 4.93 (m, 2H), 3.65 (m, 2H), 3.50 (m, 1H), 3.23 (m, 2H), 2.22 (m, 2H), 1.98 (s, 3H), 1.62 (m, 1H), 1.43 (s, 9H), 1.15–1.40 (m, 7H), 0.80 (m, 6H)

MS (M+H)$^+$=447.

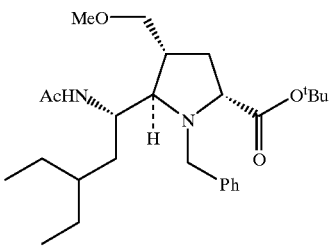

1I. (±)-(2R,3R,5R,1'S)-1-Benzyl-2-(1-acetamido-3-ethyl)pentyl-3-(methoxy-methyl)-pyrrolidine-5-carboxylic Acid t-Butyl Ester A mixture of (±)-(2R,3R,5R,1'S)-1-benzyl-2-(1-aetamido-3-ethyl)pentyl-3-(hydroxymethyl)-pyrrolidine-5-carboxylic acid t-butyl ester (40 mg, 0.09 mmole) and silver oxide (200 mg, 0.90 mmole) in 3 mL of iodomethane was heated at reflux for three hours. The reaction was cooled, filtered, and the solvent was removed in vacuo, to provide the title product as a crude oil.

MS (M+H)$^+$=461.

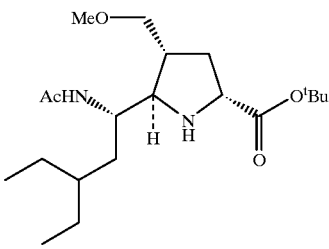

1J. (±)-(2R,3R,5R,1'S)-2-(1-Acetamido-3-ethyl)pentyl-3-(methoxymethyl)-pyrrolidine-5-carboxylic Acid t-Butyl Ester A mixture of the crude (±)-(2R,3R,5R,1'S)-1-benzyl-2-(1-acetamido-3-ethyl)pentyl-3-(methoxymethyl-pyrrolidine-5-carboxylic acid t-butyl ester (32 mg, 0.07 mmole), prepared according to the method described in Example 1I, and ammonium formate (130 mg, 2.1 mmole) in ethanol (5 mL) was heated at reflux in the presence of a catalytic amount of 10% palladium, on activated carbon, for 1.5 hours. The reaction was filtered and concentrated in vacuo. The residue was purified by chromatography on silica gel using 50% ethyl acetate/hexanes followed by 10% methanol/dichloromethane to provide the title compound as a colorless oil (yield: 16 mg, 47%).

MS (M+H)$^+$=371.

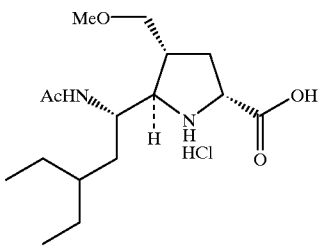

1K. (±)-(2R,3R,5R,1'S)-2-(1-Acetamido-3-ethyl) pentyl-3-(methoxymethyl)-pyrrolidine-5-carboxylic Acid Hydrochloride A solution of the (±)-(2R,3R,5R,1'S)-2-(1-acetamido-3-ethyl)pentyl-3-(methoxymethyl)-pyrrolidine-5-carboxylic acid t-butyl ester (15 mg) was dissolved in 6 N HCl in water (1 mL) and stirred at room temperature for 3 hours. The solvent was removed under high vacuum to provide the title compound as a white solid.

$^1$H NMR($d_6$-DMSO) δ8.10 (d, J=14 Hz, 1H), 4.28 (m, 1H), 4.18 (m,1H), 3.45 (m, 1H), 3.22 (s, 3H), 2.47 (m, 1H), 2.38(m, 1H), 1.90 (m, 1H), 1.88 (s, 3H), 1.15–1.42 (m, 7H), 0.82 (t, J=12.5 Hz, 3H), 0.79 (t, J=12.5 Hz, 3H)

MS (M+H)$^+$=315, (M−H)$^−$=313.

EXAMPLE 2

(±)-(2R,3R,5R,1'S)-2-(1-Acetamido-3-ethyl)pentyl-3-methoxycarbonyl-pyrrolidine-5-carboxylic Acid Hydrochloride

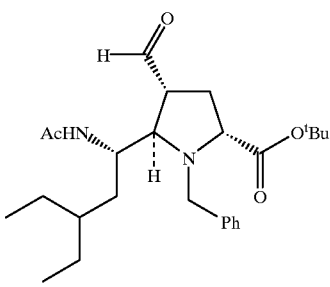

2A. (±)-(2R,3R,5R,1'S)-1-Benzyl-2-(1-acetamido-3-ethyl)pentyl-3-formyl-pyrrolidine-5-carboxylic Acid t-Butyl Ester A solution of oxalyl chloride (0.11 mL, 2M in CH$_2$Cl$_2$) in 5 mL of anhydrous dichloromethane was prepared and maintained, under a nitrogen atmosphere, at −78° C. DMSO (32 mg, 0.42 mmole) was added slowly to the solution. The mixture was stirred for 15 minutes and treated with (±)-(2R,3R,5R,1'S)-1-benzyl-2-(1-acetamido-3-ethyl)pentyl-3-hydroxymethyl-pyrrolidine-5-carboxylic acid t-butyl ester (38 mg, 0.085 mmole) in 5 mL of dichloromethane. The solution was stirred for 1 hour and triethylamine (86 mg, 0.85 mmole) was added slowly to the reaction mixture. The solution was allowed to warm to room temperature and diluted with dichloromethane. The organic layer was washed with water and brine, dried over MgSO$_4$, filtered and concentrated. The residue was purified by chromatography on silica gel using 3% ethyl acetate/hexanes to provide the title compound as a colorless oil (yield: 39 mg, 97%).

$^1$H NMR (CDCl$_3$) δ9.68 (d,J=1.0 Hz, 1H), 7.28 (m,5H), 5.06 (d, J=14 Hz, 1H), 4.38 (m, 1H), 4.10 (m, 1H), 3.75 (m, 2H), 3.45 (m, 1H), 2.62 (m, 1H), 2.20 (m, 2H), 1.98 (s, 3H), 1.42 (g, 9H), 1.25–1.40 (m, 7H), 0.82 (m, 6H)

MS (M+H)$^+$=445.

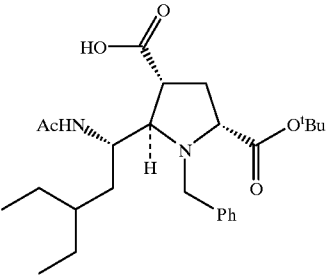

2B. (±)-(2R,3R,5R,1'S)-1-Benzyl-2-(1-acetamido-3-ethyl)pentyl-3-carboxyl-pyrrolidine-5-carboxylic Acid t-Butyl Ester A solution of NaClO$_2$ (0.16 g) and NaH$_2$PO$_4$.H$_2$O (0.17 g) in water (1 mL) was added to a solution of (±)-(2R,3R,5R,1'S)-1-benzyl-2-(1-acetamido-3-ethyl)pentyl-3-formyl-pyrrolidine-5-carboxylic acid t-butyl ester (35 mg, 0.079 mmole) and 2-methyl-2-butene (0.5 mL) dissolved in t-BuOH (1.5 mL) and acetonitrile (1.5 mL) at 0° C. After 1 hour the reaction was quenched with 10% aqueous Na$_2$S$_2$O$_3$ and extracted with dichloromethane. The organic layer was washed with water and brine, dried (MgSO$_4$) and concentrated to provide the title product (yield: ~30 mg).

MS (M+H)$^+$=461.

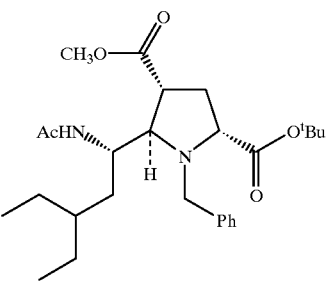

2C. (±)-(2R,3R,5R,1'S)-1-Benzyl-2-(1-acetamido-3-ethyl)pentyl-3-methoxycarbonyl-pyrrolidine-5-carboxylic Acid t-Butyl Ester A solution of Diazald™ (0.5 g, 2.33 mmole) in 5 mL of ether was added slowly to a solution of aqueous KOH (0.5 g in 1 mL of water) and 1 mL of ethanol maintained at 65° C. Diazomethane was distilled into a receiving flask charged with a solution of (±)-(2R,3R,5R,1'S)-1-benzyl-2-(1-acetamido-3-ethyl)pentyl-3-carboxyl-pyrrolidine-5-carboxylic acid t-butyl ester (30 mg, 0.065 mmole) in 3 mL of THF. The receiving flask was cooled to 0° C. in an ice/water bath. The condenser was cooled with dry ice/acetone and 3 mL of ether was added the distilling flask until the distillate was colorless. The reaction was stirred for an additional 0.5 hours at 0° C. The yellowish reaction mixture was quenched with acetic acid (0.1 mL) and diluted with ethyl acetate. The organic layer was washed with 10% NaHCO$_3$ and brine, dried with MgSO$_4$ and concentrated in vacuo. The residue was purified by chromatography on silica gel using 50% ethyl acetate/hexanes to provide the title compound as a colorless oil (yield: 20 mg, 65%).

¹H NMR (CDCl₃) δ7.25 (m, 5H), 5.10 (d, J=14 Hz, 1H), 4.23 (m, 1H), 4.08 (m,1H), 3.85 (m, 1H), 3.72 (m, 1H), 3.69 (s, 3H), 3.40 (m, 1H), 2.75 (m, 1H), 2.33 (m, 1H), 2.15 (m, 1H), 1.98 (s, 3H), 1.42 (s, 9H), 1.20–1.40 (m, 7H), 0.83 (m, 6H)

MS (M+H)⁺=475.

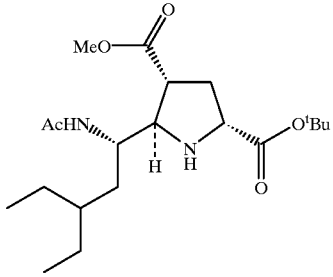

2D. (±)-(2R,3R,5R,1'S)-2-(1-Acetamido-3-ethyl) pentyl-3-methoxycarbonyl-pyrrolidine-5-carboxylic Acid t-Butyl Ester A mixture of (±)-(2R,3R,5R,1'S)-1-benzyl-2-(1-acetamido-3-ethyl)pentyl-3-methoxycarbonyl-pyrrolidine-5-carboxylic acid t-butyl ester (14 mg, 0.03 mmole) and ammonium formate (0.3 g) in ethanol (1.5 mL) with a catalytic amount of 10% palladium on activated carbon was heated at about 75° C., for 1 hour. After filtration to remove the catalyst, the solvent was removed in vacuo. The residue was purified by chromatography on silica gel to provide the title compound as a colorless oil (yield: 8.5 mg, 73%).

MS (M+H)⁺=385.

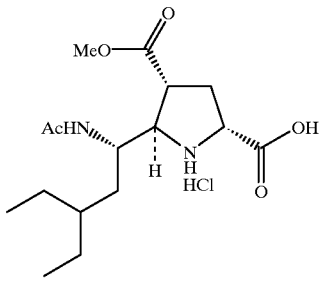

2E. (±)-(2R,3R,5R,1'S)-2-(1-Acetamido-3-ethyl) pentyl-3-methoxycarbonyl-pyrrolidine-5-carboxylic Acid Hydrochloride A solution of (±)-(2R,3R,5R,1'S)-2-(1-acetamido-3-ethyl) pentyl-3-methoxy-carbonylpyrrolidine-5-carboxylic acid t-butyl ester (8.5 mg, 0.022 mmole) in 4 N HCl in dioxane (1 mL) was stirred at room temperature for 24 hours. The solvent was removed in vacuo to provide the title compound as an off-white solid (yield 8 mg, 100%).

¹H NMR (d₆-DMSO) δ8.02 (d, J=14 Hz, 1H), 4.40 (m, 1H), 4.22 (m, 1H), 3.85 (t, J=13 Hz, 1H), 3.70 (m, 1H), 3.65 (s, 3H), 3.15 (m, 1H), 2.55 (m, 1H), 2.20 (m, 1H), 1.84 (s, 3H), 1.12–1.42 (m, 7H), 0.82 (t, J=12.5 Hz, 3H), 0.68 (t, 3H)

MS (M+H)⁺=329, (M–H)⁻=327.

EXAMPLE 3

(±)-(2R,3R,5R,1'S)-2-(1-Acetamido-3-ethyl)Pentyl-3-cyano-pyrrolidine-5-carboxylic Acid Hydrochloride

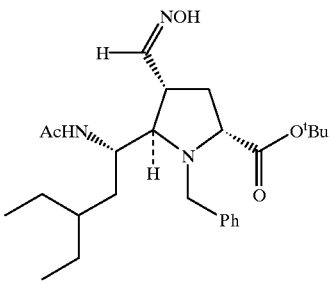

3A. (±)-(2R,3R,5R,1'S)-1-Benzyl-2-(1-acetamido-3-ethyl)pentyl-3-(hydroxyiminoformyl)-pyrrolidine-5-carboxylic Acid t-Butyl Ester The title compound is prepared by reacting a solution of (±)-(2R,3R,5R,1'S)-1-benzyl-2-(1-acetamido-3-ethyl) pentyl-3-formyl-pyrrolidine-5-carboxylic acid t-butyl ester with hydroxylamine hydrochloride and 10% aqueous potassium carbonate in methanol according to the procedure described by Chelucci et al., *Tetrahedron: Asymmetry* 5:1973 (1994).

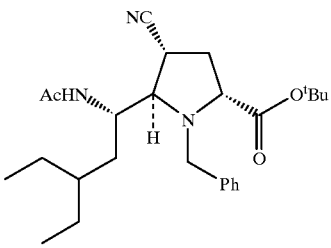

3B. (±)-(2R,3R,5R,1'S)-1-Benzyl-2-(1-acetamido-3-ethyl)pentyl-3-cyano-pyrrolidine-5-carboxylic Acid t-Butyl Ester The title compound is prepared by reacting a solution of (±)-(2R,3R,5R,1'S)-1-benzyl-2-(1-acetamido-3-ethyl) pentyl-3-(hydroxyiminoformyl)-pyrrolidine-5-carboxylic acid t-butyl ester with 1,1'-carbonyldiimidazole in dichloromethane according to the procedure described by Chelucci et al., *Tetrahedron: Asymmetry* 5:1973 (1994).

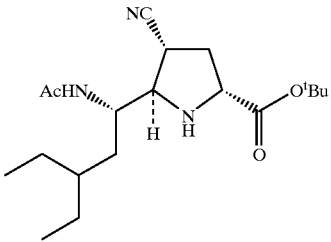

3C. (±)-(2R,3R,5R,1'S)-2-(1-Acetamido-3-ethyl) pentyl-3-cyano-pyrrolidine-5-carboxylic Acid t-Butyl Ester The title compound is prepared according to the method described in Example 1J, substituting (±)-(2R,3R,5R,1'S)-

1-benzyl-2-(1-acetamido-3-ethyl)pentyl-3-cyano-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

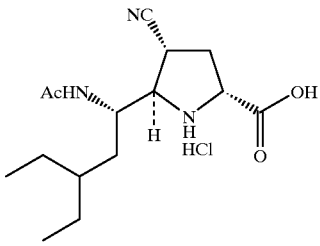

3D. (±)-(2R,3R,5R,1'S)-2-(1-Acetamido-3-ethyl)pentyl-3-cyano-pyrrolidine-5-carboxylic Acid Hydrochloride The title compound is prepared according to the method described in Example 1K, substituting (±)-(2R,3R,5R,1'S)-2-(1-acetamido-3-ethyl)pentyl-3-cyano-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

EXAMPLE 4

(±)-(2R,3R,5R,1'S,)-2-(1-Acetamido-3-ethyl)pentyl-3-propionyl-pyrrolidine-5-carboxylic Acid Hydrochloride

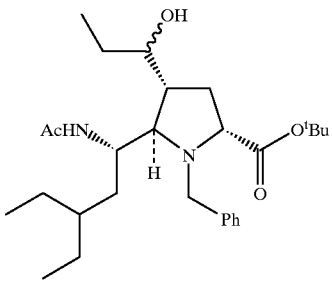

4A. (±)-(2R,3R,5R,1'S,1"R)- and (±)-(2R,3R,5R,1'S,1"S)-1-Benzyl-2-(1-acetamido-3-ethyl)pentyl-3-(1-hydroxy)propyl-pyrrolidine-5-carboxylic Acid t-Butyl Ester Ethyl magnesium bromide (0.070 mL, 3M in ether) was added to a solution of (±)-(2R,3R,5R,1'S)-1-benzyl-2-(1-acetamido-3-ethyl)pentyl-3 -formyl-pyrrolidine-5-carboxylic acid t-butyl ester (18 mg, 0.041 mmole) in 3 mL of tetrahydrofuran. The reaction mixture was maintained at 0° C., and stirred for 1 hour. The reaction wag quenched with aqueous ammonium chloride and partitioned between ethyl acetate and water. The organic layer was dried over MgSO$_4$ filtered and concentrated to provide the title product (crude yield: 20 mg, 100%).

MS (M+H)$^+$=475.

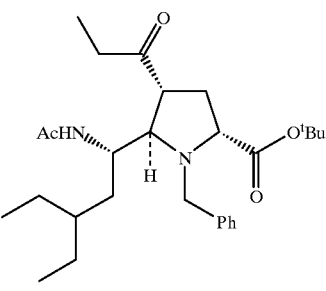

4B. (±)-(2R,3R,5R,1'S)-1-Benzyl-2-(1-acetamido-3-ethyl)pentyl-3-propionyl-pyrrolidine-5-carboxylic Acid t-Butyl Ester The title compound was prepared according to the method described in Example 2A substituting (±)-(2R,3R,5R,1'S,1"R)- and (±)-(2R,3R,5R,1'S,1"S)-1-benzyl-2-(1-acetamido-3-ethyl)pentyl-3-(1-hydroxy)propyl-pyrrolidine-5-carboxylic acid t-butyl ester, 20 mg 0.041 mmole), in place of (±)-(2R,3R,5R,1'S)-1-benzyl-2-(1-acetamido-3-ethyl)pentyl-3-hydroxymethyl-pyrrolidine-5-carboxylic acid t-butyl ester (yield: 11 mg, 56%).

MS (M+H)$^+$=473.

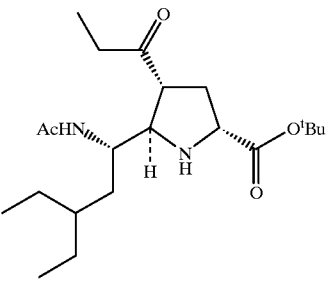

4C. (±)-(2R,3R,5R,1'S,)-2-(1-Acetamido-3-ethyl)pentyl-3-propionyl-pyrrolidine-5-carboxylic Acid t-Butyl Ester A mixture of (±)-(2R,3R,5R,1'S,)-1-benzyl-2-(1-acetamido-3-ethyl)pentyl-3-propionyl-pyrrolidine-5-carboxylic acid t-butyl ester (11 mg, 0.023 mmole), ammonium formate (250 mg) and palladium (15 mg, 10% on carbon) in ethanol (1.5 mL) was heated at 70° C. for 20 minutes. The reaction was filtered, to remove the catalyst and concentrated. The residue was purified by chromatography on silica gel using 5% methanol/chloroform to provide the title compound (yield: 8.5 mg, 95%).

MS (M+H)$^+$=383.

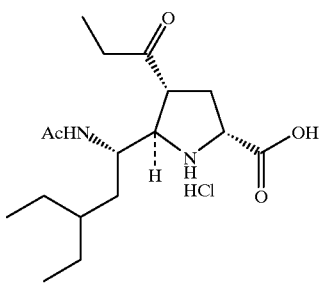

4D. (±)-(2R,3R,5R,1'S,)-2-(1-Acetamido-3-ethyl) pentyl-3-propionyl-pyrrolidine-5-carboxylic Acid Hydrochloride A solution of (±)-(2R,3R,5R,1'S,)-2-(1-acetamido-3-ethyl)pentyl-3-propionyl-pyrrolidine-5-carboxylic acid t-butyl ester (8 mg) was dissolved in 4 N HCl in dioxane (1 mL) and stirred at room temperature for 24 hours. The reaction was concentrated in vacuo to provide the title compound as an off white solid (yield: 8 mg, 100%).

$^1$H NMR (DMSO-d$_6$) δ8.03 (d, J=14 Hz, 1H), 4.41 (m, 1H), 4.20 (m, 1H), 3.92 (m, 1H), 3.68 (m, 1H), 3.46 (m, 1H), 2.65 (m, 2H), 2.00 (m, 1H)1.84 (s, 3H), 1.10–1.35 (m, 9H), 0.95 (t, J=Hz,3H), 0.81 (t, J=12.5 Hz, 3H), 0.75 (t, J=12.5 Hz, 3H)

MS: (M−H)$^-$=325, (M+35)$^+$=361, (2M−H)$^-$=651; (M+H)$^+$=327, (2M+1)$^+$=653, (2M+Na)$^+$=675.

EXAMPLE 5

(±)-(2R,3R,5R,1'S)-2-(1-Acetamido-3-ethyl)pentyl-3-(N-methylcarbamoyl)-pyrrolidine-5-carboxylic Acid Hydrochloride

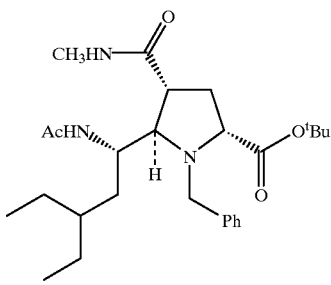

5A. (±)-(2R,3R,5R,1'S)-1-Benzyl-2-(1-acetamido-3-ethyl)pentyl-3-(N-methyl-carbamoyl)pyrrolidine-5-carboxylic Acid t-Butyl Ester A solution of (±)-(2R,3R,5R,1'S)-1-benzyl-2-(1-acetamido-3-ethyl)pentyl-3-carboxyl-pyrrolidine-5-carboxylic acid t-butyl ester (0.175 mmole) and triethylamine (18 mg, 0.175 mmole) in 10 mL THF was cooled in an ice-bath. Isobutylchloroformate (24 mg, 0.175 mmole) was added and stirred for 30 min. Then methylamine (2.0 M in THF, 0.35 mL, 0.70 mmole) was added. The mixture was stirred while allowed to warm up to room temperature overnight. The reaction was then diluted with ethyl acetate. The organic layer was washed with water, and brine, dried over MgSO$_4$, filtered and concentrated in vacuo. The residue was purified by chromatography on silica gel using 5% methanol/methylene chloride to provide the title compound, as an oil (yield: 17.2 mg, 21%).

MS: (M+H)$^+$=474

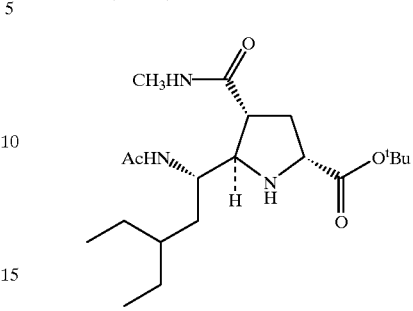

5B. (±)-(2R,3R,5R,1'S)-2-(1-Acetamido-3-ethyl) pentyl-3-(N-methylcarbamoyl)-pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)pentyl-3-(N-methylcarbamoyl)pyrrolidine-5-carboxylic acid t-butyl ester in a place of (±)-(2R,3R,5R,1'S)-1-benzyl-2-(1-acetamido-3-ethyl)pentyl-3-methoxy-methyl-pyrrolidine-5-carboxylic acid t-butyl ester (yield: 13 mg, 94%).

MS: (M+H)$^+$=384

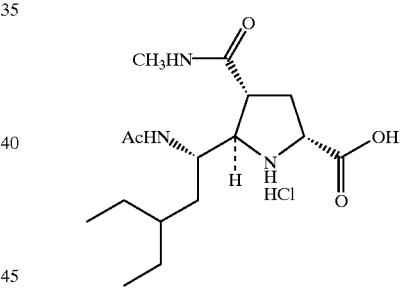

5C. (±)-(2R,3R,5R,1'S)-2-(1-Acetamido-3-ethyl) pentyl-3-(N-methylcarbamoyl)-pyrrolidine-5-carboxylic Acid Hydrochloride The title compound was prepared according to the method described in Example 1K, substituting (±)-(2R,3R,5R,1'S)-2-(1-acetamido-3-ethyl)pentyl-3-(N-methylcarbamoyl)pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (D$_2$O): δ4.43 (t, J=10 Hz, 1H), 4.36 (m, 1H), 4.09 (dd, 1H), 3.08 (q, J=10 Hz, 1H), 2.75 (m, 4H), 2.25 (m, 4H), 2.02 (s, 3H), 1.5–1.15 (br, 7H), 0.80 (m, 6H).

MS: (M+H)$^+$=328.

EXAMPLE 6

(±)-(2R,3R,5R,1'S)-2-(1-Acetamido-3-ethyl)pentyl-
3-(N-aminocarbamoyl)-pyrrolidine-5-carboxylic
Acid Hydrochloride

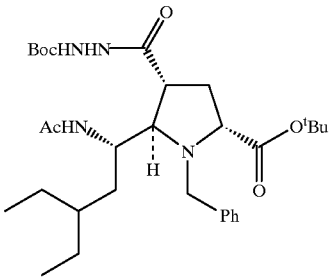

6A. (±)-(2R,3R,5R,1'S)-1-Benzyl-2-(1-acetamido-3-ethyl)pentyl-3-(N-(t-butoxycarbonyl)aminocarbamoyl)-pyrrolidine-5-carboxylic Acid t-Butyl Ester A solution of (±)-(2R,3R,5R,1'S)-1-benzyl-2-(1-acetamido-3-ethyl)pentyl-3-carboxyl-pyrrolidine-5-carboxylic acid t-butyl ester (60 mg, 0.13 mmole), t-butyl carbazate (21 mg, 0.16 mmole), 1-(3-dimethylaminopropyl)-3-ethylcarbodiimide hydrochloride (EDC, 31 mg, 0.16 mmole) and 1-hydroxybenzotriazole (9 mg, 0.065 mmole) in 3 mL anhydrous THF was stirred at room temperature for 6 hours. The reaction was then diluted with ethyl acetate. The organic layer was washed with water and brine, dried over MgSO$_4$, filtered and concentrated in vacuo. The residue was purified by chromatography on silica gel using 2% methanol/methylene chloride to provide the title compound, as an oil (yield: 45.6 mg, 61%).

MS: (M+H)$^+$=575

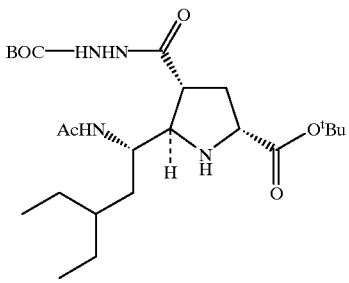

6B. (±)-(2R,3R,5R,1'S)-2-(1-Acetamido-3-ethyl)pentyl-3-(N-(t-butoxycarbonyl)aminocarbamoyl)pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)pentyl-3-(N-(t-butoxycarbonyl)aminocarbamoyl)pyrrolidine-5-carboxylic acid t-butyl ester in place of (±)-(2R,3R,5R,1'S))-1-benzyl-2-(1-acetamido-3-ethyl)pentyl-3-methoxymethyl-pyrrolidine-5-carboxylic acid t-butyl ester (yield: 28 mg, 75%).

MS: (M+H)$^+$=484

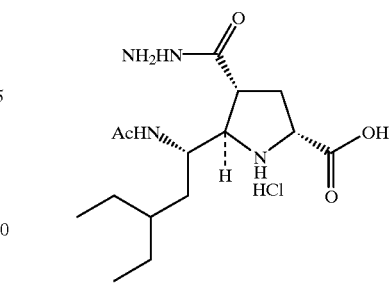

6C. (±)-(2R,3R,5R,1'S)-2-(1-Acetamido-3-ethyl)pentyl-3-(N-aminocarbamoyl)-pyrrolidine-5-carboxylic Acid Hydrochloride The title compound was prepared according to the method described in Example 1K, substituting (±)-(2R,3R,5R,1'S)-2-(1-acetamido-3-ethyl)pentyl-3-(N-(t-butoxycarbonyl)aminocarbamoyl)-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (D$_2$O): δ4.32 (m, 2H), 4.18 (dd, 1H), 3.14 (q, J=8.4 Hz, 1H), 2.75 (m, 1H), 2.26 (m, 1H), 2.01 (s, 3H), 1.50–1.15 (m, 7H), 0.80 (q, J=7.5 Hz, 6H)

MS: (M+H)$^+$=329

EXAMPLE 7

(±)-(2R,3R,5R,1'S)-2-(1-Acetamido-3-ethyl)pentyl-
3-ethoxycarbonyl-pyrrolidine-5-carboxylic Acid
Hydrochloride

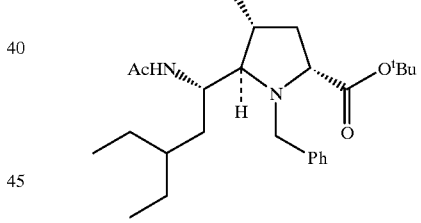

7A. (±)-(2R,3R,5R,1'S)-1-Benzyl-2-(1-acetamido-3-ethyl)pentyl-3-ethoxycarbonyl-pyrrolidine-5-carboxylic Acid t-Butyl Ester A solution of (±)-(2R,3R,5R,1'S)-1-benzyl-2-(1-acetamido-3-ethyl)pentyl-3-carboxyl-pyrrolidine-5-carboxylic acid t-butyl ester (42 mg, 0.091 mmole), ethanol (0.5 mL), 1-(3-dimethylaminopropyl)-3-ethylcarbodiimide hydrochloride (EDC, 36 mg, 0.188 mmole) and 1-hydroxybenzotriazole (7 mg, 0.05 mmole) in 2 mL anhydrous THF was stirred at room temperature overnight. The reaction was then diluted with ethyl acetate. The organic layer was washed with water,and brine, dried over MgSO$_4$, filtered and concentrated in vacuo. The residue was purified by chromatography on silica gel using 2% methanol/methylene chloride to provide the title compound, as an oil (yield: 36 mg, 33%).

$^1$H NMR (CDCl$_3$): δ7.50–7.20 (br, 5H), 5.12 (d, J=9 Hz, 1H), 4.60–4.30 (br, 2H), 4.14 (q, J=6 Hz, 2H), 4.08 (m, 1H), 3.85 (br, 1H), 3.72 (m, 1H), 3.40 (m, 1H), 2.75 (m, 1H), 2.32 (m, 1H), 1.97 (s, 3H), 1.40 (s, 9H), 1.37 (t, J=6 Hz, 3H), 1.20–1.50 (m, 7H), 0.83 (m, 6H).

Mass spectrum: $(M+H)^+=489$

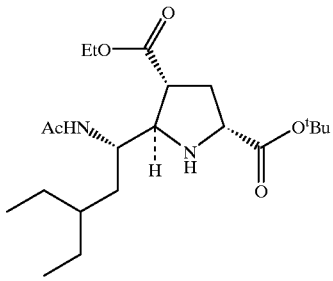

7B. (±)-(2R,3R,5R,1'S)-2-(1-Acetamido-3-ethyl)pentyl-3-ethoxycarbonyl-pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)-pentyl-3-ethoxycarbonyl-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

Mass spectrum: $(M+H)^+=399$.

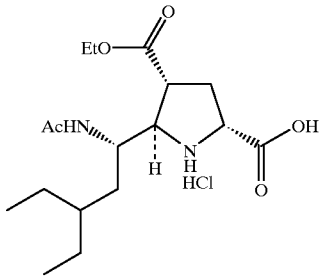

7C. (±)-(2R,3R,5R,1'S)-2-(1-Acetamido-3-ethyl)pentyl-3-ethoxycarbonyl-pyrrolidine-5-carboxylic Acid Hydrochloride The title compound was prepared according to the method described in Example 2E, substituting (±)-(2R,3R,5R,1'S)-2-(1-acetamido-3-ethyl)pentyl-3-ethoxycarbonyl-pyrrolidine-5-carboxylic acid t-butyl ester in place of (±)-(2R,3R,5R,1'S)-2-(1-acetamido-3-ethyl)pentyl-3-methoxycarbonyl-pyrrolidine-5-carboxylic acid t-butyl ester.

$^1$H NMR (D$_2$O): δ4.35 (m, 1H), 4.20 (q, J=7.5 Hz, 2H), 3.87–3.55 (m, 2H), 3.20 (q, J=7.5 Hz, 1H), 2.67 (m, 1H), 2.42 (m, 1H), 2.02 (s, 3H), 1.24 (t, J=7.5 Hz, 3H), 1.54–1.15 (m, 7H), 0.82 (m, 6H).

Mass spectrum: $(M+H)^+=343$, $(M-H)^-=341$.

EXAMPLE 8

(±)-(2R,3R,5R,1'S)-2-(1-Acetamido-3-ethyl)pentyl-3-acetyl-pyrrolidine-5-carboxylic Acid Hydrochloride

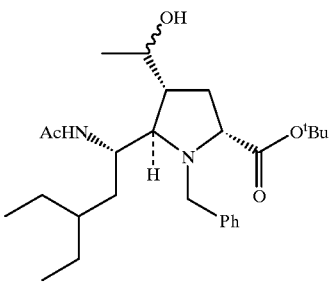

8A. (±)-(2R,3R,5R,1'S,1"R) and (±)-(2R,3R,5R,1'S,1"S)-1-Benzyl-2-(1-acetamido-3-ethyl)pentyl-3-(1-hydroxy)ethyl-pyrrolidine-5-carboxylic Acid t-Butyl Ester The title compound was prepared according to the method described in Example 4A substituting methyl magnesium bromide in place of ethyl magnesium bromide.

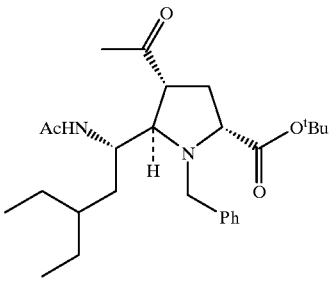

8B (±)-(2R,3R,5R,1'S)-1-Benzyl-2-(1-acetamido-3-ethyl)pentyl-3-acetyl-pyrrolidine-5-carboxylic Acid t-Butyl Ester The title compound was prepared according to the method described in Example 2A, substituting (±)-(2R,3R,5R,1'S,1"R)- and (±)-(2R,3R,5R,1'S,1"S)-1-benzyl-2-(1-acetamido-3-ethyl)pentyl-3-(1-hydroxy)ethyl-pyrrolidine-5-carboxylic acid t-butyl ester, prepared according to the procedure described in Example 8A, in place of (±)-(2R,3R,5R,1'S)-1-benzyl-2-(1-acetamido-3-ethyl)pentyl-3-hydroxy-methyl-pyrrolidine-5-carboxylic acid t-butyl ester.

$^1$H NMR(CDCl$_3$) δ5.00(d, J=9.7 Hz, 1H), 3.94(m, 2H), 3.68(m, 1H), 3.55(m, 1H), 2.64(m, 1H), 2.32(m, 1H), 2.29(s, 3H),2.20(m, 1H), 1.94(s, 3H), 1.43(s, 9H), 1.15–11.35(m, 7H), 0.80(m, 6H).

MS $(M+H)^+=459$

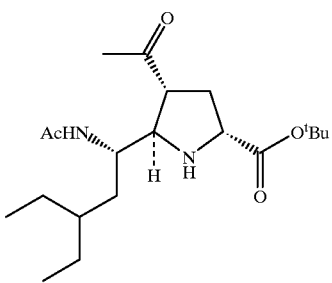

8C. (±)-(2R,3R,5R,1'S)-2-(1-Acetamido-3-ethyl)pentyl-3-acetyl-pyrrolidine-5-carboxylic Acid t-Butyl Ester The title compound is prepared according to the method described in Example 4C, substituting (±)-(2R,3R,5R,1'S)-1-benzyl-2-(1-acetamido-3-ethyl)pentyl-3-acetyl-pyrrolidine-5-carboxylic Acid t-butyl ester, prepared according to the procedure described in Example 8B, in place of (±)-(2R,3R,5R,1'S)-1-benzyl-2-(1-acetamido-3-ethyl)pentyl-3-propionyl-pyrrolidine-5-carboxylic acid t-butyl ester.

MS: (M+H)$^+$=369

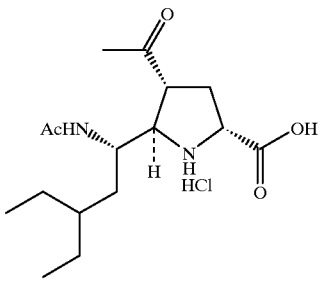

8D. (±)-(2R,3R,5R,1'S)-2-(1-Acetamido-3-ethyl)pentyl-3-acetyl-pyrrolidine-5-carboxylic Acid Hydrochloride The title compound is prepared according to the method described in Example 1K, substituting (±)-(2R,3R,5R,1'S)-2-(1-acetamido-3-ethyl)pentyl-3-acetyl-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR(DMSO-d$_6$) δ8.20(m, 1H), 4.35(m, 1H), 4.15(m, 1H), 4.03(m, 1H), 2.43(m, 1H), 2.03(m, 1H), 1.91 (s, 3H), 1.77(s, 3H), 1.55(m, 1H), 1.46(m, 1H), 1.35(m, 2H), 1.12(m, 4H), 0.84(m, 3H), 0.79(m, 3H)

MS: (M+H)$^+$=314, (M−H)$^-$=312

EXAMPLE 9

(±)-(2S,3R,5R,1'S)-2-(1-Acetamido-3-ethyl)pentyl-3-amino-pyrrolidine-5-carboxylic Acid Dihydrochloride

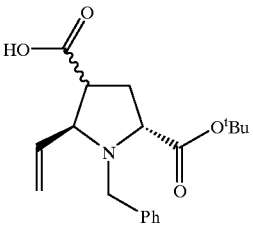

9A. (±)-(2S,3R,5R)- and (±)-(2S,3S,5R)-1-Benzyl-2-vinyl-3-carboxyl-pyrrolidine-5-carboxylic Acid Butyl Ester A solution of (±)-(2S,3R,5R)- and (±)-(2S,3S,5R)-1-benzyl-2-vinyl-3-formyl-pyrrolidine-5-carboxylic acid t-butyl ester (10 g, 31.7 mmole) (8:1 ratio), in 39 mL of ethanol was prepared. The solution was treated with a suspension of silver oxide (8.83 g, 38.1 mmole) and potassium hydroxide (10.86 g, 194 mmole) in 65 mL of water. The reaction was stirred at room temperature for 1 hour and filtered through a pad of Celite®. The ethanol was removed in vacuo. The aqueous solution was acidified with acetic acid to about pH 4. The acidic solution was extracted with ethyl acetate. The organic layer was washed with brine, dried over Na$_2$SO$_4$, filtered and concentrated to provide the title compound as a brownish oil (crude yield: 8.2 g, 77%). The crude acid was used for the next step without further purification.

MS (M+H)$^+$=332, (M−H)$^-$=330.

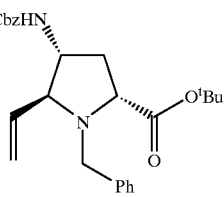

9B. (±)-(2S,3R,5R)-1-Benzyl-2-vinyl-3-benzyloxycarbonylamino-pyrrolidine-5-carboxylic Acid t-Butyl Ester A mixture of (±)-(2S,3R,5R)- and (±)-(2S,3S,5R)-1-benzyl-2-vinyl-3-carboxyl-pyrrolidine-5-carboxylic acid t-butyl ester (1.0 g, 3.02 mmole), diphenylphosphoryl azide (0.83 g, 3.32 mmole), benzyl alcohol (0.36 g, 4.53 mmole) and triethylamine (0.32 g, 3.32 mmole) in 30 mL of toluene was heated at reflux for 16 hours. The solvent was evaporated and the residue was purified by chromatography on silica gel using 10% ethyl acetate/hexanes to provide the title compound as a colorless oil (yield: 0.86 g, 65%).

$^1$H NMR (CDCl$_3$) δ7.20–7.40(m, 10H), 5.70(m, 2H), 5.10–5.23(m, 3H), 4.10(m, 1H), 3.85(m, 1H), 3.62(m, 1H), 3.45(m, 2H), 2.50(m, 1H), 1.70(m, 1H), 1.41 (s, 9H).

MS (M+H)$^+$=437.

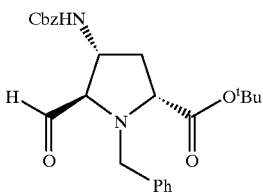

9C. (±)-(2R,3R,5R)-1-Benzyl-2-formyl-3-benzyloxycarbonylamino-pyrrolidine-5-carboxylic Acid t-Butyl Ester Osmium tetroxide (3 crystals) was added to a stirred solution of the (±)-(2S,3R,5R)-1-benzyl-2-vinyl-3-benzyloxycarbonylamino-pyrrolidine-5-carboxylic acid t-butyl ester (1.10 g, 2.52 mmole), N-methylmorpholine N-oxide (0.95 g, 8.07 mmole), in 27 mL of acetone/water (8:1), maintained at room temperature. After 6 hours, 10% aqueous $Na_2S_2O_3$ was added and stirring continued for an additional 15 minutes. The reaction was extracted with dichloromethane and the organic layer was concentrated to provide the crude diol intermediate. The diol product was used in the next step without additional purification.

MS $(M+H)^+$=471.

Sodium periodate (1.0 g, 4.52 mmole) was added in portions to a stirred solution of the crude diol (~1.25 g, 2.66 mmole) in 21 mL of THF/water (6:1). The reaction was stirred for 1 hour then diluted with ethyl acetate. The organic layer was washed with water and brine, dried over $MgSO_4$, filtered and concentrated. The residue was purified by chromatography on silica gel using 15% ethyl acetate/hexanes to provide the title compound as a colorless oil (yield: 0.66 g, 60%).

$^1$H NMR (CDCl$_3$) δ9.44(d, J=1.2 Hz, 1H), 7.20–7.40(m, 10H), 5.98(d, J=14 Hz, 1H), 5.10(m, 2H), 4.45(m, 1H), 3.90(m, 2H), 3.70(m, 1H), 3.60(m, 1H), 2.43(m, 1H), 1.70 (m, 1H), 1.45(s, 9H),

MS $(M+H)^+$=439.

9D. (±)-(2R,3R,5R,1'R)- and (±)-(2R,3R,5R,1'S)-1-Benzyl-2-(1-hydroxy-3-ethyl)pentyl-3-benzyloxycarbonylamino-pyrrolidine-5-carboxylic Acid t-Butyl Ester 1-Bromo-2-ethylbutane (1.7 g, 10.3 mmole) was added a solution of dibromoethane (3 drops) in 15 mL of dry THF, under argon, in a flask charged with magnesium (0.25 g, 10.3 mmole). The reaction mixture was heated at reflux for 45 minutes, until most of the magnesium reacted. The solution was allowed to cool to room temperature and transferred via cannula to a suspension of CuBr.SMe$_2$ (2.12 g, 10.3 mmole) in 15 mL of dry THF, maintained under argon, at −10° C. The mixture was stirred for 0.5 hours until the solution turned dark. A solution of (±)-(2R,3R,5R)-1-benzyl-2-formyl-3-benzyloxycarbonylamino-pyrrolidine-5-carboxylic acid t-butyl ester (0.45 g, 1.03 mmole) in 10 mL of THF was added dropwise and stirred for 1.5 hours, while maintaining the temperature at 0° C. The reaction was quenched with aqueous ammonium chloride, diluted with ethyl acetate, washed with water and brine, dried over MgSO$_4$, filtered and concentrated. The residue was purified by chromatography on silica gel using 10% ethyl acetate/hexanes to provide alcohol adducts as a pale yellow oil (yield: 160 mg, 30%).

$^1$H NMR (CDCl$_3$) δ7.20–7.40(m, 10H), 6.10(d, J=14 Hz, 1H), 5.10(m, 2H), 4.22(m, 1H), 4.01 (m, 1H), 3.71 (m, 1H), 3.65(m, 2H), 3.55(m, 1H), 3.20(m, 1H), 2.00–2.30(m, 2H), 1.45(s 9H), 1.15–1.40(m, 7H), 0.84(m, 6H)

MS $(M+H)^+$=525.

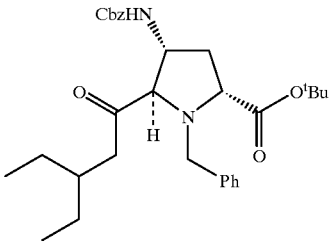

9E. (±)-(2R,3R,5R)-1-Benzyl-2-(1-oxo-3-ethyl)pentyl-3-benzyloxycarbonylamino-pyrrolidine-5-carboxylic Acid t-Butyl Ester A solution of oxalyl chloride (0.29 ml, 2 M in CH$_2$Cl$_2$) in 5 mL of dry dichloromethane was prepared and maintained under a nitrogen atmosphere at −78° C. DMSO (90 mg, 1.14 mmole) was added to the solution. The mixture was stirred for 15 minutes. The alcohol adduct, prepared above, (150 mg, 0.286 mmole), in 5 mL of dichloromethane, was added dropwise to the cold (−78° C.) reaction mixture. The solution was stirred, at −78° C., for 1 hour. Triethylamine (250 mg, 2.29 mmole) was added slowly. The reaction was allowed to slowly warm to room temperature and then diluted with dichloromethane. The organic layer was washed with water and brine, dried over MgSO$_4$, filtered and concentrated. The residue was purified by chromatography on silica gel using 5% ethyl acetate/hexanes to provide the title compound (yield: 100 mg, 67%).

$^1$H NMR (CDCl$_3$) δ7.26(m, 10H), 6.10(m, 2H), 4.28(m, 1H), 3.95(m, 2H), 2.60(m, 1H), 2.40(m, 1H), 2.03(m, 1H), 1.70(m, 2H), 1.45(s, 9H), 1.10–1.30(m, 7H), 0.70(m, 6H)

MS $(M+H)^+$=523.

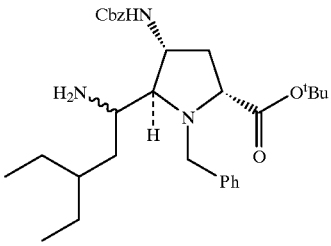

9F. (±)-(2S,3R,5R,1'R)- and (±)-(2S,3R,5R,1'S)-1-Benzyl-2-(1-amino-3-ethyl)pentyl-3-benzyloxycarbonylamino-pyrrolidine-5-carboxylic Acid t-Butyl Ester A mixture of (±)-(2R,3R,5R)-1-benzyl-2-(1-oxo-3-ethyl)pentyl-3-benzyloxy-carbonylamino-pyrrolidine-5-carboxylic acid t-butyl ester (90 mg, 0.172 mmole), ammonium acetate (400 mg, 5.17 mmole) and sodium cyanoborohydride (65 mg, 1.03 mmole) in 5 mL in methanol was heated at reflux for 18 hours. Additional portions of ammonium acetate and sodium cyanoborohydride were added and heating continued for an additional 2 hours. The reaction was quenched with 1 N sodium hydroxide, and diluted with dichloromethane. The organic layer was washed with water and brine, dried over MgSO$_4$, filtered and concentrated. The residue was purified by chromatography on silica gel using 1:1 ethyl acetate/hexanes followed by 5% methanol/dichloromethane to provide the title compounds. (yield: 58 mg, 64%)

MS (M+H)$^+$=524.

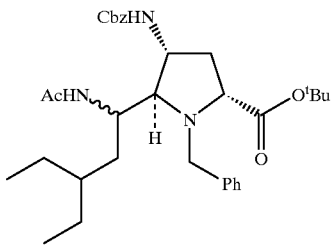

9G. (±)-(2S,3R,5R,1'R)- and (±)-(2S,3R,5R,1'S)-1-Benzyl-2-(1-acetamido-3-ethyl)pentyl-3-benzyloxycarbonylamino-pyrrolidine-5-carboxylic Acid t-Butyl Ester A solution of (±)-(2S,3R,5R,1'R)- and (±)-(2S,3R,5R,1'S)-1-benzyl-2-(1-amino-3-ethyl)pentyl-3-benzyloxycarbonylamino-pyrrolidine-5-carboxylic acid t-butyl ester (50 mg, 0.096 mmole) and acetic anhydride (117 mg, 1.15 mmole) in 5 mL of dichloromethane was stirred for 1 hour at room temperature. The solvent was evaporated in vacuo and the residue purified by chromatography on silica gel using 30–50% ethyl acetate/hexanes to provide the title compound as a colorless oil (yield: 51 mg, 97%).

$^1$H NMR (CDCl$_3$) δ7.72–7.35(m, 10H), 5.82(d, J=14 Hz, 1H), 5.10(m, 2H), 4.38(m, 1H), 4.15(m, 2H), 3.63(m, 1H), 3.38(m, 1H), 3.10(m, 1H),2.15(m, 1H), 2.00(s, 3H), 1.65(m, 1H), 1.42(s, 9H), 1.20–1.35(m, 7H), 0.80(m, 6H)

MS (M+H)$^+$=567.

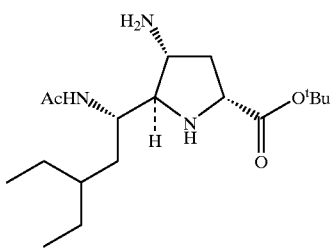

9H. (±)-(2S,3R,5R,1'S)-2-(1-Acetamido-3-ethyl)pentyl-3-amino-pyrrolidine-5-carboxylic Acid t-Butyl Ester A solution of (±)-(2S,3R,5R,1'R)- and (±)-(2S,3R,5R,1'S)-1-benzyl-2-(1-acetamido-3-ethyl)pentyl-3-benzyloxycarbonylamino-pyrrolidine-5-carboxylic acid t-butyl ester (49 mg, 0.087 mmole), ammonium formate (150 mg, 0.22 mmole) and 10% palladium on activated carbon in ethanol (5 mL) was heated at 80° C. for 45 minutes. After filtration to remove the catalyst, the solvent was removed. The residue was purified by chromatography on silica gel using 5–10% methanol/dichloromethane to furnish the diastereomers, (±)-(2S,3R,5R,1'S) (19 mg) and (±)-(2S,3R,5R,1'R) (8.6 mg) of 2-(1-acetamido-3-ethyl)pentyl-3-amino-pyrrolidine-5-carboxylic acid t-butyl ester.

$^1$H NMR (CDCl$_3$) δ6.00(d, J=14 Hz, 1H), 3.90(m, 1H), 3.73(m, 1H), 3.49(m, 1H), 3.10(m, 1H), 2.48(m, 1H), 2.03(s, 3H), 1.82(m, 1H), 1.48(s, 9H), 1.15–1.42(m, 7H), 0.85(m, 6H)

MS (M+H)$^+$=342.

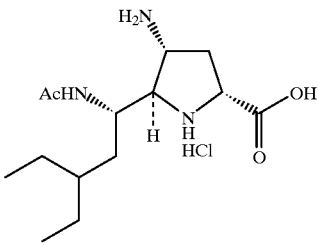

9I. (±)-(2S,3R,5R,1'S)-2-(1-Acetamido-3-ethyl)pentyl-3-amino-pyrrolidine-5-carboxylic Acid Dihydrochloride A solution of (±)-(2S,3R,5R,1'S)-2-(1-acetamido-3-ethyl)pentyl-3-amino-pyrrolidine-5-carboxylic acid t-butyl ester (17 mg, 0.050 mmole) in 1 mL of 6 N HCl was stirred at room temperature for 3 hours. The solvent was removed under high vacuum to provide the title compound as a white solid (yield: 15 mg, 100%)

$^1$H NMR (d$_6$-DMSO) δ8.28(bs, 1H), 7.90 (d, J=Hz, 1H), 4.71 (d, J=14 Hz, 1H), 4.39(m, 1H), 4.10(m, 1H), 3.92(m, 1H), 3.08(m, 1H), 2.64(m, 1H), 2.31(m, 1H), 1.95(m, 1H), 1.88(s, 3H), 1.50(m, 1H), 1.10–1.40(m, 7H), 0.72–0.90(m, 6H),

MS (M+H)$^+$=286.

EXAMPLE 10

(±)-(2S,3R,5R,1'S)-2-(1-Acetamido-3-ethyl)pentyl-3-acetamido-pyrrolidine-5-carboxylic Acid Hydrochloride

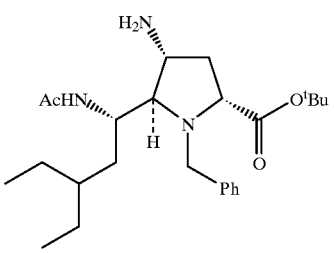

10A. (±)-(2S,3R,5R,1'S)-1-Benzyl-2-(1-acetamido-3-ethyl)pentyl-3-amino-pyrrolidine-5-carboxylic Acid t-Butyl Ester A solution of (±)-(2S,3R,5R,1'S)-1-benzyl-2-(1-acetamido-3-ethyl)pentyl-3-benzyloxycarbonylamino-pyrrolidine-5-carboxylic acid t-butyl ester (50 mg, 0.88 mmole) was stirred with 10% palladium on carbon (5 mg) in 50 mL of ethyl acetate under 1 atmosphere of hydrogen for 45 minutes. The reaction was filtered and concentrated to provide the title compound as an oil (crude yield: 35 mg, 92%).

MS (M+H)$^+$=431.

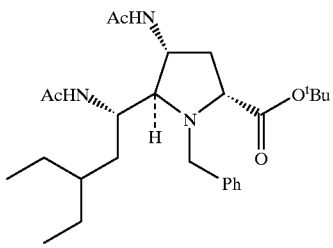

10B. (±)-(2S,3R,5R,1'S)-1-Benzyl-2-(1-acetamido-3-ethyl)pentyl-3-acetamido-pyrrolidino-5-carboxylic Acid t-Butyl Ester A solution of (±)-(2S,3R,5R,1'S)-1-benzyl-2-(1-acetamido-3-ethyl)pentyl-3-amino-pyrrolidine-5-carboxylic acid t-butyl ester (35 mg, 0.080 mmole) was reacted with acetic anhydride (0.05 mL) in 8 mL of dichloromethane for 1 hour. The reaction was concentrated and the residue purified by chromatography on silica gel using 50% ethyl acetate/hexanes followed by 3% methanol/dichloromethane to provide the title compound (yield: 30 mg, 80%).

$^1$H NMR (CDCl$_3$) δ7.20–7.35(m, 5H), 6.62(d, J=14 Hz, 1H), 5.34(d, J=14 Hz, 1H), 4.42(m, 2H), 4.20(m, 1H), 3.68(m, 1H), 3.42(m, 1H), 3.10(m, 1H), 2.18(m, 2H), 2.02(s, 3H), 1.96(s, 3H), 1.45(s, 9H), 1.25–1.42(m, 7H), 0.85(m, 6H).

MS (M+H)$^+$=474.

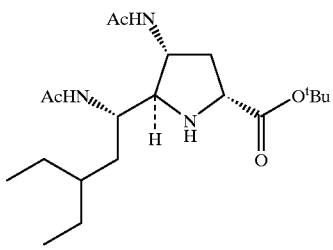

10C. (±)-(2S, 3R,5R,1S')-2-(1-Acetamido-3-ethyl)pentyl-3-acetamido-pyrrolidine-5-carboxylic Acid t-Butyl Ester The title compound was prepared according to the method described in Example 1J, substituting (±)-(2S,3R,5R,1'S)-1-benzyl-2-(1-acetamido-3-ethyl)pentyl-3-acetamido-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester. The residue was purified by chromatography on silica gel using 5% methanol/dichloromethane to provide the title compound (yield: 11.5 mg, 50%).

$^1$H NMR (CDCl$_3$) δ6.20(d, J=14 Hz, 1H), 5.94(d, J=14 Hz, 1H), 4.24(m, 1H), 4.08(m, 1H), 3.95(m, 1H), 3.75(m, 1H), 3.18(m, 1H), 2.45(m, 1H), 2.02(s, 3H), 1.96(s, 3H), 1.82(m, 1H), 1.49(s, 9H), 1.20–1.42(m, 7H), 0.85(m, 6H).

MS (M+H)$^+$=384.

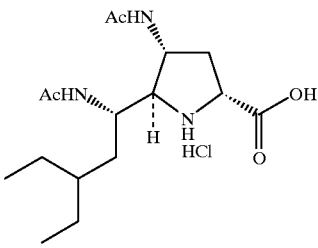

10D. (±)-(2S,3R,5R,1'S)-2-(1-Acetamido-3-ethyl)pentyl-3-acetamido-pyrrolidine-5-carboxylic Acid Hydrochloride The title compound was prepared according to the method described in Example 1K, substituting (±)-(2S,3R,5R,1'S)-2-(1-acetamido-3-ethyl)pentyl-3-acetamido-pyrrolidine-5-carboxylic acid t-butyl ester (11.0 mg, 0.029 mmole) in place of (±)-(2S,3R,5R,1'S)-2-(1-acetamido-3-ethyl)pentyl-3-(methoxymethyl)-pyrrolidine-5-carboxylic acid t-butyl ester (yield: 11.0 mg, 100%).

$^1$H NMR(d$_6$-DMSO) δ8.15(d, J=14 Hz, 1H), 8.05(d, J=14 Hz, 1H), 4.35(m, 1H), 4.28(m, 1H), 4.19(m, 1H), 3.59(m, 1H), 1.90(s, 3H), 1.81(s, 3H), 1.15–1.40(m, 7H), 0.80(m, 6H).

MS: (M−H)$^-$=326, (M+35)$^+$=362; (M+H)$^+$=328, (M+23)$^+$=350.

EXAMPLE 11

(±)-(2S,3R,5R,1'S)-2-(1-Acetamido-3-ethyl)pentyl-3-methoxycarbonylamino-pyrrolidine-5-carboxylic Acid Hydrochloride

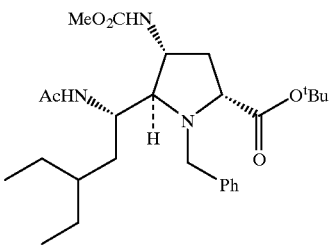

11A. (±)-(2S,3R,5R,1'S)-1-Benzyl-2-(1-acetamido-3-ethyl)pentyl-3-methoxy-carbonylamino-pyrrolidine-5-carboxylic Acid t-Butyl Ester A solution of (±)-(2S,3R,5R,1'S)-1-benzyl-2-(1-acetamido-3-ethyl)pentyl-3-amino-pyrrolidine-5-carboxylic acid t-butyl ester is reacted with methyl chloroformate and triethylamine in dichloromethane. The reaction is partitioned between dichloromethane and water. The organic layer is concentrated to provide the title compound.

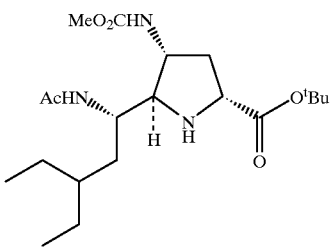

11B. (±)-(2S,3R,5R,1'S)-2-(1-Acetamido-3-ethyl)pentyl-3-methoxycarbonylamino-pyrrolidine-5-carboxylic Acid t-Butyl Ester The title compound is prepared according to the method described in Example 1J, substituting (±)-(2S,3R,5R,1'S)-1-benzyl-2-(1-acetamido-3-ethyl)-pentyl-3-methoxycarbonylaminopyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

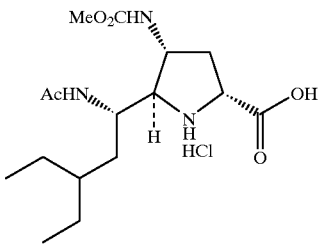

11C. (±)-(2S,3R,5R,1'S)-2-(1-Acetamido-3-ethyl)pentyl-3-methoxycarbonylamino-pyrrolidine-5-carboxylic Acid Hydrochloride The title compound is prepared according to the method described in Example 1K, substituting (±)-(2S,3R,5R,1'S)-2-(1-acetamido-3-ethyl)pentyl-3-methoxycarbonylamino-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

EXAMPLE 12

(±)-(2R,3R,5R,1'S)-2-(1-Acetamido-3-ethyl)pentyl-3-(imidazol-4-yl)-5-carboxylic Acid Dihydrochloride

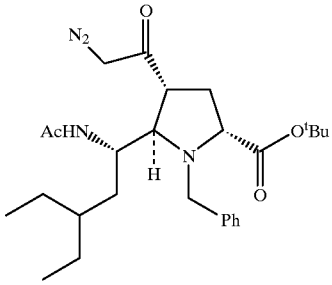

12A. (±)-(2R,3R,5R,1'S)-1-Benzyl-2-(1-acetamido-3-ethyl)pentyl-3-diazoacetyl-5-carboxylic Acid t-Butyl Ester A solution of (±)-(2R,3R,5R,1'S)-1-benzyl-2-(1-acetamido-3-ethyl)pentyl-3-carboxyl-pyrrolidine-5-carboxylic acid t-butyl ester (405.3 mg, 0.88 mmol) and N-methylmorpholine (106 µl, 0.96 mmol) in THF (20 ml) was reacted with isobutyl chloroformate (96 µl, 0.93 mmole) at −10° C. for 30 minutes. To the reaction flask was cannulated a distilled diazomethane solution in ether prepared from the reaction of diazald (2.4 g) in ether (60 ml) with a solution of potassium hydroxide (2.4 g) in ethanol (15 ml) and water (15 ml). The reaction was stirred for 3 hours at room temperature then diluted with ether. The organic layer was washed with brine, dried ($Na_2SO_4$) and concentrated to give the title compound as a thick oil (430.4 mg).

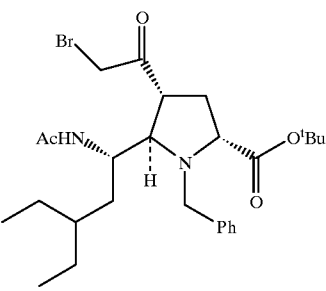

12B. (±)-(2R,3R,5R,1'S)-1-Benzyl-2-(1-Acetamido-3-ethyl)pentyl-3-bromoacetyl-5-carboxylic Acid t-Butyl Ester A solution of (±)-(2R,3R,5R,1'S)-1-benzyl-2-(1-acetamido-3-ethyl)pentyl-3-diazoacetyl-5-carboxylic acid t-butyl ester (427.4 mg, 0.88 mmol) in dioxane (50 ml) was reacted with hydrobromic acid (0.25 ml, 2.2 mmol) at 0° C. for 0.5 hours. The reaction was quenched with saturated aqueous sodium bicarbonate (25 ml) and concentrated in vacuo. The residual aqueous layer was extracted with dichloromethane (3×50 ml). The combined organic layers were washed with brine, dried over sodium sulfate, filtered and concentrated in vacuo. The residue was purified by chromatography on silica gel using 5% methanol in dichloromethane to provide the title compound as a white foamy solid (379.3 mg, 80.2%).

MS: $(M+H)^+=539$.

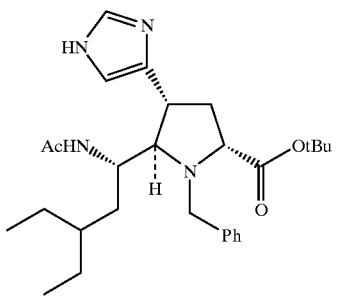

12C. (±)-(2R,3R,5R,1'S)-1-Benzyl-2-(1-acetamido-3-ethyl)pentyl-3-(imidazol-4-yl)-5-carboxylic Acid t-Butyl Ester (±)-(2R,3R,5R,1'S)-1-benzyl-2-(1-acetamido-3-ethyl)pentyl-3-bromoacetyl-5-carboxylic acid t-butyl ester (60 mg, 0.112 mmol) was treated with formamidine acetate (120 mg, 1.15 mmol) in liquid ammonia and heated at 45° C. in a sealed tube for 20 h. The reaction was concentrated in vacuo. The residue was treated with aqueous $NaHCO_3$ and extracted with dichloromethane (5×20 ml). The combined organic layers were washed with brine, dried over sodium sulfate, filtered and concentrated in vacuo. The residue was purified by chromatography on silica gel using 5% methanol in dichloromethane to provide the title compound as a white solid (21.2 mg, 39.4%).

MS: (M+H) 483.

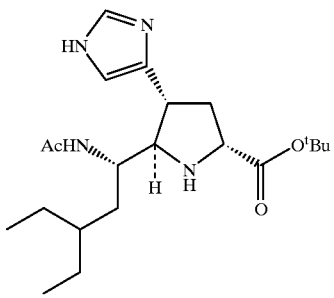

12D. (±)-(2R,3R,5R,1'S)-2-(1-Acetamido-3-ethyl) pentyl-3-(imidazol-4-yl)-5-carboxylic Acid t-Butyl Ester The title compound was prepared according to the method described in Example 1J, substituting (±)-(2R,3R,5R,1'S)-1-benzyl-2-(1-acetamido-3 -ethyl)pentyl-3-(imidazol-4-yl)-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester (yield: 12.9 mg, 66.2%).

$^1$H NMR (CDCl$_3$): δ0.75–0.81 (m, 6H), 1.17–1.42 (m, 7H), 1.47 (s, 9H), 2.03 (s, 3H), 2.66 (m,1H), 3.50 (m,1H), 3.73 (m, 1 H), 3.86 (m, 1H),4.06 (m, 1H), 7.04 (br s,1H), 7.86 (br s,1H).

MS: (M+H)$^+$=393.

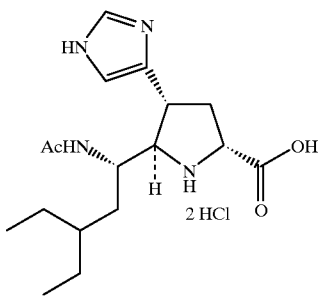

12E. (±)-(2R,3R,5R,1'S)-2-(1-Acetamido-3-ethyl) pentyl-3-(imidazol-4-yl)-5-carboxylic Acid Dihydrochloride The title compound was prepared according to the method described in Example 1K, substituting (±)-(2R,3R,5R,1'S)-2-(1-acetamido-3-ethyl)pentyl-3-(imidazol-4-yl)-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester to provide the title compound solid (yield: 12.0 mg, 96.0%).

$^1$H NMR (DMSO-d$_6$): δ0.67 (t, J=7 Hz, 3H), 0.75 (t, J=7 Hz, 3H), 1.11 (m, 3H), 1.23 (m, 4H), 1.78 (s, 3H), 2.33 (m, 1H), 2.70 (m, 1H), 3.69 (dt, 1H), 3.95 (dd,1H), 4.29 (m, 1H), 4.48 (dd,1H), 7.63 (s,1H), 8.28 (d, J=9 Hz, 1H), 9.06 (s, 1H),

MS: (M+H)$^+$=337.

EXAMPLE 13

(±)-(2R,3R,5R,1'S)-2-(1-Acetamido-3-ethyl)pentyl-3-oxazol-2-yl)-pyrrolidine-5-carboxylic Acid Dihydrochloride

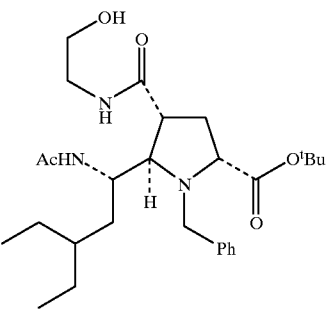

13A. (±)-(2R,3R,5R,1'S)-1-Benzyl-2-(1-acetamido-3-ethyl)pentyl-3-(N-(2-hydroxyethyl)carbamoyl)-pyrrolidine-5-carboxylic Acid t-Butyl Ester The title compound is prepared according to the method described in Example 5A, substituting ethanolamine for N-methylamine hydrochloride.

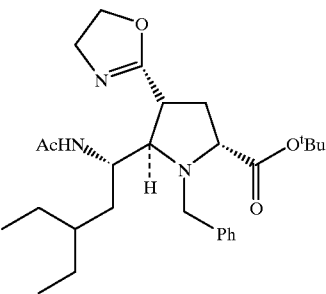

13B. (±)-(2R,3R,5R,1'S)-1-Benzyl-2-(1-acetamido-3-ethyl)pentyl-3-(oxazolin-2-yl)-pyrrolidine-5-carboxylic Acid t-Butyl Ester A solution of (±)-(2R,3R,5R,1'S)-1-benzyl-2-(1-acetamido-3-ethyl)pentyl-3-(N-(2-hydroxyethyl) carbamoyl)-pyrrolidine-5-carboxylic acid t-butyl ester, triethylamine (4 eq.), carbon tetrachloride (3.5 eq.) in acetonitrile is reacted with triphenylphosphine (3.15 eq.) for 16h at room temperature. The reaction is concentrated in vacuo. The residue is partitioned between ethyl acetate and water. The organic layer is washed with water, and brine, dried over MgSO$_4$, filtered and concentrated in vacuo. The residue is purified by chromatography on silica gel using ethyl acetate/hexanes to provide the title compound.

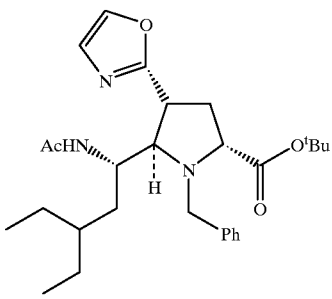

13C. (±)-(2R,3R,5R,1'S)-1-Benzyl-2-(1-acetamido-3-ethyl)pentyl-3-(oxazol-2-yl)-pyrrolidine-5-carboxylic Acid t-Butyl Ester A solution of (±)-(2R,3R,5R,1'S)-1-benzyl-2-(1-acetamido-3-ethyl)pentyl-3-(oxazolin-2-yl)-pyrrolidine-5-carboxylic acid t-butyl ester is reacted with nickel peroxide in cyclohexane according to the method described by Meyer in J. Org. Chem. 1979, 497–501 to provide the title compound.

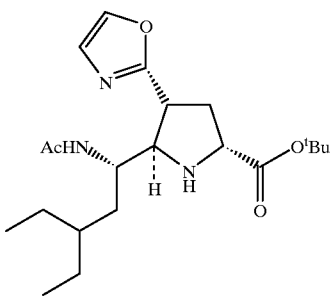

13D (±)-(2R,3R,5R,1'S)-2-(1-Acetamido-3-ethyl)pentyl-3-(oxazol-2-yl)-pyrrolidine-5-carboxylic Acid t-Butyl Ester The title compound is prepared according to the method described in Example 1J, substituting (±)-(2R,3R,5R,1'S)-1-benzyl-2-(1-acetamido-3-ethyl)-pentyl-3-(oxazol-2-yl)-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

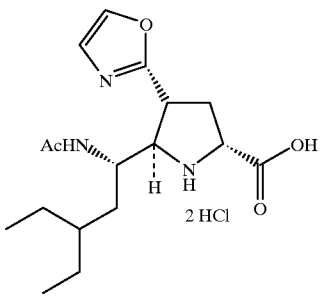

13E. (±)-(2R,3R,5R,1'S)-2-(1-Acetamido-3-ethyl)pentyl-3-(oxazol-2-yl)-pyrrolidine-5-carboxylic Acid Dihydrochloride The title compound is prepared according to the method described in Example 1K, substituting (±)-(2R,3R,5R,1'S)-2-(1-acetamido-3-ethyl)pentyl-3-(oxazol-2-yl)-pyrrolidine-5-carboxylic acid t-butyl ester in place of (±)-(2R,3R,5R,1'S)-2-(1-acetamido-3-ethyl)pentyl-3-methoxymethyl-pyrrolidine-5-carboxylic acid t-butyl ester.

EXAMPLE 14

(±)-(2R,3R,5R,1'S)-2-(1-Acetamido-3-methyl)butyl-3-(N-methylamino)pyrrolidine-5-carboxylic Acid Dihydrochloride

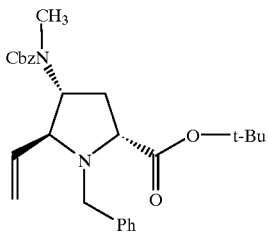

14A. (±)-(2S,3R,5R)-1-Benzyl-2-vinyl-3-(N-methyl-N-benzyloxycarbonylamino)-pyrrolidine-5-carboxylic Acid t-Butyl Ester A solution of (±)-(2R,2R,5R)-1-benzyl-2-vinyl-3-benzyloxycarbonylamino-pyrrolidine-5-carboxylic acid t-butyl ester (2.08 g, 4.77 mmole) was dissolved in 50 mL of anhydrous DMF and maintained under a nitrogen atmosphere. The solution was treated with sodium hydride (0.32 g, 8 mmole), and stirred at room temperature for 30 minutes. The solution was treated with iodomethane (0.8 ml, 12.85 mmole) and stirred for an additional 1 hour. The reaction was quenched with water and extracted with ethyl acetate. The combined organic layers were concentrated to provide the crude product which was purified by chromatography on silica gel to provide the title compound as an oil (yield: 1.75 g, 81%).

$^1$H NMR (CDCl$_3$) δ7.38–7.20 (m, 10H), 5.75–5.50 (br, 1H), 5.25–5.07 (m, 4H), 4.75–4.50 (br, 1H), 3.97 (d, J=13.5 Hz, 1H), 3.75 (m, 1H), 3.61 (d, J=13.5 Hz, 1H), 3.50 (m, 1H), 2.93 (s, 3H), 2.45 (m, 1H), 1.75 (m, 1H), 1.46 (s, 9H). MS (M+H)$^+$=451.

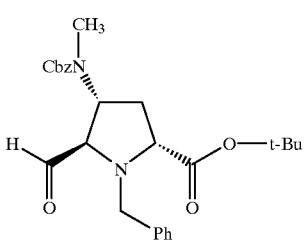

14B. (±)-(2R,3R,5R)-1-Benzyl-2-formyl-3-(N-methyl-N-benzyloxycarbonylamino)pyrrolidine-5-carboxylic Acid t-Butyl Ester The title compound was prepared according to the method described in Example 9C, substituting (±)-(2S,3R,5R)-1-benzyl-2-vinyl-3-(N-methyl-N-benzyloxycarbonylamino)pyrrolidine-5-carboxylic acid t-butyl ester in place of (±)-(2S,3R,5R)-1-benzyl-2-vinyl-3-benzyloxycarbonylamino-pyrrolidine-5-carboxylic acid t-butyl ester. (Yield: 747 mg, 42%.)

MS (M+H)$^+$=453.

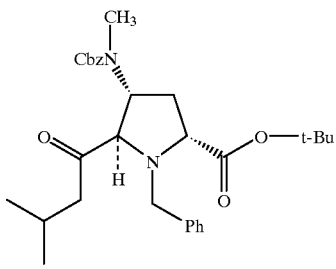

14C. (±)-(2R,3R,5R)-1-Benzyl-2-(1-oxo-3-methyl)butyl-3-(N-methyl-N-benzyloxycarbonylamino)pyrrolidine-5-carboxylic Acid t-Butyl Ester Isobutyl magnesium chloride (2.0 M in ether, 0.68 ml) was added dropwise over about 12 minutes to a solution of (±)-(2R,3R,5R)-1-benzyl-2-formyl-3-(N-methyl-N-benzyloxycarbonylamino)pyrrolidine-5-carboxylic acid t-butyl ester (196 mg, 0.43 mmole) in 5 mL of anhydrous THF, maintained at −78° C. The resulting yellow solution was stirred at −78° C. for 1 hour. The solution was quenched with saturated aqueous ammonium chloride, and extracted with ethyl acetate. The organic layer was concentrated and the crude product was oxidized according to the procedure described in Example 9D. Purification by column chromatography on silica gel, with 10–25% ethyl acetate/hexanes, provided the title compound (yield: 78 mg, 36%).

$^1$H NMR (CDCl$_3$) δ7.46–7.25 (m, 10H), 5.09 (br, 2H), 4.90–4.60 (m, 1H), 3.97–3.65 (m, 4H), 3.00 (s, 3H), 2.60 (br, 1H), 2.20–1.80 (m, 3H), 1.46 (s, 9H), 0.80–0.67 (m, 7H).

MS (M+H)$^+$=509.

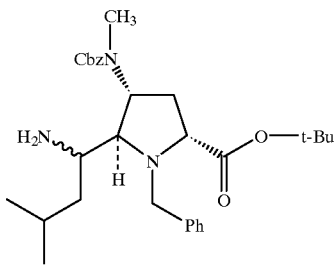

14D. (±)-(2S,3R,5R,1'R)- and (±)-(2S,3R,5R,1'S)-1-Benzyl-2-(1-amino-3-methyl)butyl-3-(N-methyl-N-benzyloxycarbonylamino)pyrrolidine-5-carboxylic Acid t-Butyl Ester The title compound was prepared according to the method described in Example 9F, substituting (±)-(2R,3R,5R)-1-benzyl-2-(1-oxo-3-methyl)butyl-3-(N-methyl-N-benzyloxycarbonylamino)pyrrolidine-5-carboxylic acid t-butyl ester in place of (±)-(2R,3R,5R)-1-benzyl-2-formyl-3-benzyloxycarbonylamino-pyrrolidine-5-carboxylic acid t-butyl ester. (Yield: 97 mg, 65%.)

MS (M+H)$^+$=5160.

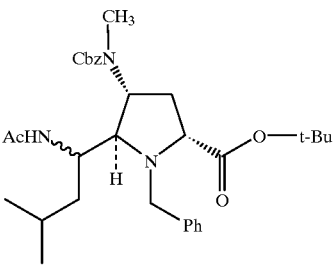

14E. (±)-(2S,3R,5R,1'R)- and (±)-(2S,3R,5R,1'S)-1-Benzyl-2-(1-acetamido-3-methyl)butyl-3-(N-methyl-N-benzyloxycarbonylamino)pyrrolidine-5-carboxylic Acid t-Butyl Ester A solution of (±)-(2S,3R,5R,1'R)- and -(2S,3R,5R,1'S) 1-benzyl-2-(1-amino-3-methyl)butyl-3-(N-methyl-N-benzyloxycarbonylamino)pyrrolidine-5-carboxylic acid t-butyl ester (47 mg, 0.094 mmole) was reacted with acetic anhydride (0.15 mL) in 4 mL of dichloromethane at room temperature for 2 hours. The reaction was concentrated in vacuo to provide the title compound.

MS (M+H)$^+$=552.

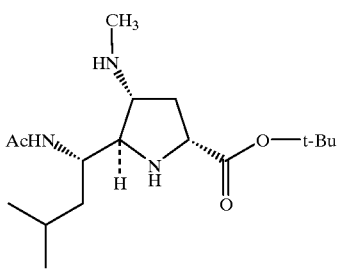

14F. (±)-(2S,3R,5R,1'S)-2-(1-Acetamido-3-methyl)butyl-3-(N-methylamino)-pyrrolidine-5-carboxylic Acid t-Butyl Ester A solution of (±)-(2S,3R,5R,1'R)- and (±)-(2S,3R,5R,1'S)-1-benzyl-2-(1-acetamido-3-methyl)butyl-3-(N-methyl-N-benzyloxycarbonylamino)pyrrolidine-5-carboxylic acid t-butyl ester (0.094 mmole), palladium (40 mg, 10% on carbon) and ammonium formate (160 mg) in 3 mL of ethanol was heated at reflux for 30 minutes. Additional palladium on carbon (15 mg) and ammonium formate (50 mg) were added. The solution was stirred for an additional 15 minutes and the mixture was then filtered to remove the solids and catalyst. The filtrate was evaporated and the residue purified by chromatography on silica gel 5% methanol/dichloromethane and 1% NH$_4$OH to provide (±)-(2S,3R,5R,1'S) (15.4 mg, lower Rf) and (±)-(2S,3R,5R,1'R) (5.4 mg, higher Rf)-2-(1-acetamido-3-methyl)butyl-3-(N-methylamino)pyrrolidine-5-carboxylic acid t-butyl esters (yield: 20.8 mg, 68%).

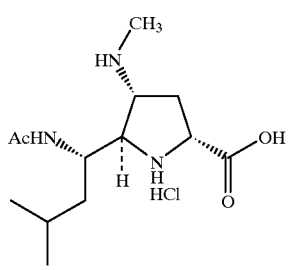

14G. (±)-(2S,3R,5R,1'S)-2-(1-Acetamido-3-methyl) butyl-3-(N-methylamino)pyrrolidine-5-carboxylic Acid Dihydrochloride A solution of (±)-(2S,3R,5R,1'S)-2-(1-Acetamido-3-methyl)butyl-3-(N-methylamino)pyrrolidine-5-carboxylic acid t-butyl ester (9.4 mg) was stirred with 4 N aqueous HCl (~1.5 mL) for 2 hours. The reaction was concentrated in vacuo to provide the title compound (yield: 10 mg, 100%).

$^1$H NMR (major peaks) (DMSO-d$_6$) δ2.57 (s, 3H), 1.90 (s, 3H), 1.47 (m, 3H), 0.91 (d, J=7.5 Hz, 3H), 0.83 (d, J=7.5 Hz, 3H)

MS:(M+H)$^+$=272.

EXAMPLE 15

(±)-(2R,3R,5R,1'S)-2-(1-Acetamido-3-ethyl)pentyl-3-(imidazol-2-yl)-pyrrolidine-5-Carboxylic Acid Dihydrochloride

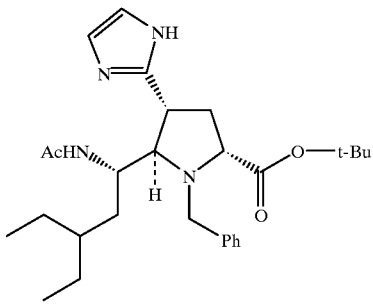

15A. (±)-(2R,3R,5R,1'S)-1-Benzyl-2-(1-acetamido-3-ethyl)pentyl-3-(imidazol-2-yl)-pyrrolidine-5-carboxylic Acid t-Butyl Ester Ammonia gas was bubbled slowly through a solution of (±)-(2R,3R,5R,1'S)-1-benzyl-2-(1-acetamido-3-ethyl) pentyl-3-formyl-pyrrolidine-5-carboxylic acid t-butyl ester (20 mg, 0.045 mmole) and glyoxal (6.2 uL, 0.054 mmole, 1.2 equiv.) in 5 mL of methanol, maintained at 0° C., for 5 minutes. After 7 hours at 0° C., additional glyoxal (10 uL) was added and ammonia was bubbled through the solution for 5 minutes. The reaction was allowed to stir at room temperature for 16 hours. A final addition of glyoxal (10 uL) and ammonia as, described above, followed by reaction at room temperature for an additional 4 hours effected a complete reaction. The reaction was concentrated in vacuo and purified by chromatography on silica gel using 50% ethyl acetate/hexanes, followed by 10% methanol/chloroform to provide the title compound as a solid (yield: 19.9 mg, 91%).

$^1$H NMR (CDCl$_3$): d 0.67 (t, J=7.2 Hz, 3H), 0.73 (t, J=7.2 Hz, 3H), 1.09–1.32 (m, 7H), 1.41 (s, 9H), 2.00 (m, 1H), 2.09 (s, 3H), 2.79 (m, 1H), 3.29 (m, 1H), 3.66 (dd, J=9.6, 2.7 Hz, 1H), 3,77 (m, 1H), 3.92 (d, J=13.4 Hz, 1H), 4.04 (d, J=13.4 Hz, 1H), 4.22 (dd, 1H), 4.49 (m, 1H), 6.08 (brs, 1H), 7.00 (s, 2H), 7.21–7.34 (m, 5H).

MS (M+H)$^+$=483.

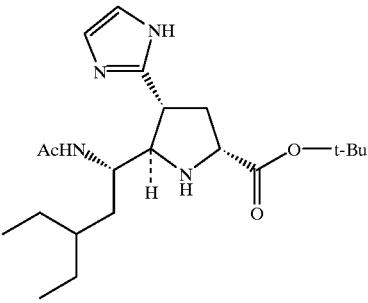

15B. (±)-(2R,3R,5R,1'S)-2-(1-Acetamido-3-ethyl) pentyl-3-(imidazol-2-yl)-pyrrolidine-5-carboxylic Acid t-Butyl Ester A mixture of (±)-(2R,3R,5R,1'S)-1-benzyl-2-(1-acetamido-3-ethyl)pentyl-3-(imidazol-2-yl)-pyrrolidine-5-carboxylic acid t-butyl ester (17 mg, 0.035 mmole), ammonium formate (250 mg) and 10% palladium on carbon (20 mg), in 5 mL of ethanol, was heated at reflux for 15 minutes The reaction was concentrated in vacuo and the residue was purified by chromatography on silica gel using 5% methanol/dichlormethane and 0.25% ammonium hydroxide to provide the title compound as a white solid (yield 11.3 mg, 81.90%).

MS (M+H)$^+$=393.

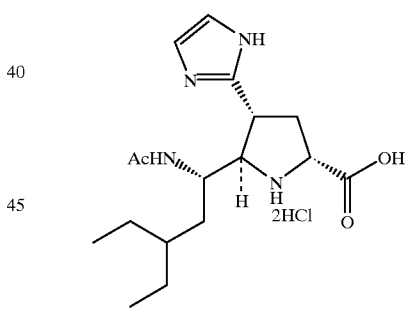

15C. (±)-(2R,3R,5R,1'S)-2-(1-Acetamido-3-ethyl) pentyl-3-(imidazol-2-yl)-pyrrolidine-5-Carboxylic Acid Dihydrochloride (±)-(2R,3R,5R,1'S)-2-(1-Acetamido-3-ethyl)pentyl-3-(imidazol-2-yl)-pyrrolidine-5-carboxylic acid t-butyl ester (11 mg, 0.028 mmole) was dissolved in 2 mL of 6N HCl and stirred at room temperature for 2 hours. The reaction was concentrated in vacuo to provide the title compound, as an off white solid (yield: 11.3 mg, 100%).

$^1$H NMR (DMSO-d$_6$): d 0.71 (t, J=7 Hz, 3H), 0.75 (t, J=7 Hz, 3H), 1.09–1.28 (m, 7H), 1.74 (s, 3H), 2.43 (m, 1H), 2.80 (m, 1H), 3.85 (m, 1H), 4.04 (M, 1H), 4.29 (m, 1H), 4.52 (m, 1H), 7.64 (s, 2H), 8.07 (br d, J=9 Hz, 1H).

MS (M+H)$^+$=337 and (M–H)$^-$=335.

EXAMPLE 16

(±)-(2R,3R,5R,1'S)-2-(1-Acetamido-3-ethyl)pentyl-3-(N,N-dimethylcarbamoyl)-pyrrolidine-5-carboxylic Acid Hydrochloride

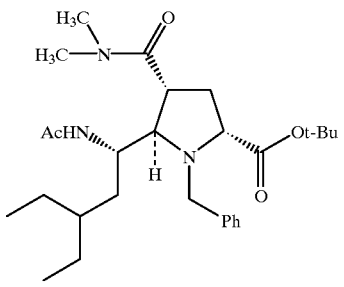

16A. (±)-(2R,3R,5R,1'S)-1-Benzyl-2-(1-acetamido-3-ethyl)pentyl-3-(N,N-dimethylcarbamoyl)pyrrolidine-5-carboxylic Acid t-Butyl Ester The title compound was prepared according to the method described in Example 5A substituting N,N-dimethylamine in place of N-methylamine (yield: 10 mg, 23%).

Mass spectrum: $(M+H)^+=488$.

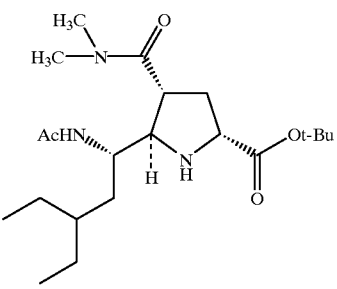

16B. (±)-(2R,3R,5R,1'S)-2-(1-Acetamido-3-ethyl)pentyl-3-(N-methylcarbamoyl)pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)pentyl-3-(N,N-dimethylcarbamoyl)pyrrolidine-5-carboxylic acid t-butyl ester in place of (±)-(2R,3R,5R,1'S)-1-benzyl-2-(1-acetamido-3-ethyl)pentyl-3-methoxy-methyl-pyrrolidine-5-carboxylic acid t-butyl ester to provide the title compound (yield: 5.5 mg, 67%).

Mass spectrum: $(M+H)^+=398$.

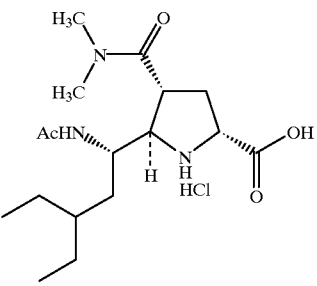

16C. (±)-(2R,3R,5R,1'S)-2-(1-Acetamido-3-ethyl)pentyl-3-(N,N-dimethyl-carbamoyl)pyrrolidine-5-carboxylic Acid Hydrochloride The title compound was prepared according to the method described in Example 1K, substituting (±)-(2R,3R,5R,1'S)-2-(1-acetamido-3-ethyl)pentyl-3-=(N,N-dimethylcarbamoyl)pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (major peaks) (D$_2$O) d 3.15 (s, 3H), 2.94 (s, 3H), 1.98 (s, 3H), 0.80 (m, 6H)

MS $(M+H)^+=342$, $(M-H)^-=340$.

EXAMPLE 17

(±)-(2R,3R,5R,1'S)-2-(1-Acetamido-3-Ethyl)pentyl-3-cyano-pyrrolidine-5-carboxylic Acid Hydrochloride

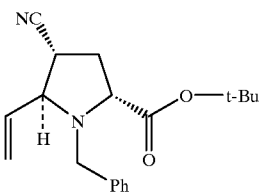

17A. (±)(2S,3R,5R)-1-Benzyl-2-vinyl-3-cyano-pyrrolidine-5-carboxylic Acid t-Butyl Ester A solution of (±)-(2S,3S,5R)-1-benzyl-2-vinyl-3-formyl-pyrrolidine-5-carboxylic acid t-butyl ester (8:1 ratio) (5 g, 15.9 mmole) with hydroxylamine hydrochloride (1.28 g, 18.5 mmole) and 10% aqueous potassium carbonate (8 mL) in 20 mL of methanol, according to the procedure described by Chelucci et al., *Tetrahedron: Asymmetry* 5:1973 (1994) provided an the intermediate oxime product.

The crude oxime, prepared above, was reacted with 1,1'-carbonyldiimidazole (3.9, 23.9 mmole) in 50 mL of dichloromethane for 3 hours, at room temperature. The reaction was concentrated in vacuo and chromatographed on silica gel with 2–10% ethyl acetate/hexanes to provide the title compound (yield: 2.5 g, 50%).

MS $(M+H)^+=313$

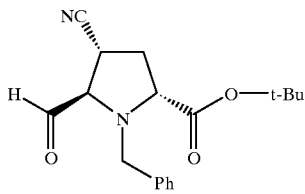

17B. (±)-(2R,3R,5R)-1-Benzyl-2-formyl-3-cyano-pyrrolidine-5-carboxylic Acid t-Butyl Ester The title compound is prepared according to the method described in Example 1D, substituting (±)(2S,3R,5R)-1-benzyl-2-vinyl-3-cyano-pyrrolidine-5-carboxylic acid t-butyl ester in place of (±)-(2S,3R,5R)-1-benzyl-2-vinyl-3-(t-butyldimethylsilyloxymethyl)-pyrrolidine-5-carboxylic acid t-butyl ester (yield: 2.2 g, 80%).

MS (M+H)$^+$=315

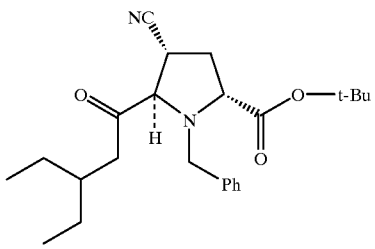

17C. (±)-(2R,3R,5R)-1-Benzyl-2-(1-oxo-3-ethyl)pentyl-3-cyano-pyrrolidine-5carboxylic Acid t-Butyl Ester The title compound was prepared according to the method described in Example 1E, substituting (±)(2S,3R,5R)-1-benzyl-2-formyl-3-cyano-pyrrolidine-5-carboxylic acid t-butyl ester in place of (±)-(2R,3R,5R)-1-benzyl-2-formyl-3-(t-butyldimethylsilyloxymethyl)-pyrrolidine-5-carboxylic acid t-butyl ester (yield 0.4 g, 27%).

MS (M+H)$^+$=399

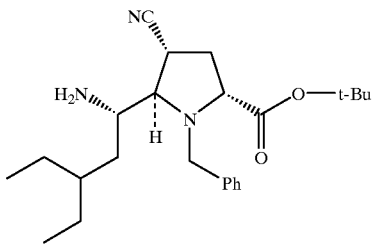

17D. (±)-(2R,3R,5R,1'S)-1-Benzyl-2-(1-amino-3-ethyl)pentyl-3-cyano-pyrrolidine-5-carboxylic Acid t-Butyl Ester The title compound was prepared according to the method described in Example 1F, substituting (±)-(2R,3R,5R)-1-benzyl-2-(1-oxo-3-ethyl)pentyl-3-cyano-pyrrolidine-5-carboxylic acid t-butyl ester in place of (±)-(2R,3R,5R)-1-benzyl-2-(1-oxo-3-ethyl)pentyl-3-(t-butyldimethylsilyloxymethyl)-pyrrolidine-5-carboxylic acid t-butyl ester (yield 0.215 g, 50%).

MS (M+H)$^+$=400

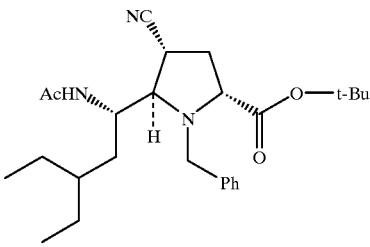

17E. (±)-(2R,3R,5R,1'S)-1-Benzyl-2-(1-acetamido-3-ethyl)pentyl-3-cyano-pyrrolidine-5-carboxylic Acid t-Butyl Ester The title compound is prepared according to the method described in Example 1G, substituting (±)-(2R,3R,5R,1'S)-1-benzyl-2-(1-amino-3-ethyl)pentyl-3-cyano-pyrrolidine-5-carboxylic acid t-butyl ester in place of (±)-(2R,3R,5R,1'R)- and (±)-(2R,3R,5R,1'S)-1-benzyl-2-(1-amino-3-ethyl)pentyl-3-(t-butyldimethylsilyloxymethyl)-pyrrolidine-5-carboxylic acid t-butyl ester (yield 0.210 g, 90%).

$^1$H NMR (CDCl$_3$) δ7.25 (m, 5H), 5.08 (m, 1H), 4.40 (m, 1H), 4.15 (m, 1H), 3.78 (m,1H), 3.48(m, 1H), 2.93 (m, 1H), 2.32 (m, 1H), 2.12 (m, 1H), 2.02 (s, 3H),1.52 (s, 9H), 1.35 (m, 7H), 0.85 (m, 6H)

MS: (M+H)$^+$=442.

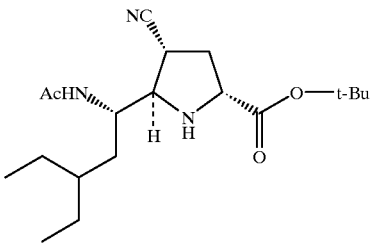

17F. (±)-(2R,3R,5R,1'S)-2-(1-Acetamido-3-ethyl)pentyl-3-cyano-pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)pentyl-3-cyano-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

$^1$H NMR (CDCl$_3$) δ5.35 (bs, 1H),4.00 (m, 1H), 3.83 (m, 1H), 3.39 (m, 1H), 3.08 (m, 1H), 2.63 (m, 1H), 2.15 (m, 1H), 2.05 (s, 3H), 1.48 (s, 9H), 1.20–1.45 (m, 7H), 0.85 (m, 6H)

MS: (M+H)$^+$=352

17G. (±)-(2R,3R,5R,1'S)-2-(1-Acetamido-3-ethyl) pentyl-3-cyano-pyrrolidine-5-carboxylic Acid Hydrochloride

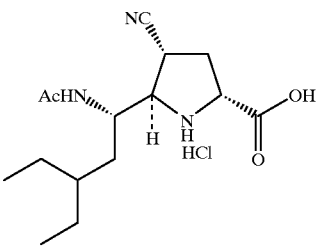

The title compound was prepared according to the method described in Example 1K, substituting (±)-(2R,3R,5R,1'S)-2-(1-acetamido-3-ethyl)pentyl-3-cyano-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (d$_6$-DMSO) δ9.12 (bs, 1H), 8.05 (m, 1H), 4.38 (m, 1H), 4.23 (m, 1H), 3.88 (m, 1H), 3.68 (m, 1H), 3.00 (m, 1H), 2.55 (m, 1H), 2.05 (m, 1H), 1.88 (s, 3H), 1.10–1.40 (m, 7H), 0.80 (m, 6H)

MS: (M+H)$^+$=296, (M−H)$^−$=294,

EXAMPLE 18

(±)-(2R,3S,5R,1'S)-2-(1-Acetamido-3-ethyl)pentyl-3-ethyl-pyrrolidine-5-carboxylic Acid Hydrochloride

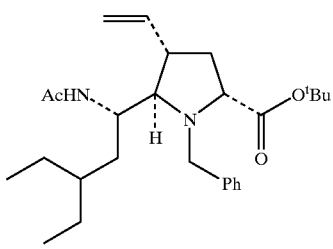

18A. (±)-(2R,3S,5R,1'S)-1-Benzyl-2-(1-acetamido-3-ethyl)pentyl-3-vinyl-pyrrolidine-5-carboxylic Acid t-Butyl Ester To an ice-cold suspension of methyl triphenylphosphonium bromide (240 mg, 0.67 mmol) in 5 mL THF was added potassium t-butoxide (60 mg, 0.54 mmol) under nitrogen. The color changed immediately to bright yellow. After stirring at room temperature for 1 h, (±)-(2R,3R,5R,1'S)-1-benzyl-2-(1-acetamido-3-ethyl)pentyl-3-formyl-pyrrolidine-5-carboxylic acid t-butyl ester (100 mg, 0.225 mmol) in 5 mL THF was added and stirred at room temperature overnight. Reaction was then quenched with saturated ammonium chloride and extracted with ethyl acetate to give the crude product which was purified by chromatography on silica gel using 30% ethyl acetate/hexanes to provide the title compound, as an oil (yield: 55 mg, 55%).

$^1$H NMR (CDCl$_3$): δ7.45–7.20 (m, 5H), 5.94 (ddd, 1H), 5.24 (d, J=12 Hz, 1H), 4.98 (d, J=18 Hz, 1H), 4.93 (d, J=10.5 Hz, 1H), 4.37 (m, 1H), 4.06 (d, J=13.5 Hz, 1H), 3.80 (d, J=13.5 Hz, 1H), 3.41 (dd, J=9 Hz, J=3 Hz, 1H), 3.31 (q, J=13.5 Hz, 1H), 2.60 (m, 1H), 2.26 (m, 1H), 2.00 (s, 3H), 1.45 (s, 9H), 1.40–1.25 (m, 7H), 0.82 (m, 6H).

MS: (M+H)$^+$=443

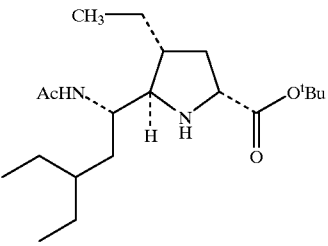

18B. (±)-(2R,3S,5R,1'S)-2-(1-acetamido-3-ethyl) pentyl-3-ethyl-pyrrolidine-5-carboxylic Acid t-Butyl Ester The title compound was prepared according to the method described in Example 1J, substituting (±)-(2R,3S,5R,1'S)-1-benzyl-2-(1-acetamido-3-ethyl)pentyl-3-vinyl-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

$^1$H NMR (CDCl$_3$): δ5.71 (br, 1H), 4.00 (br, 1H), 3.68 (t, J=8 Hz, 1H), 3.10 (m, 1H), 2.38 (m, 1H), 1.98 (s, 3H), 1.87 (m, 1H), 1.47 (s, 9H), 1.55–1.20 (m, 10H), 0.93 (t, J=7.5 Hz, 3H), 0.83 (m, 6H).

MS: (M+H)$^+$=355

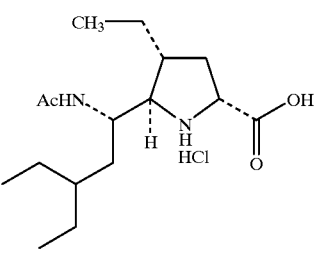

18C. (±)-(2R,3S,5R,1'S)-2-(1-acetamido-3-ethyl) pentyl-3-ethyl-pyrrolidine-5-carboxylic Acid Hydrochloride The title compound was prepared according to the method described in Example 1K, substituting (±)-(2R,3S,5R,1'S)-2-(1-acetamido-3-ethyl)pentyl-3-ethyl-pyrrolidine-5-carboxylic acid t-butyl ester in place of (±)-(2R,3R,5R,1'S)-2 -(1-acetamido-3-ethyl)pentyl-3-(methoxymethyl)-pyrrolidine-5-carboxylic acid t-butyl ester.

$^1$H NMR (D$_2$O): δ4.30 (br, 1H), 4.25 (t, J=7.5 Hz, 2H), 3.58 (br, 1H), 2.61 (m, 1H), 2.23 (br, 1H), 2.05 (s, 3H), 1.90 (m, 1H), 1.70–1.20 (m, 9H), 0.92 (t, J=-7.5 Hz, 3H), 0.81 (m, 6H).

MS: (M+H)$^+$=299

EXAMPLE 19

(±)-(2R,3S,5R,1'S)-2-(1-Acetamido-3-ethyl)pentyl-3-propyl-pyrrolidine-5-carboxylic Acid Hydrochloride

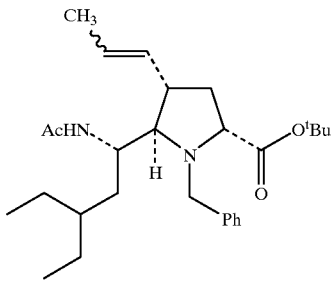

19A. (±)-(2R,3S,5R,1'S)-1-Benzyl-2-(1-acetamido-3-ethyl)pentyl-3-(cis-propen-1-yl)-pyrrolidine-5-carboxylic Acid t-Butyl Ester and (±)-(2R,3S,5R,1'S)-1-Benzyl-2-(1-acetamido-3-ethyl)pentyl-3-(trans-propen-1-yl)-pyrrolidine-5-carboxylic Acid t-Butyl Ester The title compound was prepared according the method described in Example 18A substituting ethyl triphenylphosphonium bromide for methyl triphenylphosphonium bromide.

$^1$H NMR (CDCl$_3$) δ7.24 (m, 5H), 5.59 (m, 1H), 5.36 (dd, J=11, 7 Hz, 1H), 5.28 (bs, 1H), 4.32 (m, 1H), 4.06 (d, J=12.9 Hz 1H), 3.80 (d, J=12.9 Hz, 1H), 3.42 (dd, J=8.5, 2.0 Hz, 1H), 3.30 (dd, J=6.1, 3.1 Hz, 1H), 2.88 (m, 1H), 2.29 (m, 2H), 2.01 (s, 3H), 1.64 (dd, J=6.8, 1.7 Hz, 3H), 1.44 (s, 9H), 1.30 (m, 7H), 0.81 (m, 6H).

MS: (M+H)$^+$=457, (M+Na)$^+$=479, (M−H)$^−$=455.

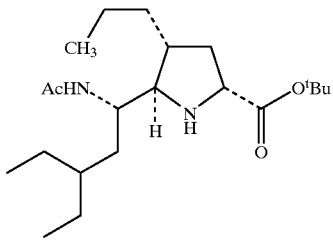

19B. (±)-(2R,3S,5R,1'S)-2-(1-acetamido-3-ethyl)pentyl-3-propyl-pyrrolidine-5-carboxylic Acid t-Butyl Ester The title compound was prepared according to the method described in Example 1J, substituting (±)-(2R,3S,5R,1'S)-1-benzyl-2-(1-acetamido-3-ethyl)pentyl-3-(cis-propen-1-yl)-pyrrolidine-5-carboxylic acid t-butyl ester and (±)-(2R,3S,5R,1'S)-1-benzyl-2-(1-acetamido-3-ethyl)pentyl-3-(trans-propen-1-yl)-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester (yield: 3.5 mg, 54%).

MS: (M+H)$^+$=369, (M+Na)$^+$=391, (M−H)$^−$=367.

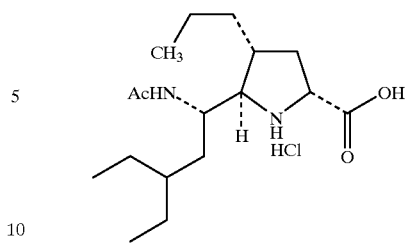

19C. (±)-(2R,3S,5R,1'S)-2-(1-acetamido-3-ethyl)pentyl-3-propyl-pyrrolidine-5-carboxylic Acid Hydrochloride The title compound was prepared according to the method described in Example 1K, substituting (±)-(2R,3S,5R,1'S)-2-(1-acetamido-3-ethyl)pentyl-3-ethyl-pyrrolidine-5-carboxylic acid t-butyl ester in place of (±)-(2R,3R,5R,1'S)-2 -(1-acetamido-3-ethyl)pentyl-3-(methoxymethyl)-pyrrolidine-5-carboxylic acid t-butyl ester (yield: 3.5 mg, 100%).

$^1$H NMR (DMSO-d6) δ8.10 (d, J=8.3 Hz, 1H), 4.24 (m, 1H), 4.17 (m, 1H), 2.43 (m, 1H), 2.19 (m, 1H), 1.89 (s, 3H), 1.70 (m, 1H), 1.50–1.20 (m, 12H), 0.87 (t, J=6.8 Hz, 3H), 0.84 (t, J=7.0 Hz, 3H), 0.79 (t, J=7.3 Hz, 3H).

MS: (M+H)$^+$=313, (M+Na)$^+$=335, (M−H)$^−$=311.

EXAMPLE 20

(±)-(2R,3S,5R,1'S)-2-(1-Acetamido-3-methyl)butyl-3-vinyl-pyrrolidine-5-carboxylic Acid Hydrochloride

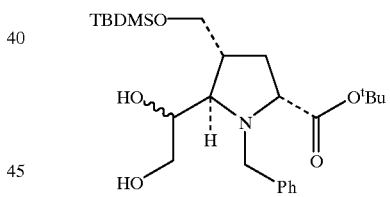

20A. (±)-(2R,3R,5R,1'RS)-1-Benzyl-2-(1 2-dihydroxy)ethyl-3-(t-butyldimethylsilyloxymethyl)-pyrrolidine-5-carboxylic Acid t-Butyl Ester Osmium tetroxide was added to a room temperature solution of (±)-(2S,3R,5R)-1-benzyl-2-vinyl-3-(t-butyldimethylsilyloxymethyl)-pyrrolidine-5-carboxylic acid t-butyl ester (3.5 g, 8.12 mmol) in 60 mL of 8:1 acetone/water and N-methylmorpholine N-oxide (3.0 g, 25.6 mmol). The reaction mixture was stirred at room temperature for 6 hours and quenched with saturated aqueous Na$_2$S$_2$O$_3$. The mixture was stirred for an additional 10 minutes and the solvent removed. The brownish residue was partitioned between dichloromethane and water. The organic layer was dried over MgSO4 and concentrated in vacuo to provide the intermediate diol as an oil (~3.8 g ) which was used without additional purification.

MS: (M+H)$^+$=466.

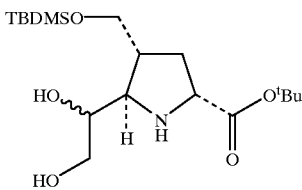

20B. (±)-(2R,3R,5R,1'RS)-2-(1 2-Dihydroxy)ethyl-3-(t-butyldimethylsilyloxymethyl)-pyrrolidine-5-carboxylic Acid t-Butyl Ester The title compound was prepared according to the method described in Example 1J, substituting (±)-(2R,3R,5R,1'RS)-1-benzyl-2-(1,2-dihydroxy)ethyl-3-(t-butyldimethylsilyloxymethyl)-pyrrolidine-5-carboxylic acid t-butyl ester (21.5 g, 46.2 mmol). in place of (±)-(2R,3R,5R,1'S)-1-benzyl-2-(1-acetamido-3-ethyl)pentyl-3-methoxymethyl-pyrrolidine-5-carboxylic acid t-butyl ester.

MS: $(M+H)^+=367$.

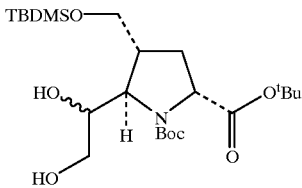

20C. (±)-(2R,3R,5R,1'RS)-1-t-Butoxycarbonyl-2-(1 2-dihydroxy)-ethyl-3-(t-butyldimethylsilyloxymethyl)-pyrrolidine-5-carboxylic Acid t-Butyl Ester (±)-(2R,3R,5R,1'RS)-2-(1,2-Dihydroxy)ethyl-3-(t-butyldimethylsilyloxymethyl)-pyrrolidine-5-carboxylic acid t-butyl ester (crude from previous step) was dissolved in 160 mL of 3:1 methanol/water and di-tert-butyl-dicarbonate (14.0 g, 64 mmol) was added. The mixture was stirred at room temperature for 72 h. Then solvent was removed and the residue was purified by chromatography on silica gel using 50% ethyl acetate/hexanes to provide the title compound as light yellow solid (yield: 15.4 g, 70%).

$^1$H NMR (CDCl$_3$): δ0.03 (s, 3H), 0.05 (s, 3H), 1.37 (s, 9H), 0.42 (s, 9H), 1.47 (s, 9H), 1.93 (d, 1H), 2.30–2.50 (m, 2H), 3.28 (d, 1H), 3.66–3.43 (m, 4H), 3.85 (dd, 1H), 4.02–4.52 (m, 1H).

MS: $(M+H)^+=476$.

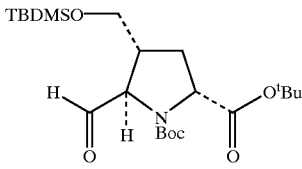

20D. (±)-(2R,3R,5R)-1-t-Butoxycarbonyl-2-formyl-3-(t-butyldimethylsilyloxymethyl)-pyrrolidine-5-carboxylic Acid t-Butyl Ester A solution of (±)-(2R,3R,5R,1'RS)-1-t-butoxycarbonyl-2-(1,2dihydroxy)ethyl-3-(t-butyldimethylsilyloxymethyl)-pyrrolidine-5-carboxylic acid t-butyl ester (6.0 g,12.6 mmol) was dissolved in 6:1 tetrahydrofuran (THF)/water (110 mL) and treated with sodium periodate (4.4 g, 20.6 mmol). The mixture was stirred at room temperature for 3 hour and diluted with ethyl acetate, washed with water, dried over MgSO$_4$, filtered, and concentrated in vacuo. The residue was purified by chromatography on silica gel using 20% ethyl acetate/hexanes to provide the title compound as a white waxy solid (yield: 4.4 g, 78.6%).

$^1$H NMR (CDCl$_3$) (mixture of two rotamers): δ0.05 and 0.06 (two s, 6H), 0.88 and 0.90 (two s, 9H), 1.42 and 1.44 (two s, 9H), 1.47 and 1.48 (two s, 9H), 1.89–1.99 (m, 1H), 2.37–2.43 (m, 2H), 3.54–3.67 (m, 2H), 4.02–4.34 (m, 2), 9.43 and 9. 53 (two d, 1H).

MS: $(M+H)^+=444$.

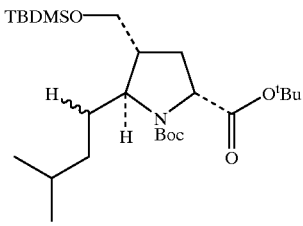

20E. (±)-(2R,3R,5R,1'RS)-1-t-Butoxycarbonyl-2-(1-hydroxy-3-methyl)butyl-3-(t-butyldimethylsilyloxymethyl)-pyrrolidine-5-carboxylic Acid t-Butyl Ester A solution of (±)-(2R,3R,5R)-1-t-butoxycarbonyl-2-formyl-3-(t-butyldimethylsilyloxymethyl)-pyrrolidine-5-carboxylic acid t-butyl ester (7.1 g, 16.03 mmol) in diethyl ether (75 mL) was reacted with isobutyl magnesium chloride (24 mL, 2.0 M in ether, 48 mmol) at 0° C. for 2.5 hours. The reaction was quenched with saturated ammonium chloride and diluted with ethyl acetate. The organic layer was washed with water, and brine, dried over MgSO$_4$, filtered and concentrated in vacuo. The residue was used in next step without further purification.

MS: $(M+H)^+=502$

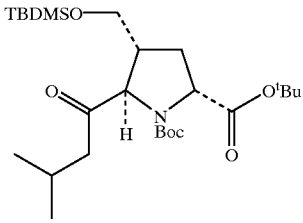

20F. (±)-(2R,3R,5R) 1-t-Butoxycarbonyl-2-(1-oxo-3-methyl)butyl-3-(t-butyldimethylsilyloxymethyl)-pyrrolidine-5-carboxylic Acid t-Butyl Ester A solution of oxalyl chloride (16 mL, 2M in CH$_2$Cl$_2$) in 100 mL of anhydrous dichloromethane was prepared and maintained under a nitrogen atmosphere, at –78° C. DMSO (4.26 mL, 64.1 mmol) was added slowly to the solution. The mixture was stirred for 15 minutes and reacted with (±)-(2R,3R,5R,1'RS)-1-t-butoxycarbonyl-2-(1-hydroxy-3-methyl)butyl-3-(t-butyldimethylsilyloxymethyl)-pyrrolidine- 5-carboxylic acid t-butyl in 30 mL of anhydrous dichloromethane. The solution was stirred for 1 hour and triethylamine (17 mL, 128 mmol) was added slowly to the reaction mixture. The solution wag allowed to warm slowly to room temperature, quenched with saturated sodium bicarbonate and diluted with dichloromethane. The organic layer was washed with water and brine, dried over $MgSO_4$, filtered and concentrated in vacuo. The residue was purified by chromatography on silica gel using 5–10% ethyl acetate/hexanes to provide the title compound (yield: 6.3 g, 78.8%).

$^1$H NMR ($CDCl_3$): δ0.07 (m, 6H), 0.81–0.96 (m, 15H), 1.40 and 1.42 (two s, 9H), 1.46 and 1.47 (two s, 9H), 1.72–1.82 (m, 1H), 2.15–2.45 (m, 4H), 3.47–3.69 (m, 1H), 4.28–4.46 (m, 2H).

MS: $(M+H)^+$=500

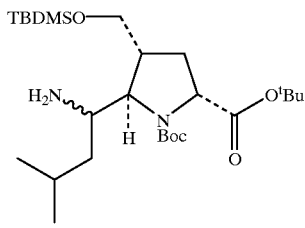

20G. (±)-(2R,3R,5R,1'RS)-1-t-Butoxycarbonyl-2-(1-amino-3-methy)butyl-3-(t-butyldimethylsilyloxymethyl)-pyrrolidine-5-carboxylic Acid t-Butyl Ester The title compound was prepared according to the method described in Example 1F, substituting (±)-(2R,3R,5R) 1-t-butoxycarbonyl-2-(1-oxo-3-methyl)butyl-3-(t-butyldimethylsilyloxymethyl)-pyrrolidine-5-carboxylic acid t-butyl ester in place of (±)-(2R,3R,5R)-1-benzyl-2-(1-oxo-3-ethyl)pentyl-3-(t-butyl-dimethylsilyloxymethyl)-pyrrolidine-5-carboxylic acid t-butyl ester (yield: 0.54 g, 34.1%).

MS: $(M+H)^+$=501.

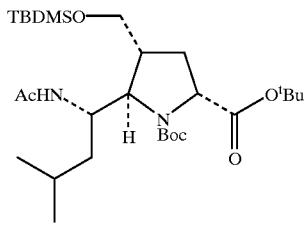

20H. (±)-(2R,3R,5R,1'S)-1-t-Butoxycarbonyl-2-(1-acetamido-3-methy)butyl-3-(t-butyldimethylsilyloxymethyl)-pyrrolidine-5-carboxylic Acid t-Butyl Ester The title compound was prepared according to the method described in Example 1G, substituting (±)-(2R,3R,1R,1'RS)-1-t-butoxycarbonyl-2-(1-amino-3-methy)butyl-3-(t-butyldimethylsilyloxymethyl)-pyrrolidine-5-carboxylic acid t-butyl ester in place of (±)-(2R,3R,5R,1'R)- and (±)-(2R,3R,5R,1'S)-1-benzyl-2-(1-amino-3-ethyl)pentyl-3-(t-butyldimethylsilyloxymethyl)-pyrrolidine-5-carboxylic acid t-butyl ester (yield: 462 mg, 79.0%).

(±)-(2R,3R,5R,1'S) $^1$H NMR ($CDCl_3$): δ0.03 and 0.04 (two s, 6H), 0.86 (s, 9H), 0.89 and 0.95 (two d, 6H), 1.04 (m, 1H), 1.17–1.25 (m, 2H), 1.44 (s, 9H), 1.46 (s, 9H), 1.86 (m, 1H), 1.99 (s, 3H), 2.07 (m, 1H), 2.30 (m, 1H), 3.48 (m, 1H), 3.61 (m, 1H), 3.67 (m, 1H), 4.16 (m, 1H), 4.27 (m, 1H), 7.35 (br d, 1H).

MS: $(M+H)^+$=543.

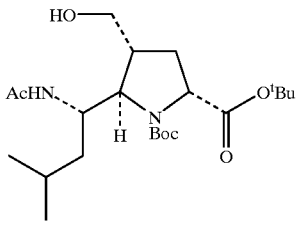

20I. (±)-(2R,3R,5R,1'S)-1-t-Butoxycarbonyl-2-(1-acetamido-3-methy)butyl-3-(hydroxymethyl)-pyrrolidine-5-carboxylic Acid t-Butyl Ester The title compound was prepared according to the method described in Example 1H, substituting (±)-(2R,3R,5R,1'S)-1-t-butoxycarbonyl-2-(1-acetamido-3-methy)butyl-3-(t-butyldimethylsilyloxymethyl)-pyrrolidine-5-carboxylic acid t-butyl ester in place (±)-(2R,3R,5R,1'S)-1-benzyl-2-(1-acetamido-3-ethyl)butyl-3-t-butyldimethylsilyloxymethyl-pyrrolidine-5-carboxylic acid t-butyl ester.

MS: $(M+H)^+$=429.

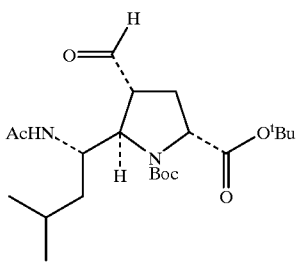

20J. (±)-(2R,3R,5R,1'S)-1-t-Butoxycarbonyl-2-(1-acetamido-3-methy)butyl-3-formyl-pyrrolidine-5-carboxylic Acid t-Butyl Ester The title compound was prepared according to the method described in Example 2A, substituting (±)-(2R,3R,5R,1'S)-1-t-butoxycarbonyl-2-(1-acetamido-3-methy)butyl-3-hydroxymethyl-pyrrolidine-5-carboxylic acid t-butyl ester in place of (±)-(2R,3R,5R,1'S)-1-benzyl-2-(1-acetamido-3-ethyl)pentyl-3-hydroxymethyl-pyrrolidine-5-carboxylic acid t-butyl ester (yield: 1.5 g, 91%).

$^1$H NMR ($CDCl_3$); δ0.92 and 0,94 (two d, 6H), 1.07 (m 1H), 1.23–1.33 (m, 2H), 1.43 (s, 9H), 1.44 (s, 9H), 1.64 (m,1H), 2.03 (s, 3H), 2.39 (m,1H), 2.46 (m, 1H), 3.18 (m, 1H), 4.19 (m, 1H), 4.32 (m, 1H), 4.39 (m, 1H), 7.12 (br d, 1H).

MS: $(M+H)^+$=427

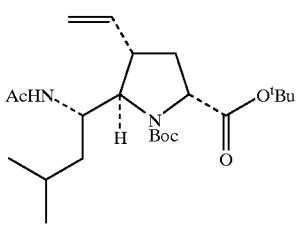

20K. (±)-(2R,3S,5R,1'S)-1-t-Butoxycarbonyl-2-(1-acetamido-3-methy)butyl-3-vinyl-pyrrolidine-5-carboxylic Acid t-Butyl Ester To a suspension of methyl triphenylphosphonium bromide (125.6 mg, 0.35 mmol) in 3 ml of anhydrous toluene wag added potassium t-butoxide (1.0 M in THF, 0.31 mmol) dropwise at room temperature. After stirring for 16 hours, (±)-(2R,3R,5R,1'S)-1-t-butoxycarbonyl-2-(1-acetamido-3-methyl)butyl-3-formyl-pyrrolidine-5-carboxylic acid t-butyl ester (30 mg, 0.070 mmol) in 3 ml of toluene was added dropwise and stirred for 0.5 hour. The reaction was quenched with saturated ammonium chloride and diluted with methylene chloride. The organic layer was washed with water and brine, dried over MgSO$_4$, filtered and concentrated in vacuo. The residue was purified by chromatography on silica gel using ethyl acetate to provide the title compound, as an white foamy solid (yield: 23.7 mg, 79.4%).

$^1$H NMR (CDCl$_3$): δ0.92 (m, 6H), 1.26 (m, 2H), 1.44 (s, 9H), 1.47 (s, 9H), 1.65 (m, 1H), 1.97 (s, 3H), 2.43 (m, 2H), 3.56 (m, 1H), 4.15 (m, 2H), 4.32 (m, 1H), 5.11 (m, 1H), 5.15 (m, 1H), 5.75 (m, 1H), 7.35 (br, 1H).

MS: (M+H)$^+$=425.

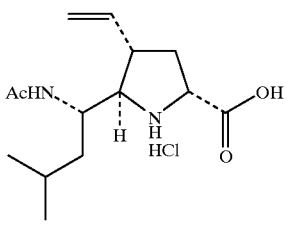

20L. (±)-(2R,3S,5R,1'S)-2-(1-Acetamido-3-methyl)butyl-3-vinyl-pyrrolidine-5-carboxylic Acid Hydrochloride The title compound was prepared according to the method described in Example 1K, substituting (±)-(2R,3S,5R,1'S)-1-t-butoxycarbonyl-2-(1-acetamido-3-methy)butyl-3-vinyl-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester (yield: 16.0 mg, 99.1%).

$^1$H NMR (DMSO-d$_6$): δ0.82 (d, 3H), 0.88 (d, 3H), 1.29 (m, 1H), 1.42 (m, 1H), 1.57 (m, 1H), 1.87 (s, 3H), 1.91 (m, 1H), 2.40 (m, 1H), 2.90 (m, 1H), 4.20 (m, 1H), 4.32 (m, 1H), 5.08 (dd, 1H), 5.17 (dd, 1H), 5.72 (ddd, 1H), 8.09 (d, 1H), 9.16 (br s, 1H), 9.28 (br s, 1H).

MS: (M+H)$^+$=269.

EXAMPLE 21

(±)-(2R,3R,5R,1'S)-2-(1-Acetamido-3-ethyl)pentyl-3-hydroxymethyl-pyrrolidine-5-carboxylic Acid Hydrochloride

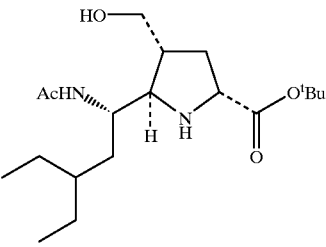

21A. (±)-(2R,3R,5R,1'S)-2-(1-Acetamido-3-ethyl)pentyl-3-hydroxymethyl-pyrrolidine-5-carboxylic Acid t-Butyl Ester The title compound was prepared according to the method described in Example 1J, substituting (±)-(2R,3R,5R,1'S)-1-benzyl-2-(1-acetamido-3-ethyl)pentyl-3-hydroxymethyl-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

MS: (M+H)$^+$=471

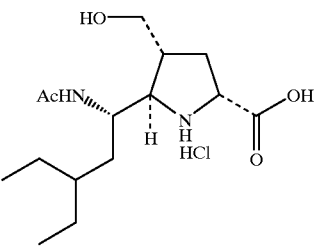

21B. (±)-(2R,3R,5R,1'S)-2-(1-Acetamido-3-ethyl)pentyl-3-hydroxymethyl-pyrrolidine-5-carboxylic Acid Hydrochloride The title compound was prepared according to the method described in Example 1K, substituting (±)-(2R,3R,5R,1'S)-2-(1-acetamido-3-ethyl)pentyl-3-hydroxymethyl-pyrrolidine-5-carboxylic acid t-butyl ester in place of (±)-(2R,3R,5R,1'S)-2-(1-acetamido-3-ethyl)pentyl-3-methoxymethyl-pyrrolidine-5-carboxylic acid t-butyl ester $^1$H NMR (DMSO-d$_6$): δ8.15 (d, J=9 Hz, 1H), 4.28–4.15 (m, 2H), 3.95–3.45 (m, 4H), 2.35 (m, 1H), 1.98 (m, 1H), 1.89 (s, 3H), 1.50–1.45 (m, 7H), 0.81 (t, J=7.4 Hz, 3H), 0.77 (t, J=7.5 Hz, 3H).

MS: (M+H)$^+$=301, (M–H)$^-$=299

EXAMPLE 22

(±)-(2R, 3R,5R,1'S)-2-(1-Acetamido-3-ethyl)pentyl-3-(pyrrol-1-yl)-pyrrolidine-5-carboxylic Acid Hydrochloride

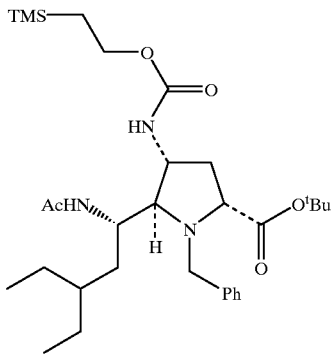

22A. (±)-(2R, 3R,5R,1'S)-1-Benzyl-2-(1-Acetamido-3-ethyl)pentyl-3-(2-trimethylsilylethoxycarbonylamino)-pyrrolidine-5-carboxylic Acid t-Butyl Ester (±)-(2R,3R,5R,1'S)-1-Benzyl-2-(1-acetamido-3-ethyl)pentyl-3-carboxyl-pyrrolidine-5-carboxylic acid t-butyl ester (80 mg, 0. 18 mmol) prepared according to the procedure of Example 2B was reacted with diphenylphosphoryl azide (0.047 mL, 0.216 mmol), 2trimethylsilylethanol (0.034 mL, 0.234 mmol), and triethylamine (0.030 mL, 0.216 mmol) in toluene (2 mL) at 75° C. for 15 hours. The reaction was concentrated in vacuo and the resulting residue purified by chromatography on silica gel using 25% ethyl acetate/hexanes to provide the title compound, as a light yellow oil (yield: 46 mg, 45%).

MS: $(M+H)^+=576$, $(M+Na)^+=598$, $(M-H)^-=574$.

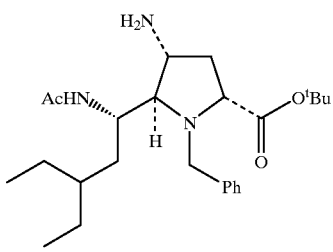

22B. (±)-(2S,3R,5R,1'S)-1-Benzyl-2-(1-acetamido-3-ethyl)pentyl-3-amino-pyrrolidine-5-carboxylic Acid t-Butyl Ester The title compound is prepared according to the method described in Example 1H, substituting (±)-(2S,3R,5R,1'S)-1-benzyl-2-(1-acetamido-3-ethyl)pentyl-3-(2-trimethylsilylethoxycarbonylamino)-pyrrolidine-5-carboxylic acid t-butyl ester in place of (±)-(2R,3R,5R,1'S)-2-(1-acetamido-3-ethyl)pentyl-3-(t-butyldimethylsilyloxymethyl)-pyrrolidine-5-carboxylic acid t-butyl ester.

MS: $(M+H)^+=432$, $(M-H)^-=430$.

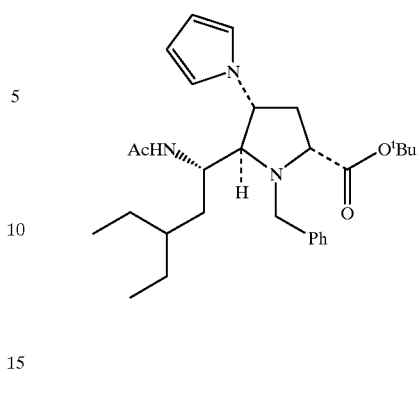

22C. (±)-(2R, 3R,5R,1'S)-1-Benzyl-2-(1-Acetamido-3-ethyl)pentyl-3-(pyrrol-1-yl)-pyrrolidine-5-carboxylic Acid t-Butyl Ester (±)-(2S, 3R,5R,1'S)-1-Benzyl-2-(1-acetamido-3-ethyl)pentyl-3-amino-pyrrolidine-5-carboxylic acid t-butyl ester (34 mg, 0.078 mmol) was reacted with 40% succinic dialdehyde in water (50 mg, 0.234 mmol), acetic acid (0.00044 mL, 0.0078 mmol), and 4A molecular sieves (200 mg) in toluene (2 mL) at RT for 3 hours. The reaction was concentrated in vacuo and the resulting residue purified by chromatography on silica gel using 50% ethyl acetate/hexanes to provide the title compound, as an oil (yield: 7.1 mg, 19%).

MS: $(M+H)^+=482$, $(M+Na)^+=504$, $(M-H)^-=480$.

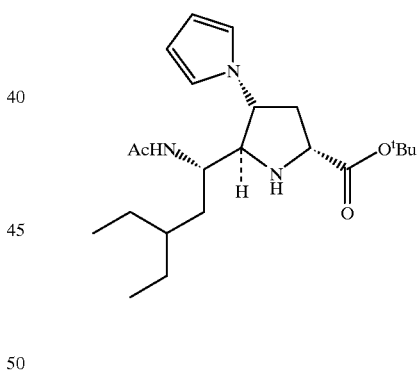

22D. (±)-(2S,3R,5R,1'S)-2-(1-Acetamido-3-ethyl)pentyl-3-(pyrrol-1-yl)-pyrrolidine-5-carboxylic Acid t-Butyl ester The title compound is prepared according to the method described in Example 1J, substituting (±)-(2S,3R,5R,1'S)-1-benzyl-2-(1-acetamido-3-ethyl)pentyl-3-(pyrrol-1-yl)-pyrrolidine-5-carboxylic acid t-butyl ester in place of (±)-(2R,3R,5R,$_1$'S)-1-benzyl-2-(1-acetamido-3-ethyl)pentyl-3-methoxymethyl-pyrrolidine-5-carboxylic acid t-butyl ester (yield: 3.5 mg, 61%).

MS: $(M+H)^+=392$, $(M-H)^-=390$.

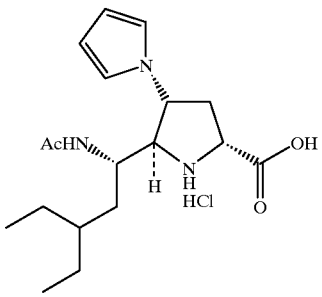

22E. (±)-(2S,3R,5R,1'S)-2-(1-Acetamido-3-ethyl) pentyl-3-(pyrrol-1-yl)-pyrrolidine-5-carboxylic Acid Hydrochloride The title compound was prepared according to the method described in Example 1K, substituting (±)-(2S,3R,5R,1'S)-2-(1-acetamido-3-ethyl)pentyl-3-(pyrrol-1-yl)-pyrrolidine-5-carboxylic acid t-butyl ester in place of (±)-(2R,3R,5R,1'S)-2-(1-acetamido-3-ethyl)pentyl-3-methoxymethyl-pyrrolidine-5-carboxylic acid t-butyl ester (yield: 3.5 mg, 100%).

$^1$H NMR (D$_2$O) δ7.48 (bs, 1H), 6.77 (bs, 2H), 5.97 (bs, 2H), 4.33 (m, 1H), 3.70 (m, 1H), 3.07 (m, 1H), 2.43 (m, 1H), 1.92 (m, 1H), 1.75 (s, 3H), 1.55 (m, 1H), 1.35–1.10 (m, 7H), 0.81 (m, 3H), 0.75 (m, 3H).

MS: (M+H)$^+$=336, (M–H)$^-$=334.

EXAMPLE 23

(±)-(2R,3R,5R,1'S)-2-(1-Acetamido-3-ethyl)pentyl-3-(1-cis-N-hydroxyimino)ethyl-pyrrolidine-5-carboxylic Acid Hydrochloride

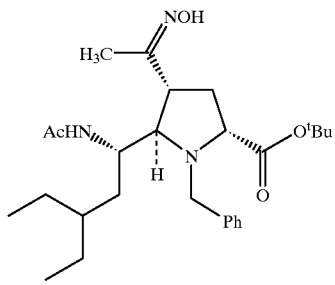

23A. (±)-(2R,3R,5R,1'S)-1-Benzyl-2-(1-acetamido-3-ethyl)pentyl-3-(1-cis-N-hydroxyimino)ethyl-pyrrolidine-5-carboxylic Acid t-Butyl Ester (±)-(2R,3R,5R,1'S) 1-Benzyl-2-(1-acetamido-3-ethyl)pentyl-3-acetyl-pyrrolidine-5-carboxylic acid t-butyl ester (45 mg, 0.1 mmol) prepared according to the method of Example 8B in methanol/methylene chloride (3/1) was reacted with a solution of hydroxylamine hydrochloride (21 mg, 0.3 mmol) and sodium hydroxide (12 mg, 0.3 mmol) in methanol (2 mL) for 2 h. The reaction was diluted with ethyl acetate. The organic layer was washed with water, and brine, dried over MgSO$_4$, filtered and concentrated in vacuo. The residue was purified by chromatography on silica gel using 40% ethyl acetate/hexanes to provide the cis-oxime title compound (lower Rf spot on TLC), as an oil (yield: 35 mg, 75%), as well as the trans-oxime title compound (higher Rf spot on TLC), as an oil (yield: 13 mg, 25%).

MS: (M+H)$^+$=474

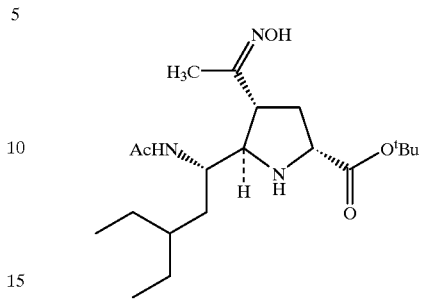

23B (±)-(2R,3R,5R,1'S)-2-(1-acetamido-3-ethyl) pentyl-3(1-cis-N-hydroxyimino)ethyl pyrrolidine-5-carboxylic Acid t-Butyl Ester The title compound is prepared according to the method described in Example 1J, substituting (±)-(2R,3R,5R,1'S)-1-benzyl-2-(1-acetamido-3-ethyl)pentyl-3-(1-cis-N-hydroxyimino)ethyl-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester.

$^1$H NMR (CDCl$_3$): δ3.92 (br, 1H), 3.70 (m, 2H), 2.82 (m, 1H), 2.38 (m, 1H), 1.88 (s, 3H), 1.78 (s, 3H), 1.39 (s, 9H), 1.40–1.20 (m, 7H), 0.76 (m, 6H).

MS: (M+H)$^+$=384

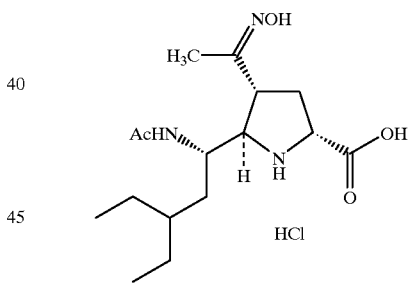

23C. (±)-(2R,3R,5R,1'S)-2-(1-acetamido-3-ethyl) pentyl-3-(1-cis-N-hydroxyimino)ethyl-pyrrolidine-5-carboxylic Acid Hydrochloride The title compound is prepared according to the method described in Example 1K, substituting (±)-(2R,3R,5R,1'S)-2-(1-acetamido-3-ethyl)pentyl-3-(1-cis-N-hydroxyimino) ethyl-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (D$_2$O): δ4.35 (m, 1H), 4.00 (m, 1H), 3.80 (m, 1H), 3.71 (m, 1H), 3.63 (m, 1H), 3.13 (q, J=8.4 Hz, 1H), 2.64 (m, 1H), 2.18 (m, 1H), 1.97 (s, 3H), 1.85 (s, 3H), 1.50–1.10 (m, 7H), 0.77 (m, 6H).

MS: (M+H)$^+$=328

EXAMPLE 24

(±)-(2R,3R,5R,1'S)-2-(1-Acetamido-3-ethyl)pentyl-3-(N-hydroxyimino)methyl-pyrrolidine-5-carboxylic Acid Hydrochloride

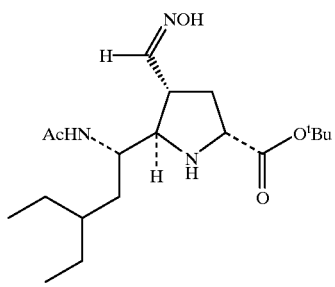

24A. (±)-(2R,3R,5R,1'S)-2-(1-Acetamido-3-ethyl)pentyl-3-(N-hydroxyimino)methyl-pyrrolidine-5-carboxylic Acid t-Butyl Ester (±)-(2R,3R,5R,1'S)-1-Benzyl-2-(1-acetamido-3-ethyl)pentyl-3-formyl-pyrrolidine-5-carboxylic acid t-butyl ester (18 mg, 0.051 mmol) prepared according to the method of Example 2A was reacted with hydroxylamine hydrochloride (7 mg, 0.11 mmol) in 1N NaOH in methanol (3 mL) at 25° C. for 1.5 hours. The reaction was quenched with aqueous ammonium chlororide (3ml) and water (3 ml) and taken by dichloromethane (2×10 ml). The organic layer was washed with water,and brine, dried over $MgSO_4$, filtered and concentrated in vacuo. The residue was purified by chromatography on silica gel using 5% methanol in dichloromethane to provide the title compound, as an oil (yield: 6 mg, 32%).

MS: $(M+H)^+=370$

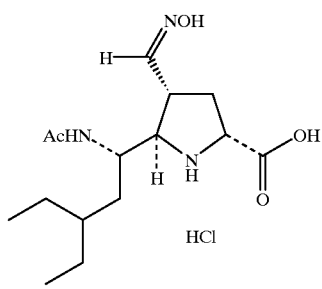

24B (±)-(2R,3R,5R,1'S)-2-(1-Acetamido-3-ethyl)pentyl-3-(N-hydroxyimino)methyl-pyrrolidine-5-carboxylic Acid Hydrochloride The title compound is prepared according to the method described in Example 1K, substituting (±)-(2R,3R,5R,1'S)-2-(1-acetamido-3-ethyl)pentyl-3-(N-hydroxyimino)methyl-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

EXAMPLE 25

(±)-(2R,3R,5R,1'S)-2-(1-Acetamido-3-ethyl)pentyl-3-(methoxyimino)methyl-pyrrolidine-5-carboxylic Acid

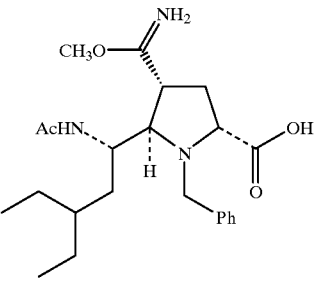

25A. (±)-(2R, 3R,5R,1'S) 1-Benzyl-2-(1-acetamido-3-ethyl)pentyl-3-(methoxyimino)methyl-pyrrolidine-5-carboxylic Acid (±)-(2R,3R,5R,1'S) 1-Benzyl-2-(1-acetamido-3-ethyl)pentyl-3-cyano-pyrrolidine-5-carboxylic acid t-butyl ester (20 mg, 0.045 mmol) prepared according to the method of Example 17E was reacted with hydrogen chloride (0.45 mmol) in ether (2 mL) and methanol (0.1 mL) at 0° C. for 5 hours. The reaction was neutralized with aqueous ammonium hydroxide and purified on silica gel with 3% methanol in dichloromethane to provide the title compound, as a white solid (yield: 5 mg, 26%).

MS: $(M+H)^+=418$

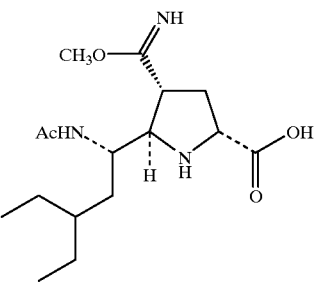

25B. (±)-(2R,3R,5R,1'S)-2-(1-Acetamido-3-ethyl)pentyl-3-(methoxyimino)methyl-pyrrolidine-5-carboxylic Acid The title compound is prepared according to the method described in Example 1J, substituting (±)-(2R,3R,5R,1'S) 1-Benzyl-2-(1-acetamido-3-ethyl)pentyl-3-(iminomethoxymethyl)-pyrrolidine-5-carboxylic acid t-butyl ester, in place of (±)-(2R,3R,5R,1'S)-1-benzyl-2-(1-acetamido-3-ethyl)pentyl-3-methoxymethyl-pyrrolidine-5-carboxylic acid t-butyl ester (yield: 3.9 mg, 96%).

$^1$H NMR (DMSO-$d_6$) δ7.52(d, J=8.7 HZ, 1H), 7.15(s, 1H),6.77(s, 1H), 3.68(m, 1H),3.61(s, 3H), 3.22(m,1H), 2.51 (m, 1H), 2.23(m,1H), 1.82(m, 1H), 1.78(s, 3H), 1.40(m, 1H), 1.26(m, 3H), 1.13(m, 3H), 0.78(t, J=6.5 HZ, 3H), 0.72(t, J=6.5 HZ, 3H)

MS: $(M+H)^+=328$

EXAMPLE 26

(±)-(2R,3R,5R,1'S)-2-(1-Acetamido-3-methyl)butyl-3-(hydroxyacetyl)-pyrrolidine-5-carboxylic Acid Hydrochloride

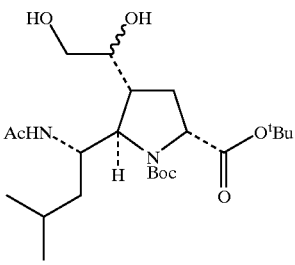

26A. (±)-(2R,3R,5R,1'S,1"RS)-1-t-Butoxycarbonyl-2-(1-acetamido-3-methyl)butyl-3-(1,2-dihydroxy)ethyl-pyrrolidine-5-carboxylic Acid t-Butyl Ester The title compound is prepared according to the method described in Example 20A substituting (±)-(2R,3R,5R,1'S)-1-t-butoxycarbonyl-2-(1-acetamido-3-methy)butyl-3-vinyl-pyrrolidine-5-carboxylic acid t-butyl ester for (±)-(2S,3R,5R)-1-benzyl-2-vinyl-3-(t-butyldimethylsilyloxymethyl)-pyrrolidine-5-carboxylic acid t-butyl ester.

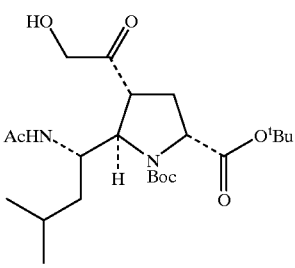

26B. (±)-(2R,3R,5R,1'S)-1-t-Butoxycarbonyl-2-(1-acetamido-3-methy)butyl-3-(hydroxyacetyl)-pyrrolidine-5-carboxylic Acid t-Butyl Ester (±)-(2R,3R,5R,1'S,1"RS)-1-t-Butoxycarbonyl-2-(1-acetamido-3-methy)butyl-3-(1,2-dihydroxy)ethyl-pyrrolidine-5-carboxylic acid t-butyl ester is reacted with dibutyltin oxide in methanol according to the procedure of Kong in J. Carbohydrate Chem. 1993, p. 557. The reaction is concentrated and the residue is redissolved in dichloromethane and reacted with bromine as described in the above reference to give the title compound.

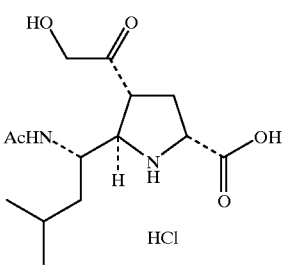

26C. (±)-(2R,3R,5R,1'S)-2-(1-Acetamido-3-methy)butyl-3-(hydroxyacetyl)-pyrrolidine-5-carboxylic Acid Hydrochloride The title compound is prepared according to the method described in Example 1K, substituting (±)-(2R,3R,5R,1'S)-1-t-butoxycarbonyl-2-(1-acetamido-3-methy)butyl-3-hydroxyacetyl-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

EXAMPLE 27

(±)-(2S,3R,5R,1'S)-2-(1-Acetamido-3-methy)butyl-3-amino-pyrrolidine-5-carboxylic Acid Dihydrochloride

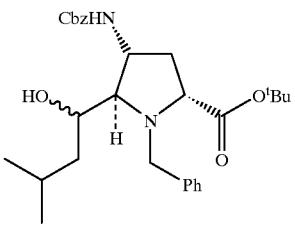

27A. (±)-(2S,3R,5R,1'RS)-1-Benzyl-2-(1-hydroxy-3-methyl)butyl-3-benzyloxycarbonylamino-pyrrolidine-5-carboxylic Acid t-Butyl Ester The title compound was prepared according to the method described in Example 9D, substituting isobutylmagnesium bromide in place of 3-pentylmagnesium bromide.

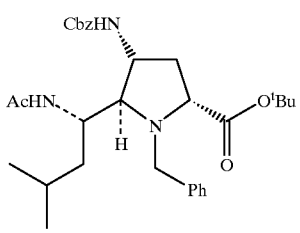

27B. (±)-(2S,3R,5R,1'S)-1-Benzyl-2-(1-acetamido-3-methyl)butyl-3-benzyloxycarbonylamino-pyrrolidine-5-carboxylic Acid t-Butyl Ester The title compound was prepared according to the method described in Examples 9E–H substituting (±)-(2R,3R,5R,1'RS)-1-benzyl-2-(1-hydroxy-3-methyl)butyl-3-benzyloxycarbonylamino-pyrrolidine-5-carboxylic acid t-butyl ester for (±)-(2R,3R,5R,1'RS)-1-benzyl-2-(1-hydroxy-3-ethyl)pentyl-3-benzyloxycarbonylamino-pyrrolidine-5-carboxylic acid t-butyl ester as the starting material of the sequence in Example 9E.

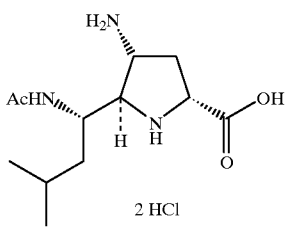

27C. (±)-(2S,3R,5R,1'S)-2-(1-acetamido-3-methyl)butyl-3-amino-pyrrolidine-5-carboxylic Acid Dihydrochloride The title compound was prepared according to the method described in Example 1K, substituting (±)-(2S,3R,5R,1'S)-

2-(1-acetamido-3-methyl)butyl-3-amino-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester.

$^1$H NMR (d$_6$-DMSO) δ8.64(bs, 1H), 8.32 (bs, 1H), 8.23 (bs, 1H), 8.18 (d, J=6 Hz, 1H), 4.79 (d, J=7 Hz, 1H), 4.42 (m, 1H), 4.33 (m, 1H), 4.21 (m, 1H), 4.07 (m, 1H), 3.76 (m, 2H), 2.73 (m, 2H), 1.92 (m, 3H), 0.80–0.97 (m, 7H).

MS (M+H)$^+$–258

EXAMPLE 28

(±)-(2R,3R,5R,1'S)-2-(1-Acetamido-3-methyl)butyl-3-methoxycarbonyl-pyrrolidine-5-carboxylic Acid Hydrochloride

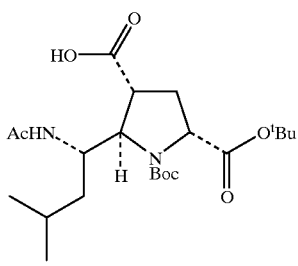

28A. (±)-(2R,3R,5R,1'S)-1-t-Butoxycarbonyl-2-(1-acetamido-3-methyl)butyl-3-carboxyl-pyrrolidine-5-carboxylic Acid t-Butyl Ester The title compound was prepared according to the method described in Example 2B, substituting (±)-(2R,3R,5R,1'S)-1-t-butoxycarbonyl-2-(1-acetamido-3-methyl)butyl-3-formyl-pyrrolidine-5-carboxylic acid t-butyl ester in place of (±)-(2R,3R,5R,1'S)-1-benzyl-2-(1-acetamido-3-ethyl)pentyl-3-formyl-pyrrolidine-5-carboxylic acid t-butyl ester.

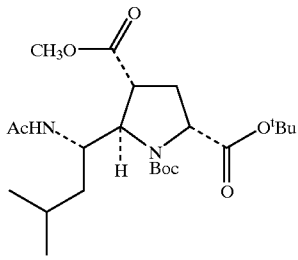

28B. (±)-(2R,3R,5R,1'S)-1-t-Butoxycarbonyl-2-(1-acetamido-3-methyl)butyl-3-methoxycarbonyl-pyrrolidine-5-carboxylic Acid t-Butyl Ester The title compound was prepared according to the method described in Example 2C, substituting (±)-(2R,3R,5R,1'S)-1-t-butoxycarbonyl-2-(1-acetamido-3-methyl)butyl-3-carboxyl-pyrrolidine-5-carboxylic acid t-butyl ester in place of (±)-(2R,3R,5R,1'S)-1-benzyl-2-(1-acetamido-3-ethyl)pentyl-3-carboxyl-pyrrolidine-5-carboxylic acid t-butyl ester.

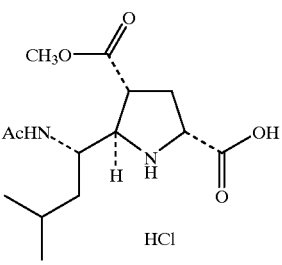

28C. (±)-(2R,3R,5R,1'S)-2-(1-Acetamido-3-methyl)butyl-3-methoxycarbonyl-pyrrolidine-5-carboxylic Acid Hydrochloride The title compound was prepared according to the method described in Example 2E, substituting (±)-(2R,3R,5R,1'S)-1-t-butoxycarbonyl-2-(1-acetamido-3-methyl)butyl-3-methoxycarbonyl-pyrrolidine-5-carboxylic acid t-butyl ester in place of (±)-(2R,3R,5R,1'S)-2-(1-acetamido-3-ethyl)pentyl-3-methoxycarbonyl-pyrrolidine-5-carboxylic acid t-butyl ester.

$^1$H NMR (DMSO-d$_6$): δ8.24, 8.08 (d, J=9 Hz, 1H), 4.44, 4.36 (m, 1H), 4.25, 4.15 (m, 1H), 3.98, 3.88 (m, 1H), 3.65, 3.64 (s, 3H), 3.18, 3.10 (m, 1H), 2.57, 2.20 (m, 2H), 1.87, 1.83 (s, 3H), 1.57 (m, 2H), 1.36 (m, 1H), 0.88 (d, J=7.5 Hz, 3H), 0.82 (d, J=7.5 Hz, 3H).

MS: (M+H)$^+$=301

EXAMPLE 29

(±)-(2R,3R,5R,1'S)-2-(1-Acetamido-3-methyl)butyl-3-(imidazol-2-yl)-pyrrolidine-5-Carboxylic Acid Dihydrochloride

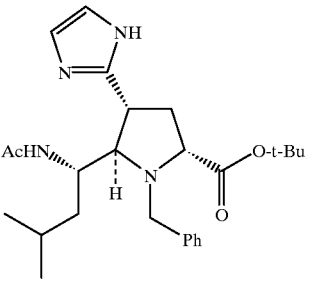

29A. (±)-(2R,3R,5R,1'S)-1-Benzyl-2-(1-acetamido-3-methyl)butyl-3-(imidazol-2-yl)-pyrrolidine-5-carboxylic Acid t-Butyl Ester The title compound was prepared according to the method described in Example 15A, substituting (±)-(2R,3R,5R,1'S)-1-benzyl-2-(1-acetamido-3-methyl)butyl-3-formyl-pyrrolidine-5-carboxylic acid t-butyl ester in place of (±)-(2R,3R,5R,1'S)-1-benzyl-2-(1-acetamido-3-ethyl)pentyl-3-formyl-pyrrolidine-5-carboxylic acid t-butyl ester (yield: 27.4 mg, 83. %).

MS: (M+H)$^+$=455.

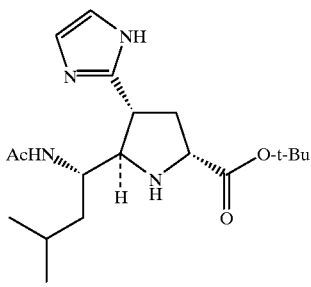

29B. (±)-(2R,3R,5R,1'S)-2-(1-Acetamido-3-methyl)butyl-3-(imidazol-2-yl)-pyrrolidine-5-carboxylic Acid t-Butyl Ester The title compound was prepared according to the method described in Example 15B, substituting (±)-(2R,3R,5R,1'S)-1-benzyl-2-(1-acetamido-3-methyl)butyl-3-(imidazol-2-yl)-pyrrolidine-5-carboxylic acid t-butyl ester in place of (±)-(2R,3R,5R,1'S)-1-benzyl-2-(1-acetamido-3-ethyl)pentyl-3-(imidazol-2-yl)-pyrrolidine-5-carboxylic acid t-butyl ester (yield: 19.1 mg, 95.5%).

MS: $(M+H)^+=365$.

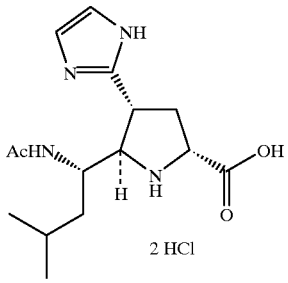

29C (±)-(2R,3R,5R,1'S)-2-(1-Acetamido-3-methyl)butyl-3-(imidazol-2-yl)-pyrrolidine-5-Carboxylic Acid Dihydrochloride The title compound was prepared according to the method described in Example 15B, substituting (±)-(2R,3R,5R,1'S)-1-benzyl-2-(1-acetamido-3-methyl)butyl-3-(imidazol-2-yl)-pyrrolidine-5-carboxylic acid t-butyl ester in place of (±)-(2R,3R,5R,1'S)-1-benzyl-2-(1-acetamido-3-ethyl)pentyl-3-(imidazol-2-yl)-pyrrolidine-5-carboxylic acid t-butyl ester.

$^1$H NMR (DMSO-$d_6$): δ0.76 (d, J=6.6 Hz, 3H), 0.82 (d, J=6.6 Hz, 3H), 1.18 (t, 2H), 1.44 (m, 1H), 1.71 (s, 3H), 2.43–2.47 (m, 1H), 2.80 (m, 1H), 3.83 (m, 1H), 4.05 (m, 1H), 4.28 (m, 1H), 4.55 (t, 1H), 7.65 (s, 2H), 8.03 (d, J=8.4 Hz, 1H).

MS: $(M+H)^+=326$.

EXAMPLE 30

(±)-(2R,3R,5R,1'S)-2-(1-Acetamido-3-methyl)butyl-3-(imidazol-4-yl)-pyrrolidine-5-carboxylic Acid Dihydrochloride

30A. (±)-(2R,3R,5R,1'S)-1-t-Butoxycarbonyl-2-(1-acetamido-3-methyl)butyl-3-carboxyl-pyrrolidine-5-carboxylic Acid t-Butyl Ester

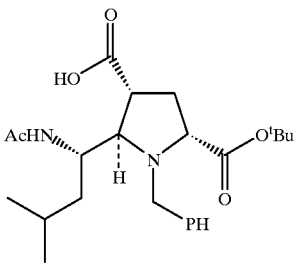

The title compound was prepared according to the method described in Example 2B, substituting (±)-(2R,3R,5R,1'S)-1-t-butoxycarbonyl-2-(1-acetamido-3-methy)butyl-3-formyl-pyrrolidine-5-carboxylic acid t-butyl ester prepared according to the method described in Example 20J in place (±)-(2R,3R,5R,1'S)-1-benzyl-2-(1-acetamido-3-ethyl)pentyl-3-formyl-pyrrolidine-5-carboxylic acid t-butyl ester (yield: 129.5 mg,>100%).

MS. $(M+H)^+=443$.

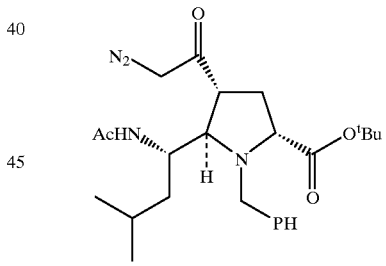

30B. (±)-(2R,3R,5R,1'S)-1-Benzyl-2-(1-acetamido-3-methyl)butyl-3-diazoacetyl-pyrrolidine-5-carboxylic Acid t-Butyl Ester The title compound was prepared according to the method described in Example 12A, substituting (±)-(2R,3R,5R,1'S)-1-benzyl-2-(1-acetamido-3 -methyl)butyl-3-carboxyl-pyrrolidine-5-carboxylic acid t-butyl ester in place of (±)-(2R,3R,5R,1'S)-1-benzyl-2-(1-acetamido-3-ethyl)pentyl-3-carboxyl-pyrrolidine-5-carboxylic acid t-butyl ester (yield: 218.8 mg, 100%).

MS: $(M+H)^+=458$.

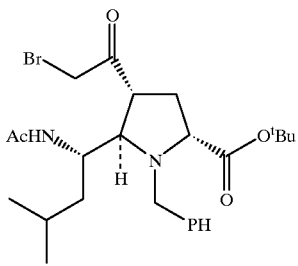

30C. (±)-(2R,3R,5R,1'S)-1-Benzyl-2-(1-acetamido-3-methyl)butyl-3-bromoacetyl-pyrrolidine-5-carboxylic Acid t-Butyl Ester The title compound was prepared according to the method described in Example 12B, substituting (±)-(2R,3R,5R,1'S)-1-benzyl-2-(1-acetamido-3-methyl)butyl-3-diazoacetyl-pyrrolidine-5-carboxylic acid t-butyl ester in place of (±)-(2R,3R,5R,1'S)-1-benzyl-2-(1-acetamido-3-ethyl)pentyl-3-diazoacetyl-pyrrolidine-5-carboxylic acid t-butyl ester (yield: 107.2 mg, 45.5%).

$^1$H NMR (CDCl$_3$): δ0.90 (d, 6H), 1.26–1.35 (m, 3H), 1.42 (s, 9H), 1.95 (s, 3H), 2.25 (m, 2H), 3.11 (m, 1H), 3.54 (dd, 1H), 3.69 (m, 1H), 3.93 (dd, 2H), 4.11 (d, 1H), 4.27 (m, 1H), 4.35 (d, 1H), 5.05 (br d, 1H), 7.25–7.32 (m, 5H).

MS: (M+H)$^+$=509.

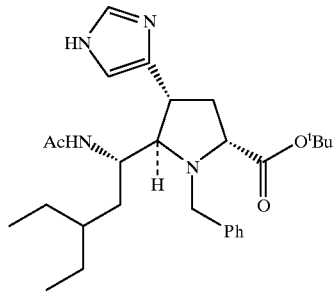

30D. (±)-(2R,3R5R,1'S)-1-Benzyl-2-(1-acetamido-3-methyl)butyl-3-(imidazol-4-yl)-pyrrolidine-5-carboxylic Acid t-Butyl Ester The title compound was prepared according to the method described in Example 12C, substituting (±)-(2R,3R,5R,1'S)-1-benzyl-2-(1-acetamido-3-methyl)butyl-3-bromoacetyl-pyrrolidine-5-carboxylic acid t-butyl ester in place of (±)-(2R,3R,5R,1'S)-1-benzyl-2-(1-acetamido-3-ethyl)pentyl-3-bromoacetyl-pyrrolidine-5-carboxylic acid t-butyl ester (yield: 32.3 mg, 60.4%).

MS: (M+H)$^+$=455.

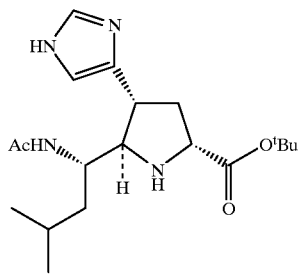

30E. (±)-(2R,3R,5R,1'S)-2-(1-Acetamido-3-methyl)butyl-3-(imidazol-4-yl)-pyrrolidine-5-carboxylic Acid t-Butyl Ester The title compound was prepared according to the method described in Example 1J, substituting (±)-(2R,3R,5R,1'S)-1-benzyl-2-(1-acetamido-3-methyl)butyl-3-(imidazol-4-yl)-pyrrolidine-5-carboxylic acid t-butyl ester in place of (±)-(2R,3R,5R,1'S)-1-benzyl-2-(1-acetamido-3-ethyl)pentyl-3-methoxymethyl-pyrrolidine-5-carboxylic acid t-butyl ester (yield: 23.9 mg, 96.2%).

$^1$H NMR (CDCl$_3$): δ0.87 (d, 3H), 0.89 (d, 3H), 1.26 (m, 1H), 1.41 (m, 2H), 1.46 (s, 9H), 1.59 (m, 1H), 1.93 (s, 3H), 2.62 (m, 1H), 3.30 (m, 1H), 3.54 (m, 1H), 3.79 (m, 1H), 4.01 (m, 1H), 6.11 (br d, 1H), 6.89 (s, 1H), 7.63 (s, 1H).

MS: (M+H)$^+$=365.

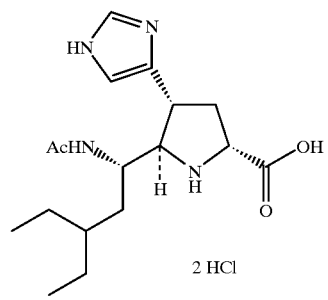

30F. (±)-(2R,3R,5R,1'S)-2-(1-Acetamido-2-methyl)butyl-3-(imidazol-4-yl)-pyrrolidine-5-carboxylic Acid Dihydrochloride The title compound was prepared according to the method described in Example 1K, substituting (±)-(2R,3R,5R,1'S)-2-(1-acetamido-3-methyl)butyl-3-(imidazol-4-yl)-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester to provide the title compound solid (yield: 24.4 mg, 100%).

$^1$H NMR (DMSO-d$_6$): δ0.76 (d, J=3.6 Hz, 3H), 0.88 (d, J=3.6 Hz, 3H), 1.22 (m, 1H), 1.28 (m, 1H), 1.48 (m, 1H), 1.79 (s, 3H), 2.32 (dt, 1H), 2.71 (dt, 1H), 3.68 (m, 1H), 3.96 (m, 1H), 4.28 (m, 1H), 4.51 (t, 1H), 7.63 (s, 1H), 8.23 (d, J=5.1 Hz, 1H), 9.10 (s, 1H), 9.67 (brs, 1H), 14.51 (brs, 1H).

MS: (M+H)$^+$=309.

EXAMPLE 31

(±)-(2R,3R,5R,1'S)-2-(1-Acetamido-3-methyl)butyl-3-(thiazol-4-yl)-pyrrolidine-5-carboxylic Acid Dihydrochloride

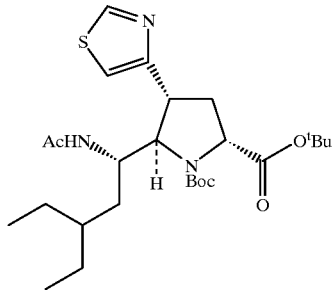

31A. (±)-(2R,3R,5R,1'S)-1-t-Butoxycarbonyl-2-(1-acetamido-3-methyl)butyl-3-(thiazol-4-yl)-pyrrolidine-5-carboxylic Acid t-Butyl Ester (±)-(2R,3R,5R,1'S)-1-t-Butoxycarbonyl-2-(1-acetamido-3-methyl)butyl-3-bromoacetyl-pyrrolidine-5-carboxylic acid t-butyl ester (36.5 mg, 0.07 mmol) was reacted with thioformamide (21.4 mg, 0.35 mmol) in ethanol (5 ml) at reflux for 4 hours. The reaction was concentrated in vacuo. The residue was treated with 5 ml of aqueous $NaHCO_3$ and extracted with dichloromethane (4×5 ml). The organic layers were washed with brine, dried over $Na_2SO_4$, filtered and concentrated in vacuo. The residue was purified by chromatography on silica gel using ethyl acetate to provide the title compound, as a white solid (yield: 23.8 mg, 70.4%).

MS: $(M+H)^+=482$.

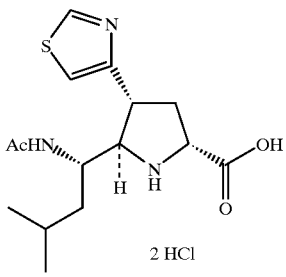

2 HCl

31B. (±)-(2R,3R,5R,1'S)-2-(1-Acetamido-3-methyl)butyl-3-(thiazol-4-yl)-pyrrolidine-5-carboxylic Acid Dihydrochloride The title compound was prepared according to the method described in Example 1K, substituting (±)-(2R,3R,5R,1'S)-1-t-butoxycarbonyl-2-(1-acetamido-3-methyl)butyl-3-(thiazol-4-yl)-pyrrolidine-5-carboxylic acid t-butyl ester in place of (±)-(2R,3R,5R,1'S)-2-(1-acetamido-3-ethyl)pentyl-3-methoxymethyl-pyrrolidine-5-carboxylic acid t-butyl ester (yield: 18.5 mg, 100%).

$^1$H NMR (DMSO-$d_6$): δ0.62 (d, J=4.2 Hz, 3H), 0.72 (d, J=4.2 Hz, 3H), 1.05 (m, 1H), 1.12 (m, 1H), 1.30 (m, 1H), 1.72 (s, 3H), 2.14 (dt, 1H), 2.59 (dt, 1H), 3.69 (m, 1H), 3.92 (br m, 1H), 4.21 (m, 1H), 4.38 (br m, 1H), 7.46 (d, J=1.2 Hz, 1H), 8.02 (d, J=5.1 Hz, 1H), 9.04 (d, =1.2 Hz, 1H), 9.39 (brs, 1H), 9.48 (br s, 1H).

MS: $(M+H)^+=326$.

EXAMPLE 32

(±)-(2R,3R,5R,1'S)-2-(1-Acetamido-3-methyl)butyl-3-(thiazol-2-yl)-pyrrolidine-5-carboxylic Acid Dihydrochloride

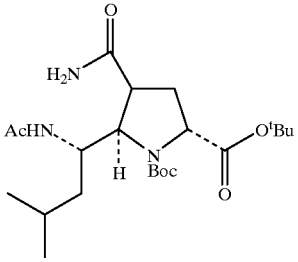

32A. (±)-(2R,3R,5R,1'S)-1-t-Butoxycarbonyl-2-(1-acetamido-3-methyl)butyl-3-carbamoyl-pyrrolidine-5-carboxylic Acid t-Butyl Ester (±)-(2R,3R,5R,1'S)-1-t-Butoxycarbonyl-2-(1-acetamido-3-methyl)butyl-3-carboxyl-pyrrolidine-5-carboxylic acid t-butyl ester (0.258 g, 0.584 mmol) was reacted with isobutyl chloroformate (80 mg, 0.84 mmol) and N-methylmorpholine (59 mg, 0.584 mmol) in THF (10 mL) at 0° C. for 0.25 hours. Aqueous ammonium hydroxide (0.39 mL) was added and the reaction was stirred at 0° C. for 0.5 hours. The reaction was diluted with ethyl acetate. The organic layer was washed with water, and brine, dried over $MgSO_4$, filtered and concentrated in vacuo. The residue was purified by chromatography on silica gel using 100% ethyl acetate to 5% methanol-ethyl acetate to provide the title compound, as a glass (yield: 182 mg, 70.7%).

$^1$H NMR ($CD_3OD$) δ4.70(m, 1H), 4.36 (q, J=3 Hz, 1H), 4.05 (m, 1H),2.87(q of t, J=9 and 3 Hz, 1H), 2.52 (m, 1H), 2.36 (m, 1H) 1.94 (d, 3H),1.63 (m, 1H), 1.41–1.53 (m, 18H), 1.3 (m, 2H), 0.9–0.18 (m, 6H)

MS: $(M+H)^+=442$

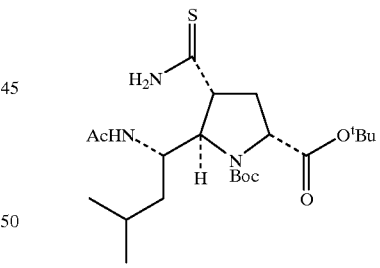

32B. (±)-(2R,3R,5R,1'S)-1-t-Butoxycarbonyl-2-(1-acetamido-3-methyl)butyl-3-thiocarbamoyl-pyrrolidine-5-carboxylic Acid t-Butyl Ester (±)-(2R,3R,5R,1'S)-1-t-Butoxycarbonyl-2-(1-acetamido-3-methy)butyl-3-carbamoyl-pyrrolidine-5-carboxylic acid t-butyl ester (70 mg, 0.159 mmol) was reacted with $P_2S_{10}$ (8.5 mg, 0.019 mmol) in 4 ml tetrahydrofuran and 1 ml of methylene chloride at room temperature. After 1.25 hrs, 9.6 mg of $P_2S_{10}$ was added. The starting material had been consumed after 2 hrs. The mixture was diluted with ethyl acetate, washed with water and brine, dried over $MgsO_4$, filtered and concentrated. The analysis showed two spots and the mass spectrum indicated it was a mixture of monothio and di-thio compounds. The material was used in the next reaction without further purification.

MS: (M+H)⁺=458, 474

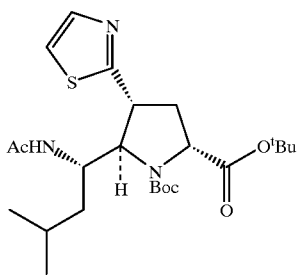

32C. (±)-(2R,3R,5R,1'S)-1-t-Butoxycarbonyl-2-(1-acetamido-3-methyl)butyl-3-(thiazol-2-yl)-pyrrolidine-5-carboxylic Acid t-Butyl Ester (±)-(2R,3R,5R,1'S)-1-t-Butoxycarbonyl-2-(1-acetamido-3-methy)butyl-3-thiocarbamoyl-pyrrolidine-5-carboxylic acid t-butyl ester (73 mg, o.16 mmol) was reacted with chloroacetaldehyde (50% in water) (0.02 ml, 0.16 mmol) in 5 ml of acetone at 75° C. Magnesium sulfate (0.9 g) and additional chloroacetaldehyde was added at intervals over the next 5 hr when till complete conversion of starting material. The reaction was diluted with ethyl acetate, washed with water, and brine, dried over MgSO₄, filtered and concentrated in vacuo The residue was purified by chromatography on silica gel using 100% ethyl acetate to provide the title compound, as a glass (yield: 12.6 mg, 16.3%).

¹H NMR (CDCl₃) δ7.69(m, 1H), 7.45(m, 1H), 4.44 (m, 1H), 4.28 (m, 2H), 3.52(m, 1H), 2.7 (m, 1H), 2.5 (m, 1H), 1.99 (s, 3H), 1.44 (s, 9H), 1.37 (s, 9H), 1.27 (m, 3H), 0.95 (m, 6H).

MS: (M+H)⁺=482

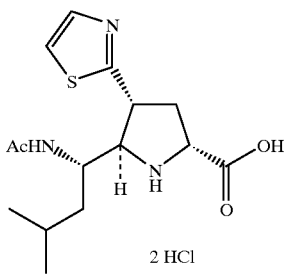

2 HCl

32D. (±)-(2R,3R,5R,1'S)-1-t-Butoxycarbonyl-2-(1-acetamido-3-methyl)butyl-3-(thiazol-2-yl)-pyrrolidine-5-carboxylic Acid Dihydrochloride The title compound was prepared according to the method described in Example 1K, substituting (±)-(2R,3R,5R,1'S)-1-t-butoxycarbonyl-2-(1-acetamido-3-methyl)butyl-3-(thiazol-2-yl)-pyrrolidine-5-carboxylic acid t-butyl ester in place of (±)-(2R,3R,5R,1'S)-2-(1-acetamido-3-ethyl)pentyl-3-methoxymethyl-pyrrolidine-5-carboxylic acid t-butyl ester (yield: 10.1 mg, 82%).

¹H NMR (DMSO-d₆) δ8.1 (d, J=10 Hz, 1H), 7.79 (d, J=4 Hz, 1H), 7.69 (d=4 Hz, 1H), 4.49 (t, J=7.5, 1H), 4.22 (m, 1H), 4.14 (t, J=9 Hz, 1H), 4.01 (q, J=10 Hz, 1H), 2.80 (m, 1H), 2.25 (m, 1H), 1.78 (s, 3H), 1.47 (m, 1H), 1.25 (m, 2H), 0.83 (d, J=6.2 Hz, 3H), 0.75 (d, J=6.2 Hz, 3H)

MS: (M−H)⁻=324, (2M−1)⁻=649, (M+35)⁺=360

EXAMPLE 33

(±)-(2R,3S,5R,1'S)-2-(1-acetamido-3-methyl)butyl-3-(cis-2-chloro-vin-1-yl)-pyrrolidine-5-carboxylic Acid Trifluoroacetic Acid Salt

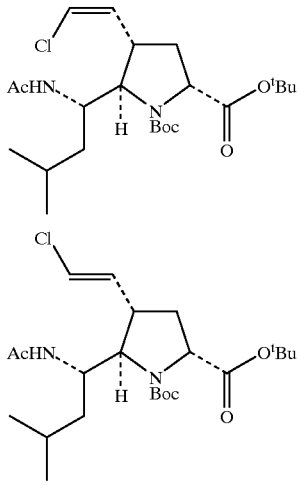

33A. (±)-(2R,3S,5R,1'S)-1-t-Butoxycarbonyl-2-(1-acetamido-3-methyl)butyl-3-(cis-2-chloro-vin-1-yl)-pyrrolidine-5-carboxylic Acid t-Butyl Ester and (±)-(2R,3S,5R,1'S)-1-t-Butoxycarbonyl-2-(1-acetamido-3-methyl)butyl-3-(trans-2-chloro-vin-1-yl)-pyrrolidine-5-carboxylic Acid t-Butyl Ester The title compound was prepared according to the method described in Example 20K substituting (chloromethyl) triphenylphosphonium chloride in place of methyltriphenylphosphonium bromide. The higher Rf 0.73 (ethyl acetate) new spot was identified to be the cis-isomer (yield: 38.4 mg, 40%) and the lower Rf 0.57 (ethyl acetate) spot trans- isomer (yield: 42 mg, 43%).

cis-isomer ¹H NMR (CDCl₃): δ7.44 (br, 1H), 6.13 (d, J=7.5 Hz, 1H), 5.32 (dd, J=9 Hz, J=7.5 Hz, 1H), 4.31–4.16 (m, 2H), 3.65 (m, 1H), 3.12 (m, 1H), 2.50 (m, 1H), 1.98 (s, 3H), 1.62 (m, 1H), 1.47 (s, 9H), 1.45 (s, 9H), 1.30–1.07 (m, 2H), 0.82 (m, 6H)

MS: (M+H)⁺=459 trans-isomer ¹H NMR (CDCl₃): δ6.12–5.90 (m, 2H), 4.30–4.07 (m, 2H), 3.64 (m, 1H), 2.62–2.37 (m, 2H), 1.98 (s, 3H), 1.69 (m, 1H), 1.48 (s, 9H), 1.45 (s, 9H), 1.26 (m, 2H), 0.91 (m, 6H).

MS: (M+H)⁺=459

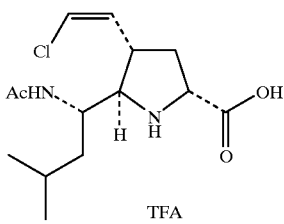

33B. (±)-(2R,3S,5R,1'S)-2-(1-acetamido-3-methyl) butyl-3-(cis-2-chloro-vin-1-yl)-pyrrolidine-5-carboxylic Acid Trifluoroacetic Acid Salt (±)-(2R,3S,5R,1'S)-1-t-Butoxycarbonyl-2-(1-acetamido-3-methyl)butyl-3-(cis-2-chloro-vin-1-yl)-pyrrolidine-5-carboxylic acid t-butyl ester (10 mg, 0.022 mmol) was reacted with trifluoroacetic acid (1.8 mL) in dichloromethane (0.4 mL) at room temperature for 7 hours. The reaction was concentrated in vacuo. The residue was dried on high vacuum to provide the title compound.

$^1$H NMR (DMSO-d$_6$): δ8.015 (d, J=7.63 Hz, 1H), 6.42 (d, J=7.02 Hz, 1H), 5.89 (dd, J=7.02 Hz, J=8.7 Hz, 1H), 4.42 (m, 1H), 4.17 (m, 1H), 3.59 (m, 1H), 3.31 (m, 1H), 2.47 (m,1H), 1.88 (s, 3H), 1.84 (m, 1H), 1.58 (m, 1H), 1.39 (m, 1H), 1.29 (m, 2H), 0.885 (d, J=6.71 Hz, 3H), 0.83 (d, J=6.41, 3H).

MS: (M+H)$^+$=303

EXAMPLE 34

(±)-(2R,3S,5R,1'S)-2-(1-acetamido-3-methyl)butyl-3-(trans-2-chloro-vin-1-yl)-pyrrolidine-5-carboxylic Acid Trifluoroacetic Acid Salt

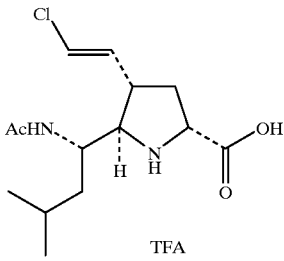

34B. (±)-(2R,3S,5R,1'S)-2-(1-acetamido-3-methyl) butyl-3-(trans-2-chloro-vinyl)-pyrrolidine-5-carboxylic Acid Trifluoroacetic Acid Salt The title compound was prepared according to the method described in Example 33B, substituting (±)-(2R,3S,5R,1'S)-1-t-butoxycarbonyl-2-(1-acetamido-3-methyl)butyl-3-(trans-2-chloro-vin-1-yl)-pyrrolidine-5-carboxylic acid t-butyl ester in place of (±)-(2R,3S,5R,1'S)-1-t-butoxycarbonyl-2-(1-acetamido-3-methyl)butyl-3-(cis-2-chloro-vin-1-yl)-pyrrolidine-5-carboxylic acid t-butyl ester.

$^1$H NMR (DMSO-d$_6$): δ8.04 (d, J=7.93 Hz, 1H), 6.355 (d, J=13.1 Hz, 1H), 5.93 (dd, J=13.1 Hz, J=9.32 Hz, 1H), 4.33 (m, 1H), 4.19 (m, 1H), 2.95 (m, 1H), 2.40 (m, 1H), 1.94 (m, 1H), 1.88 (s, 3H), 1.58 (m, 1H), 1.39 (m,1H), 1.29 (m, 1H), 0.89 (d, J=6.7 Hz, 3H), 0.825 (d, J=6.7 Hz, 3H).

MS: (M+H)$^+$=303

EXAMPLE 35

(±)-(2R,3S,5R,1'S)-2-(1-acetamido-3-methyl)butyl-3-(cis-propen-1-yl)-pyrrolidine-5-carboxylic Acid Trifluoroacetic Acid Salt

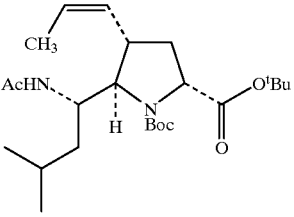

35A. (±)-(2R,3R,5R,1'S)-1-t-Butoxycarbonyl-2-(1-acetamido-3-methyl)butyl-3-(cis-propen-1-yl)-pyrrolidine-5-carboxylic Acid t-Butyl Ester To a suspension of ethyl triphenylphosphonium bromide (479 mg, 1.29 mmol) in 3 mL anhydrous toluene was added potassium t-butoxide (1.0 M in THF, 0.94 mmol) dropwise at room temperature. After stirring for 2.5 hours, (±)-(2R, 3R,5R,1'S)-1-t-Butoxycarbonyl-2-(1-acetamido-3-methyl) butyl-3-formyl-pyrrolidine-5-carboxylic acid t-butyl ester (90 mg, 0.211 mmol) in 5 mL toluene was added dropwise and stirred for 1 hour. The reaction was quenched with saturated aqueous ammonium chloride and diluted with ethyl acetate. The organic layer was washed with water, and brine, dried over MgSO$_4$, filtered and concentrated in vacuo. The residue was purified by chromatography on silica gel using 50% ethyl acetate/hexanes to provide the title compound, as an oil (yield: 70.6 mg, 76%).

MS: (M+H)$^+$=439

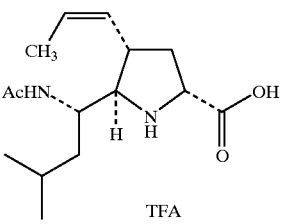

35B. (±)-(2R,3S,5R,1'S)-2-(1-acetamido-3-methyl) butyl-3-(cis-propen-1-yl)-pyrrolidine-5-carboxylic Acid Trifluoroacetic Acid Salt The title compound was prepared according to the method described in Example 33B, substituting (±)-(2R,3S,5R,1'S)-1-t-butoxycarbonyl-2-(1-acetamido-3-methyl)butyl-3-(cis-propen-1-yl)-pyrrolidine-5-carboxylic acid t-butyl ester in place of (±)-(2R,3S,5R,1'S)-1-t-butoxycarbonyl-2-(1-acetamido-3-methyl)butyl-3-(cis-2-chloro-vinyl)-pyrrolidine-5-carboxylic acid t-butyl ester.

$^1$H NMR (DMSO-d$_6$): δ8.04 (d, J=7.5 Hz, 1H), 5.51 (m, 1H), 5.26 (m, 1H), 4.32 (m, 1H), 4.18 (m, 1H), 3.45 (m, 1H), 3.18 (m, 1H), 2.39 (m, 1H), 1.88 (s, 3H), 1.73 (m, 1H), 1.63 (dd, 3H), 1.58 (m, 1H), 1.38 (m, 1H), 1.28 (m, 1H), 0.88 (d, J=6 Hz, 3H), 0.81 (dd, J=6 Hz, 3H).

MS: (M+H)$^+$=283

EXAMPLE 36

(±)-(2R,3S,5R,1'S)-2-(1-acetamido-3-methyl)butyl-3-(2,2-dimethyl-vin-1-yl)-pyrrolidine-5-carboxylic Acid Trifluoroacetic Acid Salt

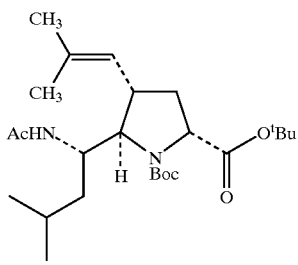

36A. (±)-(2R,3S,5R,1'S)-1-t-Butoxycarbonyl-2-(1-acetamido-3-methyl)butyl-3-(2,2-dimethyl-vin-1-yl)-pyrrolidine-5-carboxylic Acid t-Butyl Ester The title compound was prepared according to the method described in Example 20K substituting isopropyl triphenylphosphonium iodide in place of methyltriphenylphosphonium bromide (yield: 22.6 mg, 33%).

$^1$H NMR (CDCl$_3$): δ7.77 (d, 1H), 5.06 (d, J=10 Hz, 1H), 4.18 (m, 2H), 3.50 (m, 1H), 2.69 (m, 1H), 2.32 (m, 1H), 1.97 (s, 3H), 1.70 (s, 3H), 1.64 (s, 3H), 1.65 (m, 1H), 1.47 (s, 9H), 1.44 (s, 9H), 1.30–1.00 (m, 3H), 0.93 (d, J=6 Hz, 3H), 0.88 (d, J=6 Hz, 3H).

MS: (M+H)$^+$=453

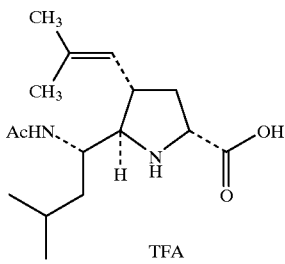

36B. (±)-(2R,3S,5R,1'S)-2-(1-acetamido-3-methyl)butyl-3-(2,2-dimethyl-vin-1-yl)-pyrrolidine-5-carboxylic Acid Trifluoroacetic Acid Salt The title compound was prepared according to the method described in Example 33B, substituting (±)-(2R,3S,5R,1'S)-1-t-butoxycarbonyl-2-(1-acetamido-3-methyl)butyl-3-(2,2-dimethyl-vin-1-yl)-pyrrolidine-5-carboxylic acid t-butyl ester in place of (±)-(2R,3S,5R,1'S)-1-t-butoxycarbonyl-2-(1-acetamido-3-methyl)butyl-3-(cis-2-chloro-vin-1-yl)-pyrrolidine-5-carboxylic acid t-butyl ester.

$^1$H NMR (DMSO-d$_6$): δ8.01 (d, J=7.5 HZ, 1H), 4.99 (d, J=10 Hz, 1H), 4.30 (m, 1H), 4.14 (m, 1H), 3.40 (m, 1H), 3.06 (m, 1H), 2.36 (m, 1H), 1.86 (s, 3H), 1.66 (s, 3H), 1.63 (s, 3H), 1.57 (m, 1H), 1.39–1.20 (m, 3H), 0.88 (d, J=6 Hz, 3H), 0.81 (d, J=6 Hz, 3H).

MS: (M+H)$^+$=297

EXAMPLE 37

(±)-(2R,3S,5R,1'S)-2-(1-acetamido-3-methyl)butyl-3-(2,2-difluoro-vin-1-yl)-pyrrolidine-5-carboxylic Acid Trifluoroacetic Acid Salt

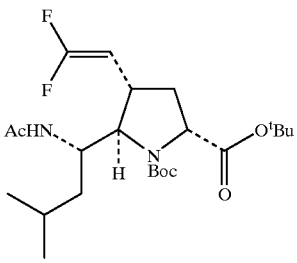

37A. (±)-(2R,3S,5R,1'S)-1-t-Butoxycarbonyl-2-(1-acetamido-3-methyl)butyl-3-(2,2-difluoro-vin-1-yl)-pyrrolidine-5-carboxylic Acid t-Butyl Ester n-Butyllithium (1.6M in hexanes, 0.61 mL, 0.97 mmol) was added to diisopropylamine (136 μL, 0.97 mmol) in 4 mL THF at −78° C. and stirred for 30 min. diethyl difluoromethylphosphonate (182 mg, 0.97 mmol) was added, the colorless solution changed slowly to yellow after stirring at −78° C. for 2 hours. (±)-(2R,3R,5R,1'S)-1-t-Butoxycarbonyl-2-(1-acetamido-3-methyl)butyl-3-formyl-pyrrolidine-5-carboxylic acid t-butyl ester (59 mg, 0.138 mmol) in 3 mL THF wag added, stirred at −78° C. for 30 min, then warm up to room temperature. The mixture was then heated at reflux for 1.5 hour, and stirred at room temperature overnight. The reaction was quenched with saturated aqueous ammonium chloride, and diluted with ethyl acetate. The organic layer was washed with water, and brine, dried over MgSO$_4$, filtered and concentrated in vacuo. The residue was purified by chromatography on silica gel using 50% ethyl acetate/hexanes to provide the title compound, as a light yellow oil (23.4 mg, 37%).

$^1$H NMR (CDCl$_3$): δ7.44 (d, 1H), 5.92 (ddd, 1H), 4.30–4.00 (m, 2H), 3.55 (m, 1H), 2.69 (m, 1H), 2.45 (m, 1H), 2.00 (s, 3H), 1.47 (s, 9H), 1.43 (s, 9H), 1.45–1.00 (m, 4H), 0.91 (m, 6H).

MS: (M+H)$^+$=461

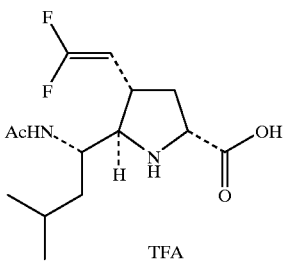

37B. (±)-(2R,3S,5R,1'S)-2-(1-acetamido-3-methyl)butyl-3-(2,2-difluoro-vin-1-yl)-pyrrolidine-5-carboxylic Acid Trifluoroacetic Acid Salt The title compound was prepared according to the method described in Example 33B, substituting (±)-(2R,3S,5R,1'S)-1-t-butoxycarbonyl-2-(1-acetamido-3-methyl)butyl-3-(2,2-difluoro-vin-1-yl)-pyrrolidine-5-carboxylic acid t-butyl ester in place of (±)-(2R,3S,5R,1'S)-1-t-butoxycarbonyl-2-

(1-acetamido-3-methyl)butyl-3-(cis-2-chloro-vin-1-yl)-pyrrolidine-5-carboxylic acid t-butyl ester.

$^1$H NMR (DMSO-d$_6$): δ8.04 (d, J=7.5 Hz, 1H), 4.59 (ddd, 1H), 4.23 (m, 1H), 4.14 (m, 1H), 3.48 (m, 1H), 3.39 (m, 1H), 2.91 (m, 1H), 2.43 (m, 1H), 1.85 (s, 3H), 1.58 (m, 1H), 1.40 (m, 1H), 1.1 (m, 1H), 1.22 (m, 1H), 0.89 (d, J=7.5 Hz, 3H), 0.83 (d, J=7.5 Hz, 3H).

MS: (M+H)$^+$=305

EXAMPLE 38

(±)-(2R,3R,5R,1'S)-2-(1-acetamido-3-methyl)butyl-3-(pyrazol-3-yl)-pyrrolidine-5-carboxylic Acid Trifluoroacetic Acid Salt

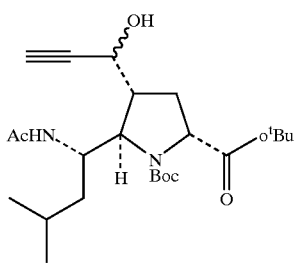

38A. (±)-(2R,3R,5R,1'S,1"RS)-1-t-Butoxycarbonyl-2-(1-acetamido-3-methyl)butyl-3-(1-hydroxy-2-propyn-1-yl)-pyrrolidine-5-carboxylic Acid t-Butyl Ester The title compound was prepared according to the method described in Example 4A substituting 2-propynyl magnesium bromide in place of ethyl magnesium bromide and substituting (±)-(2R,3R,5R,1'S)-1-t-Butoxycarbonyl-2-(1-acetamido-3-methyl)butyl-3-formyl-pyrrolidine-5-carboxylic acid t-butyl ester (250 mg, 0.587 mmol) in place of (±)-(2R,3R,5R,1'S)-1-benzyl-2-(1-acetamido-3-ethyl)pentyl-3-formyl-pyrrolidine-5-carboxylic acid t-butyl ester the crude product was used directly in the next reaction.

MS: (M+H)$^+$=453

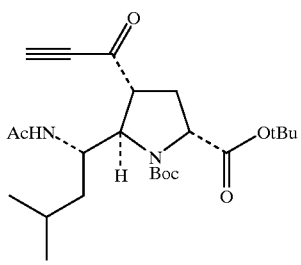

38B. (±)-(2R,3R,5R,1'S)-1-t-Butoxycarbonyl-2-(1-acetamido-3-methyl)butyl-3-(1-oxo-2-propyn-1-yl)-pyrrolidine-5-carboxylic Acid t-Butyl Ester (±)-(2R,3R,5R,1'S)-1-t-Butoxycarbonyl-2-(1-acetamido-3-methyl)butyl-3-(1-hydroxy-2-propyn-1-yl)-pyrrolidine-5-carboxylic acid t-butyl ester was reacted with Jones reagent (3.0 M in acetone, 0.33 mL) in acetone (90 mL) at 0° C. to room temperature for 1 hour. The reaction was diluted with ethyl acetate. The organic layer was washed with water, and brine, dried over MgSO$_4$, filtered and concentrated in vacuo. The residue was purified by chromatography on silica gel using 50% ethyl acetate/hexanes to provide the title compound, as a white solid (yield: 143 mg, 54%).

MS: (M+H)$^+$=491

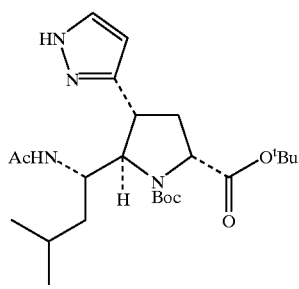

38C. (±)-(2R,3R,5R,1'S)-1-t-Butoxycarbonyl-2-(1-acetamido-3-methyl)butyl-3-(pyrazol-3-yl)-pyrrolidine-5-carboxylic Acid t-Butyl Ester (±)-(2R,3R,5R,1'S)-1-t-Butoxycarbonyl-2-(1-acetamido-3-methyl)butyl-3-(1-oxo-1-ethynyl)methyl-pyrrolidine-5-carboxylic acid t-butyl ester (140 mg, 0.311 mmol) was reacted with hydrazine monohydrate (0.24 mL, 4.944 mmol) in ethanol (12 mL) at room temperature for 4 hours. The reaction was concentrated in vacuo. The residue was purified by chromatography on silica gel using ethyl acetate to provide the title compound, as a white solid (yield: 131 mg, 91%).

MS: (M+H)$^+$=465

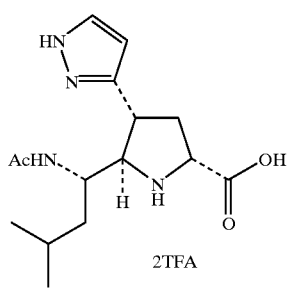

38D. (±)-(2R,3R,5R,1'S)-2-(1-acetamido-3-methyl)butyl-2-(pyrazol-2-yl)-pyrrolidine-5-carboxylic Acid Trifluoroacetic Acid Salt The title compound was prepared according to the method described in Example 33B, substituting (±)-(2R,3R,5R,1'S)-1-t-butoxycarbonyl-2-(1-acetamido-3-methyl)butyl-3-(pyrazol-3-yl)-pyrrolidine-5-carboxylic acid t-butyl ester in place of (±)-(2R,3R,5R,1'S)-1-t-butoxycarbonyl-2-(1-acetamido-3-methyl)butyl-3-(cis-2-chloro-vinyl)-pyrrolidine-5-carboxylic acid t-butyl ester.

$^1$H NMR (DMSO-d$_6$): δ8.13 (d, J=7.5 Hz, 1H), 7.65 (d, J=2.2 Hz, 1H), 6.20 (d, J=2.2 Hz, 1H), 4.39 (m, 1H), 4.25 (m, 1H), 3.94 (m, 1H), 3.56 (q, J=7.5 Hz, 1H), 2.62(m, 1H), 2.17 (m, 1H), 1.87 (s, 3H), 1.42 (m, 1H), 1.21 (m, 1H), 1.11 (m, 1H), 0.80 (d, J=6.6 Hz, 3H), 0.71 (d, J=6.6 Hz, 3H).

MS: (M+H)$^+$=309

EXAMPLE 39

(±)-(2R,3R,5R,1'S)-2-(1-acetamido-3-methyl)butyl-3-(isoxazol-3-yl)-pyrrolidine-5-carboxylic Acid Trifluoroacetic Acid Salt and (±)-(2R,3R,5R,1'S)-2-(1-acetamido-3-methyl)butyl-3-(isoxazol-5-yl)-pyrrolidine-5-carboxylic Acid Trifluoroacetic Acid Salt

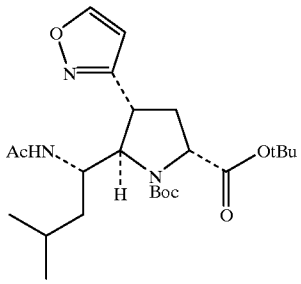

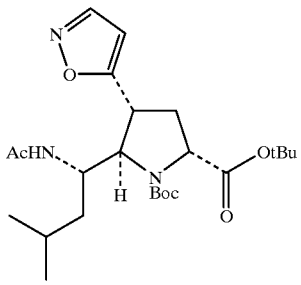

39A. (±)-(2R,3R,5R,1'S)-1-t-Butoxycarbonyl-2-(1-acetamido-3-methyl)butyl-3-(isoxazol-3-yl)-pyrrolidine-5-carboxylic Acid t-Butyl Ester and (±)-(2R,3R,5R,1'S)-1-t-Butoxycarbonyl-2-(1-acetamido-3-methyl)butyl-3-(isoxazol-5-yl)-pyrrolidine-5-carboxylic Acid t-Butyl Ester (±)-(2R,3R,5R,1'S)-1-t-Butoxycarbonyl-2-(1-acetamido-3-methyl)butyl-3-(1-oxo-1-ethynyl)methyl-pyrrolidine-5-carboxylic acid t-butyl ester (31 mg, 0.07 mmol) was reacted with hydroxyamine hydrochloride (4.9 mg, 0.07 mmol) and sodium carbonate (3.7 mg, 0.035 mmol) in ethanol (3 mL) at reflux for 30 hours. The reaction was concentrated in vacuo. The residue was purified by chromatography on silica gel using 3% methanol/dichloromethane to provide the title compound, as an oil (yield: 11.5 mg, 36%).

MS: (M+H)$^+$=466

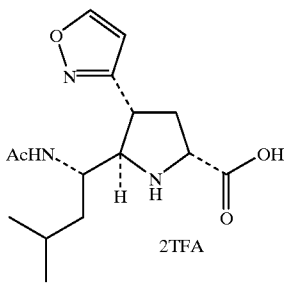

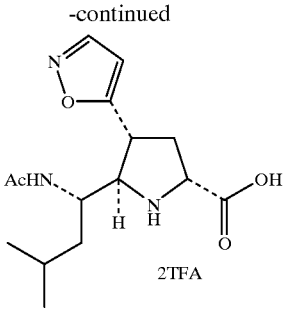

39B. (±)-(2R,3R,5R,1'S)-2-(1-acetamido-3-methyl)butyl-3-(isoxazol-3-yl)-pyrrolidine-6-carboxylic Acid Trifluoroacetic Acid Salt and (±)-(2R,3R,5R,1'S)-2-(1-acetamido-3-methyl)butyl-3-(isoxazol-5-yl)-pyrrolidine-5-carboxylic Acid Trifluoroacetic Acid Salt The title compound was prepared according to the method described in Example 33B, substituting (±)-(2R,3R,5R,1'S)-1-t-butoxycarbonyl-2-(1-acetamido-3-methyl)butyl-3-(isoxazol-3-yl)-pyrrolidine-5-carboxylic acid t-butyl ester and (±)-(2R,3R,5R,1'S)-1-t-butoxycarbonyl-2-(1-acetamido-3-methyl)butyl-3-(isoxazol-5-yl)-pyrrolidine-5-carboxylic acid t-butyl ester in place of (±)-(2R,3R,5R,1'S)-1-t-butoxycarbonyl-2-(1-acetamido-3-methyl)butyl-3-(cis-2-chloro-vinyl)-pyrrolidine-5-carboxylic acid t-butyl ester.

$^1$H NMR (DMSO-d$_6$): δ8.91, 8.54 (d,1H), 8.12, 8.05 (d, J=7.5 Hz, 1H), 6.64, 6.43 (d, 1H), 4.48, 4.51 (m, 1H), 4.28 (m, 1H), 3.97, 3.89 (m, 1H), 3.70, 3.81 (m, 1H), 2.72 (m, 1H), 2.20, 2.25 (m, 1H), 1.83, 1.80 (s, 3H), 1.48 (m, 1H), 1.34–1.10 (m, 2H), 0.83, 0.84 (d, J=6 Hz, 3H), 0.77, 0.78 (d, J=6 Hz, 3H).

MS: (M+H)$^+$=310

EXAMPLE 40

(±)-(2R,3S,5R,1'R)-2-(1-Acetamido-2-hydroxy)ethyl-3-(cis-propen-1-yl)-pyrrolidine-5-carboxylic Acid Trifluoroacetic Acid Salt

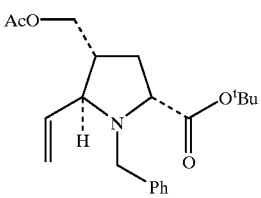

40A. (±)-(2R,3R,5R)-1-Benzyl-2-vinyl-3-(acetoxymethyl)-pyrrolidine-5-carboxylic Acid t-Butyl Ester (±)-(2R,3R,5R)-1-Benzyl-2-vinyl-3-(hydroxymethyl)-pyrrolidine-5-carboxylic acid t-butyl ester (54.2 g, 0.17 mol) and 4-(dimethylamino)pyridine (0.5 g, 4.1 mmol), in anhydrous pyridine (400 mL) was reacted with acetic anhydride (30 mL, 0.32 mol) at 0° C. for 1 hour then allowed to warm to room temperature. The reaction was stirred an additional 16 hours. The pyridine was removed in vacuo at 30° C. The residue was partitioned between ethyl acetate (100 mL) and of water (400 mL). The aqueous layer was extracted with ethyl acetate (3×100 mL) and the combined ethyl acetate layers were washed with brine, dried with MgSO$_4$, filtered, and concentrated. The crude product was purified by chromatography on silica gel using 10% ethyl acetate/hexanes to provide the title compound as a colorless oil (yield: 49.6 g, 81%).

$^1$H NMR (CDCl$_3$) δ7.28 (m, 4H), 7.21 (m,1H), 5.68 (m,1H), 5.21 (m, 2H), 4.16 (dd, J=6.3, 10.7 Hz, 1H), 4.10 (dd, J=7.3, 10.7 Hz, 1H), 3.92 (d, J=13.7 Hz, 1H), 3.64 (d, J=13.7 Hz, 1H), 3.52 (m, 1H), 3.50 (m, 1H), 2.33 (m, 1H), 2.26 (m, 1H), 2.02 (s, 3H), 1.62 (m, 1H), 1.45 (s, 9H).

MS (M+H)$^+$=360.

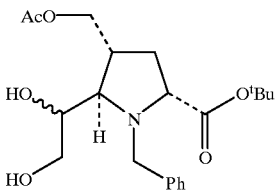

40B. (±)-(2R,3R,5R,1'R)-and (±)-(2R,3R,5R,1'S)-1-Benzyl-2-(1,2-dihydroxy)ethyl-3-(acetoxymethyl)-pyrrolidine-5-carboxylic Acid t-Butyl Ester (±)-(2R,3R,5R)-1-benzyl-2-vinyl-3-(acetoxymethyl)-pyrrolidine-5-carboxylic acid t-butyl ester. (52.5 g, 0.15 mol) and 4-methylmorpholine N-oxide (54.7 g, 0.47 mol) in acetone (540 mL) and water (60 mL) was reacted with osmium tetroxide (200 mg, 0.8 mmol). After 24 hours, the reaction was quenched with 10% sodium thiosulfate (250 mL) concentrated in vacuo. The aqueous layer was extracted with ethyl acetate (3×300 mL) and the combined organic layers were washed with brine, dried over MgSO$_4$, filtered and concentrated. The residue was purified by chromatography on silica gel using a gradient elution of ethyl acetate and dichloromethane to provide the title compound as a viscous oil (yield: 41.2 g, 72%).

$^1$H NMR (DMSO) δ7.32 (m, 3H), 7.30 (m, 1H), 7.22 (m, 1H), 4.48 (t, J=5.4 Hz, 1H), 4.42 (d, J=5.4 Hz, 1H), 4.04 (m, 1H), 4.01 (m, 1H), 3.97 (m, 1H), 3.80 (d, J=13.2 Hz, 1H), 3.78 (m, 1H), 3.43 (m, 1H), 3.39 (m, 1H), 3.32 (m, 1H), 3.07 (t, J=4.9 Hz, 1H), 2.48 (m, 1H), 2.19 (m, 1H), 1.99 (s, 3H), 1.57 (dt, J=13.7, 2.0 Hz, 1H), 1.38 (s, 9H).

MS (M+H)$^+$=394.

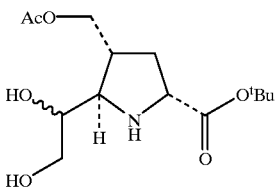

40C. (±)-(2R,3R,5R,1'R) and (±)-(2R,3R,5R,1'S)-2-(1,2-Dihydroxy)ethyl-3-(acetoxymethyl)-pyrrolidine-5-carboxylic Acid t-Butyl Ester (±)-(2R,3R,5R,1'R) and (±)-(2R,3R,5R,1'S)-1-Benzyl-2-(1,2-dihydroxy)ethyl-3-(acetoxymethyl)-pyrrolidine-5-carboxylic acid t-butyl ester (24 g, 61 mmol) in ethanol (300 mL) was reacted with ammonium formate (38.5 g, 0.61 mol) and 10% Pd/C (2 g) for 2 hours at reflux. The reaction was cooled and the catalyst removed by filtration through Celite. The filtrate was concentrated in vacuo to provide the title compound (yield: 16.7 g, 90%).

$^1$H NMR (DMSO) δ4.56 (m, 1H), 4.30 (m, 1H), 4.06 (dd, J=5.8, 10.9 Hz, 2H), 3.79 (dd, J=8.8, 10.5 Hz, 2H), 3.49 (m, 4H), 3.00 (m, 1H), 2.35 (m, 1H), 2.16 (dt, J=12.6, 8.5 Hz, 1H), 2.01 (s, 3H), 1.52 (m, 1H), 1.40 (s, 9H).

MS (M+H)$^+$=304.

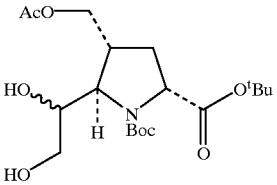

40D. (±)-(2R,3R,5R,1'R) and (±)-(2R,3R,5R,1'S)-1-t-Butoxycarbonyl 2-(1,2-dihydroxy)ethyl-3-(acetoxymethyl)-pyrrolidine-5-carboxylic Acid t-Butyl Ester (±)-(2R,3R,5R,1'R) and (±)-(2R,3R,5R,1'S)-2-(1,2-Dihydroxy)ethyl-3-(acetoxymethyl)-pyrrolidine-5-carboxylic acid t-butyl ester (33.4 g, 0.11 mol) in methanol (250 mL) and water (50 mL) was reacted with di-t-butyl dicarbonate (33.6 g, 0.15 mol) for 48 hours at room temperature. The methanol was removed in vacuo and the residue diluted with water (500 mL), and extracted with ethyl acetate (3×200 mL). The combined ethyl acetate layers were washed with brine, dried with MgSO$_4$, filtered and concentrated. The residue was chromatographed on silica gel using methanol/dichloromethane to provide the title compound as a white solid (yield: 32.8 g, 78%)

$^1$H NMR (DMSO) δ4.80 (m, 1H), 4.45 (m, 1H), 4.08 (m, 1H), 3.91 (m, 2H), 3.82 (m, 1H), 3.71 (m, 1H), 3.28 (m, 2H), 2.48 (m, 1H), 2.07 (m, 2H), 2.01 (m, 3H), 1.39 (m, 18H).

MS (M+H)$^+$=404.

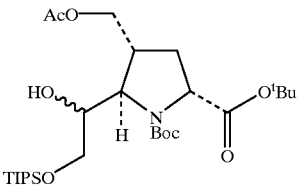

40E (±)-(2R,3R,5R,1'R) and (±)-(2R,3R,5R,1'S)-1-t-Butoxycarbonyl 2-(1-hydroxy-2-triisopropylsilyloxy)ethyl-3-(acetoxymethyl)-pyrrolidine-5-carboxylic Acid t-Butyl Ester (±)-(2R,3R,5R,1'R) and (±)-(2R,3R,5R,1'S)-1-t-Butoxycarbonyl 2-(1,2-dihydroxy)ethyl-3-(acetoxymethyl)-pyrrolidine-5-carboxylic acid t-butyl ester. (26.5 g, 66 mmol) in anhydrous dimethylformamide (200 mL ) was reacted with imidazole (8.9 g, 0.13 mol) and triisopropylsilyl chloride (19.0 g, 99 mmol) for 4 hours at room temperature. The solvent was removed under vacuum and the residue partitioned between 300 mL of water and 150 mL of ethyl acetate. The aqueous layer was extracted with ethyl acetate (2×100 mL), and the combined ethyl acetate layers extracted with brine, dried with MgSO$_4$, filtered and concentrated. The residue was purified by chromatography on silica gel using 10% ethyl acetate/hexanes to provide the title compound as a colorless oil (yield: 28.9 g, 79%).

$^1$H NMR (CDCl$_3$) δ4.22 (m, 1H), 4.04 (m, 3H), 3.87 (t, J=2.0 Hz, 1H), 3.74 (dd, J=4.9, 9.8 Hz, 1H), 3.58 (dd, J=7.8, 10.2 Hz, 1H), 3.39 (bs, 1H), 2.61 (m, 2H). 2.03 (s, 3H), 1.75 (m, 1H), 1.46 (m, 18H), 1.07 (m ,18H).

MS (M+H)⁺=560.

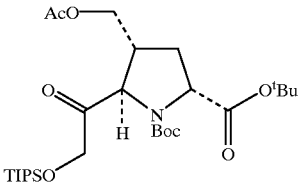

40F (±)-(2R,3R,5R)-1-t-Butoxycarbonyl-2-(1-oxo-2-triisopropylsilyloxy)ethyl-3-(acetoxymethyl)-pyrrolidine-5-carboxylic Acid t-Butyl Ester Dimethylsulfoxide (6 mL, 85 mmol) was added slowly to a solution of oxalyl chloride (2 M) (19.3 mL, 38.6 mmol) in dry dichloromethane (70 mL) at −78° C. After 10 minutes, a solution of (±)-(2R,3R,5R,1'R) and (±)-(2R,3R,5R,1'S)-1-t-butoxycarbonyl 2-(1-hydroxy-2-triisopropylsilyloxy)ethyl-3-(acetoxymethyl)-pyrrolidine-5-carboxylic acid t-butyl ester (14.4 g, 26 mmol) in dry dichloromethane (75 mL) was added at a rate such that the temperature did not exceed −70° C. After 1.5 hours, triethylamine (18 mL, 0.13 mol) was added and the temperature allowed to rise to 0° C. The reaction was quenched with a solution of ammonium chloride, diluted with water, and extracted with dichloromethane (3×100 mL). The combined dichloromethane layers were extracted with brine, dried with MgSO₄, filtered and concentrated. The residue was purified by chromatography on silica gel using 10% ethyl acetate/hexanes to provide the title compound as a colorless oil: (yield: 11 g, 77%).

¹H NMR (CDCl₃) δ4.32 (m, 6H), 2.43 (m, 2H), 2.04 (s, 3H), 1.78 (m, 1H), 1.48 (s, 9H), 1.41 (s, 9H), 1.1 (m, 1H).

MS (M+H)⁺=558.

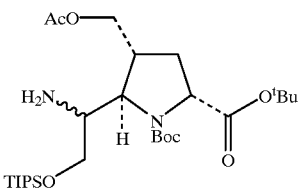

40G (±)-(2R,3R,5R,1'R) and (±)-(2R,3R,5R,1'S)-1-t-Butoxycarbonyl 2-(1-amino-2-triisopropylsilyloxy)ethyl-3-(acetoxymethyl)-pyrrolidine-5-carboxylic Acid t-Butyl Ester (±)-(2R,3R,5R)-1-t-Butoxycarbonyl 2-(1-oxo-2-triisopropylsilyloxy)ethyl-3-(acetoxymethyl)-pyrrolidine-5-carboxylic acid t-butyl ester. (22 g, 39 mmol) in methanol (1 L) was reacted with ammonium acetate (77 g, 1.0 mol) and sodium cyanoborohydride (24.8 g, 0.39 mol) at reflux for 2 hours. The solvent was removed under in vacuo, and the residue was partitioned between water (300 mL) and dichloromethane (300 mL). The aqueous layer was extracted with dichloromethane (2×100 mL) and the combined organic layers were washed with brine, dried with MgSO₄, filtered and concentrated to provide the title compound (crude yield. 22.0 g, 100%).

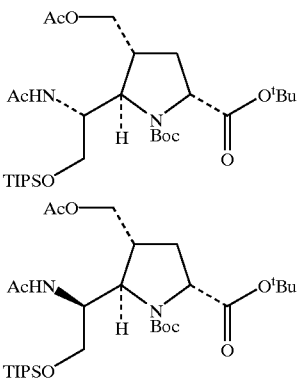

40H (±)-(2R,3R,5R,1'R) and (±)-(2R,3R,5R,1'S)-1-t-Butoxycarbonyl-2-(1-acetamido-2-triisopropylsilyloxy)ethyl-3-(acetoxymethyl)-pyrrolidine-5-carboxylic Acid t-Butyl Ester (±)-(2R,3R,5R,1'R) and (±)-(2R,3R,5R,1'S)-1-t-Butoxycarbonyl-2-(1-amino-2-triisopropylsilyloxy)ethyl-3-(acetoxymethyl)-pyrrolidine-5-carboxylic acid t-butyl ester (approx 39 mmol) in dichloromethane (500 mL) was reacted with acetic anhydride (18 mL, 0.19 mol), triethylamine (27.5 mL, 0.20 mol) and dimethylaminopyridine (50 mg, 0.39 mmol) for 18 hours at room temperature. The reaction was quenched with a solution of ammonium chloride. The aqueous layer was extracted with dichloromethane (3×100 mL) and the combined organic layers extracted with brine, dried with MgSO₄, filtered, and concentrated. The residue was chromatographed on silica gel using ethyl acetate/hexanes to provide the title compound (±)-(2R,3R,5R,1'R)-1-t-butoxycarbonyl 2-(1-acetamido-2-triisopropylsilyloxy)ethyl-3-(acetoxymethyl)-pyrrolidine-5-carboxylic acid t-butyl ester (9.14 g, 39%) and (±)-(2R,3R,5R,1'S)-1-t-butoxycarbonyl 2-(1-acetamido-2-triisopropylsilyloxy)ethyl-3-(acetoxymethyl)-pyrrolidine-5-carboxylic acid t-butyl ester (9.75 g, 41% ) as white solids.

(±)-(2R,3R,5R,1'R) ¹H NMR (CDCl₃) δ7.38 (d, J=8.3 Hz, 1H), 4.34 (m, 1H), 4.20 (dd, J=2.4, 10.3 Hz, 1H), 4.09 (dd, J=8.8, 10.2 Hz. 1H), 4.02 (dd, J=7.3, 10.1 Hz, 1H), 3.88 (m, 1H), 3.71 (dd, J=4.4, 10.3 Hz, 1H), 3.65 (dd, J=7.9, 10.13 Hz, 1H), 2.74 (m, 1H), 2.60 (m, 1H), 2.04 (s, 3H), 1.98 (s, 3H), 1.69 (dt, J=14.1, 2.5 Hz, 1H), 1.46 (s, 9H), 1.42 (s, 9H), 1.07 (m, 21H).

MS (M+H)⁺=601

(±)-(2R,3R,5R,1'S) ¹H NMR (CDCl₃) δ6.82 (d, 1H), 4.10 (m, 4H), 3.81 (m, 3H), 2.55 (m, 2H), 1.98 (m, 7H), 1.46 (s, 9H), 1.42 (s, 9H), 1.07 (m, 21H).

MS (M+H)⁺=601.

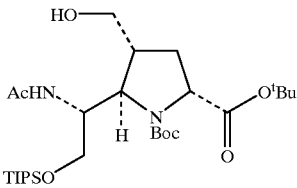

40I (±)-(2R,3R,5R,1'R)-1-t-Butoxycarbonyl 2-(1-acetamido-2-triisopropylsilyloxy)ethyl-3-hydroxymethyl-pyrrolidine-5-carboxylic Acid t-Butyl Ester (±)-(2R,2R,5R,1'R)-1-t-Butoxycarbonyl 2-(1-acetamido-2-triisopropylsilyloxy)ethyl-3-(acetoxymethyl)-pyrrolidine- 5-carboxylic acid t-butyl ester. (8.2 g, 13.66 mmol) in methanol (200 mL) and water (50 mL) was reacted with potassium carbonate (19 g, 136 mmol) at room temperature for 2 hr. The solvent was then removed in vacuo and the residue was partitioned between water (100 mL) and dichloromethane (3×100 mL). The organic extracts were dried over magnesium sulfate, filtered and concentrated in vacuo to provide the title compound as a colorless oil.

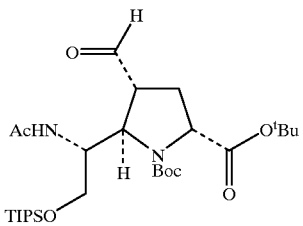

40J (±)-(2R,3R,5R,1'R)-1-t-Butoxycarbonyl 2-(1-acetamido-2-triisopropylsilyloxy)ethyl-3-formyl-pyrrolidine-5-carboxylic Acid t-Butyl Ester The title compound was prepared according to the method described in Example 2A substituting (±)-(2R,3R,5R,1'R)-1-t-butoxycarbonyl 2-(1-acetamido-(2-triisopropylsilyloxy)ethyl-3-hydroxymethyl-pyrrolidine-5-carboxylic acid t-butyl ester in place of (±)-(2R,3R,5R,1'S)-1-benzyl-2-(1-acetamido-3-ethyl)pentyl-3-hydroxymethyl-pyrrolidine-5-carboxylic acid t-butyl ester (yield; 5.9 g, 78%).

$^1$H NMR (CDCl$_3$) δ1.04–1.07 (m, 21H), 1.42 (s, 9H), 1.43 (s, 9H), 1.99 (s, 3H), 2.42 (m, 1H), 2.62 (m, 1H), 3.04 (m, 1H), 3.69 (m, 1H), 3.82 (m, 1H), 4.08 (m, 1H), 4.38 (m, 1H), 4.57 (t, 1H), 7.33 (br d, 1H), 9.65 (s, 1H).

MS: (M+H)$^+$=557.

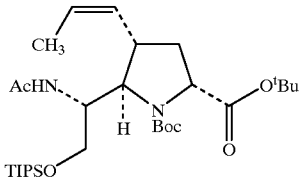

40K (±)-(2R,3S,5R,1'R)-1-t-Butoxycarbonyl 2-(1-acetamido-2-triisopropylsilyloxy)ethyl-3-(cis-propen-1-yl)-pyrrolidine-5-carboxylic Acid t-Butyl Ester The title compound was prepared according to the method described in Example 35A substituting (±)-(2R,3R,5R,1'R)-1-t-butoxycarbonyl 2-(1-acetamido-2-triisopropylsilyloxy-)ethyl-3-formyl-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester (yield: 5.9 g, 78%).

$^1$H NMR (CDCl$_3$) δ1.03–1.10 (m, 21H), 1.44 (s, 9H), 1.47 (s, 9H), 1.55 (m,1H), 1.64 (dd, 3H), 1.96 (s, 3H), 2.55 (m,1H), 3.42 (m, 1H), 3.62–3.71 (m, 3H), 4.20 (dd, 1H), 4.30 (m, 1H), 5.39 (m, 1H), 5.48 (m, 1H), 7.73 (br d, 1H).

MS: (M4H)$^+$=569

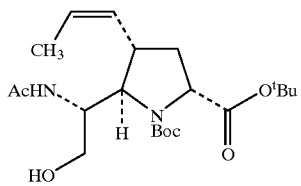

40L (±)-(2R,3S,5R,1'R)-1-t-Butoxycarbonyl 2-(1-acetamido-2-hydroxy-)ethyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-triisopropylsilyloxy)ethyl-3-(cis-propen-1-yl)-pyrrolidine-5-carboxylic acid t-butyl ester (4.85 g, 8.54 mmol) in THF (100 mL) was reacted with tetrabutyl ammonium fluoride (1M in THF) (12.8 mL, 12.8 mmol) for 30 minutes at room temperature. Water (100 mL) was added followed by extraction using dichloromethane (2×100 mL). This organic layers were dried over magnesium sulfate, filtered and concentrated in vacuo. The residue was purified by column chromatography on silica gel using 2/1: ethyl acetate/hexane to provide the title compound as a colorless solid (yield: 3.1 g, 89%).

$^1$H NMR (CDCl$_3$): d 1.44 (s, 9H), 1.47 (s, 9H), 1.56 (dd, 3H), 1.80 (m, 1H), 2.02 (s, 3H), 2.67 (m, 1H), 3.11 (t, 3H), 3.44 (dd, 1H), 3.b9 (dd, 1H), 3.74–3.84 (m, 2H), 4.15 (dd, 1H) 5.39 (m, 1H), 5.58 (m, 1H), 6.42 (br d, 1H).

MS: (M+H)$^+$=413.

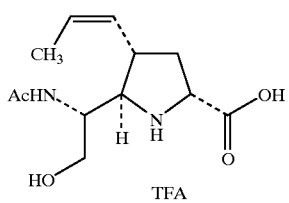

40M (±)-(2R,3S,5R,1'R)-2-(1-Acetamido-2-hydroxy)ethyl-3-(cis-propen-1-yl)-pyrrolidine-5-carboxylic Acid Trifluoroacetic Acid Salt The title compound was prepared according to the method described in Example 33B, substituting (±)-(2R,3S,5R,1'R)-1-t-butoxycarbonyl-2-(1-acetamido- 2-hydroxy)ethyl-3-(cis-propen-1-yl)-pyrrolidine-5-carboxylic acid t-butyl ester in place of (±)-(2R,3S,5R,1'S)-1-t-butoxycarbonyl-2-(1-acetamido-3-methyl)butyl-3-(trans-2-chloro-vinyl)-pyrrolidine-5-carboxylic acid t-butyl ester (yield: 18.0 mg, 100%).

$^1$H NMR (DMSO-d$_6$): d 1.66 (dd, 2H), 1.71 (dt, 1H), 1.87 (g, 3H), 2.41 (dt, 1H), 3.18 (m, 1H), 3.43 (dd, 1H), 3.61 (m, 1H), 4.13 (m, 1H), 4.35 (m, 1H), 5.25 (m, 1H), 5.51 (m, 1H), 8.05 (d, 1H), 9.16 (br s, 2H).

MS: (M+H)$^+$=257.

EXAMPLE 41

(±)-(2R,3S,5R,1'R,2'S)-2-(1-Acetamido-2-hydroxy)
butyl-3-(cis-propen-1-yl)-pyrrolidine-5-carboxylic
Acid Trifluoroacetic Acid Salt

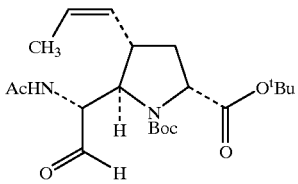

41A (±)-(2R,3S,5R,1'R)-1-t-Butoxycarbonyl 2-(1-acetamido-1-formyl)methyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-hydroxy)ethyl-3-(cis-propen-1-yl)-pyrrolidine-5-carboxylic acid t-butyl ester. (600 mg, 1.46 mmol) in dichloromethane (50 mL) was reacted with Dess-Martin Periodinane (928 mg, 2.18 mmol) for 1 hour at room temperature. The reaction was quenched with 1M aqueous sodium thiosulfate (50 mL), stirred for 20 minutes then extracted with dichloromethane (3×100 mL). The organic layer was dried over magnesium sulfate, concentrated in vacuo. The residue was purified by column chromatography on silica gel using 2/1: ethyl acetate/hexane to provide the title compound (yield: 547 mg, 92%).

$^1$H NMR (CDCl$_3$) d 9.40 (d, J=1 Hz, 1H), 7.88 (bd), 5.69 (m, 1H), 5.27 (m, 1H), 4.78 (dd, J=9.5, 1. Hz, 1H), 4.21 (t, J=8. Hz, 1H), 3.45 (m, 2H), 2.41 (m, 1H), 2.09 (s, 3H), 1.69 (dd, J=7.0, 1. Hz, 3H), 1.55 (m, 1H), 1.46 (s, 9H), 1.40 (s, 9H).

MS: (M+H)$^+$=411, (M−H)−=409.

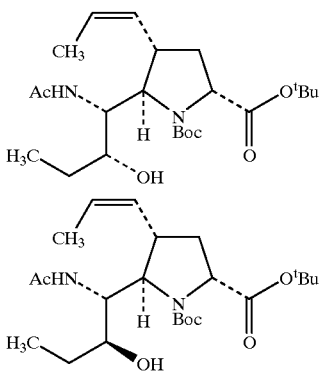

41B (±)-(2R,3S,5R,1'R,2'R) and (±)-(2R,3S,5R1'R,2'S)-1-t-Butoxycarbonyl-2-(1-acetamido-2-hydroxy)butyl-3-(cis-propen-1-yl)-pyrrolidine-5-carboxylic Acid t-Butyl Ester (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester (780 mg, 1.90 mmol) in THF (20 mL) was added dropwise to 2 solution of ethylmagnesium bromide (3M in ether) (3.17 mL, 9.51 mmol) in THF (15 mL) at room temperature and reacted for 40 minutes. The reaction was quenched with water (20 mL) and saturated aqueous ammonium chloride (20 mL) followed by extraction using dichloromethane (3×50 mL). The organic layer was dried over magnesium sulfate, filtered and concentrated in vacuo. The residue was purified by column chromatography on silica gel using 2/1: ethyl acetate/hexane to provide the title compounds (±)-(2R,3S,5R,1'R,2'R)-1-t-butoxycarbonyl 2-(1-acetamido-2-hydroxy)butyl-3-(cis-propen-1-yl)-pyrrolidine-5-carboxylic acid t-butyl ester (yield: 472 mg, 56%) and (±)-(2R,3S,5R,1'R,2'S)-1-t-butoxycarbonyl 2-(1-acetamido-2-hydroxy)butyl-3-(cis-propen-1-yl)-pyrrolidine-5-carboxylic acid t-butyl ester (yield: 82 mg, 10%) as a colorless oils.

(±)-(2R,3S,5R,1'R,2'R)=MS: (M+H)$^+$=441, (M+Na)+=463, (M−H)−=439.

(±)-(2R,3S,5R,1'R,2'S)=MS: (M+H)$^+$=441, (M+Na)+=463, (M−H)−=439.

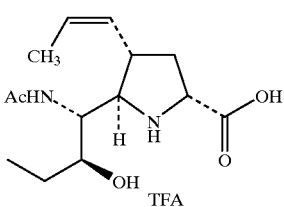

41C (±)-(2R,3S,5R,1'R,2'S)-2-(1-Acetamido-2-hydroxy)butyl-3-(cis-propen-1-yl)-pyrrolidine-5-carboxylic Acid Trifluoroacetic Acid Salt (±)-(2R,3S,5R,1'R,2'S)-1-t-Butoxycarbonyl-2-(1-acetamido-2-hydroxy)butyl-3-(cis-propen-1-yl)-pyrrolidine-5-carboxylic acid t-butyl ester (300 mg, 0.68 mmol) was reacted with trifluoroacetic acid (8 mL) in dichloromethane (2 mL) at room temperature for 6 hrs. The reaction was concentrated in vacuo overnight to provide the title compound (yield: 311 mg) as a colorless solid.

$^1$H NMR (500 MHz, DMSO-d$_6$) δ: 7.89 (d, J=8.7 Hz, 1H), 5.48 (m, 1H), 5.29 (m, 1H), 4.30 (m, 1H), 4.02 (m, 1H), 3.73 (m, 1H), 3.43 (m, 1H), 3,15 (m, 1H), 2.41 (m, 1H), 1.82 (s, 3H), 1.63 (m, 1H), 1.59 (dd, J=6.8, 1.9 Hz, 3H), (m,1H), 1.27 (m, 1H), 0.85 (t, J=7.3 Hz, 3H).

MS: (M+H)$^+$=285, (M+Na)$^+$=307, (M−H)$^−$=283.

EXAMPLE 42

(±)-(2R,3S,5R,1'R,2'S)-2-(1-Acetamido-2-hydroxy)
butyl-3-(cis-propen-1-yl)-pyrrolidine-5-carboxylic
Acid Trifluoroacetic Acid Salt

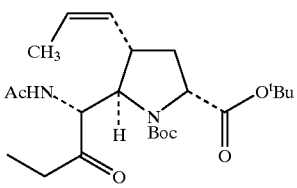

42A (±)-(2R,3S,5R,1'R)-1-t-Butoxycarbonyl-2-(1-acetamido-2-oxo)butyl-3-(cis-propen-1-yl)-pyrrolidine-5-carboxylic Acid t-Butyl Ester (±)-(2R,3S,5R,1'R,2'R)-1-t-Butoxycarbonyl-2-(1-acetamido-2-hydroxy)butyl-3-(cis-propen-1-yl)-pyrrolidine-5-carboxylic acid t-butyl ester. (460 mg, 1.05 mmol) was reacted with Dess-Martin Periodinane (666 mg, 1.57 mmol) in dichloromethane (30 mL) at room temperature for 17 hours. The reaction was quenched with 1M aqueous sodium thiosulfate (60 mL and stirred for 20 minutes. The reaction was was extracted with dichloromethane (3×100 mL). The organic layer was dried over magnesium sulfate, filtered, and concentrated in vacuo. The residue was purified by column chromatography on silica gel using 2:1: ethyl acetate/hexane to provide the title compound as a colorless semi-solid (yield: 440 mg, 96%).

MS: $(M+H)^+=439$, $(M+Na)+=461$, $(M-H)-=437$.

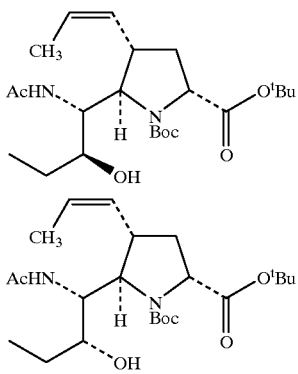

42B (±)-(2R,3S,5R,1'R,2'R) and (±)-(2R,3S,5R,1'R, 2'S)-1-t-Butoxycarbonyl-2-(1-acetamido-2-hydroxy) butyl-3-(cis-propen-1-yl)-pyrrolidine-5-carboxylic Acid t-Butyl Ester (±)-(2R,3S,5R,1'R)-1-t-Butoxycarbonyl-2-(1-acetamido-2-oxo)butyl-3-(cis-propen-1-yl)-pyrrolidine-5-carboxylic acid t-butyl ester (435 mg, 0.99 mmol) in methanol (30 mL) was reacted with sodium borohydride (188 mg, 4.97 mmol) at room temperature for 0.5 hours. The solvent was removed in vacuo and water (30 mL) was added. The aqueous layer was extracted with dichloromethane (3×50 mL). This organic layer was dried over magnesium sulfate, filtered and concentrated in vacuo. The residue was purified by column chromatography on silica gel using 2:1 ethyl acetate/hexane to provide the title compounds (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. (yield: 305 mg, 70%) and compounds (±)-(2R,3S,5R,1'R, 2'R)-1-t-butoxycarbonyl-2-(1-acetamido-2-hydroxy)butyl-3-(cis-propen-1-yl)-pyrrolidine-5-carboxylic acid t-butyl ester (yield: 17 mg, 4%).

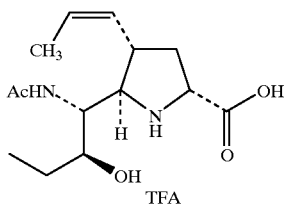

42C (±)-(2R,3S,5R,1'R,2'S)-2-(1-Acetamido-2-hydroxy)butyl-3-(cis-propen-1-yl)-pyrrolidine-5-carboxylic Acid Trifluoroacetic Acid Salt (±)-(2R,3S,5R,1'R,2'S)-1-t-Butoxycarbonyl-2-(1-acetamido-2-hydroxy)butyl-3-(cis-propen-1-yl)-pyrrolidine-5-carboxylic acid t-butyl ester (300 mg, 0.68 mmol) was reacted with trifluoroacetic acid (8 mL) in dichloromethane (2 mL) at room temperature for 6 hrs. The reaction was concentrated in vacuo overnight and triturated with acetonitrile (2×5 mL) to provide the title compound (yield: 311 mg) as a colorless solid.

$^1$H NMR (500 MHz, DMSO-d$_6$) δ: 7.89 (d, J=8.7 Hz, 1H), 5.48 (m, 1H), 5.29 (m, 1H), 4.30 (m, 1H), 4.02 (m, 1H), 3.73 (m, 1H), 3.43 (m, 1H), 3.15 (m, 1H), 2.41 (m, 1H), 1.82 (s, 3H), 1.63 (m, 1H), 1.59 (dd, J=6.8, 1.9 Hz, 3H), 1.55 (m, 1H), 1.27 (m, 1H), 0.85 (t, J 7.3 Hz, 3H).

MS: $(M+H)^+=285$, $(M+Na)+=307$, $(M-H)-=283$.

EXAMPLE 43

(±)-(2R,3S,5R,1'R,2'R)-2-(1-Acetamido-2-hydroxy) butyl-3-(cis-propen-1-yl)-pyrrolidine-5-carboxylic Acid Trifluoroacetic Acid Salt

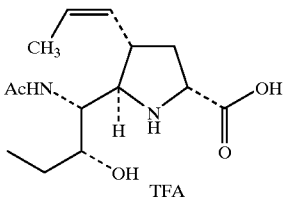

The title compound was prepared according to the method described in Example 41C, substituting (±)-(2R,3S,5R,1'R, 2'R)-1-t-butoxycarbonyl-2-(1-acetamido-2-hydroxy)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0065 g, 100%).

$^1$H NMR (DMSO-d$_6$) δ7.90 (d, J=8.8 Hz, 1H), 5.47 (m, 1H), 5.29 (t, J=9.8 Hz, 1H), 4.29 (t, J=8.8 Hz, 1H), 4.02 (q, J=6.8 Hz, 1H), 3.71 (bt, J=8 Hz, 1H), 3.43 (m, 1H), 3.15 (quint., J=8.8 Hz, 1H), 2.41 (dt, J=12.7,7.8 Hz, 1H), 1.82 (s, 3H), 1.64 (m, 1H), 1.58 (dd, J=6.8, 1.5 Hz, 3H), 1.53 (m, 1H), 0.85 (t, J=7.3 Hz, 3H).

MS: $(M+H)^+=285$, $(M+Na)+=307$, $(M-H)^-=283$, $(M+CF_3COOH)^-=397$, $(2M-1)^-=563$

EXAMPLE 44

(±)-(2R,3S,5R,1'R,2'S)-2-(1-Acetamido-2-hydroxy-3-cyano)propyl-3-(cis-propen-1-yl)-pyrrolidine-5-carboxylic Acid Trifluoroacetic Acid Salt

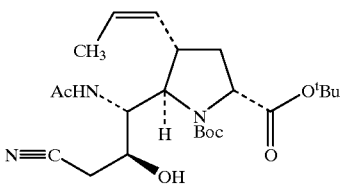

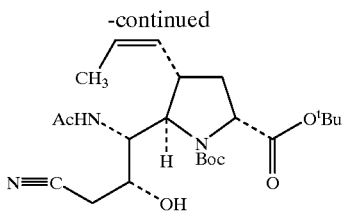

44A (±)-(2R,3S,5R,1'R,2'R) and (±)-(2R,3S,5R,1'R, 2'S)-1-t-Butoxycarbonyl-2-(1-acetamido-2-hydroxy-3-cyano)propyl-3-(cis-propen-1-yl)-pyrrolidine-5-carboxylic Acid t-Butyl Ester (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester (150 mg, 0.37 mmol) in THF (10 mL) was added dropwise to a solution of the lithium enolate of acetonitrile (1.83 mmol, 5 equivalents) in THF (15 mL) at −78° C. and reacted for 15 minutes. The reaction was quenched with saturated aqueous ammonium chloride (10 mL) and water (10 mL) followed by extraction using dichloromethane (2×50 mL). The organic layer was dried over magnesium sulfate, filtered and concentrated in vacuo. The residue was purified by column chromatography on silica gel using 211: ethyl acetate/hexane to provide the title compounds (±)-(2R,3S,5R,1'R,2'R)-1-t-butoxycarbonyl 2-(1-acetamido-2-hydroxy-3-cyano)propyl-3-(cis-propen-1-yl)-pyrrolidine-5-carboxylic acid t-butyl ester (yield: 95mg, 58%) and (±)-(2R,3S,5R,1'R,2'S)-1-t-butoxycarbonyl 2-(1-acetamido-2-hydroxy-3-cyano)propyl-3-(cis-propen-1-yl)-pyrrolidine-5-carboxylic acid t-butyl ester(yield: 30 mg, 18%) as a colorless oils.

(±)-(2R,3S,5R,1'R,2'R)=MS: $(M+H)^+$=452, $(M−H)^−$=450

(±)-(2R,3S,5R,1'R,2'S)=$^1$H NMR (CDCl$_3$) δ8.14 (d, J=8.9 Hz, 1H), 5.51 (m, 1H), 5.38 (m, 1H), 4.25 (m, 1H), 4.19 (m, 1H), 3.94 (m, 1H), 3.74 (m, 1H), 3.22 (m, 1H), 2.54 (m, 1H), 2.47 (m, 2H), 2.04 (s, 3H), 1.69 (m, 1H),1.65 (dd, J=6.5, 1.8 Hz, 3H), 1.47 (s, 9H), 1.45 (s, 9H)

MS: $(M+H)^+$=452, $(M−H)^−$=450

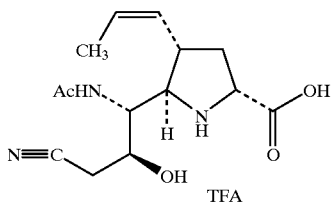

44B (±)-(2R,3S,5R,1'R,2'S)-2-(1-Acetamido-2-hydroxy-3-cyano)propyl-1-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'S)-1-t-butoxycarbonyl-2-(1-acetamido-2-hydroxy-3-cyano)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.5 mg, 95%%).

$^1$H NMR (DMSO-d$_6$) δ7.98 (d, J=10.0 Hz, 1H), 5.49 (m, 1H), 5.27 (m, 1H), 4.30 (m, 1H), 4.15 (m, 1H), 3.75(m, 1H), 3.18 (m, 1H), 2.72–2.58 (m, 2H), 2.41 (m, 1H), 1.85 (s, 3H), 1.65 (m, 1H), 1.61 (dd, J=6.70, 1.80 Hz, 3H)

MS $(M+H)^+$=298, $(M−H)^−$=204

EXAMPLE 45

(±)-(2R,3S,5R,1'R2'R)-2-(1-Acetamido-2-hydroxy-3-cyano)propyl-3-(cis-propen-1-yl-pyrrolidine-5-carboxylic Acid Trifluoroacetic Acid Salt

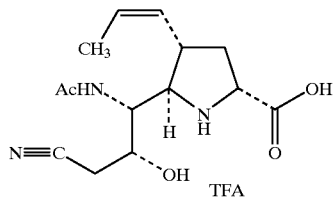

The title compound was prepared according to the method described in Example 41C, substituting (±)-(2R,3S,5R,1'R, 2'R)-1-t-butoxycarbonyl-2-(1-acetamido-2-hydroxy-3-cyano)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 8 mg, 95%).

$^1$H NMR (DMSO-d6) δ7.75(d, J=9.0 Hz, 1H), 5.47(m, 1H), 5.25(m, 1H), 4.46(m, 1H), 4.20(m, 1H), 4.13(m, 1H), 3.56(m, 1H), 3.15(m, 1H), 2.55(m, 2H), 2.42(m, 1H), 1.82(s, 3H), 1.72(m, 1H), 1.55(dd, J=6.71, 1.83, 3H)

MS: $(M+H)^+$=296, $(M+23)^+$=318, $(M−H)^−$=294

EXAMPLE 46

(±)-(2R,3S,5R,1'R2'R)-2-(1-Acetamido-2-hydroxy-3-ethoxycarbonyl)propyl-3-(cis-propen-1-yl)-pyrrolidine-5-carboxylic Acid Trifluoroacetic Acid Salt

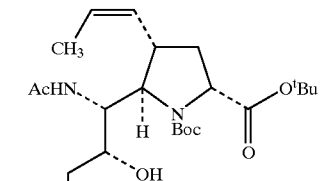

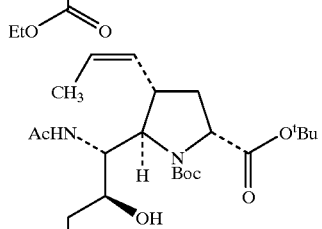

46A (±)-(2R,3S,5R,1'R,2'R) and (±)-(2R,3S,5R,1'R, 2'S)-1-t-Butoxycarbonyl-(1-acetamido-2-hydroxy-3-ethoxycarbonyl)propyl-3-(cis-propen-1-yl)-pyrrolidine-5-carboxylic Acid t-Butyl Ester (±)-(2R,3S,5R,1'R)-1-t-Butoxycarbonyl-2-(1-acetamido-1-formyl)methyl-3-(cis-propen-1-yl)-pyrrolidine-5- carboxylic acid t-butyl ester (900 mg, 2.187 mmol) in THF (40 mL) was added dropwise to a solution of the lithium enolate of ethyl acetate (8.75 mmol, 4 equivalents) in THF (40 mL) at −78° C. and reacted for 15 minutes. The reaction was quenched with saturated aqueous ammonium chloride followed by extraction using dichloromethane (3×). The organic layer was dried over magnesium sulfate, filtered and concentrated in vacuo. The residue was purified by column chromatography on silica gel using 1:1 ethyl acetate/hexane to provide the title compounds (±)-(2R,3S,5R,1'R,2'R)-1-t-butoxycarbonyl-2-(1-acetamido-2-hydroxy-3-ethoxycarbonyl)propyl-3-(cis-propen-1-yl)-pyrrolidine-5-carboxylic acid t-butyl ester (yield: 690 mg, 63%) and (±)-(2R,3S,5R,1'R,2'S)-1-t-butoxycarbonyl-2-(1-acetamido-2-hydroxy-3-ethoxycarbonyl)propyl-3-(cis-propen-1-yl)-pyrrolidine-5-carboxylic acid t-butyl ester (yield: 246 mg, 22.5%).

(±)-(2R,3S,5R,1'R,2'R) $^1$H NMR (CDCl$_3$): δ5.99 (d, 1H), 5.60 (m, 1H), 5.36 (m, 1H), 4.81 (m, 1H), 4.15 (m, 4H), 3.74 (m, 1H), 3.07 (m, 1H), 2.68 (m, 1H), 2.48 (m, 1H), 2.33 (m, 1H), 2.03 (s, 3H), 1.54 (dd, 3H), 1.47 (s, 9H), 1.46 (s, 9H), 1.24 (t, J=7.5 Hz, 3H).

MS: (M+H)$^+$=499

(±)-(2R,3S,5R,1'R,2'S) $^1$H NMR (CDCl$_3$): δ7.93 (d, 1H), 5.44 (m, 2H), 4.19 (m, 4H), 4.03 (m, 1H), 3.72 (m, 1H), 3.37 (m, 1H), 2.63 (m. 1H), 2.48 (m, 2H), 2.01 (s, 3H), 1.65 (dd, 3H), 1.48 (s, 9H), 1.46 (s, 9H), 1.26 (t, J=7.5 Hz, 3H).

MS: (M+H)$^+$=499

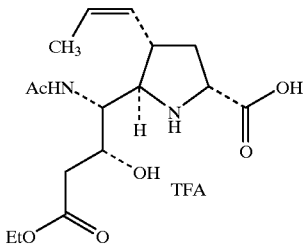

46B (±)-(2R,3S,5R,1'R,2'R)-2-(1-Acetamido-2-hydroxy-3-ethoxycarbonyl)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-3-ethoxycarbonyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

$^1$H NMR (DMSO-d$_6$): δ7.74 (d, J=9 Hz, 1H), 5.48 (m, 1H), 5.25 (m, 1H), 4.43 (m, 1H), 4.24 (m, 1H), 4.14 (m, 1H), 4.06 (q, J=7.5 Hz, 2H), 3.54 (m, 1H), 3.16 (m, 1H), 2.41 (m, 1H), 2.36 (m, 2H), 1.82 (s, 3H), 1.77 (m, 1H), 1.56 (dd, 3H), 1.18 (t, J=7.5 Hz, 3H).

MS: (M+H)$^+$=343

EXAMPLE 47

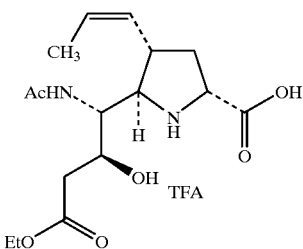

(±)-(2R,3S,5R,1'R,2'S)-2-(1-Acetamido-2-hydroxy-3-ethoxycarbonyl)propyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'S)-1-t-butoxycarbonyl-2-(1-acetamido-2-hydroxy-3-ethoxycarbonyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-cis-propen-1-yl)-pyrrolidine-5-carboxylic acid t-butyl ester.

$^1$H NMR (DMSO-d$_6$): δ7.93 (d, J=9 Hz, 1H), 5.48 (m, 1H), 5.30 (m, 1H), 4.19 (m, 1H), 4.09 (m, 1H), 4.06 (q, J=7.5 Hz, 2H), 3.94 (m, 1H), 3.73 (m, 1H), 3.18 (m, 1H), 2.54 (dd, 1H), 2.40 (m, 1H), 2.27 (m, 1H), 1.82 (s, 3H), 1.65 (m, 1H), 1.60 (dd, 3H), 1.19 (t, J=7.5 Hz, 3H).

MS: (M+H)$^+$=343

EXAMPLE 48

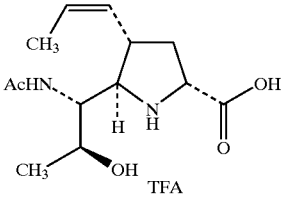

(±)-(2R,3S,5R,1'R,2'S)-2-(1-Acetamido-2-hydroxy)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0030 g, 100%).

$^1$H NMR (DMSO-d$_6$) δ8.97 (bs, 1H), 7.88 (d, J=8.5 Hz, 1H), 5.45 (m, 1H), 5.28 (t, J=9.1 Hz, 1H), 4.30 (t, J=8.6 Hz, 1H), 3.94 (q, J=7.3 Hz, 1H), 3.71 (t, J=8.0 Hz, 1H), 3.62 (m, 1H), 3.15 (quint., J=9.0 Hz, 1H), 2.40 (dt, J=12.8, 7.6 Hz, 1H), 1.88 (s, 2H), 1.65 (m, 1H), 1.59 (dd, J=7.0, 1.5 Hz, 3H), 1.08 (d, J=5.5 Hz, 3H).

MS: (M+H)$^+$=271, (M+Na)+=293, (M−H)$^−$=269.

EXAMPLE 49

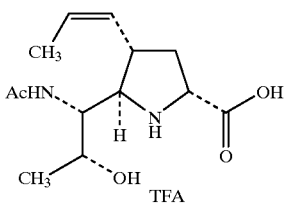

(±)-(2R,3S,5R,1'R,2'R)-2-(1-Acetamido-2-hydroxy) propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'R)-1-t-butoxycarbonyl-2-(1-acetamido-2hydroxy)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0143 g, 100%).

$^1$H NMR (DMSO-d$_6$) δ7.70 (d, J=9.1 Hz, 1H), 5.49 (m, 1H), 5.25 (t, J=9.1 Hz, 1H), 4.43 (t, J=8.6 Hz, 1H), 4.03 (m, 1H), 3.92 (m, 1H), 3.55 (t, J=8.5 Hz, 1H), 3.17 (quint., J=8.5 Hz, 1H), 2.42 (dt, J=12.8,7.3 Hz, 1H), 1.85 (s, 3H), 1.72 (dt, J=12.8, 10.0 Hz, 1H), 1.57 (dd, J=6.7,1.8 Hz, 3H), 1.04 (d, J=6.1 Hz, 3H).

MS: (M+H)$^+$=271, (M+Na)$^+$=293, (M−H)$^-$=269

EXAMPLE 50

(±)-(2R,3S,5R,1'R,2'S)-2-(1-Acetamido-2-hydroxy-2-vinyl)ethyl-3-(cis-propen-1-yl)-pyrrolidine-5-carboxylic Acid Trifluoroacetic Acid Salt

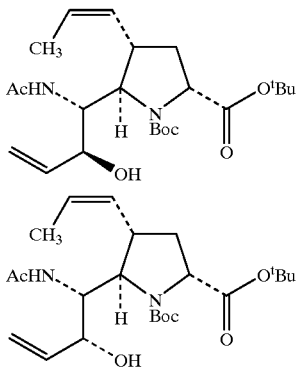

50A (±)-(2R,3S,5R,1'R,2'S) and (±)-(2R,3S,5R,1'R, 2'R)-1-t-Butoxycarbonyl-2-(1-acetamido-2-hydroxy-2-vinyl)ethyl-3-(cis-propen-1-yl)-pyrrolidine-5-carboxylic Acid t-Butyl Ester The title compounds were prepared according to the method described in Example 41B, substituting vinyl magnesium bromide for ethyl magnesium bromide to provide (±)-(2R,3S,5R,1'R,2'S)-1-t-butoxycarbonyl-2-(1-acetamido-2-hydroxy-2-vinyl)ethyl-3-(cis-propen-1-yl)-pyrrolidine-5-carboxylic acid t-butyl ester (yield: 6.5 mg, 18%) and (±)-(2R,3S,5R,1'R,2'R)-1-t-butoxycarbonyl-2-(1-acetamido-2-hydroxy)ethyl-3-(cis-propen-1-yl)-pyrrolidine-5-carboxylic acid t-butyl ester (yield: 22 mg, 59%).

(±)-(2R,3S,5R,1'R,2'S) MS: (M+H)$^+$=439, (M−H)$^-$=437

(±)-(2R,3S,5R,1'R,2'R) MS: (M+H)$^+$=439, (M−H)$^-$=437

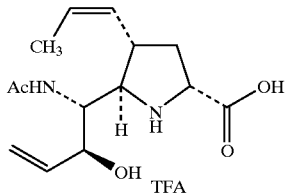

50B (±)-(2R,3S,5R,1'R,2'S),-2-(1-Acetamido-2-hydroxy-2-vinyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'S)-1-t-butoxycarbonyl-2-(1-acetamido-2-hydroxy-2-vinyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 5 mg, 96%).

$^1$H NMR (DMSO-d$_6$) δ7.85 (d, J=9.1 Hz, 1H), 5.76 (m, 1H), 5.47(m, 1H), 5.25 (m, 2H), 5.14 (m, 1H), 4.29 (m, 1H), 4.05 (m, 1H), 3.96 (m, 1H), 3.71 (m, 1H), 3.18 (m, 1H), 2.41 (m, 1H), 1.78 (s, 3H), 1.64 (m, 1H), 1.59 (dd, J=6.71, 1.21 Hz, 3H)

MS: (M+H)$^+$=283, (M+23)$^+$=305 , (M−H)$^-$=281

EXAMPLE 51

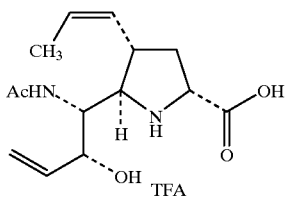

(±)-(2R,3S,5R,1'R,2'R)-2-(1-Acetamido-2-hydroxy-2-vinyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'R)-1-t-butoxycarbonyl-2-(1-acetamido-2-hydroxy-2-vinyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 6 mg, 95%).

$^1$H NMR (DMSO-d$_6$) δ7.84 (d, J=9.7 Hz, 1H), 5.78 (m, 1H), 5.48 (m, 1H), 5.23 (m, 34.43 (m, 1H), 4.26 (m, 1H), 4.20 (m, 1H), 3.55 (m, 1H), 3.18 (m, 1H), 2.43 (m, 1H), 1.81 (s, 3H), 1.73 (m, 1H), 1.57 (dd, J=6.72, 1.83 HZ, 3H)

MS: (M+H)$^+$=283, (M+23)$^-$=305, (M−H)$^-$=281, (2M−H)$^-$=563

EXAMPLE 52

(±)-(2R,3S,5R,1'R,2'S)-2-(1-Acetamido-2-hydroxy-2-vinyl)propyl-3-(cis-propen-1-yl)-pyrrolidine-5-carboxylic Acid Trifluoroacetic Acid Salt

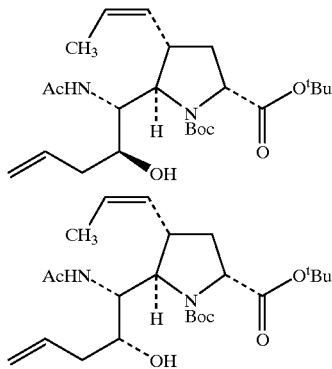

52A (±)-(2R,3S,5R,1'R,2'S) and (±)-(2R,3S,5R,1'R,2'R)-1-t-Butoxycarbonyl-2-(1-acetamido-2-hydroxy-3-vinyl)propyl-3-(cis-propen-1-yl)-pyrrolidine-5-carboxylic Acid t-Butyl Ester The title compounds were prepared according to the method described in Example 41B, substituting allyl magnesium bromide for ethyl magnesium bromide to provide (±)-(2R,3S,5R,1'R,2'S)-1-t-butoxycarbonyl-2-(1-acetamido-2-hydroxy-2-vinyl)propyl-3-(cis-propen-1-yl)-pyrrolidine-5-carboxylic acid t-butyl ester (yield: 2.0 mg, 5%) and (±)-(2R,3S,5R,1'R,2'R)-1-t-butoxycarbonyl-2-(1-acetamido-2-hydroxy)propyl-3-(cis-propen-1-yl)-pyrrolidine-5-carboxylic acid t-butyl ester (yield: 9.0 mg, 22%).

(±)-(2R,3S,5R,1'R,2'S) MS: (M+H)⁺=453; (M−H)⁻=451.

(±)-(2R,3S,5R,1'R,2'R) ¹H NMR (DMSO-d₆) δ7.70 (d, J=9.3 Hz, 1H), 5.80 (m, 1H), 5.51 (m, 1H), 5.30 (m, 1H), 5.00 (m, 2H), 4.58 (br d, 1H), 3.93 (m, 2H), 3.50 (m, 1H), 3.22 (br t, 1H), 2.02 (m, 3H), 1.88 (s, 3H), 1.56 (m, 4H), 1.41 (s, 9H), 1.36 (s, 9H)

MS: (M−H)⁻=451; (M+H)⁺=452, (M+Na)⁺=475.

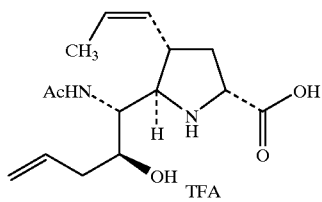

52B (±)-(2R,3S,5R,1'R,2'S)-2-(1-Acetamido-2-hydroxy-3-vinyl)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-2-vinyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 2 mg, 100%).

¹H NMR (DMSO-d₆) δ7.85 (d, J=9.3 Hz, 1H), 5.81 (m, 1H), 5.42 (m, 1H), 5.28 (t, J=7.3 Hz, 1H), 5.01 (br d, 2H), 3.99 (m, 2H), 3.57 (m, 2H), 3.08 (m, 1H), 2.33 (m, 1H), 2.26 (m, 1H), 2.07 (m, 1H), 1.81 (s, 3H), 1.57 (dd, J=1.4, 5.4 Hz, 4H)

MS: (M−H)⁻=295; (M+H)⁺=297, (M+Na)⁺=319.

EXAMPLE 53

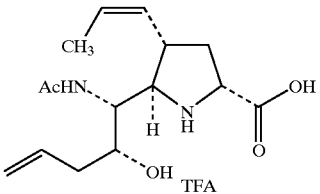

(+)-(2R,3S,5R,1'R,2'R)-2-(1-Acetamido-2-hydroxy-3-vinyl)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-3-vinyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 6 mg, 100%).

¹H NMR (DMSO-d₆) δ7.68 (d, J=9.2 Hz, 1H), 5.78 (m, 1H), 5.48 (m, 1H), 5.24 (t, J=7.8 Hz, 1H), 5.04 (m, 2H), 4.38 (t, J=7.0, 1H), 4.09 (t, J=7.0, 1H), 3.81 (t, J=4.7, 1H), 3.53 (t, J=8.5, 1H), 3.16 (m, 1H), 2.40 (m, 1H), 2.11 (m, 2H), 1.83 (s, 3H), 1.70 (m, 1H), 1.55 (dd, J=5.4, 1.4 Hz, 3H)

MS: (M−H)⁻=295; (M+H)⁺=297, (M+Na)⁺=319.

EXAMPLE 54

(±)-(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt

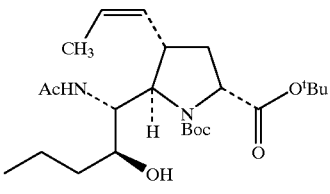

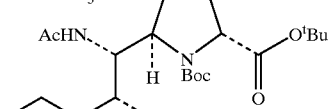

54A (±)-(2R,3S,5R,1'R,2'S) and (±)-(2R,3S,5R,1R,2'R)-1-t-Butoxycarbonyl-2-(1-acetamido-2-hydroxy)pentyl-3-(cis-propen-1-yl)-pyrrolidine-5-carboxylic Acid t-Butyl Ester The title compounds were prepared according to the method described in Example 41B, substituting propyl magnesium bromide for ethyl magnesium bromide to provide (±)-(2R,3S,5R,1'R,2'S)-1-t-butoxycarbonyl-2-(1-acetamido-2-hydroxy)pentyl-3-(cis-propen-1-yl)-pyrrolidine-6-carboxylic acid t-butyl ester (yield: 1 mg, 1%) and (±)-(2R,3S,5R,1'R,2'R)-1-t-butoxycarbonyl-2-(1-acetamido-2-hydroxy)pentyl-3-(cis-propen-1-yl)-pyrrolidine-5-carboxylic acid t-butyl ester (yield: 32 mg, 39%).

(±)-(2R,3S,5R,1'R,2'S) $^1$H NMR (CDCl$_3$) δ7.51 (d, J=8.2 Hz, 1H), 5.46 (m, 2H), 4.17 (dd, J=3.1, 6.8 Hz, 1H), 4.05 (m, 1H) 3.81 (t, J=3.4 Hz, 1H), 3.54 (m, 1H), 3.21 (m, 1H), 2.60 (m, 1H), 2.02 (s, 3H), 1.70 (dt, J=3.0, 7.4 Hz, 1H), 1.61 (d, J=5.4 Hz, 3H), 1.54 (m, 1H), 1.47 (s, 9H), 1.44 (s, 9H), 1.32 (m, 4H), 0.90 (t, J=7.1 Hz, 3H)

MS: (M+H)$^+$=455, (M+Na)$^+$=477; (M−H)$^−$=453.

(±)-(2R,3S,5R,1'R,2'R) $^1$H NMR (CDCl$_3$) δ5.98 (d, J=9.5 Hz, 1H), 5.60 (t, J=9.8 Hz, 1H), 5.36 (m, 1H), 4.16 (m, 1H), 3.75 (d, J=10.1 Hz, 1H), 3.64 (m, 1H), 3.51 (m, 1H), 3.09 (br t, 1H), 2.68 (m, 1H), 2.02 (s, 3H), 1.81 (d, J=13.9 Hz, 1H), 1.57 (m, 4H), 1.54 (dd, J=1.7, 5.1 Hz, 3H), 1.46 (s, 9H), 1.45 (s, 9H), 0.88 (t, J=6.8 Hz, 3H)

MS: (M−H)$^−$=453; (M+H)$^+$=455.

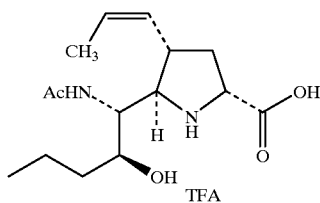

54B (±)-(2R,3S,5R,1'R,2'S)-2-(1-Acetamido-2-hydroxy)pentyl-1-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 1 mg, 100%).

$^1$H NMR (DMSO-d$_6$) δ7.83 (d, J=9.2 Hz, 1H), 5.43 (m, 1H), 5.23 (m, 1H), 3.98 (m, 1H), 3.56 (br t, 1H), 3.46 (m, 1H), 3.08 (m, 2H), 2.32 (m, 1H), 1.80 (s, 3H), 1.57 (dd, J=1.4, 5.4 Hz, 4H), 1.43 (m, 2H), 1.23 (m, 2H), 0.85 (br t, 3H)

MS: (M+H)$^+$=299, (M+Na)$^+$=321.

EXAMPLE 55

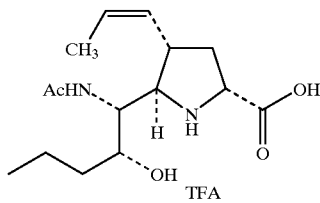

(±)-(2R,3S,5R,1'R,2'R)-2-(1-Acetamido-2-hydroxy)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-g-carboxylic acid t-butyl ester (yield: 0.0190 g, 100%).

$^1$H NMR (DMSO-d$_6$) δ7.64 (d, J=9.3 Hz, 1H), 5.48 (m, 1H), 5.24 (m, 1H), 4.38 (t, J=8.8 Hz, 1H), 4.06 (m, 1H), 3.75 (m, 1H), 3.53 (t, J=8.5 Hz, 1H), 3.16 (quint., J=8.5 Hz, 1H), 2.41 (dt, J=12.8,7.3 Hz, 1H), 1.82 (s, 3H), 1.70 (dt, 12.8,9.9 Hz, 1H), 1.55 (dd, J=7.0,1.6 Hz, 3H), 1.35 (m, 2H), 1.26 (m, 2H), 0.86 (t, J=6.7 Hz, 3H).

MS (M4H)$^+$=299, (M+Na)$^+$=321, (M−H)$^−$297.

EXAMPLE 56

(±)-(2R,3S,5R,1'R,2'S)-2-(1-Acetamido-2-hydroxy-3-methyl)butyl-3-(cis-propen-1-yl)-pyrrolidine-5-carboxylic Acid Trifluoroacetic Acid Salt

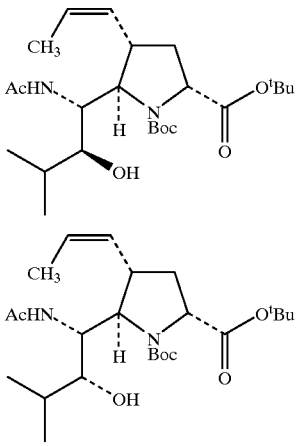

56A (±)-(2R,3S,5R,1'R,2'S) and (±)-(2R,3S,5R 1'R,2'R)-1-t-Butoxycarbonyl-2-(1-acetamido-2-hydroxy-3-methyl)butyl-3-(cis-propen-1-yl)-pyrrolidine-5-carboxylic Acid t-Butyl Ester The title compounds were prepared according to the method described in Example 41B, substituting isopropyl magnesium bromide for ethyl magnesium bromide to provide (±)-(2R,3S,5R,1'R,2'S)-1-t-butoxycarbonyl-2-(1-acetamido-2-hydroxy-3-methyl)butyl-3-(cis-propen-1-yl)-pyrrolidine-5-carboxylic acid t-butyl ester (yield: 0.0092 g, 10%) and (±)-(2R,3S,5R,1'R,2'R)-1-t-butoxycarbonyl-2-(1-acetamido-2-hydroxy-3-methyl)butyl-3-(cis-propen-1-yl)-pyrrolidine-5-carboxylic acid t-butyl ester (yield: 0.0385 g, 40%).

(±)-(2R,3S,5R,1'R,2'S) MS: (M+H)$^+$=455, (M+Na)$^{+−}$477, (2M+Na)$^+$=931, (M−H)$^−$=453.

(±)-(2R,3S,5R,1'R,2'R) MS: (M+H)$^+$=455, (M+Na)$^{+−}$477, (2M+Na)$^{+−}$931, (M−H)$^−$=453.

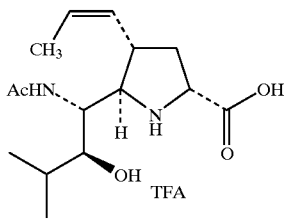

56B (±)-(2R,3S,5R,1'R,2'S)-2-(1-Acetamido-2-hydroxy-3-methyl)butyl-3-(cis-propen-1-yl)-pyrrolidine-5-carboxylic Acid Trifluoroacetic Acid Salt The title compound wag prepared according to the method described in Example 41C, substituting (±)-(2R,3S,5R,1'R,2'S)-1-t-butoxycarbonyl-2-(1-acetamido-2-hydroxy-3-methyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.010 g, 100%).

$^1$H NMR (DMSO-$d_6$) δ7.63 (d, J=9.2 Hz, 1H), 5.48 (m, 1H), 5.23 (m, 1H), 4.44 (m, 1H), 4.24 (m, 1H), 3.57 (t, J=8.7 Hz,1H), 3.33 (dd, J=8.5,2.5 Hz,1 H), 3.21 (quint., J=9.1 Hz, 1H), 2.43 (dt, J=12.8,7.6 Hz, 1H), 1.81 (s, 3H), 1.73 (dt, J=12.8,10.4 Hz, 1H), 1.56 (dd, J=6.7,1.9 Hz, 3H), 1.55 (m, 1H), 0.94 (d, J=6.7 Hz, 3H), 0.78 (d, J=6.7 Hz, 3H).

MS: (M+H)$^+$=299, (M+Na)$^+$=321, (M−H)$^-$=297, (M+CF$_3$COOH)$^-$=411, (2M−H)$^-$=595.

EXAMPLE 57

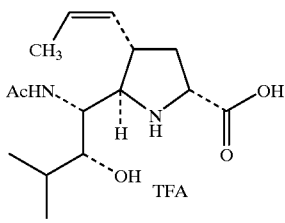

(±)-(2R,3S ,5R,1'R,2'R)-2-(1-Acetamido-2-hydroxy-3-methyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,$_1$'R,2'R)-1-t-butoxycarbonyl-2-(1-acetamido-2-hydroxy-3-methyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0433 g, 100%).

$^1$H NMR (DMSO-$d_6$) δ7.88 (d, J=9.2 Hz, 1H), 5.46 (m, 1H), 5.29 (m, 1H), 4.26 (t, J=8.5 Hz, 1H), 4.11 (m, 1H), 3.67 (m, 1H), 3.39 (dd, J=9.8,1.8 Hz, 1H), 3.15 J=9.1 Hz, 1H), 2.42 (dt, J=12.8,7.9 Hz, 1H), 1.81 (s, 3H), 1.73 (m, 1H), 1.62 (m, 1H), 1.57 (dd, J=7.0,1.6 Hz, 3H), 0.88 (d, J=6.7 Hz, 3H), 0.75 (d, J=6.7 Hz, 3H).

MS: (M+H)$^+$=299, (M+Na)$^+$=321, (M−H$_2$O)$^+$=281, (M−H)$^-$=297, (M+CF$_3$COOH)$^-$=411, (2M−H)$^-$=595.

EXAMPLE 58

(±)-(2R,3S,5R,1'R,2'S)-2-(1-Acetamido-2-hydroxy)hexyl-3-(cis-propen-1- -yl-pyrrolidine-5-carboxylic Acid Trifluoroacetic Acid Salt

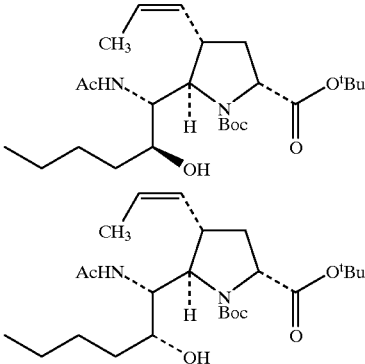

58A (±)-(2R,3S,5R,1'R,2'S) and (±)-(2R,3S,5R,1'R,2'R)-1-t-Butoxycarbonyl-(1-acetamido-2-hydroxy)hexyl-3-(cis-propen-1-yl)-pyrrolidine-5-carboxylic Acid t-Butyl Ester The title compounds were prepared according to the method described in Example 41B, substituting butyl magnesium bromide for ethyl magnesium bromide to provide (±)-(2R,3S,5R,1'R,2'S)-1-t-butoxycarbonyl-2-(1-acetamido-2-hydroxy)hexyl-3-(cis-propen-1-yl)-pyrrolidine-5-carboxylic acid t-butyl ester (yield: 2.0 mg, 8%) and (±)-(2R,3S,5R,1'R,2'R)-1-t-butoxycarbonyl-2-(1-acetamido-2-hydroxy)hexyl-3-(cis-propen-1-yl)-pyrrolidine-5-carboxylic acid t-butyl ester (yield: 6.0 mg, 24%).

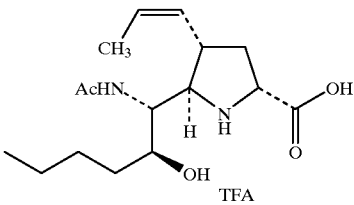

58B (±)-(2R,3S,5R,1'R,2'S)-2-(1-Acetamido-2-hydroxy)hexyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy)hexyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 2.0 mg, 100%).

$^1$H NMR (DMSO-$d_6$) δ8.34 (d, J=9.3 Hz, 1H), 5.24 (m, 1H), 5.12 (m, 1H), 3.90 (m, 1H), 3.78 (m, 1H), 3.23 (m, 1H), 2.90 (m, 1H), 2.14 (m, 1H), 1.80 (m, 1H), 1.75 (s, 3H), 1.52 (m, 3H), 1.45 (m, 1H), 1.08 (br s, 6H), 0.83 (br t, 3H).

MS: (M−H)$^-$=311; (M+H)$^+$=313.

EXAMPLE 59

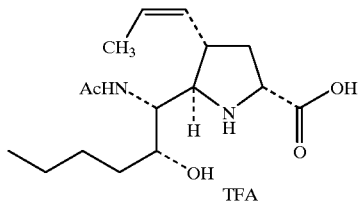

TFA (±)-(2R,3S,5R,1'R,2'R)-2-(1-Acetamido-2-hydroxy)hexyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy)hexyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 6.0 mg, 100%).

$^1$H NMR (DMSO-d$_6$) δ7.60 (d, J=9.3 Hz, 1H), 5.46 (m, 1H), 5.24 (t, J=9.2 Hz, 1H), 4.21 (t, J=8.3 Hz, 1H), 4.02 (t, J=7.9 Hz, 1H), 3.74 (m, 1H), 3.47 (t, J=8.8, 1H), 3.12 (m, 1H), 2.37 (m, 1H), 1.81 (s, 3H), 1.64 (m, 1H), 1.55 (dd, J=1.5, 5.4 Hz, 3H), 1.29 (m, 6H), 0.86 (t, J=6.9, 3H)

MS: (M−H)$^−$=311; (M+H)$^+$=313, (M+Na)$^+$=335.

EXAMPLE 60

(±)-(2R,3S,5R,1'R,2'S)-2-(1-Acetamido-2-hydroxy-4-methyl)pentyl-3-(cis-propen-1-yl)-pyrrolidine-5-carboxylic Acid Trifluoroacetic Acid Salt

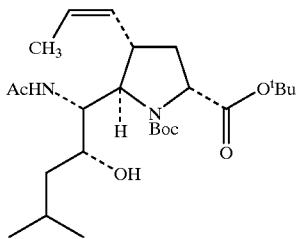

60A (±)-(2R,3S,5R,1'R,2'R)-1-t-Butoxycarbonyl-2-(1-acetamido-2-hydroxy-4-methyl)pentyl-3-(cis-propen-1-yl)-pyrrolidine-5-carboxylic Acid t-Butyl Ester The title compounds were prepared according to the method described in Example 41B, substituting isobutyl magnesium bromide for ethyl magnesium bromide to provide (±)-(2R,3S,5R,1'R,2'R)-1-t-butoxycarbonyl-2-(1-acetamido-2-hydroxy-4-methyl)pentyl-3-(cis-propen-1-yl)-pyrrolidine-5-carboxylic acid t-butyl ester (yield: 31 mg, 51%).

(±)-(2R,3S,5R,1'R,2'R) $^1$H NMR (CDCl$_3$) δ5.98 (d, J=9.5 Hz, 1H), 5.61 (t, J=8.2 Hz, 1H), 5.35 (m, 1H), 4.51 (dd, J=1.3, 3.1 Hz, 1H), 4.15 (m, 1H), 3.74 (d, J=10.5 Hz, 1H), 3.61 (m, 2H), 3.09 (t, J=7.5 Hz, 1H), 2.71 (m, 1H), 2.02 (s, 3H), 1.81 (d, J=13.9 Hz, 1H), 1.58 (brs, 1H), 1.54 (dd, J=1.7, 5.1 Hz, 3H), 1.47 (s, 9H), 1.45 (s, 9H), 1.42 (m, 1H), 0.87 (dd, J=2.4, 6.7 Hz, 6H)

MS: (M−H)$^−$=467; (M+H)$^+$=469, (M+Na)$^+$=491.

60B (±)-(2R,3S,5R,1'R)-1-t-Butoxycarbonyl-2-(1-acetamido-4-methyl-2-oxo)pentyl-3-(cis-propen-1-yl)-pyrrolidine-5-carboxylic Acid t-Butyl Ester

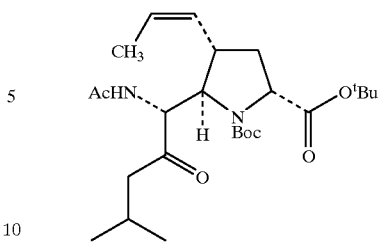

(±)-(2R,3S,5R,1'R,2'R)-1-t-Butoxycarbonyl-2-(1-acetamido-2-hydroxy-4-methyl)butyl-3-(cis-propen-1-yl)-pyrrolidine-5-carboxylic acid t-butyl ester (8.0 mg, 0.02 mmol) was reacted with Dess-Martin Periodinane (10 mg, 0.03 mmol) in dichloromethane (0.1 mL) at room temperature for 1 hour. The reaction was quenched with 1M aqueous sodium thiosulfate 1 mL and stirred for 20 minutes. The reaction was extracted with dichloromethane (3×1 mL). The organic layer was dried over magnesium sulfate, filtered, and concentrated in vacuo. The residue was purified by column chromatography on silica gel using 1:1: ethyl acetate/hexane to provide the title compound as a colorless semi-solid (yield: 4.8 mg, 61%).

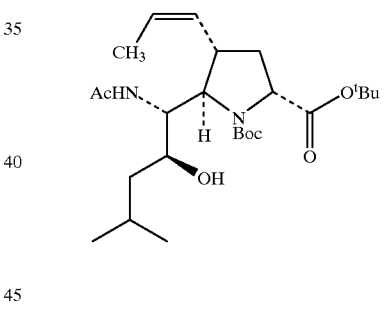

60C (±)-(2R,3S,5R,1'R,2'S)-1-t-Butoxycarbonyl-2-(1-acetamido-2-hydroxy-4-methyl)pentyl-3-(cis-propen-1-yl)-pyrrolidine-5-carboxylic Acid t-Butyl Ester (±)-(2R,3S,5R,1'R)-1-t-Butoxycarbonyl-2-(1-acetamido-4-methyl-2-oxo)pentyl-3-(cis-propen-1-yl)-pyrrolidine-5-carboxylic acid t-butyl ester (4.8 mg, 0.01 mmol) in methanol (0.1 mL) was reacted with sodium borohydride (2.0 mg, 0.05 mmol) at room temperature for 0.5 hours. The solvent was removed in vacuo and water (1 mL) was added. The aqueous layer was extracted with dichloromethane (3×1 mL). This organic layer was dried over magnesium sulfate, filtered and concentrated in vacuo. The residue was purified by column chromatography on silica gel using 1:1 ethyl acetate/hexane to provide the title compound (±)-(2R,3S,5R,1'R,2'S)-1-t-butoxycarbonyl-2-(1-acetamido-2-hydroxy-4-methyl)pentyl-3-(cis-propen-1-yl)-pyrrolidine-5-carboxylic acid t-butyl ester (yield: 2.4 mg, 51%).

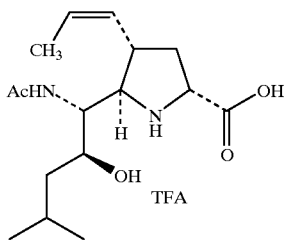

60B (±)-(2R,3S,5R,1'R,2'S)-2-(1-Acetamido-2-hydroxy-4-methyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-4-methyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.4 mg, 100%).

$^1$H NMR (D$_2$O) δ5.45 (m, 1H), 5.15 (t, J=11.0 Hz, 1H), 3.88 (m, 1H), 3.62 (t, J=8.0 Hz, 1H), 3.43 (br t, 1H), 2.98 (m, 1H), 2.36 (m, 1H), 1.81 (s, 3H), 1.60 (m, 1H), 1.51 (m, 1H), 1.45 (dd, J=1.3, 5.4 Hz, 3H), 1.17 (m, 3H), 0.74 (dd, J=6.7, 14 Hz, 6H)

MS: (M−H)$^-$=311; (M+H)$^+$=313, (M+Na)$^+$=335.

EXAMPLE 61

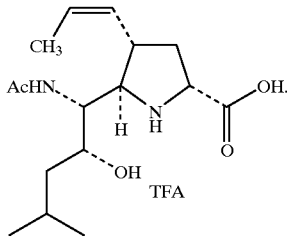

(±)-(2R,3S,5R,1'R,2'R)-2-(1-Acetamido-2-hydroxy-4-methyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-4-methyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 1.7 mg, 85%).

$^1$H NMR (DMSO-d$_6$) δ7.61 (d, J=9.8 Hz, 1H), 5.45 (m, 1H), 5.24 (t, J=7.4 Hz,1H), 4.29 (br t, 1H), 4.0 (br t, 1H), 3.83 (m, 1H), 3.49 (t, J=8.8 Hz, 1H), 3.13 (m, 1H), 2.39 (m, 1H), 1.82 (s, 3H), 1.68 (m, 2H), 1.55 (dd, J=1.4, 5.4 Hz, 3H), 1.31 (m, 1H), 1.04 (m, 1H), 0.86 (dd, J=6.4, 8.3 Hz, 6H)

MS: (M−H)$^-$=311; (M+H)$^+$=313, (M+Na)$^+$=335.

EXAMPLE 62

(±)-(2R,3S,5R,1'R,2'S)-2-(1-Acetamido-2-hydroxy)pent-3-ynyl)-3-(cis-propen-1-yl)-pyrrolidine-5-carboxylic Acid Trifluoroacetic Acid Salt

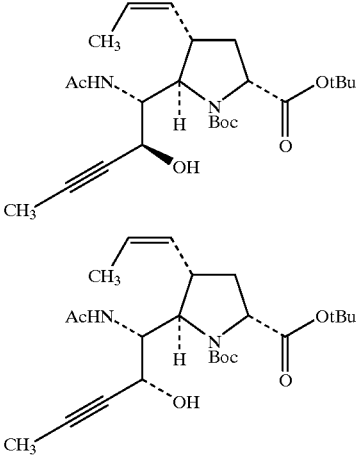

62A (±)-(2R,3S,5R,1'R,2'S) and (±)-(2R,3S,5R,1'R,2'R)-1-t-Butoxycarbonyl-2-(1-Acetamido-2-hydroxy)pent-3-ynyl)-3-(cis-propen-1-yl)-pyrrolidine-5-carboxylic Acid t-Butyl Ester The title compounds were prepared according to the method described in Example 41B, substituting propyn-1-yl zinc for ethyl magnesium bromide to provide (±)-(2R,3S,5R,1'R,2'S)-1-t-butoxycarbonyl-2-(1-acetamido-2-hydroxy)pent-3-ynyl-3-(cis-propen-1-yl)-pyrrolidine-5-carboxylic acid t-butyl ester (yield: 0.0073 g, 16%) and (±)-(2R,3S,5R,1'R,2'R)-1-t-butoxycarbonyl-2-(1-acetamido-2-hydroxy)pent-3-ynyl-3-(cis-propen-1-yl)-pyrrolidine-5-carboxylic acid t-butyl ester (yield: 0.0349 g, 77%).

(±)-(2R,3S,5R,1'R,2'S) MS: (M+H)$^+$=451, (M+Na)$^+$=473, (2M+Na)$^+$=923, (M−H)$^-$=449

(±)-(2R,3S,5R,1'R,2'R) MS: (M+H)$^+$=451, (M+Na)$^+$=473, (2M+Na)$^+$=923, (M−H)$^-$=449.

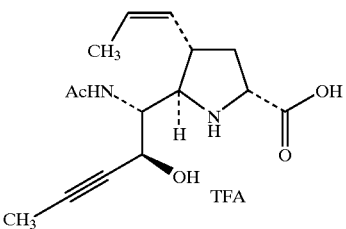

62B (±)-(2R,3S,5R,1'R,2'S)-2-(1-Acetamido-2-hydroxy)pent-3-ynyl)-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy)pent-3-ynyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0052 g, 100%).

¹H NMR (DMSO-d₆) d 7.97 (d, J=8.3 Hz, 1H), 5.48 (m, 1H), 5.25 (m, 1H), 4.35–4.20 (m, 3H), 3.67 (m, 1H), 3.18 (quint., 8.8 Hz, 1H), 2.41 (dt, J=12.7,7.8 Hz, 1H), 1.84 (s, 3H), 1.81 (d, J=1.9 Hz, 3H), 1.63 (m, 1H), 1.59 (dd, J=6.9,2.0 Hz, 3H).

MS: (M+H)⁺=295, (M+Na)⁺=317, (M−H)⁻=293, (M+CF₃COO⁻)−=407, (2M−H)⁻=587.

EXAMPLE 63

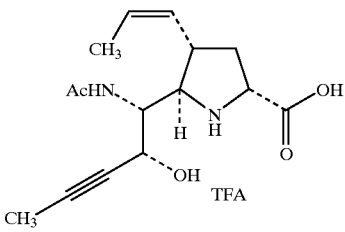

(±)-(2R,3S,5R,1'R,2'R)-2-(1-Acetamido-2-hydroxy) pent-3-ynyl)-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy)pent-3-ynyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0540 g, 100%).

¹H NMR (DMSO-d₆) d 7.90 (d, J=8.8 Hz, 1H), 5.50 (m, 1H), 5.25 (m, 1H), 4.40–4.35 (m, 2H), 4.28 (m, 1H), 3.71 (t, J=8.0 Hz, 1H), 3.18 (quint., 8.3 Hz, 1H), 2.42 (dt, J=13.2,7.4 Hz, 1H), 1.87 (s, 3H), 1.82 (d, J=1.9 Hz, 3H), 1.71 (dt, J=12.7,10.0 Hz, 1H), 1.57 (dd, J=6.9,1.5 Hz, 3H).

MS: (M+H)⁺=295, (M+Na)⁺=317, (M−H)⁻=293, (M+CF₃COO⁻)⁻=407.

EXAMPLE 64

(±)-(2R,3S,1'R,2'R)-2-(1-Acetamido-2-hydroxy-2-heptafluoropropyl)ethyl-3-(cis-propen-1-yl)-pyrrolidine-5-carboxylic Acid Trifluoroacetic Acid Salt

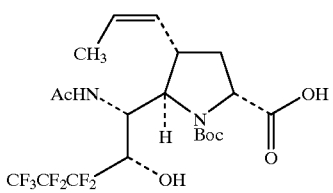

64A (±)-(2R,3S,5R,1'R,2'R)-1-t-Butoxycarbonyl-2-(1-acetamido-2-hydroxy-2-heptafluoropropyl)ethyl-3-(cis-propen-1-yl)-pyrrolidine-5-carboxylic Acid t-Butyl Ester (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester (41 mg, 0.10 mmol) and heptafluoropropyl iodide (0.144 mL, 1.0 mmol, 10 equivalents) in THF (2 mL) were reacted with 1M phenylmagnesium bromide (0.90 mL, 0.90 mmol, 9 equivalents) at −78° C. for 5 minutes. The reaction mixture was allowed to warm to room temperature over 1 h. The reaction was quenched with saturated aqueous ammonium chloride (10 mL) and water (10 mL) followed by extraction using ethyl acetate (3×25 mL). The organic layer was dried over magnesium sulfate, filtered and concentrated in vacuo. The residue was purified by column chromatography on silica gel using 1/2: ethyl acetate/hexane to provide the title compound (±)-(2R,3S, 5R,1'R,2'R)-1-t-butoxycarbonyl 2-(1-acetamido-2-hydroxy-2-heptafluoropropyl)ethyl-3-(cis-propen-1-yl)-pyrrolidine-5-carboxylic acid t-butyl ester (yield: 12.6 mg, 22%).

(±)-(2R,3S,5R,1'R,2'R) MS: (M+H)⁺=581, (M+Na)⁺=603, (2M+Na)⁺=1183, (M−H)⁻=579.

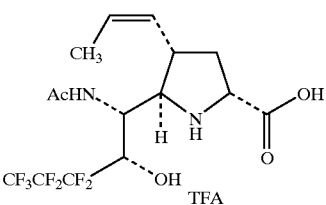

64B (±)-(2R,3S,5R,1'R,2'R)-2-(1-Acetamido-2-hydroxy-2-heptafluoropropyl)ethyl-3-(cis-propen-1-yl)pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-2-heptafluoropropyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.003 g,₁ 00%).

¹H NMR (DMSO-d₆) d 7.84 (d, J=9.3 Hz, 1H), 5.45 (m, 1H), 5.26 (m, 1H), 4.71 (t, J=9.7 Hz, 1H), 4.63 (d, J=22.0 Hz, 1H), 4.51 (m, 1H), 3.59 (t, J=9.3 Hz, 1H), 3.19 (quint., 8.3 Hz, 1H), 2.43 (dt, J=12.7,7.3 Hz, 1H), 1.76 (s, 3H), 1.74 (m, 1H), 1.53 (dd, J=6.8,1.4 Hz, 3H).

MS: (M+H)⁺=425, (M+Na)⁺=447, (M−H)⁻=423, (2M−1)⁻=847.

EXAMPLE 65

(±)-(2R,3S,5R,1'R,2'S)-2-(1-Acetamido-2,4-dihydroxy)butyl-3-(cis-propen-1-yl)-pyrrolidine-5-carboxylic Acid Trifluoroacetic Acid Salt

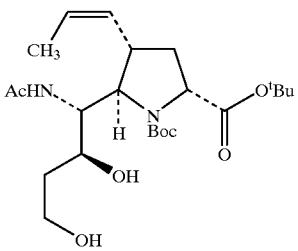

65A (±)-(2R,3S,5R,1'R,2'S)-1-t-Butoxycarbonyl-2-(1-acetamido-2,4-dihydroxy)butyl-3-(cis-propen-1-yl)-pyrrolidine-5-carboxylic Acid t-Butyl Ester (±)-(2R,3S,5R,1'R,2'S)-1-t-Butoxycarbonyl-2-(1-acetamido-2-hydroxy-3-ethoxycarbonyl)ethyl-3-(cispropen-1-yl)-pyrrolidine-5-carboxylic acid t-butyl ester (35 mg, 0.07 mmol) was reacted with lithium borohydride (8 mg, 0.35 mmol) in THF (5 mL) at 25° C. and reacted for 3 hours. The reaction was quenched with saturated aqueous ammonium chloride (2 mL) and water (2 mL) followed by extraction using dichloromethane (2×10 mL). The organic layer was dried over magnesium sulfate, filtered and concentrated in vacuo. The residue was purified by column chromatography on silica gel using 5% methanol in dichloromethane to provide the title compound (±)-(2R,3S,5R,1'R,2'S)-1-t-butoxycarbonyl 2-(1-acetamido-2,4-dihydroxy)butyl-3-(cis-propen-1-yl)-pyrrolidine-5-carboxylic acid t-butyl ester (yield: 14 mg, 440).

(±)-(2R,3S,5R,1'R,2'S)=MS: (M+H)$^+$=457, (M−H)$^-$=455

2'R)-1-t-butoxycarbonyl-2-(1-acetamido-2-hydroxy-3-ethoxycarbonyl)ethyl3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy-3-ethoxycarbonyl)ethyl-3-(cis-propen-1-yl)-pyrrolidine-5-carboxylic acid t-butyl ester. (yield: 11 mg, 70%).

$^1$H NMR (CDCl$_3$) δ5.58(m, 1H), 5.38(m, 1H),4.16(m, 1H), 4.05(m, 1H), 3.97(m, 1H), 3.78(m, 2H), 3.20(m,$_1$H), 2.66(m, 1H) 2.54(m,$_1$H), 2.04(s, 3H), 1.80(m,$_1$H), 1.55(m, 2H), 1.47(s, 9H), 1.44(s, 9H)

MS: (M+H)$^+$=467, (M−H)$^-$=455

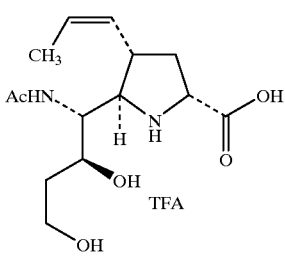

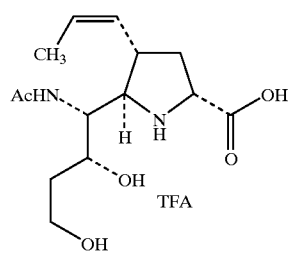

65B (±)-(2R,3S,5R,1'R,2'S)-2-(1-Acetamido-2,4-dihydroxy)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2,4-dihydroxy)butyl 3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

$^1$H NMR (DMSO-d$_6$) δ7.93 (d, J=9.0 Hz, 1H), 5.56(m, 1H), 5.31(m, 1H), 4.43 (m, 1H), 4.14 (m, 1H), 3.69 (m, 1H), 3.63 (m, 1H), 3.23 (m, 2H), 3.07 (m, 1H), 2.43 (m, 1H), 2.06 (s, 3H), 1.83 (m, 2H), 1.79 (m, 1H), 1.62 (dd, J=6.71, 1.22 Hz, 3H)

MS: (M+H)$^+$=301, (M−H)$^-$=299.

EXAMPLE 66

(±)(2R,3S,5R,1'R,2'R)-2-(1-Acetamido-2,4-dihydroxy)butyl-3-(cis-propen-1-yl)-pyrrolidine-5-carboxylic Acid Trifluoroacetic Acid Salt

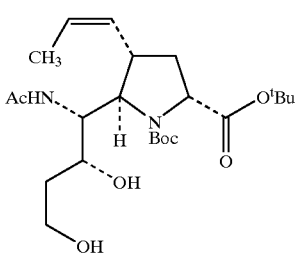

66A (2R,3S,5R,1'R,2'R)-1-t-Butoxycarbonyl-2-(1-acetamido-2,4-dihydroxy)butyl-3-(cis-propen-1-yl)-pyrrolidine-5-carboxylic Acid t-Butyl Ester The title compound was prepared according to the method described in Example 65A Substituting (±)-(2R,3S,5R,1'R,

66B (±)-(2R,3S,5R,1'R,2'R)-2-(1-Acetamido-2,4-dihydroxy)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2,4-dihydroxy)butyl 3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 8 mg, 96%).

$^1$H NMR (DMSO-d$_6$) δ7.91 (d, J=9.1 Hz, 1H), 5.50 (m, 1H), 5.25 (m, 1H), 4.43 (m, 1H), 4.30 (m, 1H), 4.22 (m, 1H), 3.94 (m, 1H), 3.86 (m, 1H), 3.62 (m, 1H), 3.18 (m, 1H), 2.43 (m, 1H), 1.85 (s, 3H), 1.75 (m, 1H), 1.65 (m, 2H), 1.58 (dd, J=6.70, 1.81 Hz, 3H).

MS: (M+H)$^+$=301, (M−H)$^-$=299.

EXAMPLE 67

(±)-(2R,3S,5R,1'R,2'S)-2-(1-Acetamido-2-hydroxy-2-(phenylacetylen-1-yl))ethyl-3-(cis-propen-1-yl)-pyrrolidine-5-carboxylic Acid Trifluoroacetic Acid Salt

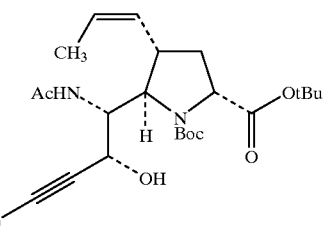

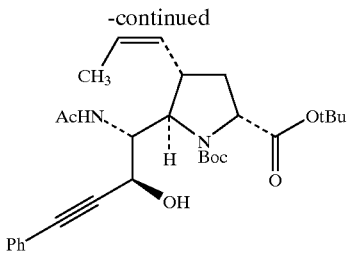

67A (±)-(2R,3S,5R,1'R,2'R) and (±)-(2R,3S,5R,1'R, 2'S)-1-t-Butoxycarbonyl-2-(1-acetamido-2-hydroxy-2-(phenylacetylen-1-yl))ethyl-3-(cis-propen-1-yl)-pyrrolidine-5-Carboxylic Acid t-Butyl Ester The title compounds were prepared according to the method described in Example 41B, substituting lithium phenylacetylide for ethyl magnesium bromide to provide (±)-(2R,3S,5R,1'R,2'S)-1-t-butoxycarbonyl-2-(1-acetamido-2-hydroxy-2-(phenylacetylen-1-yl))ethyl-3-(cis-propen-1-yl)-pyrrolidine-5-carboxylic acid t-butyl ester (yield: 0.0010 g, 4%) and (±)-(2R,3S,5R,1'R,2'R)-1-t-butoxycarbonyl-2-(1-acetamido-2-hydroxy-2-(phenylacetylen-1-yl))ethyl-3-(cis-propen-1-yl)-pyrrolidine-5-carboxylic acid t-butyl ester (yield: 0.0050 g, 21%).

(±)-(2R,3S,5R,1'R,2'S) MS: $(M+H)^+=513$, $(M+Na)^+=535$, $(2M+Na)^+=1047$, $(M-H)^-=511$.

(±)-(2R,3S,5R,1'R,2'R) MS: $(M+H)^+=513$, $(M+Na)^+=535$, $(2M+Na)^+=1047$, $(M-H)^-=511$.

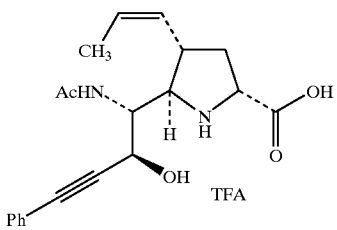

67B (±)-(2R,3S,5R,1'R,2'S)-2-(1-Acetamido-2-hydroxy-2-(phenylacetylen-1-yl))ethyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'S)-1-t-butoxycarbonyl-2-(1-acetamido-2-hydroxy-2-(phenylacetylen-1-yl))ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

EXAMPLE 68

(±)-(2R,3S,5R,1'R,2'R)-2-(1-Acetamido-2-hydroxy-2-(phenylacetylen-1-yl))ethyl-3-(cis-propen-1-yl)-pyrrolidine-5-carboxylic Acid Trifluoroacetic Acid Salt

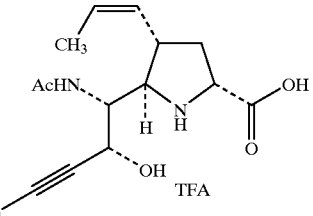

68A (±)-(2R,3S,5R,1'R,2'R)-2-(1-Acetamido-2-hydroxy-2-(phenylacetylen-1-yl))ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-2-(phenylacetylen-1-yl))ethyl-3-(cis-propen-1-yl)-pyrrolidine- 5-carboxylic acid t-butyl ester in place of (±)-(2R,3S, 5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0034 g, 100%).

$^1$H NMR (DMSO-d$_6$) δ 9.2 (bs, 1H), 8.04 (d, J=9.2 Hz, 1H), 7.45–7.35 (m, 5H), 5.50 (m, 1H), 5.29 (m, 1H), 4.64 (d, J=4.9, 1H), 4.5–4.4 (m, 2H), 3.81 (m, 1H), 3.22 (quint., J=8.5 Hz, 1H), 2.45 (dt, J=12.8,7.3 Hz, 1H), 1.89 (s, 3H), 1.74 (dt, J=12.7, 10.0 Hz, 1H), 1.58 (dd, J=7.3,1.8 Hz, 3H).

MS: $(M+H)^+=357$, $(M+Na)^+=379$, $(M-H)^-=355$.

EXAMPLE 69

(±)-(2R,3S,5R,1'R,2'S)-2-(1-Acetamido-2-hydroxy-3-ethyl)pentyl-3-(cis-propen-1-yl)-pyrrolidine-5-carboxylic Acid Trifluoroacetic Acid Salt

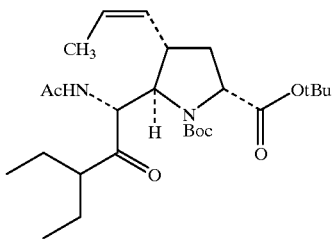

69A (±)-(2R,3S,5R,1'R)-1-t-Butoxycarbonyl-2-(1-Acetamido-2-oxo-3-ethyl)pentyl-3-(cis-propen-1-yl)-pyrrolidine-5-carboxylic Acid t-Butyl Ester The title compound was prepared according to the method described in Example 42A, substituting (±)-(2R,3S,5R,1'R, 2'R)-1-t-butoxycarbonyl-2-(1-acetamido-2-hydroxy-3-ethyl)pentyl-3-(cis-propen-1-yl)-pyrrolidine-5-carboxylic acid t-butyl ester in place of (2R,3S,5R,1'R,2'R)-1-t-butoxycarbonyl-2-(1-acetamido-2-hydroxy)butyl-3-(cis-propen-1-yl)-pyrrolidine-5-carboxylic acid t-butyl ester (yield: 8 mg, 81%).

MS: $(M+H)^+=481$, $(M-H)^-=479$

EXAMPLE 70

(±)-(2R,3S,5R,1'R,2'R)-2-(1-Acetamido-2-hydroxy-3-ethyl)pentyl-3-(cis-propen-1-yl)-pyrrolidine-5-carboxylic Acid Trifluoroacetic Acid Salt

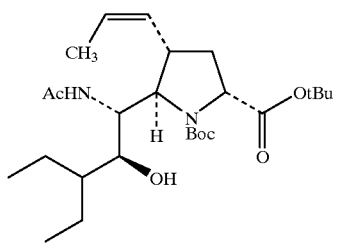

69B (±)-(2R,3S,5R,1'R,2'S)-1-t-Butoxycarbonyl-2-(1-Acetamido-2-hydroxy-3-ethyl)pentyl-3-(cis-propen-1-yl)-pyrrolidine-5-carboxylic Acid t-Butyl Ester The title compound was prepared according to the method described in Example 42B, substituting (±)-(2R,3S,5R,1'R)-1-t-butoxycarbonyl-2-(1-acetamido-2-oxo-3-ethyl)pentyl-3-(cis-propen-1-yl)-pyrrolidine-5-carboxylic acid t-butyl ester in place of (2R,3S,5R,1'R)-1-t-butoxycarbonyl 2-(1-acetamido-2-oxo)butyl-3-(cis-propen-1-yl)-pyrrolidine-5-carboxylic acid t-butyl ester (yield: 5 mg, 63%).

MS: $(M+H)^+=483$, $(M-H)^-=481$

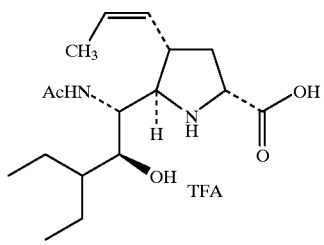

69C (±)-(2R,3S,5R,1'R,2'S)-2-(1-Acetamido-2-hydroxy-3-ethyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-3-ethyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4 mg, 95%).

$^1$H NMR (DMSO-$d_6$) δ7.67(d, J=8.9 Hz, 1H), 5.48(m, 1H), 5.23(m, 1H), 4.42(m, 1H), 4.21(m, 1H), 3.58(m, 2H), 3.22(m, 1H), 2.43(m, 1H), 1.82(s, 3H), 1.74(m, 1H), 1.58 (dd, J=6.71, 1.23 Hz, 3H), 1.52(m, 1H), 1.38(m, 1H), 1.29(m, 2 Hz), 1.13(m, 1H), 0.80(m, 6H)

MS: $(M+H)^+=327$, $(M-H)^-=325$

EXAMPLE 70

(±)-(2R,3S,5R,1'R,2'R)-2-(1-Acetamido-2-hydroxy-3-ethyl)pentyl-3-(cis-propen-1-yl)-pyrrolidine-5-carboxylic Acid Trifluoroacetic Acid Salt

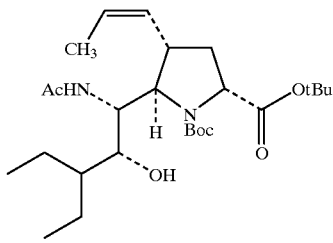

70A (±)-(2R,3S,5R,1'R,2'R)-1-t-Butoxycarbonyl-2-(1-Acetamido-2-hydroxy-3-ethyl)pentyl-3-(cis-propen-1-yl)-pyrrolidine-5-carboxylic Acid t-Butyl Ester The title compound was prepared according to the method described in Example 41B. substituting 3-pentyl magnesium bromide in place of ethyl magnesium bromide (yield: 13mg, 45%).

MS: $(M+H)^+=483$, $(M-H)^-=481$

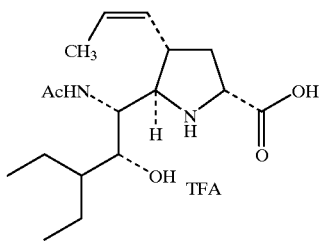

70B (±)-(2R,3S,5R,1'R,2'R)-2-(1-Acetamido-2-hydroxy-3-ethyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-3-ethyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 3 mg, 96%).

$^1$H NMR (DMSO-$d_6$) δ 7.85 (d, J=9.2 Hz, 1H), 5.47 (m, 1H), 5.30 (m, 1H), 4.28 (m, 1H), 4.19 (m, 1H), 3.67 (m, 1H), 3.58 (m, 1H), 3.17 (m, 1H), 2.43 (m, 1H), 1.81 (s, 3H), 1.63 (m, 1H), 1.58 (dd, J=6.71, 1.82 Hz, 3H), 1.40 (m, 2H), 1.28 (m, 1H), 1.10 (m, 1H), 1.05 (m, 1H), 0.83 (m, 6H)

MS: $(M+H)^+=327$, $(M-H)^-=325$

EXAMPLE 71

(±)-(2R,3S,5R,1'R,2'R)-2-(1-Acetamido-2-hydroxy-2-phenyl)ethyl-3-(cis-propen-1-yl)-pyrrolidine-5-carboxylic Acid Trifluoroacetic Acid Salt

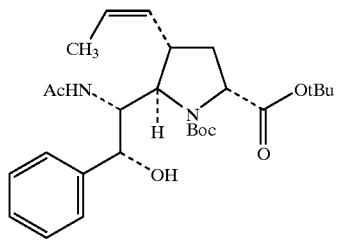

71A (±)-(2R,3S,5R,1'R,2'R)-1-t-Butoxycarbonyl-2-(1-Acetamido-2-hydroxy-2-phenyl)ethyl-3-(cis-propen-1-yl)-pyrrolidine-5-carboxylic Acid t-Butyl Ester The title compound wag prepared according to the method described in Example 41B, substituting phenyl magnesium bromide in place of ethyl magnesium bromide (yield: 36 mg, 60%).

MS: (M+H)⁺=489, (M+Na)⁺=511, (M–H)⁻487.

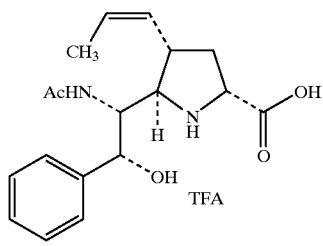

71B (±)-(2R,3S,5R,1'R,2'R)-2-(1-Acetamido-2-hydroxy-2-phenyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-2-phenyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 5.5 mg, 100%).

¹H NMR (DMSO-d₆) d 7.79 (d, J=9.2 Hz, 1H), 7.36 (m, 2H), 7.31 (m, 2H), 7.22 (m, 1H), 5.49 (m, 1H), 5.22 (m, 1H), 4.94 (d, J=3.0 Hz, 1H), 4.52 (m, 1H), 4.35 (m, 1H), 3.62 (t, J=8.5 Hz, 1H), 3.22 (m, 1H), 2.46 (m, 1H), 1.77 (m, 1H), 1.65 (s, 3H), 1.57 (dd, J=6.7, 0.8 Hz, 3H).

MS: (M+H)+=333, (M+Na)+355, (M–H)–=331.

EXAMPLE 72

(±)-(2R,3S,5R,1'R,2'S)-2-(1-Acetamido-2-hydroxy-2-phenyl)ethyl-3-(cis-propen-1-yl)-pyrrolidine-5-carboxylic Acid Trifluoroacetic Acid Salt

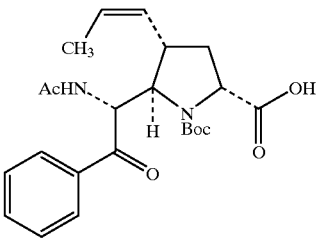

72A (±)-(2R,3S,5R,1'R)-1-t-Butoxycarbonyl-2-(1-Acetamido-2-oxo-2-phenyl)ethyl-3-(cis-propen-1-yl)-pyrrolidine-5-carboxylic Acid t-Butyl Ester The title compound was prepared according to the method described in Example 42A, substituting (±)-(2R,3S,5R,1'R,2'R)-1-t-butoxycarbonyl-2-(1-acetamido-2-hydroxy-2-phenyl)ethyl-3-(cis-propen-1-yl)-pyrrolidine-5-carboxylic acid t-butyl ester in place of (2R,3S,5R,1'R,2'R)-1-t-butoxycarbonyl 2-(1-acetamido-2-hydroxy)butyl-3-(cis-propen-1-yl)-pyrrolidine-5-carboxylic acid t-butyl ester (yield; 24 mg, 84%).

MS: (M+H)⁺=487, (M+Na)⁺=509, (M–H)⁻=485.

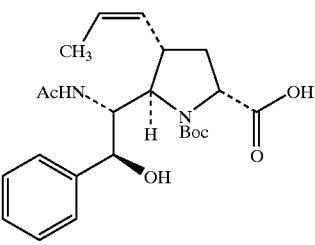

72B (±)-(2R,3S,5R,1'R,2'S)-1-t-Butoxycarbonyl-2-(1-Acetamido-2-hydroxy-2-phenyl)ethyl-3-(cis-propen-1-yl)-pyrrolidine-5-carboxylic Acid t-Butyl Ester The title compound was prepared according to the method described in Example 42B, substituting (±)-(2R,3S,5R,1'R)-1-t-butoxycarbonyl-2-(1-acetamido-2-oxo-2-phenyl)ethyl-3-(cis-propen-1-yl)-pyrrolidine-5-carboxylic acid t-butyl ester in place of (2R,3S,5R,1'R)-1-t-butoxycarbonyl 2-(1-acetamido-2-oxo)butyl-3-(cis-propen-1-yl)-pyrrolidine-5-carboxylic acid t-butyl ester (yield: 7.9 mg, 52%).

MS: (M+H)⁺=489, (M+Na)⁺=520, (M–H)⁻=487.

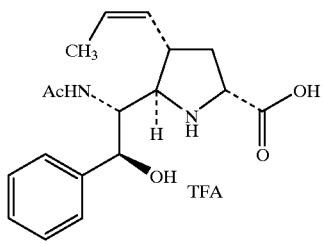

72C (±)-(2R,3S,5R,1'R,2'S)-2-(1-Acetamido-2-hydroxy-2-phenyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-2-phenyl)ethyl-3-(cis-propen-1-yl)pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 7.5 mg, 100%).

$^1$H NMR (DMSO-d$_6$) d 7.83 (d, J=9.2 Hz, 1H), 7.36 (m, 2H), 7.32 (m, 2H), 7.25 (m, 1H), 5.47 (m, 1H), 5.33 (m, 1H), 4.54 (d, J=9.8 Hz, 1H), 4.36 (m, 1H), 4.23 (m, 1H), 3.78 (m, 1H), 3.20 (m, 1H), 2.43 (m, 1H), 1.63 (m, 1H), 1.56 (dd, J=6.7, 1.2 Hz, 3H), 1.53 (s, 3H).

MS: (M+H)$^+$=333, (M+Na)$^+$=355, (M–H)$^-$=331.

EXAMPLE 73

(±)-(2R,3S,5R,1'R,2'R)-2-(1-Acetamido-2-hydroxy-2-(thiophen-2-yl))ethyl-3-(cis-propen-1-yl)-pyrrolidine-5-carboxylic Acid Trifluoroacetic Acid Salt

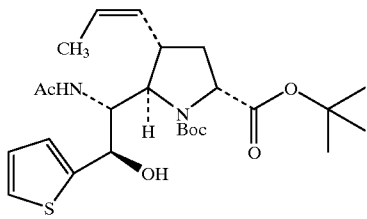

73A (±)-(2R,3S,5R,1'R,2'R)-1-t-Butoxycarbonyl-2-(1-acetamido-2-hydroxy-2-(thiophen-2-yl))ethyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-formyl)ethyl-3-(cis-propen-1-yl)-pyrrolidine-5-carboxylic acid t-butyl ester (40 mg, 0.098 mmol) in THF (2 mL) was added dropwise to a solution of 2-thienyllithium (1M in THF, 0.505 mmol, 5 equivalents) in THF (1 mL) at 25° C. and reacted for 20 minutes. The reaction was quenched with saturated aqueous ammonium chloride (2 mL) and water (5 mL) followed by extraction using dichloromethane (2×10 mL). The organic layer was dried over magnesium sulfate, filtered and concentrated in vacuo. The residue was purified by column chromatography on silica gel using 1/1: ethyl acetate/hexane to provide the title compound (yield: 9.5 mg, 20%).

MS: (M+H)$^+$=495, (M+Na)$^+$=517, (M–H)$^-$=493.

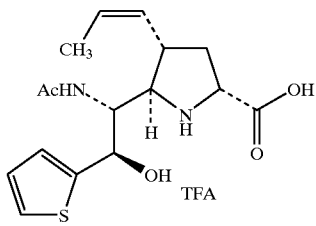

73B (±)-(2R,3S,5R,1'R,2'R)-2-(1-Acetamido-2-hydroxy-2-(thiophen-2-yl))ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-2-(thiophen-2-yl))ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.3 mg, 100%).

$^1$H NMR (DMSO-d$_6$) δ7.86 (d, J=9.8 Hz, 1H), 7.63 (dd, J=5.4, 1.0 Hz, 1H), 7.07 (m, 1H), 6.98 (m, 1H), 5.58 (m, 1H), 5.43 (m, 1H), 4.55 (m, 1H), 4.39 (m, 1H), 3.72 (m, 1H), 3.11 (m, 2H), 2.43 (m, 1H), 2.04 (s, 3H), 1.80 (m, 1H), 1.57 (m, 3H).

MS: (M+H)$^+$=339, (M+Na)$^+$=361, (M–H)$^-$=337.

EXAMPLE 74

(±)-(2R,3S,5R,1'R,2'S)-2-(1-Acetamido-2-hydroxy-3-(4-methylthiazol-2-yl))propen-3-(cis-propen-1-yl)-pyrrolidine-5-carboxylic Acid Trifluoroacetic Acid Salt

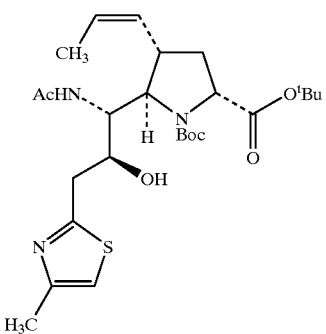

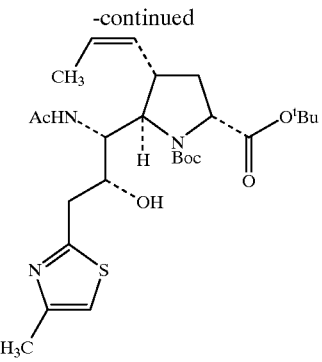

74A (±)-(2R,3S,5R,1'R,2'S) and (±)-(2R,3S,5R,1'R,2'R)-1-t-Butoxycarbonyl-2-(1-Acetamido-2-hydroxy-3-(4-methylthiazol-2-yl))propyl-3-(cis-propen-1yl)-pyrrolidine-5-carboxylic Acid t-Butyl Ester 1.6 M n-Butyllithium (0.125 mL, 0.20 mmol, 4 equivalents) was added to a solution of 2,4-dimethylthiazole (28.3 mg, 0.25 mmol, 5 equivalents) in 1 mL of THF at −78 and reacted for 30 minutes. ((±)-(2R,3S,5R,1'R)-1-t-butoxycarbonyl 2-(1-acetamido-2-formyl)ethyl-3-(cis-propen-1-yl)-pyrrolidine-5-carboxylic acid t-butyl ester (20.5 mg, 0.050 mmol) in THF (1 mL) was added dropwise to the above solution and reacted for 80 minutes at −78° C. and then for 30 minutes at room temperature. The reaction mixture was quenched with saturated aqueous ammonium chloride (5 mL) and water (5 mL) followed by extraction using dichloromethane (3×25 mL). The organic layer was dried over magnesium sulfate, filtered and concentrated in vacuo. The residue was purified by column chromatography on silica gel using 1/2: ethyl acetate/hexane to provide (±)-(2R,3S,5R,1'R,2'S)-1-t-butoxycarbonyl-2-(1-acetamido-2-hydroxy-3-(4-methylthiazol-2-yl))propyl-3-(cis-propen-1-yl)-pyrrolidine-5-carboxylic acid t-butyl ester (yield: 3.3 mg, 13%) and (±)-(2R,3S,5R,1'R,2'R)-1-t-butoxycarbonyl-2-(1-acetamido-2-hydroxy-3-(4-methylthiazol-2-yl))propyl-3-(cis-propen-1-yl)-pyrrolidine-5-carboxylic acid t-butyl ester (yield: 7.5 mg, 29%).

(2R,3S,5R,1'R,2'S) MS: $(M+H)^+=524$, $(M+Na)^+=546$, $(2M+Na)^+=1069$, $(M-H)^-=522$.

(2R,3S,5R,1'R,2'R) MS: $(M+H)^+=524$, $(M+Na)^+=546$, $(2M+Na)^+=1069$, $(M-H)^-=522$.

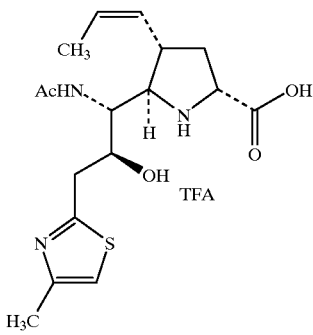

74B (±)-(2R,3S 5R,1'R,2'S)-2-(1-Acetamido-2-hydroxy-3-(4-methylthiazol-2-yl))propyl-3-(cis-propen-1-yl)-pyrrolidine-5-carboxylic Acid Trifluoroacetic Acid The title compound was prepared according to the method described in Example 41C, substituting (±)-(2R,3S,5R,1'R, 2'S)-1-t-butoxycarbonyl-2-(1-acetamido-2-hydroxy-3-(4-methylthiazol-2-yl))propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0030 g, 100%).

$^1$H NMR (DMSO-$d_6$) δ9.0 (bs, 1H), 8.10 (d, J=8.3 Hz, 1H), 7.11 (d, J=1.0 Hz, 1H), 5.48 (m, 1H), 5.30 (m, 1H), 4.30 (m, 1H), 4.10 (m, 1H), 3.88 (dt, J=9.4,2.6 Hz, 1H), 3.78 (m, 1H), 3.25–3.15 (m, 2H), 2.93 (dd, J=15.1,8.3 Hz, 1H), 2.41 (dt, J=12.3,7.3 Hz, 1H), 2.33 (d, J=1.0 Hz, 3H), 1.86 (s, 3H), 1.66 (dt, J=12.7, 10.3 Hz, 1H), 1.61 (dd, J=6.8,1.5 Hz, 3H).

MS: $(M+H)^+=368$, $(M+Na)^+=390$, $(M-H)^-=366$.

EXAMPLE 75

(±)-(2R,3S,5R,1'R,2'R)-2-(1-Acetamido-2-hydroxy-3-(4-methylthiazol-2-yl))propen-3-(cis-propen-1-yl-pyrrolidino-5-carboxylic Acid Trifluoroacetic Acid Salt

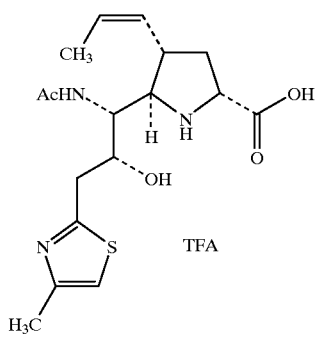

The title compound was prepared according to the method described in Example 41C, substituting (±)-(2R,3S,5R,1'R, 2'R)-1-t-butoxycarbonyl-2-(1-acetamido-2-hydroxy-3-(4-methylthiazol-2-yl))propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0030 g, 100%).

$^1$H NMR (DMSO-$d_6$) d 9.0 (bs, 1H), 7.77 (d, J=9.3 Hz, 1H), 7.11 (s, 1H), 5.47 (m, 1H), 5.25 (m, 1H), 4.45 (m, 1H), 4.20 (m, 2H), 3.58 (t, J=9.1 Hz, 1H), 3.19 (m, 1H), 2.96 (m, 2H), 2.41 (m, 1H), 2.33 (d, J=1.0 Hz, 3H), 1.85 (s, 3H), 1.73 (dt, J=12.7, 10.3 Hz, 1H), 1.54 (dd, J=6.9,1.5 Hz, 3H).

MS: $(M+H)^+=368$, $(M+Na)^+=390$, $(M-H)^-=366$, $(M+CF_3COOH)^-=480$, $(2M-H)^-=722$.

EXAMPLE 76

(±)-(2R,3S,5R,1'R,2'RS)-2-(1-Acetamido-2-hydroxy-3-(thiazolin-2-yl))1propyl-3-(cis-propen-1-yl)-pyrrolidine-5-carboxylic Acid Trifluoroacetic Acid Salt

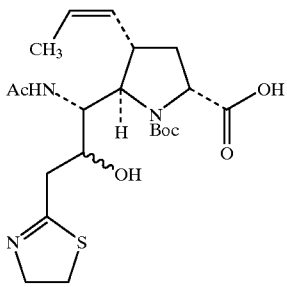

76A (±)-(2R,3S,5R,1'R,2'RS)-1-t-Butoxycarbonyl-2-(1-Acetamido-2-hydroxy-3-(thiazolin-2-yl))propyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-formyl)ethyl-3-(cis-propen-1-yl)-pyrrolidine-5-carboxylic acid t-butyl ester (20.5 mg, 0.05 mmol) in THF (1 mL) was added dropwise to a solution of the (thiazolin-2-yl)methyl lithium (0.20 mmol, 4 equivalents, prepared from 0.025 g of 2-methylthiazoline and 0.125 mL of 1.6 M n-BuLi at −78° C.) in THF (2 mL) at −78° C. and reacted for 30 minutes. The reaction was quenched with saturated aqueous ammonium chloride (5 mL) and water (5 mL) followed by extraction using dichloromethane (3×20 mL). The organic layer was dried over magnesium sulfate, filtered and concentrated in vacuo. The residue was purified by column chromatography on silica gel using 1/1 ethyl acetate/hexane to provide the title compound as a mixture of isomers (yield: 10 mg, 40%).

MS: $(M+H)^+=512$, $(M+Na)^+=534$, $(M-H)^-=510$.

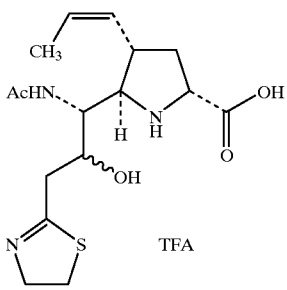

76B (±)-(2R,3S,5R,1'R,2'RS)-2-(1-Acetamido-2-hydroxy-3-(thiazolin-2-yl))propyl-3-(cis-propen-1-yl)-pyrrolidine-5-carboxylic Acid Trifluoroacetic Acid Salt The title compounds were prepared according to the method described in Example 41C, substituting (±)-(2R,3S,5R,1'R,2'RS)-1-t-butoxycarbonyl-2-(1-acetamido-2-hydroxy-3-(thiazolin-2-yl))propyl-3-(cis-propen-1-yl)-pyrrolidine-5-carboxylic acid t-butyl ester n place of (±)-(2R,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.003 g, 100%).

Major isomer $^1$H NMR (DMSO-d$_6$) δ8.88 (m, 1H), 7.76 (d, J=8.8 Hz, 1H), 5.46 (m, 1H), 5.19 (m, 1H), 4.69 (m, 1H), 3.90 (m1H), 3.85 (m, 1H), 3.49 (m, 2H), 3.35 (t, J=9.0 Hz, 1H), 3.29 (dd, J=17.6,5.9 Hz, 1H), 3.04 (t, J=8.9 Hz, 1H), 2.78 (dd, J=17.6,8.1 Hz, 1H), 2.7–2.55 (m, 2H), 1.75 (s, 3H), 1.70 (m, 1H), 1.56 (dd, J=6.8,1.5 Hz, 3H).

MS: $(M+H)^+=356$, $(M+Na)^+=378$, $(2M+Na)^+=733$, $(M-H)^-=354$.

EXAMPLE 77

(±)-(2R,3S,5R,1'R,2'S)-2-(1-Acetamido-2-hydroxy-3,3-difluoro-3-vinyl)propyl-3-(cis-propen-1-yl)-pyrrolidine-5-carboxylic Acid Trifluoroacetic Acid Salt

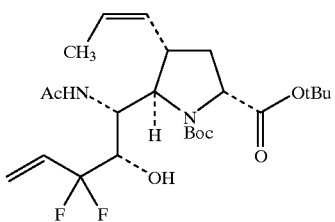

77A (±)-(2R,3S,5R,1'R,2'S)-1-t-Butoxycarbonyl-2-(1-acetamido-2-hydroxy-3,3-difluoro-3-vinyl)propyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-formyl)ethyl-3-(cis-propen-1-yl)-pyrrolidine-5-carboxylic acid t-butyl ester (41 mg, 0.10 mmol) and 1,1-difluoroallyl iodide (94 mg, 0.60 mmol, 6 equivalents) in THF (2 mL) was reacted with zinc dust (33 mg, 0.50 mmol, 5 equivalents) at 0° C. for 5 minutes and then at room temperature for 4 hours. The reaction mixture was quenched with saturated aqueous ammonium chloride (15 mL) and water (15 mL) and extracted with 3×25 mL dichloromethane. The organic layer was dried over magnesium sulfate, filtered and concentrated in vacuo. The residue was purified by column chromatography on silica gel using 1/3: ethyl acetate/hexane to provide the title compound (yield, 35 mg, 71%).

MS: $(M+H)^+=489$, $(M+Na)^+=511$, $(2M+Na)^+=999$, $(M-H)^-=487$.

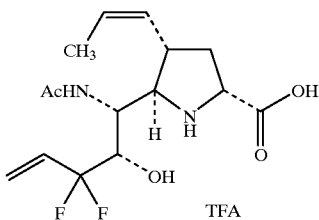

77B (±)-(2R,3S,5R,1'R,2'S)-2-(1-Acetamido-2-hydroxy-3,3-difluoro-3-vinyl)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-3,3- difluoro-3-vinyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0026 g, 96%).

$^1$H NMR (DMSO-$d_6$) δ7.68 (d, J=7.8 Hz, 1H), 5.97 (m, 1H), 5.55–5.45 (m, 2H), 5.43 (m, 1H), 5.23 (m, 1H), 4.45 (m, 2H), 4.10 (m, 1H), 3.16(quint. J=9.1 Hz, 1H), 2.41 (dt, J=12.8,7.3 Hz, 1H), 1.72 (s, 3H), 1.70 (dt, J=12.8, 10.3 Hz, 1H), 1.61 (dd, J=6.7,1.2 Hz, 3H).

MS: $(M+H)^+$=333, $(M+Na)^+$=355, $(M-H)^-$=331, $(2M-H)^-$=663.

EXAMPLE 78

(±)-(2R,3S,5R,1'R,2'R)-2-(1-Acetamido-2-hydroxy-3,3-difluoro-3-vinyl)propyl-3-(cis-propen-1-yl)-pyrrolidine-5-carboxylic Acid Trifluoroacetic Acid Salt

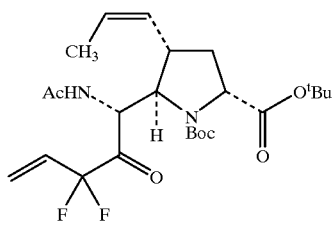

78A (±)-(2R,3S,5R,1'R)-1-t-Butoxycarbonyl-2-(1-Acetamido-2-oxo-3,3-difluoro-3-vinyl)propyl-3-(cis-propen-1-yl)-pyrrolidine-5-carboxylic Acid t-Butyl Ester The title compound was prepared according to the method described in Example 42A, substituting (±)-(2R,3S,5R,1'R,2'S)-1-t-butoxycarbonyl-2-(1-acetamido-2-hydroxy-3,3-difluoro-3-vinyl)propyl-3-(cis-propen-1-yl)-pyrrolidine-5-carboxylic acid t-butyl ester in place of (2R,3S,5R,1'R,2'R)-2-(1-acetamido-2-hydroxy)butyl-3-(cis-propen-1-yl)-pyrrolidine-5-carboxylic acid t-butyl ester to provide (±)-(2R,3S,5R,1'R)-1-t-butoxycarbonyl-2-(1-acetamido-2-oxo-3,3-difluoro-3,3-difluoro-3-vinyl)propyl-3-(cis-propen-1-yl)-pyrrolidine-5-carboxylic acid t-butyl ester (yield: 0.0050 g, 44%).

MS: $(M+H)^+$=487, $(M+Na)^+$=509, $(M-2F)^+$=448, $(M-H)^-$=485.

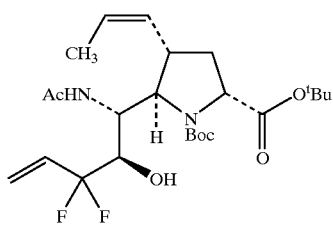

78B (±)-(2R,3S,5R,1'R,2'R)-1-t-Butoxycarbonyl-2-(1-Acetamido-2-hydroxy-3,3-difluoro-3-vinyl)propyl-3-(cis-propen-1-yl)-pyrrolidine-5-carboxylic Acid t-Butyl Ester The title compound is prepared according to the method described in Example 42B, substituting (±)-(2R,3S,5R,1'R)-1-t-butoxycarbonyl-2-(1-acetamido-2-oxo-3-difluoro-3-vinyl)propyl-3-(cis-propen-1-yl)-pyrrolidine-5-carboxylic acid t-butyl ester in place of (2R,3S,5R,1'R)-2-(1-acetamido-2-oxo)butyl-3-(cis-propen-1-yl)-pyrrolidine-5-carboxylic acid t-butyl ester.

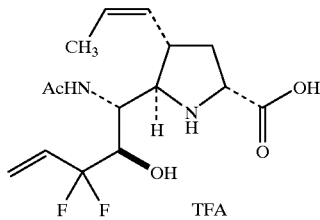

78C (±)-(2R,3S,5R,1'R,2'R)-2-(1-Acetamido-2-hydroxy-3,3-difluoro-3-vinyl)propyl-3-(cis-propen-1-yl)-pyrrolidine-5-carboxylic Acid Trifluoroacetic Acid The title compound is prepared according to the method described in Example 41C, substituting (±)-(2R,3S,5R,1'R,2'R)-1-t-butoxycarbonyl-2-(1-acetamido-2-hydroxy-3,3-difluoro-3-vinyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1acetamido-2-hydroxy)butyl-3-(cis-propen-1-yl)-pyrrolidine-5-carboxylic acid t-butyl ester.

EXAMPLE 79

(±)-(2R,3S,5R,1'R,2'R)-2-(1-Acetamido-2-hydroxy-2-(cis-buten-2-yl))ethyl-3-propen-1-yl)-pyrrolidine-5-carboxylic Acid Trifluoroacetic Acid Salt

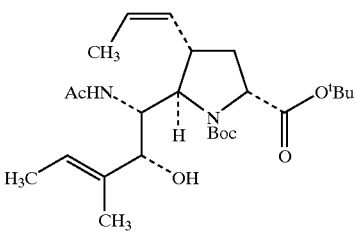

79A (±)-(2R,3S,5R,1'R,2'R)-1-t-Butoxycarbonyl-2-(1-Acetamido-2-hydroxy-2-(cis-buten-2-yl))ethyl-3-(cis-propen-1-yl)-pyrrolidine-5-carboxylic Acid t-Butyl Ester (±)-(2R,3S,5R,1'R)-1-t-Butoxycarbonyl 2-(1-acetamido-2-formyl)ethyl-3-(cis-propen-1-yl)-pyrrolidine-5-carboxylic acid t-butyl ester (30 mg, 0.073 mmol) in THF (5 mL) was reacted with cis-2-buten-2-yl lithium (0.75 mL (0.5M), 0.37 mmol) at 25° C. for 45 min. The reaction was quenched with saturated aqueous ammonium chloride (5 mL) and water (5 mL) followed by extraction using dichloromethane (2×10 mL). The organic layer was dried over magnesium sulfate, filtered and concentrated in vacuo. The residue was purified by column chromatography on silica gel using 1/1: ethyl acetate/hexane to provide the title compound (yield: 20 mg, 59%).

$^1$H NMR (CDCl$_3$) δ6.19 (d, J=8.9 Hz, 1H), 5.61 (m, 1H), 5.35 (m, 1H), 5.27 (m, 1H), 4.48 (m, 1H), 4.18 (m,1H), 4.77 (m, 2H), 3.10 (m,1H), 2.72 (m 1H), 1.99 (s, 3H), 1.82 (m, 1H), 1.73 (m, 3H), 1.55 (m, 6H), 1.47(s, 9H), 1.44 (s, 9H)

MS: $(M+H)^+$=467, $(M-H)^-$=465

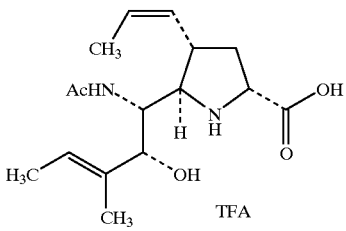

79B (±)-(2R,3S,5R,1'R,2'R)-2-(1-Acetamido-2-hydroxy-2-(cis-buten-2-yl))ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-2-(cis-buten-2-yl))ethyl-3-(cis-propen-1-yl)-pyrrolidine-5-carboxylic acid t-butyl ester in place of (±)-(2R,3S,5R,1'R,2'S)1-t-butoxycarbonyl-2-(1-acetamido-2-hydroxy)butyl-3-(cis-propen-1-yl)-pyrrolidine-5-carboxylic acid t-butyl ester (yield: 4 mg, 96%).

$^1$H NMR (DMSO-d$_6$) δ8.09 (d, J=9.0 Hz, 1H), 5.50 (m, 1H), 5.32 (m, 1H), 5.16 (m, 1H), 4.50 (m, 1H), 4.38 (m, 1H), 4.19 (m, 1H), 3.43 (m, 1H), 3.20 (m, 1H), 2.43 (m, 1H), 1.88 (s, 3H), 1.74 (m, 1H), 1.70 (s, 3H), 1.62(m, 3H), 1.58 (m, 3H)

MS: (M+H)$^+$=311, (M−H)$^−$=309

EXAMPLE 80

(±)-(2R,3S,5R,1'R,2'R,3'R) and (±)-(2R,3S,5R,1'R,2'R,3'S)-2-(1-Acetamido-2-hydroxy-3-methyl)pentyl-3-(cis-propen-1-yl)-pyrrolidine-5-carboxylic Acid Trifluoroacetic Acid Salt

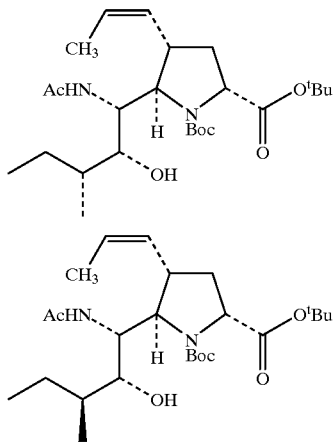

80A (±)-(2R,3S,5R,1'R,2'R,3'R) and (±)-(2R,3S,5R,1'R,2'R,3'S)-1-t-Butoxycarbonyl-2-(1acetamido-2-hydroxy-3-methyl)pentyl-3-(cis-propen-1-yl)-pyrrolidine-5-carboxylic Acid t-Butyl Ester (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester (60 mg, 0.15 mmol) in THF (1 mL) was added dropwise to a solution of 2-butylmagnesium bromide (3M in ether) (0.45 mL, 0.85 mmol) at room temperature and reacted for 40 minutes. The reaction was quenched with saturated NH$_4$Cl (1 mL) followed by extraction using dichloromethane (3×1 mL). The organic layer was dried over magnesium sulfate, filtered and concentrated in vacuo. The residue was purified by column chromatography on silica gel using 1/4: ethyl acetate/hexane to provide the title compounds (±)-(2R,3S,5R,1'R,2'R,3'S)-1-t-butoxycarbonyl 2-(1-acetamido-2-hydroxy-3-methyl)pentyl-3-(cis-propen-1-yl)-pyrrolidine-5-carboxylic acid t-butyl ester R$_f$=0.65 (1:1ethyl acetate: hexanes) (yield: 19 mg, 27%) and (±)-(2R,3S,5R,1'R,2'R,3'R)-1-t-butoxycarbonyl 2-(1-acetamido-2-hydroxy-3-methyl)pentyl-3-(cis-propen-1-yl)-pyrrolidine-5-carboxylic acid t-butyl ester R$_f$=0.5) (1:1ethyl acetate: hexanes) (yield: 19 mg, 27%).

R$_f$=0.65 $^1$H NMR (CDCl$_3$) δ5.98 (d, J=8.8 Hz, 1H), 5.62 (t, J=10.5 Hz, 1H), 5.35 (m, 1H), 4.66 (d, J=4.4 Hz, 1H), 4.16 (d, J=9.5 Hz, 1H), 3.78 (m, 3H), 3.12 (m, 2H), 2.73 (m, 1H), 2.0 (s, 3H), 1.81(d, J=13.2 Hz, 1H), 1.54 (br s, 3H), 1.47 (s, 9H), 1.44 (s, 9H), 1.25 (m, 1H), 0.81 (m, 6H)

MS: (M−H)$^−$=467; (M+H)$^+$=469.

R$_f$=0.5 $^1$H NMR (CDCl$_3$) δ6.00 (d, J=10.2 Hz, 1H), 5.61 (br t, 1H), 5.36 (m, 1H), 4.58 (d, J=4.7 Hz, 1H), 4.14 (d, J=8.8 Hz, 1H), 3.82 (m, 3H), 3.13 (m, 2H), 2.73 (m, 1H), 1.99 (s, 3H), 1.80 (d, J=13.9 Hz,1H), 1.54 (br s, 3H), 1.46 (s, 9H), 1.44 (s, 9H), 1.43 (m, 1H), 0.97 (d, J=6.8 Hz, 3H), 0.81 (t, J=7.2 Hz, 3H)

MS: (M−H)$^−$=467; (M+H)$^+$=469.

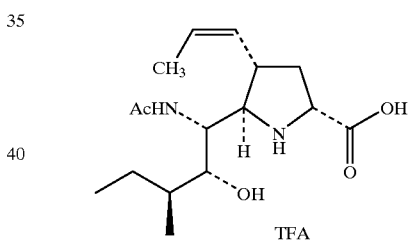

80B (±)-(2R,3S,5R,1'R,2'R,3'S)-2-(1-Acetamido-2-hydroxy-3-methyl)pentyl-3-(cis-propen-1-yl)-pyrrolidine-5-carboxylic Acid Trifluoroacetic Acid Salt (±)-(2R,3S,5R,1'R,2'R,3'S)-1-t-Butoxycarbonyl-2-(1-acetamido-2-hydroxy-3-methyl)pentyl-3-(cis-propen-1-yl)-pyrrolidine-5-carboxylic acid t-butyl ester (2.5 mg, 0.005 mmol) was reacted with trifluoroacetic acid (0.8 mL) in dichloromethane (0.2 mL) at room temperature for 6 hrs, The reaction was concentrated in vacuo overnight and triturated with acetonitrile (2×1 mL) to provide the title compound (yield: 2.0 mg, 100%).

$^1$H NMR (DMSO-d6) δ7.68 (d, J=8.8 Hz, 1H), 5.45 (m, 1H), 5.23 (t, J=7.3 Hz, 1H), 4.24 (br t, 1H), 4.18 (m, 1H), 3.52 (t, J=7.3 Hz, 1H), 3.45 (m, 1H), 3.16 (m, 1H), 2.38 (m, 1H), 1.83 (s, 3H), 1.68 (m, 1H), 1.58 (dd, J=2.0, 4.8 Hz, 3H), 1.37 (m, 2H), 0.99 (m, 1H), 0.89 (d, J=6.8 Hz, 3H), 0.79 (t, J=7.4 Hz, 3H),

MS: (M−H)−=311; (M+H)+=313, (M+Na)+=335.

EXAMPLE 81

(±)-(2R,3S,5R,1'R,2'R,3'R)-2-(1-Acetamido-2-hydroxy-3-methy)pentyl-3-(cis-propen-1-yl)-pyrrolidine-5-carboxylic Acid Trifluoroacetic Acid Salt

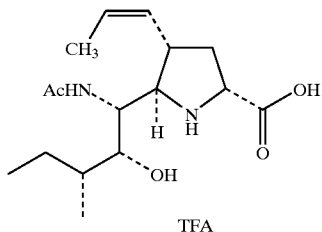

TFA

The title compound was prepared according to the method described in Example 41C),substituting (±)-(2R,3S,5R,1'R,2'R,3'R)-1-t-butoxycarbonyl-2-(1-acetamido-2-hydroxy-3-methyl)pentyl-3-(cis-propen-1-yl)-pyrrolidine-5-carboxylic acid t-butyl ester (R$_f$=0.5,1:1, ethyl acetate:hexanes) in place of (±)-(2R,3S,5R,1'R,2'S)-1-t-butoxycarbonyl-2-(-acetamido-2-hydroxy )butyl-3-(cis-propen-1-yl)-pyrrolidine-5-carboxylic acid t-butyl ester (yield: 1.6 mg, 76%).

$^1$H NMR (DMSO-d$_6$) δ7.55 (d, J=9.3 Hz, 1H), 5.45 (m, H), 5.23 (m 1H), 4.31 (br t, 1H), 4.20 (t, J=8.3 Hz, 1H), 3.5 (t, J=9.3 Hz, 1H), 3.43 (d, J=7.4 Hz, 1H), 3.17 (m, 1H), 2.40 (m, 1H), 1.80 (s, 3H), 1.70 (m, 1H), 1.55 (dd, J=1.4, 5.4 Hz, 3H), 1.36 (m, 2H), 1.14 (m, 1H), 0.84 (t, J=7.3 Hz, 3H), 0.73 (d, J=6.9 Hz, 3H)

MS: (M−H)$^−$=311; (M+H)$^+$=313, (M+Na)$^+$=335.

EXAMPLE 82

(±)-(2R,3S,5R,1'R,2'S,3'S)-2-(1-Acetamido-2-hydroxy-3-methyl)pentyl-3-(cis-propen-1-yl)-pyrrolidine-5-carboxylic Acid Trifluoroacetic Acid Salt

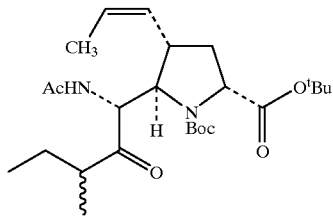

82A (±)-(2R,3S,5R,1'R,3'RS)-1-t-Butoxycarbonyl-2-(1-acetamido-2-oxo-3-methyl)pentyl-3-(cis-propen-1-yl)-pyrrolidine-5-carboxylic Acid t-Butyl Ester The title compound was prepared according to the method described in Example 42A, substituting (±)-(2R,3S,5R,1'R,2'R,3'RS)-1-t-butoxycarbonyl-2-(1-acetamido-2-hydroxy-3-methyl)pentyl-3-(cis-propen-1-yl)-pyrrolidine-5-carboxylic acid t-butyl ester in place of (±)-(2R,3S,5R,1'R,2'R) 1-t-butoxycarbonyl-2-(1-acetamido-2-hydroxy)butyl-3-(cis-propen-1-yl)-pyrrolidine-5-carboxylic acid t-butyl (yield: 12 mg, 63%).

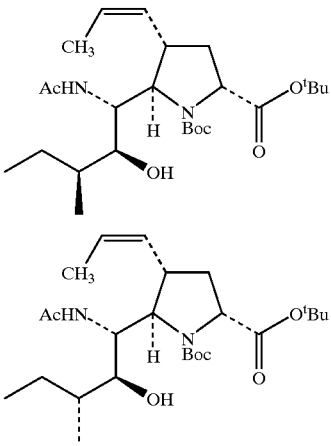

82B (±)-(2R,3S,5R,1'R,2'S,3'S) and (±)-(2R,3S,5R,1'R,2'S,3'R)-1-t-Butoxycarbonyl-2-(1-acetamido-2-hydroxy-3-methyl)pentyl-3-(cis-propen-1-yl)-pyrrolidine-5-carboxylic Acid t-Butyl Ester The title compounds were prepared according to the method described in Example 42B, substituting (±)-(2R,3S,5R,1'R,3'RS)-1-t-butoxycarbonyl-2-(1-acetamido-2-oxo-3-methyl)pentyl-3-(cis-propen-1-yl)-pyrrolidine-5-carboxylic acid t-butyl ester (R$_f$=0.5 and 0.65,1:1, ethyl acetate: hexanes) in place of (2R,3S,5R,1'R)-2-(1-acetamido-2-oxo)butyl-3-(cis-propen-1-yl)-pyrrolidine-5-carboxylic acid t-butyl ester to give (±)-(2R,3S,5R,1'R,2'S,3'S)-1-t-butoxycarbonyl-2-(1-acetamido-2-hydroxy-3-methyl)pentyl-3-(cis-propen-1-yl)-pyrrolidine-5-carboxylic acid t-butyl ester (R$_f$=0.15,1:1, ethyl acetate: hexanes) (yield: 6.0 mg, 50%) and (±)-(2R,3S,5R,1'R,2'S,3'R)-1-t-butoxycarbonyl-2-(1-acetamido-2-hydroxy-3-methyl)pentyl-3-(cis-propen-1-yl)-pyrrolidine-5-carboxylic acid t-butyl ester(R$_f$=0.10,1:1, ethyl acetate: hexanes) (yield: 2.5 mg, 63%).

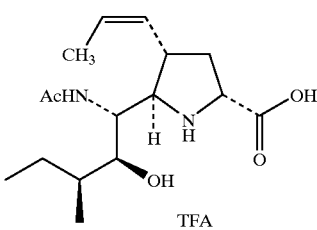

TFA 82C (±)-(2R,3S,5R,1'R,2'S,3'S)-2-(1-Acetamido-2-hydroxy-3-methyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S,3'S)-1-t-butoxycarbonyl-2-(1-acetamido-2-hydroxy-3-methyl)pentyl-3-(cis-propen-1-yl)-pyrrolidine-5-carboxylic acid t-butyl ester (R$_f$=0.15, 1:1, ethyl acetate: hexanes) in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 6.0 mg,100%).

$^1$H NMR (DMSO-d$_6$) δ7.78 (d, J=9.2 Hz, 1H), 5.42 (m, 1H), 5.29 (t, J=10.3 Hz, 1H), 4.08 (m, 1H), 3.96 (br t, 1H), 3.51 (m, 2H), 3.08 (m, 1H), 2.33 (m, 1H), 1.78 (s, 3H), 1.56 (d, J=6.3 Hz, 3H), 1.52 (m, 1H), 1.40 (m, 1H), 1.29 (m 1H), 1.21 (m, 1H), 0.84 (t, J=7.3 Hz, 3H), 0.73 (d, J=6.9 Hz, 3H)

MS: (M−H)⁻=311; (M+H)⁺=313, (M+Na)⁺=335.

Example 83

(±)-(2R,3S,5R,1'R,2'S,3'R)-2-(1-Acetamido-2-hydroxy-3-methyl)pentyl-3-(cis-propen-1-yl)-pyrrolidine-5-carboxylic Acid Trifluoroacetic Acid Salt

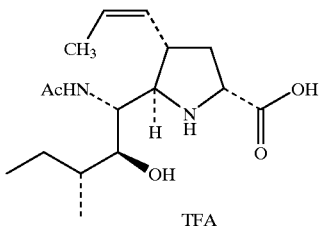

TFA

The title compound was prepared according to the method described in Example 41C, substituting(±)-(2R,3S,5R,1'R,2'S,3'R)-1-t-butoxycarbonyl-2-(1-acetamido-2-hydroxy-3-methyl)pentyl-3-(cis-propen-1-yl)-pyrrolidine-5-carboxylic acid t-butyl ester (R$_f$=0.10, 1:1ethyl acetate; hexanes) in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 2.5 mg, 100%).

¹H NMR (DMSO-d$_6$) δ7.85 (d, J=8.7 Hz, 1H), 5.45 (m 1H), 5.29 (t, J=9.3 Hz, 1H), 4.20 (m, 2H), 3.63 (t, J=8.3 Hz, 1H), 3.42 (br d, 1H), 3.14 (m, 1H), 2.41 (m, 1H), 1.79 (s, 3H), 1.62 (m, 1H), 1.58 (d, J=5.4 Hz, 3H), 1.43 (m, 2H), 1.0 (m, 1H), 0.88 (d, J=6.8 Hz, 3H), 0.80 (t, J=7.3 Hz, 3H)

MS: (M−H)⁻=311; (M+H)⁺=313, (M+Na)⁺=335.

EXAMPLE 84

(±)-(2R,3S,R 1'R,2'S)-2-(1-Acetamido-2-methoxy)butyl-3-(cis-propen-1-yl)-pyrrolidine-5-carboxylic Acid Trifluoroacetic Acid Salt

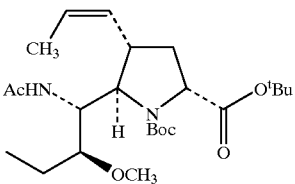

84A (±)-(2R,3S,5R,1'R,2'S)-1-t-Butoxycarbonyl-2-(1-acetamido-2-methoxy)butyl-3-(cis-propen-1-yl)-pyrrolidine-5-carboxylic Acid t-Butyl Ester (±)-(2R,3S,5R,1'R,2'S)-1-t-Butoxycarbonyl-2-(1-acetamido-2-hydroxy)butyl-3-(cis-propen-1-yl)-pyrrolidine-5-carboxylic acid t-butyl ester (22 mg, 0.05 mmole) was reacted with methyl iodide (0.016 mL, 0.25 mmole), potassium hydroxide (14 mg, 0.25 mmole) and 18-crown-6 (0.7 mg, 0.0025 mmole) in N,N-dimethylformamide (2 mL) at room temperature for 23 hours. Water (5 mL) was then added to the reaction mixture, followed by extraction with ether (2×10 mL). The organic layer was washed with water, and brine, dried over MgSO$_4$, filtered and concentrated in vacuo. The residue was purified by chromatography on silica gel using 66% ethyl acetate/hexanes to provide the title compound, as a colorless oil (yield: 5.2 mg, 23%).

MS: (M+H)⁺=455, (M−H)−=453.

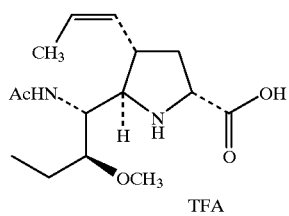

TFA 84B (±)-(2R,3S,5R,1'R,2'S)-2-(1-Acetamido-2-methoxy)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-methoxy)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield; 4.7 mg, 98%).

¹H NMR (DMSO-d6) δ7.96 (d, J=9.2 Hz, 1H), 5.50 (m, 1H), 5.24 (m, 1H), 4.25 (m, 2H), 3.70 (m, 1H), 3.23 (s, 3H), 3.19 (m, 2H), 2.40 (m, 2H), 1.86 (s, 3H), 1.68 (m, 2H), 1.62 (dd, J=7.0, 1.8 Hz, 3H), 1.39 (m, 1H), 0.77 (t, J=7.3 Hz, 3H),

MS: (M+H)⁺=299, (M+Na)+=321, (M−H)−=297

EXAMPLE 85

(±)-(2R,3S,R,1'R,2'R)-2-(1-Acetamido-2-methoxy)butyl-3-(cis-propen-1-yl)-pyrrolidine-5-carboxylic Acid Trifluoroacetic Acid Salt

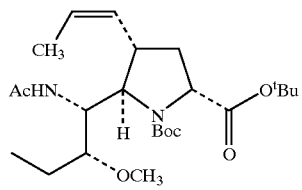

85A (±)-(2R,3S,5R,1'R,2'R)-1-t-Butoxycarbonyl-2-(1-acetamido-2-methoxy)butyl-3-(cis-propen-1-yl)-pyrrolidine-5-carboxylic Acid t-Butyl Ester (±)-(2R,3S,5R,1'R,2'R)-1-t-Butoxycarbonyl-2-(1acetamido-2-hydroxy)butyl-3-(cis-propen-1-yl)-pyrrolidine-5-carboxylic acid t-butyl ester (17 mg, 0.04 mmole) was reacted with methyl iodide (28 mg, 0.19 mmole), potassium hydroxide (8 mg, 0.19 mmole) and 18-crown-6 (0.002 mmole) in N,N-dimethylformamide (1.5 mL) at room temperature for 6 hours. Water (5 mL) was then added to the reaction mixture, followed by extraction with ether (2×10 mL). The organic layer was washed with water, and brine, dried over MgSO$_4$, filtered and concentrated in vacuo. The residue was purified by chromatography on silica gel using 50% ethyl acetate/hexanes to provide the title compound, (yield: 5 mg, 29%).

MS: (M+H)⁺=455, (M−H)⁻=453

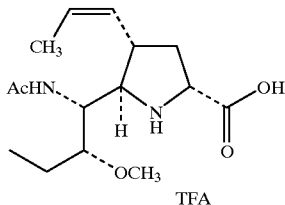

TFA

85B (±)-(2R,3S,5R,1'R,2'R)-2-(1-Acetamido-2-methoxy)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'R)-1-t-butoxycarbonyl-2-(1-acetamido-2-methoxy)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4 mg, 95%).

$^1$H NMR (DMSO-d6) δ8.00 (d, J=9.8HZ, 1H), 5.57(m, 1H), 5.35(m, 1H), 4.42(m, 1H), 4.28(m,1H),3.95(m, 1H), 3.54(m, 1H), 3.28(s, 3H), 2.80(m, 1H), 2.30(m, 1H), 1.92(s, 3H), 1.65(m, 1H), 1.60(m, 3H), 1.43(m, 2H), 0.82(t, J=7.31HZ, 3H).

MS: (M+H)+=299, (M−H)−=297

EXAMPLE 86

(±)-(2R,3S,5R,1'R,2'S)-2-(1-Acetamido-2-methoxy-3-methyl)butyl-3-(cis-propen-1-yl)-pyrrolidine-5-carboxylic Acid Trifluoroacetic Acid Salt

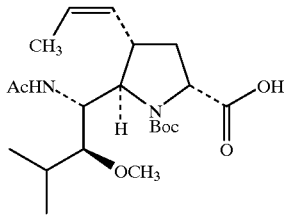

86A (±)-(2R,3S,5R,1'R,2'S)-1-t-Butoxycarbonyl-2-(1-acetamido-2-methoxy-3-methyl)butyl-3-(cis-propen-1-yl)-pyrrolidine-5-carboxylic Acid t-Butyl Ester The title compound is prepared according to the method described in Example 84A, substituting (±)-(2R,3S,5R,1'R, 2'S)-1-t-butoxycarbonyl-2-(1-acetamido-2-hydroxy-3-methyl)butyl-3-(cis-propen-1-yl)-pyrrolidine-5-carboxylic acid t-butyl ester in place of (±)-(2R,3,S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

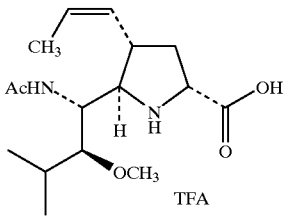

TFA

86B (±)-(2R,3S,5R,1'R,2'S)-2-(1-Acetamido-2-methoxy-3-methyl)butyl-3-(cis-propen-1-yl)-pyrrolidine-5-carboxylic Acid Trifluoroacetic Acid Salt The title compound is prepared according to the method described in Example 41C, substituting (±)-(2R,3S,5R, 1'R, 2'S)-1-t-butoxycarbonyl-2-(1-acetamido-2-methoxy-3-methyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1 -acetamido-2-hydroxy)butyl-3-(cis-propen-1-yl)-pyrrolidine-5-carboxylic acid t-butyl ester.

EXAMPLE 87

(±)-(2R,3S,5R,1'R,2'R)-2-(1-Acetamido-2-methoxy-3-methyl)butyl-3-(cis-propen-1-yl)-pyrrolidine-5-carboxylic Acid Trifluoroacetic Acid Salt

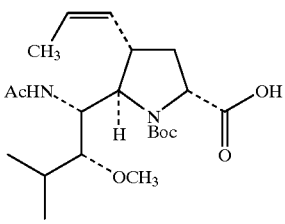

86A (±)-(2R,3S,5R,1'R,2'R)-1-t-Butoxycarbonyl-2-(1-acetamido-2-methoxy-3-methyl)butyl-3-(cis-propen-1-yl)-pyrrolidine-5-carboxylic Acid t-Butyl Ester The title compound was prepared according to the method described in Example 84A, substituting (±)-(2R,3S,5R,1'R, 2'R)-1-t-butoxycarbonyl-2-(1-acetamido-2-hydroxy-3-methyl)butyl-3-(cis-propen-1-yl)-pyrrolidine-5-carboxylic acid t-butyl ester in place of (±)-(2R,3,S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 6.8 mg, 33%).

MS: (M+H)+=469, (M+Na)+=491, (M−H)−=467.

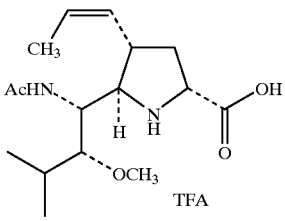

TFA

87B (±)-(2R,3S,5R,1'R,2'R)-2-(1-Acetamido-2-methoxy-3-methyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R, 2'R)-1-t-butoxycarbonyl-2-(1-acetamido-2-methoxy-3-methyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 6.6 mg, 100%).

$^1$H NMR (DMSO-d$_6$) δ7.65 (d, J=9.2 Hz, 1H), 5.43 (m, 1H), 5.23 (m, 1H), 4.42 (m, 1H), 4.37 (m, 1H), 3.56 (m, 1H), 3.46 (s, 3H), 3.17 (m, 2H), 2.44 (m, 1H), 1.80 s, 3H), 1.78 (m, 1H), 1.70 (m, 1H), 1.57 (dd, J=6.7, 1.2 Hz, 3H), 0.94 (d, J=6.7 Hz, 3H), 0.82 (d, J=6.7 Hz, 3H).

MS: (M+H)$^+$=313, (M+Na)+=335, (M−H)−=311.

EXAMPLE 88

(±)-(2R,3,5R,1'R,2'S)-2-(1Acetamido-2-methoxy) pentyl-3-(cis-propen-1-yl)-pyrrolidine-5-carboxylic Acid Trifluoroacetic Acid Salt

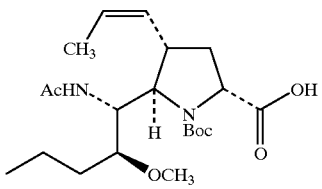

88A (±)-(2R,33 5R,1'R,2'S)-1-t-Butoxycarbonyl-2-(1-acetamido-2-methoxy)pentyl-3-(cis-propen-1-yl)-pyrrolidine-5-carboxylic Acid t-Butyl Ester The title compound was prepared according to the method described in Example 84A, substituting (±)-(2R,3S,5R,1'R,2'S)-1-t-butoxycarbonyl-2-(1-acetamido-2-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 11.9 mg, 36%).

MS: (M+H)$^+$=469, (M+Na)+=491, (M−H)−=467.

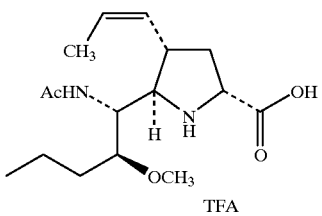

88B (±)-(2R,3S,5R,1'R,2'S)-2-(1-Acetamido-2-methoxy)pentyl-3-(cis-propen-1-yl)-pyrrolidine-5-carboxylic Acid Trifluoroacetic Acid Salt The title compound was prepared according to the method described in Example 41C, substituting (t)-(2R,3S,5R,1'R,2'S)-1-t-butoxycarbonyl-2-(1-acetamido-2-methoxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1 -acetamido-2-hydroxy)butyl-3-(cis-propen-1-yl)-pyrrolidine-5-carboxylic acid t-butyl ester. (yield: 11.5 mg, 100%).

$^1$H NMR (DMSO-d6) δ7.95 (d, J=9.8 Hz 1H), 5.49 (m, 1H), 5.23 (m, 1H), 4.25 (m, 2H), 3.68 (m, 1H), 3.24 (s, 3H), 3.22 (m, 1H), 3.18 (m, 1H), 2.40 (m, 1H), 1.85 (s, 3H), 1.66 (m, 1H), 1.62 (m, 3H), 1.58 (m, 1H), 1.38 (m, 1H), 1.27 (m, 2H), 0.86 (t, J=7.3 Hz, 3H).

MS: (M+H)$^+$=313, (M+Na)+=335, (M−H)−=311.

EXAMPLE 89

(±)-(2R,3S,5R,1'R,2'R)-2-(1-Acetamido-2-methoxy) pentyl-3-(cis-propen-1-yl)-pyrrolidine-5-carboxylic Acid Trifluoroacetic Acid Salt

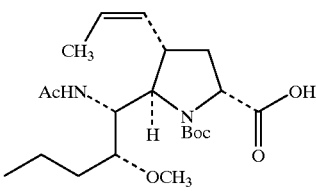

89A (±)-(2R,3S,5R,1'R,2'R)-1-t-Butoxycarbonyl-2-(1acetamido-2-methoxy)pentyl-3-(cis-propen-1-yl)-pyrrolidine-5-carboxylic Acid t-Butyl Ester The title compound was prepared according to the method described in Example 84A, substituting (±)-(2R,3S,5R,1'R,2'R)-1-t-butoxycarbonyl-2-(1-acetamido-2-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.3 mg, 21%).

MS: (M+H)$^+$=469, (M+Na)$^+$=491, (M−H)$^−$=467.

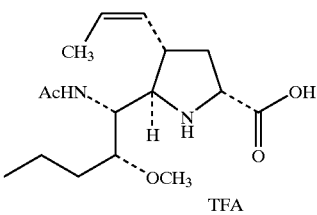

89B (±)-(2R,3S,5R,1'R,2'R)-2-(1-Acetamido-2-methoxy)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-methoxy) pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.8 mg, 100%).

$^1$H NMR (DMSO-d6) δ7.70 (d, J=9.8 Hz, 1H), 5.45 (m, 1H), 5.24 (m, 1H), 4.40 (m, 1H), 4.25 (m, 1H), 3.57 (t, J=8.5 Hz, 1H), 3.40 (m, 1H), 3.35 (s, 3H), 3.17 (m, 1H), 2.42 (m, 1H), 1.82 (s, 3H), 1.69 (m, 1H), 1.56 (dd, J=7.1, 1.2 Hz 3H), 1.24 (m, 4H), 0.88 (t, J=7.0 Hz, 3H).

MS: (M+H)$^+$=313, (M+Na)+=335, (M−H)−=311

EXAMPLE 90

(±)-(2R,3S,5R,1'R,2'S)-2-(1Acetamido-2-methoxy-2-allyl)ethyl-3-(cis-propen-1-yl)-pyrrolidine-5-carboxylic Acid Trifluoroacetic Acid Salt

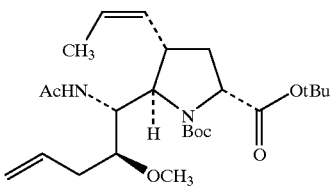

90A (±)-(2R,3S,5R,1'R,2'S)-1-t-Butoxycarbonyl-2-(1-acetamido-2-methoxy-2-allyl)ethyl-3-(cis-propen-1-yl)-pyrrolidine-5-carboxylic Acid t-Butyl Ester The title compound was prepared according to the method described in Example 84A, substituting (±)-(2R,3S,5R,1'R,2'S)-1-t-butoxycarbonyl-2-(1-acetamido-2-hydroxy-2-allyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 8 mg, 31%).

MS: $(M+H)^+=467$, $(M-H)^-=465$

90B (±)-(2R,3S,5R,1'R,2'S)-2-(1-Acetamido-2-methoxy-2-allyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-methoxy-2-allyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 6 mg, 96%).

$^1$H NMR (DMSO-d$_6$) δ8.02(d, J=8.6 HZ, 1H), 5.75 (m, 1H), 5.51(m, 1H), 5.24(m, 1H), 5.05(m, 2H), 4.27(m, 1H), 4.22(m, 1H), 3.74(m, 2H), 3.26(s, 3H), 3.18(m, 1H), 2.47(m, 1H), 2.39(m 1H), 2.17(m, 1H), 1.87(s, 3H), 1.67(m, 1H), 1.63(dd, J=6.71, 1.23 HZ, 3H).

MS: $(M+H)^+=311$, $(M-H)^-=309$

EXAMPLE 91

(±)-(2R,3S5R,1'R,2'R)-2-(1-Acetamido-2-methoxy-2-allyl)ethyl-3-(cis-propen-1-yl)-pyrrolidine-5-carboxylic Acid Trifluoroacetic Acid Salt

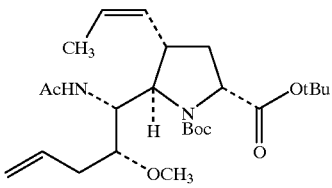

91A (±)-(2R,3S5R,1'R,2'R)-1-t-Butoxycarbonyl-2-(1-acetamido-2-methoxy-2-allyl)ethyl-3-(cis-propen-1-yl)-pyrrolidine-5-carboxylic Acid t-Butyl Ester The title compound was prepared according to the method described in Example 84A, substituting (±)-(2R,3S,5R,1'R, 2'R)-1-t-butoxycarbonyl-2-(1-acetamido-2-hydroxy-2-allyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.0 mg, 16%).

MS: $(M+H)^+=487$, $(M-H)^-=465$

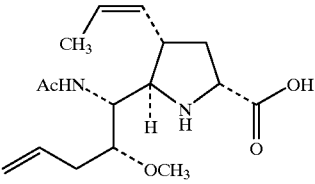

91B (±)-(2R,3S,5R,1'R,2'R)-2-(1-Acetamido-2-methoxy-2-allyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-methoxy-2-allyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 3 mg, 96%).

$^1$H NMR (DMSO-d$_6$) δ7.75 (d, J=9.2 HZ, 1H), 5.75(m 1H), 5.47(m, 1H), 5.24(m, 1H), 5.06(m, 2H), 4.42(m, 1H), 4.25(m, 1H), 3.58(m, 1H), 3.50(m, 1H), 3.37(s, 3H), 3.17(m, 1H), 2.42(m, 1H), 2.36(m, 1H), 1.83(s, 3H), 1.71(m, 1H), 1.55(dd, J=6.73, 1.83 HZ, 3H)

MS: $(M+H)^+=311$, $(M-H)^-=309$

EXAMPLE 92

(±)-(2R,3S,5R,1'R,2'S)-2-(1-Acetamido-2-hydroxy-4-vinyl)butyl-3-(cis-propen-1-yl)-pyrrolidine-5-carboxylic Acid Trifluoroacetic Acid Salt

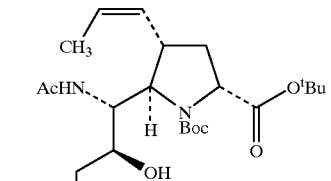

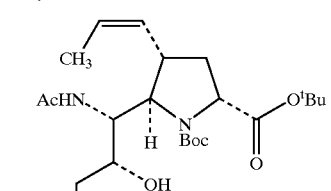

92A (±)-(2R,3S,5R,1'R ,2'S) and (±)-(2R,3S,5R,1'R,2'R)-1-t-Butoxycarbonyl-2-(1-acetamido-2-hydroxy-4-vinyl)butyl-3-(cis-propen-1-yl)-pyrrolidine-5-carboxylic Acid t-Butyl Ester The title compounds were prepared according to the method described in Example 41B, substituting 1-buten-4-yl magnesium bromide for ethyl magnesium bromide to provide (±)-(2R,3S,5R,1'R,2'S)-1-t-butoxycarbonyl-2-(1-acetamido-2-hydroxy-4-vinyl)butyl-3-(cis-propen-1-yl)-pyrrolidine-5-carboxylic acid t-butyl ester (yield: 0.0030 g, 6%) and (±)-(2R,3S,5R,1'R,2'R)-1-t-butoxycarbonyl-2-(1-acetamido-2-hydroxy-4-vinyl)butyl-3-(cis-propen-1-yl)-pyrrolidine-5-carboxylic acid t-butyl ester (yield: 0.0145 g, 28%).

(±)-(2R,3S,5R,1'R,2'S) MS: (M+H)$^+$=467, (M+Na)$^+$=489, (2M+Na)$^+$=955, (M–H)$^-$=465.

(±)-(2R,3S,5R,1'R,2'R)—MS: (M+H)$^+$=467, (M+Na)$^+$=489, (2M+Na)$^+$=955, (M–H)$^-$=465.

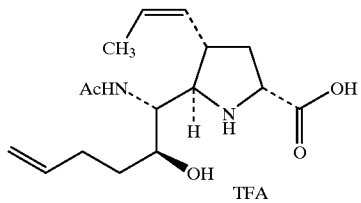

92B (±)-(2R,3S,5R,1'R,2'S)-2-(1-Acetamido-2-hydroxy-4-vinyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-4-vinyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0027 g, 100%).

$^1$H NMR (DMSO-d$_6$) δ8.93 (bs, 1H), 7.90 (d, J=9.2 Hz, 1H), 5.80 (m, 1H), 5.48 (m, 1H), 5.28 (m, 1H), 5.00 (dd, J=17.1, 1.8 Hz, 1H), 4.94 (dd, J=10.4,1.8 Hz, 1H), 4.29 (bt, J=8.3 Hz, 1H), 4.03 (m, 1H), 3.71 (m, 1H), 3.49 (m, 1H), 3.15 (quint., J=8.5 Hz, 1H), 2.41 (dt, J=12.8,7.3 Hz, 1H), 2.16 (M, 1H), 2.05 (m, 1H), 1.83 (s, 3H), 1.79–1.75 (m, 1H), 1.64 (m 1H), 1.58 (dd, J=6.7,1.8 Hz, 3H), 1.34 (m,2H).

MS: (M+H)$^+$=311, (M+Na)$^+$=333, (M–H)$^-$=309, (M+CF$_3$COO$^-$)$^-$=423

EXAMPLE 93

(±)-(2R,3S,5R,1'R,2'R)-2-(1-Acetamido-2-hydroxy-4-vinyl)butyl-3-(cis-propen-1-yl)-pyrrolidine-5-carboxylic Acid Trifluoroacetic Acid Salt

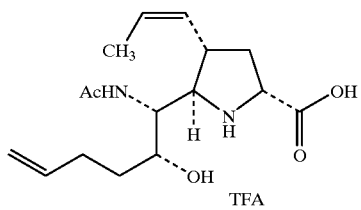

93A (±)-(2R,3S,5R,1'R,2'R)-2-(1-Acetamido-2-hydroxy-4-vinyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-2-hydroxy-4-vinyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0027 g, 100%).

$^1$H NMR (DMSO-d$_6$) δ7.68 (d, J=9.6 Hz, 1H), 5.81 (m, 1H), 5.48 (m, 1H), 5.25 (m, 1H), 5.01(dd, J=17.1, 1.8 Hz, 1H), 4.95 (dd, J=10.3,1.7 Hz, 1H), 4.43 (t, J=8.5 Hz, 1H), 4.10 (m, 1H), 3.74 (m, 1H), 3.56 (t, J=8.9 Hz, 1H), 3.16 (quint., J=8.9 Hz, 1H), 2.42 (dt, J=12.8,7.3 Hz, 1H), 2.11 (M, 1H), 2.07 (m, 1H), 1.83 (s, 3H), 1.72 (dt, J=12.8, 9.8 Hz, 1H), 1.55 (dd, J=6.7,1.8 Hz, 3H), 1.5–1.35 (m, 2H).

MS: (M+H)$^+$=311, (M+Na)$^+$=333, (M–H)$^-$=309, (M+CF$_3$COO$^-$)$^-$=423, (2M–H)$^-$=619.

EXAMPLE 94

(±)-(2R,3S,5R,1'R,2'S,3'S)-2-(1-Acetamido-2-methoxy-3-methyl)pentyl-3-(cis-propen-1-yl)-pyrrolidine-5-carboxylic Acid Trifluoroacetic Acid Salt

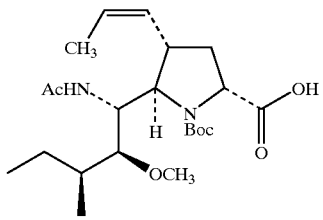

94A (±)-(2R,3S,5R,1'R,2'S,3'S)-1-t-Butoxycarbonyl-2-(1-acetamido-2-methoxy-3-methyl)pentyl-3-(cis-propen-1-yl)-pyrrolidine-5-carboxylic Acid t-Butyl Ester The title compound is prepared according to the method described in Example 84A, substituting (±)-(2R,3S,5R,1'R,2'S,3'S)-1-t-butoxycarbonyl-2-(1-acetamido-2-hydroxy-3-methyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

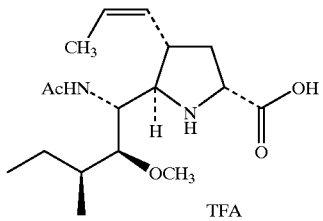

94B (±)-(2R,3S,5R,1'R,2'S2'S3'S)-2-(1-Acetamido-2-methoxy-3-methyl)pentyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'S,3'S)-1-t-butoxycarbonyl-2-(1-acetamido-2-methoxy-3-methyl)pentyl-3-(cis-propen-1-yl)-pyrrolidine-5-carboxylic acid t-butyl ester in place of (±)-(2R,3S,5R,1'R,2'S)-1-t- butoxycarbonyl-2-(1-acetamido-2-hydroxy)butyl-3-(cis-propen-1-yl)-pyrrolidine-5-carboxylic acid t-butyl ester

EXAMPLE 95

(±)-(2R,3S,5R,1'RS)-2-(1-Acetamido-2-oxo-2-heptafluoropropyl)ethyl-3-(cis-propen-1-yl)-pyrrolidine-5-carboxylic Acid Trifluoroacetic Acid Salt

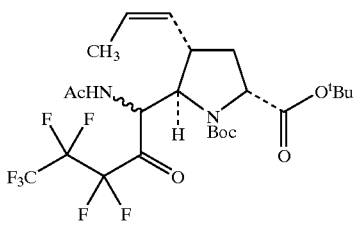

95A (±)-(2R,3S,5R,1'RS)-1-t-Butoxycarbonyl-2-(1-Acetamido-2-oxo-3-heptafluoropropyl)ethyl-3-(cis-propen-1-yl)-pyrrolidine-5-carboxylic Acid t-Butyl Ester The title compound was prepared according to the method described in Example 42A, substituting (±)-(2R,3S,5R,1'R,2'RS)-1-t-butoxycarbonyl-2-(1-acetamido-2-hydroxy-3-heptafluoropropyl)ethyl-3-(cis-propen-1-yl)-pyrrolidine-5-carboxylic acid t-butyl ester for (±)-(2R,3S,5R,1'R,2'R)-1-t-butoxycarbonyl-2-(1-acetamido-2-hydroxy)butyl-3-(cis-propen-1-yl)-pyrrolidine-5-carboxylic acid t-butyl ester (yield: 6.8 mg, 88%).

MS: (M+H)$^+$=579, (M−H)$^-$=577.

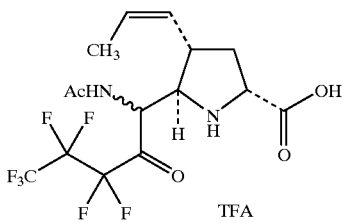

95B (±)-(2R,3S,5R,1'RS)-2-(1-Acetamido-2-oxo-2-heptafluoropropyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'RS)-1-t-butoxycarbonyl-2-(1-acetamido-2-oxo-3-heptafluoropropyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0037 g, 100%).

MS: (M+H)$^+$=423, (M−H)$^-$=421.

EXAMPLE 96

(±)-(2R,3S,5R,1'RS)-2-(1-Acetamido-2-oxo-2-heptafluoropropyl)ethyl-3-(cis-propen-1-yl)-pyrrolidine-5-carboxylic Acid Trifluoroacetic Acid Salt

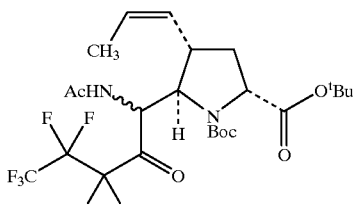

96A (±)-(2R,3S,5R,1'RS)-1-t-Butoxycarbonyl-2-(1-Acetamido-2-oxo-3-heptafluoropropyl)ethyl-3-(cis-propen-1-yl)-pyrrolidine-5carboxylic Acid t-Butyl Ester The title compound was prepared according to the method described in Example 42A, substituting (±)-(2R,3S,5R)1'R,2'S)-1-t-butoxycarbonyl-2-(1-acetamido-2-hydroxy-3-heptafluoropropyl)ethyl-3-(cis-propen-1-yl)-pyrrolidine-5-carboxylic acid t-butyl ester for (±)-(2R,3S,5R,1'R,2'R)-1-t-butoxycarbonyl-2-(1-acetamido-2-hydroxy)butyl-3-(cis-propen-1-yl)-pyrrolidine-5-carboxylic acid t-butyl ester (yield: 6.8 mg, 88%).

MS: (M+H)$^+$=579, (M−H)$^-$=577.

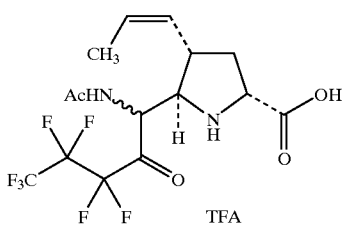

96B (±)-(2R,3S,5R,1'RS)-2-(1-Acetamido-2-oxo-2-heptafluoropropyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-3-heptafluoropropyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0037 g, 100%).

MS: (M+H)$^+$=423, (M−H)$^-$=421.

EXAMPLE 97

(±)-(2R,3S,5R,1'R)-2-(1-Acetamido-2-oxo)pentyl-3-(cis-propen-1-yl)-pyrrolidine-5-carboxylic Acid Trifluoroacetic Acid Salt

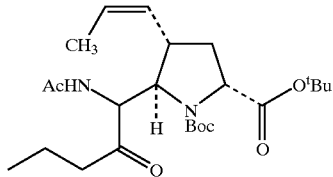

97A (±)-(2R,3S,5R,1'R)-1-t-Butoxycarbonyl-2-(1-acetamido-2-oxo)pentyl-3-(cis-propen-1-yl)-pyrrolidine-5-carboxylic Acid t-Butyl Ester The title compound was prepared according to the method described in Example 42A, substituting (±)-(2R,3S,5R,1'R,2'R)-1-t-butoxycarbonyl-2-(1-acetamido-2-hydroxy)pentyl-3-(cis-propen-1-yl)-pyrrolidine-5-carboxylic acid t-butyl ester in place of (2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 14 mg, 58%).

MS: $(M+H)^+=453$, $(M+Na)^+=475$; $(M-H)^-=451$.

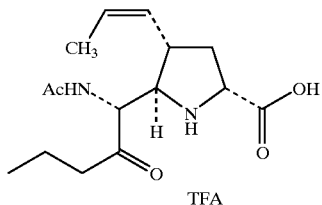

97B (±)-(2R,3S,5R,1'R)-2-(1-Acetamido-2-oxo)pentyl-3-(cis-propen-1-yl)-pyrrolidine-5-carboxylic Acid Trifluoroacetic Acid Salt The title compound was prepared according to the method described in Example 41C, substituting (+)-(2R,3S,5R,1'R)-1-t-butoxycarbonyl-2-(1-acetamido-2-oxo)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 1.4 mg, 28%).

$^1$H NMR (DMSO-d$_6$) δ8.31(d, J=8.3 Hz, 1H), 5.40 (m, 1H), 5.19 (br t, 1H), 4.26 (t, J=6.8 Hz, 1H), 3.63 (t, J=8.3 Hz, 1H), 3.35 (m, 1H), 2.97 (m, 1H), 2.45 (m, 1H), 2.34 (dt, J=3.4, 7.4 Hz, 1H), 2.20 (m, 1H), 1.84 (s, 3H), 1.58 (dd, J=2, 4.3 Hz, 3H), 1.43 (m, 3H), 0.82 (t, J=7.3 Hz, 3H)

MS: $(M-H)^-=295$; $(M+H)^+=297$, $(M+Na)^+=319$.

EXAMPLE 98

(±)-(2R,3S,5R,1'R)-2-(1-Acetamido-2-oxo)butyl-3-(cis-propen-1-yl)-pyrrolidine-5-carboxylic Acid Trifluoroacetic Acid Salt

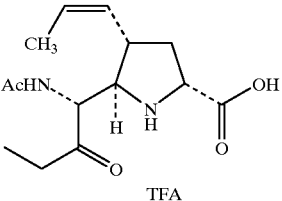

The title compound was prepared according to the method described in Example 41C, substituting (±)-(2R,3S,5R,1'R)-1-t-butoxycarbonyl-2-(1-acetamido-2-oxo)butyl-3-(cis-propen-1-yl)-pyrrolidine-5-carboxylic acid t-butyl ester prepared in Example 42A in place of (±)-(2R,3S,5R,1'R,2'S)-1-t-butoxycarbonyl-2-(1acetamido-2-hydroxy)butyl-3-(cis-propen-1-yl)-pyrrolidine-5-carboxylic acid t-butyl ester (yield, 5.0 mg, 100%).

1H NMR (DMSO-d$_6$) δ8.52 (d, J=8.6 Hz, 1H), 5.47 (m, 1H), 5.15 (m, 1H), 4,54 (m, 1H), 4.39 (dd, J=11.0, 6.7 Hz, 1H), 3.84 (t, J=9.2 Hz, 1H), 3.17 (m, 1H), 2.50 (m, 1H), 2.38 (m, 1H), 2.33 (m, 1H), 1.83 (s, 3H), 1.63 (m,1H), 1.58 (dd, J=6.7, 1.8 Hz, 3H), 0.94 (t, J=7.5 Hz, 3H).

MS: $(M+H)^+=283$, $(M+Na)^+=305$, $(M-H)^-=281$.

EXAMPLES 99–115

The title compounds were prepared according to the methods described in Examples 20 and 40–42 by substituting the respective reactants.

EXAMPLE 99

(±)-(2R,3S5R 1'R)-2-(1-Acetamido-2-oxo-2-allyl)ethyl-3-(cis-propen-1-yl)-pyrrolidine-5-carboxylic Acid Trifluoroacetic Acid Salt $^1$H NMR (DMSO-d$_6$) δ8.38 (d, J=8.5 Hz, 1H), 5.73 (m, 1H), 5.37 (m, 1H), 5.05 (m, 3H), 4.32 (t, J=7.9 Hz, 1H), 3.90 (m, 1H), 3.49 (m, 1H), 3.13 (m, 2H), 2.98 (m, 1H), 3.18 (m, 1H), 1.78 (s, 3H), 1.51 (dd, J=5.5, 1.2 Hz, 3H), 1.44 (m, 1H).

MS: $(M+H)^+=295$, (M–H)–=293.

EXAMPLE 100

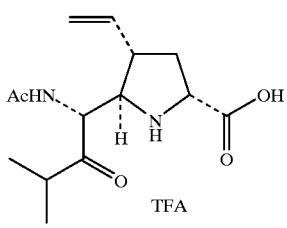

TFA (±)-(2R,3S, 5R,1'R)-2-(1-Acetamido-2-oxo-3-methyl)butyl-3-vinyl-pyrrolidine-5-carboxylic Acid Trifluoroacetic Acid Salt $^1$H NMR (DMSO-d$_6$) δ8.64 (d, J=8.5 Hz, 1H), 5.59 (m, 1H), 5.08 (d, J=17.1 Hz, 1H), 5.02 (d, J=9.8 Hz, 1H), 4.65 (t, J=8.6 Hz, 1H), 4.32 (m, 1H), 3.82 (t, J=9.2 Hz, 1H), 2.82 (m 2H), 2.36 (m,1H), 1.83 (s, 3H), 1.80 (m,1H), 1.03 (d, J=6.7 Hz, 3H), 0.97 (d, J=6.7 Hz, 3H).

MS: (M+H)$^+$=283, (M+Na)$^+$=305, (M−H)$^−$=281.

EXAMPLE 101

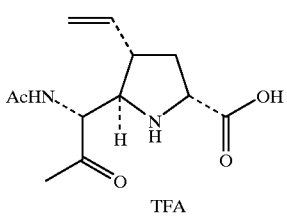

TFA (±)-(2R,3S,5R,1'R)-2-(1-Acetamido-2-oxo)propyl-3-vinyl-pyrrolidine-5-carboxylic Acid Trifluoroacetic Acid Salt 1H NMR (DMSO-d$_6$) δ8.96 (d, J=7.9 Hz, 1H), 5.71 (m, 1H), 5.27 (d, J=17.7 Hz, 1H), 5.17 (d, J=11.0 Hz, 1H), 4.38 (m, 1H), 4.29 (m, 1H), 3.81 (m, 1H), 2.61 (m, 1H), 2.22 (m, 1H), 2.13 (s, 3H), 2.01 (s, 3H), 1.24 (m, 1H).

MS: (M+H)$^+$=255, (M+Na)$^{−+}$277, (M−H)$^−$=253.

EXAMPLE 102

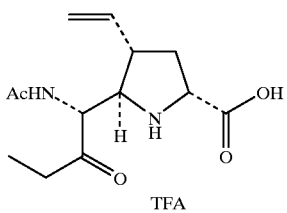

TFA (±)-(2R,3S,5R,1'R)-2-(1-Acetamido-2-oxo)butyl-3-vinyl-pyrrolidine-5-carboxylic Acid Trifluoroacetic Acid Salt $^1$H NMR (DMSO-d$_6$) δ8.61 (d, J=8.5 Hz, 1H), 5.60 (m, 1H), 5.10 (d, J=17.7 Hz, 1H), 5.03 (dd, J=10.4, 1.2 Hz, 1H), 4.54 (t, J=8.5 Hz, 1H), 4.38 (dd, J=11.0, 6.7 Hz, 1H), 3.86 (m, 1H), 2.84 (m, 1H), 2.52 (m, 1H), 2.37 (m, 2H), 1.85 (s, 3H), 1.82 (m, 1H), 0.94 (t, J=7.0 Hz, 3H).

MS: (M+H)$^+$=269, (M+Na)$^+$=291, (M−H)$^−$=267.

EXAMPLE 103

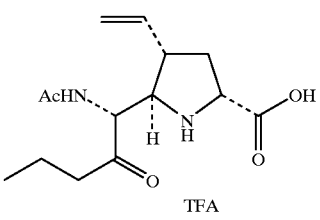

TFA (±)-(2R,3S,5R,1'R)-2-(1-Acetamido-2-oxo)pentyl-3-vinyl-pyrrolidine-5-carboxylic Acid Trifluoroacetic Acid Salt $^1$H NMR (DMSO-d$_6$) δ8.60 (d, J=9.7 Hz, 1H), 5.60 (m, 1H), 5.07 (m, 2H), 4.65 (m, 1H), 4.54 (m, 1H), 4.38 (m, 1H), 3.86 (m, 1H), 2.84 (m, 1H), 2.45 (m, 1H), 2.36 (m, 1H), 1.86 (s, 3H), 1.82 (m, 1H), 1.47 (m, 2H), 0.87 (t, J=5.8 Hz, 3H).

MS: (M+H)$^+$=283, (M+Na)$^+$=305, (M−H)$^−$=281.

EXAMPLE 104

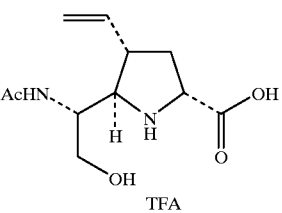

TFA (±)-(2R,3S,5R,1'R)-2-(1-Acetamido-2-hydroxy)ethyl-3-vinyl-pyrrolidine-5-carboxylic Acid Trifluoroacetic Acid Salt $^1$H NMR (DMSO-d$_6$) δ8.00 (d, J=9.9 Hz, 1H), 5.63 (m, 1H), 5.08 (m, 1H), 4.98 (m, 1H), 4.35 (m, 1H), 4.25 (m, 1H), 4.08 (m, 1H), 3.55 (m, 1H), 3.45 (m, 1H), 3.38 (m, 1H), 2.83 (m, 1H), 2.33 (m, 1H), 1.78 (s, 3H).

MS: (M+H)$^+$=243, (M+Na)+=265, (M−H)−=241.

EXAMPLE 105

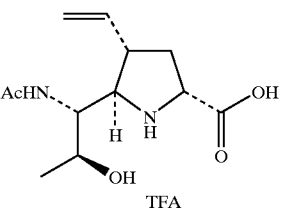

TFA (±)-(2R,3S,5R,1'R,2'S)-2-(1-Acetamido-2-hydroxy)propyl-3-vinyl-pyrrolidine-5-carboxylic Acid Trifluoroacetic Acid Salt $^1$H NMR (DMSO-d$_6$) δ7.96 (d, J=9.7 Hz, 1H), 5.74 (m, 1H), 5.12 (m, 1H), 5.03 (m, 1H), 4.27 (m, 1H), 3.96 (m, 1H), 3.77 (m, 1H), 3.65 (m, 1H), 2.87 (m, 1H), 2.38 (m, 1H), 1.82 (s, 3H), 1.80 (m, 1H), 1.08 (d, J=6.0 Hz, 3H).

MS: (M+H)$^+$=257, (M+Na)$^+$=279, (M−H)$^−$=255.

EXAMPLE 106

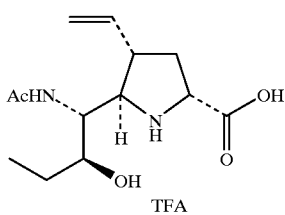

(±)-(2R,3S,5R,1'R,2'S)-2-(1-Acetamido-2-hydroxy)
butyl-3-vinyl-pyrrolidine-5-carboxylic Acid
Trifluoroacetic Acid Salt $^1$H NMR (DMSO-d$_6$) δ7.99 (d, J=9.0 Hz, 1H), 5.75 (m, 1H), 5.13 (d, J=17.1 Hz, 1H), 5.04 (d, J=10.5 Hz, 1H), 4.27 (t, J=8.4 Hz, 1H), 4.04 (m, 1H), 3,78 (m, 1H), 3.48 (m, 1H), 2.89 (m, 1H), 2.40 (m, 1H), 1.88 (m, 1H), 1.85 (s, 3H), 1.54 (m, 1H), 1.28 (m, 1H), 0.86 (t, J=7.2 Hz, 3H).
MS: (M+H)$^+$=271, (M+Na)+=293, (M–H)–=269.

EXAMPLE 107

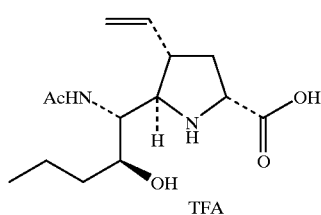

(±)-(2R,3S,5R,1'R,2'S)-2-(1Acetamido-2-hydroxy)
pentyl-3-vinyl-pyrrolidine-5-carboxylic Acid
Trifluoroacetic Acid Salt $^1$H NMR (DMSO-d$_6$) δ7.99 (d, J=9.9 Hz, 1H), 5.75 (m, 1H), 5.08 (m, 2H), 4.28 (m, 1H), 4.03 (m, 1H), 3.77 (m 1H), 3.52 (m, 1H), 2.88 (m, 1H), 2.40 (m, 1H), 1.86 (s, 3H), 1.75 (m, 1H), 1.45 (m, 2H), 1.25 (m, 2H), 0.87 (t, J=5.9 Hz, 3H).
MS: (M+H)$^+$=285, (M+Na)$^+$=307, (M–H)$^-$=283.

EXAMPLE 108

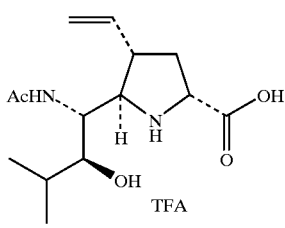

(±)-(2R,3S,5R 1'R,2'S)-2-(1-Acetamido-2-hydroxy-
3-methyl)butyl-3-vinyl-pyrrolidine-5-carboxylic
Acid Trifluoroacetic Acid Salt $^1$H NMR (DMSO-d$_6$) δ7.97 (d, J=9.3 Hz, 1H), 5.75 (m, 1H), 5.12 (d, J=17.1 Hz, 1H), 5.04 (d, J=11.2 Hz, 1H), 4.24 (m, 1H), 4.13 (m, 1H), 3.74 (dd, J=9.8, 6.1 Hz, 1H), 3.44 (dd, J=10.3, 2.0 Hz, 1H), 2.87 (m, 1H), 2.40(m, 1H), 1.84 (m,1H), 1.83 (s, 3H), 1.75 (m, 1H), 0.89 (d, J=6.8, 3H), 0.75 (d, J=6.8 Hz, 3H).
MS: (M+H)$^+$=285, (M+Na)$^+$=307, (M–H)$^-$=283.

EXAMPLE 109

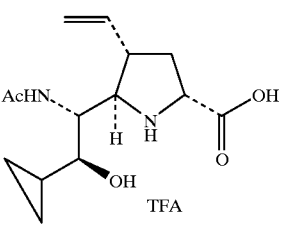

(±)-(2R,3S,5R,1'R,2'S)-2-(1-Acetamido-2-hydroxy-
2-cyclopropyl)ethyl-3-vinyl-pyrrolidine-5-carboxylic
Acid Trifluoroacetic Acid Salt $^1$H NMR (DMSO-d$^6$) δ7.81 (d, J=10.0 Hz, 1H), 5.73 (m, 1H), 5.05 (m, 2H), 4.39 (m, 1H), 4.20 (m, 1H), 3.90 (m, 1H), 3.61 (m, 1H), 3.08 (m, 1H), 2.86 (m, 1H), 2.42 (m, 1H), 1.85 (s, 3H), 0.88 (m, 1H), 0.45 (m, 1H), 0.35 (m, 2H), 0.11 (m, 1H),
MS: (M+H)$^+$=283, (M+Na)$^+$=305, (M–H)$^-$=281.

EXAMPLE 110

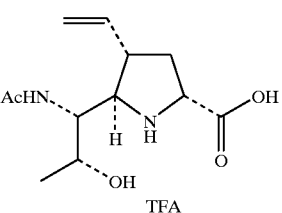

(±)-(2R,3S, 5R,1'R,2'R)-2-(1-Acetamido-2-hydroxy)
propyl-3-vinyl-pyrrolidine-5-carboxylic Acid
Trifluoroacetic Acid Salt $^1$H NMR (DMSO-d$_6$) δ7.77 (d, J=9.7 Hz, 1H), 5.72 (m, 1H), 5.07 (m, 2H), 4.40 (m, 1H), 4.03 (m, 1H), 3.95 (m 1H), 3.57 (m, 1H), 2.86 (m, 1H), 2.43 (m, 1H 1.88 (m, 1H), 1.84 (s, 3H), 1.04 (d, J=6.0 Hz, 3H).
MS: (M+H)$^+$=257, (M+Na)$^+$=279, (M–H)$^-$=255.

EXAMPLE 111

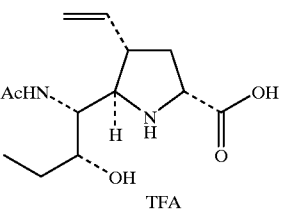

(±)-(2R,3S 5R,1'R,2'R)-2-(1-Acetamido-2-hydroxy)
butyl-3-vinyl-pyrrolidine-5-carboxylic Acid
Trifluoroacetic Acid Salt $^1$H NMR (DMSO-d$_6$) δ7.72 (d, J=9.8 Hz,1H), 5.73 (m 1H), 5.08 (d, J=17.1 Hz, 1H), 5.03 (d, J=10.4 Hz, 1H), 4.41(m, 1H), 4.13 (m 1H), 3.68 (m, 1H), 3.63 (m,1H), 2.88 (m, 1H), 2.44 (m,1H), 1.90 (m, 1H), 1.83 (s, 3H), 1.38 (m, 2H), 0.84 (t, J=7.3 Hz, 3H).
MS: (M+H)$^+$=271, (M+Na)$^+$=293, (M–H)$^-$=269.

EXAMPLE 112

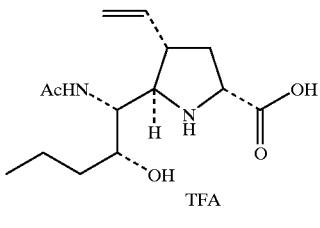

(±)-(2R,3S,5R,1'R,2'R)-2-(1-Acetamido-2-hydroxy)pentyl-3-vinyl-pyrrolidine-5-carboxylic Acid Trifluoroacetic Acid Salt $^1$H NMR (DMSO-d$_6$) δ7.72 (d, J=9.9 Hz, 1H), 5.72 (m 1H), 5.06 (m, 2H), 4.42 (m, 1H), 4.09 (m, 1H), 3.77 (m, 1H), 3.61 (m, 1H), 2.87 (m, 1H), 2.43 (m, 1H), 1.90 (m, 1H), 1.83 (s, 3H), 1.37 (m, 2H), 1.27 (m, 2H), 0.87 (t, J=5.9 Hz, 3H), MS: (M+H)$^+$=285, (M+Na)$^+$=307, (M–H)$^-$=283.

EXAMPLE 113

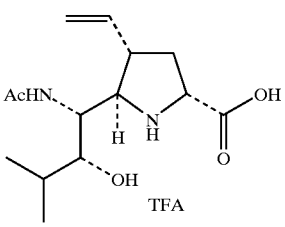

(±)-(2R,3S,5R,1'R,2'R)-2-(1-Acetamido-2-hydroxy-3-methy)butyl-3-vinyl-pyrrolidine-5-carboxylic Acid Trifluoroacetic Acid Salt $^1$H NMR (DMSO-d6) δ7.71(d, J=9.3 Hz, 1H), 5.70 (m, 1H), 5.08 (d, J=17.1 Hz, 1H), 5.03 (d, J=10.3 Hz, 1H), 4.42 (m, 1H), 4.25 (m, 1H), 3.61(m, 1H), 3.35 (dd, J=8.3, 2.5 Hz, 1H), 2.90 (m, 1H), 2.44 (m, 1H), 1.92 (m, 1H), 1.82 (s, 3H), 1.58 (m, 1H), 0.95 (d, J=6.8 Hz, 3H), 0.79 (d, J=6.4 Hz, 3H).
MS: (M+H)$^+$=285, (M+Na)$^+$=307, (M–H)$^-$=283.

EXAMPLE 114

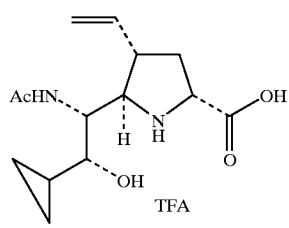

(±)-(2R,3S,5R,1'R,2'R)-2-(1-Acetamido-2-hydroxy-2-cyclopropyl)ethyl-3-vinyl-pyrrolidine-5-carboxylic Acid Trifluoroacetic Acid Salt $^1$H NMR (DMSO-d$_6$) δ7.94 (d, J=9.6 Hz, 1H), 5.76 (m, 1H), 5.12 (m, 2H), 4.40 (m, 1H), 4.21 (m, 1H), 3.90 (m, 1H), 3.53 (m, 1H), 3.13 (m, 1H), 2.81 (m, 1H), 2.25 (m, 1H), 1.87 (s, 3H), 0.90 (m, 1H), 0.47 (m, 1H), 0.37 (m, 2H), 0.15 (m, 1H).
MS: (M+H)$^+$=283, (M+Na)$^+$=305, (M–H)$^-$=281.

EXAMPLE 115

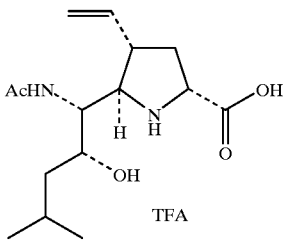

(±)-(2R,3S 5R,1'R,2'R)-2-(1-Acetamido-2-hydroxy-4-methyl)pentyl-3-vinyl-pyrrolidine-5-carboxylic Acid Trifluoroacetic Acid Salt $^1$H NMR (DMSO-d$_6$) δ7.71(d, J=9.7 Hz, 1H), 5.83 (m, 1H), 5.06 (d, J=17.1 Hz, 1H), 5.02 (d, J=10.3 Hz, 1H), 4.41 (m, 1H), 4.06 (m, 1H), 3.83 (m, 1H), 3.59 (t, J=8.8 Hz, 1H), 2,84 (m, 1H), 2.42 (m, 1H), 1.90 (m, 1H), 1.82 (s, 3H), 1.71 (m, 1H), 1.34 (m, 1H), 1.07 (m, 1H), 0.89 (d, J=6.8 Hz, 3H), 0.86 (d, J=6.3 Hz, 3H).

MS: (M+H)$^+$=299, (M+Na)$^+$=21, (M–H)$^-$=297.

EXAMPLE 116

(±)-(2R,3S,5R,1'R)-2-(1-Acetamido-2-hydroxy-2-methyl)propyl-3-vinyl-pyrrolidine-5-carboxylic Acid Trifluoroacetic Acid Salt

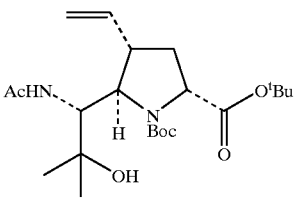

116A (±)-(2R,3S,5R,1'R)-t-Butoxycarbonyl-2-(1-Acetamido-2-hydroxy-2-methyl)propyl-3-vinyl-pyrrolidine-5-carboxylic Acid t-Butyl Ester (±)-(2R,3S,5R,1'R)-t-Butoxycarbonyl 2-(1-acetamido-2-oxo)propyl-3-vinyl-pyrrolidine-5-carboxylic acid t-butyl ester (11 mg, 0.027 mmol) was reacted with methyl magnesium bromide (3 M) (0.05 mL, 0.134 mmol) in THF (2 mL) at 25° C. for 2 hours. The reaction was quenched with saturated aqueous ammonium chloride (2 mL) and water (2 mL) followed by extraction using dichloromethane (2×5 mL). The organic layer was dried over magnesium sulfate, filtered and concentrated in vacuo. The residue was purified by column chromatography on silica gel using 2/1: ethyl acetate/hexane to provide the title compound (yield: 1.9 mg, 17%).

MS: (M+H)$^+$=427, (M–H)$^-$=425

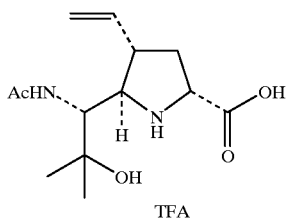

TFA

116B (±)-(2R,3S,5R,1'R)-2-(1Acetamido-2-hydroxy-2-methyl)propyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-acetamido-2-hydroxy-2-methyl)propyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 1.6 mg, 99%).

$^1$H NMR (DMSO-d$_6$) δ7.70(d, J=9.9 Hz, 1H), 5.75(m, 1H), 5.02(m, 2H), 4.37(m, 1H), 4.15(m, 1H), 3.61(m, 1H), 2.78(m, 1H), 2.41(m, 1H), 1.81(s, 3H), 1.20(s, 3H), 1.12(s, 3H)

MS (M+H)$^+$=271, (M+23)$^+$=293, (M−H)$^−$=269

EXAMPLE 117

(±)-(2R,3S,5R 1'R)-2-(1-Acetamido-2-hydroxy-2-ethyl)butyl-3-vinyl-pyrrolidine-5-carboxylic Acid Trifluoroacetic Acid Salt

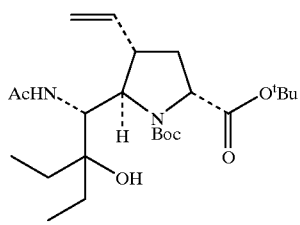

117A (±)-(2R,3S,5R,1'R)-t-Butoxycarbonyl-2-(1-Acetamido-2-hydroxy-2-ethyl)butyl-3-vinyl-pyrrolidine-5-carboxylic Acid t-Butyl Ester (±)-(2R,3S,5R,1'R)-t-Butoxycarbonyl-2-(1-acetamido-2-oxo)butyl-3-vinyl-pyrrolidine-5-carboxylic acid t-butyl ester (37 mg, 0.087 mmol) was reacted with ethyl magnesium bromide (3 M) (0.15 mL, 0.44 mmol) in THF (5 mL) at 25° C. for 2 hours. The reaction was quenched with saturated aqueous ammonium chloride 5 mL) and water (5 mL) followed by extraction using dichloromethane (2×10 mL). The organic layer was dried over magnesium sulfate, filtered and concentrated in vacuo. The residue was purified by column chromatography on silica gel using 2/1: ethyl acetate/hexane to provide the title compound (yield: 14 mg, 35%).

MS: (M+H)$^+$=455, (M−H)$^−$=453

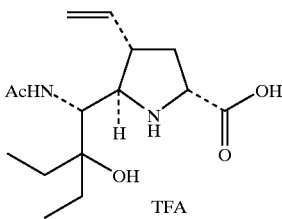

TFA

116B (±)-(2R,3S,5R,1'R)-2-(1-Acetamido-2-hydroxy-2-ethyl)butyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-acetamido-2-hydroxy-2-ethyl)butyl-3vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 5.8 mg, 98%).

$^1$H NMR (DMSO-d$_6$) δ7.62(d, J=9.6 HZ, 1H), 5.75(m, 1H), 5.03(m, 2H), 4.39(m, 1H), 4.31(m, 2H), 3.87(m, 11H), 3.38(m, 1H), 2.88(m, 1H), 2.40(m, 1H), 1.83(s, 3H), 1.55–1.30(m, 4H), 0.86(m, 6H)

MS: (M+H)$^+$=299, (M−H)$^−$=297

EXAMPLE 118

(±)-(2R,3S,5R,1'S)-2-(1-Acetamido)allyl-3-(cis-propen-1-yl)-pyrrolidine-5-carboxylic Acid Trifluoroacetic Acid Salt

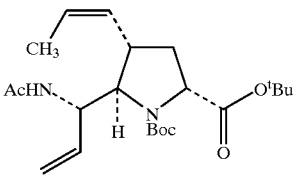

118A (±)-(2R,3S,5R,1'S)-1-t-Butoxycarbonyl-2-(1-acetamido)allyl-3-(cis-propen-1-yl)-pyrrolidine-5-carboxylic Acid t-Butyl Ester The title compound was prepared according to the method described in Example 20K, substituting (±)-(2R,3S,5R,1'S)-1-t-butoxycarbonyl-2-(1-acetamido-2-formyl)methyl-3-(cis-propen-1-yl)-pyrrolidine-5-carboxylic acid t-butyl ester in place of (±)-(2R,3S,5R,1'S)-1-t-butoxycarbonyl-2-(1-acetamido-3-methyl)butyl-3-formyl-pyrrolidine-5-carboxylic acid t-butyl ester (yield: 15.3 mg, 61.4%).

MS: (M+H)$^+$=409.

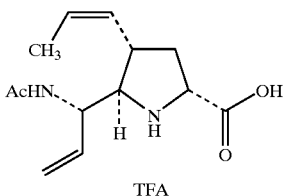

TFA 118B (±)-(2R,3S,5R,1'S)-2-(1l-Acetamido)allyl-3-(cis-propen-1-yl)pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1-acetamido)allyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 13.1 mg, 100%).

$^1$H NMR (DMSO-d6): δ1.58 (dd, 3H), 1.74 (dt, 1H), 1.88 (s, 3H), 2.41 (dt, 1H), 3.17 (m, 1H), 3.56 (dd, 1H), 4.35 (dd, 1H), 4.70 (dd, 1H), 5.22–5.30 (m, 3H), 5.51(m, 1H), 5.82 (m, 1H), 8.15 d, 1H), 9.18 (brs, 2H).

MS: (M+H)$^+$=253.

EXAMPLE 119

(±)-(2R,3S,5R 1'S)-2-(1-Acetamido-2-(cis and trans)buten-1-yl)-3-(cis-propen-1-yl)-pyrrolidine-5-carboxylic Acid Trifluoroacetic Acid Salt

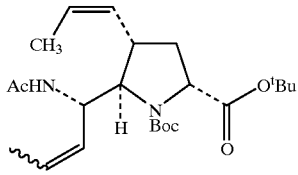

119A (±)-(2R,3S,5R,1'S)-1-t-Butoxycarbonyl-2-(1-Acetamido-2-(cis and trans)buten-1-yl)-3-(cis-propen-1-yl)-pyrrolidine-5-carboxylic Acid t-Butyl Ester The title compound was prepared according to the method described in Example 20K, substituting (±)-(2R,3S,5R,1'S)-1-t-butoxycarbonyl-2-(1-acetamido-2-formyl)methyl-3-(cis-propen-1-yl)-pyrrolidine-5-carboxylic acid t-butyl ester in place of (±)-(2R,3S,5R,1'S)-1-t-butoxycarbonyl-2-(1-acetamido-3-methyl)butyl-3-formyl-pyrrolidine-5-carboxylic acid t-butyl ester and ethyltriphenylphosphonium bromide for methyltriphenylphosphonium bromide (yield: 12.4 mg, 48.2%).

MS: (M+H)$^+$=423

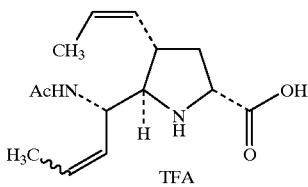

TFA 119B (±)-(2R,33S5R,1'S)-2-(1-Acetamido-2-(cis and trans)buten-1-yl)-3-(cis-propen-1-yl)-pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1acetamido-2-(cis and trans)buten-1-yl)-3-(cis-propen-1-yl)-pyrrolidine-5-carboxylic acid t-butyl ester in place of (±)-(2R,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 11.8 mg, 100%).

$^1$H NMR (DMSO-d$_6$): δ1.63 (dd, 3H), 1.66 (dd, 3H), 1.74 (m, 1H), 1.88 (s, 3H), 2.41(dt, 1H), 3.17 (m, 1H), 3.50 (dd, 1H), 4.34 (dd, 1H), 4.95 (m 1H), 5.23 (m, 1H), 5.39 (m, 1H), 5.53 (m, 1H), 5.68 (m, 1H), 8.21(d, 1H), 9.18 (brs, 2H),

MS: (M+H)$^+$=267

EXAMPLE 120

(±)-(2R,3S,5R,1'S)-2-(1-Acetamido-3,3-dimethyl) allyl-3-(cis-propen-1-yl)-pyrrolidine-5-carboxylic Acid Trifluoroacetic Acid Salt

120A (±)-(2R,3S,5R 1'S)-1-t-Butoxycarbonyl-2-(1-acetamido-3,3-dimethyl)allyl-3-(cis-propen-1-yl)-pyrrolidine-5-carboxylic Acid t-Butyl Ester The title compound was prepared according to the method described in Example 20K, substituting (±)-(2R,3S,5R,1'S)-1-t-butoxycarbonyl-2-(1-acetamido-2-formyl)methyl-3-(cis-propen-1-yl)-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester and isopropyltriphenylphosphonium bromide for methyltriphenylphosphonium bromide (yield: 8.2 mg, 25.9%). MS: (M+H)$^+$=437

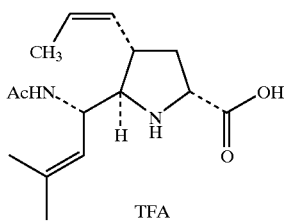

120B (±)-(2R,3S,5R,1'S)-2-(1-Acetamido-3,3-dimethyl)allyl-3-(cis-propen-1-yl)-pyrrolidine-5-carboxylic Acid Trifluoroacetic Acid Salt The title compound was prepared according to the method described in Example 41 C, substituting (±)-(2R,3S,5R,1'S)-1-t-butoxycarbonyl-2-(1-acetamido-3,3-dimethyl)allyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester ester (yield: 7.5 mg, 100%).

$^1$H NMR (DMSO-d$_6$): δ1.53 (dd, 3H), 1.57 (s, 3H), 1.61 (s, 3H), 1.66 (m, 1 H), 1.77 (s, 3H), 2.32 (dt, 1H), 3.07 (m, 1 H), 3.39 (dd, 1 H), 4.26 (m, 1H), 4.75 (m, 1H), 5.07 (d, 1H), 5.15 (m, 1H), 5.44 (m, 1H), 8.06 (d, 1H).

MS: (M+H)$^+$=281.

EXAMPLE 121

(±)-(2R,3S,5R,1'S)-2-(1-Acetamido-2-(cis and trans)penten-1-yl)-3-(cis-propen-1-yl)-pyrrolidine-5-carboxylic Acid Trifluoroacetic Acid Salt

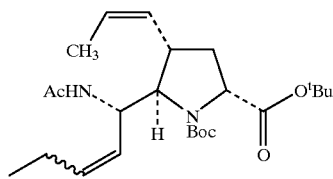

121A (±)-(2R,3S,5R,1'S)-1-t-Butoxycarbonyl-2-(1-Acetamido -2-(cis and trans)penten-1-yl)-3-(cis-propen-1-yl)-pyrrolidine-5-carboxylic Acid t-Butyl Ester The title compound was prepared according to the method described in Example substituting (±)-(2R,3S,5R,1'S)-1-t-butoxycarbonyl-2-(1-acetamido-2-formyl)methyl-3-(cis-propen-1-yl)-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester and n-butyl-triphenylphosphonium bromide for methyltriphenylphosphonium bromide (yield: 21.0 mg, 66.2%).

MS: (M+H)$^+$=437.

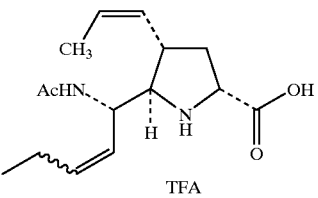

121B (±)-(2R,3S,5R,1'S)-2-(1-Acetamido-2-(cis and trans)penten-1-yl)-3-(cis-propen-1-yl)-pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1-acetamido-2-(cis and trans)penten-1-yl)-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 16.0 mg, 98.1%).

$^1$H NMR (DMSO-d$_6$): δ0.93 (t, 3H), 1.62 (dd, 3H), 1.75 (m, 1H), 1.87 (s, 3H), 2.07 (m, 2H), 2.40 (m, 1H), 3.17 (m, 1H), 3.50 (m, 1H), 4.34 (m, 1H), 4.94 (m, 1H), 5.23 (m, 1H), 5.34 (m, 1H), 5.53 (m, 1H), 5.58 (m, 1H), 8.24 (d, 1H) 9.25 (br s, 2H).

MS: (M+H)$^+$=281.

EXAMPLE 122

(±)-(2R,3S,5R,1'S)-2-(1-Acetamido-4-hydroxy-2-(cis and trans)buten-1-yl)-3-(cis-propen-1-yl)-pyrrolidine-5-carboxylic Acid Trifluoroacetic Acid Salt

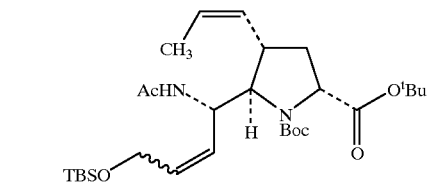

122A (±)-(2R,3S,5R,1'S)-1-t-Butoxycarbonyl-2-(1-Acetamido-4-(t-butyldimethylsilyloxy)-2-(cis and trans)buten-1-yl)-3-(cis-propen-1-yl)-pyrrolidine-5-carboxylic Acid t-Butyl Ester The title compound was prepared according to the method described in Example substituting (±)-(2R,3S,5R,1'S)-1-t-butoxycarbonyl-2-(1-acetamido-2-formyl)methyl-3-(cis-propen-1-yl)-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester and 4-(t-butyldimethylsilyloxy)-butyltriphenylphosphonium bromide for methyltriphenylphosphonium bromide (yield: 23.1 mg, 66.9%).

MS: (M+H)⁺=567.

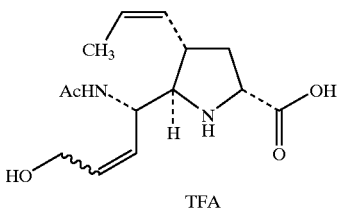

TFA

122B (±)-(2R,3S,5R,1'S)-2-(1-Acetamido-4-hydroxy-2-(cis and trans)buten-1-yl)-3-(cis-propen-1-yl)-pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1-acetamido-2 -(cis and trans)-4-hydroxy-butenyl-2-yl)-3-(cis-propen-1-yl)-pyrrolidine-5-carboxylic acid t-butyl ester in place of (±)-(2R,3S,5R,1'R, 2'S)-1-t-butoxycarbonyl-2-(1-acetamido-2-hydroxy)butyl-3-(cis-propen-1-yl)-pyrrolidine-5-carboxylic acid t-butyl ester (yield: 16.9 mg, >100%).

¹H NMR (DMSO-d₆): δ1.67 (dd, 3H), 1.78 (dt, 1H), 1.91 (m, 3H), 2.44 (m, 1H), 2.50 (m, 1H), 2.56 (m, 1H), 2.65 (m, 1H), 3.23 (m, 1H), 3.54 (m, 1H), 4.40 (m, 1H), 4.47 (m, 2H), 5.01 (m, 1H), 5.26 (m, 1H), 5.54 (m, 2H), 5.63 (m, 1H), 8.32 (d, 1H), 9.27 (br s, 2H).

MS: (M+H)⁺=297.

EXAMPLE 123

(±)-(2R,3S,5R,1'S)-2-(1-Acetamido)butyl-3-vinyl-pyrrolidine-5-carboxylic Acid Hydrochloride

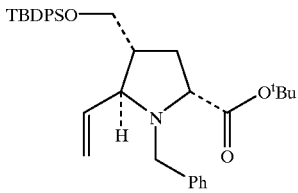

123A (±)-(2R,3R,5R)-1-Benzyl-2-vinyl-3-t-butyldiphenylsilyloxymethyl-pyrrolidine-5-carboxylic Acid t-Butyl Ester (±)-(2R,3R,5R)-1-Benzyl-2-vinyl-3-hydroxymethyl-pyrrolidine-5-carboxylic acid t-butyl ester (30.8 g, 97.1 mmol) was reacted with t-butyldiphenylsilyl chloride (49.5 mL, 190.4 mmol) and imidazole in dichloromethane (650 mL) at 0° C. for 1 hour. The reaction was quenched methanol followed by extraction with dichloromethane (600 mL). The organic layer was dried over magnesium sulfate, filtered and concentrated in vacuo. The residue was purified by column chromatography on silica gel using 2/1: chloroform/hexane to provide the title compound (yield: 52.9 g, 98%).

¹H NMR (CDCl₃) 7.62–7.67 (m, 4H), 7.32–7.44 (m, 6H), 7.25–7.30 (m, 5H), 5.58–5.72 (m, 1H), 5.06–5.14 (m, 2H), 3.90 (d, 1H), 3.72–3.78 (m, 1H), 3.58–3.68(m, 2H), 3.44–3.52 (m, 2H), 2.26–2.40 (m, 1H), 2.10–2.23 (m, 1H), 1.68–1.7 (m, 1H), 1.38 (m, 9H), 1.03 (s, 9H).

MS: (M+H)⁺=556

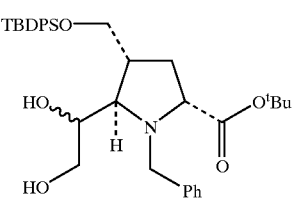

123B (±)-(2R,3R,5R,1'RS)-1-Benzyl-2-(1,2-dihydroxy)ethyl-3-t-butyldiphenylsilyloxymethyl-pyrrolidine-5-carboxylic Acid t-Butyl Ester (±)-(2R,3R,5R)-1-Benzyl-2-vinyl-3-t-butyldiphenylsilyloxymethyl-pyrrolidine-5-carboxylic acid t-butyl ester (22.7 g, 41 mmol) was reacted with OsO4 (4%) (2.5 mL, 0.7 mol. %) and N-methyl morpholine N-oxide (18.5 g, 2.77 eq.) in acetone (500 mL) and water (60 mL) for 48 h at room temperature. The reaction was quenched with 10% aqueous Na₂S₂O₃ (200 mL). The reaction was concentrated in vacuo and the residue was partitioned between ethyl acetate/water. The organic layer was dried over magnesium sulfate, filtered and concentrated in vacuo. The residue was purified by column chromatography on silica gel using 35% ethyl acetate/hexane to provide the title compound (yield: 11 g, 55%).

¹H NMR (DMSO-d₆) δ7.58–7.63 (m, 5H), 7.40–7.48 (m, 7H), 7.20–7.35 (m, 3H), 4.41–4.45 (m, 2H), 3.98 (d, 1H), 3.75–3.84 (m, 2H), 3.50–3.68 (m, 2H), 3.4–3.46 (m, 1H), 3.16–3.25 (m, 1H), 2.97–3.0 (m, 1H), 2.09–2.28 (m, 1H), 1.62–1.89 (m, 1H), 1.34–1.39 (m, 1H), 1.30 (m, 9H), 0.98,0.96 (2s, 9H).

MS: (M+H)⁺=590

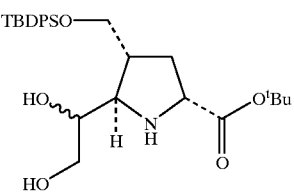

123C (±)-(2R,3R,5R,1'RS)-2-(1,2-dihydroxy)ethyl-3-t-butyldiphenylsilyloxymethyl-pyrrolidine-5-carboxylic Acid t-Butyl Ester (±)-(2R,3R,5R,1'RS)-1-Benzyl-2-(1,2-dihydroxy)ethyl-3-t-butyldiphenylsilyloxymethyl-pyrrolidine-5-carboxylic acid t-butyl ester (11 g, 18.7 mmol) was reacted under 1 atmosphere of hydrogen with 20% Pd(OH)₂/C (5 g) and in ethanol (40 mL) vigorously stirred for 2.5 days at room temperature. The reaction was filtered, and the catalyst was washed with methanol (3×30 mL). The filtrate was evaporated in vacuo to give the title compound as an oil (yield: 8 g, 94%)

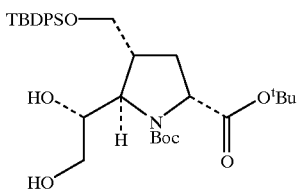

123D (±)-(2R,3R,5R,1'R)-1-t-Butoxycarbonyl-2-(1,2-dihydroxy)ethyl-3-t-butyldiphenylsilyloxymethyl-pyrrolidine-5-carboxylic Acid t-Butyl Ester The title compound was prepared according to the method described in Example 40D, substituting (±)-(2R,3R,5R,1'R)-2-(1,2-dihydroxy)ethyl-3-t-butyldiphenylsilyloxymethyl-pyrrolidine-5-carboxylic acid t-butyl ester in place of (2R,3R,5R,1'RS)-2-(1,2-dihydroxy)ethyl-3-acetoxymethyl-pyrrolidine-5-carboxylic acid t-butyl ester. The residue was purified by column chromatography on silica gel using 35% ethyl acetate/hexane to provide the title compound (yield: 20.5 g, 60%).

$^1$H NMR (DMSO-$d_6$) 7.57–7.60 (m, 4H), 7.38–7.48 (m, 6H), 4.85,4.77 (2d, 1H), 4.45–4.50 (m, 1H), 4.02–4.10 (m, 1H), 3.80–3.95 (m, 1H), 3.73,3.68 (2s, 1H), 3.45–3.67 (m, 2H), 3.18–3.28 (m, 2H), 2.36–2.46 (m, 2H), 1.88,1.70 (2d,1H), 1.40,1.35 (2s, 9H), 1.32,1.26 (2s, 9H), 1.0,0.98 (2s, 9H).

MS: $(M+H)^+=600$

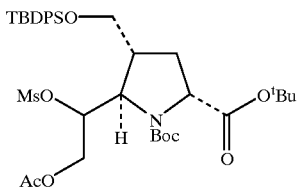

123E (±)-(2R,3R,5R,1'R)-1-t-Butoxycarbonyl-2-(1-methanesulfonyloxy-2-acetoxy)ethyl-3-t-butyldiphenylsilyloxymethyl-pyrrolidine-5-carboxylic Acid t-Butyl Ester (±)-(2R,3R,5R,1'R)-1-t-Butoxycarbonyl-2-(1,2-dihydroxy)ethyl-3-t-butyldiphenylsilyloxymethyl-pyrrolidine-5-carboxylic acid t-butyl ester (20.5 g, 34.2 mmole) was reacted with acetic anhydride (16.1 mL, 171 mmole) and triethylamine (47.7 mL, 342 mmole) in dichloromethane (360 mL) at 0° C. for 16 h.

The reaction was treated with methanol (35 mL) for 10 minutes and diluted with dichloromethane (1300 mL). The organic layer was washed with water,and brine, dried over MgSO$_4$, filtered and concentrated in vacuo. The residue was reacted with methanesulfonyl chloride (4.0 mL, 51.3 mmole) and triethylamine (14.3 mL, 103 mmole) in dichloromethane (350 mL) at 0° C. for 1.5 hours. The reaction was quenched with water (300 mL) and diluted with dichloromethane (1200 mL). The organic layer was washed with water,and brine, dried over MgSO$_4$, filtered and concentrated in vacuo. The residue was purified by chromatography on silica gel using 30% ethyl acetate/hexanes to provide the title compound (yield: 23.8 g, 97%).

$^1$H NMR (DMSO-$d_6$) δ7.58–7.62 (m, 4H), 7.38–7.50 (m, 6H), 5.12–5.26 (2m, 1H), 4.06–4.25 (m, 3H), 4.00 (d,1H), 3.46–3.68 (m, 2H), 3.20,3.18 (2s, 3H), 2.40–2.48 (m, 1H), 2.02,1.99, (2s, 3H), 1.68–1.88 (m, 1H), 1.42,1.36 (2s, 9H), 1.31,1.25 (2s, 9H), 1.00,0.9 (2s, 9H).

MS: $(M+H)^+=720$, $(M+NH_4)^+=737$

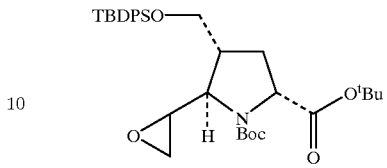

123F (±)-(2R,3R,5R,1'S)-1-t-Butoxycarbonyl-2-oxiranyl-3-t-butyldiphenylsilyloxymethyl-pyrrolidine-5-carboxylic Acid t-Butyl Ester (±)-(2R,3R,5R,1'S)-1-t-Butoxycarbonyl-2-(1-methanesulfonyloxy-2-acetoxy)ethyl-3-t-butyldiphenylsilyloxymethyl-pyrrolidine-5-carboxylic acid t-butyl ester (23.8 g, 33.1 mmole) was reacted with potassium carbonate (10.1 g, 66.2 mmole) in methanol (160 mL) and THF (160 mL) at 25° C. for 18 hours. The reaction was concentrated in vacuo. The residue was dissolved in ethyl acetate and washed with water,and brine, dried over MgSO$_4$, filtered and concentrated in vacuo. The residue was purified by chromatography on silica gel using 25% ethyl acetate/hexanes to provide the title compound, as an oil (yield: 16.7 g, 87%).

$^1$H NMR (CDCl$_3$) δ7.60–7.68 (m, 4H), 7.32–7.45 (m, 6H), 4.02–4.28 (m, 2H), 3.67–3.78 (m, 1H), 3.52–3.62 (m, 1H), 3.0–3.08 (m, 1H), 2.68–2.75 (m, 1H), 2.47–2.52 (m, 3H), 1.80–1.90 (m, 1H), 1.48,1.42 (2s, 9H), 1.37,1.35 (2s, 9H), 1.07,1.03 (2s, 9H).

MS: $(M+H)^+=582$

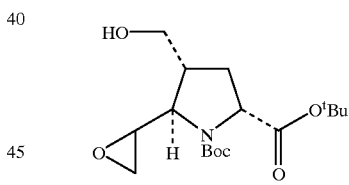

123G (±)-(2R,3R,5R,1'S)-1-t-Butoxycarbonyl-2-oxiranyl-3-hydroxymethyl-pyrrolidine-5-carboxylic Acid t-Butyl Ester (±)-(2R,3R,5R,1'S)-1-t-Butoxycarbonyl-2-oxiranyl-3-t-butyldiphenylsilyloxymethyl-pyrrolidine-5-carboxylic acid t-butyl ester (4.17 g, 7.2 mmole) was reacted with tetrabutylammonium fluoride (1M) (14 mL, 14.0 mmole) in THF (7 mL) for 20 minutes at 0° C. then for 1.5 hours at 25° C. The reaction was concentrated in vacuo the residue was dissolved in ethyl acetate and washed with pH 7.0 buffer and brine, dried over MgSO$_4$, filtered and concentrated in vacuo. The residue was purified by chromatography on silica gel using 50% ethyl acetate/hexanes to provide the title compound, as an oil (yield: 2.4 g, 97%).

$^1$H NMR (DMSO-$d_6$) δ4.72–4.78 (m, 1H), 3.94–4.05 (m, 2H), 3.35–3.47 (m, 1H), 3.18–3.28 (m, 1H), 3.03–3.08 (m, 1H), 2.63–2.73 (m, 1H), 2.37–2.44 (m, 1H), 2.30–2.36 (m,

1H), 2.08–2.20 (m, 1H), 1.58–1.75 (m, 1H), 1.40 (s, 9H), 1.37,1.34 (2s, 9H).

MS: (M+H)⁺=344, (M+Na)⁺=366

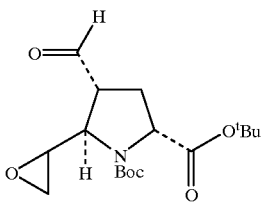

123H (±)-(2R,3R,5R,1'S)-1-t-Butoxycarbonyl-2-oxiranyl-3-formyl-pyrrolidine-5-carboxylic Acid t-Butyl Ester (±)-(2R,3R,5R,1'S)-1-t-Butoxycarbonyl-2-oxiranyl-3-hydroxymethyl-pyrrolidine-5-carboxylic acid t-butyl ester (2.4 g, 7.0 mmole) and triethylamine (3.9 mL 28.0 mmole) in dichloromethane (70 mL) at 0° C. was reacted with sulfur trioxide pyridine complex (3.35 g, 21.0 mmole) in dimethylsulfoxide (21 mL) by dropwise addition followed by reaction for an additional 3 hours. The reaction was quenched with water (50 mL) and diluted with ethyl acetate (200 mL). The organic layer was washed with water,and brine, dried over MgSO₄, filtered and concentrated in vacuo to provide the title compound (yield: 2.2 g,).

¹H NMR (DMSO-d₆) (rotamers) δ9.58 and 9.56 (2s, 1H), 4.70 and 4.53 (2m, 1H), 3.96 (dd, J=1.4, 9.2 Hz, 1H), 3.25–3.20 (m, 1H), 2.91 (m, 1H), 2.71 (m, 1H), 2.50–2.28 (m, 3H), 1.42, 1.37, 1.34, and 1.30 (4s, 18H)

MS: (M–H)⁻=340

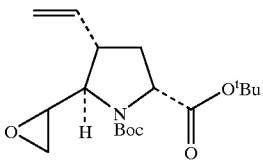

123I(±)-(2R,3S,5R 1'S)-1-t-Butoxycarbonyl-2-oxiranyl-3-vinyl-pyrrolidine-5-carboxylic Acid t-Butyl Ester Triphenylphosphoranylidenemethyl ylide (17.6 mmole) prepared by reacting methyltriphenylphosphonium bromide (12.63 g, 35.4 mmole) and potassium tert-butoxide (1M) (17.6 mL, 17.6 mmole) in THF (70 mL) for 1 hour at 25° C. (±)-(2R,3R,5R,1'S)-1-t-Butoxycarbonyl-2-oxiranyl-3-formyl-pyrrolidine-5-carboxylic acid t-butyl ester (2.2 g, 6.5 mmole) in THF (10 mL) was added to the above solution at 0° C. and stirred for 0.5 hours. The reaction was quenched with saturated ammonium chloride (50 mL) and diluted with ethyl acetate (200 mL). The organic layer was washed with water,and brine, dried over MgSO₄, filtered and concentrated in vacuo. The residue was purified by chromatography on silica gel using 10% ethyl acetate/hexanes to provide the title compound (yield: 2 g, 84%).

¹H NMR (DMSO-d₆) δ5.80–5.95 (m, 1H), 5.08 (d, 1H), 4.94–5.04 (1H), 4.00–4.07 (m, 1H), 3.59,3.90 (2t, 1H), 3.07–3.16 (m, 1H), 2.73–2.81 (m, 1H), 2.65–2.72 (m, 1H), 2.35–2.48 (m, 1H), 1.59–1.76 (m, 1H), 1.42 (s, 9H), 1.38, 1.35 (2s, 9H).

MS: (M+H)⁺=340

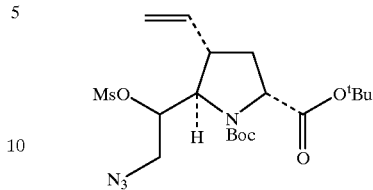

123J (±)-(2R,3S,5R, 1'R)-1-t-Butoxycarbonyl-2-(1-methanesulfonyloxy-3-azido)ethyl-3-vinyl-pyrrolidine-5-carboxylic Acid t-Butyl Ester (±)-(2R,3S,5R,1'S)-1-t-Butoxycarbonyl-2-oxiranyl-3-vinyl-pyrrolidine-5-carboxylic acid t-butyl ester (1.72 g, 5.1 mmole) and ammonium chloride (1.36 g, 25.4 mmole) in ethanol (45 mL) and water (5 mL) was reacted with lithium azide (1.2 g, 24.5 mmole) for 7 hours at 50° C. The reaction was concentrated in vacuo and diluted with ethyl acetate (200 mL). The organic layer was washed with water,and brine, dried over MgSO₄, filtered and concentrated in vacuo. The residue (2.15 g) was dissolved in dichloromethane (50 mL) and reacted with methanesulfonyl chloride (0.8 mL, 10.2 mmole) and triethylamine (2.8 mL, 20.4 mmole) for 0.5 hours at 0° C. The reaction was quenched with aqueous sodium bicarbonate (50 mL) and diluted with ethyl acetate (200 mL). The organic layer was washed with water,and brine, dried over MgSO₄, filtered and concentrated in vacuo. The residue was purified by chromatography on silica gel using 10% ethyl acetate/hexanes to provide the title compound (yield: 1.87 g, 80%).

¹H NMR (DMSO-d₆) δ5.77–5.98 (m, 1H), 4.94–5.11 (m, 3H), 4.12–4.19 (m, 1H), 3.99–4.06 (m, 1H), 3.66,3.71 (2d, 1H), 3.25,3.22 (2s, 3H), 2.92–3.02 (m, 1H), 2.55–2.63 (m, 1H), 1.68–1.82 (m, 1H), 1.45,1.42 (2s, 9H), 1.38,1.36 (2s,

MS: (M+H)⁺=461

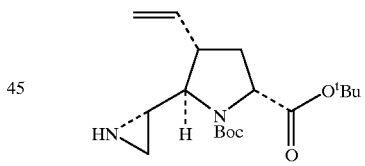

123K (±)-(2R,3S,5R,1'S)-1-t-Butoxycarbonyl-2-aziridinyl-3-vinyl-pyrrolidine-5-carboxylic Acid t-Butyl Ester (±)-(2R,3S,5R,1'S)-1-t-Butoxycarbonyl-2-(1-methanesulfonyloxy-3-azido)ethyl-3-vinyl-pyrrolidine-5-carboxylic acid t-butyl ester (2.12 g, 4.6 mmole) was reacted with triphenylphosphine (1.81 g, 6.9 mmole) in THF (30 mL) and water (7.5 mL) at 65° C. for 1 hour. The reaction was concentrated in vacuo and redissolved in ethyl acetate (200 mL). The organic layer was washed with water,and brine, dried over MgSO₄, filtered and concentrated in vacuo. The residue was purified by chromatography on silica gel using 4% methanol in dichloromethane to provide 2 g of the crude title compound containing approximately 60% product and 40% Ph₃PO which was used directly for acylation.

¹H NMR (DMSO-d₆) δ5.78–5.5.98 (m, 1H), 4.12 (d, 1H), 3.42,3.19 (2d, 1H), 2.53–2.73 (m, 2H), 2.00–2.15 (m, 1H), 1.68–1.76 (m, 1H), 1.62–1.68 (m, 1H), 1.41 (s, 9H), 1.37, 1.36 (2s, 9H).

MS: (M+H)⁺=339, (M+Na)⁺=361

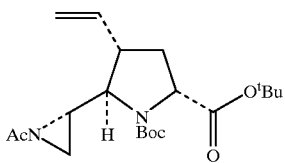

123L (±)-(2R,3S,5R,1'S)-1-t-Butoxycarbonyl-2-(N-acetylaziridinyl)-3-vinyl-pyrrolidine-5-carboxylic Acid t-Butyl Ester (±)-(2R,3S,5R,1'S)-1-t-Butoxycarbonyl-2-aziridinyl-3-vinyl-pyrrolidine-5-carboxylic acid t-butyl ester (1.03 g, 3.1 mmole) was reacted with acetic anhydride (0.42 mL, 4.7 mmole) and triethylamine (1.3 mL, 9.3 mmole) in dichloromethane (30 mL) at 26° C. for 1 hours. The reaction was quenched with water (50 mL) and diluted with ethyl acetate (200 mL). The organic layer was washed with water, and brine, dried over MgSO₄, filtered and concentrated in vacuo. The residue was purified by chromatography on silica gel using 20% ethyl acetate/hexanes to provide the title compound (yield: 0.75 g, 64%).

$^1$H NMR (DMSO-d₆) δ5.78–5.98 (m, 1H), 5.05 (d, 1H), 4.98,4.94 (2d, 1H), 4.12–4.20 (m, 1H), 3.54,3.42 (2dd, 1H), 2.54–2.98 (m, 3H), 2.40,2.49 (2d, 1H), 2.15,2.19 (2d, 1H), 2.02,2.04 (2s, 3H), 1.68–1.82 (m, 1H), 1.42 (s, 9H), 1.48, 1.45 (2s, 9H).

MS: (2M+Na)⁺=783

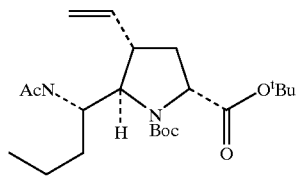

123M (±)-(2R,3S,5R, 1'S)-1-t-Butoxycarbonyl-2-(1-acetamido)butyl-3-vinyl-pyrrolidine-5-carboxylic Acid t-Butyl Ester To a suspension of copper(I) bromide-dimethyl sulfide complex (0.051 g, 0.248 mmol) in THF (1.0 ml) at 0° C., was added ethylmagnesium bromide (1M) (1.0 ml, 1.0 mmol) in THF. After stirring for 10 minutes at 0° C., a portion of this solution (0.60 ml) was added dropwise to a solution of (±)-(2R,3S,5R,1'S)-1-t-Butoxycarbonyl-2-(N-acetylaziridinyl)-3-vinyl-pyrrolidine-5-carboxylic acid t-butyl ester (0.020 g, 0.053 mmole) in THF (0.40 ml) at −78° C. After stirring for 20 minutes at −78° C., the reaction was warmed to 0 ° C. and stirred for 30 minutes. The reaction was quenched with saturated ammonium chloride (1.0 mL) and diluted with ethyl acetate (10 mL). The organic layer was washed with water and brine, dried over MgSO₄, filtered and concentrated in vacuo. The residue was purified by chromatography on silica gel using a gradient of 0–75% ethyl acetate/hexanes to provide the title compound (yield: 0.004 g, 19%).

$^1$H NMR (DMSO-d₆) (rotamers) δ7.48 (d, J=9.5 Hz, 1H), 5.98–5.80 (m, 1H), 5.00–4.90 (m, 2H), 4.45–4.25 (m, 1H), 3.96–3.91 (m, 1H), 3.60–3.57 and 3.53–3.50 (2m, 1H), 2.91–2.76 (m, 1H), 2.59–2.42 (m, 1H), 1.80 (s, 3H), 1.73–1.59 (m, 1H), 1.42 and 1.41 (2s, 9H), 1.40–1.15 (m, 4H), 1.37 and 1.34 (2s, 9H), 0.89–0.82 (m, 3H)

MS: (M−H)⁻=409, (M+H)⁺=411

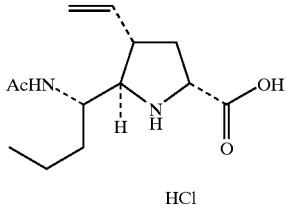

123N (±)-(2R,3S,5R,1'S)-2-(1-Acetamido)butyl-3-vinyl-pyrrolidine-5-carboxylic Acid Hydrochloric Acid Salt The title compound was prepared according to the method described in Example 1K, substituting (±)-(2R,3S,5R,1'S)-1-t-butoxycarbonyl-2-(1-acetamido)butyl-3-vinyl-pyrrolidine-5-carboxylic acid t-butyl ester in place of (2R, 3R,5R,1'S)-2-(1-acetamido-3-ethyl)pentyl-3-methoxymethyl-pyrrolidine-5-carboxylic acid t-butyl ester (yield: 3.1 mg, 99%).

$^1$H NMR (DMSO-d₆) δ8.11 (d, J=7.3 Hz, 1H), 5.76–5.69 (m, 1H), 5.16 (d, J=17.1 Hz, 1H), 5.07 (dd, J=1.5, 10.3 Hz, 1H), 4.30 (dd, J=7.3, 9.8 Hz, 1H), 4.13 (m, 1H), 3.50 (dd, J=5.9, 9.8 Hz, 1H), 2.90 (m, 1H), 2.39 (m, 1H), 1.92–1.85 (m, 1H), 1.87 (m, 3H), 1.52–1.18 (m, 4H), 0.85 (t, J=7.3, 3H)

MS: (M−H)⁻=253, (M+H)⁺=255

EXAMPLES 124–130

The following title compounds were prepared in two steps according to the methods described in Examples 123M and 123N, the denoted reagents and their respective methods of preparation are substituted in place of diethylcuprate and its preparation in Example 123M for step 1.

EXAMPLE 124

(±)-(2R,3S,5R,1'S)-2-(1-Acetamido)hexyl-3-vinyl-pyrrolidine-5-carboxylic Acid Hydrochloric Acid Salt The organocuprate reagent was prepared from a Grignard reagent and a catalytic quantity of copper(I) bromide-dimethyl sulfide complex according to the methods described in Example 123M, substituting 2M butylmagnesium chloride for 1M ethylmagnesium bromide.

$^1$H NMR (MeOD-d$_3$) δ5.82–5.70 (m, 1H), 5.29 (d, J=17.0 Hz, 1H), 5.17 (dd, J=1.3, 10.2 Hz, 1H), 4.35 (dd, J=7.5, 10.2 Hz, 1H), 4.19 (m, 1H), 3.65 (dd, J=3.4, 9.8 Hz, 1H), 3.01 (m, 1H), 2.55 (m, 1H), 2.08–1.97 (m, 1H), 2.04 (s, 3H), 1.6–1.31 (m, 8H), 0.91 (t, J=6.4 Hz, 3H)

MS: (M−H)$^−$=281, (M+H)$^+$=283

EXAMPLE 125

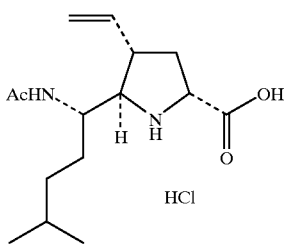

(±)-(2R,3S,5R,1'S)-2-(1-Acetamido-4-methyl)pentyl-3-vinyl-pyrrolidine-5-carboxylic Acid Hydrochloric Acid Salt The organocuprate reagent was prepared from a Grignard reagent and a catalytic quantity of copper(I) bromide-dimethyl sulfide complex according to the methods described in Example 123M, substituting iso-butylmagnesium chloride for ethylmagnesium bromide.

$^1$H NMR (MeOD-d$_3$) δ5.83–5.71 (m, 1H), 5.29 (dd, J=0.7,17.0 Hz, 1H), 5.17 (dd, J=0.7, 10.2 Hz, 1H), 4.34 (dd, J=7.5, 10.2 Hz, 1H), 4.15 (m, 1H), 3.66 (dd, J=3.4, 9.8 Hz, 1H), 3.01 (m, 1H), 2.55 (m, 1H), 2.08–1.97 (m, 1H), 2.04 (m, 3H), 1.65–1.10 (m, 5H), 0.91 (d, J=6.4 Hz, 3H), 0.91 (d, J=6.5 Hz, 3H)

(M+H)$^+$=283

EXAMPLE 126

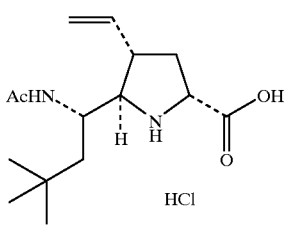

(±)-(2R,3S,5R,1'S)-2-(1-Acetamido-3,3dimethyl)butyl-3-vinyl-pyrrolidine-5-carboxylic Acid Hydrochloric Acid Salt The organocuprate reagent was prepared from a Grignard reagent and a catalytic quantity of copper(I) bromide-dimethyl sulfide complex according to the methods described in Example 123M, substituting 1M tert-butylmagnesium chloride for 1 M ethylmagnesium bromide.

$^1$H NMR (MeOD-d$_3$) δ5.84–5.71 (m, 1H), 5.31 (d, J=17.0 Hz, 1H), 5.19 (d, J=10.2 Hz, 1H), 4.39–4.33 (m, 2H), 3.66 (dd, J=3.4, 9.8 Hz, 1H), 3.02 (m, 1H), 2.57 (m, 1H), 2.08–1.97 (m, 1H), 2.02 (s, 3H), 1.55 (dd, J=9.5, 14.6 Hz, 1H), 1.42 (dd J=1.4, 14.6 Hz, 1H), 0.95 (s, 9H)

(M+H)$^+$=283

EXAMPLE 127

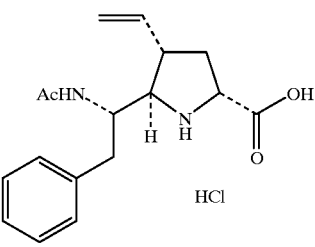

(±)-(2R,3S,5R,1'S)-2-(1-Acetamido-2-phenyl)ethyl-3-vinyl-pyrrolidine-5-carboxylic Acid Hydrochloric Acid Salt Lithium diphenylcurpate was prepared according to the method described by Lipshutz, B. H. in *Organometallics in Synthesis*; Schlosser, M., Ed.; Wiley and Sons: New York, 1994; p.292. This cuprate was used according to the methods described in Example 123M, substituting lithium diphenyl-cuprate for the Grignard derived diethylcuprate complex.

$^1$H NMR (MeOD-d$_3$) δ7.35–7.21 (m, 5H), 5.87–5.75 (m, 1H), 5.37 (d, J=16.6 Hz, 1H), 5.26 (dd, J=1.0, 10.2 Hz, 1H), 4.53 (m, 1H), 4.37 (dd, J=7.5, 9.8 Hz, 1H), 3.70 (dd, J=3.7, 9.8 Hz, 1H), 3.11 (m, 1H), 2.97 (dd, J=6.1, 14.2 Hz, 1H), 2.84 (dd, J=9.5, 14.2 Hz, 1H), 2.59 (m, 1H), 2.08–1.99 (m, 1H), 1.93 (s, 3H)

(M−H)$^−$=301, (M+H)$^{30}$=303

EXAMPLE 128

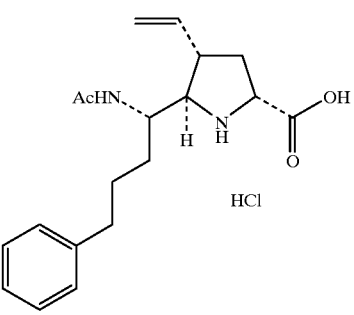

(±)-(2R,3S,5R,1'S)-2-(1-Acetamido4-phenyl)butyl-3-vinyl-pyrrolidine-5-carboxylic Acid Hydrochloric Acid Salt The organocuprate reagent was prepared from a Grignard reagent and a catalytic quantity of copper(I) bromide-dimethyl sulfide complex according to the methods described in Example 123M, substituting 1M phenethyl-magnesium chloride for 1M ethylmagnesium bromide.

$^1$H NMR (MeOD-d$_3$) δ7.29–7.13 (m, 5H), 5.77–5.65 (m, 1H), 5.24 (d, J=16.6 Hz, 1H), 5.13 (dd, J=1.0, 9,8 Hz, 1H), 4.33 (dd, J=7.5, 10.2 Hz, 1H), 4.22 (m, 1H), 3.62 (dd, J=3.4, 9.8 Hz, 1H), 2.98 (m, 1H), 2.63 (m, 2H), 2.54 (m, 1H), 2.06–1.95 (m, 1H), 2.03 (s, 3H), 1.79–1.55 (m, 4H)

(M−H)$^−$=329, (M+H)$^+$=331

EXAMPLE 129

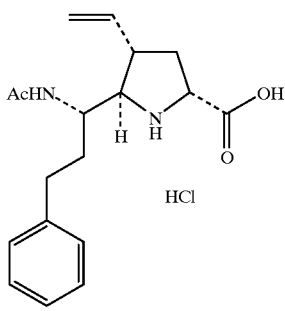

(±)-(2R,3S,5R,1'S)-2-(1-Acetamido-3-phenyl)butyl-3-vinyl-pyrrolidine-5-carboxylic Acid Hydrochloric Acid Salt The organocuprate reagent was prepared from a Grignard reagent and a catalytic quantity of copper(I) bromide-dimethyl sulfide complex according to the methods described in Example 123M, substituting 2M benzylmagnesium chloride for 1M ethylmagnesium bromide.

1H NMR (MeOD-$d_3$) δ7.30–7.17 (m, 5H), 5.82–5.70 (m, 1H), 5.28 (d, J=17.0 Hz, 1H), 5.17 (d, J=11.2 Hz, 1H), 4.33 (dd, J=7.5, 10.2 Hz, 1H), 4.18 (m, 1H), 3.64 (dd, J=3.4, 9.8 Hz, 1H), 3.01 (m, 1H), 2.78 (m, 1H), 2.66–2.50 (m, 2H), 2.07 (s, 3H), 2.07–1.85 (m, 3H)

$(M-H)^-=315$, $(M+H)^+=317$

EXAMPLE 130

(±)-(2R,3S,5R,1'S)-2-(1-Acetamido-2-propen-2-yl)ethyl-3-vinyl-pyrrolidine-5-carboxylic Acid Trifluoroacetic Acid Salt

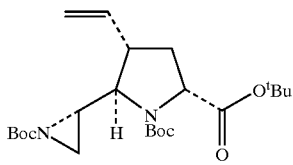

130A (±)-(2R,3S,5R,1'S)-1-t-Butoxycarbonyl-2-(N-t-Butoxycarbonylaziridinyl)-3-vinyl-pyrrolidine-5-carboxylic Acid t-Butyl Ester (±)-(2R,3S,5R,1'S)-1-t-Butoxycarbonyl-2-aziridinyl-3-vinyl-pyrrolidine-5-carboxylic acid t-butyl ester (0.058 g, 0.17 mmole) was reacted with di-t-butyldicarbonate (95 mg, 0.44 mmole) and triethylamine (0.12 mL, 0.86 mmole) in dichloromethane (2.0 mL) at room temperature for 1 hour. The reaction was quenched with saturated sodium bicarbonate (1.0 mL) and diluted with ethyl acetate (20 mL). The organic layer was washed with water, and brine, dried over $MgSO_4$, filtered and concentrated in vacuo. The residue was purified by chromatography on silica gel using a gradient of 0–15% ethyl acetate/dichloromethane to provide the title compound (yield: 0.060 g, 80%).

$^1$H NMR (DMSO-$d_6$) (rotamers) δ5.97–5.78 (m, 1H), 5.06–4.93 (m, 2H), 4.15 (dd, J=2.0, 9.8 Hz, 1H), 3.40–3.28 (m, 1H), 2.94–2.49 (m, 3H), 2.39 and 2.33 (2d, J=6.1, 6.4 Hz, 1H), 2.17 and 2.11 (2d, J=3.7, 3.4, 1H), 1.81–1.69 (m, 1H), 1.42–1.36 (m, 27H)

MS: $(M+Na)^+=461$ (weak)

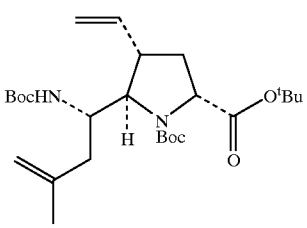

130B (±)-(2R,3S,5R,1'S)-1-t-Butoxycarbonyl-2-(1-N-t-butoxycarbonylamino-2-propen-2-yl)ethyl-3-vinyl-pyrrolidine-5-carboxylic Acid t-Butyl Ester To a suspension of copper(I) bromide-dimethyl sulfide complex (0.026g, 0.127 mmol) in THF (1.0 ml) at 0° C. was added isopropenylmagnesium bromide (0.5M) (1.0 ml, 0.50 mmol) in THF. After stirring for 10 minutes at 0° C., the mixture was cooled to −78° C. and a solution of (±)-(2R, 3S,5R,1'S)-1-t-butoxycarbonyl-2-(N-t-butoxycarbonylaziridinyl)-3-vinyl-pyrrolidine-5-carboxylic acid t-butyl ester (0.030 g, 0.068 mmole) in THF (1.0 ml) was added dropwise. After stirring for 10 minutes at −78° C., the reaction was warmed to 0° C. and stirred for 2 hours. The reaction was quenched with saturated ammonium chloride (1.0 mL) and diluted with ethyl acetate (10 mL). The organic layer was washed with water, and brine, dried over $MgSO_4$, filtered and concentrated in vacuo. The residue was purified by chromatography on silica gel using a gradient of 0–10% ethyl acetate/dichloromethane to provide the title compound (yield: 0.026 g, 79%).

$^1$H NMR (DMSO-$d_6$) (rotamers) δ6.64 (m, 1H), 5.96–5.76 (m, 1H), 4.98–4.89 (m, 2H), 4.76–4.68 (m, 2H), 4.40–4.25 (m, 1H), 3.94 (m, 1H), 3.60–3.53 (m, 1H), 3.02–2.86 (m, 1H), 2.62–2.42 (m, 1H), 2.10–1.99 (m, 2H), 1.72 and 1.70 (2s, 3H), 1.72–1.55 (m, 1H), 1.44–1.34 (m, 27H)

MS: $(M-H)^-479$, $(M+H)^+=481$

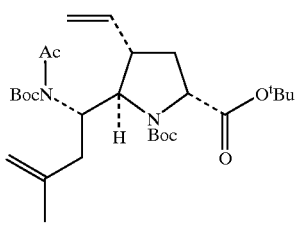

130C (±)-(2R,3S,5R,1'S)-1-t-Butoxycarbonyl-2-(1-N-t-butoxycarbonylacetamido-2-propen-2-yl)ethyl-3-vinyl-pyrrolidine-5-carboxylic Acid t-Butyl Ester (±)-(2R,3S,5R,1'S)-1-t-Butoxycarbonyl-2-(1-N-t-butoxycarbonylamino-2-propen-2-yl)ethyl-3-vinyl-pyrrolidine-5-carboxylic acid t-butyl ester (0.024 g, 0.050 mmole) was reacted with lithium hexamethyldisilazide (1 M) (0.60 mL, 0.60 mmole) in THF (2.0 mL) at −25° C. for 1 hour. To the above reaction was then added acetyl chloride (0.085 mL, 1.20 mmole) at −25° C. and the mixture was stirred for 30 minutes. The reaction was quenched with saturated sodium bicarbonate (2.0 mL) and stirred for 30 minutes at room temperature. The reaction was diluted with ethyl acetate (20 mL). The organic layer was washed with water, and brine, dried over MgSO₄, filtered and concentrated in vacuo. The residue was purified by chromatography on silica gel using a gradient of 0–15% ethyl acetate/hexanes to provide the title compound (yield: 0.015 g, 58%) along with unreacted starting material.

¹H NMR (DMSO-d₆) (rotamers) δ6.01–5.84 (m, 1H), 4.99–4.89 (m, 2H), 4.76–4.58 (m, 3H), 4.33 and 4.23 (2d, J=7.8, 8.1 Hz, 1H), 4.13–4.04 (m, 1H), 2.69 (m, 1H), 2.62–2.42 (m, 1H), 2.29 (br s, 3H), 2.35–2.14 (m, 2H), 1.76–1.55 (m, 1H), 1.60 (s, 3H), 1.50–1.35 (m, 27H)

MS: (M+H)⁺=523

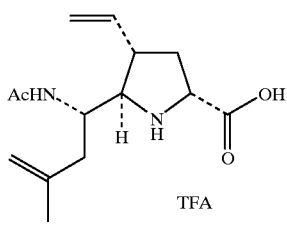

TFA 130D (±)-(2R,3S,5R,1'S)-2-(1-Acetamido-2-propen-2-yl) ethyl -3-vinyl-pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1-N-t-butoxycarbonylacetamido-2-propen-2-yl)ethyl -3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. (yield: 12 mg, 99%).

¹H NMR (MeOD-d₃) δ5.83–5.70 (m, 1H), 5.30 (dd, J=0.7, 17.0 Hz, 1H), 5.19 (d, J=10.2Hz, 1H), 4.79 (s, 1H), 4.71 (s, 1H), 4.46 (m, 1H), 4.30 (dd, J=7.8, 9.8 Hz, 1H), 3.66 (dd, J=3.7, 9.8 Hz, 1H), 3.03 (m, 1H), 2.56 (m, 1H), 2.40–2.19 (m, 2H), 2.08–1.96 (m, 1H), 2.01 (s, 3H), 1.76 (s, 3H)

(M–H)⁻=265, (M+H)⁺=267

EXAMPLES 131–135

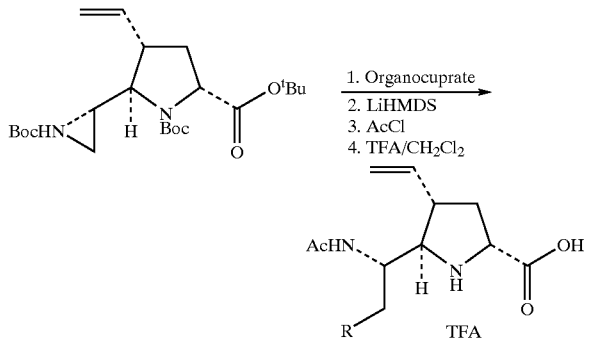

The following title compounds were prepared in 4 steps according to the methods described in Example 130 the denoted reagents for step 1 and their respective methods of preparation are substituted in place of isopropenyl cuprate and its preparation in 130B

EXAMPLE 131

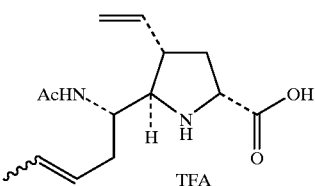

TFA (±)-(2R,3S,5R,1'S)-2(1-Acetamido-1-(cis and trans)-propen-1-yl)ethyl-3-vinyl-pyrrolidine-5-carboxylic Acid Trifluoroacetic Acid Salt The organocuprate reagent was prepared from a Grignard reagent and a catalytic quantity of copper(I) bromide-dimethyl sulfide complex according to the methods described in Example 130B, substituting 0.5M 1-propenylmagnesium bromide (mixture of cis and trans isomers) for 0.5M isopropenylmagnesium bromide.

¹H NMR (MeOD-d₃) (2:1 trans:cis ratio) δ5.81–5.54 (m, 2H), 5.43–5.30 (m, 1H), 5.33–5.27 (m, 0.33H, cis isomer), 5.31–5.25 (m, 0.66H, trans isomer), 5.20–5.15 (m, 1H), 4.26–4.17 (m, 2H), 3.65 (dd, J=3.4, 9.8 Hz, 1H), 2.98 (m, 1H), 2.58–2.48 (m, 1H), 2.45–2.19 (m, 2H), 2.08–1.94 (m, 1H), 2.02 (s, 3H), 1.68 (m, 2H, trans isomer), 1.63 (m, 1H, cis isomer)

(M–H)⁻=265, (M+H)⁺=267

EXAMPLE 132

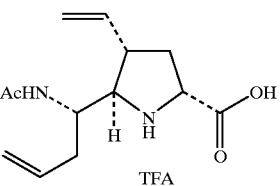

TFA (±)-(2R,3S,5R,1'S)-2-(1-Acetamido-2-allyl)methyl-3-vinyl-pyrrolidine-5-carboxylic Acid Trifluoroacetic Acid Salt The organocuprate reagent was prepared from a Grignard reagent and a catalytic quantity of copper(I) bromide-dimethyl sulfide complex according to the methods described in Example 130B, substituting 1M vinylmagnesium bromide for 0.5M isopropenylmagnesium bromide.

¹H NMR (MeOD-d₃) δ5.83–5.70 (m, 2H), 5.28 (d, J=17.0 Hz, 1H), 5.19–5.13 (m, 3H), 4.28 (m,1H), 4.19 (dd, J=8.5, 9.1 Hz, 1H), 3.66 (dd, J=3.4, 9.5 Hz, 1H), 2.99 (m, 1H), 2.57–2.48 (m, 1H), 2.44–2.26 (m, 2H), 2.05–1.93 (m, 1H), 2.01 (s, 3H)

(M+H)⁺=253

EXAMPLE 133

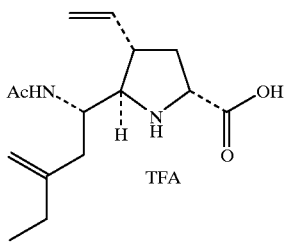

(±)-(2R,3S,5R,1'S)-2-(1-Acetamido)-2-(1-buten-2-yl)ethyl-3-vinyl-pyrrolidine-5-carboxylic Acid Trifluoroacetic Acid Salt The organocuprate reagent was prepared from a Grignard reagent and a catalytic quantity of copper(I) bromide-dimethyl sulfide complex according to the methods described in Example 130B, substituting 0.5M 1-buten-2-ylmagnesium bromide for 0.5M isopropenylmagnesium bromide.

$^1$H NMR (MeOD-d$_3$) δ5.81–5.73 (m, 1H), 5.30 (d, J=17.1 Hz, 1H), 5.19 (d, J=10.0 Hz, 1H), 4.93 (s, 1H), 4.83 (s, 1H), 4.45 (m, 1H), 4.31 (dd, J=7.6, 9.8 Hz, 1H), 3.69 (dd, J=3.2, 9.8 Hz, 1H), 3.03 (m, 1H), 2.59–2.53 (m, 1H), 2.38 (dd, J=5.9, 14.9 Hz, 1H), 2.30 (dd, J=9.5, 14.9 Hz, 1H), 2.07 (q, J=7.6 Hz, 2H), 2.05–1.99 (m, 1H), 2.01 (s, 3H), 1.05 (t, J=7.6 Hz, 3H)

(M+H)$^+$=281

EXAMPLE 134

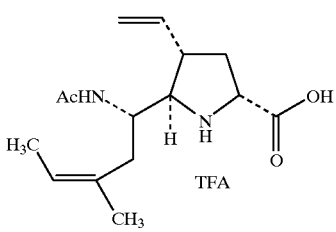

(±)-(2R,3S,5R,1'S)-2-(1-Acetamido-2-(trans-2-buten-2-yl)ethyl-3-vinyl-pyrrolidine-5-carboxylic Acid Trifluoroacetic Acid Salt The organocuprate reagent was prepared from a Grignard reagent and a catalytic quantity of copper(I) bromide-dimethyl sulfide complex according to the methods described in Example 130B, substituting 0.5M 1-methyl-1-propenylmagnesium bromide for 0.5M isopropenylmagnesium bromide.

$^1$H NMR (MeOD-d$_3$) δ5.83–5.71 (m, 1H), 5.41 (q, J=6.8 Hz, 1H), 5.31 (d, J=17.3 Hz, 1H), 5.19 (d, J=10.2 Hz, 1H), 4.42 (m, 1H), 4.31 (dd, J=7.5, 9.8 Hz, 1H), 3.61 (dd, J=4.0, 9.8 Hz, 1H), 3.01 (m, 1H), 2.62–2.52 (m, 1H), 2.46 (dd, J=9.5, 13.9 Hz, 1H), 2.26 (dd, J=5.8, 13.9 Hz, 1H), 2.09–1.99 (m, 1H), 2.00 (s, 3H), 1.72 (s, 3H), 1.59 (d, J=6.8 Hz, 3H)

(M+H)$^+$=281

EXAMPLE 135

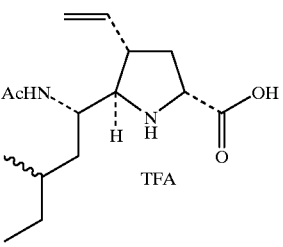

(±)-(2R,3S,5R,1'S,3'RS)-2-(1-Acetamido-3-methyl)pentyl-3-vinyl-pyrrolidine-5-carboxylic Acid Trifluoroacetic Acid Salt The organocuprate reagent was prepared from a Grignard reagent and a catalytic quantity of copper(I) bromide-dimethyl sulfide complex according to the methods described in Example 130B, substituting 2M sec-butylmagnesium bromide for 0.5M isopropenylmagnesium bromide.

$^1$H NMR (MeOD-d$_3$) (1:1 mixture of methyl isomers) δ5.82–5.69 (m, 1H), 5.27 (d, J=17.0 Hz, 0.5H), 5.25 (d, J=17.0 Hz, 0.5H), 5.15 (d, J=10.2 Hz, 1H), 4.33 (m, 1H), 4.18 (dd, J=2.7, 7.5 Hz, 0.5H), 4.15 (dd, J=3.0, 7.8 Hz, 0.5H), 3.62 (dd, J=3.1, 9.8 Hz, 0.5H), 3.57 (dd, J=4.07, 9.8 Hz, 0.5H), 2.97 (m, 1H), 2.57–2.47 (m, 1H), 2.03–1.92 (m, 1H), 2.03 (m, 1.5H), 2.02 (s, 1.5H), 1.72–1.06 (m, 5H), 0.95–0.86 (m, 6H)

(M+H)$^+$=283

EXAMPLE 136

(±)-(2R,3S,5R,1'RS)-2-(1-Acetamido-1-(N-methyl-N-benzylcarbamoyl)methyl-3-vinyl-pyrrolidine-5-carboxylic Acid Trifluoroacetic Acid Salt

136A (±)-(2R,3S,5R,1'R)-1-t-Butoxycarbonyl-2-(1-acetamido-1-carboxyl)methyl-3-vinyl-pyrrolidine-5-carboxylic Acid t-Butyl Ester The title compound was prepared according to the method of Example 2B substituting (±)-(2R,3S,5R,1'R)-1-t-butoxycarbonyl-2-(1-acetamido-1-formyl)methyl-3-vinyl-pyrrolidine-5-carboxylic acid t-butyl ester for (±)-(2R,3R,5R,1'S) -1-benzyl-2-(1-acetamido-3-ethyl)pentyl-3-formyl-pyrrolidine-5-carboxylic acid t-butyl ester.

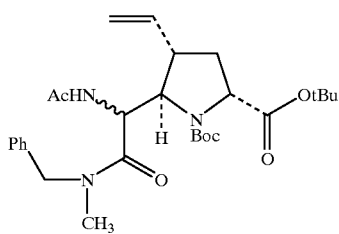

136B (±)-(2R,3S,5R,1'RS)-1-t-Butoxycarbonyl-2-(1-acetamido-2-(N-methyl-N-benzylcarbamoyl)methyl-3-vinyl-pyrrolidine-5-carboxylic Acid t-Butyl Ester

(±)-(2R,3S,5R,1'R)-1-t-Butoxycarbonyl-2-(1-acetamido-1-carboxyl)methyl-3-vinyl-pyrrolidine-5-carboxylic acid t-butyl ester (36 mg, 0.09 mmole) was reacted with N-methyl-N-benzylamine (32 mg, 0.26 mmole), dimethylaminopyridine (1 mg, 0.008 mmole) and 1-(3-dimethylaminopropyl)-3-ethylcarbodiimide hydrochloride (30mg, 0.16mmole) in DMF (3 mL) at 25° C. for 16 hours. The reaction was quenched with water (3 mL) and diluted with ethyl acetate (20 mL). The organic layer was washed with water, and brine, dried over MgSO$_4$, filtered and concentrated in vacuo. The residue was purified by chromatography on silica gel using 50% ethyl acetate/hexanes to provide the title compound.

MS: (M+H)$^+$=516, (M−H)$^-$514

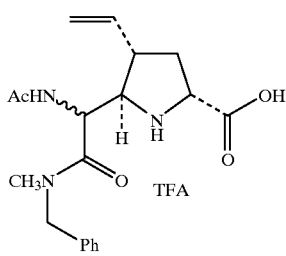

136C (±)-(2R,3S,5R,1'RS)-2-(1-Acetamido-1-(N-methyl-N-benzylcarbamoyl)methyl-3-vinyl-pyrrolidine-5-carboxylic Acid Trifluoroacetic Acid Salt

The title compound was prepared according to the method described in Example 41C, substituting (±)-(2R,3S,5R,1'RS)-1-t-butoxycarbonyl-2-(1-acetamido-2-(N-methyl-N-benzylcarbamoyl)methyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 7 mg, 95%).

$^1$H NMR (DMSO-d$_6$) δ8.52( d, J=9.7 HZ, 1H), 7.30( m, 5H), 5.65( m, 1H), 5.12(m, 4H), 4.62(m, 1H), 4.40(m, 2H), 3.70(m, 1H), 2.90(s, 3H), 2.20(m, 2H), 1.96(s, 3H),

MS: (M+H)$^+$360, (M+23)$^+$382

EXAMPLE 138

(±)-(2R,3S,5R,1'R)-2-(1-Acetamido-2-(N-phenyl-carbonyloxy)ethyl-3-vinyl-pyrrolidine-5-carboxylic Acid Trifluoroacetic Acid Salt

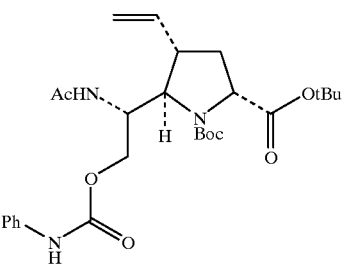

138A (±)-(2R,3S,5R,1'R)-1-t-Butoxycarbonyl-2-(1-acetamido-2-N-phenyl-carbonyloxy)ethyl-3-vinyl-pyrrolidine-5-carboxylic Acid t-Butyl Ester

(±)-(2R,3S,5R,1'R)-1-t-Butoxycarbonyl-2-(1-acetamido-2-hydroxy)ethyl-3-vinyl-pyrrolidine-5-carboxylic acid t-butyl ester (18 mg, 0.045 mmole) was reacted with phenylisocyanate (16 mg, 0.14 mmole) and pyridine(0.1 ml) in THF (3 mL) at 25° C. for 16 hours. The reaction was quenched with water (2 mL) and diluted with ethyl acetate (10 mL). The organic layer was washed with water, and brine, dried over MgSO$_4$, filtered and concentrated in vacuo. The residue was purified by chromatography on silica gel using 50% ethyl acetate/hexanes to provide the title compound (yield;7.5 mg, 33%).

MS: (M+H)$^+$=518, (M−H)$^-$516

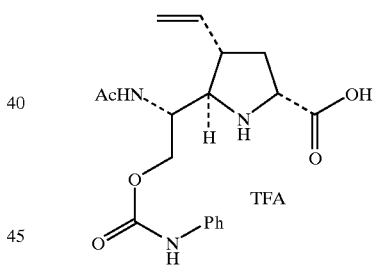

138B (±)-(2R,3S,5R,1 R)-2-(1-Acetamido-1-(N-phenylcarbonyloxy)ethyl-3-vinyl-pyrrolidine-5-carboxylic Acid Trifluoroacetic Acid Salt

The title compound was prepared according to the method described in Example 41C, substituting (±)-(2R,3S,5R,1'R)-1-t-butoxycarbonyl-2-(1-acetamido-2-N-phenyl-carbonyloxy)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4 mg, 95%).

$^1$H NMR (DMSO-d$_6$) d 8.36( d, J=9.7 HZ, 1H), 7.30(m, 5H), 5.78(m, 1H), 5.22(m, 1H), 5.10(m, 1H), 4.58(m, 1H), 4.45(m, 1H), 4.14(2H), 3.58(m, 1H), 2.88( m, 1H), 2.27(m, 1H), 2.12 (m, 1H), 1.88(s, 3H)

MS: (M+H)$^+$=362, (M+23)$^+$=384, (M−H)$^-$=360, (M+35)$^-$396

EXAMPLE 139

(±)-(2R,3S,5R,1'R)-2-(1-Acetamido-1-isobutyryloxy)ethyl-3-vinyl-pyrrolidine-5-carboxylic Acid Trifluoroacetic Acid Salt

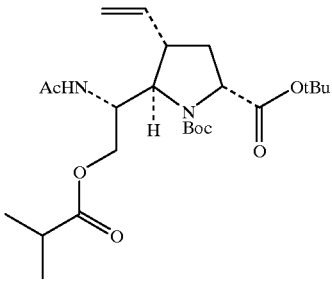

139A (±)-(2R,3S,5R,1'R)-1-t-Butoxycarbonyl-2-(1-acetamido-2-isobutyryloxy)ethyl-3-vinyl-pyrrolidine-5-carboxylic Acid t-Butyl Ester (±)-(2R,3S,5R,1'R)-1-t-Butoxycarbonyl-2-(1-acetamido-2-hydroxy)ethyl-3-vinyl-pyrrolidine-5-carboxylic acid t-butyl ester (15 mg, 0.04 mmole) was reacted with isobutyryl chloride (8 mg, 0.08 mmole) and triethylamine (8 mg, 0.08 mmole) in dichloromethane (4 mL) at 0° C. for 2 hours. The reaction was quenched with water (3 mL) and diluted with ethyl acetate (20 mL). The organic layer was washed with water, and brine, dried over MgSO$_4$, filtered and concentrated in vacuo. The residue was purified by chromatography on silica gel using 30% ethyl acetate/hexanes to provide the title compound (yield: 11 mg, 63%).

MS: (M+H)$^+$=469, (M−H)$^−$467

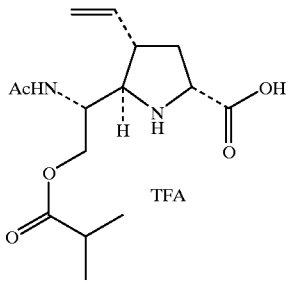

139B (±)-(2R,3S,5R,1'R)-2-(1-Acetamido-1-isobutyryloxy)ethyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-acetamido-2-isobutyryloxy)ethyl-3-vinyl-pyrrolidine-5-carboxylic acid t-butyl ester in place of (±)-(2R,3S,5R,1'S,2'S)-1-t-butoxycarbonyl-2-(1-acetamido-2-hydroxy)butyl-3-(cis-propen-1-yl)-pyrrolidine-5-carboxylic acid t-butyl ester (yield: 6.0 mg, 96%).

$^1$H NMR (DMSO-d$_6$) δ8.00 ( d, J=9.9 HZ, 1H), 5.63(m, 1H), 5.08(m, 1H), 4.98(m, 1H), 4.35(m, 1H), 4.25(m, 1H), 4.08(m, 1H), 3.55(m, 1H), 3.45(m, 1H), 3.38(m, 1H), 2.83 (m, 1H), 2.33(m, 1H), 1.78(s, 3H)

MS: (M+H)$^+$=243, (M+23)$^+$=265, (M−H)$^−$241

EXAMPLE 140

(±)-(2R,3S,5R,1'R)-2-(1-Acetamido-2-N-ethyl-thiocarbonyloxy)ethyl-3-vinyl-pyrrolidine-5-carboxylic Acid Trifluoroacetic Acid Salt

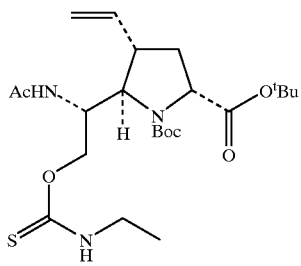

140A (±)-(2R,3S,5R,1'R)-1-t-Butoxycarbonyl-2-(1-Acetamido-2-N-ethyl-thiocarbonyloxy)ethyl-3-vinyl-pyrrolidine-5-carboxylic Acid t-Butyl Ester (±)-(2R,3S,5R,1'R)-1-t-Butoxycarbonyl-2-(1-acetamido-2-hydroxy)ethyl-3-vinyl-pyrrolidine-5-carboxylic acid t-butyl ester (17 mg, 0.04 mmole) was reacted with ethyl-isothiocyanate (19 mg, 0.21 mmole) in pyridine (2 mL) at 70° C. for 17 hours. The reaction was quenched with water (3 mL) and diluted with ethyl acetate (20 mL). The organic layer was washed with water, and brine, dried over MgSO$_4$, filtered and concentrated in vacuo. The residue was purified by chromatography on silica gel using 70% ethyl acetate/hexanes to provide the title compound (yield: 10 mg, 48%).

MS: (M+H)$^+$=486, (M+23)$^+$=508, (M−H)$^−$=485

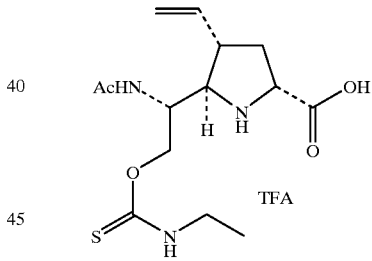

140B (±)-(2R,3S,5R,1'R)-2-(1-Acetamido-2-N-ethyl-thiocarbonyloxy)ethyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-acetamido-2-N-ethyl-thiocarbonyloxy)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 7 mg, 94%).

$^1$H NMR (DMSO-d$_6$) δ8.30 (d, J=9.7 HZ, 1H), 5.78 (m, 1H), 5.25(m, 1H), 5.12(m, 1H), 4.50(m, 1H), 4.33(m, 1H), 4.18(m, 2H), 3.72(m, 1H),3.55 (m, 2H), 2.30 (m, 1H), 2.10(m, 1H), 1.82(m, 3H), 1.17 (m, 3H)

MS: (M+H)$^+$=330, (M−H)$^−$=328

EXAMPLE 141

(±)-(2R,3S,5R,1'S)-2-(1-Acetamido-2-amino)ethyl-3-vinyl-pyrrolidine-5-carboxylic Acid Hydrochloride Salt

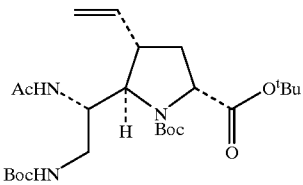

141A (±)-(2R,3S,5R,1'S)-1-t-Butoxycarbonyl-2-(1-acetamido-2-t-butoxycarbonylamino)ethyl-3-vinyl-pyrrolidine-5-carboxylic Acid t-Butyl Ester (±)-(2R,3S,5R,1'S)-1-t-Butoxycarbonyl-2-(1-acetamido-2-azido)ethyl-3-vinyl-pyrrolidine-5-carboxylic acid t-butyl ester (9.5 mg, 0.022 mmole) was reacted with triphenylphosphine (23.5 mg, 0.090 mmole) in ethanol (180 μL) and water (45 μL) at 70° C. for 30 minutes. The reaction mixture was concentrated in vacuo. The residue was dissolved in dichloromethane (220 μL) and to it was added di-tert-butyl dicarbonate (7.3 mg, 0.034 mmol) and N,N-diisopropylethylamine (11.7 mL, 0.067 mmol) at 25° C. After 1 hour the reaction mixture was diluted with water and extracted with ethyl acetate. The organic layers were combined, washed with brine, dried over $MgSO_4$, and concentrated in vacuo. The residue was purified by chromatography on silica gel using 100% dichloromethane to 50% dichloromethane/ethyl acetate to provide the title compound (yield 7.5 mg, 67%).

$^1$H NMR (DMSO-$d_6$)(rotamers) δ7.51(d, J=10.5 Hz, 1H), 6.80–6.66(m, 1H), 5.90–5.76(m, 1H), 5.02–4.90(m, 2H), 4.38–4.19(m, 1H), 3.98–3.94(m, 1H), 3.62–3.62(m, 1H), 3.09–2.73(m, 2H), 2.6–2.42(m, 1H), 1.80 (s, 3H), 1.72–1.62 (m, 1H), 1.42–1.34(m, 27H).

MS: $(M+H)^+$=498, $(M+Na)^+$=520, $(M-H)^-$=496, $(M+Cl)^-$=532

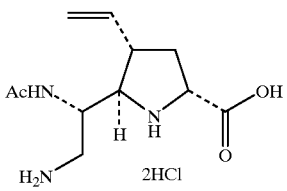

141B (±)-(2R,3S,5R,1'S)-2-(1-Acetamido-2-amino) ethyl-3-vinyl-pyrrolidine-5-carboxylic Acid DiHydrochloride The title compound was prepared according to the method described in Example 1K, substituting (±)-(2R,3S,5R,1'S)-1-t-butoxycarbonyl-2-(1-acetamido-2-t-butoxycarbonylamino)ethyl-3-vinyl-pyrrolidine-5-carboxylic acid t-butyl ester in place of (+)(2R,3R,5R,1'S)-2-(1-acetamido-3-ethyl)pentyl-3-methoxymethyl-pyrrolidine-5-carboxylic acid t-butyl ester (yield: 3.65 mg, 99%).

$^1$H NMR (DMSO-$d_6$) δ8.24(d, J=7.9 Hz, 1H), 5.75–5.68 (m, 1H), 5.16 (d, J=17.1 Hz, 1H), 5.06(d, J=10.4 Hz, 1H), 4.37–4.27(m, 2H), 3.60–3.16(m, 2H), 3.00–2.88(m, 2H), 2.46–2.36(m, 1H), 1.91–1.81(m, 1H), 1.86(s, 3H).

MS: $(M+H)^+$=242, $(M+Na)^+$=264, $(M-H)^-$=240, $(2M-H)^-$=481

EXAMPLE 142

(±)-(2R,3S,5R,1'S)-2-(1-Acetamido-2-acetamido) ethyl-3-vinyl-pyrrolidine-5-carboxylic Acid Hydrochloride

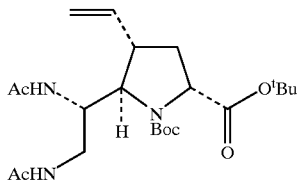

142A (±)-(2R,3S,5R,1'S)-1-t-Butoxycarbonyl-2-(1-acetamido-2-acetamido)ethyl-3-vinyl-pyrrolidine-5-carboxylic Acid t-Butyl Ester (±)-(2R,3S,5R,1'S)-1-t-Butoxycarbonyl-2-(1-acetamido-2-amino)ethyl-3-vinyl-pyrrolidine-5-carboxylic acid t-butyl ester (9.4 mg, 0.024 mmole) was reacted with acetic anhydride (11.2 μL) and triethylamine (33.1 μL) in dichloromethane (0.23 mL) at 0° C. for 1 hour. The reaction was diluted with water (3 mL), extracted with ethyl acetate (12 mL), washed with brine, dried over $MgSO_4$, and concentrated in vacuo. The residue was purified by chromatography on silica gel using 100% ethyl acetate to 90% ethyl acetate/methanol to provide the title compound (yield: 6.8mg, 66%).

$^1$H NMR (DMSO-$d_6$) (rotamers) δ7.79–7.74 (m, 1H), 7.54 (d, J=9.8 Hz, 1H), 5.97–5.81 (m, 1H), 5.01–4.91(m, 2H), 4.36–4.27(m, 1H), 3.97–3.90(m, 1H), 3.68–3.63(m, 1H), 3.21–3.15(m, 1H), 3.10–2.76(m, 1H), 2.88–2.78(m, 1H), 2.58–2.45(m, 1H), 1.81(m, 3H), 1.78(m, 3H), 1.76–1.64(m, 1H), 1.42–1.36(m, 18H).

MS: $(M+H)^+$=439, $(M+Na)^+$=462, $(M-H)^-$=438, $(M+35)^-$=474

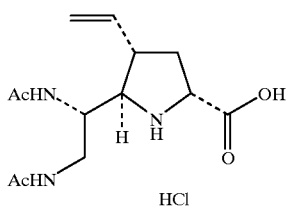

142B (±)-(2R,3S,5R,1'S)-2-(1-Acetamido-2-acetamido)ethyl-3-vinyl-pyrrolidine-5-carboxylic Acid Hydrochloride The title compound was prepared according to the method described in Example 1K, substituting (±)-(2R,3S,5R,1'S)-2-(1,2-di-acetamido)butyl-3-vinyl-pyrrolidine-5-carboxylic acid Hydrochloridesalt in place of (±)(2R,3R,5R,1'S)-2-(1-acetamido-3-ethyl)pentyl-3-methoxymethyl-pyrrolidine-5-carboxylic acid t-butyl ester (yield: 3.30 mg, 80%).

MS: $(M+H)^+$=284, $(M-H)^-$=282, $(M+Cl)^-$=318

EXAMPLE 143

(±)-(2R,3S,5R,1'S)-2-(1-Acetamido-2-azido)ethyl-3-vinyl-pyrrolidine-5-carboxylic Acid Hydrochloride

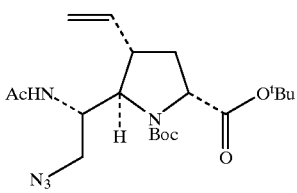

143A (±)-(2R,3S,5R,1'S)-1-t-Butoxycarbonyl-2-(1-N-acetamido-2-azido)ethyl-3-vinyl-pyrrolidine-5-carboxylic Acid t-Butyl Ester (±)-(2R,3S,5R,1'S))-1-t-Butoxycarbonyl-2-(N-acetylaziridinyl)-3-vinyl-pyrrolidine-5-carboxylic acid t-butyl ester (21.6 mg, 0.064 mmole) was reacted with sodium azide (41.6 mg, 0.64 mmole) and ammonium chloride (34.2 mg, 0.64 mmol) in ethanol (270 μL) and water (30 μL) at 75° C. for 1 hour. The ethanol was then removed in vacuo and the remaining aqueous was extracted with ethyl acetate. The combined organics were washed with brine, dried over $MgSO_4$, and concentrated in vacuo (crude yield: 20 mg, 82%). To the crude mixture was added acetic anhydride (31 μL, 0.33 mmol) and triethylamine (92 μL, 0.66 mmol) in dichloromethane (330 μL) at 0° C. for 30 minutes. The reaction mixture was then concentrated in vacuo. The residue was purified by chromatography on silica gel using 100% dichloromethane to 50% dichloromethane/ethyl acetate to provide the title compound (yield: 10 mg, 60%).

$^1$H NMR (DMSO-$d_6$)(rotamers) δ7.85 and 7.81(d, J=9.5 Hz and 9.8 Hz, 1H), 5.94–5.80(m, 1H), 5.04–4.93(m, 2H), 4.58–4.38(m, 1H), 4,04–3.96 (m, 1H), 3.72–3.66(m, 1H), 3.41–3.21(m, 2H), 3.09–2.79(m, 1H), 2.59–2.46(m, 1H), 1.84–1.82(m, 3H), 1.79–1.53(m, 1H), 1.43–1.35(m, 18H).

MS: $(M+H)^+$=424, $(M+Na)^+$=446, $(2M+Na)^+$=869, $(M-H)^-$=422, $(M+Cl)^-$=458

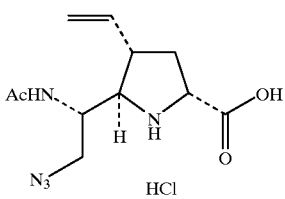

143B (±)-(2R,3S,5R,1'S)-2-(1-Acetamido-2-azido)ethyl-3-vinyl-pyrrolidine-5-carboxylic Acid Hydrochloric Salt The title compound was prepared according to the method described in Example 1K, substituting (±)-(2R,3S,5R,1'S)-1-t-butoxycarbonyl-2-(1-acetamido-2-azido)ethyl-3-vinyl-pyrrolidine-5-carboxylic acid t-butyl ester in place of (±) (2R,3R,5R,1'S)-2-(1-acetamido-3-ethyl)pentyl-3-methoxymethyl-pyrrolidine-5-carboxylic acid t-butyl ester (yield: 2.94 mg, 93%).

$^1$H NMR (DMSO-$d_6$) δ8.24(d, J=8.55 Hz, 1H), 5.74–5.67 (m, 1H), 5.14(d, J=17.1 Hz, 1H), 5.06(d, J=10.4 Hz, 1H), 4.41–4.35(m, 2H), 3.57–3.36(m, 3H), 2.93–2.90(m, 1H), 2.44–2.38(m, 1H), 1.96–1.84(m, 1H), 1.84 (s, 3H).

MS: $(M+H)^+$=268, $(M-H)^-$=266, $(M+Cl)^-$=302

EXAMPLE 144

(±)-(2R,3S,5R,1'S)-2-(1-Acetamido-2-N-methylamino)ethyl-3-vinyl-pyrrolidine-5-carboxylic Acid Dihydrochloride

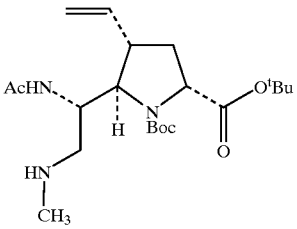

144A (±)-(2R,3S,5R,1'S)-1-t-Butoxycarbonyl-2-(1-N-acetamido-2-N-methylamino)ethyl-3-vinyl-pyrrolidine-5-carboxylic Acid t-Butyl Ester Methylamine (0.016 g, 0.39 mmole) was reacted with N,O-bis-trimethylsilylacetamide (0.079 g, 0.39 mmole) in DMSO (0.8 mL) at 0° C. for 1 hour. (±)-(2R,3S,5R,1'S)-1-t-Butoxycarbonyl-2-(N-acetylaziridinyl)-3-vinyl-pyrrolidine-5-carboxylic acid t-butyl ester (0.040 g, 0.11 mmole) was then reacted with the above reagent N-trimethylsilylmethylamine at 75° C. for 18 hours. The reaction was diluted with ethyl acetate (7 mL) washed with water and brine, dried over magnesium sulfate, filtered and concentrated in vacuo. The residue was purified by chromatography on silica gel using chloroform-methanol-ammonia to provide the title compound (yield: 0.011 g, 25%).

$^1$H NMR (CDCl$_3$) δ5.78–5.98 (m, 1H), 5.90–5.04 (2m, 2H), 4.40–4.55 (brm, 1H), 3.90–4.02 (m, 1H), 3.64–3.75 (2m, 1H), 2.25–2.40 (brm 3H), 2.83,2.85 (2d, 3H), 1.42,1.44 (2m, 9H), 1.34,1.37 (2m, 9H).

Ms: $(M+H)^+$=412

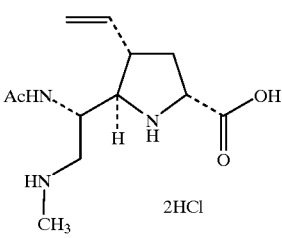

144B (±)-(2R,3S,5R,1'S)-2-(1-Acetamido-2-N-methylamino)ethyl-3-vinyl-pyrrolidine-5-carboxylic Acid Dihydrochloride Salt The title compound was prepared according to the method described in Example 1K, substituting (±)-(2R,3S,5R,1'S)-1-t-butoxycarbonyl-2-(1-acetamido-2-N-methylamino) ethyl-3-vinyl-pyrrolidine-5-carboxylic acid t-butyl ester in place of (±)(2R,3R,5R,1'S)-2-(1-acetamido-3-ethyl)pentyl-3-methoxymethyl-pyrrolidine-5-carboxylic acid t-butyl ester (yield: 7.2 mg, 99%).

$^1$H NMR (DMSO-$d_6$) δ8.25 (d, 1H), 5.70 (m, 1H), 5.10 (m, 2H), 4.50 (m,1H), 4.40 (m, 1H), 2.55 (s, 3H), 1.85 (s, 3H).

MS: $(M+H)^+$=256

EXAMPLES 145–164

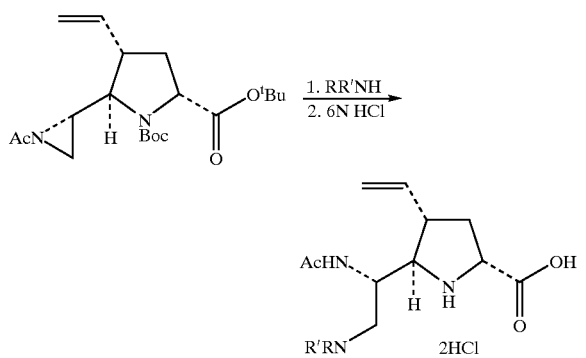

The following title compounds were prepared according to the methods described in Examples 141–144 where R' is equal to hydrogen. Where R or R' are not equal to hydrogen the corresponding amine is used directly without the intermediacy of trimethylsilylation.

EXAMPLE 145

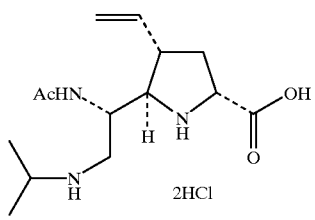

(±)-(2R,3S,5R,1'S)-2-(1-Acetamido-2-N-isopropylamino)ethyl-3-vinyl-pyrrolidine-5-carboxylic Acid Dihydrochloride Salt $^1$H NMR (DMSO-$d_6$) δ8.30 (d, 1H), 5.70 (m, 1H), 5.10 (m, 2H), 4.40 (br, 2H), 3.52–3.68 (br, 1H), 3.10–3.20 (br, 1H), 2.82–2.97 (br, 1H), 2.37–2.47 (br, 1H) 1.88 (s, 3H), 1.25 (d, 6H).
MS: (M+H)$^+$=284

EXAMPLE 146

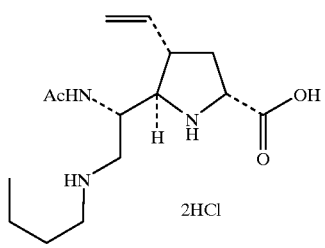

(±)-(2R,3S,5R,1'S)-2-(1-Acetamido-2-N-butylamino)ethyl-3-vinyl-pyrrolidine-5-carboxylic Acid Dihydrochloride Salt $^1$H NMR (DMSO-$d_6$) δ8.25 (d, 1H), 5.70 (m, 1H), 5.10 (m, 2H), 4.50 (m, 1H), 4.38 (m, 1H), 3.60 (m, 1H), 2.90 (m, 3H), 2.40 (m, 2H), 1.87 (s, 3H), 1.62 (m, 2H), 1.33 (m, 2H), 0.90 (t, 3H).
MS: (M+H)$^+$=298

EXAMPLE 147

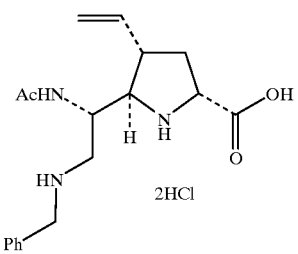

(±)-(2R,3S,5R,1'S)-2-(1-Acetamido-2-N-benzylamino)ethyl-3-vinyl-pyrrolidine-5-carboxylic Acid Hydrochloride Salt $^1$H NMR (DMSO-$d_6$) δ7.56–7.43 (m, 5H), 5.74–5.67 (m, 1H), 5.15–4.99(m, 2H), 4.56(m, 1H), 4.27–3.93(m, 3H), 3.66–3.15(m, 3H), 2.91–2.88(m, 1H), 2.64–2.34(m, 2H), 1.86(m, 3H).
MS: (M+H)$^+$=332, (M+Na)$^+$=354, (M–H)$^-$=330, (2M–H)$^-$=661

EXAMPLE 148

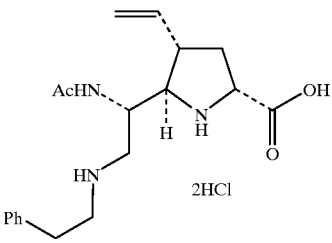

(±)-(2R,3S,5R,1'S)-2-(1-Acetamido-2-N-phenethylamino)ethyl-3-vinyl-pyrrolidine-5-carboxylic Acid Dihydrochloride Salt $^1$H NMR (DMSO-$d_6$) δ8.25 (d, 1H), 7.30 (m, 5H), 5.70 (m, 1H), 5.10 (m, 2H), 4.50 (br, 1H), 4.35 (br, 1H), 3.61 (m, H), 3.17 (m, 3H), 2.98 (m, 3H), 2.42 (m, 1H), 1.88 (m, 3H).
MS: (M+H)$^+$=346

EXAMPLE 149

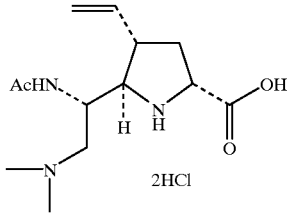

(±)-(2R,3S,5R,1'S)-2-(1-Acetamido-2-N,N-dimethylamino)ethyl-3-vinyl-pyrrolidine-5-carboxylic Acid Dihydrochloride Salt $^1$H NMR (DMSO-$d_6$) δ8.34 (d, J=9.2 Hz, 1H), 5.74–5.67 (m, 1H), 5.12(d, J=17.1 Hz, 1H), 5.04(d, J=10.4 Hz, 1H), 4.67–4.62(m, 1H), 4.40(dd, J=73, 10.4 Hz, 1H), 3.60–3.11

(m, 3H), 2.96–2.83(m, 1H), 2.50(m, 6H), 2.44–2.38(m, 1H), 1.94 –1.84(m, 1H), 1.84(m, 3H).

MS: (M+H)⁺=270, (M+Na)⁺=292, (M−H)⁻=268.

EXAMPLE 150

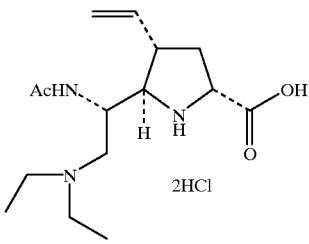

(±)-(2R,3S,5R,1′S)-2-(1-Acetamido-2-N,N-diethylamino)ethyl-3-vinyl-pyrrolidine-5-carboxylic Acid Dihydrochloride Salt ¹H NMR (DMSO-d₆) δ8.23 (d, 1H), 5.70 (m, 1H), 5.10 (m, 2H), 4.60 (br, 1H), 4.40 (br, 1H), 3.12 (m, 4H), 2.88 (m, 1H), 2.42 (m, 1H), 1.85 (m, 3H), 122 (t, 3H).

MS: (M+H)⁺=298

EXAMPLE 151

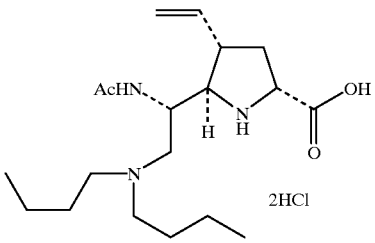

(±)-(2R,3S,5R,1′S)-2-(1-Acetamido-2-N,N-dibutylamino)ethyl-3-vinyl-pyrrolidine-5-carboxylic Acid Dihydrochloride Salt ¹H NMR (DMSO-d₆) δ8.24 (d, 1H), 5.70 (m, 1H), 5.08 (m, 2H), 4.48–4.62 (br, 1H), 4.28–4.43 (1H), 3.05 (m, 4H), 2.77–2.92 (br, 1H), 2.34–2.46 (br, 2H), 1.84 (s, 3H), 1.64 (m, 4H), 1.30 (m, 4H), 0.93 (t, 6H).

MS: (M+H)⁺=354

EXAMPLE 152

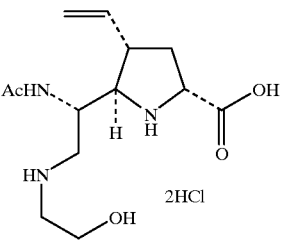

(±)-(2R,3S,5R,1′S)-2-(1-Acetamido-2-(N-2-hydroxyethylamino))ethyl-3-vinyl-pyrrolidine-5-carboxylic Acid Dihydrochloride Salt ¹H NMR (DMSO-d₆) δ8.20 (d, 1H), 5.70 (m, 1H), 5.15 (d, 1H), 5.08 (d, 1H), 4.50 (brm, 1H), 4.38 (brm, 1H), 3.68 (M, 1H), 3.0 (brm, 2H), 2.90 (m, 1H), 2.41 (m, 1H), 1.85 (s, 3H).

MS: (M+H)⁺=286

EXAMPLE 153

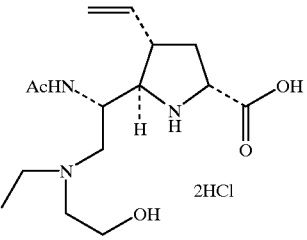

(±)-(2R,3S,5R,1S)-2-(1-Acetamido-2-(N-2-hydroxyethyl-N-ethylamino))ethyl-3-vinyl-pyrrolidine-5-carboxylic Acid Dihydrochloride Salt ¹H NMR (DMSO-d₆) δ5.81–5.74(m, 1H), 5.38(d, J=17.1 Hz, 1H), 5.22(d, J=10.0 Hz, 1H), 4.92–4.88(m, 1H), 4.48 (dd, J=7.6, 9.8 Hz, 1H), 3.91(t, J=4.9 Hz, 2H), 3.85(dd, J=5.6, 10.0 Hz, 1H), 3.63–3.53(m, 2H), 3.46–3.39(m, 4H), 3.16–3.13(m, 1H), 2.66–2.61(m, 1H), 2.08(m, 3H), 2.06–2.01(m, 1H), 1.38(t, J=7.33, 3H).

MS: (M+H)⁺=314, (M+Na)⁺=336, (M−H)⁻=312, (M+Cl)⁻=348, (2M−H)⁻=625

EXAMPLE 154

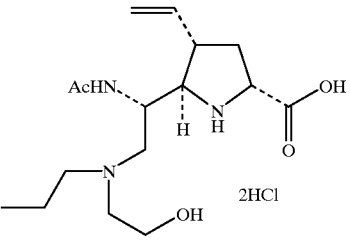

(±)-(2R,3S,5R,1′S)-2-(1-Acetamido-2-(N-2-hydroxyethyl-N-propylamino))ethyl-3-vinyl-pyrrolidine-5-carboxylic Acid Dihydrochloride Salt ¹H NMR (DMSO-d₆) δ8.36(d, J=8.5 Hz, 1H), 5.75–5.68 (m, 1H), 5.13(d, J=17.1 Hz, 1H), 5.04(d, J=10.4 Hz, 1H), 4.62(m, 1H), 4.36(m, 1H), 3.77(t, J=4.9 Hz, 2H), 3.63–3.59 (m, 1H), 3.50–3.23(m, 3H), 3.22–3.19(m, 2H), 3.08(t, J=7.3 Hz, 2H), 2.91–2.87(m, 1H), 2.44–2.39(m, 1H), 1.99–1.88 (m, 1H), 1.84(s, 3H), 1.75–1.70 (m, 2H), 0.90(t, J=6.7 Hz, 3H).

MS: (M+H)⁺=328, (M+Na)⁺=350, (M−H)⁻=326, (M+Cl)⁻=362, (2M−H)⁻=653

EXAMPLE 155

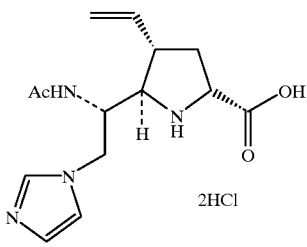

2HCl (±)-(2R,3S,5R,1'S)-2-(1-Acetamido-2-(imidazol-1-yl))ethyl-3-vinyl-pyrrolidine-5-carboxylic Acid DiHydrochloride $^1$H NMR (MeOD-d$_3$) δ.9.06(s, 1H), 7.72(s, 1H), 7.58(s, 1H), 5.84–5.76(m, 1H), 5.39(d, J=17.1 Hz, 1H), 5.23(d, J=10.25 Hz, 1H), 4.70–4.66(m, 1H), 4.52– 4.43(m, 2H), 3.92–3.89(m, 1H), 3.20–3.17(m, 1H), 2.67–2.62(m, 1H), 2.11–2.04(m, 1H), 1.95–1.89(m, 1H), 1.91(s, 3H).

MS: (M+H)$^+$=293, (M–H)$^-$=291, (M+35)$^+$=327.

EXAMPLE 156

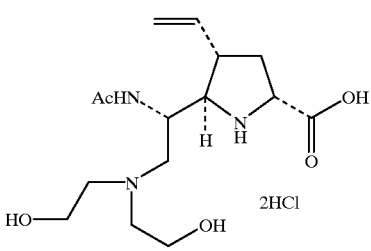

2HCl (±)-(2R,3S,5R,1'S)-2-(1-Acetamido-2-(N,N-di-(2-hydroxyethylamino))ethyl-3-vinyl-pyrrolidine-5-carboxylic Acid Dihydrochloride Salt MS: (M+H)$^+$=330, (M+Na)$^+$=352, (M–H)$^-$=328, (M+Cl)$^-$=364

EXAMPLE 157

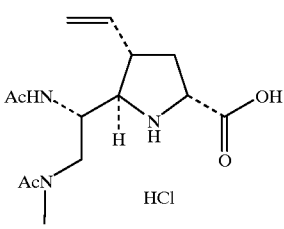

HCl (±)-(2R,3S,5R,1'S)-2-(1-Acetamido-2-(N-acetyl-N-methylamino)ethyl-3-vinyl-pyrrolidine-5-carboxylic Acid Hydrochloride Salt $^1$H NMR (DMSO-d$_6$) δ8.01,7.95 (2d, 1H), 5.68–5.80 (m,1 H), 5.02–5.22 (m, 2H), 4.30–4.45 (brm, 2H), 3.26,3.21 (2d, 1H), 2.82–2.95 (brm, 1H), 2.38–2.48 (m, 1H), 1.98,2.02 (2s, 3H),1.79,1.82 (2s, 3H).

MS: (M+H)$^+$=298

EXAMPLE 158

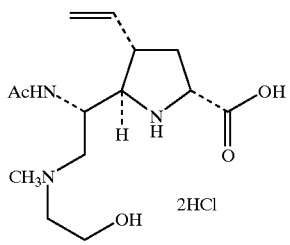

2HCl (±)-(2R,3S,5R,1'S)-2-(1-Acetamido-2-(N-2-hydroxyethyl-N-methylamino))ethyl-3-vinyl-pyrrolidine-5-carboxylic Acid Dihydrochloride Salt $^1$H NMR (DMSO-d$_6$) δ8.35(d, J=9.15 Hz, 1H), 5.74–5.67 (m, 1H), 5.12(d, J=17.1 Hz, 1H), 5.04(d, J=10.4 Hz, 1H), 4.70(m, 1H), 4.39(dd, J=7.3, 10.4 Hz, 1H), 3.80–3.75(m, 3H), 3.61–3.43(m, 3H), 3.23–3.16(m, 2H), 2.91–2.82(m, 1H), 2.82(s, 3H), 2.44–2.39(m, 1H), 1.92–1.84(m, 1H), 1.84(s, 3H).

MS: (M+H)$^+$=300, (M+Na)$^+$=322, (2M+H—H$_2$O)$^+$=581

EXAMPLE 159

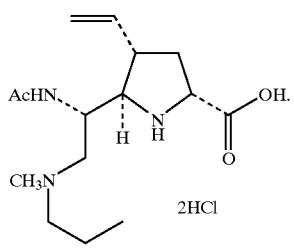

2HCl (±)-(2R,3S,5R,1'S)-2-(1-Acetamido-2-(N-propyl-N-methylamino)ethyl-3-vinyl-pyrrolidine-5-carboxylic Acid Dihydrochloride Salt $^1$H NMR (DMSO-d$_6$) (broad) δ8.3(1H), 5.7(1H), 5.12–5.04(2H), 4.6(1H), 4.35(1H), 2.61–2.35(11H), 1.9 (3H), 1.78–1.63(2H), 1.9(3H).

MS: (M+H)$^+$=298, (M+Na)$^+$=320, (M–H)$^-$=296, (M+Cl)$^-$=332, (2M–H)$^-$=593

EXAMPLE 160

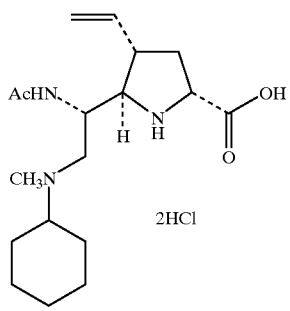

2HCl (±)-(2R,3S,5R,1'S)-2-(1-Acetamido-2-(N-cyclohexyl-N-methylamino))ethyl-3-vinyl-pyrrolidine-5-carboxylic Acid Hydrochloride Salt $^1$H NMR (DMSO-d$_6$) δ8.26(m, 1H), 5.75–5.65(m, 1H), 5.08(d, J=17.1 Hz, 1H), 5.02(d, J=10.3 Hz, 1H), 4.62(m, 1H), 4.43–4.40(m, 1H), 3.62–3.58(m, 3.46–3.16(m, 2H), 2.89–2.84(m, 1H), 2.72(s, 3H), 2.44–2.39(m, 1H), 2.07–1.80(m, 5H), 1.81 (s, 3H), 1.63(m, 1H), 1.45–1.06(m, 6H).

MS: $(M-+H)^+=338$, $(M+Na)^+=360$, $(M-H)^-=336$, $(M+Cl)^-=372$

EXAMPLE 161

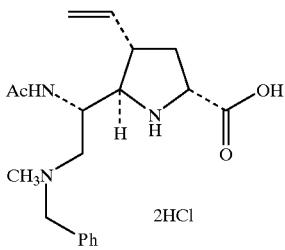

(±)-(2R,3S,5R,1'S)-2-(1-Acetamido-2-(N-benzyl-N-methylamino))ethyl-3-vinyl-pyrrolidine-5-carboxylic Acid Dihydrochloride Salt $^1$H NMR (DMSO-d$_6$) δ8.36(m, 1H), 7.61–7.46(m, 5H), 5.69–5.64(m, 1H), 5.07(d, J=17.1 Hz, 1H), 4.99(d, J=10.1 Hz, 1H), 4.77(m, 1H), 4.44–4.39(m, 2H), 4.25(d, J=12.9, 1H), 3.61(m, 1H), 3.43(m, 1H), 3.22(m, 1H), 2.93–2.85(m, 1H), 2.73(s, 3H), 2.44–2.38(m, 1H), 1.92–1.85(m, 1H), 1.85(s, 3H).

MS: $(M+H)^+=346$

EXAMPLE 162

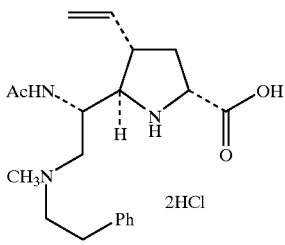

(±)-(2R,3S,5R,1'S)-2-(1-Acetamido-2-(N-phenethyl-N-methylamino))ethyl-3-vinyl-pyrrolidine-5-carboxylic Acid Dihydrochloride Salt $^1$H NMR (DMSO-d$_6$) δ8.34(d, J=8.55 Hz, 1H), 7.37–7.26 (m, 5H), 5.76–5.69(m, 1H), 5.14(d, J=17.1 Hz, 1H), 5.06(d, J=10.4 Hz, 1H), 4.72(m, 1H), 4.46–4.42(m, 1H), 3.83–3.20 (m, 6H), 3.13–2.99(m, 2H), 2.86(s, 3H), 2.95–2.83(m, 1H), 2.46–2.40(m, 1H), 1.95–1.81(m, 1H), 1.86(s, 3H).

MS: $(M-+H)^+=360$

EXAMPLE 163

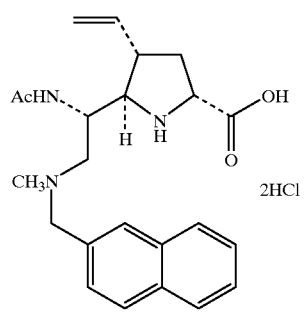

(±)-(2R,3S,5R,1'S)-2-(1-Acetamido-2-(N-naphthylmethyl-N-methylamino))ethyl-3-vinyl-pyrrolidine-5-carboxylic Acid Dihydrochloride Salt $^1$H NMR (DMSO-d$_6$) δ8.41(d, J=7.3 Hz, 1H), 8.32–7.59 (m, 7H), 5.60(m, 1H), 5.04(d, J=17.1 Hz, 1H), 4.91(d, J=9.8 Hz, 1H), 4.97–4.73(m, 3H), 4.39(m, 1H), 3.70–3.13(m, 3H), 2.90(m, 1H), 2.72(s, 3H), 2.43–2.41(m, 1H), 2.01–1.74(m, 1H), 1.87(s, 3H).

MS: $(M+H)^+=395$, $(M+Na)^+=418$, $(M-H)^-=394$, $(M+Cl)^-=430$, $(2M-H)^-=789$

EXAMPLE 164

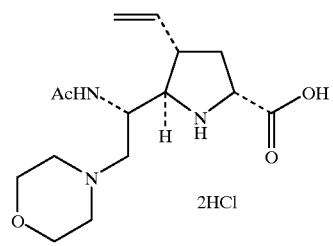

(±)-(2R,3S,5R,1'S)-2-(1-Acetamido-2-(N-morpholinyl))ethyl-3-vinyl-pyrrolidine-5-carboxylic Acid Dihydrochloride Salt $^1$H NMR (DMSO-d$_6$) δ8.28 (d, 1H), 5.75–5.78 (m, 1H), 5.15 (d,1H), 5.05 (d, 1H), 4.65 (brm, 1H), 4.42 (m, 1H), 3.72–3.98 (brm, 3H), 3.62 (m, 1H), 2.90 (m, 1H), 2.38–2.48 (m, 1H), 1.85 (s, 3H).

MS: $(M+H)^+=312$

EXAMPLE 165

(±)-(2R,3S,5R,1'S,3'R)-2-(1-Acetamido-2-(N-methyl-N-t-butylamino-N-oxide))ethyl-3-vinyl-pyrrolidine-5-carboxylic Acid Hydrochloride Salt

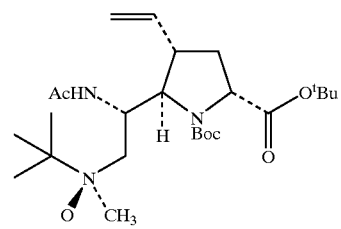

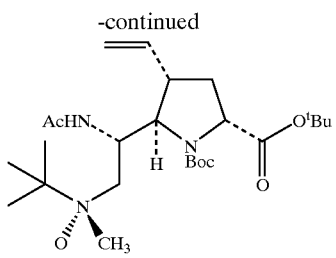

165A (±)-(2R,3S,5R,1'S,3'R) and (±)-(2R,3S,5R,1'S, 3'S)-1-t-Butoxycarbonyl-2-(1-acetamido-2-(N-methyl-N-t-butylamino-N-oxide))ethyl-pyrrolidine-5-carboxylic Acid t-Butyl Ester (±)-(2R,3S,5R,1'S)-1-t-Butoxycarbonyl-2-(1-acetamido-2-(N-methyl-N-t-butylamino))ethyl-3-vinyl-pyrrolidine-5-carboxylic acid t-butyl ester (37 mg, 0.08 mmole) was reacted with the m-chloroperoxybenzoic acid (20 mg, 0.08 mmole) in $CH_2Cl_2$ (0.9 mL) at 0° C. for 1 hour. The reaction was chromatographed directly on silica gel eluting with a gradient of acetone to acetone/30% MeOH to provide the title compounds isomer (±)-(2R,3S,5R,1'S,3'R) (yield: 0.010 g, 27%) and isomer (±)-(2R,3S,5R,1'S,3'R) (yield: 0.011 g, 29%).

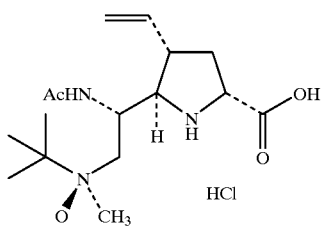

165B (±)-(2R,3S,5R,1'S,3'R)-2-(1-Acetamido-2-(N-methyl-N-t-butylamino-N-oxide))ethyl-3-vinyl-pyrrolidine-5-carboxylic Acid Hydrochloride Salt The title compound was prepared according to the method described in Example 15C substituting (±)-(2R,3S,5R,1'S, 3'R)-1-t-butoxycarbonyl-2-(1-acetamido-2-(N-methyl-N-t-butylamino-N-oxide))ethyl-pyrrolidine-5-carboxylic acid t-butyl ester for (±)-(2R,3S,5R,1'S)-2-(1-acetamido-3-ethyl)pentyl-3-(imidazol-2-yl)-pyrrolidine-5-carboxylic acid t-butyl ester (yield; 6 mg, 80%).

$^1$H NMR ($CD_3OD$) δ5.72–5.87 (m, 1H), 5.40 (d, 1H), 5.20–5.28 (m, 2H), 4.44–4.53 (dd, 1H), 3.73–3.95 (m, 3H), 3.57 (s, 3H), 3.08–3.19 (m, 1H), 2.59–2.72 (m, 1H), 2.05–2.15 (m, 1H), 2.04 (s, 3H), 1.54 (s, 9H).

MS: $(M+H)^+$=328

EXAMPLES 166–178

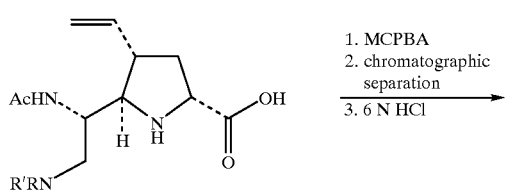

The following title compounds were prepared according to the method described in Example 165.

EXAMPLE 166

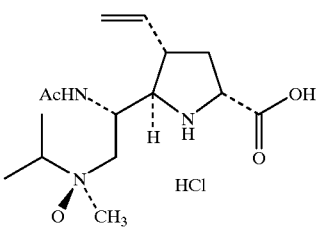

(±)-(2R,3S,5R,1'S,3'R)-2-(1-Acetamido-2-(N-methyl-N-isopropylamino-N-oxide))ethyl-3-vinyl-pyrrolidine-5-carboxylic Acid Hydrochloride Salt $^1$H NMR (MeOD-$d_3$) δ5.87–5.74 (m, 1H), 5.46–5.40 (m, 1H), 5.27–5.23 (m, 1H), 5.21–5.18 (m, 1H), 4.50 (dd, J=8.1, 9.8 Hz, 1H), 4.04–3.87 (m, 4H), 3.54 (s, 3H), 3.20–3.14 (m, 1H), 2.69–2.60 (m, 1H), 2.12–2.01 (m, 1H), 2.05 (s, 3H), 1.50 (d, J=6.4 Hz, 3H), 1.48(d, J=6.4 Hz, 3H).

MS: $(M+H)^+$=314, $(M+Na)^+$=336, $(2M+1)^+$=627, $(2M+Na)^+$=649.

EXAMPLE 167

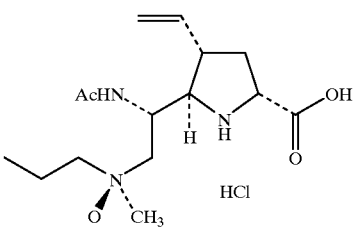

(±)-(2R,3S,5R,1'S,3'S)-2-(1-Acetamido-2-(N-methyl-N-propylamino-N-oxide)ethyl-3-vinyl-pyrrolidine-5-carboxylic Acid HydrochlorideSalt $^1$H NMR (MeOD-$d_3$) δ5.87–5.74 (m, 1H), 5.46–5.40 (m, 1H), 5.27–5.23 (m, 1H), 5.21–5.18 (m, 1H), 4.50 (dd, J=8.1, 9.8 Hz, 1H), 4.04–3.87 (m, 4H), 3.54 (s, 3H), 3.20–3.14 (m, 1H), 2.69–2.60 (m, 1H), 2.12–2.01 (m, 1H), 2.05 (s, 3H), 1.50 (d, J=6.4 Hz, 3H), 1.48(d, J=6.4 Hz, 3H).

MS: $(M+H)^+$=314, $(M+H-H_2O)^-$=295

EXAMPLE 168

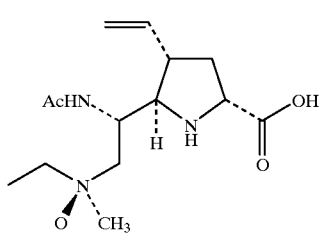

(±)-(2R,3S,5R,1'S,3'S)-2-(1-Acetamido-2-(N-methyl-N-ethylamino-N-oxide))ethyl-3-vinyl-pyrrolidine-5-carboxylic Acid HydrochlorideSalt $^1$H NMR (MeOD-d$_3$) δ5.82–5.75 (m, 1H), 5.44(d, J=17.1 Hz, 1H), 5.26(d, J=10.4 Hz, 1H), 5.14–5.11(m, 1H), 4.48–4.45(m, 1H), 4.9(d, J=4.9 Hz, 2H), 3.87(dd, J=4.9, 10.4 Hz, 1H), 3.76(q, J=6.7 Hz, 2H), 3.54(s, 3H), 3.17–3.09 (m, 1H), 2.68–2.62 (m, 1H), 2.06(s, 3H), 2.09–2.03 (m, 1H), 1.45(t, J=7.3 Hz, 3H).
MS: (M+H)$^+$=300, (M+Na)$^+$=322, (M+H—H$_2$O)$^+$=282

EXAMPLE 169

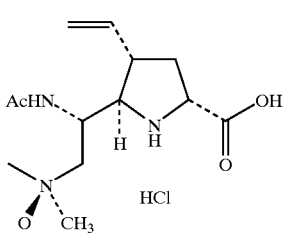

(±)-(2R,3S,5R,1'S)-2-(1-Acetamido-2-(N,N-dimethylamino-N-oxide)ethyl-3-vinyl-pyrrolidine-5-carboxylic Acid Hydrochloride Salt $^1$H NMR (DMSO-d$_6$) δ8.58 (d, 1H), 5.67–5.78 (m, 1H), 5.20 (d, 1H), 5.08 (d, 1H), 4.62–4.78 (brm, 1H), 4.25–4.42 (brm, 1H), 4.06 (d, 1H), 3.85–3.95 (brm, 1H), 3.88–3.98 (brm, 1H), 3.35–3.50 (brs, 6H), 2.36–2.48 (m, 1H), 1.92 (m, 1H), 1.85 (s, 3H).
MS: (M+H)$^+$=286

EXAMPLE 170

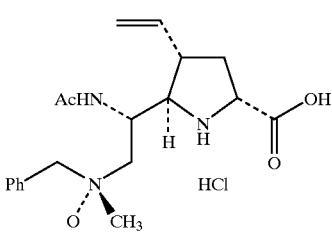

(±)-(2R,3S,5R,1'S,3'S)-2-(1-Acetamido-2-(N-methyl-N-benzylamino-N-oxide))ethyl-3-vinyl-pyrrolidine-5-carboxylic Acid HydrochlorideSalt $^1$H NMR (MeOD-d$_3$) δ7.60–7.47(m, 5H), 5.75–5.65(m, 1H), 5.39(d, J=6.35 Hz, 1H), 5.21(d, J=8.8 Hz, 1H), 5.18–5.11(m, 1H), 5.00–4.70(m, 2H), 4.35–4.27(m, 1H), 4.00–3.94(m, 2H), 3.86–3.79(m, 1H), 3.20(s, 3H), 3.14–3.05(m, 1H), 2.77–2.50(m, 1H), 2.08(s, 3H), 2.10–2.94(m, 1H).

MS: (M+H)$^+$=362, (M+Na)$^+$=385, (M–H)$^-$=360, (M+35)$^-$=396

EXAMPLE 171

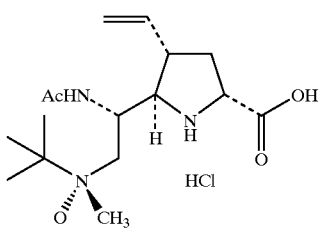

(±)-(2R,3S,5R,1'S,3'S)-2-(1-Acetamido-2-(N-methyl-N-t-butylamino-N-oxide)ethyl-3-vinyl-pyrrolidine-5-carboxylic Acid HydrochlorideSalt $^1$H NMR (CD$_3$OD) δ5.80 (m, 1H), 5.44 (d, 1H), 5.27 (d, 1H), 5.08 (m, 1H), 4.34–4.44 (dd, 1H), 3.83–3.94 (m, 3H), 3.38 (s, 3H), 3.02–3.18 (m, 1H), 2.58–2.72 (m, 1H), 2.08 (s, 3H), 1.97–2.08 (m, 1H), 1.55 (s, 9H).

MS: (M+H)$^+$=328

EXAMPLE 172

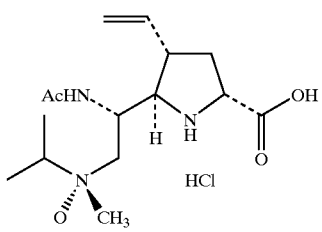

(±)-(2R,3S,5R,1'S,3'S)-2-(1-Acetamido-2-(N-methyl-N-isopropylamino-N-oxide))ethyl-3-vinyl-pyrrolidine-5-carboxylic Acid Hydrochloride Salt $^1$H NMR (MeOD-d$_3$) δ5.86–5.74 (m, 1H), 5.53–5.47 (m, 1H), 5.29–5.25 (m, 1H), 5.22–5.19 (m, 1H), 4.50 (dd, J=8.1, 9.5 Hz, 1H), 4.13–4.04 (m, 2H), 3.96 (dd, J=4.1, 10.5 Hz, 1H), 3.87–3.82 (m, 1H), 3.39 (s, 3H), 3.23–3.17 (m, 1H), 2.70–2.61 (m, 1H), 2.11 (s, 3H), 2.08–2.00 (m, 1H), 1.50 (d, J=6.4 Hz, 3H), 1.49(d, J=6.4 Hz, 3H).

MS: (M+H)$^+$=314, (M+Na)$^+$=336, (2M+1)$^+$=627, (2M+Na)$^+$=649.

EXAMPLE 173

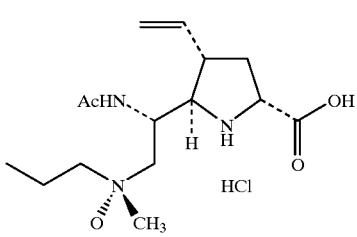

(±)-(2R,3S,5R,1'S,3'R)-2-(1-Acetamido-2-(N-methyl-N-propylamino-N-oxide))ethyl-3-vinyl-pyrrolidine-5-carboxylic Acid Hydrochloride Salt $^1$H NMR (MeOD-d$_3$) δ5.82–5.75(m, 1H), 5.45(d, J=17.1 Hz, 1H), 5.26(d, J=10.4 Hz, 1H), 5.07–5.13(m, 1H), 4.48–4.42(m, 1H), 3.98(d, J=5.5 Hz, 2H), 3.86(dd, J=4.3, 9.8 Hz, 1H), 3.67–3.64(m, 2H), 3.46(s, 3H), 3.16–3.01(m, 1H), 2.68–2.62(m, 1H), 2.09–2.02(m, 1H), 2.06(s, 3H), 1.92–1.86(m, 2H), 1.04(t, J=7.3 Hz, 3H).
MS: (M+H)$^+$=314, (M+H—H$_2$O)$^-$=295

EXAMPLE 174

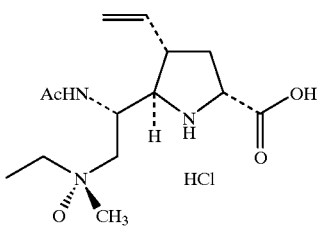

(±)-(2R,3S,5R,1'S,3'R)-2-(1-Acetamido-2-(N-methyl-N-ethylamino-N-oxide))ethyl-3-vinyl-pyrrolidine-5-carboxylic Acid Hydrochloride Salt $^1$H NMR (MeOD-d$_3$) δ5.82–5.75(m, 1H), 5.45(d, J=17.1 Hz, 1H), 5.26(d, J=10.4 Hz, 1H), 5.13–5.10(m, 1H), 4.48–4.44(m, 1H), 4.02–3.94(m, 2H), 3.89(dd, J=4.3, 9.8 Hz, 1H), 3.82(q, J=7.3 Hz, 2H), 3.46(s, 3H), 3.18–3.10(m, 1H), 2.68–2.62 (m, 1H), 2.09(s, 3H), 2.07–2.02(m, 1H), 1.46(t, J=7.3 Hz, 3H).
MS: (M+H)$^+$=300, (M+Na)$^+$=322, (M+H—H$_2$O)$^+$=282

EXAMPLE 175

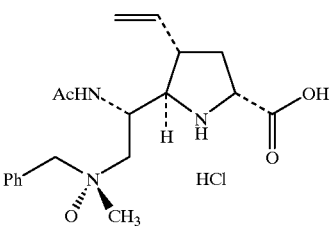

(±)-(2R,3S,5R,1'S,3'S)-2-(1-Acetamido-2-(N-methyl-N-benzylamino-N-oxide))ethyl-3-vinyl-pyrrolidine-5-carboxylic Acid HydrochlorideSalt $^1$H NMR (MeOD-d$_3$) δ7.60–7.47(m, 5H), 5.75–5.65(m, 1H), 5.39(d, J=6.35 Hz, 1H), 5.21(d, J=8.8 Hz, 1H), 5.18–5.11(m, 1H), 5.00–4.70(m, 2H), 4.35–4.27(m, 1H), 4.00–3.94(m, 2H), 3.86–3.79(m, 1H), 3.40(s, 3H), 3.14–3.05(m, 1H), 2.77–2.50(m, 1H), 2.08(s, 3H), 2.10–2.94(m, 1H).

MS: (M+H)$^+$=362, (M+Na)$^+$=385, (M−H)$^-$=360, (M+35)$^-$=396

EXAMPLE 176

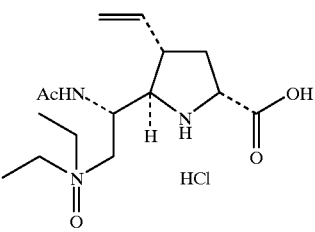

(±)-(2R,3S,5R,1'S)-2-(1-Acetamido-2-(N,N-diethylamino-N-oxide))ethyl-3-vinyl-pyrrolidine-5-carboxylic Acid Hydrochloride Salt $^1$H NMR (MeOD-d$_3$) δ5.84–5.78(m, 1H), 5.45(d, J=16.85 Hz, 1H), 5.26(d, J=10.0 Hz, 1H), 5.09–5.05(m, 1H), 4.45–4.42(m, 1H), 3.96–3.86(m, 3H), 3.76(q, J=6.6 Hz, 2H), 3.70(q, J=7.3 Hz, 2H), 3.15–3.11(m, 1H), 2.68–2.62(m, 1H), 2.08–2.02(m, 1H), 2.08(s, 3H), 1.44–1.38(m, 6H).

MS: (M+H)$^+$=314, (M+Na)$^+$=336, (M+2Na)$^+$=358

EXAMPLE 177

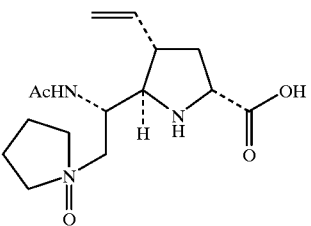

(±)-(2R,3S,5R,1'S,3'R)-2-(1-Acetamido-2-(N-pyrrolidinyl-N-oxide))ethyl-3-vinyl-pyrrolidine-5-carboxylic Acid Hydrochloride Salt $^1$H NMR (DMSO-d$_6$) δ8.74 (d, 1H), 5.65–5.80 (m,1H), 5.28 (d, 1H), 5.10 (d,1H), 4.82 (m, 1H), 4.40–4.50 (dd, 1H), 4.30 (d, 1H), 3.60–4.12 (brm, 5H), 2.98–3.15 (m, 1H), 2.38–2.48 (m, 1H), 2.05–2.20 (brm, 5H), 1.88–1.98 (m, 1H), 1.87 (s, 3H).

MS: (M+H)$^+$=312

EXAMPLE 178

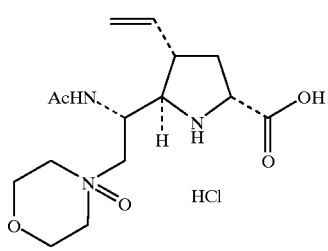

(±)-(2R,3S,5R,1'S)-2-(1-Acetamido-2-(N-morpholinyl-N-oxide)ethyl-3-vinyl-pyrrolidine-5-carboxylic Acid Hydrochloride Salt $^1$H NMR (DMSO-d$_6$) δ8.65 (d,1H), 5.66–5.80 (m, 1H), 5.22 (d, 1H), 5.09 (d, 1H), 4.78 (brs, 1H), 4.32–4.42 (dd, 1H), 4.10–4.17 (brm, 2H), 3.50–4.02 (brm, 9H), 2.92–3.04 (brm, 1H), 2.37–2.48 (m, 1H), 1.88–1.96 (m, 1H), 1.87 (s, 3H).

MS: (M+H)$^+$=328

EXAMPLE 179

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid HydrochlorideSalt

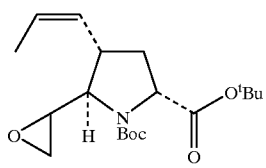

179A (±)-(2R,3S,5R,1'S)-1-t-Butoxycarbonyl-2-oxiranyl-3-(cis-propen-1-yl)-pyrrolidine-5-carboxylic Acid t-Butyl Ester The title compound was prepared according to the method described in EXAMPLE 123I, substituting ethyltriphenylphosphonium bromide in place of methyltriphenylphosphonium bromide (yield: 350 mg, 77%).

$^1$H NMR (CDCl$_3$) (rotamers) δ5.55–5.43 (m, 2H), 4.13–4.04 (m, 2H), 3.14–3.11 (m, 2H), 2.76–2.50 (m, 3H), 1.75–1.70 (m, 1H), 1.64(d, 3H), 1.48–1.43(m, 18H).

MS: (M+H)$^+$=354, (M+Na)$^+$=376, (2M+Na)$^+$=729

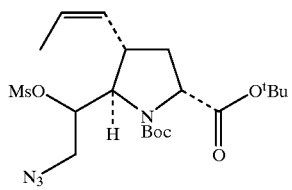

179B (±)-(2R,3S,5R,1'R)-1-t-Butoxycarbonyl-2-(1-methanesulfonyloxy-3-azido)ethyl-3-(cis-propen-1-yl)-pyrrolidine-5-carboxylic Acid t-Butyl Ester The title compound was prepared according to the method described in EXAMPLE 123J, substituting (±)-(2R,3S,5R, 1'S)-1-t-butoxycarbonyl-2-oxiranyl-3-(cis-propen-1-yl)-pyrrolidine-5-carboxylic acid t-butyl ester in place of (±)-(2R,3S,5R,1'S)-1-t-butoxycarbonyl-2-(1-acetamido)butyl-3-vinyl-pyrrolidine-5-carboxylic acid t-butyl ester (yield: 1.08 g, 84%).

$^1$H NMR (DMSO-d$_6$) (rotamers) δ5.53–5.33 (m, 2H), 5.05–4.93 (m, 1H), 4.20–3.90 (m, 2H), 3.76–3.62 (m, 2H), 3.24 (s, 3H), 2.59–2.49(m, 1H), 1.64–1.55(m, 5H), 1.43–1.36(m, 18H).

MS: (M+H)$^+$=475, (M+Na)$^+$=497, (2M+Na)$^+$=971

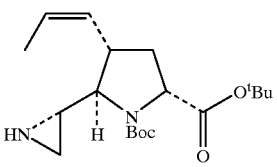

179C (±)-(2R,3S,5R,1'S)-1-t-Butoxycarbonyl-2-aziridinyl-3-(cis-propen-1-yl)-pyrrolidine-5-carboxylic Acid t-Butyl Ester The title compound was prepared according to the method described in EXAMPLE 123K, substituting (2R,3S,5R,1'S)-1-t-butoxycarbonyl-2-(1-methanesulfonyloxy-3-azido) ethyl-3-(cis-propen-1-yl)-pyrrolidine-5-carboxylic acid t-butyl ester in place of (2R,3S,5R,1'S)-1-t-butoxycarbonyl-2-(1-methanesulfonyloxy-3-azido)ethyl-3-vinyl-pyrrolidine-5-carboxylic acid t-butyl ester(crude yield: 564 mg, 71%).

$^1$H NMR(DMSO-d$_6$) (rotamers) δ5.45–5.30 (m, 2H), 4.15–3.99 (m, 1H), 3.30–3.08 (m, 1H), 3.07–2.84 (m, 1H), 2.68–2.51 (m, 1H), 2.13–1.85(m, 1H), 1.80–1.05(m, 3H), 1.57(d, J=5.4 Hz, 3H), 1.41–1.35(m, 18H).

MS: (M+H)$^+$=352, (M+23)$^+$=375, (2M+H)$^+$=705, (2M+23)$^+$=727

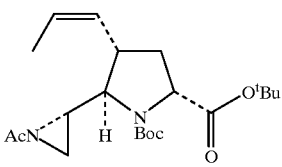

179D (±)-(2R,3S,5R,1'S)-1-t-Butoxycarbonyl-2-(N-acetylaziridinyl)-3-(cis-propen-1-yl)-pyrrolidine-5-carboxylic Acid t-Butyl Ester The title compound was prepared according to the method described in Example 123L, substituting (±)-(2R,3S,5R, 1'S)-1-t-butoxycarbonyl-2-aziridinyl-3-(cis-propen-1-yl)-pyrrolidine-5-carboxylic acid t-butyl ester in place of (±)-(2R,3S,5R,1'S)-1-t-butoxycarbonyl-2-aziridinyl-3-vinyl-pyrrolidine-5-carboxylic acid t-butyl ester(yield: 455 mg, 72%).

$^1$H NMR(DMSO-d$_6$) (rotamers) δ5.74–5.34(m, 2H), 4.17 (dd, J=2.4, 6.35 Hz, 1H), 3.41(dd, J=1.95, 6.35 Hz, 1H), 3.14–2.99(m, 1H), 2.73–2.58(m, 2H), 2.40(d, J=6.35 Hz, 1H), 2.17–2.12(m, 1H), 2.05–2.00(m, 3H), 1.66–1.55(m, 1H), 1.56(d, J=6.8 Hz, 3H), 1.41–1.31(m, 18H).

MS: (M+H)⁺=395, (M+Na)⁺=417, (M+H+Na)⁺=418,

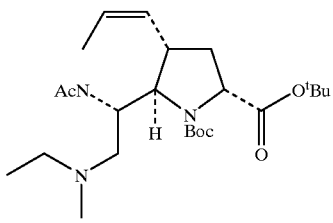

179E (±)-(2R,3S,5R,1'S)-1-t-Butoxycarbonyl-2-(1-acetamido-2-N-ethyl-N-methylamino)ethyl-3-(cis-propen-1-yl)-pyrrolidine-5-carboxylic Acid t-Butyl Ester The title compound was prepared according to the method described in Example 150, substituting N-ethyl-N-methylamine in place of diethylamine (yield: 30 mg, 87%).

MS: (M+H)⁺=454, (M+Na)⁺=476, (M−H)⁻=452, (M+35)⁻=488

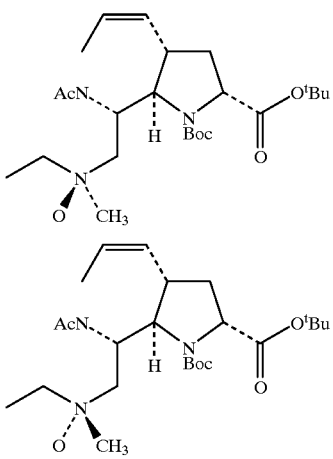

179E (±)-(2R,3S,5R,1'S,3'R) and (±)-(2R,3S,5R,1'S,3'S)-1-t-Butoxycarbonyl-2-(1-acetamido-2-(N-ethyl-N-methylamino-N-oxide))ethyl-3-(cis-propen-1-yl)-pyrrolidine-5-carboxylic Acid t-Butyl Ester The title compound was prepared according to the method described in Example 165A, substituting (±)-(2R,3S,5R,1'S)-1-t-butoxycarbonyl-2-(1-acetamido-2-(N-ethyl-N-methylamino))ethyl-3-(cis-propen-1-yl)-pyrrolidine-5-carboxylic acid t-butyl ester in place of (±)-(2R,3S,5R,1'S)-1-t-butoxycarbonyl-2-(1-acetamido-2-N-methyl-N-t-butylamino)ethyl-3-(cis-propen-1-yl)-pyrrolidine-5-carboxylic acid t-butyl ester (yield: 15.2 mg, 51%).

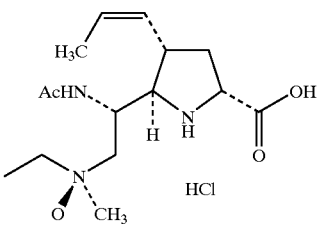

179F (±)-(2R,3S,5R,1'S,3'R)-2-(1-Acetamido-2-(N-ethyl-N-methylamino-N-oxide))ethyl-3-(cis-propen-1-yl)-pyrrolidine-5-carboxylic Acid Hydrochloride Salt The title compound was prepared according to the method described in Example 1K, substituting (±)-(2R,3S,5R,1'S,3'R)-1-t-butoxycarbonyl-2-(1-acetamido-2-(N-methyl-N-ethyl-N-oxide))ethyl-pyrrolidine-5-carboxylic acid t-butyl ester for (±)-(2R,3R,5R,1'S)-2-(1-acetamido-3-ethyl)pentyl-3-methoxymethyl-pyrrolidine-5-carboxylic acid t-butyl ester (yield: 8.7 mg, 29%).

¹H NMR (MeOD-d₃) δ5.75–5.69(m, 1H), 5.37–5.30(m, 1H), 5.07–5.04(m, 1H), 4.49(dd, J=7.8, 10.2 Hz, 1H), 4.05–3.74(m, 4H), 3.61–3.32 (m, 1H), 3.55(s, 3H), 2.69–2.60(m, 1H), 2.04(s, 3H), 1.95–1.84(m, 1H), 1.75(dd, J=2.0, 7.1 Hz, 3H), 1.44 (t, J=7.1 Hz, 3H).

MS: (M+H)⁺=314, (M+35)⁺=348

EXAMPLES 179–184

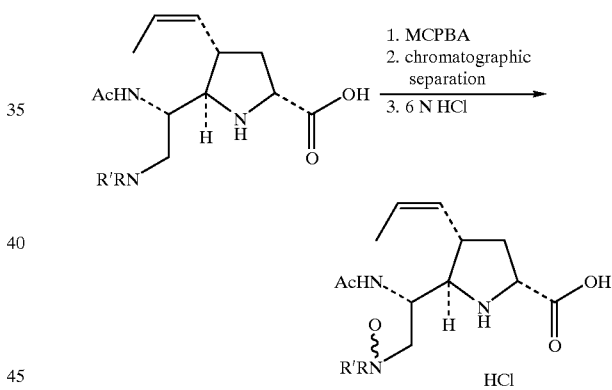

The following title compounds were prepared according to the method described in Example 179.

EXAMPLE 180

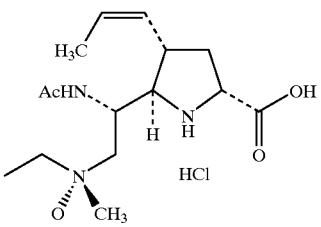

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid Hydrochloride Salt ¹H NMR (MeOD-d₃) δ5.75–5.69(m, 1H), 5.38–5.30(m, 1H), 5.02–4.98(m, 1H), 4.47(dd, J=7.8, 9.8 Hz,1H), 4.02–3.77(m, 4H), 3.56–3.39(m, 1H), 3.47(s, 3H), 2.69–2.59(m, 1H), 2.07(s, 3H), 1.95–1.84(m, 1H), 1.76(dd, J=1.7, 7.1 Hz, 3H), 1.46(t, J=7.1 Hz, 3H).

MS: (M+H)⁺=314, (M+35)⁺=348

EXAMPLE 181

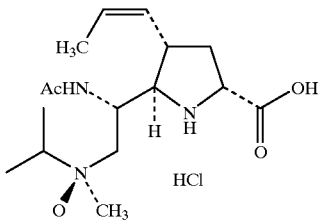

(±)-(2R,3S,5R,1'S,3'R)-2-(1-Acetamido-2-(N-isopropyl-N-methylamino-N-oxide))ethyl-3-(cis-propen-1-yl)-pyrrolidine-5-carboxylic Acid Hydrochloride Salt ¹H NMR (MeOD-d₃) δ5.76–5.66(m, 1H), 5.39–5.31(m, 1H), 5.17–5.11(m, 1H), 4.51(dd, J=7.5, 10.2 Hz, 1H), 4.07–3.76(m, 4H), 3.55(S, 3H), 3.52–3.39(m, 1H), 2.69–2.60(m, 1H), 2.02 (S, 3H), 2.08–1.84(m, 1H), 1.75(dd, J=1.7, 7.1Hz, 3H), 1.50(d, J=6.1 Hz, 3H), 1.48(d, J=6.4 Hz, 3H).

MS: (M+H)⁺=314, (M+35)⁺=348

EXAMPLE 182

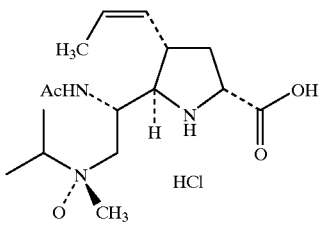

(±)-(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid Hydrochloride Salt ¹H NMR (MeOD-d₃) δ5.76–5.68(m, 1H), 5.39–5.31(m, 1H), 5.10–5.05(m, 1H), 4.49(dd, J=7.8, 9.8 Hz, 1H), 4.12–3.84(m, 4H), 3.55–3.44(m, 1H), 3.41(S, 3H), 2.69–2.60(m, 1H), 2.08(S, 3H), 2.07–1.84(m, 1H), 1.76(dd, J=1.7, 6.8 Hz, 3H), 1.51(d, J=2.4 Hz, 3H), 1.49(d, J=2.4 Hz, 3H).

MS (M+H)⁺=314, (M+35)⁺=348

EXAMPLE 183

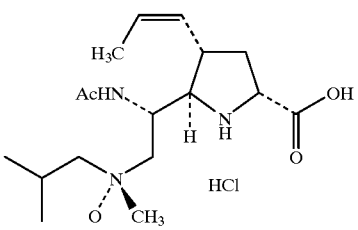

(±)-(2R,3S,5R,1'S,3'S)-2-(1-Acetamido-2-(N-isobutyl-N-methylamino-N-oxide))ethyl-3-(cis-propen-1-yl)-pyrrolidine-5-carboxylic Acid Hydrochloride Salt ¹H NMR (MeOD-d₃) δ5.75–5.69(m, 1H), 5.38–5.31(m, 1H), 5.18–5.12(m, 1H), 4.53(dd, J=7.5, 9.8 Hz, 1H), 4.25–3.42(m, 6H), 3.65 (s, 3H), 2.68–2.58(m, 1H), 2.44–2.36(m, 1H), 2.05(s, 3H), 1.94–1.87(m, 1H), 1.76(d, J=2.7 Hz, 3H), 1.14 (d, J=6.8 Hz, 6H).

MS: (M+H)⁺=342, (M+Na)⁺=364, (M–H)⁻=340

EXAMPLE 184

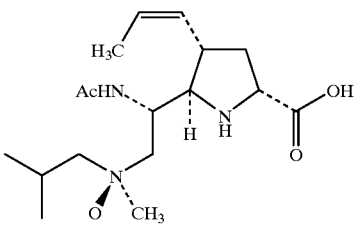

(±)-(2R,3S,5R,1'S,3'R)-2-(1-Acetamido-2-(N-isobutyl-N-methylamino-N-oxide))ethyl-3-(cis-propen-1-yl)-pyrrolidine-5-carboxylic Acid Hydrochloride Salt ¹H NMR (MeOD-d₃) δ5.75–5.69(m, 1H), 5.38–5.31(m, 1H), 5.06–5.02(m, 1H), 4.48(dd, J=7.5, 9.8 Hz, 1H), 4.08–3.85(m, 3H), 3.70–3.57 (m, 2H), 3.52(s, 3H), 3.48–3.41(m, 1H), 2.70–2.60(m, 1H), 2.40–2.36(M, 1H), 2.08(s, 3H), 1.95–1.84(m, 1H), 1.75(dd, J=1.7, 7.1 Hz, 3H), 1.14 (d, J=6.8 Hz, 6H).

MS: (M+H)⁺=342, (M+Na)⁺=364, (M–H)⁻=340

EXAMPLE 185

(±)-(2R,3S,5R,1'S)-2-(1-Acetamido-2-(N-isopropyl-N-hydroxyamino))ethyl-3-vinyl-pyrrolidine-5-carboxylic Acid Hydrochloride Salt

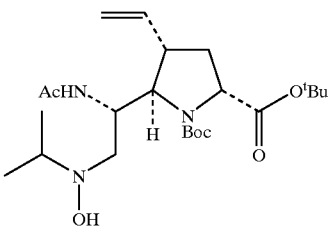

165A (±)-(2R,3S,5R,1'S)-1-t-Butoxycarbonyl-2-(1-acetamido-2-(N-isopropyl-N-hydroxyamino))ethyl-3-vinyl-pyrrolidine-5-carboxylic Acid t-Butyl Ester (±)-(2R,3S,5R,1'S)-1-t-Butoxycarbonyl-2-(1-acetamido-2-isopropylamino)ethyl-3-vinyl-pyrrolidine-5-carboxylic acid t-butyl ester (21 mg, 0.048 mmole) was dissolved in 0.95 mL of acetone. It was then titrated with 0.14 mL of a solution of dimethyldioxirane (0.1 M) in acetone at −45° C. for 0.5 hour. The reaction was stopped by concentrating the mixture in vacuo. The residue was purified by chromatography on silica gel using 100% dichloromethane to 90% dichloromethane/methanol to provide the title compound (yield: 5.3 mg, 24%) and recovered starting material (yield 12 mg, 57%).

$^1$H NMR (MeOD-$d_3$) δ5.95–5.89(m, 1H), 5.08–4.94(m, 2H), 4.75–4.68(m, 1H), 4.13–3.83(m, 2H), 2.85–2.47(m, 4H), 1.96(s, 3H), 1.82–1.76(m, 1H), 1.52–1.44(m, 18H), 1.45–1.29(m, 1H), 1.07–1.04(m, 6H).

MS: $(M+H)^+=456$, $(M+Na)^+=478$, $(M-H)^-=454$, $(M+35)^-=490$.

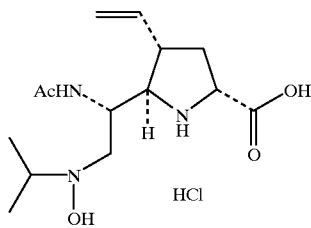

185B (±)-(2R,3S,5R,1'S)-2-(1-Acetamido-2-(N-isopropyl-N-hydroxyamino))ethyl-3-vinyl-pyrrolidine-5-carboxylic Acid Hydrochloride Salt The title compound was prepared according to the method described in Example 1K, substituting (±)-(2R,3R,5R,1'S)-1-t-butoxycarbonyl-2-(1-acetamido-2-(N-isopropyl-N-hydroxyamino))ethyl-3-vinyl-pyrrolidine-5-carboxylic acid t-butyl ester in place of (±)(2R,3R,5R,1'S)-2-(1-acetamido-3-ethyl)pentyl-3-methoxymethyl-pyrrolidine-5-carboxylic acid t-butyl ester (yield: 3.0 mg, 87%).

$^1$H NMR (MeOD-$d_3$) δ5.83–5.71(m, 1H), 5.40(d, J=17.3 Hz, 1H), 5.24(d, J=10.2 Hz, 1H), 4.48(dd, J=7.8, 10.2 Hz, 1H), 3.88–3.59(m, 4H), 3.17–3.10(m, 1H), 2.67–2.58(m, 1H), 2.10–1.99(m, 1H), 2.09(s, 3H), 1.33–1.17(m, 1H), 1.38(d, J=6.4 Hz, 6H).

MS: $(M+H)^+=300$, $(M-H)^-=298$, $(2M-H)^-=597$

EXAMPLE 186

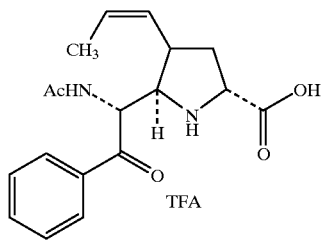

(±)-(2R,3S,5R,1'R)-2-(1-Acetamido-2-oxo-2-phenyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-oxo-2-phenyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 5.9 mg, 100%).

$^1$H NMR (DMSO-$d_6$) δ8.62 (d, J=9.8 Hz, 1H), 7.93 m, 2H), 7.68 (m, 1H), 7.55 (t, J=7.9 Hz, 2H), 5.61 (m, 1H), 5.48 (m, 1H), 5.19 (m, 1H), 4.50 (m, 1H), 3.98 (t, J=9.8 Hz, 1H), 3.30 (m, 1H), 2.38 (m, 1H), 1.73 (m, 1H), 1.71 (s, 3H), 1.59 (m, 3H).

MS: $(M+H)^+=331$, $(M+Na)+=353$, $(M-H)-=329$.

EXAMPLE 187

(±)-(2R,3S,5R,1'R,2'R)-2-(1-Acetamido-2-methoxy-4-vinyl)butyl-3-(cis-propen-1-yl)-pyrrolidine-5-carboxylic Acid Trifluoroacetic Acid Salt

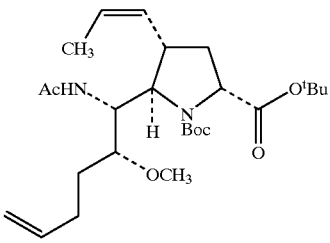

187A (±)-(2R,3S,5R,1'R,2'R)-1-t-Butoxycarbonyl-2-(1-acetamido-2-methoxy-4-vinyl)butyl-3-(cis-propen-1-yl)-pyrrolidine-5-carboxylic Acid t-Butyl Ester The title compound is prepared according to the method described in Example 84A, substituting (±)-(2R,3S,5R,1'R,2'R)-1-t-butoxycarbonyl-2-(1-acetamido-2-hydroxy-4-vinyl)butyl-3-(cis-propen-1-yl)-pyrrolidine-5-carboxylic acid t-butyl ester for (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

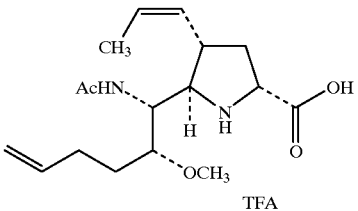

187B (±)-(2R,3S,5R,1'R,2'R)-2-(1-Acetamido-2-methoxy-4-vinyl)butyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'R)-1-t-butoxycarbonyl-2-(1-acetamido-2-methoxy-4-vinyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

EXAMPLE 188

(±)-(2R,3S,5R,1'R,2'S)-2-(1-Acetamido-2-methoxy-4-vinyl)butyl-3-(cis-propen-1-yl)-pyrrolidine-5-carboxylic Acid Trifluoroacetic Acid Salt

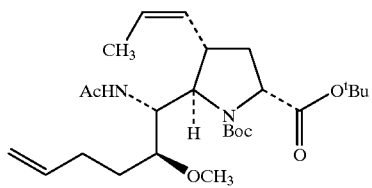

188A (±)-(2R,3S,5R,1'R,2'S)-1-t-Butoxycarbonyl-2-(1-acetamido-2-methoxy-4-vinyl)butyl-3-(cis-propen-1-yl)-pyrrolidine-5-carboxylic Acid t-Butyl Ester The title compound was prepared according to the method described in Example 84A, substituting (±)-(2R,3S,5R,1'R,2'S)-1-t-butoxycarbonyl-2-(1-acetamido-2-hydroxy-4-vinyl)butyl-3-(cis-propen-1-yl)-pyrrolidine-5-carboxylic acid t-butyl ester for (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0044 g, 22%).

MS: $(M+H)^+=481$, $(M-H)^-=479$.

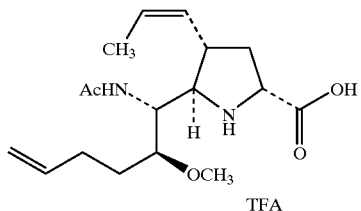

188B (±)-(2R,3S,5R,1'R,2'S)-2-(1-Acetamido-2-methoxy-4-vinyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-methoxy-4-vinyl)butyl-3-(cis-propen-1-yl)-pyrrolidine-5-carboxylic acid t-butyl ester in place of (±)-(2R,3S,5R,1'R,2'S)-1-t-butoxycarbonyl-2-(1 -acetamido-2-hydroxy)butyl-3-(cis-propen-1-yl)-pyrrolidine-5-carboxylic acid t-butyl ester (yield: 0.0031 g, 100%).

$^1$H NMR (DMSO-$d_6$) δ7.93 (d, J=9.2 Hz, 1H), 5.81 (m, 1H), 5.49 (m, 1H), 5.26 (m, 1H), 5.1–4.9 (m, 2H), 4.29 (m 1H), 4.03 (m, 2H), 3.68 (m, 1H), 3.26 (m, 1H), 3.25 (s, 3H), 3.18 (quint., J=8.5 Hz, 1H), 2.40 (dt, J=12.7,7.3 Hz, 1H), 2.32 (M, 1H), 2.20 (m, 1H), 2.02 (m, 1H), 1.85 (s, 3H), 1.68 (m, 1H), 1.64 (m, 1H), 1.61 (dd, J=6.7,1.8 Hz, 3H), 1.55–1.40 (m, 2H).

MS: $(M+H)^+=325$, $(M+Na)^+=347$, $(M-H)^-=323$.

EXAMPLE 189

(±)-(2R,3R,5R,1'R,2'S)-2-(1-Acetamido-2,3-dihydroxy)propyl-3-(cis-propen-1-yl)-pyrrolidine-5-carboxylic Acid Trifluoroacetic Acid Salt

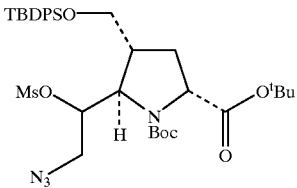

189A (±)-(2R,3R,5R,1'S)-1-t-Butoxycarbonyl-2-(1-methanesulfonyloxy-3-azido)ethyl-3-t-butyldiphenylsilyloxymethyl-pyrrolidine-5-carboxylic Acid t-Butyl Ester The title compound was prepared according to the method described in Example 123J substituting (±)-(2R,3R,5R,1'S)-1-t-butoxycarbonyl-2-oxiranyl-3-t-butyldiphenylsilyloxymethyl-pyrrolidine-5carboxylic acid t-butyl ester in place of (2R,3S,5R,1'S)-2-oxiranyl-3-vinyl-pyrrolidine-5-carboxylic acid t-butyl ester (yield: 9.0 g, 90%).

$^1$H NMR (DMSO-$d_6$) (rotamers) δ7.62–7.58 (m, 4H), 7.49–7.38 (m 6H), 4.97–4.79 (m, 1H), 4.19–4.02 (m, 2H), 3.79–3.48 (m, 2H), 3.15 and 3.13 (2s, 3H), 2.49–2.39 (m, 2H), 1.98–1.74 (m, 1H), 1.43–1.25 (m, 18H), 1.02 and 1.00 (2s, 9H)

MS: $(M+H)^+=703$, $(M+Na)^+=725$

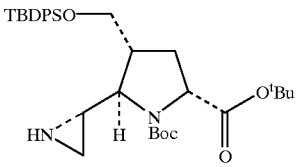

189B (±)-(2R,3R,5R,1'S)-1-t-butoxycarbonyl-2-aziridinyl-3-t-butyldiphenylsilyloxymethyl-pyrrolidine-5-carboxylic acid t-butyl ester The title compound was prepared according to the method described in Example 123K substituting (±)-(2R,3R,5R,1'S)-1-t-butoxycarbonyl-2-(1-methanesulfonyloxy-3-azido)ethyl-3-t-butyldiphenylsilyloxymethyl-pyrrolidine-5-carboxylic acid t-butyl ester in place of (±)-(2R,3S,5R,1'S)-1-t-butoxycarbonyl-2-(1-methanesulfonyloxy-3-azido)ethyl-3-vinyl-pyrrolidine-5-carboxylic acid t-butyl ester (yield: 5.9 g, 79%).

$^1$H NMR (DMSO-$d_6$) (rotamers) δ7.60–7.56 (m, 4H), 7.49–7.39 (m 6H), 4.11–4.05 (m, 1H), 3.67–3.48 (m, 2H), 3.42–3.30 (m, 1H), 2.49–2.39 (m, 1H), 2.25–1.61 (m, 5H), 1.40, 1.35, 1.33, and 1.27 (4s, 18H), 0.99 and 0.98 (2s, 9H)

MS: (M+H)⁺=581, (M+Na)⁺=603

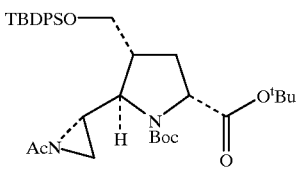

189C (±)-(2R,3R,5R,1'S)-1-t-Butoxycarbonyl-2-N-acetylaziridinyl-3-t-butyldiphenylsilyloxymethyl-pyrrolidine-5-carboxylic Acid t-Butyl Ester The title compound was prepared according to the method described in Example 123L substituting (±)-(2R,3R,5R,1'S)-1-t-butoxycarbonyl-2-aziridinyl-3-t-butyldiphenylsilyloxymethyl-pyrrolidine-5-carboxylic acid t-butyl ester in place of (±)-(2R,3S,5R,1'S)-1-t-butoxycarbonyl-2-aziridinyl-3-vinyl-pyrrolidine-5-carboxylic acid t-butyl ester (yield: 3.1 g, 96%).

¹H NMR (DMSO-d₆) (rotamers) δ7.60–7.57 (m, 4H), 7.49–7.39 (m 6H), 4.18–4.11 (m, 1H), 3.71–3.51 (m, 3H), 2.76–2.68 (m, 1H), 2.58–2.45 (m, 1H), 2.46 and 2.39 (2d, J=6.1, 6.1Hz, 1H), 2.40 and 2.47 (2m, 1H), 2.08 and 2.05 (2d, J=3.1, 3.1 Hz, 1H), 2.02 and 1.99 (2s, 3H), 1.94–1.79 (m, 1H), 1.41, 1.36, 1.35 and 1.29 (4s, 18H), 0.99 and 0.98 (2s, 9H)

MS: (M+H)⁺=623, (M+Na)⁺=645

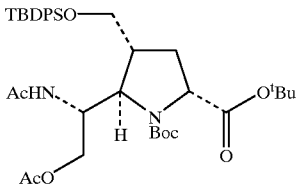

189D (±)-(2R,3R,5R,1'R)-1-t-Butoxycarbonyl-2-(1-acetamido-2-acetoxy)ethyl-3-t-butyldiphenylsilyloxymethyl-pyrrolidine-5-carboxylic Acid t-Butyl Ester (±)-(2R,3R,5R,1'S)-1-t-butoxycarbonyl-2-N-acetylaziridinyl-3-t-butyldiphenylsilyloxymethyl-pyrrolidine-5-carboxylic acid t-butyl ester (2.75g, 4.40 mmole) was reacted with potassium acetate (2.49 g, 25.37 mmole) and acetic acid (1.45 mL, 25.37 mmole) in DMSO (45 mL) at 100° C. for 16 hours. The reaction was quenched with 1N NaHCO₃ (100 mL) and diluted with ethyl acetate (300 mL). The organic layer was washed with water, and brine, dried over MgSO₄, filtered and concentrated in vacuo. The residue was purified by chromatography on silica gel using 100% dichloromethane to 50% dichloromethane/ethyl acetate to provide the title compound (yield: 2.45 g, 81%).

MS: (M+H)⁺=683, (M+Na)⁺=705, (M–H)⁻=681, (M+Cl)⁻=717

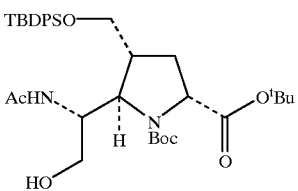

189E (±)-(2R,3R,5R,1'R)-1-t-Butoxycarbonyl-2-(1-acetamido-2-hydroxy)ethyl-3-t-butyldiphenylsilyloxymethyl-pyrrolidine-5-carboxylic Acid t-Butyl Ester (±)-(2R,3R,5R,1'R)-1-t-Butoxycarbonyl-2-(1-acetamido-2-acetoxy)ethyl-3-t-butyldiphenylsilyloxymethyl-pyrrolidine-5-carboxylic acid t-butyl ester (2.45 g, 3.58 mmole) was reacted with potassium carbonate (1.48 g, 10.73 mmole) in methanol (18 mL) and THF (18 mL) at 25° C. for 45 minutes. The reaction was quenched with water (100 mL) and diluted with ethyl acetate (200 mL). The organic layer was washed with water, and brine, dried over MgSO₄, filtered and concentrated in vacuo. The residue was purified by chromatography on silica gel using 85% dichloromethane/ethyl acetate to 100% ethyl acetate to provide the title compound (yield: 2.05 g, 90%).

MS: (M+H)⁺=641, (M+Na)⁺=663, (2M+Na+H)⁺=304, (M–H)⁻=639, (M+Cl)⁻=675

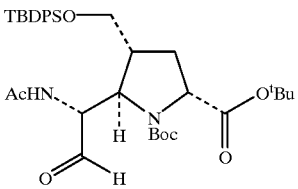

189F (±)-(2R,3R,5R,1'R)-1-t-Butoxycarbonyl-2-(1-acetamido-2-formyl)ethyl-3-t-butyldiphenylsilyloxymethyl-pyrrolidine-5-carboxylic Acid t-Butyl Ester The title compound was prepared according to the method described in Example 41A substituting (±)-(2R,3R,5R,1'R)-1-t-butoxycarbonyl-2-(1-acetamido-2-hydroxy)ethyl-3-t-butyldiphenylsilyloxymethyl-pyrrolidine-5-carboxylic acid t-butyl ester in place of (±)-(2R,3S,5R,1'R)-1-t-butoxycarbonyl 2-(1-acetamido-2-hydroxy)ethyl-3-(cis-propen-1-yl)-pyrrolidine-5-carboxylic acid t-butyl ester.

¹H NMR (DMSO-d₆) (rotamers) 9.49(d, J=16.3, 1H), 8.33 and 8.29(2d, J=8.8 and 8.8 Hz, 1H), 7.58–7.38(m, 10H), 4.94 and 4.84(2dd, J=4.4, 8.8 Hz and 4.4, 8.8 Hz, 1H), 4.26–3.37(m, 4H), 2.47–2.30(m, 1H), 1.97–1.83(m, 1H), 1.92(s, 3H), 1.42–1.18(m, 18H), 1.42–1.18(m, 1H), 1.00–0.97(m, 9H).

MS: (M+H)⁺=639, (M–H)⁻=637

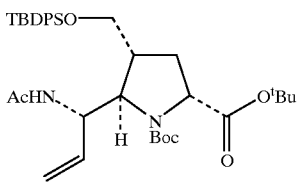

189G (±)-(2R,3R,5R,1'S)-1-t-Butoxycarbonyl-2-(1-acetamido-1-vinyl)methyl-3-t-butyldiphenylsilyloxymethyl-pyrrolidine-5-carboxylic Acid t-Butyl Ester The title compound was prepared according to the method described in Example 118A substituting (±)-(2R,3R,5R,1'R)-1-t-butoxycarbonyl-2-(1-acetamido-2-formyl)ethyl-3-t-butyldiphenylsilyloxymethyl-pyrrolidine-5-carboxylic acid t-butyl ester in place of (±)-(2R,3S,5R,1'R)-1-t-butoxycarbonyl 2-(1-acetamido-2-formyl)ethyl-3-(cis-propen-1-yl)-pyrrolidine-5-carboxylic acid t-butyl ester.

¹H NMR (DMSO-d₆) (rotamers) 7.99–7.74(m, 1H), 7.59–7.39(m, 10H), 5.80–5.68(m, 1H), 5.21–5.01(m, 3H), 3.97–3.31(m, 1H), 3.78–3.74(m, 1H), 3.60–3.46(m, 2H), 2.53–2.37(m, 1H), 2.09–1.72(m, 1H), 1.87(s, 3H), 1.42–1.23(m, 19H), 1.00–0.99(m, 9H).

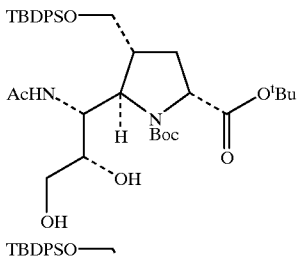

189H (±)-(2R,3R,5R,1'R,2'R) and (±)-(2R,3R,5R,1'R,2'S)-1-t-Butoxycarbonyl-2-(1-acetamido-2,3-dihydroxy)propyl-3-t-butyldiphenylsilyloxymethyl-pyrrolidine-5-carboxylic Acid t-Butyl Ester The title compounds were prepared according to the method described in Example 20A substituting (±)-(2R,3R,5R,1'S)-1-t-butoxycarbonyl-2-(1-acetamido-2-vinyl)ethyl-3-t-butyldiphenylsilyloxymethyl-pyrrolidine-5-carboxylic acid t-butyl ester in place of (±)-(2R,3S,5R)-1-benzyl-2-vinyl-3-t-butyldimethylsilyloxymethyl-pyrrolidine-5-carboxylic acid t-butyl ester (±)-(2R,3R,5R,1'R,2'S) isomer (yield: 311 mg, 24%) (±)-(2R,3R,5R,1'R,2'R) isomer (yield: 700 mg, 54%).

(±)-(2R,3R,5R,1'R,2'S) ¹H NMR (DMSO-d₆) (rotamers) 7.62–7.39(m, 11H), 4.56 and 4.51 (d, J=4.8, 1H), 4.46–4.39 (m, 2H), 3.97–3.82(m, 1H), 3.74–3.47(m, 3H), 3.28–3.21 (m, 2H), 2.89–2.64(m, 1H), 2.51–2.45(m, 1H), 2.05–1.8(m, 1H), 1.87–1.86(m, 3H), 1.43–1.23(m, 19H), 0.99–0.98(m, 9H).

(±)-(2R,3R,5R,1'R,2'R) ¹H NMR (DMSO-d₆) (rotamers) 7.63–7.40(m, 11H), 4.56–4.54(d, J=4.8, 1H), 4.47–4.33(m, 2H), 3.94–3.80(m, 1H), 3.85–3.80(m, 1H), 3.76–3.68(m, 1H), 3.60–3.51(m, 1H), 3.44–3.35(m, 1H), 3.30–3.21(m, 1H), 2.78–2.62(m, 1H), 2.46–2.31(m, 1H), 2.07–1.98(m 1H), 1.83(s, 3H), 1.39–1.29(m, 19H), 1.00–0.99(m, 9H).

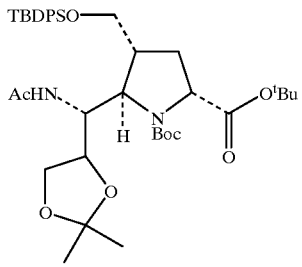

189I (±)-(2R,3R,5R,1'R,2'R)-1-t-Butoxycarbonyl-2-(1-acetamido-1-(2,2-dimethyl-1,3-dioxolan-4-yl))methyl-3-t-butyldiphenylsilyloxymethyl-pyrrolidine-5-carboxylic Acid t-Butyl Ester (±)-(2R,3R,5R,1'R,2'R)-1-t-Butoxycarbonyl-2-(1-acetamido-2,3-dihydroxy)propyl-3-t-butyldiphenylsilyloxymethyl-pyrrolidine-5-carboxylic acid t-butyl ester was reacted with 2,2-dimethoxypropane (1.1 ml, 9.09 mmole) and p-Toluenesulfonic acid (4.3 mg, 0.023 mmole) in tetrahydrofuran (4.5 mL) at 25° C. for 45 minutes. The reaction was quenched with triethylamine (3 mL). Stirring was continued for an additional 10 minutes. The reaction was then diluted with 10% NaHCO₃ (15 mL) and extracted with ethyl acetate (45 ml). The organic layer was washed with water, and brine, dried over MgSO₄, filtered and concentrated in vacuo. The residue was carried over to the next step purified by chromatography on silica gel using 100% dichlormethane to 94% dichloromethane/methanol to provide the title compound (yield: 194 mg, 91%).

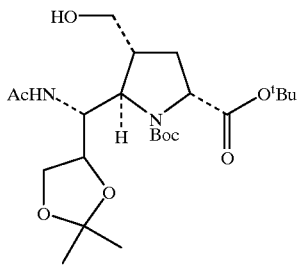

189J (±)-(2R,3R,5R,1'R,2'S)-1-t-Butoxycarbonyl-2-(1-acetamido-1-(2,2-dimethyl-1,3-dioxolan-4-yl))methyl-3-hydroxymethyl-pyrrolidine-5-carboxylic Acid t-Butyl Ester The title compound was prepared according to the method described in Example 123G substituting (±)-(2R,3R,5R,1'R,2'S)-1-t-butoxycarbonyl-2-(1-acetamido-1-(2,2-dimethyl-1 3-dioxolan-4-yl))methyl-3-t-butyldiphenylsilyloxymethyl-pyrrolidine-5-carboxylic acid t-butyl ester for (±)-(2R,3R,5R,1'S)-1-t-butoxycarbonyl-2-oxiranyl-3-t-butyldiphenylsilyloxymethyl-pyrrolidine-5-carboxylic acid t-butyl ester. The resulting residue was purified by chromatography on silica gel using 100% dichlormethane to 94% dichloromethane/methanol to provide the title compound (yield: 194 mg, 91%).

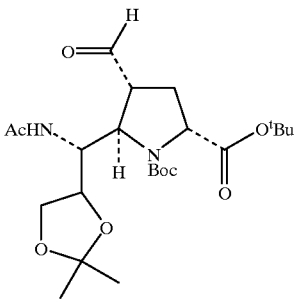

189JJ (±)-(2R,3R,5R,1'R,2'S)-1-t-Butoxycarbonyl-2-(1-acetamido-1-(2,2-dimethyl-1,3-dioxolan-4-yl))methyl-3-formyl-pyrrolidine-5-carboxylic Acid t-Butyl Ester The title compound was prepared according to the method described in Example 123H substituting (±)-(2R,3R,5R,1'R,2'S)-1-t-butoxycarbonyl-2-(1-acetamido-1-(2,2-dimethyl-1,3-dioxolan-4-yl))methyl-3-hydroxymethyl-pyrrolidine-5-carboxylic acid t-butyl ester for (±)-(2R,3R,5R,1'S)-1-t-butoxycarbonyl-2-oxiranyl-3-hydroxymethyl-pyrrolidine-5-carboxylic acid t-butyl ester.

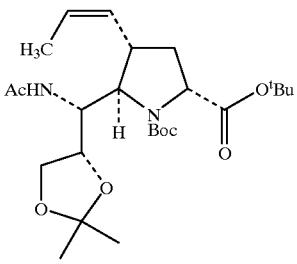

189K (±)-(2R,3S,5R,1'R,2'S)-1-t-Butoxycarbonyl-2-(1-acetamido-1-(2,2-dimethyl-1,3-dioxolan-4-yl))methyl-3-(cis-propen-1-yl))-pyrrolidine-5-carboxylic Acid t-Butyl Ester The title compound was prepared according to the method described in Example 35A substituting (±)-(2R,3R,5R,1'R,2'S)-1-t-butoxycarbonyl-2-(1-acetamido-1-(2,2-dimethyl-1,3-dioxolan-4-yl))methyl-3-formyl-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester (yield: 11.5 mg, 59%).

$^1$H NMR (CDCl$_3$): δ6.62 (d, 1H), 5.56 (m, 1H), 5.40 (m, 1H), 4.43 (m, 1H), 4.25 (m, 1H), 4.16 (m, 1H), 4.02 (m, 1H), 3.88 (m, 1H), 3.54 (m 1H), 3.14 (m, 1H), 2.54 (m 1H), 2.04 (s, 3H), 1.71 (m 1H), 1.60 (dd, 3H), 1.46 (s, 9H), 1.45 (s, 9H), 1.40 (s, 3H), 1.32 (s, 3H).

MS: (M+H)$^+$=483

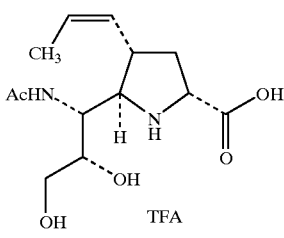

189L (±)-(2R,3S,5R,1'R,2'S)-2-(1-Acetamido-2,3-dihydroxy)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-1-(2,2-dimethyl-1,3-dioxolan-4-yl))methyl-3-(cis-propen-1-yl)-pyrrolidine-5-carboxylic acid t-butyl ester in place (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

$^1$H NMR (DMSO-d$_6$): δ7.84 (d, J=9 Hz, 1H), 5.49 (m, 1H), 5.27 (m, 1H), 4.47 (m, 1H), 4.25 (m, 1H), 4.17 (m, 1H), 3.75 (m, 1H), 3.59 (m, 1H), 3.35 (m, 1H), 3.18 (m, 1H), 2.43 (m, 1H), 1.81 (s, 3H),1.55 (dd, 3H).

MS: (M+H)$^+$=287

EXAMPLE 190

(±)-(2R,3R,5R,1'R,2'R)-2-(1-Acetamido-2,3-dihydroxy)propyl-3-(cis-propen-1-yl)-pyrrolidine-5-carboxylic Acid Trifluoroacetic Acid Salt

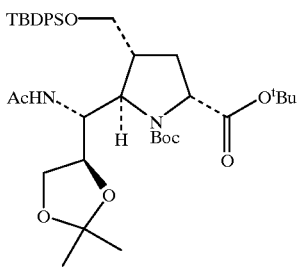

190A (±)-(2R,3R,5R,1'R,2'R)-1-t-Butoxycarbonyl-2-(1-acetamido-1-(2,2-dimethyl-1,3-dioxolan-4-yl))methyl-3-t-butyldiphenylsilyloxymethyl-pyrrolidine-5-carboxylic Acid t-Butyl Ester The title compound was prepared according to the method described in Example 189I substituting (±)-(2R,3R,5R,1'R,2'R)-1-t-butoxycarbonyl-2-(1-acetamido-2,3-dihydroxy)propyl-3-t-butyldiphenylsilyloxymethyl-pyrrolidine-5-carboxylic acid t-butyl ester in place of (±)-(2R,3R,5R,1'R,2'S)-1-t-Butoxycarbonyl-2-(1-acetamido-2,3-dihydroxy)propyl-3-t-butyldiphenylsilyloxymethyl-pyrrolidine-5-carboxylic acid t-butyl ester.

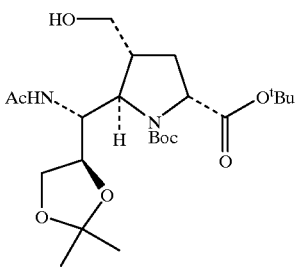

190B (±)-(2R,3R,5R,1'R,2'R)-1-t-Butoxycarbonyl-2-(1-acetamido-1-(2,2-dimethyl-1,3-dioxolan-4-yl))methyl-3-hydroxymethyl-pyrrolidine-5-carboxylic Acid t-Butyl Ester The title compound was prepared according to the method described in Example 123G substituting (±)-(2R,3R,5R,1'R,2'R)-1-t-butoxycarbonyl-2-(1-acetamido-1-(2,2-dimethyl-1,3-dioxolan-4-yl))methyl-3-t-butyldiphenylsilyloxymethyl-pyrrolidine-5-carboxylic acid t-butyl ester for (±)-(2R,3R,5R,1'S)-1-t-butoxycarbonyl-2-oxiranyl-3-t-butyldiphenylsilyloxymethyl-pyrrolidine-5-carboxylic acid t-butyl ester.

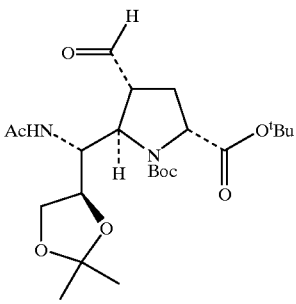

190C (±)-(2R,3R,5R,1'R,2'R)-1-t-Butoxycarbonyl-2-(1-acetamido-1-(2,2-dimethyl-1,3-dioxolan-4-yl))methyl-3-formyl-pyrrolidine-5-carboxylic Acid t-Butyl Ester The title compound was prepared according to the method described in Example 123H substituting (±)-(2R,3R,5R,1'R,2'R)-1-t-butoxycarbonyl-2-(1-acetamido-1-(2,2-dimethyl-1,3-dioxolan-4-yl))methyl-3-hydroxymethyl-pyrrolidine-5-carboxylic acid t-butyl ester for (±)-(2R,3R,5R,1'S)-1-t-butoxycarbonyl-2-oxiranyl-3-hydroxymethyl-pyrrolidine-5-carboxylic acid t-butyl ester.

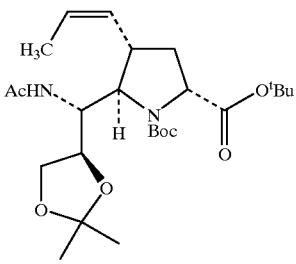

190D (±)-(2R,3S,5R,1'R,2'R)-1-t-Butoxycarbonyl-2-(1-acetamido-1-(2,2-dimethyl-1,3-dioxolan-4-yl))methyl-3-(cis-propen-1-yl)-pyrrolidine-5-carboxylic Acid t-Butyl Ester The title compound was prepared according to the method described in Example 35A substituting (±)-(2R,3R,5R,1'R,2'R)-1-t-butoxycarbonyl-2-(1-acetamido-1-(2,2-dimethyl-1,3-dioxolan-4-yl))methyl-3-formyl-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester (yield: 42 mg, 61%).

$^1$H NMR (CDCl$_3$): δ7.88 (d, 1H), 5.52 (m, 1H), 5.34 (m, 1H), 4.33 (m, 1H), 4.21 (m, 1H), 3.96 (m, 2H), 8.88 (m, 1H), S8.0 (m, 1H), 8.40 (m, 1H), 2.53 (m, 1H), 1.98 (s, 3H), 1.66 (dd, 3H), 1.46 (s, 9H), 1.44 (s, 9H), 1.41 (s, 3H), 1.33 (s, 3H).

MS: (M+H)$^+$=483

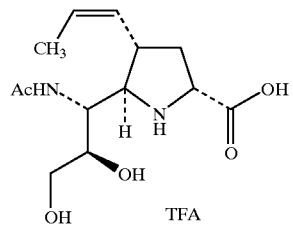

190E (±)-(2R,3S,5R,1'R,2'R)-2-(1-Acetamido-2,3-dihydroxy)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'R)-1-t-butoxycarbonyl-2-(1-acetamido-1-(2,2-dimethyl-1,3-dioxolan-4-yl))methyl-3-(cis-propen-1-yl))-pyrrolidine-5-carboxylic acid t-butyl ester in place of (±)-(2R,3S,5R,1'R,2'R)-1-t-butoxycarbonyl-2-(1-acetamido-2-hydroxy)butyl-3-(cis-propen-1-yl)-pyrrolidine-5-carboxylic acid t-butyl ester.

$^1$H NMR (DMSO-d$_6$): δ7.98 (d, J=9 Hz, 1H), 5.48 (m, 1H), 5.29 (m, 1H), 4.60 (m, 1H), 4.30 (m, 1H), 4.12 (m, 1H), 3.76 (m, 1H), 3.52 (m, 1H), 3.46 (m, 1H), 3.32 (m, 1H), 3.18 (m, 1H), 2.40 (m, 1H), 1.84 (s, 3H), 1.60 (dd, 3H).

MS: (M+H)$^+$=287

EXAMPLE 193

(±)-(2R,3S,5R,1'R,2'S)-2-(1-Acetamido-2-ethoxy)pentyl-3-(cis-propen-1-yl)-pyrrolidine-5-carboxylic Acid Trifluoroacetic Acid Salt

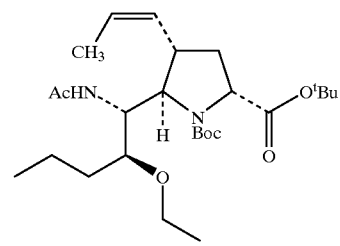

193A (±)-(2R,3S,5R,1'R,2'S)-1-t-Butoxycarbonyl-2-(1-acetamido-2-ethoxy)pentyl-3-(cis-propen-1-yl)-pyrrolidine-5-carboxylic Acid t-Butyl Ester The title compound was prepared according to the method described in Example 88A, substituting ethyl iodide for methyl iodide (yield: 3.6 mg, 28%).

MS: (M+H)$^+$=483, (M+Na)$^+$=505, (M−H)$^−$=481.

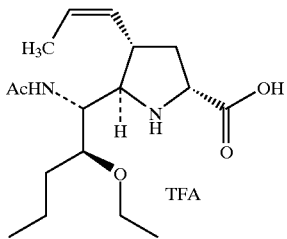

193B (±)-(2R,3S,5R,1'R,2'S)-2-(1-Acetamido-2-ethoxy)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-ethoxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester ester (yield: 3.2 mg, 100%).

$^1$H NMR (DMSO-$d_6$) δ7.92 (d, J=9.2 Hz, 1H), 5.47 (m, 1H), 5.25 (m, 1H), 4.25 (m, 2H), 3.70 (m, 1H), 3.52 (m, 1H), 3.33 (m, 2H), 3.18 (m, 1H), 2.39 (m, 1H), 1.85 (s, 3H), 1.66 (m, 1H), 1.61 (dd, J=6.7, 1.8 Hz, 3H), 1.56 (m, 1H), 1.37 (m, 1H), 1.28 (m, 2H), 1.13 (m, 3H), 0.86 (t, J=7.3 Hz, 3H).

MS: (M+H)$^+$=327, (M+Na)$^+$=349, (M−H)$^−$=325.

EXAMPLE 194

(±)-(2R,3S,5R,1'R,2'R)-2-(1-Acetamido-2-ethoxy)pentyl-3-(cis-propen-1-yl)-pyrrolidine-5-carboxylic Acid Trifluoroacetic Acid Salt

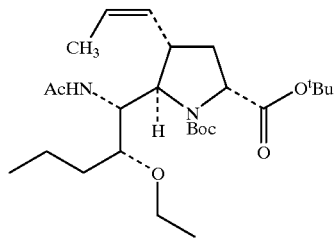

194A (±)-(2R,3S,5R,1'R,2'R)-1-t-Butoxycarbonyl-2-(1-acetamido-2-ethoxy)pentyl-3-(cis-propen-1-yl)-pyrrolidine-5-carboxylic Acid t-Butyl Ester The title compound is prepared according to the method described in Example 88A, substituting ethyl iodide for methyl iodide.

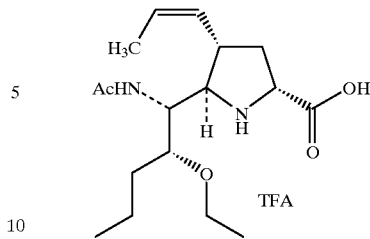

194B (±)-(2R,3S,5R,1'R,2'R)-2-(1-Acetamido-2-ethoxy)pentyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'R)-1-t-butoxycarbonyl-2-(1-acetamido-2-ethoxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

EXAMPLE 195

(±)-(2R,3S,5R,1'S)-2-(1-Acetamido-2-hydroxy)ethyl-3-vinyl-pyrrolidine-5-carboxylic Acid Trifluoroacetic Acid Salt

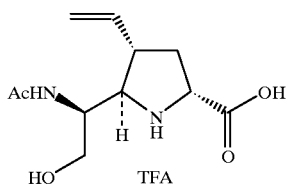

The title compound was prepared according to the method described in Example 41C, substituting (±)-(2R,3S,5R,1'S)-1-t-butoxycarbonyl-2-(1-acetamido-2-hydroxy)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 19.9 mg, 100%).

$^1$H NMR (DMSO-$d_6$) δ7.80 (d, J=8.8 Hz, 1H), 5.76 (m, 1H), 5.23 (d, J=17.1 Hz, 1H), 5.15 (m, 1H), 4.31 (m, 1H), 4.03 (m, 1H), 3.62 (m, 1H), 3.53 (m, 2H), 2.79 (m, 1H), 2.42 (m, 1H), 1.90 (s, 3H), 1.85 (m, 1H).

MS (M+H)$^+$=243, (M+Na)$^+$=265, (M−H)$^−$=241.

EXAMPLE 196

(±)-(2R,3S,5R,1'R,2'S)-2-(1-Acetamido-2-hydroxy-3-dimethylphosphonyl)propyl-3-(cis-propen-1-yl)-pyrrolidine-5-carboxylic Acid Trifluoroacetic Acid Salt

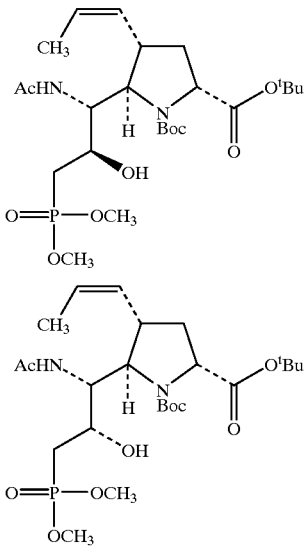

196A (±)-(2R,3S,5R,1'R,2'S) and (±)-(2R,3S,5R,1'R,2'R)-1-t-Butoxycarbonyl-2-(1-acetamido-2-hydroxy-3-dimethylphosphonyl)propyl-3-(cis-propen-1-yl)-pyrrolidine-5-carboxylic Acid t-Butyl Ester (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester (78 mg, 0.19 mmol) in THF (5 mL) was added dropwise to a solution of dimethylphosphonylmethyl lithium (3M) (0.32 mL, 0.95 mmol) in THF (20 mL) at −78° C. and reacted for 40 minutes. The reaction was quenched with water (10 mL) and saturated aqueous ammonium chloride (10 mL) followed by extraction using dichloromethane (2×50 mL). The organic layer was dried over magnesium sulfate, filtered and concentrated in vacuo. The residue was purified by column chromatography on silica gel using 5–10% methanol in dichloromethane to provide the title compounds (±)-(2R,3S,5R,1'R,2'R) isomer (yield: 27 mg, 27%) and (±)-(2R,3S,5R,1'R,2'S) isomer (yield: 5.5 mg, 6%).

(±)-(2R,3S,5R,1'R,2'R) $^1$H NMR (CDCl$_3$) δ5.98 (m, 1H), 5.58(m, 1H), 5.35(m, 1H), 4.94(m, 1H), 4.14(m, 2H), 3.74 (m, 8H), 3.06(m, 1H), 2.64(m, 1H), 2.03(s, 3H), 1.95(m, 1H), 1.83(m, 3H), 1.53(s, 9H), 1.46(s, 9H)

MS: (M+H)$^+$=535, (M−H)$^−$=533

(±)-(2R,3S,5R,1'R,2'S) MS: (M+H)$^+$=535, (M−H)$^−$=533

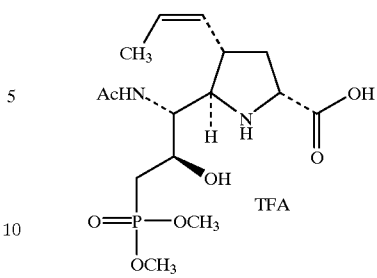

196B (±)-(2R,3S,5R,1'R,2'S)-2-(1-Acetamido-2-hydroxy-3-dimethylphosphonyl)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-dimethylphosphonyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield 3 mg, 96%).

$^1$H NMR (DMSO-d$_6$) δ7.98(d, J=9.2 Hz, 1H), 5.48(M, 1H), 5.28(m, 1H), 4.36(m, 1H), 4.30(m, 1H), 4.08(m, 2H), 3.70(m, 2H), 3.60(m, 6H), 3.18(m, 1H), 2.40(m, 1H), 2.05 (m, 1H), 1.85(s, 3H), 1.60(dd, J=6.2, 1.2 Hz, 3H) MS: (M+H)$^+$=379, (M−H)$^−$=377

EXAMPLE 197

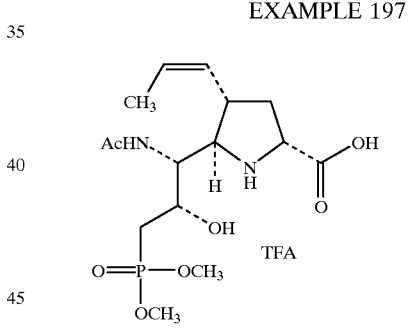

(±)-(2R,3S,5R, 1'R,2'R)-2-(1-Acetamido-2-hydroxy-3-dimethylphosphonyl)propyl-3-(cis-propen-1-yl)-pyrrolidine-5-carboxylic Acid Trifluoroacetic Acid Salt The title compound was prepared according to the method described in EXAMPLE 41C, substituting (±)-(2R,3S,5R,1'R,2'R)-1-t-butoxycarbonyl-2-(1-acetamido-2-hydroxy-dimethylphosphonyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 13 mg, 96%).

$^1$H NMR (DMSO-d$_6$) δ7.72 (d, J=9.2 HZ, 1H), 5.48(m, $_1$H), 5.24(m, 1H), 4.44(m, 1H), 4.15(m, 2H), 3.62(m, 7H), 3.54(m, 1H), 3.15(m, 1H), 2.40(m, 1H), 1.95(m, 1H), 1.82(s, 3H), 1.72(m, 1H), 1.54(dd, J=6.7, 1.2 HZ, 3H)

MS: (M+H)$^+$=379, (M−H)$^−$=377

EXAMPLE 198

(±)-(2R,3S,5R,1'S)-2-(1-Acetamido-3-hydroxy)propyl-3-(cis-propen-1-yl)-pyrrolidine-5-carboxylic Acid Trifluoroacetic Acid Salt

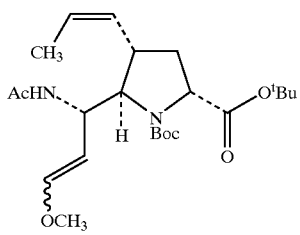

198A (±)-(2R,3S,5R,1'S)-1-t-Butoxycarbonyl-2-(1-acetamido-1-(cis and trans-2-methoxyvinyl))methyl-3-(cis-propen-1-yl)-pyrrolidine-5-carboxylic Acid t-Butyl Ester (±)-(2R,3S,5R,1'R)-1-t-Butoxycarbonyl-2-(1-acetamido-1-formyl)methyl-3-(cis-propen-1-yl)-pyrrolidine-5-carboxylic acid t-butyl ester (113 mg, 0.28 mmol) was added to a solution of (methoxymethyl)triphenylphosphonium bromide (240 mg, 0.70 mmol) and potassium t-butoxide (0.56 mL, 0.56 mmol, 1M in THF) in toluene (3 mL) at 0° C. for 15 minutes. The reaction was quenched with saturated aqueous ammonium chloride (3 mL) followed by extraction using dichloromethane (2×3 mL). The organic layer was dried over magnesium sulfate, filtered and concentrated in vacuo. The residue was purified by column chromatography on silica gel using 1/4: ethyl acetate/hexane to provide the title compounds $^1$H NMR (CDCl$_3$) δ8.65 (br d, 1H) 6.01 (d, J=5.7 Hz, 1H), 5.40 (m, 3H), 5.11 (br t, 1H), 4.15 (m, 2H), 3.72 (m, 1H) 3.61 (s, 3H), 3.00 (m, 1H), 2.42 (m, 1H), 1.94 (s, 3H), 1.64 (dd, J=1.4, 5.0 Hz, 3H), 1.45 (m, 9H), 1.25 (m, 9H)

MS: (M+H)$^+$=439.

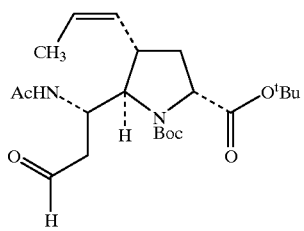

198B (±)-(2R,3S,5R,1'S)-1-t-Butoxycarbonyl-2-(1-acetamido-2-formyl)ethyl-3-(cis-propen-1-yl)-pyrrolidine-5-carboxylic Acid t-Butyl Ester (±)-(2R,3S,5R,1'S)-1-t-Butoxycarbonyl-2-(1-acetamido-2-(cis and trans-2-methoxyvinyl))methyl-3-(cis-propen-1-yl)-pyrrolidine-5-carboxylic acid t-butyl ester (21 mg, 0.048 mmol) was reacted with LiBr (37 mg, 0.43 mmol) and AG50W-X2 ion exchange resin in CH$_3$CN (2 mL) and water (0.1 mL) at room temperature for 45 minutes. The reaction was filtered and quenched with saturated aqueous sodium bicarbonate (1 mL) followed by extraction using dichloromethane (2×1 mL). The organic layer was dried over magnesium sulfate, filtered and concentrated in vacuo. The residue was purified by column chromatography on silica gel using 1/4: ethyl acetate/hexane to provide the title compound.

$^1$H NMR (CDCl$_3$) δ9.70 (dd, J=1.3, 2.4 Hz, 1H), 8.11 (d, J=7.8 Hz, 1H), 5.54 (m, 1H), 5.41 (t, J=5.8 Hz, 1H), 4.52 (m, 1H), 4.13 (dd, J=4.4, 4.8 Hz, 1H), 3.75 (dd, J=2.7, 3.1 Hz, 1H), 2.86 (m, 1H), 2.47 (m, 3H), 1.99 (s, 3H), 1.63 (dd, J=1.6, 5.1 Hz, 3H), 1.46 (s, 9H), 1.45 (m, 1H), 1.44 (s, 9H)

MS: (M+H)$^+$=425; (M−H)$^-$=423.

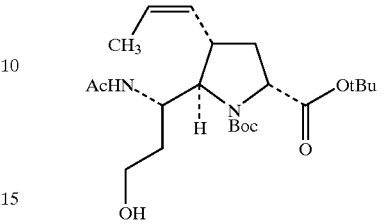

198C (±)-(2R,3S,5R,1'S)-1-t-Butoxycarbonyl-2-(1-acetamido-3-hydroxy)propyl-3-(cis-propen-1-yl)-pyrrolidine-5-carboxylic Acid t-Butyl Ester (±)-(2R,3S,5R,1'S)-1-t-Butoxycarbonyl-2-(1-acetamido-2-formyl)ethyl-3-(cis-propen-1-yl)-pyrrolidine-5-carboxylic acid t-butyl ester (9 mg, 0.02 mmol) was reacted with sodium borohydride (1 mg, 0.02 mmol) in methanol (0.1 mL) at room temperature for 20 minutes. The reaction was quenched with saturated aqueous ammonium chloride (1 mL) followed by extraction using dichloromethane (2×1 mL). The organic layer was dried over magnesium sulfate, filtered and concentrated in vacuo. The residue was purified by column chromatography on silica gel using 1/4: ethyl acetate/hexane to provide the title compound.

$^1$H NMR (CDCl$_3$) δ8.45 (d, J=7.5 Hz, 1H), 5.55 (m, 1H), 5.34 (t, J=7.8 Hz, 1H), 4.20 (dd, J=3.0, 5.4 Hz, 2H), 3.71 (d, J=6.1 Hz, 1H), 3.62 (m, 1H), 3.50 (t, J=9.1 Hz, 1H), 2.92 (m, 1H), 2.41 (m, 1H), 2.04 (s, 3H), 1.66 (dd, J=2.0, 5.1 Hz, 3H), 1.62 (m, 1H), 1.47 (s, 9H), 1.45 (m, 1H), 1.43 (s, 9H), 1.22 (m, 2H)

MS: (M+H)$^+$=427; (M−H)$^-$=425.

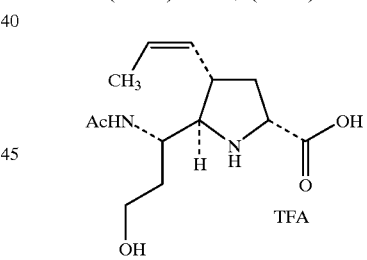

198D (±)-(2R,3S,5R,1'S)-2-(1-Acetamido-3-hydroxy)propyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'S)-1-t-butoxycarbonyl-2-(1-acetamido-2-hydroxy)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 4.6 mg, 100%).

$^1$H NMR (DMSO-d$_6$) δ9.25 (br s, 1H), 8.13 (d, J=7.3 Hz, 1H), 5.52 (m, 1H), 5.28 (br t, 1H), 4.32 (br t, 1H), 4.22 (m, 1H), 3.49 (m, 4H), 3.18 (m, 1H), 2.40 (m, 1H), 1.90 (s, 3H), 1.73 (m, 1H), 1.63 (dd, J=1.8, 5.5 Hz, 3H), 1.57 (m, 1H)

MS: (M−H)$^-$=269; (M+H)$^+$=271.

EXAMPLE 199

(±)-(2R,3S,5R,1'S,3'S)-2-(1-Acetamido-3-hydroxy)
pentyl-3-(cis-propen-1-yl)-pyrrolidine-5-carboxylic
Acid Trifluoroacetic Acid Salt

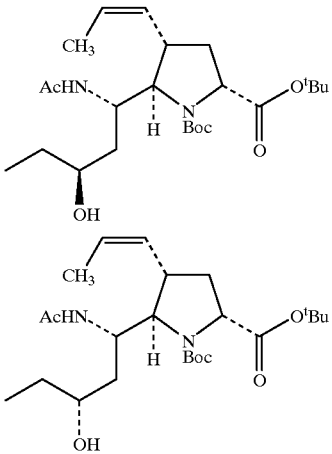

199A (±)-(2R,3S,5R,1'S,3'S) and (±-(2R,3S,1'R, 3'R)-1-t-Butoxycarbonyl-2-(1-acetamido-3-hydroxy) ethyl-3-(cis-propen-1-yl)-pyrrolidine-5-carboxylic Acid t-Butyl Ester (±)-(2R,3S,5R,1'S)-1-t-Butoxycarbonyl-2-(1-acetamido-2-formyl)ethyl-3-(cis-propen-1-yl)-pyrrolidine-5-carboxylic acid t-butyl ester (26 mg, 0.061 mmol) was reacted with ethylmagnesium bromide (3.0 M) (0.122 mL, 0.367 mmol) in THF (4 mL) at room temperature for 30 minutes. The reaction was quenched with saturated aqueous ammonium chloride (10 mL) and water (10 mL) followed by extraction using ethyl acetate (3×25 mL). The organic layer was dried over magnesium sulfate, filtered and concentrated in vacuo. The residue was purified by column chromatography on silica gel using 1/1 ethyl acetate/hexane followed by 2/1 ethyl acetate/hexane to provide the title compounds (±)-(2R,3S,5R,1'S,2'S) (yield: 6.7 mg, 24%) and (±)-(2R, 3S,5R,1'S,2'R) (yield: 6.8 mg, 24%).

(±)-(2R,3S,5R,1'S,2'S) MS: (M+H)$^+$=455, (M+Na)$^+$=477, (M−H)$^-$=453.

(±)-(2R,3S,5R,1'S,2'R) MS: (M+H)$^+$=455, (M+Na)$^+$=477, (M−H)$^-$=453.

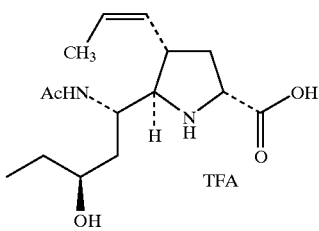

199B (±)-(2R,3S,5R,1'S,3'S)-2-(1-Acetamido-3-hydroxy)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'S, 3'S)-1-t-butoxycarbonyl-2-(1-acetamido-3-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 6.2 mg, 100%).

$^1$H NMR (DMSO-d$_6$) δ9.20 (bs, 1H), 8.18 (d, J=7.3 Hz, 1H), 5.51 (m, 1H), 5.27 (m, 1H), 4.30 (m, 1H), 4.25 (m, 1H), 3.58 (m, 1H), 3.41 (m, 1H), 3.18 (m, 1H), 2.39 (m, 1H), 1.90 (s, 3H), 1.75 (m, 1H), 1.64 (dd, J=7.5,1.5 Hz, 3H), 1.51 (M, 1H), 1.38 (m, 1H), 1.32 (m, 1H), 0.83 (t, J=7.3 Hz, 3H).

MS: (M+H)$^+$=299, (M+Na)$^+$=321, (M−H)$^-$=297, (2M−H)$^-$=595.

EXAMPLE 200

(±)-(2R,3S,5R,1'S,3'R)-2-(1-Acetamido-3-hydroxy)
pentyl-3-(cis-propen-1-yl)-pyrrolidine-5-carboxylic
Acid Trifluoroacetic Acid Salt

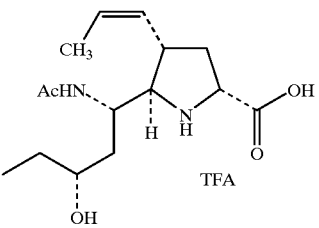

The title compound was prepared according to the method described in Example 41C, substituting (±)-(2R,3S,5R, 1'S, 3'R)-1-t-butoxycarbonyl-2-(1-acetamido-3-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 6.5 mg, 100%).

$^1$H NMR (DMSO-d$_6$) δ9.25 (bs, 1H), 8.15 (d, J=7.3 Hz, 1H), 5.52 (m, 1H), 5.27 (m, 1H), 4.31 (m, 2H), 3.52 (m, 1H), 3.36 (m, 1H), 3.19 (quint., J=8.5 Hz, 1H), 2.38 (m, 1H), 1.92 (s, 3H), 1.75 (m, 1H), 1.64 (dd, J=7.3,1.5 Hz 3H), 1.48 (m, 1H), 1.33 (m, 2H), 0.85 (t, J=7.3 Hz, 3H).

MS: (M+H)$^+$=299, (M+Na)$^+$=321, (M−H)$^-$=297, (2M−H)$^-$=595.

EXAMPLE 201

(±)-(2R,3S,5R,1'R)-2-(1-Acetamido-2-oxo-3,3-difluoro-3-vinyl)propyl-3-(cis-propen-1-yl)-pyrrolidine-5-carboxylic Acid Trifluoroacetic Acid Salt

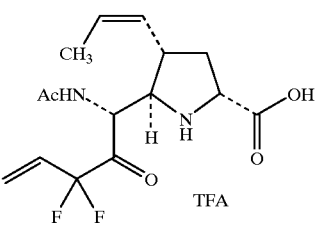

The title compound was prepared according to the method described in Example 41C, substituting (±)-(2R,3S,5R,1'R)-1-t-butoxycarbonyl-2-(1-Acetamido-2-oxo-3,3-difluoro-3- vinyl)propyl-3-(cis-propen-1-yl)-pyrrolidine-5-carboxylic Acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0050 g, 100%).

$^1$H NMR (DMSO-d$_6$) δ8.67 (d, J=8.5 Hz, 1H), 6.1–5.95 (m, 1H), 5.78 (dd, J=17.1, 2.4 Hz, 1H), 5.71 (d, 11.0 Hz, 1H), 5.45 (m, 1H), 5.12 (m, 1H), 4.94 (t, J=9.2 Hz, 1H), 4.51 (dd, J=12.2,6.1 Hz, 1H), 3.98 (m, 1H), 3.24 (m, 1H), 2.32 (m, 1H), 1.73 (s, 3H), 1.66 (q, J=11.9 Hz, 1H), 1.57 (dd, J=6.7,1.8 Hz, 3H).

MS: (M+H)$^+$=331, (M+H$_2$O)$^+$=349, (M+Na)$^+$=353, (M−H)$^−$=329, (2M−H)$^−$=659.

EXAMPLE 202

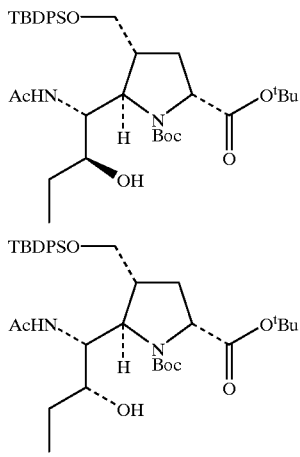

202A (±)-(2R,3R,5R,1'R,2'S) and (±)-(2R,3R,5R, 1'R,2'R)-1-t-Butoxycarbonyl-2-(1-acetamido-2-hydroxy)butyl-3-t-butyldiphenylsilyloxymethyl-pyrrolidine-5-carboxylic Acid t-Butyl Ester The title compounds were prepared according to the method described in Example 41B substituting (±)-(2R,3R, 5R,1'R)-1-t-butoxycarbonyl-2-(1-acetamido-2-formyl) ethyl-3-t-butyldiphenylsilyloxymethyl-pyrrolidine-5-carboxylic acid t-butyl ester in place of (±)-(2R,3S,5R,1'R)-1-t-butoxycarbonyl-2-(1-acetamido-2-formyl)ethyl-3-(cis-propen-1-yl)-pyrrolidine-5-carboxylic acid t-butyl ester to provide (±)-(2R,3R,5R,1'R,2'S) isomer (yield: 370 mg, 17%) and (±)-(2R,3R,5R,1'R,2'R) isomer (yield: 1.2 g, 55%).

(±)-(2R,3R,5R,1'R,2'S) $^1$H NMR(d$_6$-DMSO) δ7.4–7.65 (m, 10H), 4.47 (d, 1H), 4.32 (m, 1H), 3.87 (m, 2H), 3.68 (m, 1H), 3.55 (m, 1H), 3.25 (m,1H), 2.7 (m, 1H), 2.45 (m, 1H), 2.0 (m, 1H), 1.83 (d, 3H), 1.28–1.4 (m, 18H), 0.95 (d, 0.83 (dt, 3H).

MS: (M−H)−=667, (M+35)$^+$=703; (M+H)$^+$=669, (M+Na)+=691

(±)-(2R,3R,5R,1'R,2'R) $^1$H NMR(d$_6$-DMSO) δ7.4–7.65 (m, 10H), 4.40 (dd, 1H), 4.12–4.32 (m, 1H), 3.82–3.96 (m, 1H), 3.66 (m, 2H), 3.52 (t, 1H), 2.6–2.8 (m, 1H), 2.45 (m, 1H), 1.76–2.0 (m, 1H), 1.87 (d, 3H), 1.25–1.4 (m, 18H), 0.95 (d, 9H), 0.83 (dt, 3H).

MS: (M−H)−=667, (M+35)$^+$=703; (M+H)$^+$=669, (M+Na)+=691

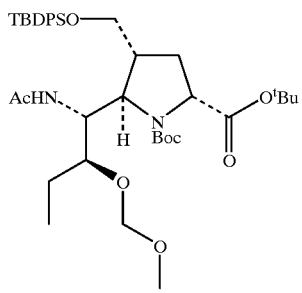

202B (±)-(2R,3R,5R,1'R,2'S)-1-t-Butoxycarbonyl-2-(1-acetamido-2-methoxymethyloxy)butyl-3-t-butyldiphenylsilyloxymethyl-pyrrolidine-5-carboxylic Acid t-Butyl Ester (±)-(2R,3R,5R,1'R,2'S)-1-t-butoxycarbonyl-2-(1-acetamido-2-hydroxy)butyl-3-t-butyldiphenylsilyloxymethyl-pyrrolidine-5-carboxylic acid t-butyl ester (0.58 g,0.87 mmole) was reacted with methoxymethyl chloride (1.15 mL, 10.07 mmole) and diisopropylethylamine (3.5 mL, 20.1 mmole) in dichloromethane (1 mL) at room temperature for 5 hours. The reaction was quenched with saturated NH$_4$Cl (100 mL) and diluted with ethyl acetate (200 mL). The organic layer was washed with water, and brine, dried over MgSO$_4$, filtered and concentrated in vacuo. The residue was purified by chromatography on silica gel using 5% methanol/methylene chloride to provide the title compound (yield, 0.64 g, 98%).

$^1$H NMR(d$_6$-DMSO) δ7.4–7.65 (m, 10H), 4.70 (s, 1H), 4.62 (s, 1H), 4.35–4.55 (m, 2H), 3.75–3.95 (m, 2H), 3.68 (m, 1H), 3.55 (m, 1H), 3.25 (m, 1H), 3.24 (s, 3H), 2.55 (m, 1H), 2.45 (m, 1H), 2.0 (m, 1H), 1.85 (s, 3H), 1.28–1.4 (m, 18H), 0.99 (d, 9H), 0.8 (dt, 3H)

MS: (M−H)−=755, (M+35)$^+$=791; (M+H)$^+$=757, (M+Na)+=779

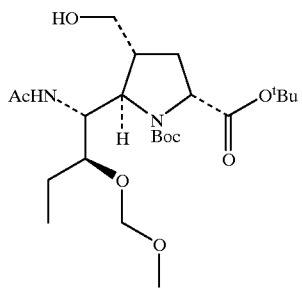

202C (±)-(2R,3R,5R,1'R,2'S)-1-t-Butoxycarbonyl-2-(1-acetamido-2-methoxymethyloxy)butyl-3-hydroxymethyl-pyrrolidine-5-carboxylic Acid t-Butyl Ester The title compound was prepared according to the method described in Example 123G substituting (±)-(2R,3R,5R,1'R, 2'S)-1-t-butoxycarbonyl-2-(1-acetamido-2-methoxymethyloxy)butyl-3-t-butyldiphenylsilyloxymethyl-pyrrolidine-5-carboxylic acid t-butyl ester in place of (±)-(2R,3R,5R,1'S)-1-t-butoxycarbonyl-2-oxiranyl-3-t-butyldiphenylsilyloxymethyl-pyrrolidine-5-carboxylic acid t-butyl ester (yield: 0.416 g, 95%).

$^1$H NMR(d$_6$-DMSO) δ7.45 (t, 1H), 4.62–4.74 (m, 3H), 4.48 (m, 1H), 3.85 (m, 2H), 3.55–3.6 (m, 2H), 3.45 (t, 1H), 3.2–3.4 (m, 2H), 3.25 (d, 3H), 2.4 (m, 2H), 1.82 (d, 3H), 1.58 (m, 3H), 1.32–1.45 (m, 18H), 0.82 (dt, 3H).

MS: (M−H)−=517, (M+35)+=553; (M+H)+=519, (M+Na)+=541

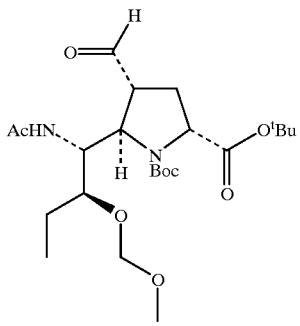

202D (±)-(2R,3R,5R,1'R,2'S)-1-t-Butoxycarbonyl-2-(1-acetamido-2-methoxymethyloxy)butyl-3-formyl-pyrrolidine-5-carboxylic Acid t-Butyl Ester The title compound was prepared according to the method described in Example 123H substituting (±)-(2R,3R,5R,1'R,2'S)-1-t-butoxycarbonyl-2-(1-acetamido-2-methoxymethyloxy)butyl-3-hydroxymethyl-pyrrolidine-5-carboxylic acid t-butyl ester in place of (±)-(2R,3R,5R,1'S)-1-t-butoxycarbonyl-2-oxiranyl-3-hydroxymethyl-pyrrolidine-5-carboxylic acid t-butyl ester (yield: 0.335 g, 80.8%).

$^1$H NMR(d$_6$-DMSO) δ9.55 (d, 1H), 7.48 (m, 1H), 4.55–4.72 (m, 4H) 3.9 (d, 1H), 3.6 (m, 2H), 3.45 (m, 3H), 3.32 (s, 3H), 3.05 (t, 1H), 2.25–2.45 (m, 4H), 1.83 (s, 3H), 1.58 (m, 3H), 1.30–1.45 (m, 18H), 0.86 (dt, 3H).

MS: (M−H)−=515, (M+35)+=551; (M+H)+=517

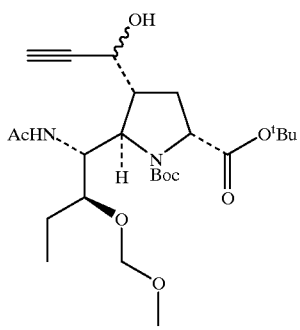

202E (±)-(2R,3R,5R,1'R,2'S,1"RS)-1-t-Butoxycarbonyl-2-(1-acetamido-2-methoxymethyloxy)butyl-3-(1-hydroxy-2-propyn-1yl)-pyrrolidine-5-carboxylic Acid t-Butyl Ester The title compound was prepared according to the method described in Example 38A substituting (±)-(2R,3R,5R,1'R,2'S)-1-t-butoxycarbonyl-2-(1-acetamido-2-methoxymethyloxy)butyl-3-formyl-pyrrolidine-5-carboxylic acid t-butyl ester in place of (±)-(2R,3R,5R,1'S)-1-t-butoxycarbonyl-2-(1-acetamido-3-methyl)butyl-3-formyl-pyrrolidine-5-carboxylic acid t-butyl ester (yield: 0.27 g, 83%).

MS: (M−H)−=541, (M+35)+=577; (M+H)+=543, (M+Na)+=565

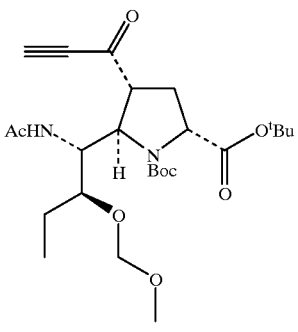

202F (±)-(2R,3R,5R,1'R,2'S)-1-t-Butoxycarbonyl-2-(1-acetamido-2-methoxymethyloxy)butyl-3-(1-oxo-2-propyn-1-yl)-pyrrolidine-5-carboxylic Acid t-Butyl Ester The title compound was prepared according to the method described in Example 38B substituting (±)-(2R,3R,5R,1'R,2'S,1"RS)-1-t-butoxycarbonyl -2-(1-acetamido-2-methoxymethyloxy)butyl-3-(1-hydroxy-2-propyn-1-yl)-pyrrolidine-5-carboxylic acid t-butyl ester in place of (±)-(2R,3R,5R,1'S,1"RS)-1-t-butoxycarbonyl-2-(1-acetamido-3-methyl)butyl-3-(1-hydroxy-2-propyn-1-yl)-pyrrolidine-5-carboxylic acid t-butyl ester (yield: 0.2 g, 74%).

$^1$H NMR(d$_6$-DMSO) δ7.49 (br d, 1H), 5.0 (d, 1H), 4.7 (br, 1H), 4.55–4.7 (m, 3H), 3.88 (br d, 1H), 3.5–3.7 (m, 2H), 3.43 (t, 2H), 3.2–3.4 (m, 2H), 3.24 (s, 3H), 2.4–2.7 (m, 2H), 1.84 (s, 3H), 1.5–1.7 (m, 2H), 1.30–1.45 (m, 18H), 0.86 (dt, 3H)

MS: (M−H)−=539, (M+35)+=575; (M+H)+=541, (M+Na)+=563

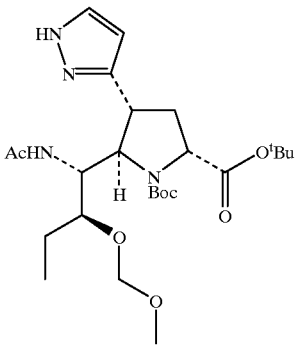

202G (±)-(2R,3R,5R,1'R,2'S)-1-t-Butoxycarbonyl-2-(1-acetamido-2-methoxymethyloxy)butyl-3-(pyrazol-3-yl)-pyrrolidine-5-carboxylic Acid t-Butyl Ester The title compound was prepared according to the method described in Example 38C substituting (±)-(2R,3R,5R,1'R,2'S)-1-t-butoxycarbonyl-2-(1-acetamido-2-methoxymethyloxy)butyl-3-(1-oxo-2-propyn-1-yl)-pyrrolidine-5-carboxylic acid t-butyl ester in place of (±)-(2R,3R,5R,1'S)-1-t-butoxycarbonyl-2-(1-acetamido-3-methyl)butyl-3-(1-oxo-2-propyn-1-yl)-pyrrolidine-5-carboxylic acid t-butyl ester (yield: 180 mg, 87%).

$^1$H NMR(d$_6$-DMSO) δ7.57 (br t, 2H), 6.1 (d, 1H), 4.50–4.7 (m, 4H) 3.95 (m, 1H), 3.4–3.6 (m, 3H), 3.3–3.4(m,

3H), 3.22 (d, 3H), 2.55–2.65 (m, 1H), 2.2 (m, 1H), 1.85 (s, 3H), 1.5–1.7 (m, 2H), 1.15–1.45 (m, 18H), 0.86 (dt, 3H).

MS: (M−H)⁻=553, (M+35)⁺=589: (M+H)⁺⁻553, (M+Na)⁺=577

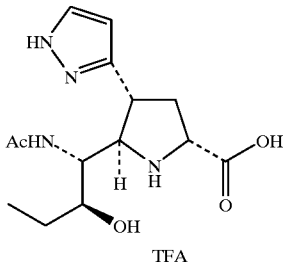

TFA

202H (±)-(2R,3R,5R,1'R,2'S)-2-(1-Acetamido-2-hydroxy)butyl-3-(pyrazol-3-yl)-pyrrolidine-5-carboxylic Acid Trifluoroacetic Acid Salt The title compound was prepared according to the method described in Example 1K, substituting (±)-(2R,3R,5R,1'R,2'S)-1-t-butoxycarbonyl-2-(1-acetamido-2-methoxymethyloxy)butyl-3-(pyrazol-3-yl)-pyrrolidine-5-carboxylic acid t-butyl ester in place of (±)-(2R,3R, 5R, 1'S)-2-(1-acetamido-3-ethyl)pentyl-3-methoxymethyl-pyrrolidine-5-carboxylic acid t-butyl ester. Chromatography on silica gel with 2-propanol:acetic acid:ethyl acetate:water 1:1:3:1 followed by the addition of 0.1% trifluoroacetic acid gave the title compound (yield: 15 mg, 55%).

¹H NMR(d₆-DMSO) δ7.95 (d, 1H), 7.65 (br s,1H), 6.18 (d, 1H), 4.37 (m, 1H), 4.23 (m, 1H), 4.38 (m, 1H), 4.56 (m, 1H), 2.63 (m, 1H), 2.10 (m, 1H), 1.78 (s, 3H), 1.50 (m, 1H), 1.25 (m, 1H), 0.83 (t, J=7.46 Hz, 3H).

MS: (M−H)−=309, (M+35)⁺=345; (M+H)⁺=311, (M+Na)+=333

EXAMPLE 203

(±)-(2R,3R,5R,1'R,2'R)-2-(1-Acetamido-2-hydroxy)butyl-3-(pyrazol-3-yl)-pyrrolidine-5-carboxylic Acid Trifluoroacetic Acid Salt

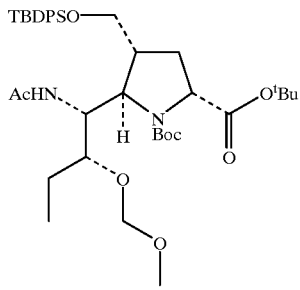

203B (±)-(2R,3R,5R,1'R,2'R)-1-t-Butoxycarbonyl-2-(1-acetamido-2-methoxymethyloxy)butyl-3-t-butyldiphenylsilyloxymethyl-pyrrolidine-5-carboxylic Acid t-Butyl Ester The title compounds were prepared according to the method described in Example 202B substituting (±)-(2R,3R,5R,1'R,2'R)-1-t-butoxycarbonyl-2-(1-acetamido-2-hydroxy)butyl-3-t-butyldiphenylsilyloxymethyl-pyrrolidine-5-carboxylic acid t-butyl ester in place of (±)-(2R,3R,5R,1'R,2'S)-1-t-butoxycarbonyl-2-(1-acetamido-2-hydroxy)butyl-3-t-butyldiphenylsilyloxymethyl-pyrrolidine-5-carboxylic acid t-butyl ester (yield: 0.217 g, 96%).

¹H NMR(d₆-DMSO) δ7.4–7.65 (m, 10H), 4.70 (s, 1H), 4.62 (s, 1H), 4.35–4.55 (m, 2H), 3.75–3.95 (m, 2H), 3.68 (m, 1H), 3.55 (m, 1H), 3.25 (m, 1H), 3.24 (s, 3H), 2.55 (m,1H), 2.45 (m, 1H), 2.0 (m, 1H), 1.85 (s, 3H), 1.28–1.4 (m, 18H), 0.99 (d, 9H), 0.8 (dt, 3H).

MS: (M−H)-=755, (M+35)⁺=791; (M+H)⁺=757, (M+Na)+=779

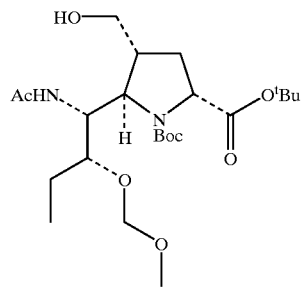

203C (±)-(2R,3R,5R,1'R,2'R)-1-t-Butoxycarbonyl-2-(1-acetamido2-methoxymethyloxy)butyl-3-hydroxymethyl-pyrrolidine-5-carboxylic Acid t-Butyl Ester The title compound was prepared according to the method described in Example 123G substituting (±)-(2R,3R,5R,1'R,2'R)-1-t-butoxycarbonyl-2-(1-acetamido-2-methoxymethyloxy)butyl-3-t-butyldiphenylsilyloxymethyl-pyrrolidine-5-carboxylic acid t-butyl ester in place of (±)-(2R,3R,5R,1'S)-1-t-butoxycarbonyl-2-oxiranyl-3-t-butyldiphenylsilyloxymethyl-pyrrolidine-5-carboxylic acid t-butyl ester (yield: 0.124 g, 83%).

¹H NMR(d₆-DMSO) δ7.42 (dd, 1H), 4.62–4.8 (m, 3H), 4.48 (m, 1H), 3.6–3.85 (m, 3H), 3.35–3.6 (m, 4H), 3.25 (s, 3H), 2.25 (m, 1H), 2.4 (m, 1H), 2.28 (m, 1H), 1.82 (s, 3H), 1.58 (m, 3H), 1.32–1.45 (m, 18H), 0.9 (dt, 3H).

MS: (M−H)⁻=517, (M+35)⁺=553; (M+H)⁺=519, (M+Na)⁺=541

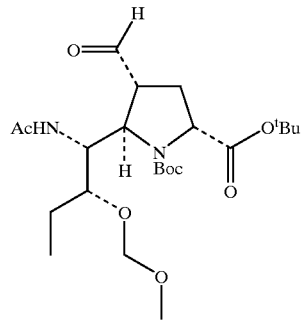

203D (±)-(2R,3R,5R,1'R,2'R)-1-t-Butoxycarbonyl-2-(1-acetamido-2-methoxymethyloxy)butyl-3-formyl-pyrrolidine-5-carboxylic Acid t-Butyl Ester The title compound was prepared according to the method described in Example 123H substituting (±)-(2R,3R,5R,1'R,2'R)-1-t-butoxycarbonyl-2-(1-acetamido-2- methoxymethyloxy)butyl-3-hydroxymethyl-pyrrolidine-5-carboxylic acid t-butyl ester in place of (±)-(2R,3R,5R,1'S)-1-t-butoxycarbonyl-2-oxiranyl-3-hydroxymethyl-pyrrolidine-5-carboxylic acid t-butyl ester (yield: 0.106 g, 86%).

$^1$H NMR(d$_6$-DMSO) δ9.58 (d, 1H), 7.58 (dd, 1H), 4.6–4.72 (m, 3H), 4.48(d, 1H), 3.88 (d, 1H), 3.4–3.65 (m, 5H), 3.24 (s, 3H), 3.15 (dd, 1H), 2.20–2.48 (m, 4H), 1.86 (s, 3H), 1.58 (m, 3H), 1.30–1.40 (m, 18H), 0.86 (t, 3H).

MS: (M−H)$^-$=515, (M+35)$^{30}$ =551; (M+H)$^+$=517

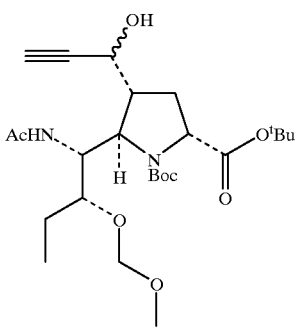

203E (±)-(2R,3R,5R,1'R,2'R,1"RS)-1-t-Butoxycarbonyl-2-(1-acetamido-2-methoxymethyloxy)butyl-3-(1-hydroxy-2-propyn-1-yl)-pyrrolidine-5-carboxylic Acid t-Butyl Ester The title compound was prepared according to the method described in Example 38A substituting (±)-(2R,3R,5R,1'R,2'R)-1-t-butoxycarbonyl-2-(1-acetamido-2-methoxymethyloxy)butyl-3-formyl-pyrrolidine-5-carboxylic acid t-butyl ester in place of (±)-(2R,3R,5R,1'S,1"RS)-1-t-butoxycarbonyl-2-(1-acetamido-3-methyl)butyl-3-formyl-pyrrolidine-5-carboxylic acid t-butyl ester (yield: 32 mg, 76%).

MS: (M−H)$^-$=541, (M+35)$^+$=577; (M+H)$^+$=543, (M+Na)$^+$=565

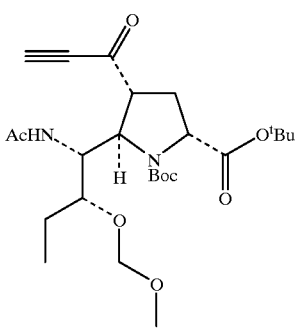

203F (±)-(2R,3R,5R,1'R,2'R)-1-t-Butoxycarbonyl-2-(1-acetamido-2-methoxymethyloxy)butyl-3-(1-oxo-2-propyn-1-yl)-pyrrolidine-5-carboxylic Acid t-Butyl Ester The title compound was prepared according to the method described in Example 38B substituting (±)-(2R,3R,5R,1'R,2'R)-1-t-butoxycarbonyl-2-(1 -acetamido-2-methoxymethyloxy)butyl-3-(1-hydroxy-2-propyn-1-yl)-pyrrolidine-5-carboxylic acid t-butyl ester in place of (±)-(2R,3R,5R,1'S,1"RS)-1-t-butoxycarbonyl-2-(1-acetamido-3-methyl)butyl-3-(1-oxo-2-propyn-1-yl)-pyrrolidine-5-carboxylic acid t-butyl ester (yield: 25 mg, 78%).

$^1$H NMR(d$_6$-DMSO) δ7.49 (br d, 1H), 5.0 (d, 1H), 4.7 (br s, 1H), 4.55–4.7 (m, 3H) 3.88 (br d, 1H), 3.5–3.7 (m, 2H), 3.43 (t, 2H), 3.2–3.4 (m, 2H), 3.24 (s, 3H), 2.4–2.7 (m, 2H), 1.84 (s, 3H), 1.5–1.7 (m, 2H), 1.30–1.45 (m, 18H), 0.86 (dt, 3H).

MS: (M−H)$^-$=539, (M+35)$^+$=575; (M+H)$^+$=541, (M+Na)$^+$=563

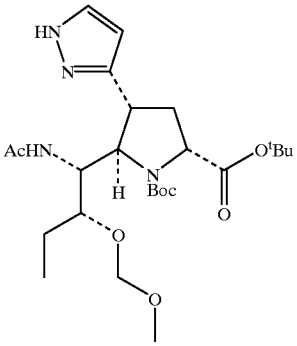

203G (±)-(2R,3R,5R,1'R,2'R)-1-t-Butoxycarbonyl-2-(1-acetamido-2-methoxymethyloxy)butyl-3-(pyrazol-3-yl)-pyrrolidine-5-carboxylic Acid t-Butyl Ester The title compound was prepared according to the method described in Example 38C substituting (±)-(2R,3R,5R,1'R,2'R)-1-t-butoxycarbonyl-2-(1-acetamido-2-methoxymethyloxy)butyl-3-(1-oxo-2-propyn-1-yl)-pyrrolidine-5-carboxylic acid t-butyl ester in place of (±)-(2R,3R,5R,1'S)-1-t-butoxycarbonyl-2-(1-acetamido-3-methyl)butyl-3-(1-oxo-2-propyn-1-yl)-pyrrolidine-5-carboxylic acid t-butyl ester (yield: 18 mg, 72%).

$^1$H NMR(d$_6$-DMSO) δ7.57 (m, 2H), 6.1 (d, 1H), 4.40–4.7 (m, 4H) 3.93 (m, 1H), 3.4–3.6 (m, 3H), 3.3–3.4(m, 3H), 3.22 (d, 3H), 2.55–2.65 (m, 1H), 2.2 (m, 1H), 1.85 (s, 3H), 1.5–1.7 (m, 2H), 1.15–1.45 (m, 18H), 0.86 (m, 3H).

MS: (M−H)$^-$=553, (M+35)$^+$=589; (M+H)$^+$=553 (M+Na)$^+$=577

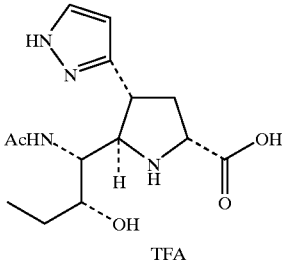

TFA

203H (±)-(2R,3R,5R,1'R,2'R)-2-(1-Acetamido-2-hydroxy)butyl-3-(pyrazol-3-yl)-pyrrolidine-5-carboxylic Acid Trifluoroacetic Acid Salt The title compound was prepared according to the method described in Example 15B, substituting (±)-(2R,3R,5R,1'R,2'R)-1-t-butoxycarbonyl-2-(1-acetamido-2-methoxymethyloxy)butyl-3-(pyrazol-3-yl)-pyrrolidine-5-carboxylic acid t-butyl ester in place of (±)-(2R,3R,5R,1'S)-

1-benzyl-2-(1-acetamido-3-ethyl)pentyl-3-(imidazol-2-yl)-pyrrolidine-5-carboxylic acid t-butyl ester. Chromatography on silica gel with 2-propanol:acetic acid:ethyl acetate:water 1:1:3:1 followed by the addition of 0.1% trifluoroacetic acid gave the title compound (yield: 4 mg, 45%).

$^1$H NMR(d$_6$-DMSO) δ7.65 (d, 1H), 7.64 (d, 1H), 6.16 (d, 1H), 4.37 (m, 1H), 4.23 (m, 1H), 4.38 (m, 1H), 4.56 (m, 1H), 2.63 (m, 1H), 2.10 (m, 1H), 1.74 (s, 3H), 1.25–1.40 (m, 2H), 0.83 (t, J=7.46 Hz, 3H).

MS: (M−H)$^−$=309, (M+35)$^+$=345; (M+H)$^+$=311, (M+Na)$^+$=333

EXAMPLE 204

(±)-(2R,3R,5R)-2-Acetamidomethyl-3-methoxycarbonyl-pyrrolidine-5-carboxylic Acid Hydrochloride

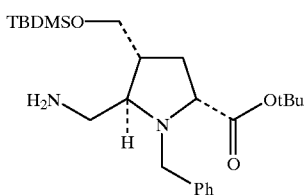

204A (±)-(2R,3R,5R)-1-Benzyl-2-aminomethyl-3-t-butyldimethylsilyloxymethyl-pyrrolidine-5-carboxylic Acid t-Butyl Ester The title compound is prepared according to the method described in Example 1F, substituting (±)-(2R,3R,5R)-1-benzyl-2-formyl-3-t-butyldimethylsilyloxymethyl-pyrrolidine-5-carboxylic acid t-butyl ester in place of (±)-(2R,3R,5R)-1-benzyl-2-(1-oxo-3-ethyl)pentyl-3-t-butyldimethylsilyloxymethyl-pyrrolidine-5-carboxylic acid t-butyl ester.

MS: (M+H)$^+$=435

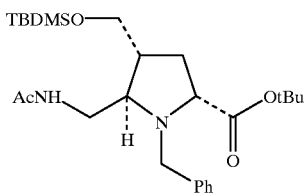

204B (±)-(2R,3R,5R)-1-Benzyl-2-acetamidomethyl-3-t-butyldimethylsilyloxymethyl-pyrrolidine-5-carboxylic Acid t-Butyl Ester The title compound is prepared according to the method described in Example 1G, substituting (±)-(2R,3R,5R)-1-benzyl-2-aminomethyl-3-t-butyldimethylsilyloxymethyl-pyrrolidine-5-carboxylic acid t-butyl ester in place of (±)-(2R,3R,5R,1'R)- and (±)-(2R,3R,5R,1'S)-1-benzyl-2-(1-amino-3-ethyl)pentyl-3-t-butyldimethylsilyloxymethyl-pyrrolidine-5-carboxylic acid t-butyl ester.

$^1$H NMR (CDCl$_3$): δ7.2–7.35 (m, 5H), 6.14 (br, 1H), 3.86 (dd, J=18 Hz, 13.5 Hz, 2H), 3.67 (m, 1H), 3.60 (m, 1H), 3.49 (m, 1H), 3.28 (m, 1H), 3.06 (m, 1H), 2.19 (m, 2H), 1.95 (s, 3H), 1.45 (s, 9H), 0.91 (s, 9H), 0.07 (s, 6H).

MS: (M+H)$^+$=477

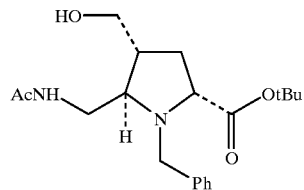

204C (±)-(2R,3R,5R)-1-Benzyl-2-acetamidomethyl-3-hydroxymethyl-pyrrolidine-5-carboxylic Acid t-Butyl Ester The title compound was prepared according to the method described in Example 1H, substituting (±)-(2R,3R,5R)-1-benzyl-2-acetamidomethyl-3-t-butyldimethylsilyloxymethyl-pyrrolidine-5-carboxylic acid t-butyl ester in place of (±)-(2R,3R,5R,1'S)-1-benzyl-2-(1-acetamido-3-ethyl)pentyl-3-t-butyldimethylsilyloxymethyl-pyrrolidine-5-carboxylic acid t-butyl ester.

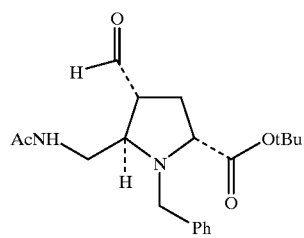

204D (±)-(2R,3R,5R)-1-Benzyl-2-acetamidomethyl-3-formyl-pyrrolidine-5-carboxylic Acid t-Butyl Ester The title compound was prepared according to the method described in Example 2A, substituting (±)-(2R,3R,5R)-1-benzyl-2-acetamidomethyl-3-hydroxymethyl-pyrrolidine-5-carboxylic acid t-butyl ester in place of (±)-(2R,3R,5R,1'S)-1-benzyl-2-(1-acetamido-3-ethyl)pentyl-3-hydroxymethyl-pyrrolidine-5-carboxylic acid t-butyl ester.

$^1$H NMR (CDCl$_3$): δ9.70 (s, 1H), 7.22–7.36 (m 5H), 5.82 (br, 1H), 3.83 (dd, J=3.3 Hz, 13.5 Hz, 2H), 3.74 (m, 1H), 3.56 (d, J=9 Hz, 1H), 3.15 (m, 1H), 2.73 (m, 1H), 2.36–2.10 (m, 2H), 1.98 (s, 3H), 1.45 (s, 9H).

MS: (M+H)$^+$=361

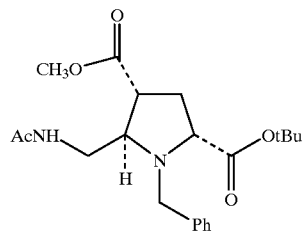

204E (±)-(2R,3R,5R)-1-Benzyl-2-acetamidomethyl-3-methoxycarbonyl-pyrrolidine-5-carboxylic Acid t-Butyl Ester The title compound was prepared according to the method described in Example 2B and 2C, substituting (±)-(2R,3R, 5R)-1-benzyl -2-acetamidomethyl-3-formyl-pyrrolidine-5-carboxylic acid t-butyl ester in place of (±)-(2R,3R,5R,1'S)-1-benzyl-2-(1-acetamido-3-ethyl)pentyl-3-formyl-pyrrolidine-5-carboxylic acid t-butyl ester.

$^1$H NMR (CDCl$_3$): δ7.45–7.20 (m, 5H), 5.96 (br, 1H), 3.90–3.73 (m, 4H), 3.71 (s, 3H), 3.52 (dd, J=9 Hz, 2 Hz, 1H), 3.13 (m, 1H), 2.84 (m, 1H), 2.36 (m, 1H), 2.18 (m, 1H), 1.97 (s, 3H), 1.45 (s, 9H).

MS: (M+H)$^+$=391

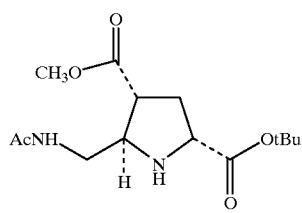

204F (±)-(2R,3R,5R)-2-Acetamidomethyl-3-methoxycarbonyl-pyrrolidine-5-carboxylic Acid t-Butyl Ester The title compound was prepared according to the method described in Example 2D, substituting (±)-(2R,3R,5R)-1-benzyl-2-acetamidomethyl-3-methoxycarbonyl-pyrrolidine-5-carboxylic acid t-butyl ester in place of (±)-(2R,3R,5R,1'S)-1-benzyl-2-(1-acetamido-3-ethyl)pentyl-3-methoxycarbonyl-pyrrolidine-5-carboxylic acid t-butyl ester.

$^1$H NMR (CDCl$_3$): δ6.19 (br, 1H), 3.72 (m, 2H), 3.70 (s, 3H), 3.43 (m, 1H), 3.28 (m, 1H), 2.74 (m, 1H), 2.44 (m 1H), 2.21 (m, 1H), 2.00 (s, 3H), 1.48 (s, 9H).

MS: (M+H)$^+$=301

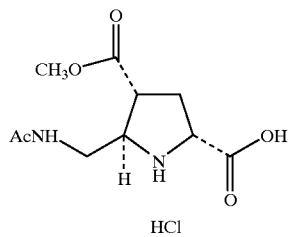

204G (±)-(2R,3R,5R)-2-Acetamidomethyl-3-methoxycarbonyl-pyrrolidine-5-carboxylic Acid Hydrochloride The title compound was prepared according to the method described in Example 2E substituting (±)-(2R,3R,5R)-2-acetamidomethyl-3-methoxycarbonyl-pyrrolidine-5-carboxylic acid t-butyl ester in place of (±)-(2R,3R,5R,1'S)-2-(1-acetamido-3-ethyl)pentyl-3-methoxycarbonyl-pyrrolidine-5-carboxylic acid t-butyl ester.

$^1$H NMR (D$_2$O): δ4.42 (t, J=8.25 Hz, 1H), 4.22 (m, 1H), 3.83 (m, 1H), 3.75 (s, 3H), 3.70–3.60 (m, 2H), 3.26 (m, 1H), 2.78 (m, 1H), 2.43 (m,1H), 2.03 (s, 3H).

MS: (M+H)$^+$=245

EXAMPLES 205–213

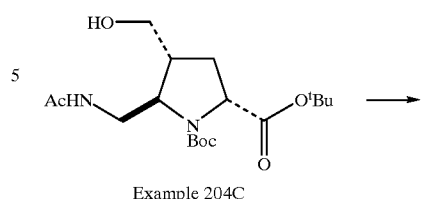

Example 204C

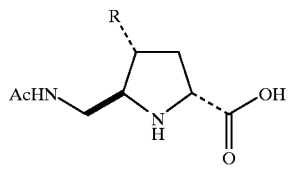

The following title compounds were prepared according to the methods described in Examples 1–39 from the common intermediate prepared as described in Example 204C.

EXAMPLE 205

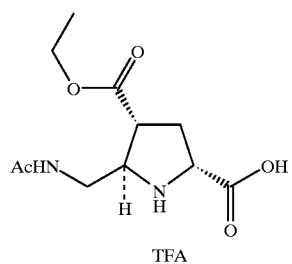

(±)-(2R,3R,5R)2-Acetamidomethyl-3-ethoxycarbonyl-pyrrolidine-5-carboxylic Acid Trifluoroacetic Acid Salt $^1$H NMR (D$_2$O) δ4.30 (t, J=8.2 Hz, 1H), 4.21 (m, 3H), 3.62 (dd, J=2.4, 3.4 Hz, 2H), 3.23 (m, 1H), 2.74 (m, 1H), 2.38 (m,1H), 2.02 (s, 3H), 1.26 (m, 3H)

MS: (M+H)$^+$=259; (M–H)$^-$=257.

EXAMPLE 206

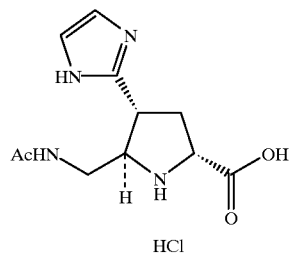

(±)-(2R,3R,5R)-2-Acetamidomethyl-3-(imidazol-2-yl)-pyrrolidine-5-carboxylic Acid Hydrochloride $^1$H NMR (D$_2$O): δ7.46 (s, 2H), 4.53 (dd, J=9.5 Hz, J=8.5 Hz, 1H), 4.28 (m, 1H), 3.96 (m, 1H), 3.65 (m, 2H), 3.03 (dt, J=13.5 Hz, J=7.6 Hz, 1H), 2.46 (m, 1H), 1.94 (s, 3H).

MS: (M+H)$^+$=253, (M–H)$^-$=251

EXAMPLE 207

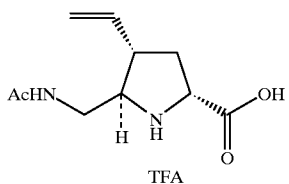

(±)-(2R,3S,5R)-2-Acetamidomethyl-3-vinyl-pyrrolidine-5-carboxylic Acid Trifluoroacetic Acid Salt $^1$H NMR (D$_2$O) δ5.74 (m, 1H), 5.24 (m, 2H), 4.20 (dd, J=1.7, 8.1 Hz, 1H), 3.65 (m, 2H), 3.50 (m, 1H), 2.84 (m, 1H), 2.61 (m, 1H), 2.03 (s, 3H), 1.95 (m, 1H)

MS: (M+H)$^+$=213.

EXAMPLE 208

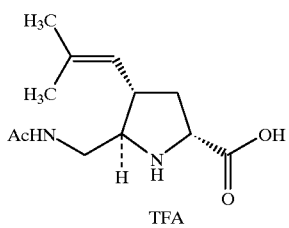

(±)-(2R,3R,5R)-2-Acetamidomethyl-3-(2,2-dimethyl-vinyl)-pyrrolidine-5-carboxylic Acid Trifluoroacetic Acid Salt $^1$H NMR (D$_2$O) δ5.01 (br d, 1H), 4.18 (dd, J=2.1, 8.1 Hz, 1H), 3.53 (m, 3H), 3.04 (m, 1H), 2.55 (m, 1H), 2.0 (s, 3H), 1.75 (m, 1H), 1.72 (s, 3H), 1.67 (s, 3H)

MS: (M+H)$^+$=241, (M+Na)$^+$=263; (M−H)$^-$=239.

EXAMPLE 209

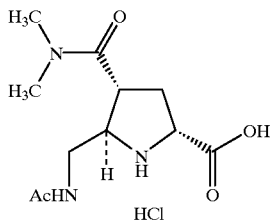

(±)-(2R,3R,5R)-2-Acetamidomethyl-3-(N,N-dimethylcarbamoyl)-pyrrolidine-5-carboxylic Acid Trifluoroacetic Acid Salt $^1$H NMR (D$_2$O) δ4.60 (t, J=8.4 Hz, 1H), 4.23 (m, 1H), 3.56 (d, J=5.8 Hz, 2H) 3.50 (m, 1H), 3.10 (s, 3H), 2.94 (s, 3H), 2.88 (m, 1H), 2.19 (m, 1H), 2.00 (s, 3H)

MS: (M+H)$^+$=258, (M−H)$^-$=256.

EXAMPLE 210

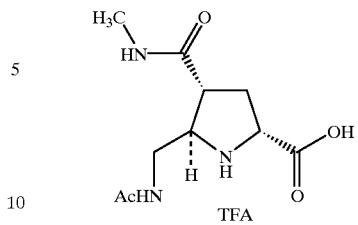

(±)-(2R,3R,5R)-2-Acetamidomethyl-3-(N-methylcarbamoyl)-pyrrolidine-5-carboxylic Acid Trifluoroacetic Acid Salt $^1$H NMR (D$_2$O) 4.49 (t, J=8.5 Hz, 1H), 4.10 (m, 1H), 3.57 (d, J=5.8 Hz, 2H), 3.03 (m, 1H), 2.76 (m, 1H), 2.74 (s, 3H), 2.29 (m, 1H), 2.00 (s, 3H)

MS: (M+H)$^+$=244.

EXAMPLE 211

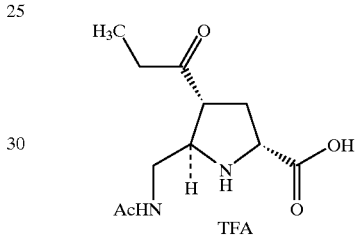

(±)-(2R,3R,5R)-2-Acetamidomethyl-3-propionyl-pyrrolidine-5-carboxylic Acid Trifluoroacetic Acid Salt $^1$H NMR (D$_2$O) δ4.24 (m, 2H), 3.55 (d, J=4.7 Hz, 1H), 3.40 (m, 1H), 2.85 (m, 1H), 2.64 (m, 3H), 2.16 (m, 1H), 2.01 (s, 3H), 1.02 (t, J=7.1 Hz, 3H)

MS: (M+H)$^+$=243; (M−H)$^-$=241.

EXAMPLE 212

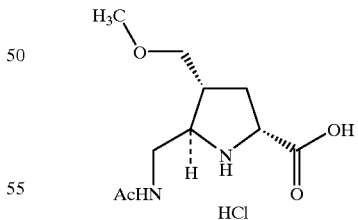

(±)-(2R,3R,5R)-2-Acetamidomethyl-3-methoxymethyl-pyrrolidine-5-carboxylic Acid Hydrochloride $^1$H NMR (D$_2$O): δ4.44 (t, J=6 Hz, 2H), 3.77 (m, 1H), 3.65–3.48 (m, 3H), 3.35 (s, 3H), 2.64 (m, 1H), 2.56 (m, 1H), 2.03 (s, 3H), 2.00 (m, 1H).

MS: (M+H)$^+$=231, (M−H)$^-$=229

EXAMPLE 213

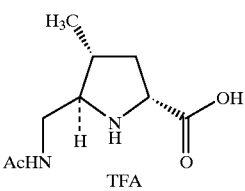

(±)-(2R,3S,5R)-2-Acetamidomethyl-3-methyl-pyrrolidine-5-carboxylic Acid Trifluoroacetic Acid Salt $^1$H NMR (D$_2$O) δ4.30 (m, 1H), 3.64 (m, 1H), 3.48 (m, 1H), 3.20 (m, 1H), 2.64 (m, 1H), 2.03 (s, 3H), 1.76 (m, 1H), 1.32 (br t, 1H), 1.12 (m, 4H)

MS: (M+H)$^+$=201, (M+Na)$^+$=223.

EXAMPLE 214

(±)-(2R,3S,5R,1'R)-2-(1-Acetamido-2-ethylthio)ethyl-3-vinyl-pyrrolidine-5-carboxylic Acid Trifluoroacetic Acid Salt

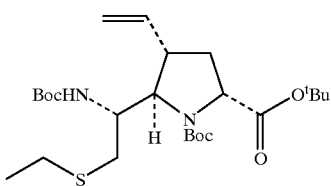

214A (±)-(2R,3S,5R,1'R)-1-t-Butoxycarbonyl-2-(1-t-butoxycarbonylamino-2-ethylthio)ethyl-3-vinyl-pyrrolidine-5-carboxylic Acid t-Butyl Ester To a solution of ethanethiol (0.047 mL, 0.63 mmol) in THF (2 mL) at 0° C. was added 2.5 M n-BuLi/hexane (0.248 mL, 0.62 mmol). The reaction mixture was stirred for 45 minutes and a solution of (±)-(2R,3S,5R,1'S)-1-t-butoxycarbonyl-2-(N-t-butoxycarbonylaziridinyl)-3-vinyl-pyrrolidine-5-carboxylic acid t-butyl ester (0.08 g, 0.182 mmole) in THF (0.5 mL) was added followed by DMF (1.5 mL) and stirred at room temperature for 2 hours. The reaction was quenched with 1N NaHCO$_3$ (10 mL) and diluted with ethyl acetate (20 mL). The organic layer was washed with water,and brine, dried over MgSO$_4$, filtered and concentrated in vacuo. The residue was purified by chromatography on silica gel using 10% ethyl acetate/hexanes to provide the title compound (yield: 61 mg, 67%).

$^1$H NMR(d$_6$-DMSO) δ6.74 (br d, 1H), 5.85 (m, 1H), 4.9–5.0 (m, 2H), 4.20 (m, 1H), 3.95 (m, 1H), 3.75 (d, 1H), 2.8–3.0 (dd, 1H), 2.5 (m, 3H), 1.65 (m, 1H), 1.32–1.45 (m, 27H), 1.17 (dt, 3H).

MS: (M−H)$^-$=499; (M+H)$^+$=501, (M+Na)$^+$=523

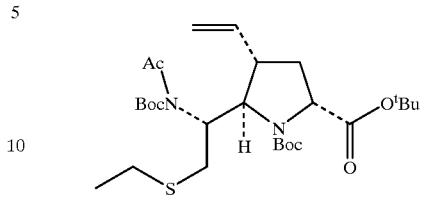

214B (±)-(2R,3S,5R,1'R)-1-t-Butoxycarbonyl-2-(1-N-t-butoxycarbonylacetamido-2-ethylthio)ethyl-3-vinyl-pyrrolidine-5-carboxylic Acid t-Butyl Ester (±)-(2R,3S,5R,1'R)-1-t-Butoxycarbonyl-2-(1-N-t-butoxycarbonylamino-2-ethylthio)ethyl-3-vinyl-pyrrolidine-5-carboxylic acid t-butyl ester (58 mg, 0.116 mmole) was reacted with lithium hexamethyldisilazide (1 M) (1.16 mL, 1.16 mmole) in THF (3 mL) at −78° C. After 0.5 hour at −78° C. and 1 hour at −40° C., the above reaction mixture was reacted with acetyl chloride (0.166 mL, 2.33 mmole) at −30° C. for 0.3 hours. The reaction was quenched with 1N NaHCO$_3$ (10 mL) and extracted with ethyl acetate (20 mL). The organic layer was washed with water, and brine, dried over MgSO$_4$, filtered and concentrated in vacuo. The residue was purified by chromatography on silica gel using 10% ethyl acetate/hexanes to provide the title compound (yield, 28 mg, 44%).

$^1$H NMR(d$_6$-DMSO) δ5.88 (m, 1H), 4.9–5.0 (m, 2H), 4.52 (m, 1H), 4.33 (m, 1H), 4.1 (m, 1H), 2.78 (dd, 1H), 2.3–2.5 (m, 6H), 1.7 (m, 1H), 1.32–1.5 (m, 27H), 1.11 (t, 3H).

MS: (M+H)$^+$=543.

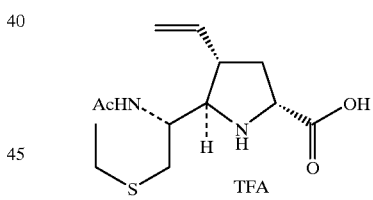

214C (±)-(2R,3R,5R,1'R)-2-(1-Acetamido-2-ethylthio)ethyl-3-vinyl-pyrrolidine-5-carboxylic Acid Trifluoroacetic Acid Salt The title compound was prepared according to the method described in Example 41C, substituting (±)-(2R,3S,5R, 1'R)-1-t-butoxycarbonyl-2-(1-N-t-butoxycarbonylacetamido-2-ethylthio)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield 7 mg, 95%).

$^1$H NMR(d$_6$-DMSO) δ8.15 (d, 1H), 5.72 (m, 1H), 5.05–5.2 (m, 2H), 4.2–4.4 (m, 2H), 4.33 (m, 1H), 2.93 (m, 1H), 2.7–2.8 (2d, 1H), 2.3–2.6(m, 3H), 1.85–1.95 (m, 1H), 1.93 (s, 3H), 1.17 (t, J=7.46 Hz, 3H)

MS: (M+H)$^+$=287.

EXAMPLE 215

(±)-(2R,3S,5R,1'R,3'S)-2-(1-Acetamido-2-ethylsulfinyl)ethyl-3-vinyl-pyrrolidine-5-carboxylic Acid Trifluoroacetic Acid Salt

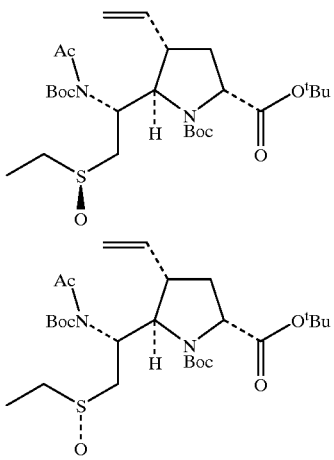

215A (±)-(2R,3S,5R,1'R,3'S) and (±)-(2R,3S,5R,1'R,3'R)-1-t-Butoxycarbonyl-2-(1-N-t-butoxycarbonylacetamido-2-ethylsulfinyl)ethyl-3-vinyl-pyrrolidine-5-carboxylic Acid t-Butyl Ester (±)-(2R,3S,5R,1'R)-1-t-Butoxycarbonyl-2-(1-N-t-butoxycarbonylacetamido-2-ethylthio)ethyl-3-vinyl-pyrrolidine-5-carboxylic acid t-butyl ester (72 mg, 0.132 mmole) was reacted with 55% m-chloroperoxybenzoic acid (41 mg, 0.132 mmole) in CHCl$_3$ (1.5 mL) at −40° C. for 30 minutes. The reaction was concentrated in vacuo. The residue was purified by chromatography on silica gel using ethyl acetate to provide the title compounds (±)-(2R,3S,5R,1'R,3'S) isomer (yield: 14 mg, 18.9%) and (±)-(2R,3S,5R,1'R,3'R) (yield: 45 mg, 60.7%).

(2R,3S,5R,1'R,3'S) $^1$H NMR(d$_6$-DMSO) δ5.88 (m, 1H), 4.9–5.0 (m, 2H), 4.50 (m, 1H), 4.0–4.15 (m, 1H), 2.7–2.9 (m, 3H), 2.55 (m, 1H), 2.37 (s, 3H), 1.7 (m, 1H), 1.32–1.5 (m, 27H), 1.12 (t, 3H)

MS: (M+H)$^+$=559, (M+Na)+581

(2R,3S,5R,1'R,3'R) $^1$H NMR(d$_6$-DMSO) δ5.88 (m, 1H), 4.9–5.0 (m, 2H), 4.50 (m, 1H), 4.03–4.15 (m, 1H), 3.2 (m, 1H) 3.1 (dd, 1H), 2.5–2.7(m, 2H), 2.38 (s, 3H), 1.75 (m, 1H), 1.32–1.5 (m, 27H), 1.12 (t, 3H)

MS: (M+H)$^+$=559, (M+Na)+=581

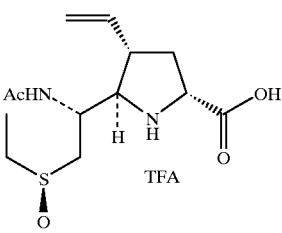

215B (±)-(2R,3S,5R,1'R,3'S)-2-(1-Acetamido-2-ethylsulfinyl)ethyl-3-vinyl-pyrrolidine-5-carboxylic Acid Trifluoroacetic Acid Salt The title compound was prepared according to the method described in Example 41C, substituting (±)-(2R,3S,5R,1'R,3'S)-1-t-butoxycarbonyl-2-(1-N-t-butoxycarbonylacetamido-2-ethylsulfinyl)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. ester (yield: 9 mg, 86%).

$^1$H NMR(d$_6$-DMSO) δ8.39 (d, 1H), 5.72 (m, 1H), 5.15–5.2 (dd, 2H), 4.5 (m, 1H), 4.37 (m, 1H), 3.65 (m, 1H), 2.85–3.04 (m, 3H), 2.6–2.85 (m, 2H), 2.4 (m, 1H), 1.83–1.95 (m, 1H), 1.86 (s, 3H), 1.20 (t, J=7.46 Hz, 3H).

MS: (M−H)$^-$=301; (M+H)$^+$=303, (M+Na)$^+$=325

EXAMPLE 216

(±)-(2R,3S,5R,1'R, 3'R)-2-(1-Acetamido-2-ethylsulfinyl)ethyl-3-vinyl-pyrrolidine-5-carboxylic Acid Trifluoroacetic Acid Salt

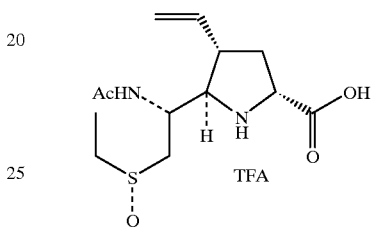

The title compound was prepared according to the method described in Example 41C, substituting (±)-(2R,3S,5R,1'R,3'R)-1-t-butoxycarbonyl-2-(1-N-t-butoxycarbonylacetamido-2-ethylsulfinyl)ethyl-3-vinyl-pyrrolidine-5-carboxylic acid t-butyl ester in place of (±)-(2R,3S,5R,1'R,2'S)-1-t-butoxycarbonyl 2-(1-acetamido-2-hydroxy)butyl-3-(cis-propen-1-yl)-pyrrolidine-5-carboxylic acid t-butyl ester (yield: 12 mg, 94%).

$^1$H NMR(d$_6$-DMSO) δ8.39 (d, 1H), 5.72 (m, 1H), 5.15–5.2 (dd, 2H), 4.53 (m, 1H), 4.41 (t, 1H), 3.65 (m, 1H), 3.2 (dd, 1H), 2.9–3.0 (m, 2H), 2.65–2.9(m, 2H), 2.4(m, 1H), 1.83–1.95 (m, 1H), 1.83 (s, 3H), 1.20 (t, J=7.46 Hz, 3H)

MS: (M−H)$^-$=301; (M+H)$^+$=303, (M+Na)$^+$=325

EXAMPLE 217

(±)-(2R,3S,5R,1'R)-2-(1-N-t-butoxycarbonylacetamido-2-ethylsulfonyl)ethyl-3-vinyl-pyrrolidine-5-carboxylic Acid Trifluoroacetic Acid Salt

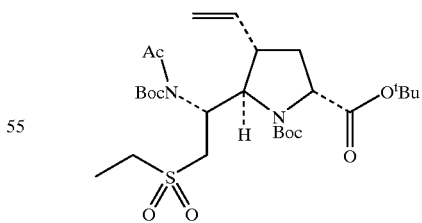

217A (±)-(2R,3S,5R,1'R)-1-t-Butoxycarbonyl-2-(1-N-t-butoxycarbonylacetamido-2-ethylsulfonyl)ethyl-3-vinyl-pyrrolidine-5-carboxylic Acid t-Butyl Eater (±)-(2R,3S,5R,1'R,3'R)-1-t-Butoxycarbonyl-2-(1-N-t-butoxycarbonylacetamido-2-ethylsulfinyl)ethyl-3-vinyl-pyrrolidine-5-carboxylic acid t-butyl ester (25 mg, 0.0448 mmole) was reacted with 55% m-chloroperoxybenzoic acid (14 mg, 0.0448 mmole) in CHCl₃ (1.5 mL) at 0° C. for one hour. The reaction was concentrated in vacuo. The residue was purified by chromatography on silica gel using 25% ethyl acetate/hexane to provide the title compound (yield: 23.7 mg, 92%).

$^1$H NMR(d$_6$-DMSO) δ5.88 (m, 1H), 4.85–5.0 (m, 2H), 4.38 (m, 1H), 4.15 (m, 1H), 3.7 (m, 1H) 3.45 (dd, 1H), 2.9–3.2 (m, 3H), 2.5–2.7 (m, 1H), 2.3–2.4 (m, 3H), 1.6–2.04 (m, 1H), 1.35–1.55 (m, 27H), 1.15 (t, 3H)

MS: (M+H)$^+$=575

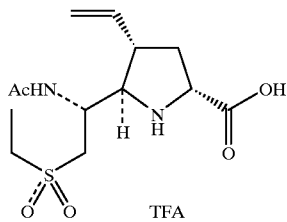

217B (±)-(2R,3S,5R,1'R)-2-(1-Acetamido-2-ethylsulfonyl)ethyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-N-t-butoxycarbonylacetamido-2-ethylsulfonyl)ethyl-3-vinyl-pyrrolidine-5-carboxylic acid t-butyl ester in place of (±)-(2R,3S,5R, 1'R,2'S)-1-t-butoxycarbonyl-2-(1-acetamido-2-hydroxy)butyl-3-(cis-propen-1-yl)-pyrrolidine-5-carboxylic acid t-butyl ester (yield: 12 mg, 94%).

$^1$H NMR(d$_6$-DMSO) δ8.34 (d, 1H), 5.72 (m, 1H), 5.05–5.25 (dd, 2H), 4.68 (m, 1H), 4.39 (dd, 1H), 3.7 (2d, 1H), 3.48 (dd, 1H), 3.3–3.4 (dd, 2H), 3.08 (q, 2H), 2.95 (m, 1H), 2.42 (m, 1H), 1.9 (m, 1H), 1.84 (s, 3H), 1.23 (t, J=7.46 Hz, 3H).

MS: (M–H)$^-$=317, (M+35)$^+$=353; (M+H)$^+$=319, (M+Na)$^+$=341

EXAMPLES 218, 220

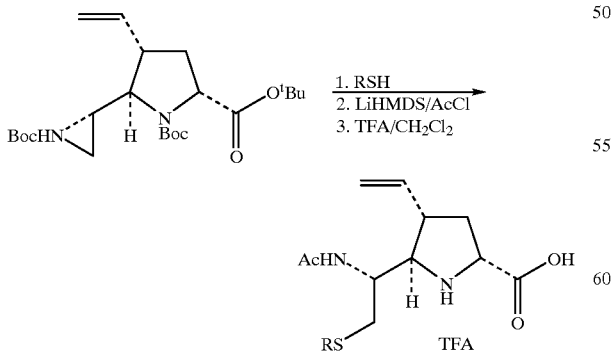

The following title compounds were prepared in 3 steps according to the methods described in Example 214.

EXAMPLE 218

(±)-(2R,3,5R,1'R)-2-(1-Acetamido-2-isopropylthio) ethyl-3-vinyl-pyrrolidine-5-carboxylic Acid Trifluoroacetic Acid Salt

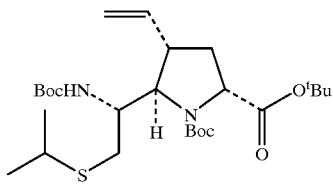

218A (±)-(2R,3S,5R,1'R)-1-t-Butoxycarbonyl-2-(1-N-t-butoxycarbonylamino-2-isopropylthio)ethyl-3-vinyl-pyrrolidine-5-carboxylic Acid t-Butyl Ester The title compound was prepared according to the method described in Example 214A, substituting isopropylthiol in place of ethanethiol (yield: 22 mg, 62%).

$^1$H NMR(d$_6$-DMSO) δ6.73 (d, 1H), 5.85 (m, 1H), 4.9–5.0 (m, 2H), 4.18 (m, 1H), 3.95 (m, 1H), 3.75 (br d, 1H), 2.8–3.0 (m, 2H), 1.65 (m, 1H), 1.32–1.45 (m, 27H), 1.18 (dd,6H)

MS: (M–H)$^-$=513; (M+H)$^+$=515, (M+Na)+=537

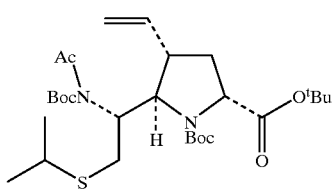

218B (±)-(2R,3S,5R,1'R)-1-t-Butoxycarbonyl-2-(1-(N-t-butoxycarbonyl-N-acetamido)-2-isopropylthio) ethyl-3-vinyl-pyrrolidine-5-carboxylic Acid t-Butyl Ester The title compound was prepared according to the method described in Example 214B, substituting (±)-(2R,3S,5R, 1'R)-1-t-Butoxycarbonyl-2-(1-N-t-butoxycarbonylamino-2-isoproylthio)ethyl-3-vinyl-pyrrolidine-5-carboxylic acid t-butyl ester in place of (±)-(2R,3S,5R,1'R)-1-t-Butoxycarbonyl-2-(1-N-t-butoxycarbonylamino-2-ethylthio)ethyl-3-vinyl-pyrrolidine-5-carboxylic acid t-butyl ester (yield: 12 mg, 50%).

$^1$H NMR(d$_6$-DMSO) δ5.86 (m, 1H), 4.88–5.0 (m, 2H), 4.54 (m, 1H), 4.33 (m, 1H), 4.13 (d, 1H), 3.05 (m, 1H), 2.73–2.84 (m, 2H), 2.38 (brs, 3H), 1.72 (m, 1H), 1.32–1.5 (m, 27H), 1.14 (dd, 6H).

MS: (M+H)$^+$=557, (M+Na)+=579

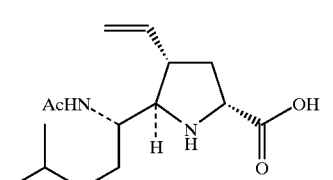

218C (±)-(2R,3S,5R,1'R)-2-(1-Acetamido-2-isopropylthio)ethyl-3-vinyl-pyrrolidine-5-carboxylic Acid Trifluoroacetic Acid Salt The title compound was prepared according to the method described in Example 15B, substituting (±)-(2R,3S,5R,1'R)-

1-t-butoxycarbonyl-2-(1-N-t-butoxycarbonylacetamido-2-isopropylthio)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 8 mg, 97%).

¹H NMR(d₆-DMSO) δ8.14 (d, 1H), 5.72 (m, 1H), 5.05–5.2 (dd, 2H), 4.2–4.4 (m, 2H), 3.68 (dd, 1H), 2.93 (m, 2H), 2.74 (dd, 1H), 2.58 (dd, 1H), 1.93 (m, 1H), 1.87 (s, 3H), 1.2 (t, 6H)

MS: (M−H)−=299; (M+H)⁺=301, (M+Na)⁺=323

EXAMPLE 219

(±)-(2R,3S,5R,1'R)-2-(1-Acetamido-2-phenylthio)ethyl-3-vinyl-pyrrolidine-5-carboxylic Acid Hydrochloride

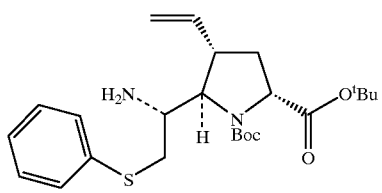

219A (±)-(2R,3S,5R,1'R)-1-t-Butoxycarbonyl-2-(1-amino-2-phenylthio)ethyl-3-vinyl-pyrrolidine-5-carboxylic Acid t-Butyl Ester (±)-(2R,3S,5R,1'S)-1-t-Butoxycarbonyl-2-aziridinyl-3-vinyl-pyrrolidine-5-carboxylic acid t-butyl ester (20.3 mg, 0.06 mmole) was reacted with the phenylthiol (19.9 mg, 0.18 mmol) and triethylamine (0.047 mL, 0.34 mmol) in MeOH (0.06 mL) at ambient temperature for 3.5 hours. The reaction solution was concentrated in vacuo. The residue was purified by preparative thin layer chromatography on silica gel using ethyl acetate/methanol/ammonium hydroxide, 99/0.05/0.05, to provide the title compound (yield: 20.7 mg, 77%).

¹H NMR (d₆-DMSO) δ7.31 (m, 4H), 7.17 (m, 1H), 5.87 (m, 1H), 5.03 (d, J=17 Hz, 0.4H), 5.01 (d, J=17 Hz, 0.6H), 4.91 (d, J=11H, 0.4H), 4.90 (d, J=11 Hz, 0.6H), 4.15 (m, 1H), 3.82 (m, 0.6H), 3.76 (m, 0.4H), 3.39(m, 1H), 2.92 (m, 2H), 2.55 (m, 1H), 1.64 (m, 2H), 1.42 (s, 5.4H), 1.37 (s, 3.6H), 1.34 (s, 5.4H), 1.22 (s, 3.6H)

MS: (M+H)⁺=449, (M+Na)⁺=471

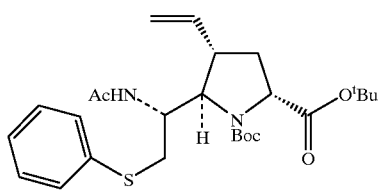

219B (±)-(2R,3S,5R,1'R)-1-t-Butoxycarbonyl-2-(1-acetamido-2-phenylthio)ethyl-3-vinyl-pyrrolidine-5-carboxylic Acid t-Butyl Ester (±)-(2R,3S,5R,1'R)-1-t-Butoxycarbonyl-2-(1-amino-2-phenylthio)ethyl-3-vinyl-pyrrolidine-5-carboxylic acid t-butyl ester (17.2 mg, 0.04 mmole) was reacted with the acetic anhydride (0.011 mL, 0.11 mmol) and triethylamine (0.092 mL, 0.23 mmol) in CH₂Cl₂ (0.3 mL) at rt for 4.25 hours. The reaction solution was concentrated in vacuo. The residue was purified by preparative thin layer chromatography on silica gel using 5% methanol/dichloromethane to provide the title compound.

¹H NMR (d₆-DMSO) d 7.75 (d, J=9 Hz, 0.6H), 7.73 (d, J=9 Hz, 0.4H), 7.32 (m, 4H), 7.19 (m, 1H), 5.87 (m, 1H), 5.04 (d, J=17 Hz, 0.4H), 5.00 (d, J=17 Hz, 0.6H), 4.95 (d, J=10 Hz, 0.6H), 4.93 (d, J=10 Hz, 0.4H), 4.59 (m, 0.4H), 4.45(m, 0.6H), 3.99 (dd, J=10 Hz, 2 Hz, 0.6H), 3.94 (dd, J=10 Hz, 2.5 Hz. 0.4H), 3.84 (m, 0.6H), 3.77 (m, 0.4H), 3.07 (dd, 13 Hz, 5 Hz, 0.6H), 2.95 (m, 1.8H), 2.83 (br t, J=8 Hz, 0.6H), 2.48 (m, 1H), 1.84 (s, 1.2H), 1.81 (s, 1.8H), 1.68 (m, 1H), 1.41 (s, 5.4H), 1.36 (s, 3.6H), 1.34 (s, 5.4H), 1.26 (s, 3.6H)

MS: (M−H)−=489, (M+35)−; (M+H)⁺=490, (M+Na)⁺=513

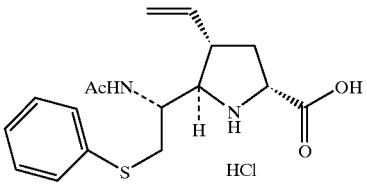

219C (±)-(2R,3S,5R,1'R)-2-(1-Acetamido-2-phenylthio)ethyl-3-vinyl-pyrrolidine-5-carboxylic Acid Hydrochloride The title compound was prepared according to the method described in Example 1K, substituting (±)-(2R,3S,5R,1'R)-1-t-butoxycarbonyl-2-(1-acetamido-2-phenylthio)ethyl-3-vinyl-pyrrolidine-5-carboxylic acid t-butyl ester in place of (±)-(2R,3R,5R,1'S)-2-(1-acetamido-3-ethyl)pentyl-3-(methoxymethyl)-pyrrolidine-5-carboxylic acid t-butyl ester (yield: 14.6 mg, 100%.)

¹H NMR(d₄-methanol) δ7.43 (m, 2H), 7.31 (m, 3H), 5.75 (ddd, J=17 Hz, 10 Hz, 8 Hz, 1H), 5.32 (br d, J=17 Hz, 1H), 5.19 (dd, J=10 Hz, 1.4 Hz, 1H), 4.58 (m, 2H), 3.89 (dd, J=10 Hz, 3 Hz, 1H), 3.19 (dd, J=14 Hz, 6 Hz, 1H), 3.09 (dd, J=14 Hz, 9 Hz, 1H), 3.04 (m, 1H), 2.57(dt, J=13 Hz, 7 Hz, 1H), 2.04 (s, 3H), 2.03 (m, 1H)

MS: (M−H)−=333; (M+H)⁺=335, (M+Na)⁺=357

EXAMPLE 220

(±)-(2R,3S,5R,1'R)-2-(1-Acetamido-2-benzylthio)ethyl-3-vinyl-pyrrolidine-5-carboxylic Acid Trifluoroacetic Acid Salt

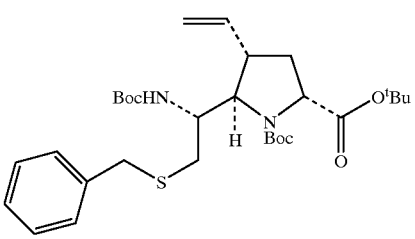

220A (±)-(2R,3S,5R,1'R)-1-t-Butoxycarbonyl-2-(1-N-t-butoxycarbonylamino-2-benzylthio)ethyl-3-vinyl-pyrrolidine-5-carboxylic Acid t-Butyl Ester The title compound was prepared according to the method described in Example 214A, substituting benzylmercaptan in place of ethanethiol (yield; 28 mg, 72%).

¹H NMR(d₆-DMSO) δ7.2–7.35 (m, 5H), 6.80 (br d, 1H), 5.84 (m, 1H), 4.86–4.96 (m, 2H), 4.25(m, 1H), 3.95 (m, 1H), 3.7–3.8 (m, 3H), 2.76–2.94 (m, 1H), 2.35–2.45 (m, 2H), 1.65 (m, 1H), 1.32–1.45 (m, 27H)

MS: (M−H)−=561; (M+H)⁺=563, (M+Na)+=585

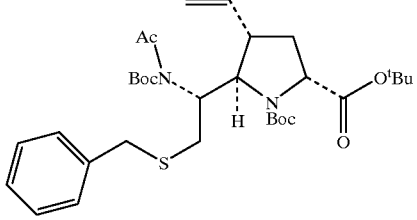

220B (±)-(2R,3S,5R,1'R)-1-t-Butoxycarbonyl-2-(1-(N-t-butoxycarbonyl-acetamido)-2-benzylthio)ethyl-3-vinyl-pyrrolidine-5-carboxylic Acid t-Butyl Ester The title compound was prepared according to the method described in Example 214B, substituting (±)-(2R,3S,5R,1'R)-1-t-Butoxycarbonyl-2-(1-N-t-butoxycarbonylamino-2-benzylthio)ethyl-3-vinyl-pyrrolidine-5-carboxylic acid t-butyl ester in place of (±)-(2R,3S,5R,1'R)-1-t-Butoxycarbonyl-2-(1-N-t-butoxycarbonylamino-2-ethylthio)ethyl-3-vinyl-pyrrolidine-5-carboxylic acid t-butyl ester (yield: 3.3 mg, 61%).

¹H NMR(d₆-DMSO) δ7.2–7.35 (m, 5H), 5.84 (m, 1H), 4.86–4.96 (m, 2H), 4.55(m, 1H), 4.32 (d, 1H), 4.05 (d, 1H), 3.56–3.65 (m, 2H), 2.9 (m, 1H), 2.3–2.65 (m, 3H), 2.42 (s, 3H), 1.76 (d, 1H), 1.25–1.55 (m, 27H)

MS: (M+H)⁺=605, (M+Na)+=627

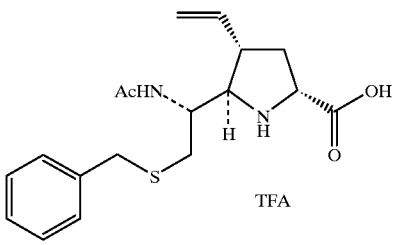

220C (±)-(2R,3S,5R,1'R)-2-(1-Acetamido-2-benzylthio)ethyl-3-vinyl-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-N-t-butoxycarbonylacetamido-2-benzylthio)ethyl-3-vinyl-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 2.2 mg, 95%).

¹H NMR(d₆-DMSO) δ8.18 (d, 1H), 7.2–7.32 (m, 5H), 5.68(m, 1H), 5.02–5.2 (m, 2H), 4.3–4.45 (m, 2H), 3.76 (s, 2H), 3.68 (dd, 1H), 2.92 (m, 1H), 2.62 (dd, 1H), 2.32–2.55 (m, 2H), 1.85–1.95 (m, 1H), 1.89 (s, 3H).

MS: (M−H)⁻=347; (M+H)⁺=349, (M+Na)⁺=371

EXAMPLE 221

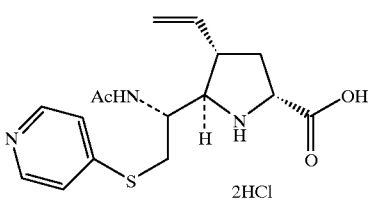

(±)-(2R,3S,5R,1'R)-2-(1-Acetamido-2-(4-pyridinethio)ethyl-3-vinyl-pyrrolidine-5-carboxylic Acid Dihydrochloride The title compound was prepared according to the method of Example 219A–C substituting 4-thiopyridine for thiophenol as the reagent in Example 219A.

¹H NMR(d₄-methanol) d 8.57 (d, J=7 Hz, 2H), 7.97 (d, J=7 Hz, 2H), 5.85 (ddd, J=17 Hz, 10 Hz, 9 Hz, 1H), 5.40 (br d, J=17 Hz, 1H), 5.25 (dd, J=17 Hz, 10 Hz, 1H), 4.67 (dt, J=10 Hz, 4 Hz, 1H), 4.47 (dd, J=10 Hz, 8 Hz, 1H), 4.01 (dd, J=10 Hz, 4 Hz, 1H), 3.68 (dd, J=14 Hz, 5 Hz, 1H), 3.45 (dd, J=14 Hz, 10 Hz, 1H), 3.16 (m, 1H), 2.65 (dt, J=14 Hz, 7 Hz, 1H), 2.07 (m, 1H), 2.04 (s, 3H)

MS: (M−H)³¹ =334; (M+H)⁺=336, (M+Na)⁺=358

EXAMPLE 222

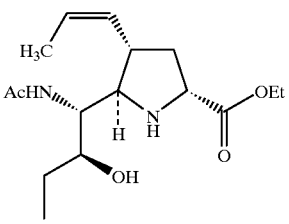

(±)-(2R,3S,5R,1'R,2'S)-2-(1-Acetamido-2-hydroxy)butyl-3-(cis-propen-1-yl)-pyrrolidine-5-carboxylic Acid Ethyl Ester Thionyl chloride (1.49 mL, 20.5 mmol) was reacted with ethanol (25 mL) at 0° C. for 10 minutes. (±)-(2R,3S,5R,1'R,2'S)-2-(1-Acetamido-2-hydroxy)butyl-3-(cis-propen-1-yl)-pyrrolidine-5-carboxylic acid trifluoroacetic acid salt (815 mg, 2.05 mmol) in ethanol (50 mL) was added to the above solution and reacted at room temperature for 17 hours. The reaction was concentrated in vacuo and the residue was purified by chromatography on silica gel with 90/10/0.5 dichloromethane/methanol/ammonium hydroxide to provide the title compound as a white solid (yield: 462 mg, 72%).

¹H NMR (DMSO-d₆) δ7.49 (d, J=9.8 Hz, 1H), 5.31 (m, 2H) 4.11 (m, 2H), 3.72 (t, J=7.7 Hz, 1H), 3.69 (m, 1H), 3.42 (m, 1H), 3.07 (m, 1H), 2.85 (m, 1H), 2.22 (m, 1H), 1.76 (s, 3H), 1.54 (d, J=5.6 Hz, 3H), 1.45 (m, 1H), 1.39 (m, 1H), 1.21 (m, 1H), 1.19 (t, J=7.0 Hz, 3H), 0.83 (t, J=7.3 Hz, 3H).

MS: (M+H)⁺=313, (M+Na)⁺=335, (M−H)⁻=311.

EXAMPLE 223

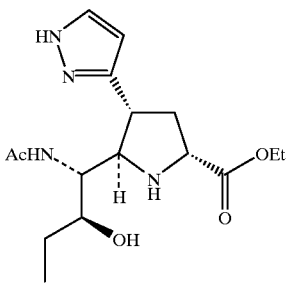

(±)-(2R,3R,5R,1'R,2'S)-2-(1-Acetamido-2-hydroxy)
butyl-3-(pyrazol-3-yl)-pyrrolidine-5-carboxylic Acid
Ethyl Ester The title compound is prepared according to the method described in Example 222, substituting (±)-(2R,3R,5R,1'R,2'S)-2-(1-acetamido-2-hydroxy)butyl-3-(pyrazol-3-yl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic trifluoroacetic acid salt (yield: 32 mg, 52%).

$^1$H NMR($d_6$-DMSO) δ7.6 (br s, 1H), 6.1 (br s, 1H), 4.08 (q, J=7.12 Hz, 2H), 3.78 (m, 1H), 3.65 (m, 1H), 3.55 (m, 1H), 3.45 (m, 1H), 3.25 (m, 1H), 3.45 (m, 1H), 1.72 (s, 3H), 1.45 (m, 1H), 1.2 (m, 1H), 1.16 (t, J=7.12 Hz, 3H), 0.82 (t, J=7.46 Hz, 3H).

MS: $(M-H)^-=337$, $(M+35)^+=373$; $(M+H)^+=339$, $(M+Na)^+=361$

EXAMPLE 224

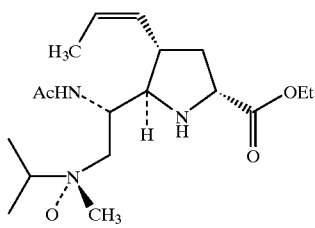

(±)-(2R,3R,5R,1'S,3'S)-2-(1-Acetamido-2-(N-isopropyl-N-methylamino-N-oxide))ethyl-3-(cis-propen-1-yl)-pyrrolidine-5-carboxylic Acid Ethyl Ester The title compound is prepared according to the method described in Example 222, substituting (±)-(2R,3S,5R,1'S,3'S)-2-(1-acetamido-2-(N-isopropyl)-N-methylamino-N-oxide))ethyl-3-(cis-propen-1-yl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic acid trifluoroacetic acid salt (yield: 25 mg, 34%).

$^1$H NMR (MeOD-$d_3$) δ5.51–5.43(m, 1H), 5.34–5.27(m, 1H), 4.36–4.30(m, 1H), 4.18(q, J=7.1 Hz, 2H), 3.88(dd, J=6.8, 8.8 Hz, 1H), 3.82–3.67(m, 2H), 3.49–3.42(m, 1H), 3.34(s, 3H), 3.14–2.96(m, 1H), 2.42–2.33(m, 1H), 1.92(s, 3H), 1.64–1.52(m, 1H), 1.63(dd, J=1.7, 6.8 Hz, 3H), 1.41–1.24(m, 1H), 1.39(d, J=6.4 Hz, 3H), 1.31(d, J=6.4 Hz, 3H), 1.26(t, J=7.1 Hz, 3H).

MS: $(M+H)^+=356$, $(M+Na)^+=378$, $(M-H)^-=354$, $(M+35)^+=390$.

EXAMPLE 225

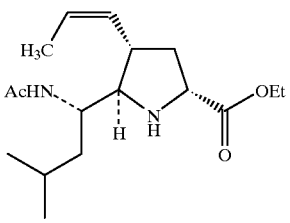

(±)-(2R,3S,5R,1'S)-2-(1-Acetamido-3-methyl)butyl-3-(cis-propen-1-yl)-pyrrolidine-5-carboxylic Acid Ethyl Ester The title compound is prepared according to the method described in Example 222, substituting (±)-(2R,3S,5R,1'S)-2-(1-acetamido-3-methyl)butyl-3-(cis-propen-1-yl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic acid trifluoroacetic acid salt (yield; 838 mg, 94%).

$^1$H NMR (CDCl$_3$): δ5.50 (m, 1H), 5.41 (m, 1H), 5.28 (m, 1H), 4.21 (q, J=7.5 Hz, 2H), 4.06 (m, 1H), 3.87 (t, J=7.5 Hz, 1H), 3.10 (m, 1H), 2.97 (m, 1H), 2.39 (m, 1H), 1.97 (s, 3H), 1.66 (dd, 3H), 1.60 (m, 1H), 1.40 (m, 2H), 0.94 (d, J=7.5 Hz, 3H), 0.93 (d, J=7.5 Hz, 3H).

MS: $(M+H)^+=311$

EXAMPLE 226

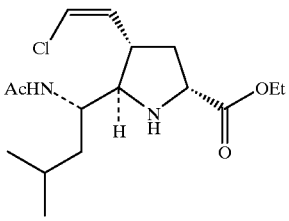

(±)-(2R,3S,5R,1'S)-2-(1-Acetamido-3-methyl)butyl-3-(cis-2-chloro-vin-1-yl)-pyrrolidine-5-carboxylic Acid Ethyl Ester The title compound is prepared according to the method described in Example 222, substituting (±)-(2R,3S,5R,1'S)-2-(1-acetamido-3-methyl)butyl-3-(cis-2-chloro-vin-1-yl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic acid trifluoroacetic acid salt (yield: 28 mg, 46%).

$^1$H NMR (CDCl$_3$): δ6.05 (d, J=7.5 Hz, 1H), 5.90 (dd, J1=9 Hz, J2=6 Hz, 1H), 5.31 (d, J=9 Hz, 1H), 4.19 (q, J=7.5 Hz, 2H), 4.06 (m, 1H), 3.82 (t, J=7.5 Hz, 1H), 3.17 (m, 2H), 2.45 (m, 1H), 1.98 (s, 3H), 1.67 (m, 1H), 1.60 (m, 1H), 1.37 (m, 2H), 1.27 (t, J=7.5 Hz, 3H), 0.91 (d, J=7.5 Hz, 3H), 0.89 (d, J=7.5 Hz, 3H).

MS: $(M+H)^+=331$

EXAMPLE 227

EXAMPLE 228

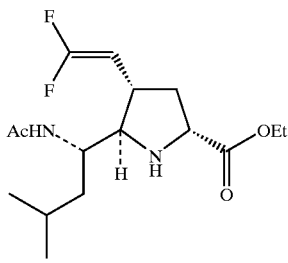

(±)-(2R,3S 5R,1'S)-2-(1-Acetamido-3-methyl)butyl-3-(2,2-difluoro-vinyl)-pyrrolidine-5-carboxylic Acid Ethyl Ester The title compound is prepared according to the method described in Example 222, substituting (±)-(2R,3S,5R,1'S)-2-(1-acetamido-3-methyl)butyl-3-(2,2-difluoro-vinyl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic acid trifluoroacetic acid salt (yield: 28 mg, 57%).

$^1$H NMR (CDCl$_3$): δ4.22 (q, J=7.5 Hz, 2H), 4.14 (m, 1H), 4.03 (m, 1H), 3.29 (br, 1H), 2.85 (m, 1H), 2.52 (m, 1H), 2.01 (s, 3H), 1.77 (m, 2H), 1.64 (m, 2H), 1.49 (m, 1H), 1.38 (m, 1H) 1.29 (t, J=7.5 Hz, 3H), 0.93 (d, J=7.5 Hz, 3H), 0.90 (d, J=7.5 Hz, 3H).

MS: (M+H)$^+$=333

EXAMPLE 229

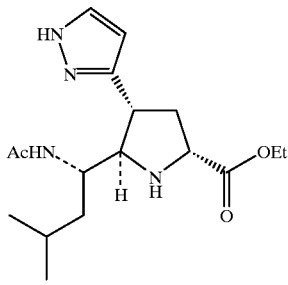

(±)-(2R,3R,5R,1'S)-2-(1-Acetamido-3-methyl)butyl-3-(pyrazol-3-yl)-pyrrolidine-carboxylic Acid Ethyl Ester The title compound is prepared according to the method described in Example 222, substituting (±)-(2R,3R,5R,1'S)-2-(1-acetamido-3-methyl)butyl-3-(pyrazol-3-yl)-pyrrolidine-5-carboxylic acid trifluoroacetic acid salt in place of (±)-(2R,3S,5R,1'R,2'S)-2-(1-acetamido-2-hydroxy)butyl-3-(cis-propen-1-yl)-pyrrolidine-5-carboxylic acid trifluoroacetic acid salt (yield: 48 mg, 75.5%).

$^1$H NMR (CDCl$_3$): δ7.49 (d, 1H), 7.26(s, 1H), 6.18 (d, 1H), 4.18 (q, J=7.5 Hz, 2H), 4.12 (m, 1H), 3.91 (t, J=7.5 Hz, 1H), 3.51 (t, J=7.5 Hz, 1H), 3.40 (q, J=9 Hz, 1H), 2.64 (m, 1H), 2.00 (m, 1H), 1.82 (s, 3H), 1.75 (m, 1H), 1.36 (m, 1H), 1.26 (t, J=9 Hz, 3H), 0.855 (d, 3H), 0.84 (d, 3H).

MS (M+H)$^+$=337

EXAMPLE 230

(±)-(2R,3S,5R,1'R)-2-(1-Acetamido-2-ethyl-2-hydroxy)butyl-3-(cis-propen-1-yl)-pyrrolidine-5-carboxylic Acid Trifluoroacetic Acid Salt

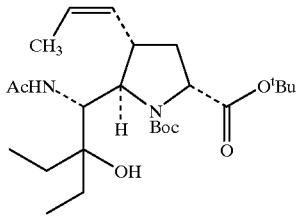

230A (±)-(2R,3S,5R,1'R)-1-t-Butoxycarbonyl-2-(1-acetamido-2-ethyl-2-hydroxy)butyl-3-(cis-propen-1-yl)-pyrrolidine-5-carboxylic Acid t-Butyl Ester The title compound was prepared according to the method described in Example 41B, substituting (±)-(2R,3S,5R,1'R)-1-t-butoxycarbonyl-2-(1-acetamido-2-oxo)butyl-3-(cis-propen-1-yl)-pyrrolidine-5-carboxylic acid t-butyl ester for (±)-(2R,3S,5R,1'R)-1-t-butoxycarbonyl 2-(1-acetamido-1-formyl)methyl-3-(cis-propen-1-yl)-pyrrolidine-5-carboxylic acid t-butyl ester to provide the title compound (yield: 0.021 g, 51%).

MS: (M+H)$^+$=469, (M+Na)$^+$=491, (2M+Na)$^+$=959, (M−H)$^-$=467.

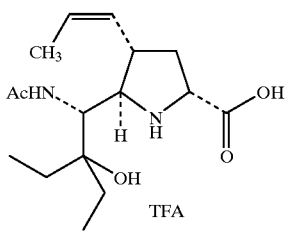

230B (±)-(2R,3S,5R,1'R)-2-(1-Acetamido-2-ethyl-2-hydroxy)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R)-1-t-butoxycarbonyl-2-(1-acetamido-2-ethyl-2-hydroxy)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0039 g, 100%).

$^1$H NMR (DMSO-d$_6$) δ7.52 (d, J=10.3 Hz, 1H), 5.45 (m, 1H), 5.28 (m, 1H), 4.32 (m, 2H), 3.68 (t, J=8.8 Hz, 1H), 3.16 (quint., J=8.5 Hz, 1H), 2.41 (dt, J=13.2,8.3 Hz, 1H), 1.81(s, 3H), 1.59 (m, 1H), 1.53 (dd, J=6.8,1.5 Hz, 3H), 1.52–1.42 (m, 3H), 1.30 (m, 1H), 0.86 (t, J=7.3 Hz, 3H), 0.83 (t, J=7.3 Hz, 3H).

MS: (M+H)$^+$=313, (M+Na)$^+$=335, (M−H)$^-$=311, (2M−H)$^-$=623.

EXAMPLE 231

(±)-(2R,3S,5R,1'R,2'S)-2-(1-Acetamido-2-hydroxy-2-methyl)pentyl-3-(cis-propen-1-yl)-pyrrolidine-5-carboxylic Acid Trifluoroacetic Acid Salt

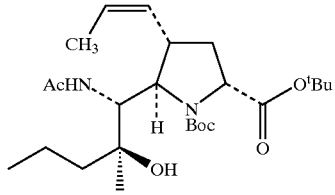

231A (±)-(2R,3S,5R,1'R,2'S)-1-t-Butoxycarbonyl-2-(1-acetamido-2-hydroxy-2-methyl)pentyl-3-(cis-propen-1-yl)-pyrrolidine-5-carboxylic Acid t-Butyl Ester The title compound was prepared according to the method described in Example 41B, substituting (±)-(2R,3S,5R,1'R)-1-t-butoxycarbonyl-2-(1-acetamido-2-oxo)pentyl-3-(cis-propen-1-yl)-pyrrolidine-5-carboxylic acid t-butyl ester for (±)-(2R,3S,5R,1'R)-1-t-Butoxycarbonyl 2-(1-acetamido-1-formyl)methyl-3-(cis-propen-1-yl)-pyrrolidine-5-carboxylic acid t-butyl ester and methylmagnesium bromide for ethylmagnesium bromide to provide the title compound (yield: 0.0285 g, 45%).

MS: $(M+H)^+=469$, $(M+Na)^+=491$.

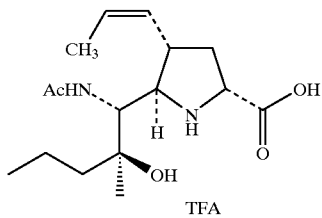

231B (±)-(2R,3S,5R,1'R,2'S)-2-(1-Acetamido-2-hydroxy-2-methyl)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-2-methyl)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0040 g, 100%).

$^1$H NMR (DMSO-$d_6$) δ9.25 (bs, 1H), 8.75 (bs, 1H), 7.54 (d, J=10.3 Hz, 1H), 5.45 (m, 1H), 5.29 (m, 1H), 4.37 (bt, J=8.3 Hz, 1H), 4.22 (t, J=9.7 Hz, 1H), 3.62 (t, J=8.8 Hz, 1H), 3,12 (quint., J=8.5 Hz, 1H), 2.41 (dt, J=12.7,7.8 Hz, 1H), 1.78 (s, 3H), 1.59 (m, 1H), 1.53 (dd, J=6.8,2.0 Hz, 3H), 1.4–1.25 (m, 4H), 1.17 (s, 3H), 0.81 (t, J=6.5 Hz, 3H).

MS: $(M+H)^+=313$, $(M+Na)^+=335$, $(M-H)^-=311$, $(2M-H)^-=623$

EXAMPLE 232

(±)-(2R,3S,5R,1'R,2'S)-2-(1-Acetamido-2-ethyl-2-hydroxy)pentyl-3-(cis-propen-1-yl)-pyrrolidine-5-carboxylic Acid Trifluoroacetic Acid Salt

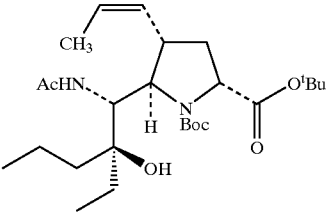

232A (±)-(2R,3S,5R,1'R,2'S)-1-t-Butoxycarbonyl-2-(1-acetamido-2-ethyl-2-hydroxy)pentyl-3-(cis-propen-1-yl)-pyrrolidine-5-carboxylic Acid t-Butyl Ester The title compound was prepared according to the method described in Example 41B, substituting (±)-(2R,3S,5R,1'R)-1-t-butoxycarbonyl-2-(1-acetamido-2-oxo)pentyl-3-(cis-propen-1-yl)-pyrrolidine-5-carboxylic acid t-butyl ester for (±)-(2R,3S,5R,1'R)-1-t-butoxycarbonyl 2-(1-acetamido-1-formyl)methyl-3-(cis-propen-1-yl)-pyrrolidine-5-carboxylic acid t-butyl ester to provide the title compound (yield: 0.0222 g, 33%).

MS: $(M+H)^+=483$, $(M+Na)^+=505$, $(M-H)^-=481$.

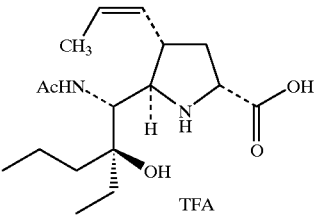

232B (±)-(2R,3S,5R,1'R,2'S)-2-(1-Acetamido-2-ethyl-2-hydroxy)pentyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-ethyl-2-hydroxy)pentyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 0.0035 g, 100%).

$^1$H NMR (DMSO-$d_6$) δ9.1 (bs, 1H), 8.75 (bs, 1H), 7.53 (d, J=9.8 Hz, 1H), 5.44 (m, 1H), 5.28 (m, 1H), 4.35–4.25 (m, 2H) 3.67 (m, 1H), 3.16 (quint., J=8.5 Hz, 1H), 2.41 (dt, J=12.8,7.9 Hz, 1H), 1.81 (s, 3H), 1.60 (m, 1H), 1.53 (dd, J=6.7,1.8 Hz, 3H), 1.46 (m, 2H), 1.4–1.20 (m, 4H), 0.86 (t, J=7.3 Hz, 3H), 0.82 (t, J=6.7 Hz, 3H).

MS: $(M+H)^+=327$, $(M-H)^-=325$, $(M+CF_3COOH)^-=439$, $(2M-H)^-=651$

EXAMPLE 233

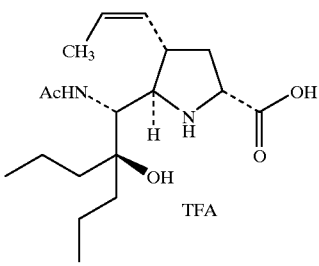

(±)-(2R,3S,5R,1'R)-2-(1-Acetamido-2-propyl-2-hydroxy)pentyl-3-(cis-propen-1-yl-pyrrolidine-5-carboxylic Acid Trifluoroacetic Acid Salt The title compound was prepared according to the method described in Example 232 substituting propyl magnesium bromide for ethyl magnesium bromide.

$^1$H NMR (DMSO-d$_6$): δ0.81 (t, 3H), 0.91 (t, 3H), 1.24–1.49 (m, 8H), 1.54 (dd, 3H), 1.60 (m, 1H), 1.81 (s, 3H), 2.41 (m, 1H), 3.15 (m, 1H), 3.69 (t, 1H), 4.28 (t, 1H), 4.35 (t, 1H), 5.17 (brs, 1H), 5.28 (td, 1H), 5.45 (dq, 1H), 7.54 (d, 1H), 8.80 (br s, 1H), 9.12 (br s, 1H).

MS: (M+H)$^+$=341.

EXAMPLE 234

(±)-(2R,3S,5R,1'R)-2-(1-Acetamido-2-ethyl-2-methoxy)butyl-3-(cis-propen-1-yl)-pyrrolidine-5-carboxylic Acid Trifluoroacetic Acid Salt

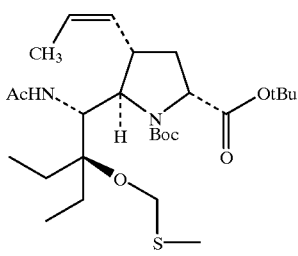

234A (±)-(2R,3S,5R,1'R)-1-t-Butoxycarbonyl-2-(1-Acetamido-2-ethyl-2-(methylthio)methyloxy)butyl-2-(cis-propen-1-yl-pyrrolidine-5-carboxylic Acid t-Butyl Ester (±)-(2R,3S,5R,1'R,2'S)-1-t-Butoxycarbonyl-2-(1-acetamido-2-ethyl-2-methoxy)butyl-3-(cis-propen-1-yl)-pyrrolidine-5-carboxylic acid t-butyl ester was reacted with dimethylsufoxide and acetic anhydride according to the method of Marshall, J. A. in J. Org. Chem. 1979, vol. 44, p 2994 to provide the title compound.

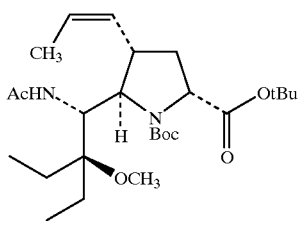

234A (±)-(2R,3S,5R,1'R,2'S)-1-t-Butoxycarbonyl-2-(1-Acetamido-2-ethyl-2-methoxy)butyl-3-(cis-propen-1-yl)-pyrrolidine-5-carboxylic Acid t-Butyl Ester (±)-(2R,3S,5R,1'R,2'S)-1-t-Butoxycarbonyl-2-(1-acetamido-2-ethyl-2-(methylthio)methyloxy)butyl-3-(cis-propen-1-yl)-pyrrolidine-5-carboxylic acid t-butyl ester is reacted with Raney Nickel according to the procedure of Marshall, J. A. in J. Org. Chem. 1979, vol. 44, p 2994 to provide the title compound.

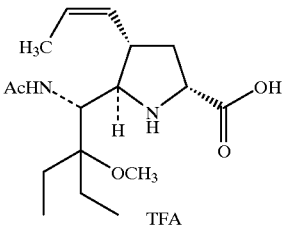

(±)-(2R,3S,5R,1'R,2'S)-2-(1-Acetamido-2-ethyl-2-methoxy)butyl-3-(cis-propen-1-yl)-pyrrolidine-5-carboxylic Acid Trifluoroacetic Acid Salt The title compound is prepared according to the method described in Example 41C, substituting (±)-(2R,3S,5R,1'R,2'S)-1-t-butoxycarbonyl-2-(1-acetamido-2-ethyl-2-methoxy)butyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester.

EXAMPLE 235

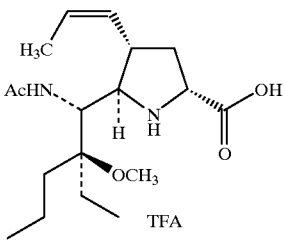

(±)-(2R,3S,5R,1'R,2'S)-2-(1-Acetamido-2-ethyl-2-methoxy)pentyl-3-(cis-propen-1-yl)-pyrrolidine-5-carboxylic Acid Trifluoroacetic Acid Salt The title compound is prepared according to the method described in Example 234 substituting (±)-(2R,3S,5R,1'R,2'S)-1-t-butoxycarbonyl-2-(1-acetamido-2-ethyl-2-hydroxy)pentyl-3-(cis-propen-1-yl)-pyrrolidine-5-carboxylic acid t-butyl ester for (±)-(2R,3S,5R,1'R)-1-t-butoxycarbonyl-2-(1-acetamido-2-ethyl-2-hydroxy)butyl-3-(cis-propen-1-yl)-pyrrolidine-5-carboxylic acid t-butyl ester in 234A.

EXAMPLE 236

(±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid Trifluoroacetic Acid Salt

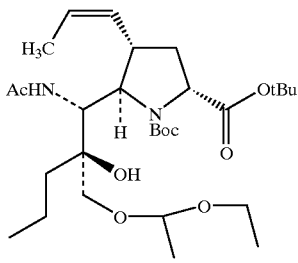

236A (±)-(2R,3S,5R,1'R,2'S)-1-t-Butoxycarbonyl-2-(1-Acetamido-2-((1-ethoxy)ethyloxymethyl)-2-hydroxy)pentyl-3-(cis-1-propen-1-yl)-pyrrolidine-5-carboxylic Acid t-Butyl Ester (±)-(2R,3S,5R,1'R,2'S)-1-t-Butoxycarbonyl-2-(1-acetamido-2-oxo)pentyl-3-(cis-propen-1-yl)-pyrrolidine-5-carboxylic acid t-butyl ester (50 mg, 0.11 mmole) was reacted with (ethoxyethyloxymethyl)tributylstannane (260 mg, 0.66 mmole) according to the method of Still, W. C. (*J. Am. Chem. soc.*, 100, 1481(1978)) to provide the title compound (yield: 26.8 mg, 43.8%).

$^1$H NMR (CDCl$_3$): δ0.89 (t, 3H), 1.19 (m, 3H), 1.29 (dd, 3H), 1.45 (s, 9H), 1.46 (s, 9H), 1.52–1.73 (m, 8H), 1.99 (s, 3H), 2.44 (m, 1H), 3.24–3.74 (m, 5H), 3.91–4.22 (m, 3H), 4.49 (m, 1H), 4.62 (m, 1H), 5.37 (m, 1H), 5.64 (m, 1H), 5.97–6.41 (m, 1H).

MS: (M+H)$^+$=557.

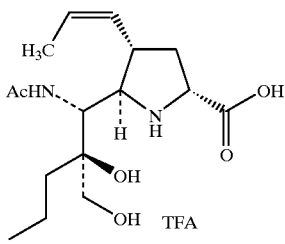

236B (±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid Trifluoroacetic Acid Salt (±)-(2R,3S,5R,1'R,2'S)-1-t-Butoxycarbonyl-2-(1-Acetamido-2-(1-ethoxy-2-ethoxymethyl)-2-hydroxy)pentyl-3-(cis-propen-1-yl)-pyrrolidine-5-carboxylic Acid t-Butyl Ester (13.5 mg, 0.024 mmol) was dissolved in THF (1 mL) and treated with 0.5 N HCl (1 mL) at room temperature for 1 hr. The solvents were removed and the resulting white solid was reacted with trifluoroacetic acid (0.8 mL) in dichloromethane (0.2 mL) at room temperature for 6 hours. The reaction was concentrated in vacuo overnight to provide the title compound (yield: 10.7 mg) as a off white solid.

$^1$H NMR (DMSO-d$_6$) δ0.81 (t, 3H), 1.24–1.38 (m, 4H), 1.52 (dd, 3H), 1.62 (m, 1H), 1.78 (s, 3H), 2.41 (m, 1H), 3.11 (m, 1H), 3.51 (q$_{AB}$, 2H), 3.77 (t, 1H), 4.23 (t, 1H), 4.40 (m, 1H), 5.27 (t, 1H), 5.45 (m, 1H), 7.55 (d, 1H), 8.87 (br s, 1H), 9.26 (br s, 1H).

MS: (M+H)$^+$=329

EXAMPLE 237

(±)-(2R,3S,5R,1'R,2'S)-2-(1-Acetamido-2-allyloxy-2-vinyl)ethyl-3-(cis-propen-1-yl)-pyrrolidine-5-carboxylic Acid Trifluoroacetic Acid Salt

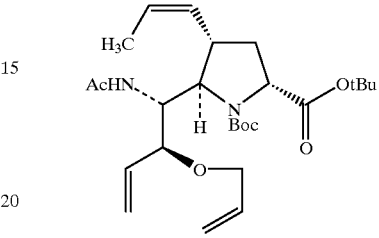

237A (±)-(2R,3S,5R,1'R,2'S)-1-t-Butoxycarbonyl-2-(1-acetamido-2-allyloxy-2-vinyl)ethyl-3-(cis-propen-1-yl-pyrrolidino-5-carboxylic Acid t-Butyl Ester (2R,3S,5R,1'R,2'S)-1-t-Butoxycarbonyl-2-(1-acetamido-2-hydroxy-2-vinyl)ethyl-3-(cis-propen-1-yl)-pyrrolidine-5-carboxylic acid t-butyl ester was reacted according to the method described in Example 84A substituting allyl iodide for methyl iodide (yield: 28 mg, 80%).

MS: (M+H)$^+$=479, (M–H)$^-$=477

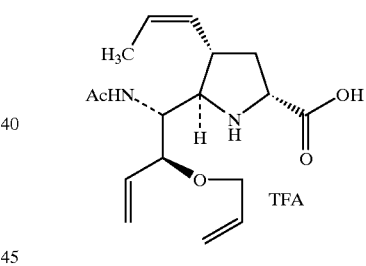

237B (±)-(2R,3S,5R,1'R,2'S)-2-(1-Acetamido-2-allyloxy-2-vinyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-allyloxy-2-vinyl)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. (yield: 4 mg, 100%).

$^1$H NMR (DMSO-d6) δ7.08 (d, J=7.8 Hz, 1H), 5.90 (m, 1H), 5.55 (m, 1H), 5.48 (m, 1H), 5.32 (m, 2H), 5.26 (m, 2H), 5.16 (m, 1H), 4.28 (m, 2H), 3.96 (m, 1H), 3.79 (m, 1H), 3.73 (m, 1H), 3.66 (m, 1H), 3.26 (m, 1H), 2.40 (m, 1H), 1.81 (s, 3H), 1.70 (m, 1H), 1.64 (dd, J=6.9, 1.5 Hz, 3H).

MS: (M+H)$^+$=323, (M–H)$^-$=321.

EXAMPLE 238

(±)-(2R,3S,5R,1'R,2'S)-2-(1-Acetamido-1-(2,5-dihydrofuran-2-yl))methyl-3-(cis-propen-1-yl)-pyrrolidine-5-carboxylic Acid Trifluoroacetic Acid Salt

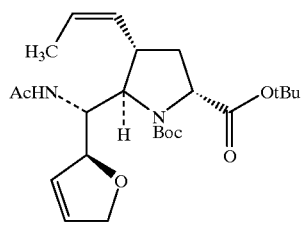

238A (±)-(2R,3S,5R,1'R,2'S)-2-(1-Acetamido-1-(2,5-dihydrofuran-2-yl))methyl-3-(cis-propen-1-yl)-pyrrolidine-5-carboxylic Acid t-Butyl Ester (±)-(2R,3S,5R,1'R,2'S)-1-t-Butoxycarbonyl-2-(1-acetamido-1-allyloxy-2-vinyl)ethyl-3-(cis-propen-1-yl)-pyrrolidine-5-carboxylic acid t-butyl ester (21 mg, 0.044 mmole) prepared according to the procedure of Example 237A was reacted with bis(tricyclohexylphosphine)benzylidine ruthenium(IV) dichloride [Grubb's catalyst] (7.5 mg, 0.009 mmole) in methylene chloride (5 mL) at 25° C. for 2 hours under a nitrogen atmosphere. The reaction was concentrated in vacuo and the resulting residue purified by chromatography on silica gel using 75% ethyl acetate/hexanes to provide the title compound (yield: 18 mg, 90%).

MS: $(M+H)^+=451$, $(M-H)^-=449$.

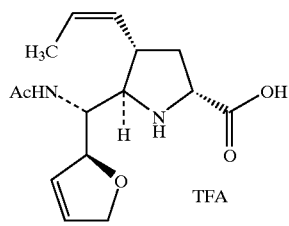

238B (±)-(2R,3S,5R,1'R,2'S)-2-(1-Acetamido-1-(2,5-dihydrofuran-2-yl))methyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-Butoxycarbonyl-2-(1-acetamido-1-(2,5-dihydrofuran-2-yl))methyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido2-hydroxy)butyl-3-(cis-propen-1-yl)-pyrrolidine-5-carboxylic acid t-butyl ester. (yield: 7 mg, 100%).

¹H NMR (DMSO-d6) δ8.09 (d, J=8.8 Hz, 1H), 6.10 (m, 1H), 5.87 (m, 1H), 5.50 (m, 1H), 5.27 (m, 1H), 4.68 (m, 2H), 4.58 (m, 1H), 4.33 (m, 1H), 4.06 (m, 1H), 3.68 (m, 1H), 3.18 (m, 1H), 2.40 (m, 1H), 1.85 (s, 3H), 1.68 (m, 1H), 1.60 (dd, J=6.8, 1.5 Hz, 3H),

MS: $(M+H)^+=295$, $(M-H)^-=293$.

EXAMPLE 239

(±)-(2R,3S,5R,1'R,2'S)-2-(1-Acetamido-2-allyloxy-2-allyl)ethyl-3-(cis-propen-1-yl)-pyrrolidine-5-carboxylic Acid Trifluoroacetic Acid Salt

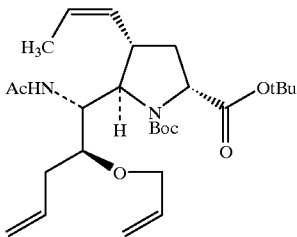

239A (±)-(2R,3S,5R,1'R,2'S)-1-t-Butoxycarbonyl-2-(1-acetamido-2-allyloxy-2-allyl)ethyl-3-(cis-propen-1-yl)-pyrrolidine-5-carboxylic Acid t-Butyl Ester (2R,3S,5R,1'R,2'S)-1-t-Butoxycarbonyl-2-(1-acetamido-2-hydroxy-2-allyl)ethyl-3-(cis-propen-1-yl)-pyrrolidine-5-carboxylic acid t-butyl ester was reacted according to the method described in Example 84A substituting allyl iodide for methyl iodide iodide (yield: 19 mg, 36%).

MS: $(M+H)^+=493$, $(M-H)^-=491$.

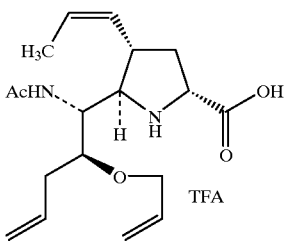

239B (±)-(2R,3S,5R,1'R,2'S)-2-(1-Acetamido-2-allyloxy-2-allyl)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-Acetamido-2-allyloxy-2-allyl)propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. (yield: 5.7 mg, 100%).

¹H NMR (DMSO-d6) δ8.06 (dd, J=8.8 Hz, 1H), 6.92 (m, 1H), 6.77 (m, 1H), 5.50 (m, 1H), 5.29 (m, 2H), 5.17 (m, 1H), 5.05 (m, 2H), 4.27 (m, 2H), 4.10 (dd, J=12.2, 5.4 Hz, 1H), 3.83 (m, 1H), 3.78 (m, 1H), 3.40 (m, 1H), 3.20 (m, 1H), 2.46 (m, 1H), 2.38 (m, 1H), 2.20 (m, 1H), 1.88 (s, 3H), 1.69 (m, 1H), 1.63 (dd, J=6.8, 1.5 Hz, 3H).

MS: $(M+H)^+=337$, $(M+Na)^+=359$, $(M-H)^-=335$.

EXAMPLE 240

(±)-(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid Trifluoroacetic Acid Salt

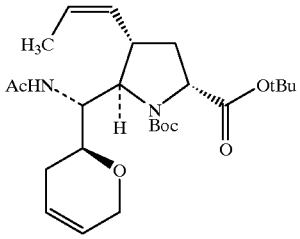

240A (±)-(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid t-Butyl Ester (±)-(2R,3S,5R,1'R,2'S)-1-t-Butoxycarbonyl-2-(1-Acetamido-2-allyloxy-2-allyl)ethyl-3-(cis-propen-1-yl)-pyrrolidine-5-carboxylic acid t-butyl ester (11.5 mg, 0.023 mmole) prepared according to the procedure of Example 239A was reacted with bis(tricyclohexylphosphine) benzylidine ruthenium(IV) dichloride [Grubb's catalyst] (3.8 mg, 0.005 mmole) in methylene chloride (3 mL) at 25° C. for 3 hours under a nitrogen atmosphere. The reaction was concentrated in vacuo and the resulting residue purified by chromatography on silica gel using 75% ethyl acetate/hexanes to provide the title compound (yield: 5.7 mg, 53%).

MS: $(M+H)^+=465$, $(M+Na)^+=487$, $(M-H)^-=463$

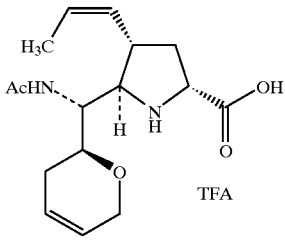

240B (±)-(2R,3S,5R,1'R,2'S)-2-(1-Acetamido-1-(3,6-dihydro-2-H-pyran-2-yl)methyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-1-(3,6-dihydro-2-H-pyran-2-yl))propyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester. (yield: 5.9 mg, 100%).

$^1$H NMR (DMSO-d6) δ8.04 (d, J=8.8 Hz, 1H), 5.77 (m, 2H), 5.50 (m, 1H), 5.25 (m, 1H), 4.21 (m, 2H), 4.14 (m, 1H), 4.04 (m, 1H), 3.81 (m, 1H), 3.40 (m, 1H), 3.23 (m, 1H), 2.41 (m, 1H), 2.09 (m, 1H), 1.88 (s, 3H), 1.83 (m, 1H), 1.70 (m, 1H), 1.63 (d, J=6.8 Hz, 3H).

MS: $(M+H)^+=309$, $(M+Na)^+=331$, $(M-H)^-=307$

The following compounds were synthesized according to the methods previously described in Examples 1–240

EXAMPLE 241

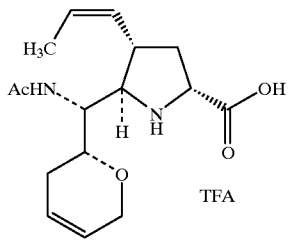

(±)-(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid Trifluoroacetic Acid Salt 1H NMR (DMSO-d6) δ7.90 (d, 9.1 Hz, 1H), 5.79 (m, 2H), 5.48 (m, 1H), 5.23 (m, 1H), 4.43 (m, 1H), 4.24 (m, 2H), 4.17 (m, 2H), 3.73 (m, 1H), 3.64 (m, 1H), 3.19 (m, 1H), 2.42 (m, 1H), 2.02 (m, 1H), 1.85 (s, 3H), 1.78 (m, 1H), 1.75 (m, 1H), 1.56 (dd, J=7.5, 1.5 Hz, 3H).

MS: $(M+H)^+=309$, $(M+Na)^+=331$, $(M-H)^-=307$.

EXAMPLE 242

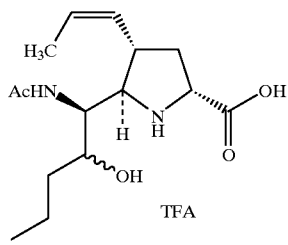

(±)-(2R,3S,5R,1'S,2'RS)-2-(1-Acetamido-2-hydroxy)pentyl-3-(cis-propen-1-yl)-pyrrolidine-5-carboxylic Acid Trifluoroacetic Acid Salt $^1$H NMR (DMSO) δ7.7 (d, J=9.8 Hz, 1H), 5.61 (m, 1H), 5.19 (dt, J=1.8, 11.0 Hz, 1H), 4.33 (dd, J=6.7, 10.3 Hz, 1H), 3.81 (m, 1H), 3.70 (dd, 1.8, 10.3 Hz, 1H), 3.54 (q, J=6.1 Hz, 1H), 3.10 (m, 1H), 2.35 (dt, J=12.8, 6.8 Hz, 1H), 1.90 (s, 3H), 1.7 (m, 1H), 1.59 (dd, J=0.7, 7.3 Hz, 3H), 1.4 (m, 3H), 1.2 (m, 2H), 0.90 (t, J=6.7 Hz, 3H).

MS: $(M+H)^+=299$

EXAMPLE 243

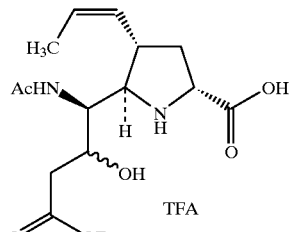

(±)-(2R,3S,5R,1'S,2'RS)-2-(1-Acetamido-2-hydroxy-3-ethoxycarbonyl)propyl-3-(cis-propen-1-yl)-pyrrolidine-5-carboxylic Acid Trifluoroacetic Acid Salt $^1$H NMR (DMSO) δ7.75 (m, 1H), 5.60 (m, 1H), 5.29 (m, 1H), 4.55–4.25 (m, 3H), 4.15–4.0 (m, 3H), 3.9–3.6 (m, 3H), 3.15 (m, 1H), 2.45–2.3 (m 2H), 1.9 (s, 3H), 1.8–1.5 (m, 5H), 1.2 (m, 3H).

MS: $(M+H)^+=343$

EXAMPLE 244

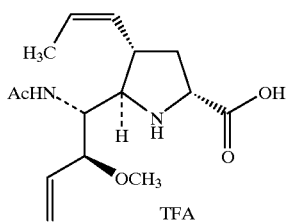

TFA (±)-(2R,3S,5R,1'R,2'S)-2-(1-Acetamido-2-methoxy-
2-vinyl)ethyl-3-(cis-propen-1-yl)-pyrrolidine-5-
carboxylic Acid Trifluoroacetic Acid Salt $^1$H NMR (DMSO-d$_6$) d 7.91(d, J=8.05 Hz, 1H), 5.50(m, 2H), 5.30(m, 3H), 4.27(m, 1H), 4.23(m, 1H), 3.75(m, 1H), 3.48(m, 1H), 3.23(m, 1H), 3.15(s, 3H), 2.40(m, 1H), 1.80(s, 3H), 1.68(m, 1H), 1.64(dd, J=1.83, 7.32 Hz, 3H)

MS: (M+H)$^+$=297, (M−H)$^-$=295

EXAMPLE 245

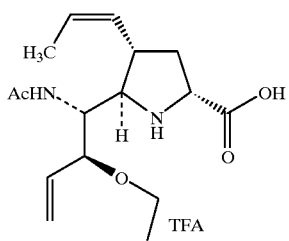

TFA (±)-(2R,3S,5R,1'R,2'S)-2-(1-Acetamido-2-ethoxy-2-
vinyl)ethyl-3-(cis-propen-1-yl)-pyrrolidine-5-
carboxylic Acid Trifluoroacetic Acid Salt $^1$H NMR(DMSO-d$_6$) d 7.90(d, J=7.85 Hz, 1H), 5.57(m, 2H), 5.48(m, 3H), 4.27(m, 1H), 4.22(m, 1H), 3.77(m, 1H), 3.60(m, 1H), 3.46(m, 1H), 3.23(m, 2H), 2.39(m, 1H), 1.80(s, 3H), 1.70(m, 1H), 1.64(dd, J=1.47, 6.73 Hz, 3H), 1.12(t, J=6.83 Hz, 3H)

MS: (M+H)$^+$=311, (M−H)$^-$=309

EXAMPLE 246

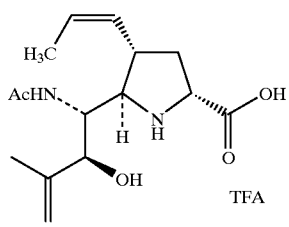

TFA (±)-(2R,3S,5R,1'R,2'S)-2-(1-Acetamido-2-hydroxy-
2-(propeny-2-yl))ethyl-3-(cis-propen-1-yl)-
pyrrolidine-5-carboxylic Acid Trifluoroacetic Acid
Salt $^1$H NMR(DMSO-d$_6$) δ7.69(d, J=9.75 Hz, 1H), 5.47(m, 1H), 5.28(m, 1H), 5.03(m, 1H), 4.86(m, 1H), 4.40(m, 1H), 4.30(m, 1H), 4.18(m, 1H), 3.97(m, 1H), 3.68(m, 1H), 3.21(m, 1H), 2.43(m, 1H), 1.82(m, 1H), 1.73(s, 3H), 1.64(s, 3H), 1.59(m, 3H)

MS: (M+H)$^+$=297, (M−H)$^-$=295

EXAMPLE 247

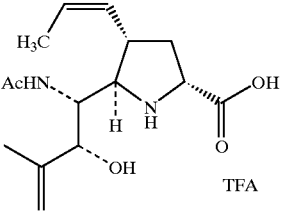

TFA (±)-(2R,3S,5R,1'R,2'R)-2-(1-Acetamido-2-hydroxy-
2-(propeny-2-yl))ethyl-3-(cis-propen-1-yl)-
pyrrolidine-5-carboxylic Acid Trifluoroacetic Acid
Salt $^1$H NMR (DMSO-d$_6$) δ7.65(d, J=9.80 HZ, 1H), 5.48(m, 1H), 5.23(m, 1H), 4.99(s, 1H), 4.88(s, 1H), 4.46(m, 1H), 4.30(m, 1H), 4.19(m, 1H), 3.55(m, 1H), 3.22(m, 1H), 2.44(m, 1H), 1.78(s, 3H), 1.75(m, 1H), 1.65(s, 3H), 1.58(dd, J×1.23, 6.70 HZ, 3H)

MS: (M+H)$^+$=297, (M−H)$^-$=295

EXAMPLE 248

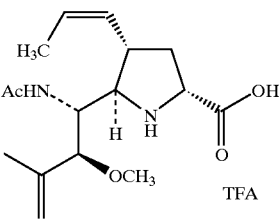

TFA (±)-(2R,3S,5R,1'R,2'S)-2-(1-Acetamido-2-methoxy-
2-(propeny-2-yl))ethyl-3-(cis-propen-1-yl)-
pyrrolidine-5-carboxylic Acid Trifluoroacetic Acid
Salt $^1$H NMR (DMSO-d$_6$) d 7.77(d, J=9.8 Hz, 1H), 5.49 (m, 1H), 5.25(m, 1H), 5.07(m, 1H), 4.94(m, 1H), 4.32(m, 1H), 4.25(m, 1H), 3.75(m, 1), 3.48(m, 1H), 3.25(m, 1H), 3.08(s, 3H), 2.40(m, 1H), 1.77(s, 3H), 1.68(m, 1H), 1.64(dd, J=1.22, 6.71 Hz, 3H), 1.56(s, 3H)

MS: (M+H)$^+$=31 1, (M−H)$^-$=309

EXAMPLE 249

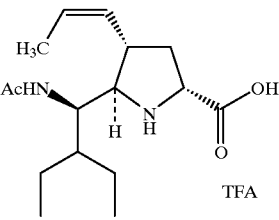

TFA (±)-(2R,3S,5R,1'R)-2-(1-Acetamido-2-ethyl)butyl-3-
(cis-propen-1-yl)-pyrrolidine-5-carboxylic Acid
Trifluoroacetic Acid Salt $^1$H NMR (DMSO-d$_6$) δ7.62(d, J=9.21 Hz, 1H), 5.58(m, 1H), 5.28(m, 1H), 4.37(m, 1H), 3.98(m, 1H), 3.57(m, 1H), 3.10(m, 1H), 2.45(m, 1H), 1.92(s, 3H), 1.76(m, 1H), 1.62 (dd, J=1.83, 6.72 Hz, 3H), 1.24(m, 5H), 0.84(t, J=7.61 Hz, 3H), 0.77(t, J=7.61 Hz, 3H)

MS: (M+H)⁺=297, (M−H)⁻=295

EXAMPLE 250

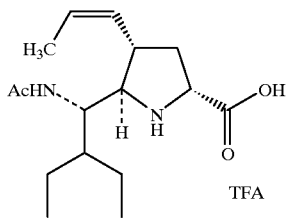

TFA (±)-(2R,3S,5R,1'S)-2-(1-Acetamido-2-ethyl)butyl-3-(cis-propen-1-yl)-pyrrolidine-5-carboxylic Acid Trifluoroacetic Acid Salt ¹H NMR (DMSO-d₆) δ7.76(d, J=9.2 Hz, 1H), 5.46(m, 1H), 5.29(m, 1H), 4.23(m, 1H), 3.63(m, 1H), 3.15(m, 1H), 3.01(m, 1H), 2.38(m, 1H), 1.87(s, 3H), 1.71(m, 1H), 1.60(m, 3H), 1.36(m, 1H), 1.20(m, 4H), 0.83 (t, J=7.3 Hz, 6H)

MS: (M+H)⁺=297, (M−H)⁻=295

EXAMPLE 251

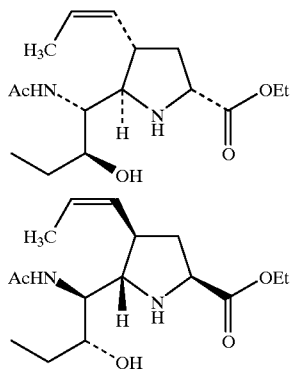

(−)-(2R,3S,5R,1'S)-2-(1-Acetamido-2-hydroxy)butyl-3-(cis-propen-1-yl)-pyrrolidine-5-carboxylic Acid Ethyl Ester and (±)-(2S,3R,5S,1'R)-2-(1-Acetamido-2-hydroxy)butyl-3-(cis-propen-1-yl)-pyrrolidine-5-carboxylic Acid Ethyl Ester (±)-(2R,3S,5R,1'S)-2-(1-Acetamido-2-hydroxy)butyl-3-(cis-propen-1-yl)-pyrrolidine-5-carboxylic acid ethyl ester (100 mg) was chromatographed in one injection on a chiral HPLC column of dimensions 5×30 cm. The column was packed with Chiralpak AD chiral stationary phase packing from Chiral Technologies. The mobile phase consisted of 1:9 ethanol:hexanes at a flow rate of 117 mL/min. Two peaks were observed at (24–36) minutes (−)-(2R,3S,5R,1'S) (yield: 45 mg) and at (60–96) min (+)-(2S,3R,5S,1'R) (yield: 45 mg).

(−)-(2R,3S,5R,1'S) [α]_D=−26° (c=0.78, dichloromethane)

EXAMPLE 252

(−)-(2R,3S,5R,1'S)-2-(1-Acetamido-2-hydroxy)butyl-3-(cis-propen-1-yl)-pyrrolidine-5-carboxylate Ammonium Salt

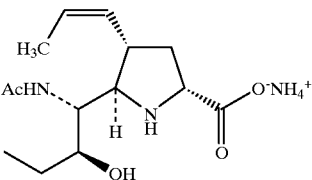

(−)-(2R,3S,5R,1'S)-2-(1-Acetamido-2-hydroxy)butyl-3-(cis-propen-1-yl)-pyrrolidine-5-carboxylic acid ethyl ester (4.9 mg, 0.0157 mmole) prepared according to the procedure of Example 251 was reacted with lithium hydroxide (0.75 mg, 0.0314 mmole) in a mixture of methanol (0.75 mL) and water (0.25 mL) at 0° C. for 7 hours. Then 0.1 N aqueous Hydrochloric acid (1 mL) was added, the reaction was concentrated in vacuo and the resulting residue purified by ion exchange chromatography on Aldrich Dowex 50WX8-400 strongly acidic resin. The residue was placed on the column and washed with water (5 mL) followed by elution using 0.5 N aqueous Ammonium hydroxide to provide the title compound as a colorless solid (yield: 3.9 mg, 83%). [α]_D=−40°, c=0.08 (water).

¹H NMR (DMSO-d₆) δ7.71 (d, J=9.2 Hz, 1H), 5.38 (m, 1H), 5.29 (m, 1H), 3.92 (m, 11H), 3.65 (t, J=8. 5 Hz, 1H), 3.43 (m, 1H), 3.33 (m, 1H), 2.98 (m, 1H), 2.23 (m, 1H), 1.76 (s, 3H), 1.54 (dd, J=6.7,1.8 Hz, 3H), 1.46 (m, 2H), 1.23 (m, 1H), 0.84 (t, J=7.3 Hz, 3H).

MS: (M+H)=285, (M+Na)+=307, (M−H)−=283.

[α]_D=−40°, (c=0.08, water).

EXAMPLE 253

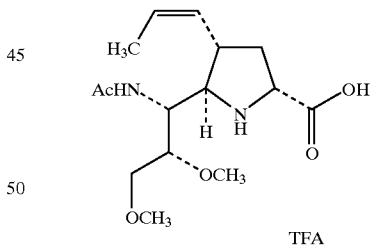

TFA (±)-(2R,3S,5R,1'R,2'S)-2-(1-Acetamido-2,3-dimethoxy)propyl-3-(cis-propen-1-yl)-pyrrolidine-5-carboxylic Acid Trifluoroacetic Acid Salt ¹H NMR (MeOD-d₃) δ.7.8(d, J=9.3 Hz, 1H), 5.49–5.43 (m, 1H), 5.25(dd, J=1.95, 9.3 Hz, 1H), 4.38–4.31(m, 2H), 3.57–3.50(m, 1H), 3.46(dd, J=4.9, 10.3 Hz, 1H), 3.42(s, 3H), 3.35–3.32(m, 2H), 3.27(s, 3H), 3.16–3.09 (m, 1H), 2.46–2.40(m, 1H), 1.80(s, 3H), 1.72–1.65(m, 1H), 1.55(d, J=6.8 Hz, 3H).

MS: (M+H)⁺=315, (M+Na)⁺=337, (M−H)⁻=313, (M+Cl)⁻=349, (2M−H)⁻=627.

EXAMPLE 254

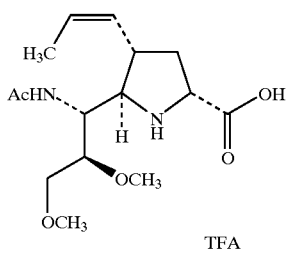

TFA (±)-(2R,3S,5R,1'R,2'R)-2-(1-Acetamido-2,3-dimethoxy)propyl-3-(cis-propen-1-yl)-pyrrolidine-5-carboxylic Acid Trifluoroacetic Acid Salt $^1$H NMR (MeOD-d$_3$) δ.8.04(d, J=8.5 Hz, 1H), 5.52–5.48 (m, 1H), 5.27–5.22(m, 1H), 4.32–4.25(m, 2H), 3.74–3.71 (m, 1H), 3.53(dd, J=2.4, 10.1 Hz, 1H), 3.33–3.25(m, 2H), 3.31(s, 3H), 3.25(s, 3H), 3.21–3.17(m, 1H), 2.42–2.36(m, 1H), 1.86(s, 3H), 1.71–1.63(m, 1H), 1.62(d, J=7.3 Hz, 3H).
MS: (M+H)$^+$=315, (M+Na)$^+$=337, (M−H)$^−$=313, (M+Cl)$^−$=349, (2M−H)$^−$=627

EXAMPLE 255

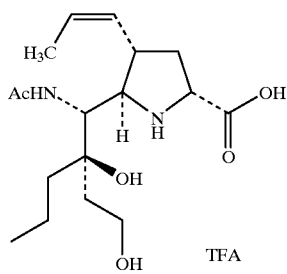

TFA (±)-(2R,3S,5R,1'R,2'R)-2-(1-Acetamido-2-hydroxyethyl-2-hydroxy)pentyl-3-(cis-propen-1-yl)-pyrrolidine-5-carboxylic Acid Trifluoroacetic Acid Salt $^1$H NMR (DMSO-d$_6$): δ7.60 (m, 1H), 5.46 (m, 1H), 5.30 (m, 1H), 4.54 (m, 1H), 4.35 (m, 1H), 4.03 (m, 1H), 3.96 (m, 1H), 3.69 (m, 1H), 3.15 (m, 1H), 2.40 (m, 1H), 1.98 (m, 2H), 1.80 (s, 3H), 1.70–1.50 (m, 5H), 1.38 (m, 3H), 0.83 (m, 3H), MS: (M+H)+=343, (M−H)$^−$=341

EXAMPLE 256

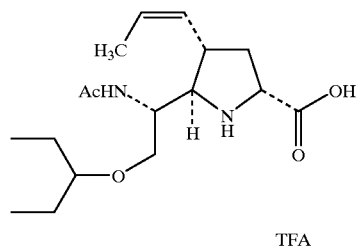

TFA (±)-(2R,3S,5R,1'R)-2-(1-Acetamido-2-(3-pentyloxy))ethyl-3-(cis-propen-1-yl)-pyrrolidine-5-carboxylic Acid Trifluoroacetic Acid Salt $^1$H NMR (MeOD-d$_3$) δ5.69–5.59 (m, 1H), 5.33–5.25 (m, 1H), 4.39 (m, 1H), 4.34 (dd, J=7.8, 10.2 Hz, 1H), 3.73 (dd, J=4.8, 10.2 Hz, 1H), 3.58–3.47 (m, 2H), 3.38–3.24 (m, 1H), 3.27–3.20 (m, 1H), 2.61–2.52 (m, 1H), 2.02 (s, 3H), 1.90–1.78 (m, 1H), 1.70 (dd, J=1.7, 6.8 Hz, 3H), 1.60–1.50 (m, 4H), 0.92 (t, J=7.5 Hz, 6H)

(M+H)$^+$=327, (M+Na)$^+$=349

EXAMPLE 257

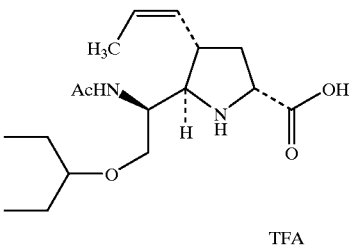

TFA (±)-(2R,3S,5R,1'S)-2-(1-Acetamido-2-(3-pentyloxy))ethyl-3-(cis-propen-1-yl)-pyrrolidine-5-carboxylic Acid Trifluoroacetic Acid Salt $^1$H NMR (MeOD-d$_3$) δ5.73–5.66 (m, 1H), 5.32–5.25 (m, 1H), 4.36 (dd, J=7.8, 10.2Hz, 1H), 4.09 (m, 1H), 3.68 (dd, J=6.1, 10.2 Hz, 1H), 3.61 (d, J=4.4Hz, 2H), 3.35–3.23 (m, 1H), 3.24–3.16 (m, 1H), 2.65–2.55 (m, 1H), 2.03 (s, 3H), 1.92–1.80 (m, 1H), 1.70 (dd, J=2.0, 7.1 Hz, 3H), 1.59–1.47 (m, 4H), 0.94–0.80 (m, 6H)

(M+H)$^+$=327, (M+Na)$^+$=349

EXAMPLE 258

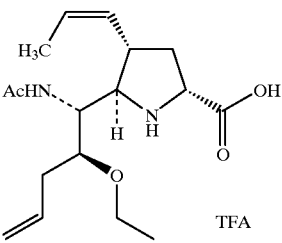

TFA (±)-(2R,3S,5R,1'R,2'S)-2-(1-Acetamido-2-ethoxy-3-vinyl)propyl-3-(cis-propen-1-yl)-pyrrolidine-5-carboxylic Acid Trifluoroacetic Acid Salt $^1$H NMR (DMSO-d$_6$) δ8.01 (d, J=8.6 Hz, 1H), 5.76 (m, 1H), 5.49 (m, 1H), 5.25 (m, 1H), 5.05 (m, 2H), 4.28 (m, 1H), 4.02 (m, 1H), 3.77 (m, 1H), 3.62 (m, 1H), 3.36 (m, 1H), 3.29 (m, 1H), 3.18 (m, 1H), 2.43 (m, 1H), 2.38 (m, 1H), 2.16 (m, 1H), 1.87 (s, 3H), 1.69 (m, 1H), 1.63 (dd, J=6.7, 1.2 Hz, 3H), 1.12 (t, J=6.7 Hz, 3H).

MS: (M+H)=325, (M−H)−=323

EXAMPLE 259

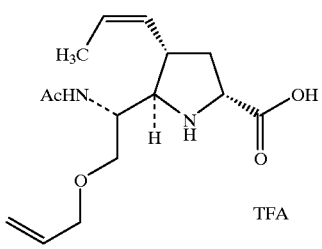

(±)-(2R,3S,5R,1'R)-2-(1-Acetamido-2-allyloxy) ethyl-3-(cis-propen-1-yl)-pyrrolidine-5-carboxylic Acid Trifluoroacetic Acid Salt $^1$H NMR (DMSO-d6) δ9.16 (m,2H), 8.1 (d,J=7.5 Hz, 1H), 5.88(m, 1H), 5.50 (m, 1H), 5.15–5.32(m, 3H), 4.35(m, 2H), 3.95(m,2H), 3.61(m, 1H), 3.40(m,2), 3.20(m, 1H), 2.40(m, 1H), 1.87(s,3H), 1.72(m, 1H), 1.62(d, J=6.2,3H)

MS: (M+1)=297, (M+23)=319, (2M+23)=615

EXAMPLE 260

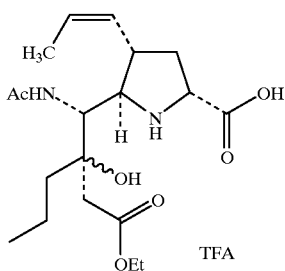

(±)-(2R,3S,5R,1'R,2'RS)-2-(1-Acetamido-2-hydroxy-2-(2-ethoxycarbonyl))pentyl-3-(cis-propen-1-yl)-pyrrolidine-5-carboxylic Acid Trifluoroacetic Acid Salt $^1$H NMR (DMSO-d$_6$): δ7.57 (d, J=10 Hz, 1H), 5.45 (m, 1H), 5.29 (m, 1H), 4.35 (m, 1H), 4.09 (m, 1H), 3.68 (m, 1H), 3.44 (m, 1H), 3.17 (m, 1H), 2.87 (m, 1H), 2.64 (m, 1H), 2.39 (m, 1H), 1.80 (s, 3H), 1.65–1.56 (m, 2H), 1.53 (m, 3H), 1.50–1.30 (m, 3H), 1.21 (t, J=7.5 Hz, 3H), 0.80 (t, J=7.5 Hz, 3H).

MS: (M+H)$^+$=385, (M−H)$^-$=383

EXAMPLE 261

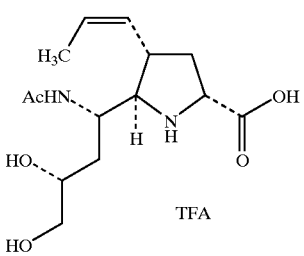

(±)-(2R,3S,5R,1'S,3'R)-2-(1-Acetamido-3,4-dihydroxy)butyl-3-(cis-propen-1yl)-pyrrolidine-5-carboxylic Acid Trifluoroacetic Acid Salt $^1$H NMR (CD$_3$OD) δ5.58–5.70 (m, 1H), 5.24–5.38 (m, 1H), 4.34–4.50 (m, 2H), 3.58–3.72 (m, 2H), 3.42–3.48 (d, 2H), 2.50–2.63 (m, 1H), 2.04 (s, 3H), 1.77–1.95 (m, 1H), 1.65–1.76 (m, 4H), 1.50–1.63 (m, 1H).

MS: (M+H)$^+$=301

EXAMPLE 262

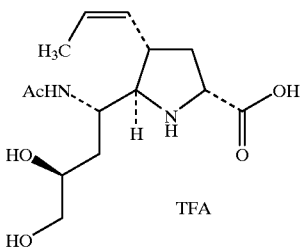

(±)-(2R,3S,5R,1'S,3'S)-2-(1-Acetamido-3,4-dihydroxy)butyl-3-(cis-propen-1-yl)-pyrrolidine-5-carboxylic Acid Trifluoroacetic Acid Salt $^1$H NMR (CD$_3$OD) δ5.58–5.72 (m, 1H), 5.25–5.37 (m, 1H), 4.30–4.45 (m, 2H), 3.63–3.77 (m, 2H), 3.44–3.49 (d, 2H), 2.50–2.63 (m, 1H), 2.03 (s, 3H), 1.76–1.95 (m, 2H), 1.65–1.75 (m, 4H).

MS: (M+H)$^+$=301

EXAMPLE 263

(±)-(2R,3S,5R,1'R)-2-(1-Acetamido-2-methoxy) ethyl-3-(cis-propen-1-yl)-pyrrolidine-5-carboxylic Acid Trifluoroacetic Acid Salt

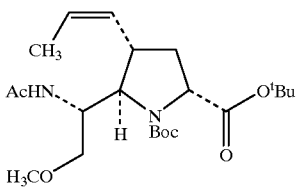

263A (±)-(2R,3S,5R,1'R)-1-t-Butoxycarbonyl-2-(1-Acetamido-2-methoxy)ethyl-3-(cis-propen-1-yl)-pyrrolidine-5-carboxylic Acid t-Butyl Ester The title compound was prepared according to the method described in Example 84A, substituting (±)-(2R,3S,5R,1'R)-1-t-butoxycarbonyl-2-(1-acetamido-2-hydroxy)ethyl-3-(cis-propen-1-yl)-pyrrolidine-5-carboxylic acid t-butyl ester for (±)-(2R,3S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 4.2 mg, 20%).

MS: (M+H)$^+$=427, (M+Na)$^+$=449, (M−H)$^{--}$425.

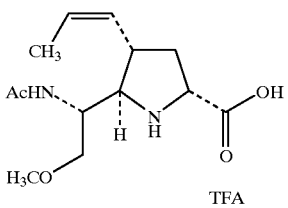

263B (±)-(2R,3S,5R,1'R)-2-(1-Acetamido-2-methoxy)ethyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R)-

1-t-butoxycarbonyl-2-(1-acetamido-2-methoxy)ethyl-3-(cis-propen-1-yl)-pyrrolidine-5-carboxylic acid t-butyl ester in place of (±)-(2R,3S,5R,1'R,2'S)-1-t-butoxycarbonyl-2-(1-acetamido- 2-hydroxy)butyl-3-(cis-propen-1-yl)-pyrrolidine-5-carboxylic acid t-butyl ester (yield: 0.0031 g, 100%).

¹H NMR (DMSO-d₆) δ8.12 (d, J=7.9 Hz, 1H), 5.50 (m, 1H), 5.23 (m, 1H), 4.33 (m, 1H), 3.56 (dd, J=9.7,8.0 Hz, 1H), 3.4–3.3 (m, 2H), 3.26 (s, 3H), 3.19 (m, 1H), 2.39 (dt, J=12.8,7.3Hz, 1H), 1.86 (s, 3H), 1.71 (m, 1H), 1.61 (dd, J=6.7,1.8 Hz, 3H).

MS: (M+H)⁺=271, (M+Na)⁺=293.

EXAMPLE 264

(±)-(2R,3S,5R,1'R,2'S)-2-(1-Acetamido-2-hydroxy-3-dimethyl)butyl-3-(cis-propen-1-yl)-pyrrolidine-5-carboxylic Acid Trifluoroacetic Acid Salt

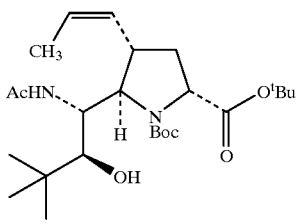

264A (±)-(2R,3S,5R,1'R,2'S)-1-t-Butoxycarbonyl-2-(1-acetamido-2-hydroxy-3-dimethyl)butyl-3-(cis-propen-1-yl)-pyrrolidine-5-carboxylic Acid t-Butyl Ester The title compounds were prepared according to the method described in Example 41B, substituting t-butyl lithium for ethyl magnesium bromide to provide (±)-(2R,3S,5R,1'R,2'S)-1-t-butoxycarbonyl-2-(1-acetamido-2-hydroxy-3-dimethyl)butyl-3-(cis-propen-1-yl)-pyrrolidine-5-carboxylic acid t-butyl ester (yield: 2.5 mg, 11%)

(±)-(2R,3S,5R,1'R,2'S) MS: (M+H)⁺=469; (M−H)⁻=467.

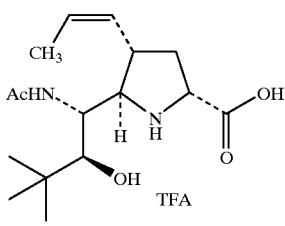

264B (±)-(2R,3S,5R,1'R,2'S)-2-(1-Acetamido-2-hydroxy-4-vinyl)butyl-3-(cis-propen-1-yl)-pyrrolidine-5-carboxylic Acid Trifluoroacetic Acid Salt The title compound was prepared according to the method described in Example 41C, substituting (±)-(2R,3S,5R,1'R,2'S)-1-t-butoxycarbonyl-2-(1-acetamido-2-hydroxy-3-dimethyl)butyl-3-(cis-propen-1-yl)-pyrrolidine-5-carboxylic acid t-butyl ester in place of (±)-(2R,2S,5R,1'R,2'S)-1-t-butoxycarbonyl-2-(1-acetamido-2-hydroxy)butyl-3-(cis-propen-1-yl)-pyrrolidine-5-carboxylic acid t-butyl ester (yield: 2.3 mg, 100%).

¹H NMR (D₂O) δ5.40 (m, 1H), 5.10 (t, J=5.5 Hz, 1H), 4.13 (t, J=9.2 Hz, 1H), 3.46 (m, 1H), 3.22 (d, J=7.3 Hz, 1H), 3.00 (m, 1H), 2.41 (m, 1H), 1.70 (s, 3H), 1.45 (m, 1H), 1.39 (d, J=4.9 Hz, 3H), 1.07 (t, J=5.5 Hz, 1H), 0.70 (s, 9H)

MS: (M+H)⁺=313.

EXAMPLE 265

(±)-(2R,3S,5R,1'R,2'S)-2-(1-acetamido-2-methoxy-2-methyl)pentyl-3-(cis-propen-1-yl)pyrrolidine-5-carboxylic Acid Trifluoroacetic acid Salt

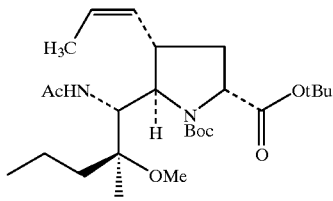

265A (±)-(2R,3S,5R,1'R,2'S)-1-t-Butoxycarbonyl-2-(1-acetamido-2-methoxy-2-methyl)pentyl-3-(cis-propen-1-yl)pyrrolidine-5-carboxylic Acid t-Butyl ester Sodium bis(trimethylsilyl)amide (7.26 mL, 1.0M in THF, 7.26 mmol) was added slowly to a solution of (±)-(2R,3S,5R,1'R,2'S)-1-t-butoxycarbonyl-2-(1-acetamido-2-hydroxy-2-methyl)pentyl-3-(cis-propen-1-yl)pyrrolidine-5-carboxylic acid t-butyl ester (3.09 g, 6.6 mmol) in THF (65 mL) at −78° C. The reaction mixture was stirred at −78° C. for 1 h and then at 0° C. for 20 min. Methyl iodide (8.2 mL, 18.8 g. 0.132 mol) was added and the mixture stirred at 0° C. for 20 min and rt for 2 h. The reaction mixture was quenched with saturated aqueous ammonium chloride (20 mL) and water (20 mL) and extracted using ethyl acetate (3×100 mL). The combined organic layer was dried over magnesium sulfate, filtered, and concentrated in vacuo. The residue was purified by column chromatography on silica gel using 99:1 dichloromethane/methanol followed by 98:2 dichloromethane/methanol to give the title compound (2.1 g, 67% yield). This compound exists as a mixture of rotamers at rt. The ¹H NMR spectrum was therefore acquired at 130° C.

¹H NMR (DMSO-d₆) δ6.9 (bs, 1H), 5.75 (m, 1H), 5.3 (m, 1H), 4.55 (m, 1H), 3.9 (m, 2H), 3.5 (m, 1H), 3.15 (s, 3H), 2.6 (m, 1H), 1.85 (s, 3H), 1.6 (d, J=6 Hz, 3H), 1.5–1.25 (m, 4H), 1.40 (bs, 18H), 1.08 (s, 3H), 0.85 (t, J=7 Hz, 3H).

MS: (M+H)⁺=483, (M+Na)⁺=505, (M−H)⁻⁻481.

265B (±)-(2R,3S,5R,1'R,2'S)-2-(1-acetamido-2-methoxy-2-methyl)pentyl-3-(cis-propen-1-yl)pyrrolidine-5-carboxylic Acid Trifluoroacetic Acid Salt

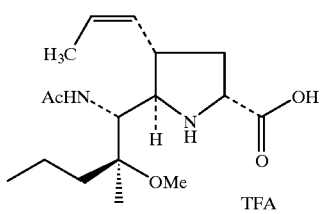

(±)-(2R,3S,5R,1'R,2'S)-1-t-Butoxycarbonyl-2-(1-acetamido-2-methoxy-2-methyl)pentyl-3-(cis-propen-1-yl)

pyrrolidine-5-carboxylic acid t-butyl ester (4.1 mg, 0.0085 mmol) was reacted with trifluoroacetic acid (0.8 mL) in dichloromethane (0.2 mL) at room temperature for 4 h. The reaction mixture was concentrated in vacuo overnight to provide the title compound (yield: 4.1 mg, 100%) as a colorless oil.

$^1$H NMR (DMSO-d$_6$) δ8.96 (bs, 1H), 8.61 (bs, 1H), 7.61 (d, J=10.3 Hz, 1H), 5.45 (m, 1H), 5.28 (m, 1H), 4.33 (t, J=9.8Hz, 1H), 4.29 (m, 1H), 3.59 (m, 1H), 3.2–3.1 (m, 1H), 3.14 (s, 3H), 2.43 (dt, J=12.8,7.9 Hz, 1H), 1.80(s, 3H), 1.6–1.4 (m, 2H), 1.53 (dd, J=6.7,1.2 Hz, 3H), 1.35–1.25 (m, 3H), 1.19 (s, 3H), 0.8 (t, J=6.7 Hz, 3H).

MS: (M+H)$^+$327, (M+Na)$^+$349, (2M+H)$^+$653, (M–H)$^-$=325, (2M–H)$^-$=651.

EXAMPLE 266

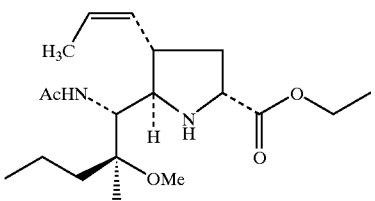

(±)-(2R,3S,5R,1'R,2'S)-2-(1-Acetamido-2-methoxy-2-methyl)pentyl-3-(cis-propen-1-yl)pyrrolidine-5-carboxylic Acid Ethyl Ester A mixture of 9.88 g (0.083 mol, 6.05 mL) thionyl chloride and 175 mL of anhydrous ethanol was stirred at rt for 15 min. To this mixture was added slowly dropwise a solution of 1.83 g (4.15 mmol) (±)-(2R,3S,5R,1'R,2'S)-2-(1-acetamido-2-methoxy-2-methyl)pentyl-3-(cis-propen-1-yl) pyrrolidine-5-carboxylic acid trifluoroacetic acid salt in 25 mL of anhydrous ethanol. The mixture was stirred at room temperature for 18 h and then the solvent was evaporated in vacuo overnight. The residue was purified by column chromatography on silica gel using 98:2:0.1 dichloromethane/methanol/ammonium hydroxide to give the title compound (1.44 g, 98% yield) as a thick colorless oil which solidified upon prolonged standing.

$^1$H NMR (CDCl$_3$) 5.48 (d, J=10.8 Hz, 1H), 5.45–5.28 (m, 2H), 4.16 (m 2H), 3.83 (t, J=7.4 Hz, 1H), 3.29 (t, J=7.1 Hz, 1H), 3.17 (s, 3H), 2.97 (quintet, J=8.1 Hz, 1H), 2.31 (dt, J=12.9,7.8 Hz, 1H), 1.95(s, 3H), 1.61 (dd, J=6.5,1.4 Hz, 3H), 1.55–1.30 (m, 3H), 1.26 (t, J=7.1 Hz, 3H), 1.11 (s, 3H), 0.90 (t, J=7.1 Hz, 3H).

MS: (M+H)$^+$=355, (M–H)$^-$=353.

EXAMPLE 267

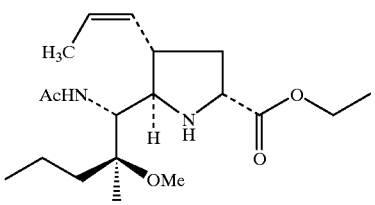

(−)-(2R,3S,5R,1'R,2'S)-2-(1-Acetamido-2-methoxy-2-methyl)pentyl-3-(cis-propen-1-yl)pyrrolidine-5-carboxylic Acid Ethyl Ester Resolution of the racemic ethyl ester was carried out by chiral HPLC using a Chiralpak AD column (10 micron particle diameter, Chiral Technologies, Exton, Pa.) eluting with 98:2 (v/v) hexane/ethanol. Thus, (±)-(2R,3S,5R,1'R,2'S)-2-(1-acetamido-2-methoxy-2-methyl)pentyl-3-(cis-propen-1-yl)pyrrolidine-5-carboxylic acid ethyl ester (14.8 g, 0.042 mol) provided 6.44 g (44% recovery) of (−)-(2R,3S,5R,1'R,2'S)-2-(1-acetamido-2-methoxy-2-methyl) pentyl-3-(cis-propen-1-yl)pyrrolidine-5-carboxylic acid ethyl ester ([α]=−76.9° in dichloromethane at room temperature) and 6.34 9 (43% recovery) of (+)-(2S,3R,5S,1'S,2'R)-2-(1-acetamido-2-methoxy-2-methyl)pentyl-3-(cis-propen-1-yl)pyrrolidine-5-carboxylic acid ethyl ester ([α]=+75.8° in dichloromethane at room temperature). The $^1$H NMR and MS data for each of these compounds matched exactly the data obtained for the racemic mixture.

EXAMPLE 268

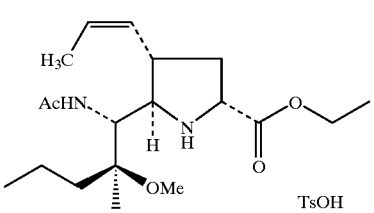

(−)-(2R,3S,5R,1'R,2'S)-2-(1-Acetamido-2-methoxy-2-methyl)pentyl-3-(cis-propen-1-yl)pyrrolidine-5-carboxylic Acid Ethyl Ester p-Toluenesulfonic Acid Salt A solution of (−)-(2R,3S,5R,1'R,2'S)-2-(1-acetamido-2-methoxy-2-methyl)pentyl-3-(cis-propen-1-yl)pyrrolidine-5-carboxylic acid ethyl ester (0.269 g, 0.759 mmol) and p-toluenesulfonic acid hydrate (0.144 g, 0.759 mmol) in dichloromethane (15 mL) was stirred at room temperature for 30 minutes. The solvent was then evaporated in vacuo to provide the title compound (yield: 0.390 g, 98%) as a white powder.

$^1$H NMR δ10.1 (bs, 1H), 9.4, (bs, 1H), 7.78 (d, J =8.1 Hz, 2H), 7.16 (d, J=7.8 Hz, 2H), 6.75 (bd, J=10 Hz, 1H), 5.6–5.4 (m, 2H), 4.49 (t, J=9.5 Hz, 1H), 4.28 (m, 1H), 4.22 (q, J=7.2 Hz, 2H), 4.14 (m, 1H), 3.32 (m, 1H), 3.24 (s, 3H), 2.48 (m, 2H), 2.35 (s, 3H), 1.94 (s, 3H), 1.93 (dt, J=13.7,10.5 Hz, 1H), 1.57 (d, J=5.4 Hz, 3H), 1.5–1.4 (m, 3H), 1.37 (s, 3H), 1.26 (t, J=7.1 Hz, 3H), 0.85 (t,J=6.8 Hz, 3H).

MS: (M+H)$^+$=355, (M–H)$^-$=353.

Anal Calcd for C$_{26}$H$_{42}$N$_2$O$_7$S: C, 59.29; H, 8.04; N, 5.32; S, 6.09. Found: C, 59.24, H, 7.87: N, 5.16; S, 6.18

EXAMPLE 269

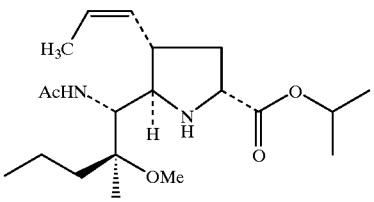

(±)-(2R,3S,5R,1'R,2'S)-2-(1-acetamido-2-methoxy-2-methyl)pentyl-3-(cis-propen-1-yl)pyrrolidine-5-carboxylic Acid Isopropyl Ester A mixture of 0.19 g (1.59 mmol, 0.12 mL) thionyl chloride and 10 mL of 2-propanol was stirred at rt for 15 min. To this mixture was added slowly dropwise a solution of 0.35 g (0.0795 mmol) (±)-(2R,3S,3R,1'R,2'S)-2-(1-acetamido-2-methoxy-2-methyl)pentyl-3-(cis-propen-1-yl)pyrrolidine-5-carboxylic acid trifluoroacetic acid salt in 2 mL of 2-propanol. The mixture was stirred at room temperature for 48 hours and then the solvent was evaporated in vacuo. The residue was purified by column chromatography on silica gel using 98:2:0.1 dichloromethane/methanol/ammonium hydroxide to provide the title compound (yield: 9.1 mg, 31%) as a colorless oil.

$^1$H NMR (CDCl$_3$) δ5.5–5.25 (m, 3H), 5.02 (septet, J=6.3 Hz, 1H), 4.15 (dd, J=10.2,7.1 Hz, 1H), 3.79 (t, J=7.5 Hz, 1H), 3.28 (t, J=7.4 Hz, 1H), 3.17 (s, 3H), 2.96 (quintet, J=8.3 Hz, 1H), 2.30 (td, J=12.5,8.2 Hz, 1H), 1.94 (s, 3H), 1.62 (dd, J=6.8,1.6 Hz, 3H), 1.65–1.30 (m, 5H), 1.24 (d, J=6.5 Hz, 3H), 1.21 (d, J=6.3 Hz, 3H), 1.11 (s, 3H), 0.90 (t, J=7.1 Hz, 3H).

MS: (M+H)$^+$=369, (M−H)$^-$=367.

EXAMPLE 270

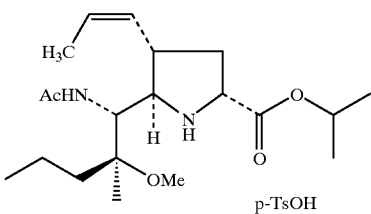

p-TsOH (±)-(2R,3S,5R,1'R,2'S)-2-(1-acetamido-2-methoxy-2-methyl)pentyl-3-(cis-propen-1-yl)pyrrolidine-5-carboxylic Acid Isopropyl Ester p-Toluenesulfonic Acid Salt A mixture of (±)-(2R,3S,5R,1'R,2'S)-2-(1-acetamido-2-methoxy-2-methyl)pentyl-3-(cis-propen-1-yl)pyrrolidine-5-carboxylic acid isopropyl ester (8.4 mg, 0.0228 mmol) and p-toluenesulfonic acid monohydrate (0.0043 g, 0.0228 mmol) in 1 mL of dichloromethane was stirred at rt for 1 h. The solvent was evaporated in vacuo to provide the desired product (yield: 12.0 mg, 97%) as a white powder.

$^1$H NMR (CDCl$_3$) δ9.9 (bs, 1H), 9.45 (bs, 1H), 7.79 (d, J=8.1 Hz, 2H), 7.15 (d, J=7.8 Hz, 2H), 6.57 (bd, J=8.9 Hz, 1H), 5.53 (m, 2H), 5.07 (quintet, J=6.3 Hz, 1H), 4.50 (t, J=9.5 Hz, 1H), 4.25 (bs, 1H), 4.10 (bs, 1H), 3.34 (m, 1H), 3.24 (s, 3H), 2.50 (m, 1H), 2.35 (s, 3H), 1.95 (s, 3H), 1.9 (m, 1H), 1.6–1.2 (m, 6H), 1.35 (s, 3H), 1.25 (d, J=6.4 Hz, 3H), 1.23 (d, 3H), 0.85 (t, J=7.0 Hz, 3H).,

MS: (M+H)$^+$=369, (M−H)$^-$=367.

EXAMPLE 271

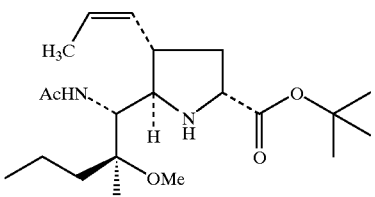

(±)-(2R,3S,5R,1'R,2'S)-2-(1-acetamido-2-methoxy-2-methyl)pentyl-3-(cis-propen-1-yl)pyrrolidine-5-carboxylic acid t-butyl ester A mixture of (±)-(2R,3S,5R,1'R,2'S)-1-t-butoxycarbonyl-2-(1-acetamido-2-methoxy-2-methyl)pentyl-3-(cis-propen-1-yl)pyrrolidine-5-carboxylic acid t-butyl ester (0.4123 g, 0.855 mmol) and trifluoroacetic acid (2.93 g, 25.7 mmol) in 10 mL dichloromethane was stirred at rt for 1.5 h. The solvent was evaporated in vacuo and the residue purified by chromatography on silica gel, eluting with 98:2:0.1 dichloromethane/methanol/ammonium hydroxide to provide the desired product (yield: 0.168 g, 51%) as a colorless oil.

$^1$H NMR (CDCl$_3$) δ5.5–5.25 (m, 3H), 4.15 (dd, J=10.1, 7.2 Hz, 1H), 3.73 (t, J=7.4 Hz, 1H), 3.26 (t, J=7.1 Hz, 1H), 3.17 (s, 3H), 2.94 (quintet, J=8.3 Hz, 1H), 2.28 (td, J=12.5, 7.8 Hz, 1H), 1.93 (s, 3H), 1.61 (dd, J=6.4,1.4 Hz, 3H), 1.58–1.20 (m, 5H), 1.44 (s, 9H), 1.11 (s, 3H), 0.90 (t, J=7.1 Hz, 3H).

MS: (M+H)$^+$=383, (M−H)$^-$=381.

EXAMPLE 272

(±)-(2R,3S,5R,1'R,2'S)-2-(1-acetamido-2-methoxy-2-methyl)pentyl-3-(cis-propen-1-yl)pyrrolidine-5-carboxylic Acid t-Butyl ester p-Toluenesulfonic Acid Salt

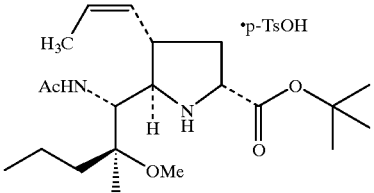

A mixture of (±)-(2R,3S,5R,1'R,2'S)-2-(1-acetamido-2-methoxy-2-methyl)pentyl-3-(cis-propen-1-yl)pyrrolidine-5-carboxylic acid t-butyl ester (0.161 g, 0.421 mmol) and p-toluenesulfonic acid monohydrate (0.080 g, 0.421 mmol) in 10 mL of dichloromethane was stirred at rt for 1 h. The solvent was evaporated in vacuo to provide the desired product (yield; 0.230 g, 99%) as a white powder.

$^1$H NMR (CDCl$_3$) δ9.2 (bs, 1H), 9.35 (bs, 1H), 7.79 (d, J=6.4 Hz, 2H), 7.15 (d, J=8.4 Hz, 2H), 6.8 (bd, J=9.9 Hz, 1H), 5.6–5.4 (m, 2H), 4.50 (t, J=9.15 Hz, 1H), 4.22 (bs, 1H), 4.10 (bs, 1H), 3.4–3.3 (m, 1H), 3.24 (s, 3H), 2.46 (m, 1H), 2.34 (s, 3H), 1.94 (s, 3H), 1.86 (m, 1H), 1.64 (s, 3H), 1.57 (d, J=5.1 Hz, 3H), 1.52 –1.40 (m, 2H), 1.46 (s, 9H), 1.38 (s, 3H), 1.3–1.2 (m, 1H), 0.84 (t, J =6.8 Hz, 3H).

MS: (M+H)$^+$=383, (M−H)$^-$=381.

Anal. Calcd for $C_{28}H_{46}N_2O_7S$: C, 60.62; H, 8.36; N, 5.05; S, 5.78. Found: C, 60.64; H, 8.14; N, 4.96; S, 5.70.

EXAMPLE 273

(-) 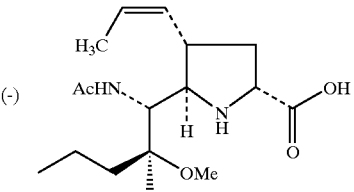

(−)-(2R,3S,5R,1'R,2'S)-2-(1-acetamido-2-methoxy-2-methyl)pentyl-3-(cis-propen-1-yl)pyrrolidine-5-carboxylic Acid A solution of (−)-(2R,3S,5R,1'R,2'S)-2-(1-acetamido-2-methoxy-2-methyl)pentyl-3-(cis-propen-1-yl)pyrrolidine-5- carboxylic acid ethyl ester (0.528 g, 1.49 mmol) and lithium hydroxide (72 mg, 3.0 mmol) in methanol (75 mL) and water (25 mL) was stirred at a for 6 h. Following the addition of 100 mL of 0.1 N HCl the mixture was evaporated in vacuo to provide a white solid. This material was dissolved in water (25 mL) and adsorbed on 15 g of DOWEX 50WX8-400 strongly acidic ion-exchange resin (resin had been prepared by washing with water followed by 0.5 N ammonium hydroxide followed by 1.0 N hydrochloric acid followed by water). After washing the resin with water (250 mL), the desired product was eluted using 0.5 N ammonium hydroxide (250 mL) to provide the desired product (yield: 0.460 g, 90%) as a white solid. [α]=−54.6° in water at rt.

$^1$H NMR (D$_2$O) δ5.61 (dq, J=8.9,7.2 Hz, 1H), 5.31 (m, 1H), 4.35 (d, J=10.2 Hz, 1H), 4.10 (t, J=8.9 Hz, 1H), 3.59 (t, J=10.0 Hz, 1H), 3.26 (s, 3H), 3.14 (quintet, J=8.5 Hz, 1H), 2.54 (dt, J=13.6, 7.8 Hz, 1H), 2.16 (m, 1H), 1.95 (s, 3H), 1.75–1.6 (m, 1H), 1.57 (dd, J=6.8, 1.3 Hz, 3H), 1.40 (m, 1H), 1.35–1.25 (m, 2H), 1.24 (s, 3H), 0.85 (t, J=7.0 Hz, 3H), 0.78 (m, 1H).

MS (M+H)$^+$=327, (M+Na)$^+$=349, (M−H)$^−$=325, (2M−H)$^−$=651.

EXAMPLE 274

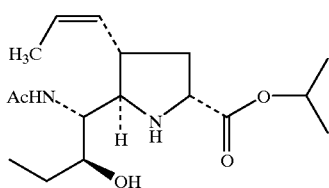

(±)-(2R,3S,5R,1'R,2'S)-2-(1-acetamido-2-hydroxy)butyl-3-(cis-propen-1-yl)pyrrolidine-5-carboxylic Acid Isopropyl Ester $^1$H NMR (CDCl$_3$, 500 MHz) δ5.50–5.45 (m, 1H), 5.35 (d, 1H, J=7 Hz), 5.30–5.25 (m, 1H), 5.10–5.0 (m, 1H), 3.80–3.75 (m, 2H), 3.62–3.57 (m, 1H), 3.11–3.12 (m, 1H), 3.10–3.02 (m, 1H), 2.42–2.37 (m, 1H), 1.93 (s, 3H), 1.61 (d, 3H, J=5 Hz), 1.52–1.42 (m, 3H), 1.28–1.20 (m, 8H), 0.98 (t, 3H, J=7 Hz)

EXAMPLE 275

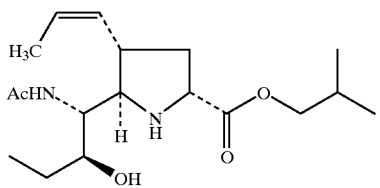

(±)-(2R,3S,5R,1'R,2'S)-2-(1-acetamido-2-hydroxy)butyl-3-(cis-propen-1-yl)pyrrolidine-5-carboxylic Acid Isobutyl Ester $^1$H NMR (DMSO-d$_6$, 500 MHz) δ7.49 (d, 1H, J=10 Hz), 5.32–5.24 (m, 2H), 3.92–3.80 (m, 2H), 3.75 (t, 1H, J=7.7 Hz), 3.48–3.32 (m, 6H), 3.10–3.04 (m, 1H), 2.90–2.83 (m, 1H), 2.45 (s, 1H), 2.29–2.2.22 (m, 1H), 2.19 (s, 1H), 1.75 (s, 2H), 1.52 (d, 2H, J=5 Hz), 1.06 (s, 3H), 0.90 (d, 6H, J=5 Hz)

EXAMPLE 276

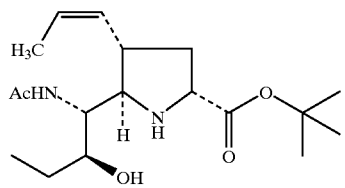

(±)-(2R,3S,5R,1'R,2'S)-2-(1-acetamido-2-hydroxy)butyl-3-(cis-propen-1-yl)pyrrolidine-5-carboxylic Acid tert-Butyl Ester $^1$H NMR (DMSO-d$_6$, 500 MHz) δ8.95 (s, br, 1H), 7.88 (d, 1H, J=9.5 Hz), 5.50–5.43 (m, 1H), 5.35–5.24 (m, 2H), 4.30–4.25 (m, 1H), 4.03–3.95 (m, 1H), 3.75–3.68 (m, 1H), 2.42–2.33 (m, 1H), 1.82 (s, 3H), 1.60 (d, 3H, J=6 Hz), 1.58 (d, 3H, J=6 Hz), 1.45 (s, 9H), 1.30–1.22 (m, 2H), 0.85 (t, 3H, J=7.5 Hz)

EXAMPLE 277

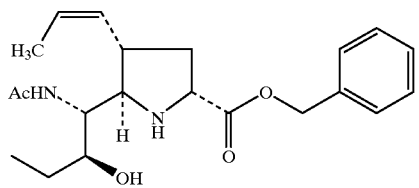

(±)-(2R,3S,5R,1'R,2'S)-2-(1-acetamido-2-hydroxy)butyl-3-(cis-propen-1-yl)pyrrolidine-5-carboxylic Acid Benzyl Ester $^1$H NMR (DMSO-d$_6$, 500 MHz) δ7.49 (d, 1H, J=9.5 Hz), 7.40–7.30 (m, 5H), 5.32–5.24 (m, 2H), 5.19–5.10 (m, 3H), 3.70 (t, 1H, J=7 Hz), 3.62–3.55 (m, 2H), 3.44–3.40 (m, 1H), 3.10–3.05 (t, 1H, J=7 Hz), 2.90–2.82 (m, 1H), 2.30–2.21 (m, 1H), 1.75 (s, 3H), 1.53 (d, 3H, J=6 Hz), 1.45–1.39 (m, 2H), 0.80 (t, 3H, J=7.5 Hz)

EXAMPLE 278

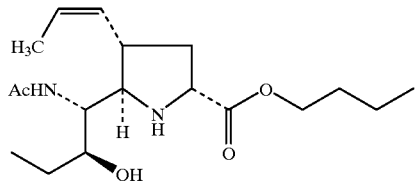

(±)-(2R,3S,5R,1'R,2'S)-2-(1-acetamido-2-hydroxy)butyl-3-(cis-propen-1-yl)pyrrolidine-5-carboxylic Acid Butyl Ester $^1$H NMR (DMSO-d$_6$, 500 MHz) δ9.2 (s, br, 1H), 7.89 (d, 1H, J=9.5 Hz), 7.48 (d, 2H, J=8 Hz), 7.10 (d, 2H, J=8 Hz), 5.50–5.42 (m, 1H), 5.35–5.25 (m, 1H), 4.42–4.37 (m, 1H), 4.21–4.13 (m, 2H), 4.07–4.00 (m, 1H), 3.75–3.69 (m, 1H), 3.47–3.40 (m, 1H), 3.20–3.10 (m, 1H), 2.47–2.40 (m, 1H), 2.27 (s, 3H), 1.81 (s, 3H), 1.68–1.57 (m, 4H), 1.38–1.22 (m, 5H), 0.92–0.81 (m, 5H).

EXAMPLE 279

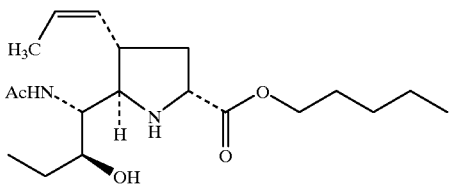

(±)-(2R,3S,5R,1'R,2'S)-2-(1-acetamido-2-hydroxy) butyl-3-(cis-propen-1-yl)pyrrolidine-5-carboxylic Acid Pentyl Ester $^1$H NMR (DMSO-d$_6$, 500 MHz) δ7.50 (d, 1H, J=9.5 Hz), 5.35–5.23 (m, 2H), 4.12–4.00 (m, 2H), 3.30 (s, 3H), 3.72 (t, 1H, J=5.0 Hz), 3.60–3.53 (m, 1H), 3.43–3.40 (m, 1H), 3.10–3.05 (m, 1H), 3.90–3.83 (m, 1H), 2.27–2.20 (m, 1H), 1.50–1.35 (m, 3H), 1.75 (s, 3H), 1.60–1.50 (m, 4H), 1.32–1.15 (m, 5H), 0.9–0.8 (m, 5H).

EXAMPLE 280

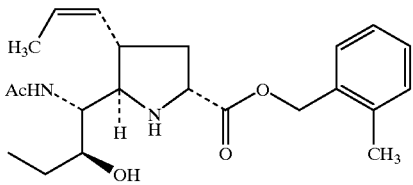

(±)-(2R,3S,5R,1'R,2'S)-2-(1-acetamido-2-hydroxy) butyl-3-(cis-propen-1-yl)pyrrolidine-5-carboxylic Acid (2-Methyl)benzyl Ester p-Toluenesulfonic Acid Salt $^1$H NMR (DMSO-d$_6$, 500 MHz) δ9.05 (d, br 1H), 7.90 (d, 1H, J=9.5 Hz), 7.47 (d, 2H, J=8.0 Hz), 7.39–7.20 (m, 4H), 7.10 (d, 2H, J=8.0 Hz), 5.50–5.42 (m, 1H), 5.29–5.20 (m, 2H), 4.05–4.00 (m, 1H), 3.75–3.70 (m, 1H), 2.45–2.40 (m, 1H), 2.22 (s, 2H), 2.29 (s, 3H), 1.81 (s, 3H), 1.67–1.50 (m, 5H), 1.30–1.22 (m, 4H), 0.88–0.82 (t, 3H, J=7.5 Hz)

EXAMPLE 281

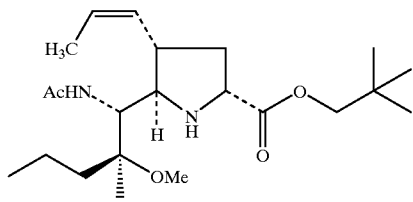

(±)-(2R,3S,5R,1'R,2'S)-2-(1-acetamido-2-methoxy-2-methyl)pentyl-3-(cis-propen-1-yl)pyrrolidine-5-carboxylic Acid t-Amyl Ester A mixture of 0.054 g (0.45 mmol, 0.033 mL) thionyl chloride and 0.64 g 2,2-dimethyl-1-propanol in 1 mL anhydrous toluene was stirred at rt for 15 min. To this mixture was added in one portion 0.011 g (0.0227 mmol) (±)-(2R, 3S,5R,1'R,2'S)-2-(1-acetamido-2-methoxy-2-methyl) pentyl-3-(cis-propen-1-yl)pyrrolidine-5-carboxylic acid trifluoroacetic acid salt. The mixture was stirred at rt for 18 h and then the solvent was evaporated in vacuo. The residue was purified by column chromatography on silica gel using 98:2:0.1 dichloromethane/methanol/ammonium hydroxide to give the title compound (6.5 mg, 66% yield) as a colorless oil.

$^1$H NMR (CDCl3) δ5.5–5.25 (m, 3H), 4.17 (dd, J=10.2, 7.1 Hz, 1H), 3.89 (t, J=7.8 Hz, 1H), 3.86 (d, J=10.5 Hz, 1H), 3.75 (d, J=10.5 Hz, 1H), 3.31 (t, J=7.7 Hz, 1H), 3.17 (s, 3H), 2.98 (quintet, J=8.3 Hz, 1H), 2.33 (dt, J=12.9,7.8 Hz, 1H), 1.94(s, 3H), 1.61 (dd, J=6.6,1.3 Hz, 3H), 1.65–1.30 (m, 5H), 1.12 (s, 3H), 0.93 (s, 9H), 0.90 (t, J=7.1 Hz, 3H).

MS: (M+H)$^+$=397, (M+Na)$^+$=419, (M–H)$^-$=395.

EXAMPLE 282

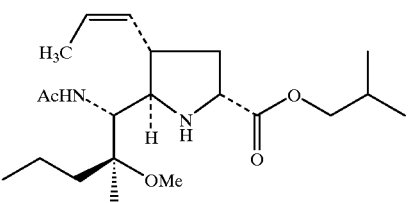

(±)-(2R,3S,5R,1'R,2'S)-2-(1-acetamido-2-methoxy-2-methyl)pentyl-3-(cis-propen-1-yl)pyrrolidine-5-carboxylic acid Isobutyl Ester A mixture of 0.0714 g (0.60 mmol, 0.044 mL) thionyl chloride and 2 mL 2-methyl-1-propanol was stirred at rt for 15 min. To this mixture was added a solution of 0.0132 g (0.030 mmol) (±)-(2R,3S,5R,1'R,2'S)-2-(1-acetamido-2-methoxy-2-methyl)pentyl-3-(cis-propen-1-yl)pyrrolidine-5-carboxylic acid trifluoroacetic acid salt in 1 mL of 2-methyl-1-propanol. The mixture was stirred at rt for 48 h and then the solvent was evaporated in vacuo. The residue was purified by column chromatography on silica gel using 98:2:0.1 dichloromethane/methanol/ammonium hydroxide to give the title compound (6.5 mg, 57% yield) as a colorless oil.

$^1$H NMR (CDCl$_3$) δ5.5–5.25 (m, 3H), 4.16 (dd, J=10.4, 7.3 Hz, 1H), 3.95–3.8 (m, 3H), 3.30 (t, J=7.3 Hz, 1H), 3.17 (s, 3H), 2.97 (quintet, J=8.3 Hz, 1H), 2.32 (dt, J=12.9,7.8 Hz, 1H), 1.95 (s, 3H), 1.93 (m, 1H), 1.61 (dd, J=6.6,1.5 Hz, 3H), 1.6–1.2 (m, 5H), 1.11 (s, 3H), 0.92 (d, J6.4 Hz, 6H), 0.90 (t, J=7.0 Hz, 3H).

EXAMPLE 283

(±)-(2R,3S,5R,1'R,2'R)-2-(1-acetamido-2-hydroxy-2-ethenyl)pentyl-3-(cis-propen-1-yl)pyrrolidine-5-carboxylic Acid Trifluoroacetic Acid Salt

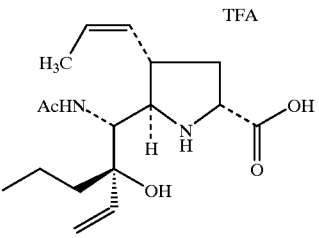

$^1$H NMR (DMSO-d$_6$) δ7.58 (d, J=10.4 Hz, 1H), 6.02 (dd, J =17.1,10.4 Hz, 1H), 5.5–5.4 (m, 2H), 5.30 (dd, J =11.0,1.8

Hz, 1H), 5.20 (m, 1H), 4.35–4.30 (m, 2H), 3.38 (t, J=9.2 Hz, 1H), 3.07 (quintet, J=8.8 Hz, 1H), 2.42 (dt, J =13.4,7.9 Hz, 1H), 1.80 (s, 3H), 1.55 (m, 1H), 1.51 (dd, J=6.7,1.8 Hz, 3H), 1.43–1.30 (m, 4H), 1.22 (m, 1H), 0.81 (t, J=7.0 Hz, 3H).

MS: (M+H)$^+$=325, (M+Na)$^+$=347, (2M+H)$^+$=649, (M–H)$^{-31}$=323, (2M–H)$^-$=647.

EXAMPLE 284

(±)-(2R,3S,5R,1'R,2'R)-2-(1-acetamido-2-methoxy-2-ethenyl)pentyl-3-(cis-propen-1-yl)pyrrolidine-5-carboxylic Acid Trifluoroacetic Acid Salt

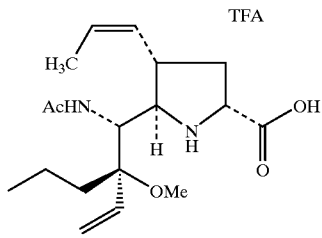

$^1$H NMR (DMSO-d$_6$) δ7.58 (d, J=10.4 Hz, 1H), 6.02 (dd, J=17.1,10.4 Hz, 1H), 5.5–5.4 (m, 2H), 5.30 (dd, J=11.0, 1.8 Hz, 1H), 5.20 (m, 1H), 4.35–4.30 (m, 2H), 3.38 (t, J=9.2 Hz, 1H), 3.07 (quintet, J=8.8 Hz, 1H), 2.42 (dt, J=13.4, 7.9 Hz, 1H), 1.80 (s, 3H), 1.55 (m, 1H), 1.51 (dd, J=6.7,1.8 Hz, 3H), 1.43–1.30 (m, 4H), 1.22 (m, 1H), 0.81 (t, J=7.0 Hz, 3H).

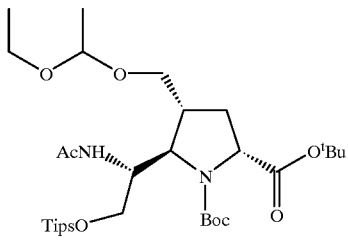

EXAMPLE 285

285A (±)-(2R,3R,5R,1'R)-1-t-Butoxycarbonyl-2-(1-acetamido-2-triisopropyl-silyloxy)ethyl-3-ethoxyethyloxymethylpyrrolidine-5-carboxylic acid t-butyl ester (±)-(2R,3R,5R,1'R)-1-t-Butoxycarbonyl 2-(1-acetamido-2-triisopropyl-silyloxy)ethyl-3-hydroxymethylpyrrolidine-5-carboxylic acid t-butyl ester (1.06 g, 1.90 mmol) in 40 ml of dichloromethane was reacted with pyridinium p-toluenesulfonate (95 mg, 0.38 mmol) and ethyl vinyl ether (0.36 ml, 3.80 mmol) 1 hour at room temperature. The reaction was quenched with saturated aqueous NaHCO$_3$, extracted with dichloromethane (5×30 ml). The combined organic layers were dried over Na$_2$SO$_4$ and concentrated to give the crude title compound (yield: 1.2 g, 100%).

MS: (M+H)$^+$=631.

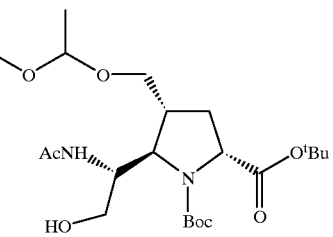

285B (±)-(2R,3R,5R,1'R)-1-t-Butoxycarbonyl-2-(1-acetamido-2-hydroxy)ethyl-3-ethoxyethyloxymethylpyrrolidine-5-carboxylic acid t-butyl ester The product of Example 285A (1.2 g, 1.90 mmol) in THF (60 ml) was reacted with tetrabutyl ammonium fluoride (1M in THF) (1.90 ml, 1.90 mmol) for 60 minutes at room temperature. Water was added followed by extraction using dichloromethane (5×40 ml). This organic layers were dried over Na$_2$SO$_4$, filtered and concentrated in vacuo. The residue was purified by column chromatography on silica gel using 10% methanol in dichloromethane to provide the title compound as a colorless oil (yield: 791.6 mg , 87.7%).

$^1$H NMR (CDCl$_3$): δ1.18 (td, 3H), 1.26 (dd,3H), 1.44 (s, 9H), 1.47 (s, 9H), 1.85 (m, 1H), 2.00 (s, 3H), 2.39 (m, 1H), 2.55 (m, 1H), 3.27–3.67 (m, 6H), 3.83 (m, 1H), 3.92 (d, 1H), 4.12 (dt, 1H), 4.26 (m, 1H), 4.64 (m, 1H), 6.36 (br d, 1H).

MS: (M+H)$^+$=475.

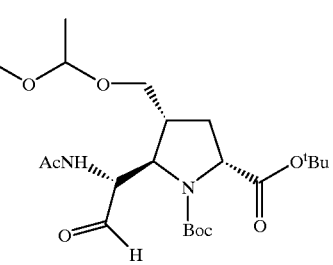

285C (±)-(2R,3R,5R,1'R)-1-t-Butoxycarbonyl-2-(1-acetamido-1-formyl)methyl-3-ethoxyethyloxymethylpyrrolidine-5-carboxylic Acid t-Butyl Ester The product of Example 285B (790.0 mg, 1.66 mmol) was reacted with Dess-Martin Periodinane (850 mg, 2.0 mmol) in dichloromethane (40 ml) at room temperature for 2 hours. The reaction was quenched with 1M aqueous sodium thiosulfate (40 ml) and extracted with dichloromethane (5×40 ml). The organic layers were dried over sodium sulfate, filtered, and concentrated in vacuo. The residue was purified by column chromatography on silica gel using ethyl acetate to provide the title compound as a white foamy solid (yield: 707.1 mg, 89.9%).

$^1$H NMR (CDCl$_3$): δ1.18 (td, 3H), 1.27 (dd, 3H), 1.42 (s, 9H), 1.47 (s, 9H), 1.71 (m, 1H), 2.08 (s, 3H), 3.34–3.67 (m,

4H), 3.92 (dd, 1H), 4.18 (dd, 1H) 4.65 (m, 1H), 4.89 (ddd, 1H), 7.15 (m, 1H), 9.46 (s, 1H).

MS: (M+H)$^+$=473.

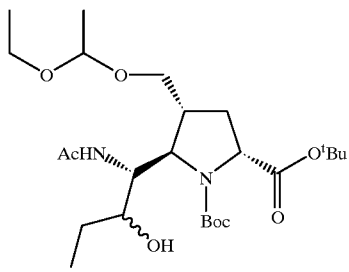

285D (±)-(2R,3R,5R,1'R,2'R and 2'S)-1-t-Butoxycarbonyl-2-(1-acetamido-2-hydroxy)butyl-3-ethoxyethyloxymethylpyrrolidine-5-carboxylic Acid t-Butyl Ester The product of Example 285C (700 mg, 1.48 mmol) in THF (15 ml) was added dropwise to a solution of ethyl-magnesium chloride (3.0M in ether) (3.0 ml, 8.9 mmol) in THF (15 ml) at room temperature and reacted for 30 minutes. The reaction was quenched with saturated aqueous ammonium chloride (15 ml) followed by extraction with dichloromethane (5×20 ml). The organic layer was dried over sodium sulfate, filtered and concentrated in vacuo, to provide the crude title compound (yield: 756.2 mg, 100%).

MS: (M+H)$^+$=503.

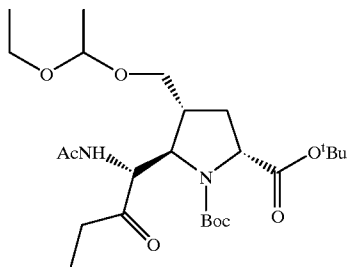

285E (±)-(2R,3R,5R,1'R)-1-t-Butoxycarbonyl-2-(1-acetamido-2-oxo)butyl-3-ethoxyethyloxymethylpyrrolidine-5-carboxylic Acid t-Butyl Ester The title compound was prepared according to the method described in Example 285C, substituting the product of Example 285D in place of the product of Example 285B (yield: 574.2 mg, 77.4%).

$^1$H NMR (CDCl$_3$): δ1.04 (t, J=7.2 Hz, 3H), 1.18 (td, J=6.9 3.6 Hz, 3H), 1.24 (dd, J=5.4, 1.2 Hz, 3H), 1.45 (s, 9H), 1.46 (s, 9H), 1.65 (m, 1H), 2.04 (s, 3H), 2.28 (m, 1H), 2,42 (m, 1H), 2,63 (qd, J=7.2, 1.5 Hz, 2H), 3.25 (dd, J=9.3, 6.3 Hz, 1H), 3.36–3.46 (m, 2H), 3.54–3.61 (m, 2H), 4.09–4.18 (m, 2H), 4.61 (t, J=5.1 Hz, 1H), 5.23 (br t, J=7.2 Hz, 1H).

MS: (M+H)$^+$=501.

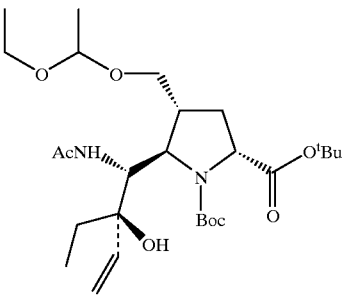

285F (±)-(2R,3R,5R,1'R,2'R)-1-t-Butoxycarbonyl-2-(1-acetamido-2-hydroxy-2-vinyl)butyl-3-ethoxyethyloxymethylpyrrolidine-5-carboxylic Acid t-Butyl Ester The title compound was prepared according to the method described in Example 285D, substituting compound the product of Example 285E in place of the product of Example 285C and substituting vinyl magnesium bromide in place of ethyl magnesium bromide (yield: 272.1 mg, 45.2%).

MS: (M+H)$^+$=529.

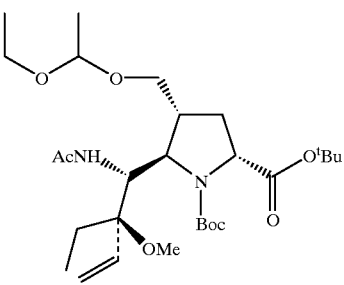

285G (±)-(2R,3R,5R,1'R,2'R)-1-t-Butoxycarbonyl-2-(1-acetamido-2-methoxy-2-vinyl)butyl-3-ethoxyethyloxymethylpyrrolidine-5-carboxylic Acid t-Butyl Ester The product of Example 285F (200 mg, 0.38 mmol) in THF (6 ml) was reacted with sodium bis(trimethylsilyl) amide (1.0M in THF, 0.76 ml, 0.76 mmol) at −78° C. for 45 minutes then at 0° C. for 15 minutes. Methyl iodide (2.4 ml, 38.0 mmol) was added to the reaction at 0° C. Stirring was continued at 0° C. for 30 minutes then at room temperature for 2 hours. The reaction was quenched with saturated aqueous ammonium chloride (10 ml) followed by extraction using dichloromethane (5×20 ml). The organic layer was dried over sodium sulfate, filtered and concentrated in vacuo. The residue was purified by column chromatography on silica gel using 5% methanol in dichloromethane to provide the title compound (yield: 202.0 mg, 98.4%).

MS: (M+H)$^+$=543.

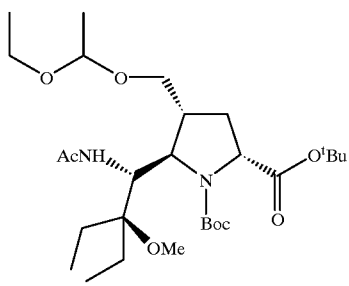

285H (±)-(2R,3R,5R,1'R)-1-t-Butoxycarbonyl-2-(1-acetamido-2-methoxy-2-ethyl)butyl-3-ethoxyethyloxymethylpyrrolidine-5-carboxylic Acid t-Butyl Ester The product of Example 285F (200 mg, 0.369 mmol) and 10% Pd—C (100 mg) were stirred under 1 atmosphere of hydrogen in ethyl acetate (50 ml) for 2 hours. The reaction was filtered and concentrated, to give the crude title compound (yield: 198.1 mg, 98.7%).

MS: (M+H)$^+$=545.

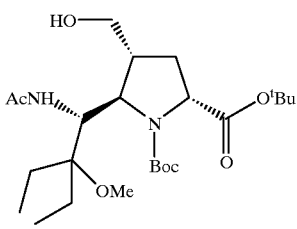

285I (±)-(2R,3R,5R,1'R)-1-t-Butoxycarbonyl-2-(1-acetamido-2-methoxy-2-ethyl)butyl-3-hydroxymethylpyrrolidine-5-carboxylic Acid t-Butyl Ester The product of Example 285H (196.0 mg, 0.36 mmol) was dissolved in THF (20 ml) and treated with 0.2N hydrochloric acid (20 ml) at room temperature for 2 hour. The reaction was quenched with saturated aqueous sodium bicarbonate followed by extraction using dichloromethane (5×20 ml). The organic layer was dried over sodium sulfate, filtered and concentrated in vacuo. The residue was purified by column chromatography on silica gel using 5% methanol in dichloromethane to provide the title compound (yield: 103.2 mg, 60.7%).

$^1$H NMR (CDCl$_3$) (mixture of two rotamers) δ: 0.87, 0.89 (two t, J=7.5 Hz, 3H), 1.06, 1.26 (two t, J=7.5 Hz, 3H), 1.45, 1.46 (two s, 9H), 1.52, 1.55 (two s, 9H), 1.73–1.94 (m, 5H), 1.98, 1.99 (two s, 3H), 2.29–2.42 (m, 1H), 2.66–2.91 (m, 1H), 3.27, 3.28 (two s, 3H), 3.51–3.72 (m, 2H), 4.00–4.11 (m, 1H), 4.18–4.29 (m, 1H), 4.67, 4.70 (two dd, 1H), 5.76, 5.81 (two br d, 1H).

MS: (M+H)$^+$=473.

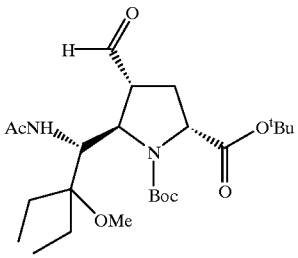

285J (±)-(2R,3R,5R,1'R)-1-t-Butoxycarbonyl-2-(1-acetamido-2-methoxy-2-ethyl)butyl-3-formylpyrrolidine-5-carboxylic Acid t-Butyl Ester The title compound was prepared according to the method described in Example 285C, substituting the product of Example 285I in place of the product of Example 285B (yield: 40.1 mg, 80.5%).

MS: (M+H)$^+$=471.

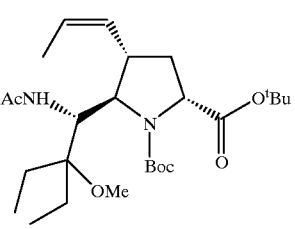

285K (±)-(2R,3R,5R,1'R)-1-t-Butoxycarbonyl-2-(1-acetamido-2-methoxy-2-ethyl)butyl-3-(cis-propen-1-yl)pyrrolidine-5-carboxylic Acid t-Butyl Ester A suspension of ethyl triphenylphosphonium bromide (180 mg, 0.48 mmol) in anhydrous toluene (2 ml) was reacted with potassium t-butoxide (1.0 M in THF, 0.32 mmol) at room temperature for 14 hours. The product of Example 285J (38 mg, 0.081 mmol) in toluene (2 ml) was added dropwise to the above mixture and stirred for 1 hour. The reaction was quenched with saturated aqueous ammonium chloride and extracted with dichloromethane (5×10 ml). The organic layer was washed with brine, dried over Na$_2$SO$_4$, filtered and concentrated in vacuo. The residue was purified by chromatography on silica gel using 50% ethyl acetate/hexanes to provide the title compound (yield: 20.1 mg, 53.8%).

$^1$H NMR (CDCl$_3$) (mixture of rotamers) δ: 0.84 0.91 (3H), 0.97–1.11 (3H), 1.42–1.47 (9H), 1.54–1.55 (9H), 1.60–1.64 (3H), 1.66 (1H), 1.72–1.80 (4H), 1.97–1.99 (3H), 2.42–2.58 (1H), 3.23–3.25 (3H), 3.50–3.73 (1H) 4.03–4.18

(2H), 4.67–4.73 (1H), 5.29–5.38 (1H), 5.57–5.71 (1H), 5.83–6.02 (1H).
MS: (M+H)⁺=483.

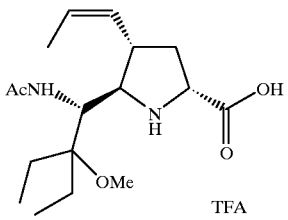

TFA

285L (±)-(2R,3R,5R,1'R)-2-(1-acetamido-2-methoxy-2-ethyl)butyl-3-(cis-propen-1-yl) pyrrolidine-5-carboxylic Acid Trifluoroacetic Acid Salt The product of Example 285K (17.0 mg, 0.035 mmol) was reacted with trifluoroacetic acid (0.8 mL) in dichloromethane (0.2 mL) at room temperature for 4 hours. The reaction was concentrated in vacuo and triturated with dichloromethane (4×0.2 ml) to provide the title compound (yield: 15.6 mg, 100%) as an off white solid.
¹H NMR (DMSO-d₆) δ0.81 (t, 3H), 0.96 (t, 3H), 1.29 (m, 1H), 1.53 (dd, 3H), 1.55–1.65 (m, 3H), 1.70 (m, 1H), 1.82 (s, 3H), 2.45 (m, 1H), 3.10 (m, 1H), 3.17 (s, 3H), 3,72 (m, 1H), 4.24 (m, 1H), 4.39 (t, 1H), 5.29 (m, 1H), 5.45 (m, 1H), 7.58 (d, 1H), 8.50 (br s, 1H), 9.03 (br s, 1H).

EXAMPLE 286

(±)-(2R,3S,5R,1'R,2'S)-2-(1-Acetamido-2-methyl-2,3-dimethoxy)ethyl-3-(cis-propen-1-yl)-pyrrolidine-5-carboxylic Acid Trifluoroacetic Acid Salt

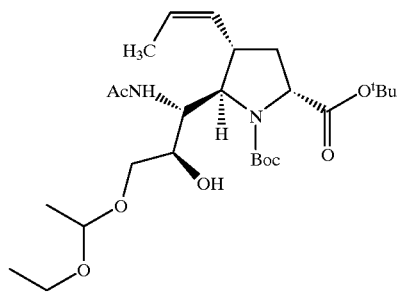

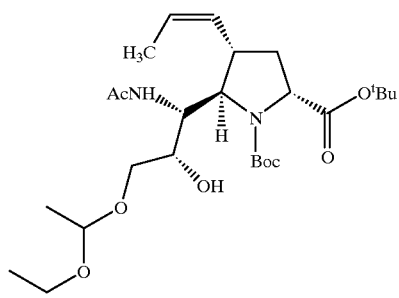

286A1 (±)-(2R,3S,5R,1'R,2'R)-1-t-Butoxycarbonyl-2-(1-acetamido-3-ethoxyethyloxy-2-hydroxy)propyl-3-(cis-propen-1-yl)-pyrrolidine-5-carboxylic Acid t-Butyl Ester and 286A2 (±)-(2R,3S,5R,1'R,2'S)-1-Butoxycarbonyl-2-(1-acetamido-3-ethoxyethyloxy-2-hydroxy)propyl-3-(cis-propen-1-yl)-pyrrolidine-5-carboxylic Acid t-Butyl Ester (Ethoxyethyloxymethyl)tributylstannane (prepared according to the procedure of W. Clark Still, *J. Am. Chem. Soc.*, 100, 1481 (1978)) (575 mg, 1.46 mmol) in THF (4 ml) was reacted with n-butyllithium (1.6M, 0.6 ml, 0.96 mmol) at −78° C. for 15 minutes followed by the product of Example 41A (70 mg, 0.17 mmol) in THF (2 ml). The mixture was stirred at −78° C. for an additional 30 minutes, quenched with saturated aqueous ammonium chloride (3 ml) followed by extraction using dichloromethane (5×10 ml). The organic layer was dried over magnesium sulfate, filtered and concentrated in vacuo. The residue was separated by column chromatography on silica gel using 5% methanol in dichloromethane to provide the title compounds 286A1 (yield: 25.1 mg, 28.7%) and 286A2 (yield: 30.9 mg, 35.3%) as white foamy solids.

286A1: ¹H NMR (CDCl₃): δ1.20 (dt, J=7.2, 2.4 Hz, 3H), 1.30 (dd, J=5.4, 3.9 Hz, 3H), 1.44 (s, 9H), 1.47 (s, 9H), 1.61 (m, 1H), 1.65 (dd, J=6.6, 1.5 Hz, 3H), 2.04 (s, 3H), 2.62 (m, 1H), 3.38–3.70 (m, 8H), 4.23 (dd, J=9.3, 5.1 Hz, 1H), 4.67 (qd, J=5.1, 2.4 Hz, 1H), 4.37–4.48 (m, 2H), 7.77 (br t, J=9.9 Hz, 1H).

286A2: ¹H NMR (CDCl₃) δ1.19 (dt, J=7.2, 2.4 Hz, 3H), 1.29 (t, J=5.1 Hz, 3H), 1.44 (s, 9H), 1.46 (s, 9H), 1.54 (dd, 3H), 1.64 (m, 1H), 2.00 (s, 3H), 2.66 (m, 1H), 3.13 (m, 1H), 3.41–3.49 (m, 2H), 3.59–3.69 (m, 2H), 3.75 (d, J=9.9 Hz, 1H), 3.89 (td, J=10.2, 3.0 Hz, 1H), 4.15 (ddd, J=10.2, 3.0, 1.2 Hz, 1H), 4.65 (dd, J=9.6, 5.1 Hz, 1H), 4.72 (dd, J=6.6, 4.8 Hz, 1H), 5.35 (m, 1H), 5.60 (br t, J=10.2 Hz, 1H), 5.99 (br d, J=10.2 Hz, 1H).

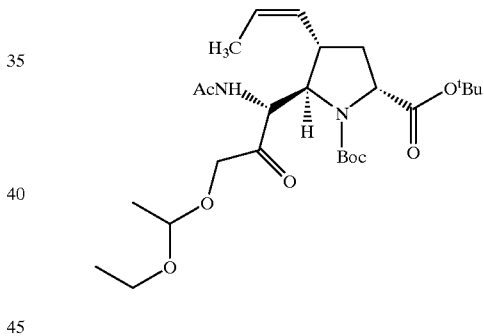

286B (±)-(2R,3S,5R,1'R)-1-t-Butoxycarbonyl-2-(1-acetamido-3-ethoxyethyloxy-2-oxo)propyl-3-(cis-propen-1-yl)-pyrrolidine-5-carboxylic Acid t-Butyl Ester The products of Example 286A (298.0 mg, 0.58 mmol) were reacted with Dess-Martin Periodinane (368.4 mg, 0.87 mmol) in dichloromethane (20 ml) at room temperature for 2 hours. The reaction was quenched with 1M aqueous sodium thiosulfate (20 ml) and extracted with dichloromethane (5×20 ml). The organic layer was dried over sodium sulfate, filtered, and concentrated in vacuo. The residue was purified by column chromatography on silica gel using ethyl acetate to provide the title compound as a white foamy solid (yield: 254.2 mg, 85.6%).

¹H NMR (CDCl₃): δ1.17 (t, 3H), 1.31 (dd, 3H), 1.41 (s, 9H), 1.46 (s, 9H), 1.56 (m, 1H), 1.64 (dt, 3H), 2.06 (s, 3H), 2.45 (m, 1H), 3.47 (m, 2H), 3.62 (m, 2H), 4.12–4.48 (m,

3H), 4.75 (m, 1H), 4.96 (ddd, 1H), 5.29 (m, 1H), 5.58 (m, 1H), 7.83 (br q, 1H).

MS: (M+H)⁺=513.

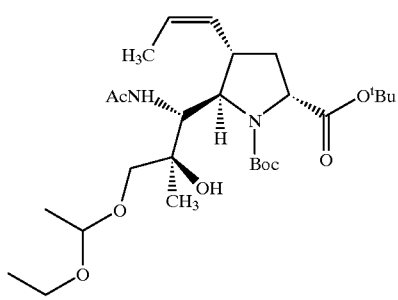

286C (±)-(2R,3S,5R,1'R,2'R)-1-t-Butoxycarbonyl-2-(1-acetamido-3-ethoxyethyloxy-2-hydroxy-2-methyl)propyl-3-(cis-propen-1-yl)-pyrrolidine-5-carboxylic Acid t-Butyl Ester The product of Example 286B (60.0 mg, 0.117 mmol) in THF (2 ml) was added dropwise to a solution of methylmagnesium bromide (3.0M in ether) (0.2 mL, 0.59 mmol) in THF (2 ml) at room temperature and reacted for 60 minutes. The reaction was quenched with saturated aqueous ammonium chloride (2 ml) followed by extraction using dichloromethane (5×10 ml). The organic layer was dried over sodium sulfate, filtered and concentrated in vacuo, to provide the title compound (yield: 56.0 mg, 90.5%).

MS: (M+H)⁺=529.

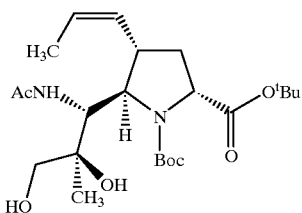

286D (±)-(2R,3S,5R,1'R,2'R)-1-t-Butoxycarbonyl-2-(1-acetamido-2,3-dihydroxy-2-methyl)propyl-3-(cis-propen-1-yl)-pyrrolidine-5-carboxylic Acid t-Butyl Ester The product of Example 286C (55.0 mg, 0.104 mmol) was dissolved in THF (5 ml) and reacted with 0.1N hydrochloric acid (5 ml) at room temperature for 0.5 hour. The reaction was quenched with saturated aqueous sodium bicarbonate followed by extraction using dichloromethane (5×10 ml). The organic layer was dried over sodium sulfate, filtered and concentrated in vacuo. The residue was purified by column chromatography on silica gel using 5% to 10% methanol in dichloromethane to provide the title compound (yield: 29.1 mg, 61.3%).

1H NMR (CDCl₃) δ: 1.17 (s, 3H), 1.43 (s, 9H), 1.46 (s, 9H), 1.63 (dd, 3H), 1.65 (m, 1H), 2.06 (s, 3H), 2.64 (s, 1H), 2.83 (m, 1H), 3.16 (m, 1H), 3.33 (m, 1H), 3.44 (m, 1H), 4.01 (br s, 1H), 4.23 (m, 2H), 4.48 (m, 1H), 5.37–5.55 (m, 2H), 8.05 (br d, 1H).

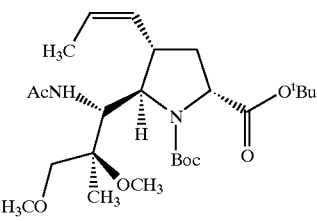

286E (±)-(2R,3S,5R,1'R,2'R)-1-t-Butoxycarbonyl-2-(1-acetamido-2,3-dimethoxy-2-methyl)propyl-3-(cis-propen-1-yl)-pyrrolidine-5-carboxylic Acid t-Butyl Ester The product of Example 286D (28.0 mg, 0.061 mmol) in THF (2 ml) was reacted with sodium bis(trimethylsilyl) amide (1.0M in THF, 184 μl, 0.184 mmol) at −78° C. for 45 minutes and then 0° C. for 15 minutes. Methyl iodide (190 μl, 3.05 mmol) was added to the mixture at 0° C. and stirred at 0° C. for 30 minutes then at room temperature for 1 h. The reaction was quenched with saturated aqueous ammonium chloride (2 ml) followed by extraction using dichloromethane (5×10 ml). The organic layer was dried over sodium sulfate, filtered and concentrated in vacuo. The residue was purified by column chromatography on silica gel using 5% methanol in dichloromethane to provide the title compound (yield: 28.2 mg, 94.5%).

¹H NMR (CDCl₃) (the major rotamer) δ: 1.28 (s, 3H), 1.44 (s, 9H), 1.48 (s, 9H), 1.63 (dd, J=7.2, 1.8 Hz, 3H), 1.70 (m, 1H), 2.01 (s, 3H), 2.49 (m, 1H), 324 (s, 3H), 3.25 (d, 1H), 3.35 (s, 3H), 3.38 (m, 2H), 3.87 (br s, 1H), 4.11 (dd, J=10.5, 1.5 Hz, 1H), 4.80 (m, 1H), 5.37 (m, 1H), 5.63 (td, J=10.2, 2.1 Hz, 1H), 6.46 (br d, J=8.7 Hz, 1H).

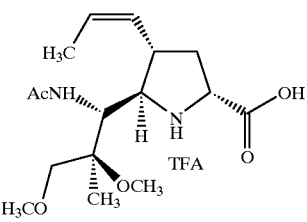

286F (±)-(2R,3S,5R,1'R,2'R)-2-(1-acetamido-2,3-dimethoxy-2-methyl)propyl-3-(cis-propen-1-yl)-pyrrolidine-5-carboxylic Acid Trifluoroacetic Acid Salt The product of Example 286E (10.2 mg, 0.021 mmol) was reacted with trifluoroacetic acid (0.8 ml) in dichloromethane (0.2 ml) at room temperature for 4 hours. The reaction was concentrated in vacuo and triturated with dichloromethane (4×0.2 ml) to provide the title compound (yield: 9.2 mg, 98.9%) as an off white solid.

¹H NMR (DMSO-d₆) δ: 1.13 (s, 3H), 1.56 (dd, 3H), 1.63 (m, 1H), 1.84 (s, 3H), 2.45 (dt, 1H), 3.18 (m, 1H), 3.19 (d$_{AB}$, J=11.0 Hz, 1H), 3.22 (s, 3H), 3.24 (s, 3H), 3.41 (d$_{AB}$, J=11.0 Hz, 1H), 3.69 (t, 1H), 4.28 (t, 1H), 4.46 (t, 1H), 5.30 (tq, 1H), 5.46 (dq, 1H), 7.46 (d, J=10.0 Hz, 1H), 8.75 (br s, 2H).

MS: (M+H)⁺=329.

EXAMPLE 287

(±)-(2R,3S,5R,1'R,2'S)-2-(1-acetamido-2-methoxy-2-methyl)butyl-3-(cis-propen-1-yl)-pyrrolidine-5-carboxylic Acid Trifluoroacetic Acid Salt

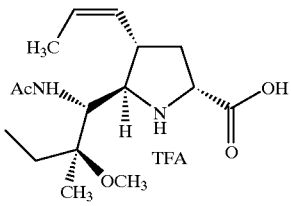

$^1$H NMR (DMSO-d$_6$) δ0.75 (t, J=4.5 Hz, 3H), 1.19 (s, 3H), 1.33 (td, J=9.0, 4.5 Hz, 1H), 1.53 (dd, J=4.2, 0.9 Hz, 3H), 1.56 (q, J=5.7 Hz, 2H), 1.79 (s, 3H) 2.43 (dt, J=8.1, 4.5 Hz, 1H), 3.14 (s, 3H), 3.15 (m, 1H), 3.59 (br m, 1H), 4.30 (br m, 1H), 4.34 (t, J=6.0, 0.9 Hz, 1H), 5.28 (td, J=6.0, 0.9 Hz, 1H), 5.46 (dq, J=6.6, 4.2 Hz, 1H), 7.59 (d, J=6.0 Hz, 1H), 8.61 (br s, 1H), 8.97 (br s, 1H).

MS: (M+H)$^+$=313.

EXAMPLE 288

(−)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt

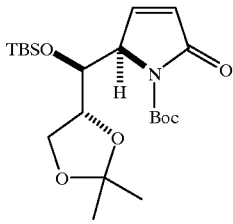

288A tert-Butyl(2R,3S)-2-((S)-((tert-butyl(dimethyl)silyl)oxy)((4R)-2,2-dimethyl-1,3-dioxolan-4-yl)methyl)-5-oxo-2,5-dihydro-1H-pyrrole-1-carboxylate The title compound was prepared according to the procedure described in Tetrahedron Asymmetry, 1996, 1167–1180.

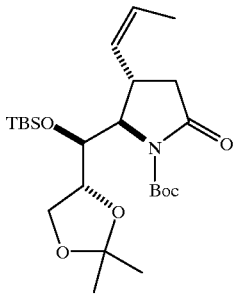

288B tert-Butyl(2R,3S)-2-((S)-((tert-butyl(dimethyl)silyl)oxy)((4R)-2,2-dimethyl-1,3-dioxolan-4-yl)methyl)-5-oxo-3-((1Z)-1-propenyl)-1-pyrrolidinecarboxylate To a solution of copper bromide/dimethyl sulfide (5.9 g, 28.8 mmol) in THF (100 mL) at −78° C. was added 1-propenylmagnesium bromide (0.5M in THF, 113 mL, 56.5 mmol) over 1.5 h followed by trimethylsilyl chloride (2.26 mL, 17.8 mmol) in THF (28 mL). To this solution was added the product of example 288A (2.44 g, 5.71 mmol) in THF (20 mL) at −78° C., and the reaction mixture was warmed to −22° C. for 2 h. The reaction mixture was quenched with sat. NH$_4$Cl and warmed to 25° C. The mixture was extracted with ethyl acetate, the organic layer was separated, dried, filtered, and the solvent was evaporated. The crude residue was purified by column chromatography on silica gel using 80% hexane/ethyl acetate to give title compound (2.5 g, 93%).

$^1$H NMR (CDCl$_3$) δ5.52–5.40 (m, 2H), 4.15–4.00 (m, 3H), 3.92 (d, 1H), 3.74 (dd, 1H), 3.33 (t, 1H), 2.92 (dd, 1H), 2.13 (dd, 1H), 2.65 (d, 3H), 1.53 (s, 9H), 1.30 (d, 6H), 0.88 (s, 9H), 0.12 (d, 6H).

MS: (M+H)$^+$=470, (M+Na)$^+$=492

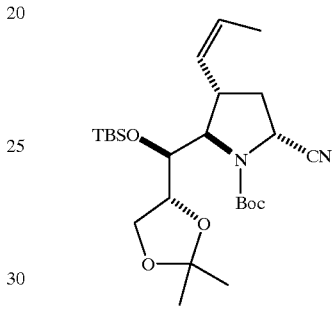

288C tert-Butyl(2R,3S,5R)-2-((S)-((tert-butyl(dimethyl)silyl)oxy)((4R)-2,2-dimethyl-1,3-dioxolan-4-yl)methyl)-5-cyano-3-((1Z)-1-propenyl)-1-pyrrolidinecarboxylate i. To a solution of the product of example 288B (2.84 g, 6.05 mmol) in THF (12 mL) at −78° C. was added diisobutylaluminum hydride (1M in hexane, 10.6 mL, 10.6 mmol). After 0.5 h the reaction was quenched at −78° C. with sat. NH$_4$Cl (45 mL), 10% sodium potassium tartrate solution (45 mL), diluted with ethyl acetate, and stirred for 1 h at 25° C. The organic layer was separated, dried, and the solvent was evaporated to give 2.85 g crude oil used directly for the next step.

ii. The above crude product was stirred in methanol (50 mL) with pyridinium p-toluenesulfonate (0.15 g, 0.59 mmol) at 25° C. for 1 h after which the mixture was quenched with brine, extracted with ethyl acetate, dried, filtered, and the solvent was evaporated to give 2.57 g of an oil which was used directly for the next step.

iii. To a solution of crude product of example 288C(ii) in dichloromethane (40 mL) at −78° C. was added trimethylsilyl cyanide (2.1 mL, 15.78 mmol) and boron trifluoride-etherate (0.98 mL, 7.76 mmol). After 1 h the reaction was quenched with sat. sodium bicarbonate and warmed to 25° C. and extracted with dichloromethane. The solvents were evaporated and the crude residue was purified by column chromatography on silica gel using 1% methanol/dichloromethane to give the title compound (2.48 g, 84% over three steps).

$^1$H NMR (CDCl3) δ5.8–5.88 (m, 1H), 5.56–5.45 (m, 1H), 4.52–4.47(dd, 1H), 4.17–4.08 (m, 2H), 4.05–3.65 (m, 3H), 3.4 (m, 1H), 2.65 (m, 1H), 1.97 (d, 1H), 1.66 (dd, 3H), 1.52 (s, 9H), 1.3 (s, 6H), 0.84 (s, 9H), 0.12 (dd, 6H)

MS: (M+H)⁺=481, (M+Na)⁺=503

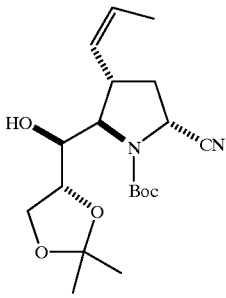

288D tert-Butyl(2R,3S,5R)-5-cyano-2-((S)-((4R)-2,2-dimethyl-1,3-dioxolan-4-yl)(hydroxy)methyl)-3-((1Z)-1-propenyl)-1-pyrrolidinecarboxylate To a solution of the product of example 288C (2.48 g, 5.16 mmol) in THF (32 mL) at 0° C. was added tetrabutylammonium fluoride (1M in THF, 10 mL, 10 mmol) over 1 h. After 0.5 h the reaction was quenched with sat. NH₄Cl and ethyl acetate. The organic layer was separated, dried, and the solvents were evaporated. The crude residue was purified by column chromatography on silica gel using 15% ethyl acetate/dichloromethane to give the title compound (1.75 g, 92.5%).

¹H NMR (CDCl₃) δ5.8–5.52(m, 2H), 4.48 (dd, 1H), 4.15–4.08 (m, 2H), 3.93 (dd, 1H), 3.86 (d, 1H), 3.62–3.45 (m, 2H), 2.63 (ddd, 1H), 2.07 (d, 1H), 1.68 (dd, 3H), 1.53 (s, 9H), 0.88 (s, 9H), 1.4 (s, 3H), 1.34 (s, 3H)

MS: (M+Cl)⁻=401; (M+H)⁺=367, (M+Na)⁺=389

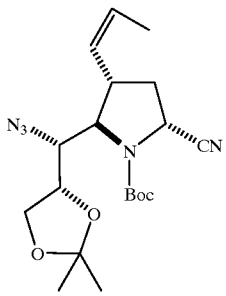

288E tert-Butyl(2R,3S,5R)-2-((R)-azido((4S)-2,2-dimethyl-1,3-dioxolan-4-yl)methyl)-5-cyano-3-((1Z)-1-propenyl)-1-pyrrolidinecarboxylate To a solution of the product of example 288D (1.75 g, 4.78 mmol) in THF (28 mL) at 0° C. was added sequentially, triphenylphosphine (2.25 g, 8.6 mmol), diethyl diazodicarboxylate (1.35 mL, 8.6 mmol), and diphenylphosphoryl azide (1.85 mL, 8.6 mmol). The reaction mixture was allowed to warm to 25° C. over 16 h before being quenched with water (100 mL), 10% citric acid (50 mL), and ethyl acetate. The organic layer was separated, dried, and the solvents were evaporated. The crude residue was purified by column chromatography on silica gel using 12% ethyl acetate/dichloromethane to give the title compound (1.25 g, 67%).

¹H NMR (CDCl₃) δ5.68–5.48 (m, 2H), 4.53 (d, 1H), 4.2–9.97 (m, 3H), 3.83 (t, 1H), 3.55–3.30 (m, 2H), 2.74 (ddd, 1H), 1.98 (dt, 1H), 1.68 (dd, 3H), 1.53 (s, 9H), 0.88 (s, 9H), 1.46 (s, 3H), 1.37 (s, 3H)

MS: (M+H)⁺=392, (M+Na)⁺=414

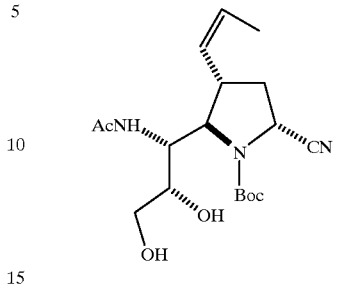

288F tert-Butyl(2R,3S,5R)-2-((1R,2S)-1-(acetylamino)-2,3-dihydroxypropyl)-5-cyano-3-((1Z)-1-propenyl)-1-pyrrolidinecarboxylate i. To a solution of the product of example 288E (1.25 g, 3.19 mmol) in THF:water (4:1) (44 mL) was added triphenylphosphine (1 g, 3.84 mmol), and the mixture was heated to 75° C. for 18 h. The solvents were evaporated and the crude amine was azeotroped with benzene (10 mL).

ii. The crude amine was dissolved in dichloromethane (30 mL) at 25° C. and combined with triethylamine (3.73 mL, 26.8 mmol), acetic anhydride (1.26 mL, 13.4 mmol), and 4-dimethylaminopyridine (0.044 g, 0.34 mmol). After 1 h, water and dichloromethane were added, and the organic layer was separated and passed through a small pad of silica gel with ethyl acetate to give 2.2 g crude acetamide containing triphenylphosphine and used directly for the next step.

iii. The crude N-acetamide (2.2 g) was dissolved in 80% acetic acid (100 mL) at 25° C. for 4 days. The solvents were evaporated, and the crude product was purified by column chromatography on silica gel using 5% methanol/ethyl acetate to give the title compound (0.92 g, 78% over three steps).

¹H NMR (CDCl₃) δ5.94 (d, 1H), 5.8–5.55 (m, 2H), 4.49 (d, 1H), 4.46 (dd, 1H), 3.88–3.54 (m, 5H), 3.34 (m, 1H), 3.28 (dd, 1H), 2.65 (m, 1H), 2.16 (d, 1H), 2.07 (s, 3H), 1.63 (dd, 3H), 1.56 (s, 9H)

MS: (M−H)⁻=366, (M+Cl)⁻=402; (M+H)⁺=368, (M+Na)⁺=390

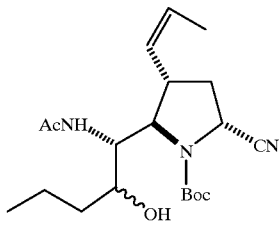

288G tert-Butyl(2R,3S,5R)-2-((1R)-1-(acetylamino)-(2R and 2S)-2-hydroxypentyl)-5-cyano-3-((1Z)-1-propenyl)-1-pyrrolidinecarboxylate i. To a solution of the product of example 288F (0.92 g, 2.51 mmol) in 30% aqueous ethanol (24 mL) at 0° C. was added sodium metaperiodate (1.6 g, 7.48 mmol). The mixture was stirred for 1 h before diluting with ethyl acetate. The organic layer was separated, dried, and the solvents were evaporated and azeotroped with toluene to give 1 g of crude aldehyde which was used directly for the next step.

ii. To a solution of propyl magnesium chloride (2M in ether, 3.65 mL, 7.3 mmol) in THF (14 mL) at 0° C. was added the product of example 288G(i) (1 g) in THF (10 mL) over 0.5 h. The mixture was stirred for 0.5 h before being quenched with sat. NH₄Cl, extracted with ethyl acetate, dried, and the solvents were evaporated. The crude residue was purified by column chromatography on silica gel using ethyl acetate to give the title compounds (0.665 g, 70% as a 3.5:1 mixture of stereoisomers).

Major isomer:

¹H NMR (CDCl₃) δ5.98 (d, 1H), 5.77–5.55 (m, 2H), 4.45 (d, 1H), 4.3 (d, 1H), 3.72–3.56 (m, 2H), 3.48 (m, 1H), 3.24 (dd, 1H), 2.7 (m, 1H), 2.14 (d, 1H), 2.03 (s, 3H), 1.62 (dd, 3H), 1.55 (s, 9H), 1.5–1.2 (m, 4H), 0.88 (t, 3H),

MS: (M−H)⁻=378, (M+Cl)⁻=414; (M+H)⁺=380, (M+Na)⁺=402

Minor isomer:

¹H NMR (CDCl₃) δ6.7 (d, 1H), 5.68–5.53 (m, 2H), 4.42 (dd, 1H), 4.02 (m, 1H), 3.76 (dd, 1H), 3.53 (m, 1H), 3.32 (m, 2H), 2.64 (m, 1H), 2.07 (d, 1H), 2.01 (s, 3H), 1.66 (d, 3H), 1.55 (s, 9H), 1.5–1.24 (m, 4H), 0.92 (t, 3H)

MS: (M−H)⁻=378, (M+Cl)⁻=414; (M+H)⁺=380, (M+Na)⁺=402

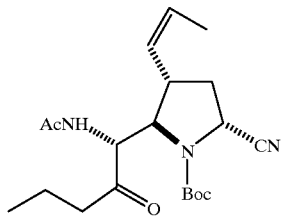

288H tert-Butyl(2R,3S,5R)-2-((1R)-1-(acetylamino)-2-oxopentyl)-5-cyano-3-((1Z)-1-propenyl)-1-pyrrolidinecarboxylate To the product alcohols of example 288G (0.665 g, 1.75 mmol) in dichloromethane (18 mL) was added Dess-Martin reagent (1.05 g, 2.47 mmol) at 25° C. After 1.5 h the reaction mixture was diluted with ether (100 mL) and filtered through Celite. The organic solution was washed with 10% sodium thiosulfate (50 mL), and the solvents were evaporated. The crude residue was purified by column chromatography on silica gel using ethyl ether to give the title compound (0.5 g, 76%).

¹H NMR (CDCl₃) δ7.56 (d, 1H), 5.63 (m, 1H), 5.43 (m, 1H), 5.02 (d, 1H), 4.45 (dd, 1H), 3.68 (d, 1H), 3.38 (m, 1H), 2.62–2.4 (m, 3H), 2.07 (s, 3H), 1.96 (m, 1H), 1.6 (dd, 3H), 1.52 (s, 9H), 1.6–1.48 (m, 2H), 0.88 (t, 3H);

MS: (M−H)⁻=376; (M+H)⁺=378, (M+Na)⁺=400

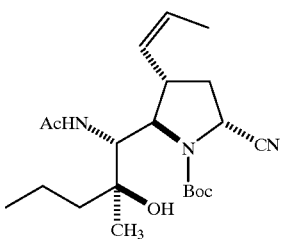

288I tert-Butyl(2R,3S,5R)-2-((1R,2S)-1-(acetylamino)-2-hydroxy-2-methylpentyl)-5-cyano-3-((1Z)-1-propenyl)-1-pyrrolidinecarboxylate A solution of the product of example 288H (20 mg, 0.053 mmol) in THF (0.5 mL) was added to methyl magnesium bromide (3M in THF, 0.105 mL, 0.318 mmol) in THF (1.0 ml) at 0° C. After 0.5 h at 0° C. the mixture was quenched with sat. NH₄Cl and extracted with ethyl acetate. The organic layer was separated, dried, and the solvent was evaporated. The crude residue was purified by column chromatography on silica gel using ethyl acetate to give the title compound (10.4 mg, 50%).

¹H NMR (CDCl₃) δ5.91 (d, J=9.5 Hz, 1H), 5.71 (m, 1H), 5.55 (m, 1H), 4.38 (d, J=8.8 Hz, 1H), 4.28 (m, 1H), 3.97 (m, 1H), 3.47 (m, 1H), 2.55 (m, 1H), 2.07–2.02 (m, 1H), 2.02 (s, 3H), 1.65 (d, J=6.8 Hz, 3H), 1.56 (s, 9H), 1.56–1.30 (m, 4H), 1.14 (s, 3H), 0.93 (m, 3H).

MS: (M+H)⁺=394, (M−H)⁻=392

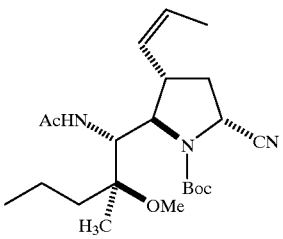

288J tert-Butyl(2R,3S,5R)-2-((1R,2S)-1-(acetylamino)-2-methoxy-2-methylpentyl)-5-cyano-3-((1Z)-1-propenyl)-1-pyrrolidinecarboxylate To a solution of the product of example 288I (16 mg, 0.041 mmol) in THF (0.5 mL) at −78° C. were added methyl iodide (0.125 mL, 2.02 mmol) and NaHMDS (1M in THF, 0.06 mL, 0.061 mmol) and the mixture was stored at −25° C. for 16 h. The reaction was quenched with sat. NH₄Cl and ethyl acetate was added. The organic layer was separated, dried and the solvent was evaporated. The crude residue was purified by column chromatography on silica gel using 50% ethyl acetate/dichloromethane to give the title compound (7.7 mg, 50%).

¹H NMR (CDCl₃) rotamers δ5.89 (m, 1H), 5.71 (m, 1H), 5.50 (m, 1H), 4.55 (dd, J=2.0, 9.2 Hz, 1H), 4.44 (t, J=9.5 Hz, 1H), 4.36 (dd, J=1.0, 9.5 Hz, 1H), 3.94 (m, 1H), 3.89 (d, J=1.0 Hz, 1H), 3.73 (dd, J=9.2, 9.8 Hz, 1H), 3.21 and 3.20 (2s, 3H), 2.49 (m, 1H), 2.00 (s, 3H), 1.95 (d, J=12.9 Hz, 1H), 1.80–1.20 (m, 4H), 1.66 (dd, J=1.7, 6.8 Hz, 1H), 1.55 (m, 9H), 1.14 and 1.12 (2s, 3H), 0.95 (t, J=6.8 Hz, 3H).

MS: (M+H)⁺=408, (M−H)⁻=406

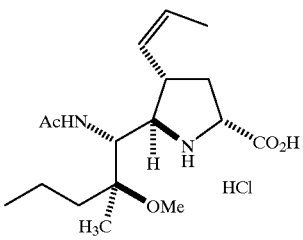

288K (−)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt The product of example 288J (2 mg, 0.005 mmol) was combined with hydrochloric acid (6N, 1 mL) and stirred at 60° C. for 16 h. The solvent was evaporated to give the title compound (1.6 mg, quant.).

¹H NMR (MeOD-d₃) δ5.60 (m, 1H), 5.30 (m, 1H), 4.48 (d, J=9.8 Hz, 1H), 4.37 (t, J=8.1 Hz, 1H), 3.65 (t, J=9.5 Hz, 1H), 3.27 (s, 3H), 3.27 (m, 1H), 2.57 (m 1H), 1.93 (s, 3H), 1.72 (m, 1H), 1.62 (dd, J=1.7, 6.8 Hz, 3H), 1.70–1.23 (m, 4H), 1.28 (s, 3H), 0.88 (t, J=6.8 Hz, 3H).

MS: (M+H)⁺=327, (M+Na)⁺=349

EXAMPLE 289

(−)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt

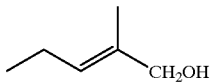

289A (2E)-2-Methyl-2-penten-1-ol

A solution of methyl 2-methyl-2-pentenoate (6.37 g, 49.6 mmol) in ether (120 mL) was added to a mixture of lithium aluminum hydride (4.72 g, 124.2 mmol) in ether (180 mL) at 0° C. and stirred at 25° C. for 1.5 h. After recooling to 0° C. the reaction was quenched (water, 4.7 mL; 15% NaOH, 4.7 mL; water, 14.1 mL). The mixture was filtered, dried, refiltered, and the solvent was evaporated. The crude product was distilled (55 torr, 85–87° C.) to give the allylic alcohol (3.96 g, 80%).

¹H NMR (CDCl₃) δ5.44–5.38 (m, 1H), 4.0 (d, J=5.42 Hz, 2H), 2.10–2.00 (m, 2H), 1.67(s, 3H), 1.0–0.95 (t, J=5.09 Hz, 3H).

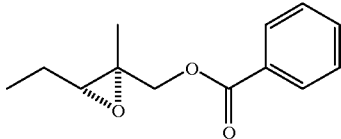

289B

A solution of the product of example 289A (5.1 g, 51 mmol) in dichloromethane (35 mL) was added to a mixture of (−)-dimethyl D-tartrate (0.545 g, 3.06 mmol), titanium tetraisopropoxide (0.76 g, 2.55 mmol), molecular sieves (4A, 1.8 g), and t-butyl hydroperoxide (5M solution in decane, 20 mL) in dichloromethane (180 mL) at −20° C., and the reaction mixture was stirred for 3.5 h. To this mixture was added trimethyl phosphite (9 mL, 76.5 mmol), triethylamine (8.5 mL, 61.2 mmol), and benzoyl chloride (5.92 mL, 51 mmol), and was stirred for 1.5 h before being washed with 10% tartaric acid (200 mL×2), saturated sodium bicarbonate (150 mL×3), and brine. The organic layer was dried, the solvent was evaporated and the residue was purified by column chromatography on silica gel using hexanes-85% hexanes/ethyl acetate to give the title compound (7.35 g, 65%).

¹H NMR (CDCl₃) δ8.18–7.42 (m, 5H), 4.31 (dd, J=11.87, 6.45 Hz, 1H), 2.94 (t, J=6.45 Hz, 1H), 1.71–1.53 (m, 2H), 1.40 (s, 3H), 1.06 (t, J=7.46 Hz, 3H).

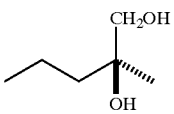

289C (2S)-2-Methyl-1,2-pentanediol

To a solution of lithium aluminum hydride (3.8 g, 0.1 mol) at 0° C. in tetrahydrofuran (THF) (160 mL) was added the product of example 289B (7.35 g, 0.099 mol) in THF (40 mL). After 0.5 h, the mixture is warmed to 25° C., recooled to 0° C. and quenched (water, 5 mL; 15% NaOH, 5 mL; water, 15 mL). The mixture was filtered, and the solvent was evaporated. The residue was purified by column chromatography on silica gel using hexanes-60% hexanes/ethyl acetate to give the title compound (2.48 g, 63%).

¹H NMR (CDCl₃) δ3.50–3.38 (m, 2H), 1.50–1.31 (m, 4H), 1.17 (s, 3H), 0.94 (t, J=7.1 Hz, 3H).

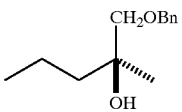

289D (2S)-1-(Benzyloxy)-2-methyl-2-pentanol

To a suspension of sodium hydride (95% powder, 5.08 g, 0.212 mol) in THF (210 mL) at 0° C. was added the product of example 289C (10.02 g, 0.085 mol) in THF (85 mL). After 1 h, benzyl bromide (12.1 mL, 0.102 mol) was added, and the reaction mixture was warmed to 25° C. for 16 h. The mixture was quenched with sat. NH₄Cl (30 mL), and the solvent was evaporated. The residue was partitioned between water and ether, the ether was separated and dried. The crude product was purified by column chromatography on silica gel using 100–85% hexanes-hexanes/ethyl acetate to give the title compound (17.26 g, 98%).

¹H NMR (CDCl₃) δ7.39–7.27 (m, 5H), s(4.56, 2H), 3.31 (dd, J=8.82, 16.96 Hz, 2H), 1.52–1.23 (m, 4H), 1.17 (s, 3H), 0.92 (t, J=7.12, 3H).

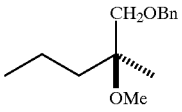

289E ((((2S)-2-Methoxy-2-methylpentyl)oxy)methyl)benzene

To a solution of the product of example 289D (17.26 g, 0.0829 mol) in THF (280 mL) at 0° C. was added sodium bis(trimethylsilyl)amide (NaHMDS) (1M in THF, 166 mL, 0.166 mol). After 1 h methyl iodide (25.8 mL, 0.415 mol) was added, and the mixture was warmed to 25° C. for 16 h. The mixture was quenched with sat. NH₄Cl (25 mL) and water (250 mL), the organic layer was separated and the aqueous layer was extracted with ether. The organic layers were combined, washed with brine, and dried. The solvent was evaporated, and the residue was purified by column chromatography on silica gel using hexanes-90% hexanes/ethyl acetate to give the title compound (18.03 g, 98%).

1H NMR (CDCl₃) δ7.35–7.26 (m, 5H), 4.55 (s, 2H), 3.32 (dd, J=9.8, 12.5 Hz, 2H), 3.22 (s, 3H), 1.58–1.42 (m, 2H), 1.34–1.22 (m, 2H), 1.14 (s, 3H), 0.90 (t, J=7.12 Hz, 3H).

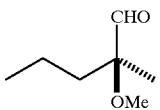

289F (2S)-2-Methoxy-2-methylpentanal

To a solution of the product of example 289E (5 g, 22.5 mmol) in dichloromethane (75 mL) was added Pd(OH)₂ (20% on carbon, 1.6 g) and the flask fitted with a hydrogen balloon. The mixture was stirred for 3.5 h after which the catalyst was filtered and rinsed with dichloromethane (75 mL). This solution was reacted directly with pyridinium chlorochromate (14.5 g, 67.5 mmol) at 0° C. with molecular sieves (4 A, 5 g) and Celite (5 g). The mixture was stirred for 1.5 h at 25° C. Ether (200 mL) was added and this solution was filtered through a short pad of silica gel with additional ether. The solvent was evaporated in a short-path distillation apparatus, and the product was distilled (60 torr, 72–75° C.) to give the title compound (1.4 g, 48% for two steps).

¹H NMR (CDCl₃) δ9.21 (s, 1H), 3.28 (s, 3H), 1.64–1.51 (m, 2H), 1.38–1.23 (m, 2H), 1.22 (s, 3H), 0.92 (t, J=7.12 Hz, 3H).

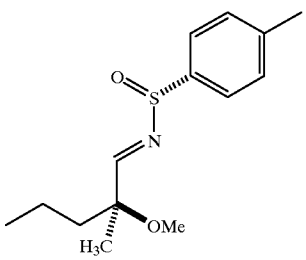

289G N-((E,2S)-2-Methoxy-2-methylpentylidene)-(4R)-methylbenzenesulfinimine

To a solution of p-toluenesulfinamide (138.42 mg, 0.892 mmol) in THF (3 mL) was added aldehyde product of example 289F (0.143 mL, 1.07 mmol) followed by titanium tetraethoxide (0.57 mL, 2.72 mmol). The solution was stirred at 25° C. overnight and quenched by pouring the solution into brine (3 mL). The mixture was filtered through a pad of Celite and rinsed with dichloromethane and water. The organic layer was separated and the aqueous layer was extracted with dichloromethane (2'20 mL). The combined organic layers was dried and the solvent was evaporated. The crude residue was purified by column chromatography on silica gel using 50–33% hexane/dichloromethane, then 1% and 2% Et₂O/dichloromethane to give the title compound (189.19 mg, 79%).

¹H NMR (CDCl₃) δ8.13 (s, 1H), 7.56 (d, J=8.48 Hz, 2H), 7.30 (d, J=8.47, 1H), 3.20 (s, 3H), 2.40 (s, 3H), 1.59 (m, 2H), 1.33 (s, 3H), 1.24 (m, 2H), 0.84 (t, J=7.29 Hz, 3H)

MS: (M+H)⁺=268

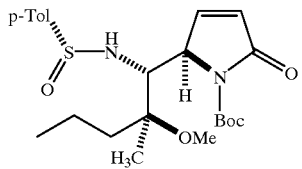

289H To a solution of the product of example 289G (0.278 g, 1.04 mmol) and N-t-butoxycarbonyl-2-t-butyldimethylsilyloxypyrrole (0.59 g, 1.98 mmol), prepared according to the procedure described in JOC, 1992, 57, 3760–3763, in dichloromethane (7 mL) at −78° C. was added trimethylsilyl triflate (0.283 mL, 1.56 mmol). After 6 h, the reaction was quenched at −78° C. with triethylamine (0.232 mL, 3.15 mmol) followed by saturated sodium bicarbonate (5 mL) and dichloromethane and warmed to 25° C. The organic layer was separated, dried, and the solvents were evaporated. The crude residue was triturated with ether and the resulted precipitation was filtered to give the title compound as a white solid (0.25 g 53%).

¹H NMR (CDCl₃) δ7.56 (d, 2H), 7.28 (d, 2H), 7.29 (dd, 1H), 5.59 (dd, 1H), 4.81 (m, 1H), 4.27 (dd, 1H), 4.18 (d, 1H), 3.18 (s, 3H), 2.39 (s, 3H), 1.92 (m, 1H), 1.38–1.72 (m, 3H), 1.69 (s, 9H), 1.43 (s, 3H), 1.03 (t, 3H)

MS: (M+H)⁺=451, (M+Na)⁺=473

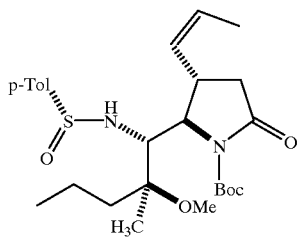

289I tert-Butyl(3S)-2-((1R,2S)-2-methoxy-2-methyl-1-(((4-methylphenyl)sulfinyl)amino)pentyl)-5-oxo-3-((1Z)-1-propenyl)-1-pyrrolidinecarboxylate To a suspension of copper bromide/dimethyl sulfide (62.53 mg, 0.30 mmol) in THF (0.6 mL) at −78° C. was added propenylmagnesium bromide (0.5 M in THF, 1.22 mL, 0.61 mmol). The solution was stirred at −78° C. for 30 min. To the solution was added trimethylsilyl chloride (0.017 mL, 0.13 mmol) followed by a solution of the product of example 289H (54.96 mg, 0.12 mmol) in dichloromethane (0.4 mL) at −78° C. The reaction mixture was stirred at −78° C. for 1.5 h. The reaction mixture was quenched with sat. NH₄Cl and warmed to 25° C. for 1 h. The mixture was partitioned between saturated NH₄Cl (10 mL) and dichloromethane (45 mL). The organic layer was washed with H₂O (10 mL) and the combined aqueous layers was extracted with dichloromethane (2×10 mL). The combined organic layers were dried, filtered, and the solvent was evaporated. The crude residue was purified by column chromatography on silica gel using 17–33% ethyl acetate/hexane to give the title compound (44.31 mg, 74%).

¹H NMR (CDCl₃) δ7.62 (d, J=8.47 Hz, 2H), 7.32 (d, J=8.48 Hz, 2H), 5.43 (m, 2H), 4.58 (d, J=7.80 Hz, 1H), 3.99 (br d, J=2.71 Hz, 1H), 3.93 (dd, J=7.80, 2.71 Hz, 1H), 3.71 (m, 1H), 3.19 (s, 3H), 2.57 (dd, J=17.81, 9.67 Hz, 1H), 2.40

(s, 3H), 1.97 (dd, J=17.80, 1.53 Hz, 1H), 1.82 (m, 1H), 1.59 (s, 12H), 1.52 (m, 1H), 1.42 (s, 3H), 1.27 (m, 2H), 0.96 (t, J=6.95 Hz, 3H)

MS: (M−H)⁻=491; (M+H)⁺=493, (M+NH₄)⁺=510, (M+Na)⁺=515

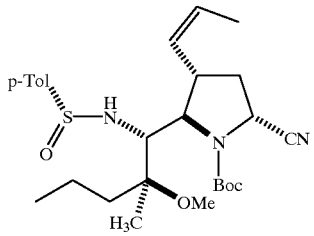

289J (1) tert-Butyl(3S,5R)-5-cyano-2-((1R,2S)-2-methoxy-2-methyl-1-(((4-methylphenyl)sulfinyl)amino)pentyl)-3-((1Z)-1-propenyl)-1-pyrrolidinecarboxylate The title compound was prepared according to the procedure described in example 288C substituting the product of example 289I for the product of example 288B.

¹H NMR (CDCl₃) δ7.53 (d, J=8.14 Hz, 2H), 7.32 (d, J=8.14 Hz, 2H), 5.73 (m, 1H), 5.48 (m, 1H), 4.58–4.46 (m, 2H), 4.01–3.69 (m, 3H), 3.18 (s, 0.6H), 3.16 (s, 2.4H), 2.42 (s, 3H), 2.38 (m, 1H), 1.81–1.66 (m, 3H), 1.61–1.59 (m, 12H), 1.26–1.17 (m, 5H), 0.92 (m, 3H)

MS: (M−H)⁻=502; (M+H)⁺=504, (M+Na)⁺=526

289J (2) Alternative Preparation of tert-Butyl(3S,5R)-5-cyano-2-((1R,2S)-2-methoxy-2-methyl-1-(((4-methylphenyl)sulfinyl)amino)pentyl)-3-((1Z)-1-propenyl)-1-pyrrolidinecarboxylate The title compound was prepared according to the procedure described in example 288C substituting the product of example 289I for the product of example 288B, with the exception that to a solution of crude alcohol resulting from step (i) (following DiBAl−H reduction) (1.21 g, 2.4 mmol) in dichloromethane (12 mL) at −78° C. was added trimethylsilyl cyanide (0.98 mL, 7.2 mmol) and trimethylsilyl triflate (0.64 mL, 3.6 mmol). After 5 minutes the reaction was quenched with sat. sodium bicarbonate and warmed to 25° C. and extracted with dichloromethane. The solvents were evaporated and the crude residue was purified by column chromatography on silica gel using 40% ethyl acetate/hexane to give the title compound (0.82 g).

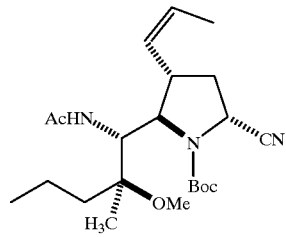

289K tert-Butyl(2R,3S,5R)-2-((1R,2S)-1-(acetylamino)-2-methoxy-2-methylpentyl)-5-cyano-3-((1Z)-1-propenyl)-1-pyrrolidinecarboxylate i. To a solution of the product of example 289J (8.4 mg, 0.017 mmol) in MeOH (0.17 mL) was added trifluoroacetic acid (0.0055 mL, 0.071 mmol) at 25° C. The solution was stirred overnight and the solvents were evaporated. The residue was azeotroped with chloroform and toluene to give an oil, which was used in the next step without purification.

ii. To the crude amine from 289K(i) in dichloromethane (0.17 mL) was added triethylamine (0.0238 mL, 0.17 mmol) followed by acetic anhydride (0.0081 mL, 0.086 mmol) at 25° C. The solution was stirred for 20 min and the solvent was evaporated. The residue was purified by column chromatography on silica gel using 33–67% ethyl acetate/hexane to give the title compound (5.16 mg, 76% over two steps).

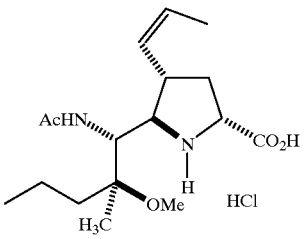

289L(−)-(2R,3S,5R,1′R,2′S)-2-(1-Acetamido-2-methoxy-2-methyl)pentyl-3-(cis-propen-1-yl)-pyrrolidine-5-carboxylic Acid Hydrochloride Salt The title compound was prepared according to the procedure of example 288K.

EXAMPLE 290

(−)-(2R,3S,5R,1′R,2′S)-2-(1-Acetamido-2-methoxy-2-methyl)pentyl-3-(cis-propen-1-yl)-pyrrolidine-5-carboxylic Acid Hydrochloride Salt

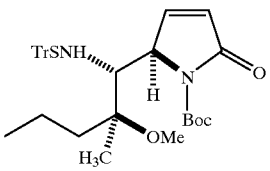

290A tert-Butyl(2R)-2-((1R,2S)-2-methoxy-2-methyl-1-((tritylsulfenyl)amino)pentyl)-5-oxo-2,5-dihydro-1H-pyrrole-1-carboxylate i. A mixture of aldehyde product of example 289F (250 mg, 1.92 mmole), triphenylmethanesulfenamide (560 mg, 1.92 mmole), MgSO₄ (750 mg, 5.7 mmole) and PPTS (10 mg, 0.04 mmole) was stirred at 25° C. for 18 hours, filtered and the solvent was evaporated.

ii. To the crude imine from 290A(i) in ether (6.0 ml) at −78° C. were added N-t-butoxycarbonyl-2-t-butyldimethylsilyoxypyrrole (1.13 g, 3.8 mmole) and BF₃-Et₂O (0.61 ml, 4.8 mmole) and the reaction was stirred at −78° C. for 2 h and then at −40° C. for 2 h. The reaction was quenched with sat. sodium bicarbonate (30 ml) and allowed to warm to 25° C. The reaction was diluted with chloroform (75 ml) and the organic layer was washed with water and brine, dried, filtered and the solvents were evaporated. The residue was purified by column chromatography on silica gel using 20% ethyl acetate/hexane to provide the title compound (higher Rf) (821 mg, 73%) and a lower Rf diastereomer (187 mg, 17%).

Major diasteomer:

¹H NMR (CDCl₃) δ7.32 (dd, J=2.0, 6.1 Hz, 1H), 7.29–7.19 (m, 15H), 6.02 (dd, J=1.4, 6.1 Hz, 1H), 4.83 (m, 1H), 3.86 (dd, J=3.1, 11.5 Hz, 1H), 3.05 (s, 3H), 2.62 (d, J=11.2 Hz, 1H), 1.62–0.98 (m, 4H), 1.36 (s, 9H), 0.92 (t, J=6.6 Hz, 3H), 0.43 (s, 3H).

MS: (M+H)⁺=587, (M+Na)⁺=609

Minor diastereomer:

¹H NMR (CDCl₃) δ7.28–7.18 (m, 16H), 6.02 (dd, J=1.7, 6.1 Hz, 1H), 4.90 (m, 1H), 3.89 (dd, J=2.0, 11.5 Hz, 1H), 3.06 (s, 3H), 2.42 (d, J=11.5 Hz, 1H), 1.54 (s, 9H), 1.28–0.85 (m, 4H), 1.16 (s, 3H), 0.57 (t, J=7.1 Hz, 3H).

MS: (M+H)⁺=587, (M+Na)⁺=609

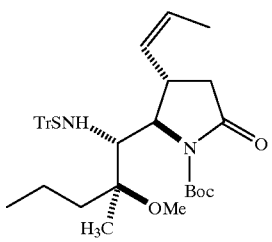

290B tert-Butyl(2R,3S)-2-((1R,2S)-2-methoxy-2-methyl-1-((tritylsulfenyl)amino)pentyl)-5-oxo-3-((1Z)-1-propenyl)-1-pyrrolidinecarboxylate The title compound was prepared according the procedure of example 288B substituting the product of example 290A for the product of example 288A yielding (747 mg, 93%).

¹H NMR (CDCl₃) δ7.30–7.19 (m, 15H), 5.44–5.33 (m, 2H), 3.99 (d, J=1.4 Hz, 1H), 3.69 (m, 1H), 3.58 (dd, J=2.4, 10.5 Hz, 1H), 3.06 (d, J=10.9 Hz, 1H), 3.03 (s, 3H), 2.81 (dd, J=9.5, 18.0 Hz, 1H), 1,95 (dd, J=1.4, 18.0 Hz, 1H), 1.58 (d, J=5.1 Hz, 3H), 1.62–1.02 (m, 4H), 1.43 (s, 9H), 0.86 (t, J=6.6 Hz, 3H), 0.51 (s, 3H).

MS: (M+H)⁺=629, (M+Na)⁺=651

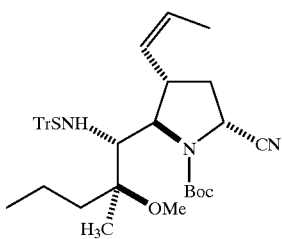

290C tert-Butyl(2R,3S,5R)-5-cyano-2-((1R,2S)-2-methoxy-2-methyl-1-((tritylsulfenyl)amino)pentyl)-3-((1Z)-1-propenyl)-1-pyrrolidinecarboxylate The title compound was prepared according the procedure of example 288C substituting the product of example 290B for the product of example 288B yielding (459 mg, 71%).

¹H NMR (CDCl₃) δ7.31–7.20 (m, 15H), 5.74–5.67 (m, 1H), 5.49–5.38 (m, 1H), 4.60 (d, J=9.2 Hz, 1H), 3.82 (dd, J=7.8, 10.5 Hz, 1H), 3.79 (d, J=1.7 Hz, 1H), 3.68 (dd, J=2.0, 10.5 Hz, 1H), 3.05 (d, J=10.5 Hz, 1H), 3.01 (s, 3H), 2.59–2.48 (m, 1H), 1.84 (d, J=13.2 Hz, 1H), 1.60 (dd, J=1.7, 6.8 Hz, 3H), 1.62–0.90 (m, 4H), 1.34 (s, 9H), 0.86 (t, J=6.6 Hz, 3H), 0.45 (s, 3H).

MS: (M+H)⁺=640, (M+Na)⁺=662, (M–H)⁻=638

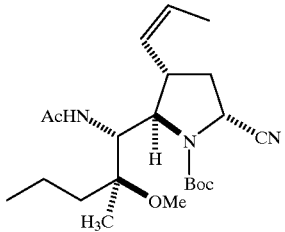

290D tert-Butyl(2R,3S,5R)-2-((1R,2S)-1-(acetylamino)-2-methoxy-2-methylpentyl)-5-cyano-3-((1Z)-1-propenyl)-1-pyrrolidinecarboxylate The product of example 290C (23.0 mg, 0.036 mmole) was suspended in methanol (1.0 ml) and PPTS (36.0 mg, 0.143 mmol) was added. The mixture was heated to reflux for 15 h and then the solvent was evaporated. To the crude residue dissolved in dichloromethane (0.5 ml) were added acetic anhydride (0.01 ml, 0.108 mmol) and triethylamine (0.03 ml, 0.216 mmol), and the mixture was stirred for 1 h. The reaction was quenched with methanol (0.05 ml) and evaporated. The residue was purified by column chromatography on silica gel using a gradient of dichloromethane up to 50% ethyl acetate/dichloromethane to give the the title compound (11.3 mg, 77%).

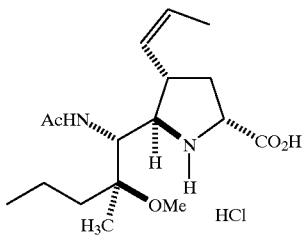

290E (–)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt The title compound was prepared according to the procedure of example 288K.

EXAMPLE 291 tert-Butyl(2R)-2-((1R,2S)-2-methoxy-2-methyl-1-(acetylamino)pentyl)-5-oxo-2,5-dihydro-1H-pyrrole-1-carboxylate

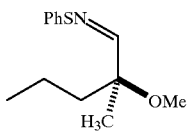

291A Ammonia gas was bubbled through a suspension of phenyl disulfide (34 mg, 0.15 mmoles) and silver nitrate (26 mg, 0.15 mmol) in methanol (2.5 mL) at 0° C. After 15 min a solution of aldehyde product of example 289F (40 mg, 0.3 mmol) in methanol (0.5 mL) was added and the mixture was stirred at 25° C. for 68 h. The reaction mixture was filtered, evaporated, dissolved in ether, refiltered. The organic layer was washed with water, dried, and the solvents were evaporated to give crude imine (42 mg, 57%).

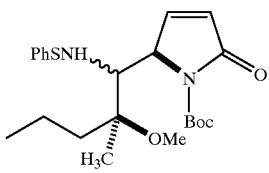

291B tert-Butyl(2R)-2-((1R,2S)-2-methoxy-2-methyl-1-(phenylsulfenylamino)pentyl)-5-oxo-2,5-dihydro-1H-pyrrole-1-carboxylate A solution of imine product of example 291A (42 mg, 0.18 mmol) and N-t-butoxycarbonyl-2-t-butyldimethylsilyloxypyrrole (53 mg, 0.18 mmol) in dichloromethane (1.5 mL) was cooled to −78° C. and boron trifluoride-etherate (0.034 mL, 0.27 mmol) was added. After 2 h at −78° C. the reaction was quenched with sat. sodium bicarbonate (2 mL), extracted with dichloromethane, dried, and the solvent was evaporated to give the title compound.

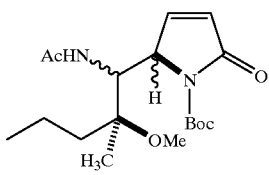

291C tert-Butyl(2R)-2-((1R,2S)-2-methoxy-2-methyl-1-(acetylamino)pentyl)-5-oxo-2,5-dihydro-1H-pyrrole-1-carboxylate The product of example 291B was treated with 80% acetic acid (2 mL) at 25° C. for 1 h and the solvent was evaporated. The crude residue was purified using 5% methanol in dichloromethane with 0.2% ammonium hydroxide to give the amine (28 mg, 50%).

The amine product (28 mg, 0.09 mmol) in dichloromethane (1 mL) was treated with acetic anhydride (0.017 mL, 0.18 mmol), triethylamine (0.028 mL, 0.2 mmol) and 4-dimethylaminopyridine (2 mg, 0.02 mmol) for 1 h. The solution was purified by column chromatography on silica gel directly by eluting with 5% methanol in dichloromethane to give the title compound (26 mg, 82%) as a 1.9–1 mixture of two inseparable diastereomers.

Major isomer:

1H NMR (CDCl$_3$) δ7.26–7.30 (dd, 1H), 9.06–6.12 (dd, 1H), 5.33 (d, 1H), 4.96–5.01 (dd, 1H), 4.88–4.92 (m, 1H), 3.25 (s, 3H), 1.88 (s, 3H), 1.61 (s, 9H), 1.4 (s, 3H), 0.9 (t, 3H).

Minor isomer:

$^1$H NMR (CDCl$_3$) δ7.31–7.35 (dd, 1H), 6.05–6.1 (dd, 1H), 5.37 (d, 1H), 4.87–4.92 (dd, 1H), 4.83–4.88 (m, 1H), 3.23 (s, 3H), 1.92 (s, 3H), 1.59 (s, 9H), 1.18 (s, 3H), 1.02 (t, 3H).

EXAMPLE 292 tert-Butyl(2R)-2-((1R,2S)-2-methoxy-2-methyl-1-((4-methoxyanilino)pentyl)-5-oxo-2,5-dihydro-1H-pyrrole-1-carboxylate

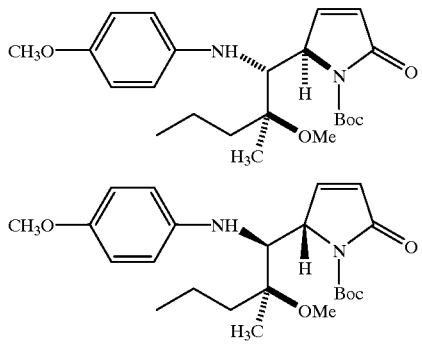

To a suspension of Yb(OTf)$_3$ (12 mg, 019 mmole) and MgSO$_4$ (70 mg, 0.58 mmole) in dichloromethane (0.50 ml) were added the aldehyde product of example 289F (22 mg, 0.19 mmole) in dichloromethane (0.50 ml) and p-anisidine (24 mg, 0.19 mmole) in dichloromethane (0.50 ml) and the mixture was stirred for 0.5 h at rt. N-t-butoxycarbonyl-2-t-butyldimethylsilyloxypyrrole (59 mg, 0.19 mmol) in dichloromethane (0.35 ml) was added and the reaction was stirred for 1 h and then quenched with water. The reaction was diluted with ethyl acetate and the organic layer was washed with water and brine, dried, filtered and the solvents were evaporated. The residue was purified by column chromatography on silica gel using mixtures of ethyl acetate/hexane to provide the title compounds two diastereomers (Yield: higher $R_f$ (25 mg, 31%), lower $R_f$ (28 mg, 35%)).

Higher $R_f$ diasteomer:

$^1$H NMR (CDCl$_3$) δ7.42 (dd, J=2.0, 6.1 Hz, 1H), 6.65 (m, 2H), 6.41 (m, 2H), 6.06 (dd, J=1.7, 6.1 Hz, 1H), 4.91 (m, 1H), 4.28 (dd, J=3.4, 10.5 Hz, 1H), 3.70 (s, 3H), 3.42 (d, J=10.8 Hz, 1H), 3.26 (s, 3H), 1.90–1.29 (m, 4H), 1.52 (s, 9H), 1.18 (s, 3H), 1.02 (t, J=7.1 Hz, 3H).

MS: (M+H)$^+$=419, (M+Na)$^+$=441

Lower $R_f$ diastereomer:

$^1$H NMR (CDCl$_3$) δ7.39 (dd, J=2.4, 6.1 Hz, 1H), 6.65 (m, 2H), 6.40 (m, 2H), 6.05 (dd, J=1.7, 6.1 Hz, 1H), 4.93 (m,1H), 4.29 (dd, J=2.4, 10.5 Hz, 1H), 3.70 (s, 3H), 3.45 (d, J=10.5 Hz, 1H), 3.26 (s, 3H), 1.58 (s, 9H), 1.55–1.10 (m, 4H), 1.39 (s, 3H), 0.69 (t, J=7.5 Hz, 3H).

MS: (M+H)$^+$=419, (M+Na)$^+$=441

EXAMPLE 293

(−)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt

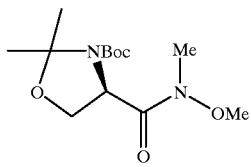

293A (R)4-(Methoxy-methyl-carbamoyl)-2,2-dimethyl-oxazolidine-3-carboxylic acid tert-butyl ester The title compound was synthesized according to the procedure of A. D. Campbell, T. M. Raynham, R, J. K.

Taylor, *Synthesis* 1998, 1707 from D-serine, yield 65% (3 steps). $[\alpha]_D=+36.220$ (c=1.8, CHCl$_3$)[ref. $[\alpha]_D=+35.8°$].

$^1$H NMR (400 MHz, CDCl3): δ4.78 (dd, 0.5H, 1/2 NCH, J=3.5 and 7.4 Hz); 4.68 (dd, 0.5H, 1/2 NCH, J=3.5 and 7.4 Hz); 4.15 (m, 1H,); 3.95 (m, 1H, OCH); 3.72 (s, 1.5H, 1/2 OMe); 3.68(s, 1.5H, 1/2OMe); 3.18(s, 3H, Nme); 1.72(s, 1.5H, 1/2Me); 1.68 (s, 1.5H, 1/2 Me); 1.58 (s, 1.5H, 1/2 Me); 1.54 (s, 1.5H, 1/2 Me); 1.48 (s, 4.5H, 1/2 CMe3); 1.40 (s, 4.5H, 1/2 CMe3).

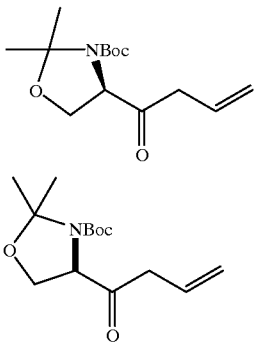

293B (R)4-But-3-enoyl-2,2-dimethyl-oxazolidine-3-carboxylic acid tert-butyl ester A solution of the product of example 293A (2.0 g, 6.96 mmol) in dry THF (20 mL) was added a 1.0 M solution of allyl magnesium chloride (14 mL, 14 mmol) at −78° C. under N$_2$. The resulting yellow solution was stirred at −65° C. TLC indicated the absence of S.M. after 1 h. The mixture was quenched with saturated. NH$_4$Cl at −65° C. and warmed up to r.t. After extraction with EtOAc, the crude product was purified by flash chromatography (EtOAc/hexane 2:8) to give the title compound as a colorless oil (1.74 g, yield 93%).

$[\alpha]_D=+67.8°$ (c=2.5, CHCl$_3$).

$^1$H NMR(400 MHz, CDCl$_3$): δ5.90 (m, 1H, =CH); 5.19 (m, 2H, =CH); 4.49 (m, 0.5H, 1/2 NCH); 4.36 (m, 0.5H, 1/2 NCH)'4.12 (m, 1H, OCH); 3.90 (m, 1H, OCH); 3.25 (m, 2H, COCH$_2$); 1.71 (s, 1.5H, 1/2 Me); 1.65 (s, 1.5H, 1/2 Me); 1.52 (s, 1.5H, 1/2 Me); 1.49 (s, 6H, 1/2 Me, 1/2 CMe$_3$); 1.41 (s, 4.5H, 1/2 Cme$_3$)

MS (FAB): 270.1(M+1), 214.1, 200.1, 170.1, 156.0, 137.0, 100.1, 83.0, 69.0

HRMS (FAB, NBA), calcd. for C$_{14}$H$_{24}$NO$_4$ (MH) 270.1705, found 270.1713

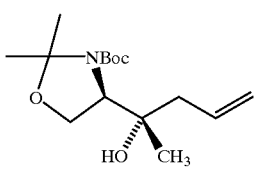

293C (4R,1')4-(1-Hydroxy-1-methyl-but-3-enyl)-2,2-dimethyl-oxazolidine 3-carboxylic acid tert-butyl ester To a solution of the product of example 293B (2.69 g, 10 mmol) in 50 mL dry THF was added a 1.4 M solution of MeMgCl (21.43 mL, 30 mmol) at −78° C. The resulting solution was stirred and allowed to warm up to 0° C. over 3 h. After quenching with sat. NH$_4$Cl, the crude product was purified by flash chromatography (EtOAc:CH$_2$Cl$_2$ 1:9) to give 1.29 g of starting material and the title compound (1.37 g, yield 48%) as a colorless oil.

$^1$H NMR(400 MHz, CDCl$_3$): δ5.94 (m, 1H, =CH); 5.05 (dd, 2H, =CH, J=6.8 and 16.3 Hz); 3.95 (m, 2H, OCH, NCH); 3.85 (d, 1H, OCH, J=7.2 Hz) 2.27 (dd, 1H, CH—C=C, J=5.8 and 13.8 Hz); 2.05 (m, 1H, CH—C=C); 1.54 (s, 3H, CMe); 1.46 (s, 3H, CMe); 1.45 (s, 9H, CMe$_3$); 1.05 (s, 3H, Me).

$^{13}$C NMR (100 MHZ, CDCl$_3$): δ155.38, 134.31, 117.46, 94.49, 81.26, 73.99, 66.19, 64.63, 41.84, 28.11, 26.05, 24.48, 24.19.

MS (FAB): 286.2(M+1), 230.1, 212.1, 200.1, 186.1, 172.1, 154.1, 144.1, 130.0, 110.1, 100.1, 83.0, 69.0.

HRMS (FAB, NBA): calcd. for C$_{15}$H$_{28}$NO$_4$ (MH) 286.2018, found 286.2013

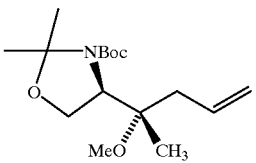

293D (4R,1'S)4-(1-Methoxy-1-methyl-but-3-enyl)-2,2-dimethyl oxazolidine 3-carboxylic acid tert-butyl ester To a stirred solution of the product of example 293C (0.5 g, 1.75 mmol) in dry THF (5 mL) was added 218 µl MeI (3.51 mmol) at 0° C., then 60% NaH (77 mg, 1.93 mmol) was added followed by Bu$_4$NBr (112 mg, 0.35 mmol). The mixture was stirred at r.t. overnight and quenched with H$_2$O at 0° C. After extraction with EtOAc, the crude oil was purified by flash chromatography (EtOAc:hexane 1:9) to give the title compound as a colorless oil (367 mg, yield 70%).

$[\alpha]_D=26.8°$ (c=4.4, CHCl$_3$).

$^1$H NMR (400 MHz, CDCl$_3$): δ5.83 (m, 1H, =CH); 5.03 (m, 2H, =CH$_2$); 4.14 (d, 2H, OCH$_2$, J=9.2 Hz); 3.82(dd, 1H, NH, J=6.5 and 9.2 Hz); 3.17 (s, 3H, OCH$_3$); 2.53 (dd, 1H, CH—C=C, J=5.9 and 14.9 Hz); 2.10 (m, 1H, CH—C=C); 1.56 (s, 3H, CMe); 1.45 (s, 12H, CMe, CMe$_3$); 1.10 (s, 3H, Me).

13C NMR(100 MHz, CDCl3): δ154.28, 134.09, 117.23, 80.08, 78.46, 63.77, 60.82, 49.35, 39.95, 28.14, 26.59, 24.32, 19.25.

MS (FAB): 300.3(M+1), 260.2, 244.2, 212.2, 200.2, 186.1, 172.1, 154.1, 144.1, 99.1.

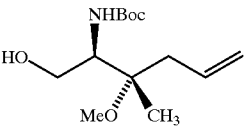

293E (1R,2S)(1-Hydroxymethyl-2-methoxy-2-methyl-pent-4-enyl)-carbamic acid ted-butyl ester To a stirred solution of the product of example 293D (1.09 g, 3.65 mmol) in dry MeOH (30 mL) was added p-toluensulfonic acid (70.4 mg, 0.37 mol) and the resulting mixture was stirred at r.t for 30 min. The reaction was quenched with sat. NaHCO$_3$. The solvent was removed under reduced pressure and 20 mL H$_2$O was added. After extraction with EtOAc, the organic layer was dried over MgSO$_4$ and evaporated to give the title compound as a white crystalline solid (850 mg, yield 90%).

[α]$_D$=−35.3°(c=0.9, CHCl$_3$).

$^1$H NMR(400 MHz, CDCl$_3$): δ5.75 (m, 1H, =CH); 5.26 (d, 1H, NH, J=8.8 Hz); 5.10 (m, 2H, =CH$_2$), 3.94 (dd, 1H, OCH, J=3.1 and 10.9 Hz); 3.60 (m, 2H, OCH, NCH); 3.21 (s, 3H, OMe); 2.54 (dd, 1H, CH—C=C, J=6.6 and 14.0 Hz); 2.29 (dd, 1H, CH—C=C, J=8.0 and 14.0 Hz); 1.43 (s, 9H, CMe$_3$); 1.24 (s, 3H, CMe).

$^{13}$C NMR(CDCl$_3$): δ156.24, 132.64, 118.82, 80.68, 79.33, 62.85, 55.78, 49.10, 40.09, 29.56, 28.23, 19.27.

MS (FAB): 260.2(M+1), 242.1, 229.1, 204.1, 172.1, 154.0, 145.1, 136.0, 119.1, 109.1, 95.1, 81.1, 69.0.

HRMS (FAB, NBA): calcd. for C$_{13}$H$_{26}$NO$_4$ (MH) 260.1 862, found 260.1867

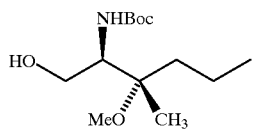

293F (1R,2S)(1-Hydroxymethyl-2-methoxy-2-methyl-pentyl)-carbamic acid tert-butyl ester To a solution of the product of example 292E (259 mg, 1.0 mmol) in MeOH (10 mL) was added 15 mmol % of 10% Pd/C. The flask was then flashed with nitrogen and finally with hydrogen. The reaction mixture was hydrogenated under atmospheric pressure at r.t. for 14 h, after which it was filtered through a pad of Celite (3×10 mL EtOH rinse) and concentrated to give the title compound as a white solid (258 mg , yield 99%).

[α]$_D$=−34.1°(c=2.2, CHCl$_3$).

$^1$H NMR(CDCl$_3$): δ5.20 (d, 1H, NH, J=8.7 Hz); 3.68 (dd, 1H, OCH, J=3.9 and 11.1 Hz); 3.55 (m, 2H, NCH, OCH); 3.13 (br, 1H, OH); 3.07 (s, 3H, OMe); 1.55 (m, 1H, CH); 1.32 (s, 9H, CMe$_3$): 1.25 (m, 3H, CH$_2$, CH): 1.06 (,, 3H, Me); 0.81 (t, 3H, CH$_3$, J=7.2 Hz).

$^3$C NMR (CDCl$_3$): δ156.28, 80.13, 78.98, 62.49, 55.77, 48.60, 37.36, 28.10, 19.11, 17.01, 14.45.

MS (FAB): 262.2(M+1), 230.2, 206.1, 174.1, 156.1, 144.1, 123.1, 113.1, 101.1 83.1, 69.1.

HRMS (FAB, NBA): calcd. for C$_{13}$H$_{28}$NO$_4$ (MH) 262.2018, found 262.2024

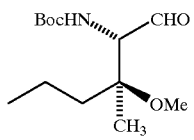

293G (1S,2S)(1-Formyl-2-methoxy-2-methyl-pentyl)-carbamic acid tert-butyl ester To a solution of the product of example 293F (190 mg, 0.73 mmol) in dry CH$_2$Cl$_2$ (12 mL) was added dry DMSO (2 mL) followed by Et$_3$N (1.01 mL, 7.3 mmol) and Py.SO$_3$ (928 mg, 5.84 mmol) at 0° C. The resulting mixture was allowed to warm up to r.t. and stirred for 2 h. The reaction was quenched with sat. NH$_4$Cl. After extraction with CH$_2$Cl$_2$, the organic layer was dried over MgSO$_4$. The solvent was evaporated to give the title compound as a crude oil (181 mg, yield 96%) which was used without further purification.

$^1$H NMR(400 MHz, CDCl$_3$): δ9.63 (s, 1H, CHO); 5.18 (d, 1H, NH, J=7.5 Hz); 4.23 (d, 1H, NCH, d=8.0 Hz); 3.09 (s, 3H, OMe); 1,50 (m, 2H, CH$_2$); 1.32 (s, 9H, CMe$_3$); 1.20 (m, 2H, CH$_2$); 1.13 (s, 3H, CMe); 0.82 (t, 3H, CH$_3$, J=7.1 Hz).

$^{13}$C NMR (400 MHz, CDCl$_3$): δ201.03, 155.67, 79.69, 79.69, 79.40, 63.58, 49.15, 37.12, 28.00, 19.41, 16.37, 14.24.

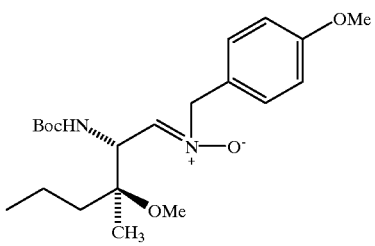

293H To a solution of the product of example 292G (272 mg, 1.05 mmol) in dichloromethane (20 mL) was added N-p-methoxybenzyl-N-hydroxylamine (153 mg, 1.0 mmol) followed by a large excess of MgSO$_4$. The mixture was stirred at r.t. for 4 h. After filtration and evaporation, the crude product was purified by flash chromatography (EtOAc:hexane 1:1) to give the nitrone title compound (335 mg, 85%) as a colorless oil.

[a]$_D$=32.30 (c=2.0, CHCl$_3$).

$^1$H NMR(400 MHz, CDCl$_3$): δ7.28 (d, 2H, ArH, J=8.5 Hz); 6.85 (d, 2H, ArH, J=8.5 Hz); 6.64 (d, 1H, NH, J=6.5 Hz); 6.05 (br, 1H, CH=N); 4.83 (m, 1H, CHN); 4.77 (s, 2H, CH$_2$Ar); 3.76 (s, 3H, OMe); 3.09 (s, 3H, OMe); 1.37 (s, 9H, Boc); 1.50–1.20 (m, 4H, 2×CH$_2$); 1.11 (s, 3H, Me); 0.78 (t, 3H, CH$_3$, J=6.2Hz).

$^{13}$C NMR (400 MHz, CDCl$_3$): δ159.94, 155.45, 136.07, 130.63, 124.98, 114.10, 80.79, 79.34, 69.51, 55.19, 58.03, 49.40, 37.07, 28.19, 19.43, 16.69, 14.56.

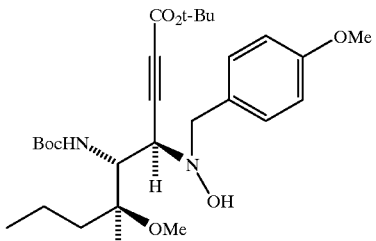

293I

To a solution of t-butyl propiolate (505 mg, 4.0 mmol) in dry THF (15 mL) at −78° C. was added n-BuLi (1.6 mL, 2.5 M in hexanes, 4.0 mmol) and the resulting solution was stirred for 1 hour. A cold (−78° C.) solution of nitrone product of example 293H (395 mg, 1.0 mmol) in dry THF (10 mL) was then added with a cannula, followed by BF$_3$.Et$_2$O (568 mg, 4.0 mmol). The reaction mixture was stirred at −78° C. for an additional 1 h. After being quenched with sat. NH₄Cl. (5 mL), the mixture was warmed up to r.t. and extracted with EtOAc (3×25 mL). The organic extracts were combined, washed with brine, dried over MgSO₄ and filtered. The solvent was removed under reduced pressure and the residue was purified by flash chromatography (EfOAc:hexane 2:8) to give the title compound (417 mg, 80%) as a pale yellow oil.

$[\alpha]_D = -106.5°$ (c=1.0, CHCl₃).

¹H NMR(400 MHz, CDCl₃): δ7.29 (d, 2H, ArH, J=8.6 Hz); 6.84 (d, 2H, ArH, J=8.6 Hz); 6.15 (br, 1H, NOH); 5.16 (d, 1H, NH, J=10.8 Hz); 4.25 (m, 1H, CHN); 4.12 ( s, 2H, CH₂Ar); 3.97 (s, 1H, CHN); 3.79 (s, 3H, OMe); 3.11 (s, 3H, OMe); 1.51 (s, 9H, t-Bu); 1.45 (s, 9H, Boc); 1.35–1.20 (m, 4H, 2×CH₂); 1.13 (s, 3H, Me); 0.86 (t, 3H, CH₃, J=7.2 Hz).

¹³C NMR (400 MHz, CDCl₃): δ158.70, 156.99, 152.35, 130.29, 130.03, 129.38, 113.44, 83.28, 81.49, 80.04, 77.93, 60.31, 55.10, 48.90, 36.56, 28.23, 27.89, 19.58, 16.34, 14.42.

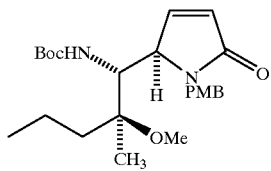

293J (2R,1'R,2'S)-1-p-Methoxybenzyl-2-(1-t-butoxycarbonylamino-2-methoxy-2-methyl)pentyl-5-oxo-2,5-dihydro-1H-pyrrole To a solution of the product of example 293I (239 mg, 0.5 mmol) in a mixture of acetic acid and methanol (1:9, 10 mL) was added zinc dust (20 eq., 10 mmol). The reaction mixture was vigorously stirred for 3 h, during which fresh zinc dust (10 eq.) was added. After filtration through a pad of celite, the residue was washed with dichloromethane (20 mL) and the filtrate was neutralized by NaHCO₃ at 0° C. The resulting crude product (after extraction into ethyl acetate, washing with brine, drying over MgSO₄ and evaporation of the solvent) was purified by flash chromatography (EtOAc:hexanes, 4:6) to give the title compound (112 mg, 50%) as colorless crystals. The structure and absolute configuration were confirmed by single crystal X-ray crystallography.

¹H NMR(400 MHz, CDCl₃): δ7.16 (d, 2H, ArH, J=8.0 Hz), 6.82 (d, 2H, ArH, J=8.0 Hz); 6.16 (d, 1H, =CH, J=6.0 Hz); 5.27 (m, 1H, =CH); 4.51 (d, 1H, NH, J=10.2Hz); 4.1 0 (m, 1H, CHN); 4.09 ( s, 2H, CH₂Ar); 3.78–3.75 (m, 1H, CHN); 3.76 (s, 3H, OMe); 3.13 (s, 3H, OMe); 1.50–1.40 (m, 2H, CH₂): 1.40 (s, 9H, Boc); 1.13 (s, 3H, Me); 1.09–0.84 (m, 2H, CH₂); 0.62 (t, 3H, CH₃).

¹³C NMR (400 MHz, CDCl₃): δ171.28, 15.883, 155.94, 145.36, 129.41, 129.33, 128.01, 113.89, 113.58, 79.57, 78.26, 60.92, 55.11, 54.09, 48.70, 42.44, 37.20, 36.69, 28.16, 27.99, 19.71, 17.13, 14.38.

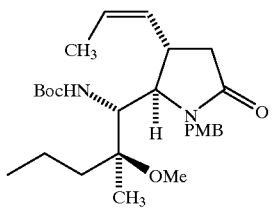

293K (2R,3S,1'R,2'S)-1-p-Methoxybenzyl-2-(1-t-butoxycarbonylamino-2-methoxy-2-methyl)pentyl-5-oxo-pyrrolidine The product of example 293J is reacted with the appropriate bis(Z-propen-1-yl)cuprate according to the procedure of Hanessian in Synthetic Letters 1990, p501–505 to provide the title compound.

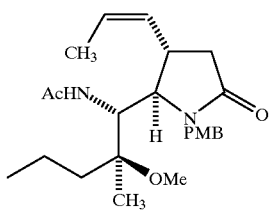

293L (2R,3S,1'R,2'S)-1-p-Methoxybenzyl-2-(1-acetamido-2-methoxy-2-methyl)pentyl-5-oxo-pyrrolidine The title compound is prepared according to the procedure of 289K substituting the product of example 293K for the product of example 289J.

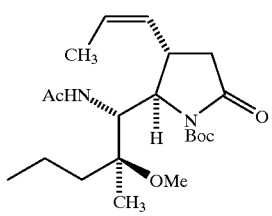

293M (2R,3S,1'R,2'S)-1-t-Butoxycarbonyl-2-(1-acetamido-2-methoxy-2-methyl)pentyl-5-oxo-pyrrolidine The product of example 293L is reacted with ceric ammonium nitrate according to the procedure of Yamaura in Bull. Chem. Soc. Japan 1985,58, 1413. The resulting product is reacted with di-t-butyldicarbonate, and N,N-dimethylaminopyridine and triethylamine to give the title compound.

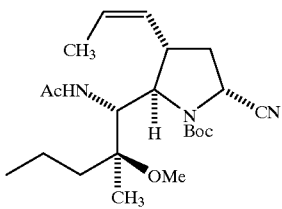

293N (2R,3S,5R,1'R,2'S)-1-t-Butoxycarbonyl-2-(1-acetamido-2-methoxy-2-methyl)pentyl-5-cyano-pyrrolidine The title compound is prepared according to the procedure described in example 288C substituting the product of example 293M for the product of example 288B.

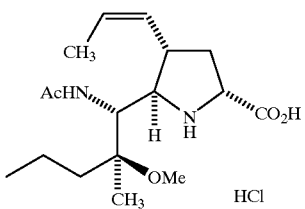

293O (−)-(2R,3S,5R,1'R,2'S)-2-(1-Acetamido-2-methoxy-2-methyl)pentyl-3-(cis-propen-1-yl)-pyrrolidine-5-carboxylic Acid Hydrochloride Salt The title compound is prepared according to the procedure of example 288K.

EXAMPLE 294

(±)-(2R,3R,5R,1'R,2'S)-2-(1-Acetamido-2-methoxy-2-methylpentyl-3-[(aminoimino)methyl]amino-pyrrolidine-5-carboxylic Acid

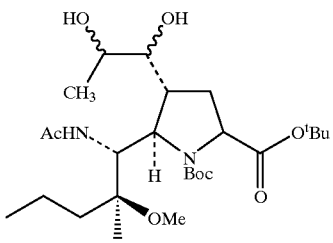

294A (±)-(2R,3R,5R 1'R,2'S)-1-t-Butoxycarbonyl-2-(1-acetamido-2-methoxy-2-methyl)pentyl-3-(1-hydroxy-2-hydroxy-propane)-pyrrolidine-5-carboxylic Acid t-Butyl Ester The product of example 265A is reacted with with osmium tetroxide (0.05 eq.) and 4-N-methylmorpholine-N-oxide (3 eq.) in acetone and water at room temperature. When complete, the reaction is quenched aqueous sodium thiosulfate and partitioned between saturated $NH_4Cl$ and ethyl acetate. The organic layer Is washed with water, and brine, dried over $MgSO_4$, filtered and concentrated in vacuo. The residue is then purified by chromatography on silica gel providing the title compound.

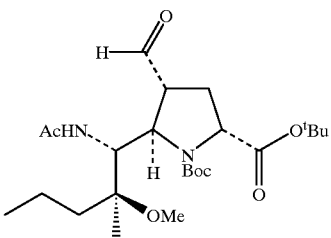

294B (±)-(2R,3R,5R,1'R,2'S)-1-t-Butoxycarbonyl-2-(1-Acetamido-2-methoxy-2-methyl)pentyl-3-formylpyrrolidine-5-carboxylic Acid t-Butyl Ester The product of example 294A with sodium periodate (1.5 eq.) in tetrahydrofuran and water at room temperature. When complete, the reaction is quenched with saturated $NH_4Cl$ and diluted with ethyl acetate. The organic layer is washed with water, and brine, dried over $MgSO_4$, filtered and concentrated in vacuo. The residue is purified by chromatography on silica gel providing the title compound.

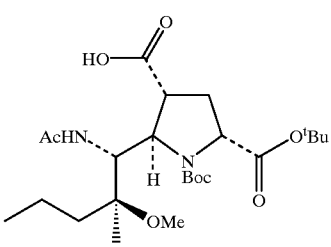

294C (±)-(2R,3R,5R,1'R,2'S)-1-t-Butoxycarbonyl-2-(1-acetamido-2-methoxy-2-methyl)pentyl-3-carboxyl-pyrrolidine-5-carboxylic Acid t-Butyl Ester The product of example 294B is reacted with with sodium chlorite (14 eq.) and sodium hydrogen phosphate (10 eq.) in 2-methyl-2-butene, tert-butanol, acetonitrile and water at 0° C. When complete, the reaction is quenched with aqueous sodium thiosulfate and diluted with ethyl acetate. The organic layer is washed with water, and brine, dried over $MgSO_4$, filtered and concentrated in vacuo to provide the title compound.

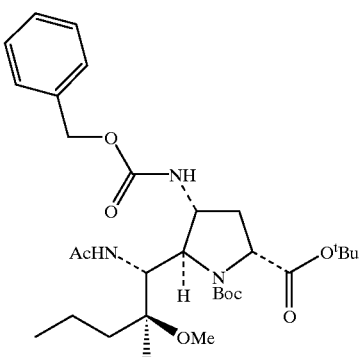

294D (±)-(2R,3R,5R,1'R,2'S)-1-t-Butoxycarbonyl 2-(1-acetamido-2-methoxy-2-methyl)pentyl-3-benzyloxycarbonylamino-pyrrolidine-5-carboxylic Acid t-Butyl Ester The product of example 294C is reacted with diphenylphosphoryl azide (1.2 eq.), triethylamine (1.2 eq.), and benzyl alcohol (1.3 eq.) in toluene at 75° C. When complete, the reaction is quenched with saturated $NH_4Cl$ and diluted with ethyl acetate. The organic layer is washed with water, and brine, dried over $MgSO_4$, filtered and concentrated in vacuo. The residue is then purified by chromatography on silica gel providing the title compound.

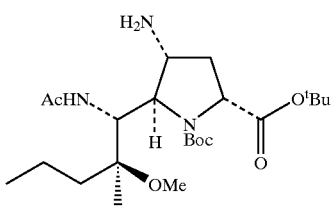

294E (±)-(2R,3R,5R,1'R,2'S)-1-t-Butoxycarbonyl-2-(1-acetamido-2-methoxy-2-methyl)pentyl-3-amino-pyrrolidine-5-carboxylic Acid t-Butyl Ester The product of example 294F is reacted with 10% palladium on carbon under an atmosphere of hydrogen in ethanol. When complete, the reaction is diluted with ethyl acetate. The organic layer is washed with water, and brine, dried over $MgSO_4$, filtered and concentrated in vacuo. The residue is then purified by chromatography on silica gel providing the title compound.

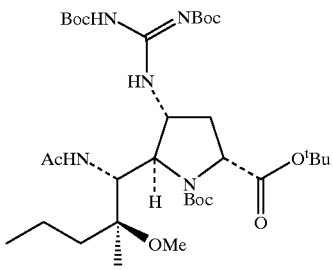

294F (±)-(2R,3R,5R,1'R,2'S)-1-t-Butoxycarbonyl 2-(1-acetamido-2-methoxy-2-methyl)pentyl-3-[(N-tert-butoxycarbonylamino-N'-tert-butoxycarbonylimino)methyl]amino-pyrrolidine5-carboxylic Acid t-Butyl Ester The product of example E is reacted with 1,3-bis(tert-butoxycarbonyl)-2-methyl-2-thiopseudourea (1.5 eq.), triethylamine (5.0 eq.), and mercury(II) chloride (1.5 eq.) in dimethyl formamide at room temperature. When complete, the reaction is diluted with ethyl acetate and filtered through a pad of celite. The organic solution is then washed with water, and brine, dried over $MgSO_4$, filtered and concentrated in vacuo. The residue is then purified by chromatography on silica gel providing the title compound.

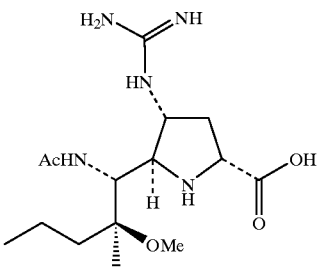

294G (±)-(2R 3R,5R,1'R,2'S)-1-t-Butoxycarbonyl-2-(1-acetamido-2-methoxy-2-methyl)pentyl-3-[(aminoimino)methyl]amino-pyrrolidine-5-carboxylic Acid The product of example 294F is reacted with 80% trifluoroacetic acid in dichloromethane at room temperature. When complete, the reaction is concentrated in vacuo and purified by cation-exchange chromatography on Dowex 50W-X8 providing the title compound.

EXAMPLE 295

(2R,3R,5R,1'R,2'S)-2-(1-Acetamido-2-methoxy-2-methyl)pentyl-3-[(aminoimino)methyl]amino-pyrrolidine-5-carboxylic Acid

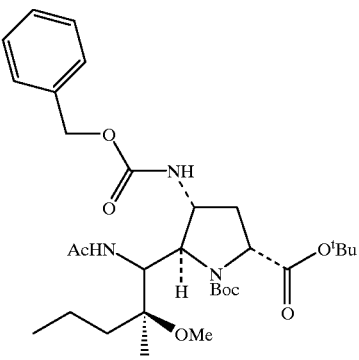

295A (2R,3R,5R,1'R,2'S)-1-t-Butoxycarbonyl-2-(1-acetamido-2-methoxy-2-methyl)pentyl-3-benzyloxycarbonylamino-pyrrolidine-5-carboxylic Acid t-Butyl Ester The title compound is prepared by chiral HPLC chromatography by the procedure of example 267 substituting the product of example 294D for the product of example 266 to provide the title compound.

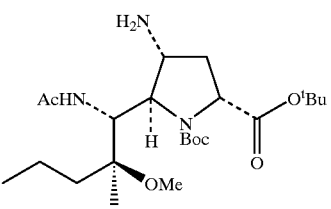

295B (2R,3R,5R,1'R,2'S)-1-t-Butoxycarbonyl-2-(1-acetamido-2-methoxy-2-methyl)pentyl-3-amino-pyrrolidine-5-carboxylic Acid t-Butyl Ester The title compound is prepared according to the procedure of example 294E substituting the product of example 295A for the product of example 294D.

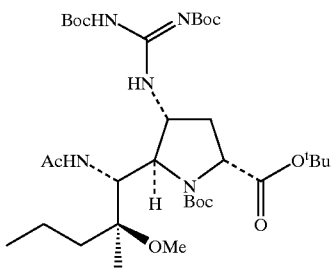

295C (2R,3R,5R,1'R,2'S)-1-t-Butoxycarbonyl 2-(1-acetamido-2-methoxy-2-methyl)pentyl-3-[(N-t-butoxycarbonylamino-N'-t-butoxycarbonylimino) methyl]amino-pyrrolidine-5-carboxylic Acid t-Butyl Ester The title compound is prepared according to the procedure of example 294F substituting the product of example 295B for the product of example 294E.

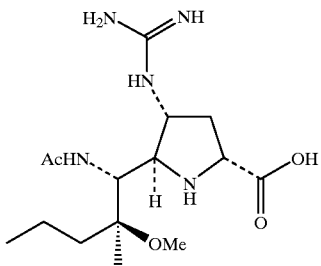

295D (2R,3R,5R,1'R,2'S)-1-t-Butoxycarbonyl 2-(1-acetamido-2-methoxy-2-methyl)pentyl-3-[(N-t-butoxycarbonylamino-N'-t-butoxycarbonylimino) methyl]amino-pyrrolidine-5-carboxylic Acid t-Butyl Ester The title compound is prepared according to the procedure of example 294G substituting the product of example 295C for the product of example 294F.

EXAMPLE 296

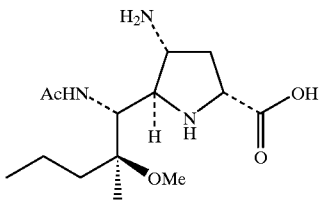

(2R,3R,5R,1'R,2'S)-2-(1-Acetamido-2-methoxy-2-methyl)pentyl-3-amino-pyrrolidine-5-carboxylic Acid The title compound is prepared according to the procedure of example 294G substituting the product of example 295B for the product of example 294F.

EXAMPLE 297

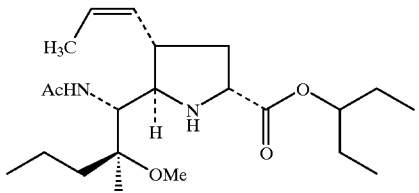

(2R,3S,5R,1'R,2'S)-2-(1-Acetamido-2-methoxy-2-methyl)pentyl-3-(cis-propen-1-yl)pyrrolidine-5-carboxylic Acid 3-Pentyl Ester A mixture of 2.92 g (24.5 mmol, 1.79 mL) thionyl chloride and 20 mL of 3-pentanol was stirred at room temperature for 45 minutes. To this mixture was adden in one portion the product of example 273 (0.40 g,1.23 mmol). The mixture was stirred at room temperature for 18 h and then the solvent was evaporated in vacuo. The residue was purified by column chromatography on silica gel using 98:2:0.1 dichloromethane/methanol/ammonium hydroxide to provide the title compound (yield: 0.325 g, 67%) as a colorless oil.

$^1$H NMR (CDCl$_3$) δ5.5–5.25 (m, 3H), 4.77 (m, 1H), 4.16 (dd, J=10.2,7.2 Hz, 1H), 3.84 (t, J=7.5 Hz, 1H), 3.29 (t, J=7.4 Hz, 1H), 3.18 (s, 3H), 2.96 (quintet, J=8.3 Hz, 1H), 2.34 (td, J=12.5,8.2 Hz, 1H), 1.94 (s, 3H), 1.62 (dd, J=6.5, 1.3 Hz 3H), 1.65–1.25 (m, 8H), 1.11 (s, 3H), 0.95–0.80 (m, 9H).

MS: (M+H)$^+$=397, (M−H)$^-$=419, (M−H)$^-$=395

EXAMPLE 298

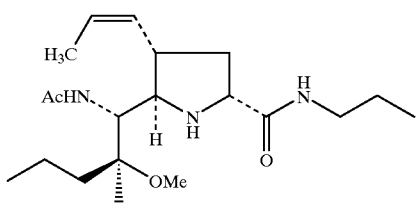

(2R,3S,5R,1'R,2'S)-2-(1-Acetamido-2-methoxy-2-methyl)pentyl-3-(cis-propen-1-yl)-5-(N-propylcarbamoyl-pyrrolidine The product of example 267 (0.375 g, 1.06 mmol) was reacted with n-propylamine (5 mL) for 5 days room temperature. The reaction was concentrated evaporated in vacuo. The residue was purified by column chromatography on silica gel using 98:2:0.1 dichloromethane/methanol/ ammonium hydroxide to provide the title compound (yield: 0.216 g, 56%) as a white solid.

$^1$H NMR (CDCl$_3$) δ7.57 (m, 1H), 5.82 (d, J=9.5 Hz, 1), 5.45–5.35 (m, 1H),5.24 (m, 1H), 4.09 (dd, J=9.5,4.8 Hz, 1H), 3.71 (t, J=8.2 Hz, 1H), 3.17 (m, 2H), 3.14 (s, 3H), 2.92 (quintet, J=8.4 Hz, 1H), 2.36 (td, J=13.2,7.8 Hz, 1H), 2.01 (s, 3H), 1.61 (dd, J=6.8,1.7 Hz, 3H), 1.6–1.25 (m, 6H), 1.12 (s, 3H), 0.94 (t, J=7.1 Hz, 3H), 0.92 (t, J=7.1 Hz, 3H).

MS: (M+H)$^+$=367.

EXAMPLE 299

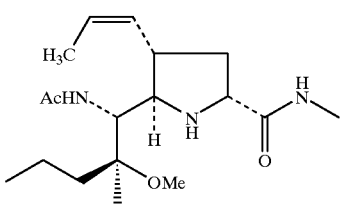

(±)-(2R,3S 5R,1'R,2'S)-2-(1-Acetamido-2-methoxy-2-methyl)pentyl-3-(cis-propen-1-yl)-5-N-methylcarbamoyl-pyrrolidine A mixture of the product of example 267 (0.0085 g, 0.024 mmol) and 3 mL of 2.0 M methylamine in water was stirred at room temperature for 24 h, and the solvent was then evaporated in vacuo. The residue was purified by column chromatography on silica gel using 98:2:0.1 dichloromethane/methanol/ammonium hydroxide to provide the desired product (yield: 0.004 g, 50%) as a colorless oil.

$^1$H NMR (CDCl$_3$) δ7.54 (m, 1H), 5.81 (d, J=9.8 Hz, 1), 5.45–5.35 (m, 1H), 5.23 (m, 1H), 4.10 (dd, J=9.5, 4.7 Hz, 1H), 3.73 (t, J=8.1 Hz, 1H), 3.17 (dd, J=7.5,4.7 Hz, 1H), 3.14 (s, 3H), 2.93 (quintet, J=8.5 Hz, 1H), 2.79 (d, J=5.1 Hz 3H), 2.36 (td, J=13.2,7.8 Hz, 1H), 2.01 (s, 3H), 1.60 (dd, J=6.8,1.7 Hz, 3H), 1.6–1.25 (m, 4H), 1.12 (s, 3H), 0.94 (t, J=7.1 Hz, 3H).

MS: (M+H)$^+$=339

EXAMPLE 300

(±)-(2R,3S,5R,1'R,2'S)-2-(1-acetamido-2-methoxy-2-methyl)pentyl-3-(cis-propen-1-yl)pyrrolidine-5-carboxamide

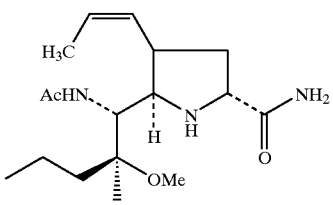

A mixture of 0.0446 g (0.126 mmol) ) (±)-(2R,3S,5R,1'R,2'S)-2-(1-acetamido-2-methoxy-2-methyl)pentyl-3-(cis-propen-1-yl)pyrrolidine-5-carboxylic acid ethyl ester and 3 mL of conc. ammonium hydroxide was stirred at room temperature for 24 h, and the solvent was then evaporated in vacuo. The residue was purified by column chromatography on silica gel using 95:5:0.1 dichloromethane/methanol/ammonium hydroxide to provide the title compound (yield: 0.0185 g, 45%) as a colorless oil.

$^1$H NMR (MeOH-d$_4$) δ5.45–5.25 (m, 2H), 4.09 (d, J=8.8 Hz, 1H), 3.75 (dd, J=8.5,7.8 Hz, 1H), 3.21 (s, 3H), 3.17 (dd, J=8.7,7.0 Hz, 1H), 2.96 (quintet, J=7.8 Hz, 1H), 2.31 (td, J=12.5,7.6 Hz, 1H), 1.90 (s, 3H), 1.59 (dd, J=6.4,1.4 Hz, 3H), 1.55–1.25 (m, 5H), 1.23 (s, 3H), 0.87 (t, J=7.1 Hz, 3H).

MS: (M+H)$^+$=326, (M+Na)$^+$=348, (M–H)$^-$=324.

EXAMPLE 301

(2R,3S,5R,1'R,2'S)-N-ethyl-2-(1-acetamido-2-methoxy-2-methyl)pentyl-3-(cis-propen-1-yl)-5-N-ethylcarbamoyl-pyrrolidine

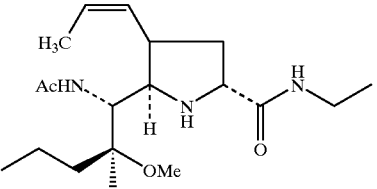

A mixture of 0.0853 g (0.162 mmol) (–)-(2R,3S,5R,1'R,2'S)-2-(1-acetamido-2-methoxy-2-methyl)pentyl-3-(cis-propen-1-yl)pyrrolidine-5-carboxylic acid ethyl ester toslyate salt and 5 mL of 70% aqueous ethylamine was stirred at rt for 24 h, and the solvent was then evaporated in vacuo. The residue was purified by column chromatography on silica gel using 97.5:2.5:0.1 dichloromethane/methanol/ammonium hydroxide to provide the desired product (yield: 0.051 g, 89%) as a white solid.

$^1$H NMR (CDCl$_3$) δ7.51 (m, 1H), 5.83 (d, J=9.5 Hz, 1H), 5.45–5.35 (m, 1H), 5.24 (m, 1H), 4.09 (dd, J=9.5,4.8 Hz, 1H), 3.70 (t, J=7.9 Hz, 1H), 3.26 (dq, J=5.8,7.5 Hz, 2H), 3.16 (m, 1H), 3.14 (s, 3H), 2.92 (quintet, J=8.4 Hz, 1H), 2.25 (td, J=12.9,7.8 Hz, 1H), 2.01 (s, 3H), 1.61 (dd, J=6.7,1.5 Hz, 3H), 1.6–1.25 (m, 5H), 1.13 (t, J=7.3 Hz, 3H), 1.12 (s, 3H), 0.94 (t, J=7.1 Hz, 3H).

MS: (M+H)$^+$=354, (M+Na)$^+$=376, (M–H)$^-$=352.

EXAMPLE 302

(2R,3S,5R,1'R,2'S)-2-(1-acetamido-2-methoxy-2-methyl)pentyl-3-(cis-propen-1-yl)-5-N-(1-propyl)carbamoyl-pyrrolidine p-Toluenesulfonic Acid Salt

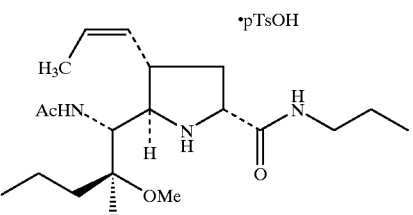

A mixture of (2R,3S,5R,1'R,2'S)-2-(1-acetamido-2-methoxy-2-methyl)pentyl-3-(cis-propen-1-yl)-5-N-(1-propyl)carbamoyl-pyrrolidine (0.213 g, 0.58 mmol) and p-toluenesulfonic acid monohydrate (0.110 g, 0.58 mmol) in 5 mL of dichloromethane was stirred at rt for 15 min. The solvent was evaporated in vacuo to provide the desired product (yield: 0.32 g, 99%) as a white powder.

$^1$H NMR (CDCl$_3$) δ9.35 (bs, 1H), 8.3 (bs, 1H), 8.21 (t, J=5.4 Hz, 1H), 7.79 (d, J=8.2 Hz, 2H), 7.16 (d, J=8.1 Hz, 2H), 6.49 (d, J=9.8 Hz, 1H), 5.51 (dq, J=10.9,7.8 Hz, 1H), 5.27 (m, 1H), 4.76 (m, 1H), 4.56 (dd, J=9.8,7.1 Hz, 1H), 3.81 (m, 1H), 3.42 (m, 1H), 3.25–3.0 (m, 2H), 3.15 (s, 3H), 2.72 (dt, J=13.2,7.5 Hz, 1H), 2.34 (s, 3H), 2.00 (s, 2H), 1.86 (m, 1H), 1.64 (s, 3H), 1.57 (dd, J=6.9,1.5 Hz, 3H), 1.5–1.2 (m, 2H), 1.19 (s, 3H), 0.84 (t, J=7.1 Hz, 3H), 0.82 (t, J=6.8 Hz, 3H).

MS: (M+H)$^+$=367.

Using the methods described above and the general knowledge of one skilled in the art, compounds of the invention (having the indicated relative stereochemistry or enantiomerically enriched and having the indicated absolute stereochemisty) can be prepared which are represented by taking one core from Table 1 (wherein Ac is acetyl), one Y substituent from Table 2, one R substituent from Table 3 and one $R^3$ substituent from Table 4a, 4b, 4c, 4d, 4e, 4f, 4g or 4h.

TABLE 2-continued
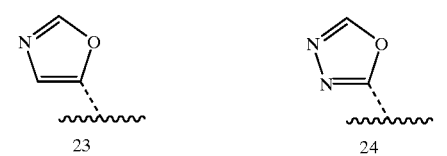
23
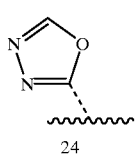
24
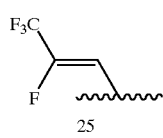
25
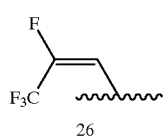
26
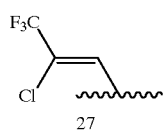
27
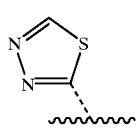
28
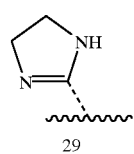
29
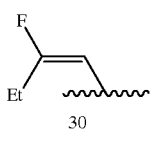
30
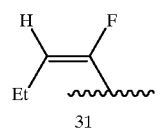
31
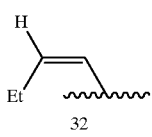
32
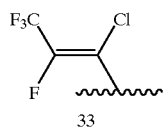
33
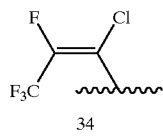
34
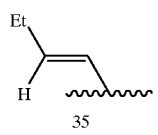
35
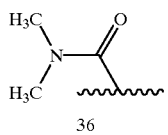
36
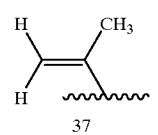
37
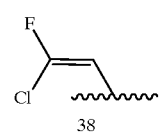
38
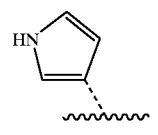
39
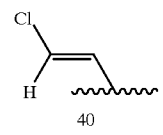
40
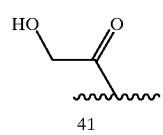
41
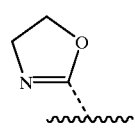
42
TABLE 2-continued
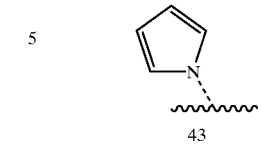
43
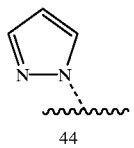
44
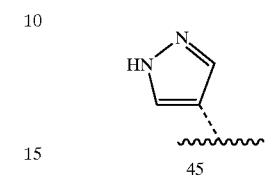
45
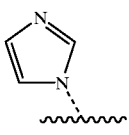
46
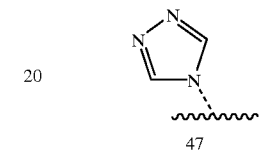
47
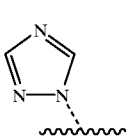
48
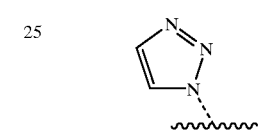
49
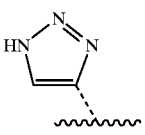
50
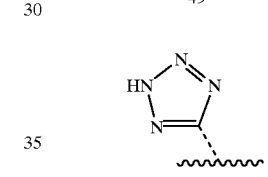
51
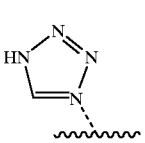
52
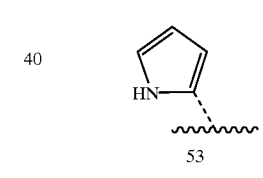
53
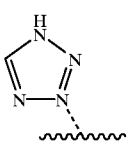
54
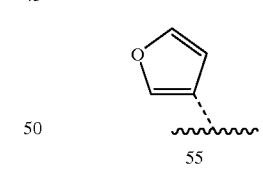
55
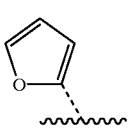
56
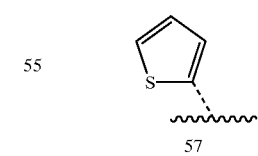
57
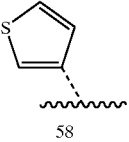
58
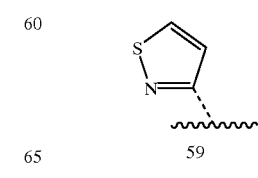
59
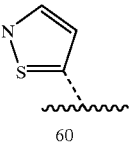
60

TABLE 2-continued
| | |
|---|---|
| 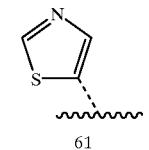 61 | 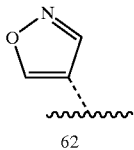 62 |
| 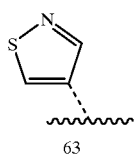 63 | 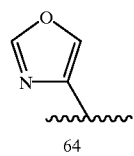 64 |
| 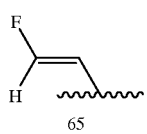 65 | 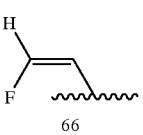 66 |
| 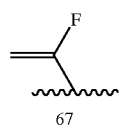 67 | 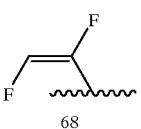 68 |
| 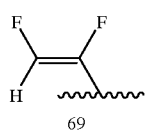 69 | 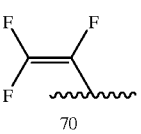 70 |
| 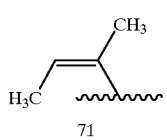 71 | 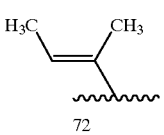 72 |
| 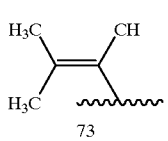 73 | 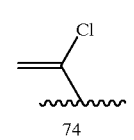 74 |
| 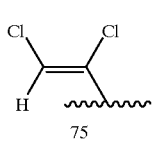 75 | 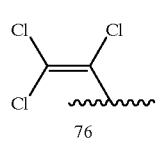 76 |
| 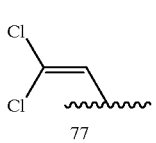 77 | 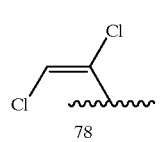 78 |
| 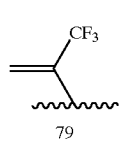 79 | 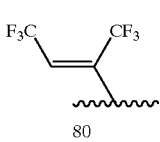 80 |
TABLE 2-continued
| | |
|---|---|
| 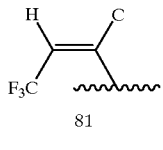 81 | 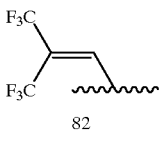 82 |
| 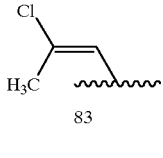 83 | 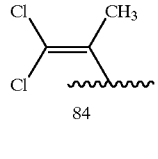 84 |
| 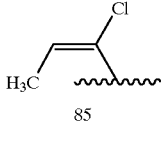 85 | 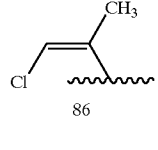 86 |
| 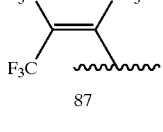 87 | 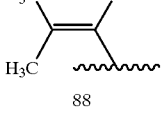 88 |
| 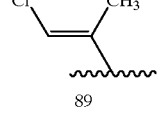 89 | 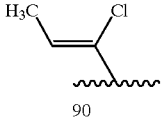 90 |
| 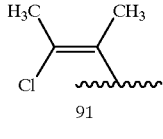 91 | 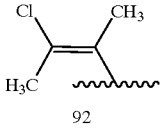 92 |
| 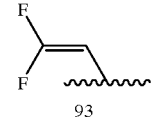 93 | 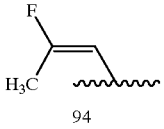 94 |
| 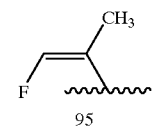 95 | 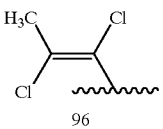 96 |
| 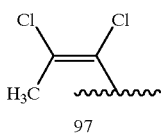 97 | 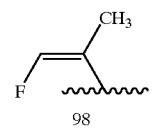 98 |
| 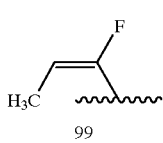 99 | 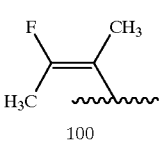 100 |

TABLE 2-continued
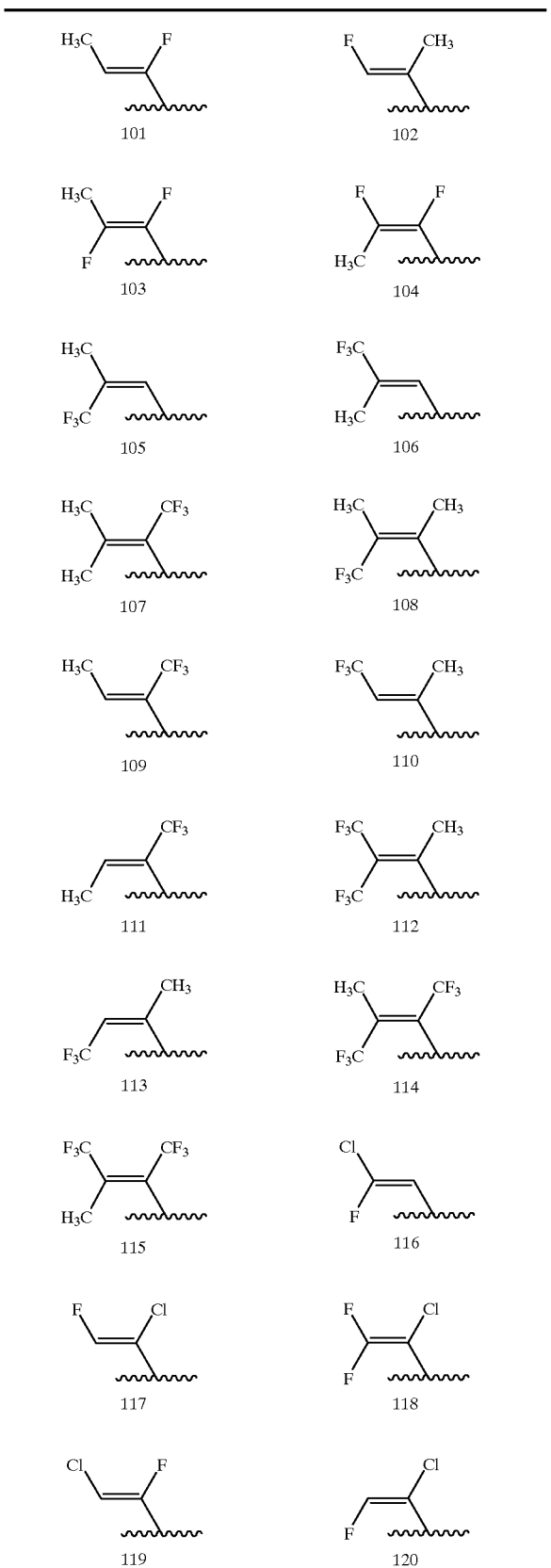
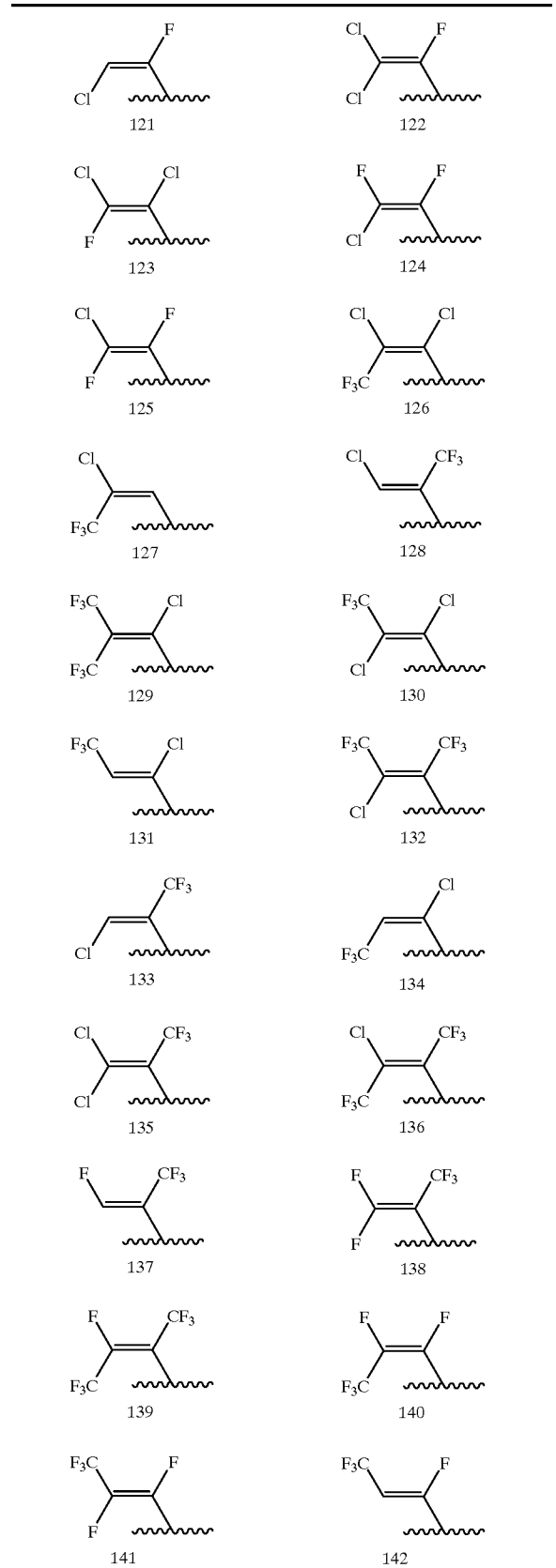

TABLE 2-continued
| | |
|---|---|
| 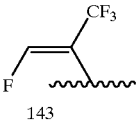 143 | 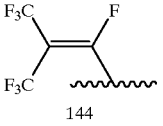 144 |
| 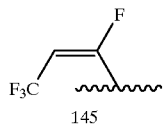 145 | 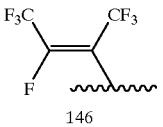 146 |
| 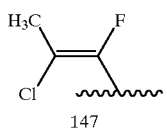 147 | 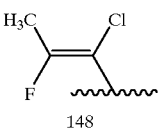 148 |
| 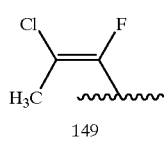 149 | 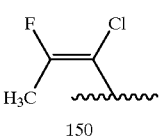 150 |
| 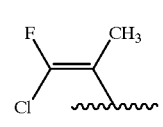 151 | 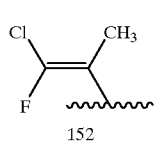 152 |
| 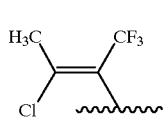 153 | 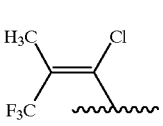 154 |
| 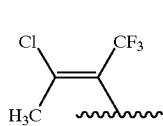 155 | 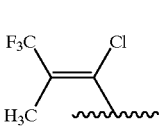 156 |
| 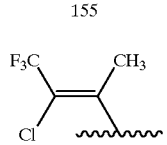 157 | 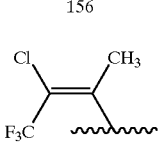 158 |
| 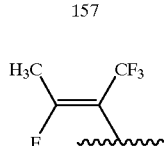 159 | 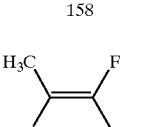 160 |
| 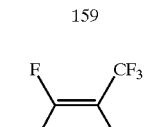 161 | 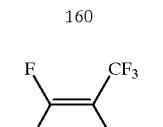 162 |
| 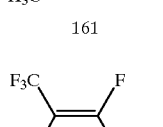 163 | 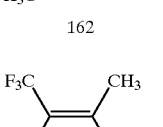 164 |
TABLE 2-continued
| | |
|---|---|
| 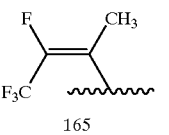 165 | 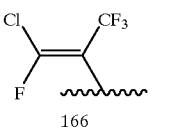 166 |
| 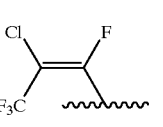 167 | 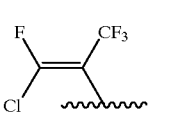 168 |
| 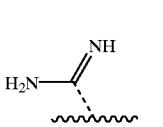 169 | 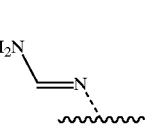 170 |
| 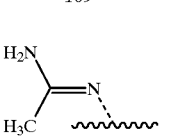 171 | 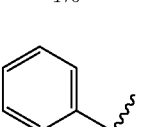 172 |
| 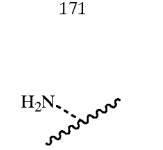 173 | 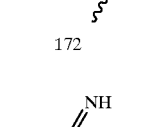 174 |
TABLE 3
| | |
|---|---|
| 1 | —OH |
| 2 | —OCH$_3$ |
| 3 | 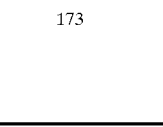 |
| 4 | 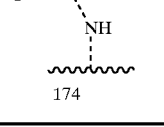 |
| 5 | 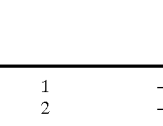 |
| 6 | 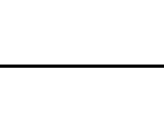 |
| 7 | 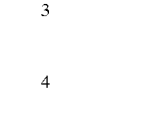 |
| 8 | 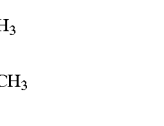 |

TABLE 3-continued

| # | Structure |
|---|---|
| 9 | —O—CH2—C(CH3)3 |
| 10 | —O—CH2—CH(CH3)2 |
| 11 | —O—CH(CH3)—CH2—CH3 (S) |
| 12 | —O—CH(CH3)—CH2—CH3 (R) |
| 13 | —O—C(CH3)3 with extra CH3 (tert-amyl type) |
| 14 | —O—CH2CH2—N(CH3)2 |
| 15 | —O—CH2CH2—N(CH2CH3)2 |
| 16 | —O—CH2—phenyl |
| 17 | —O—CH2—(2-pyridyl) |
| 18 | —O—CH2—(3-pyridyl) |
| 19 | —O—cyclohexyl |
| 20 | —O—cyclopropyl |
| 21 | —O—(1-methylpiperidin-4-yl) |

TABLE 3-continued

| # | Structure |
|---|---|
| 22 | —O—CH2CH2—(piperidin-1-yl) |
| 23 | —O—CH2CH2—(morpholin-4-yl) |
| 24 | —O—CH2CH2—(4-methylpiperazin-1-yl) |
| 25 | —O—C(CH3)2—CH2—(piperidin-1-yl) |
| 26 | —O—C(CH3)2—CH2—(morpholin-4-yl) |
| 27 | —O—C(CH3)2—CH2—(4-methylpiperazin-1-yl) |
| 28 | —O—CH2—(3H-isobenzofuran-1-one-3-yl) |
| 29 | —O—CH2—O—C(O)—C(CH3)3 |
| 30 | —O—CH2—O—C(O)—O—C(CH3)3 |
| 31 | —O—CH2CH2—phenyl |
| 32 | —O—CH2CH2—(2-pyridyl) |

TABLE 3-continued
| | |
|---|---|
| 34 | 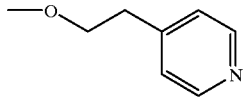 |
| 35 | 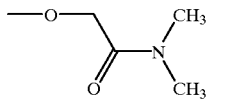 |
| 36 | 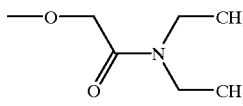 |
| 37 | 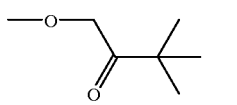 |
| 38 | 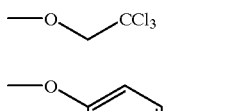 |
| 39 | 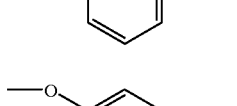 |
| 40 | 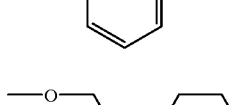 |
| 41 | 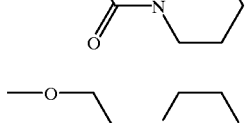 |
| 42 | 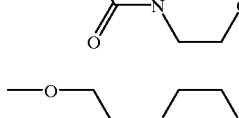 |
| 43 | 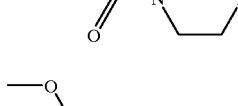 |
| 44 | 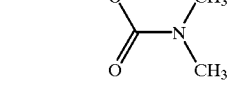 |
| 45 | 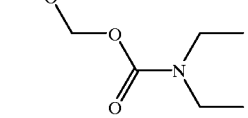 |
| 46 | 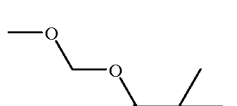 |
TABLE 3-continued
| | |
|---|---|
| 47 | —NH$_2$ |
| 48 |  |
| 49 |  |
| 50 |  |
| 51 |  |
| 52 |  |
| 53 |  |
| 54 |  |
| 55 |  |
| 56 |  |
| 57 |  |
| 58 |  |
| 59 |  |
| 60 |  |

TABLE 3-continued

| | |
|---|---|
| 61 | —NH—CH2—C(=O)—N(piperidine) |
| 62 | —NH—CH2—C(=O)—OH |
| 63 | —NH—CH2—C(=O)—OCH3 |
| 64 | —NH—CH2—C(=O)—O—Et |
| 65 | —NH—Ala-OH |
| 66 | —NH—Ala-OCH3 |
| 67 | —NH—Ala-OEt |
| 68 | —NH—Val-OH |
| 69 | —NH—Val-OCH3 |
| 70 | —NH—Val-OEt |
| 71 | —NH—Leu-OH |
| 72 | —NH—Leu-OCH3 |
| 73 | —NH—Leu-OEt |
| 74 | —NH—Ile-OH |
| 75 | —NH—Ile-OCH3 |
| 76 | —NH—Ile-OEt |
| 77 | —NH—Phe-OH |
| 78 | —NH—Phe-OCH3 |
| 79 | —NH—Phe-OEt |
| 80 | —NH—Tyr-OH |
| 81 | —NH—Tyr-OCH3 |
| 82 | —NH—Tyr-OEt |
| 83 | —NH—Asn-OH |
| 84 | —NH—Asn-OCH3 |
| 85 | —NH—Asn-OEt |
| 86 | —NH—Glu-OH |
| 87 | —NH—Glu-OCH3 |
| 88 | —NH—Glu-OEt |
| 89 | —NH—Glu-OH |
| 90 | —NH—Gln-OCH3 |
| 91 | —NH—Gln-OEt |
| 92 | —NH—Asp-OH |
| 93 | —NH—Asp-OCH3 |
| 94 | —NH—Asp-OEt |
| 95 | —NH—Lys-OH |
| 96 | —NH—Lys-OCH3 |
| 97 | —NH—Lys-OEt |
| 98 | —NH—Ser-OH |
| 99 | —NH—Ser-OCH3 |
| 100 | —NH—Ser-OEt |
| 101 | —O—CH(CH2CH3)2 |

TABLE 4a

| | |
|---|---|
| 1 | CH2=C(CH3)—CH(OH)— (wavy bond) |
| 2 | H3C—CH=CH—CH(OH)— (wavy bond) |

TABLE 4a-continued

TABLE 4a-continued
| | |
|---|---|
| 24 | 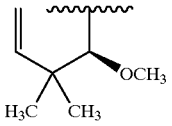 |
| 25 | 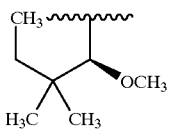 |
| 26 | 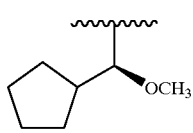 |
| 27 | 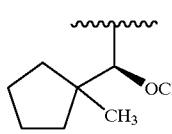 |
| 28 | 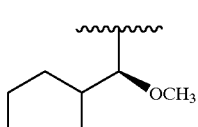 |
| 29 | 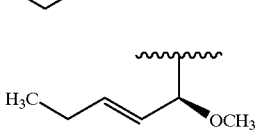 |
| 30 | 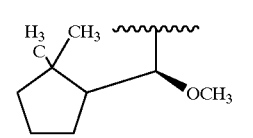 |
| 31 | 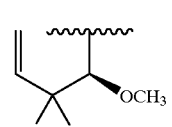 |
| 32 | 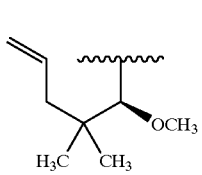 |
| 33 | 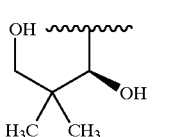 |
| 34 | 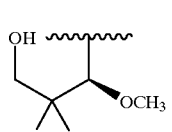 |
TABLE 4a-continued
| | |
|---|---|
| 35 | 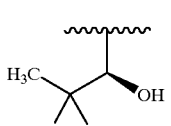 |
| 36 | 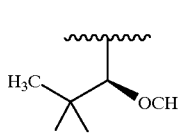 |
| 37 | 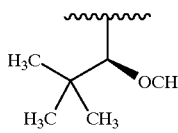 |
| 38 | 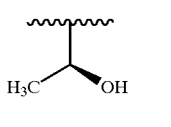 |
| 39 | 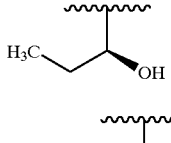 |
| 40 | 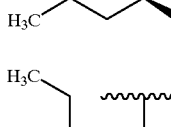 |
| 41 | 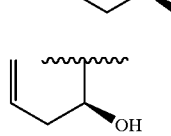 |
| 42 | 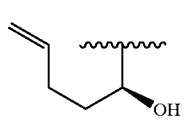 |
| 43 | 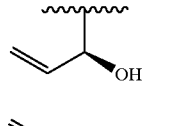 |
| 44 | 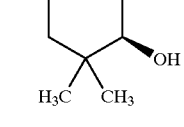 |
| 45 | 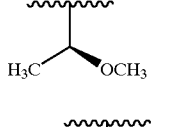 |
| 46 | 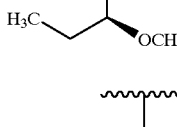 |
| 47 | 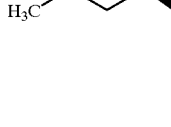 |

TABLE 4a-continued

| | |
|---|---|
| 48 | H₃C~~~OCH₃ (structure) |
| 49 | CH₂=CH-CH₂-CH(OCH₃)~ |
| 50 | CH₂=CH-CH₂-CH₂-CH(OCH₃)~ |
| 51 | CH₂=CH-CH(OCH₃)~ |
| 52 | CH₂=CH-CH₂-C(CH₃)₂-CH(OCH₃)~ |

TABLE 4b

| | |
|---|---|
| 1 | ~CH(OH)-CH₂-OH |
| 2 | ~CH(OCH₃)-CH₂-OH |
| 3 | ~CH(OCH₂CH₃)-CH₂-OH |
| 4 | ~CH(OCH₂CH₂CH₃)-CH₂-OH |
| 5 | ~CH(OH)-CH₂-OH |

TABLE 4b-continued

| | |
|---|---|
| 6 | ~CH(OCH₃)-CH₂-OH |
| 7 | ~CH(OCH₂CH₃)-CH₂-OH |
| 8 | ~CH(OCH₂CH₂CH₃)-CH₂-OH |
| 9 | ~CH(OH)-CH(OH)-CH₂-OH |
| 10 | ~CH(OCH₃)-CH(OH)-CH₂-OH |
| 11 | ~CH(OCH₂CH₃)-CH(OH)-CH₂-OH |
| 12 | ~CH(OCH₂CH₂CH₃)-CH(OH)-CH₂-OH |
| 13 | ~CH(OH)-CH(OH)-CH₂-OH |
| 14 | ~CH(OCH₃)-CH(OH)-CH₂-OH |
| 15 | ~CH(OCH₂CH₃)-CH(OH)-CH₂-OH |

TABLE 4b-continued

| # | Structure |
|---|---|
| 16 | HOCH₂-CH(OH)-CH(OPr)- (with wavy bond) |
| 17 | HOCH₂-CH(OH)-CH(OH)- |
| 18 | HOCH₂-CH(OH)-CH(OCH₃)- |
| 19 | HOCH₂-CH(OH)-CH(OEt)- |
| 20 | HOCH₂-CH(OH)-CH(OPr)- |
| 21 | HOCH₂-CH(OH)-CH(OH)- |
| 22 | HOCH₂-CH(OH)-CH(OCH₃)- |
| 23 | HOCH₂-CH(OH)-CH(OEt)- |
| 24 | HOCH₂-CH(OH)-CH(OPr)- |
| 25 | HOCH₂-CH(OAllyl)- |
| 26 | HOCH₂-CH(OAllyl)- |
| 27 | HOCH₂-CH(OH)-CH(OAllyl)- |
| 28 | HOCH₂-CH(OH)-CH(OAllyl)- |
| 29 | HOCH₂-CH(OH)-CH(OAllyl)- |
| 30 | HOCH₂-CH(OH)-CH(OAllyl)- |
| 31 | CH₃OCH₂-CH(OCH₃)- |
| 32 | CH₃OCH₂-CH(OCH₃)- |
| 33 | CH₃O-CH₂-CH(OCH₃)-CH(OCH₃)- |
| 34 | CH₃O-CH₂-CH(OCH₃)-CH(OCH₃)- |
| 35 | CH₃O-CH₂-CH(OCH₃)-CH(OCH₃)- |

TABLE 4b-continued

| No. | Structure |
|---|---|
| 36 | CH3O–CH(OCH3)–CH(OCH3)– (with stereochemistry) |
| 37 | (H3C)2C(OH)–CH(OH)– |
| 38 | (H3C)2C(OH)–CH(OCH3)– |
| 39 | (H3C)2C(OH)–CH(OCH2CH3)– |
| 40 | (H3C)2C(OH)–CH(O-propyl)– |
| 41 | H3C–C(CH2CH3)(OH)–CH(OH)– |
| 42 | H3C–C(CH2CH3)(OH)–CH(OCH3)– |
| 43 | H3C–C(CH2CH3)(OH)–CH(OCH2CH3)– |
| 44 | H3C–C(CH2CH3)(OH)–CH(O-propyl)– |
| 45 | H3C–CH(OH)–CH(OH)– |

TABLE 4b-continued

| No. | Structure |
|---|---|
| 46 | H3C–CH(OH)–CH(OCH3)– |
| 47 | H3C–CH(OH)–CH(OCH2CH3)– |
| 48 | H3C–CH(OH)–CH(O-propyl)– |
| 49 | H3C–CH2–CH(OH)–CH(OH)– |
| 50 | H3C–CH2–CH(OH)–CH(OCH3)– |
| 51 | H3C–CH2–CH(OH)–CH(OCH2CH3)– |
| 52 | H3C–CH2–CH(OH)–CH(O-propyl)– |
| 53 | H3C–CH(OH)–CH(OH)– |
| 54 | H3C–CH(OH)–CH(OCH3)– |
| 55 | H3C–CH(OH)–CH(OCH2CH3)– |

TABLE 4b-continued

| No. | Structure |
|---|---|
| 56 | 2-hydroxy-1-methylpropyl propyl ether fragment |
| 57 | 1,2-dihydroxybutyl fragment |
| 58 | 1-hydroxy-2-methoxybutyl fragment |
| 59 | 2-ethoxy-1-hydroxybutyl fragment |
| 60 | 1-hydroxy-2-propoxybutyl fragment |
| 61 | 1-hydroxy-2-methyl fragment with O |
| 62 | 1-hydroxy-2-methoxy-2-methylpropyl fragment |
| 63 | 2-ethoxy-1-hydroxy-2-methylpropyl fragment |
| 64 | 1-hydroxy-2-methyl-2-propoxypropyl fragment |
| 65 | 2-ethyl-1,2-dihydroxybutyl fragment |
| 66 | 2-ethyl-2-hydroxy-1-methoxybutyl fragment |
| 67 | 1-ethoxy-2-ethyl-2-hydroxybutyl fragment |
| 68 | 2-ethyl-2-hydroxy-1-propoxybutyl fragment |
| 69 | 1,2-dihydroxy-1-methylbutyl fragment |
| 70 | 1,2-dihydroxy-1-methylpentyl fragment |
| 71 | 2-hydroxy-1-methoxy-1-methylbutyl fragment |
| 72 | 2-hydroxy-1-methoxy-1-methylpentyl fragment |
| 73 | 1,2-dihydroxy-1-methylpentyl fragment |
| 74 | 1,2-dihydroxy-1-ethylpentyl fragment |
| 75 | 2-hydroxy-1-methoxy-1-methylpentyl fragment |

TABLE 4b-continued

| | |
|---|---|
| 76 | (structure: ethyl, OCH3, OH, CH3) |
| 77 | (structure: (H3C)2C(OH)-C(OH)(CH3)-) |
| 78 | (structure: (H3C)2C(OH)-C(OH)(CH3)-CH3) |
| 79 | (structure: (H3C)2C(OH)-C(OCH3)(CH3)-) |
| 80 | (structure: (H3C)2C(OH)-C(OCH3)(CH3)-CH3) |
| 81 | (structure with ethyl, OH, CH3, OH, ethyl) |
| 82 | (structure with CH3, ethyl, OH, CH3, OH, CH3) |
| 83 | (structure with CH3, ethyl, OCH3, CH3, OH, H3C) |
| 84 | (structure with H3C, ethyl, OCH3, CH3, OH, H3C) |

TABLE 4c

| | |
|---|---|
| 1 | H3C–CH(—)–CH3 |
| 2 | H3C–CH2–CH(—)–CH3 |
| 3 | CH3–CH2–CH2–CH(—)–CH3 |
| 4 | H3C–CH2–CH2–CH2–CH(—)–CH3 |
| 5 | CH2=CH–CH2–CH(—)–CH3 |
| 6 | CH2=CH–CH2–CH2–CH(—)–CH3 |
| 7 | CH2=CH–CH(—)–CH3 |
| 8 | CH2=C(CH3)–CH(—)–CH3 |
| 9 | CH3–CH=CH–CH(—)–CH3 (cis) |
| 10 | H3C–CH=CH–CH(—)–CH3 (trans) |
| 11 | CH3–CH=C(CH3)–CH(—)–CH3 |
| 12 | H3C–CH=C(CH3)–CH(—)–CH3 |
| 13 | CH2=C(CH2CH3)–CH(—)–CH3 |

TABLE 4c-continued

| | |
|---|---|
| 14 | CH₃ / H₃C–C=CH–CH(CH₃)– (2-methyl-2-butenyl branch) |
| 15 | (CH₃)(H₃C)C=C(CH₃)–CH(CH₃)– |
| 16 | CH₂=CH–CH₂–C(CH₃)₂–CH(CH₃)– |
| 17 | (H₃C)₂CH–CH(CH₃)– |
| 18 | (H₃C)₃C–CH(CH₃)– |
| 19 | cyclohexyl–CH(CH₃)– |
| 20 | cyclopentyl–CH(CH₃)– |
| 21 | CH₃CH₂–C(CH₃)₂–CH(CH₃)– |
| 22 | CH₃CH₂–CH(CH₃)–CH(CH₃)– (shown with lower CH₃) |
| 23 | CH₃CH₂–CH(CH₃)–CH(CH₃)– |

TABLE 4c-continued

| | |
|---|---|
| 24 | CH₂=CH–C(CH₃)₂–CH(CH₃)– |
| 25 | H₃C–CH(OH)–CH(CH₃)– |
| 26 | CH₃CH₂–CH(OH)–CH(CH₃)– |
| 27 | CH₃CH₂CH₂–CH(OH)–CH(CH₃)– |
| 28 | CH₂=CH–CH₂–CH(OH)–CH(CH₃)– |
| 29 | CH₃–CH₂–CH(OH)–CH(CH₃)– |
| 30 | CH₃–CH₂–CH(OH)–CH(CH₃)– |
| 31 | CH₃CH₂CH₂–CH(OH)–CH(CH₃)– |
| 32 | CH₂=CH–CH₂–CH(OH)–CH(CH₃)– |
| 33 | C₆H₅–CH₂–CH(CH₃)– |

TABLE 4c-continued

| | |
|---|---|
| 34 | HO-CH2-CH(OH)-CH(CH3)- |
| 35 | HO-CH2-CH(OH)-CH(CH3)- (diastereomer) |
| 36 | HO-CH2-C(CH3)2-CH(CH3)- |
| 37 | (CH3)2CH- |
| 38 | CH3CH2-CH(CH3)- |
| 39 | CH3CH2CH2-CH(CH3)- |
| 40 | CH3(CH2)3-CH(CH3)- |
| 41 | CH2=CH-CH2-CH(CH3)- |
| 42 | CH2=CH-CH2CH2-CH(CH3)- |
| 43 | CH2=CH-CH(CH3)- |
| 44 | CH2=C(CH3)-CH(CH3)- |
| 45 | cis-CH3-CH=CH-CH(CH3)- |

TABLE 4c-continued

| | |
|---|---|
| 46 | trans-CH3-CH=CH-CH(CH3)- |
| 47 | CH3-CH=C(CH3)-CH(CH3)- |
| 48 | CH3-CH=C(CH3)-CH(CH3)- (isomer) |
| 49 | CH2=C(CH2CH3)-CH(CH3)- |
| 50 | (CH3)2C=CH-CH(CH3)- |
| 51 | (CH3)2C=C(CH3)-CH(CH3)- |
| 52 | CH2=CH-CH2-C(CH3)2-CH(CH3)- |
| 53 | (CH3)2CH-CH(CH3)- |
| 54 | (CH3)3C-CH(CH3)- |
| 55 | cyclohexyl-CH(CH3)- |

TABLE 4c-continued

| # | Structure |
|---|---|
| 56 | cyclopentyl-CH(CH₃)- |
| 57 | (CH₃CH₂)(CH₃)₂C-CH(CH₃)- |
| 58 | CH₃CH₂-CH(CH₃)- attached, with CH₃ (wedge down) |
| 59 | CH₃CH₂-CH(CH₃)- attached, with CH₃ (dashed) |
| 60 | CH₂=CH-C(CH₃)₂-CH(CH₃)- |
| 61 | CH₃-CH(OH)-CH(CH₃)- |
| 62 | CH₃CH₂-CH(OH)-CH(CH₃)- |
| 63 | CH₃CH₂CH₂-CH(OH)-CH(CH₃)- |
| 64 | CH₂=CH-CH₂-CH(OH)-CH(CH₃)- |
| 65 | CH₃CH₂-CH(OH)-CH(CH₃)- |
| 66 | CH₃CH₂-CH(OH)-CH(CH₃)- |
| 67 | CH₃CH₂CH₂-CH(OH)-CH(CH₃)- |
| 68 | CH₂=CH-CH₂-CH(OH)-CH(CH₃)- |
| 69 | PhCH₂-CH(CH₃)- |
| 70 | HOCH₂-CH(OH)-CH(CH₃)- |
| 71 | HOCH₂-CH(OH)-CH(CH₃)- |
| 72 | HOCH₂-C(CH₃)₂-CH(CH₃)- |
| 73 | (CH₃)₂CH-CH(CH₂CH₃)- |
| 74 | (CH₃CH₂)₂CH- |
| 75 | CH₃CH₂CH₂-CH(CH₂CH₃)- |
| 76 | CH₃CH₂CH₂CH₂-CH(CH₂CH₃)- |
| 77 | CH₂=CH-CH₂-CH(CH₂CH₃)- |

TABLE 4c-continued
| | | | | |
|---|---|---|---|---|
| 78 | 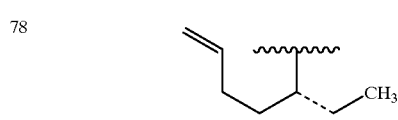 | 5 | 89 | 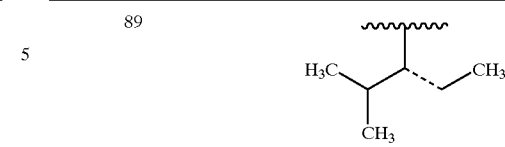 |
| 79 | 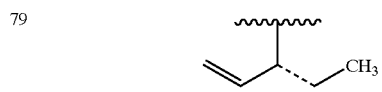 | 10 | 90 | 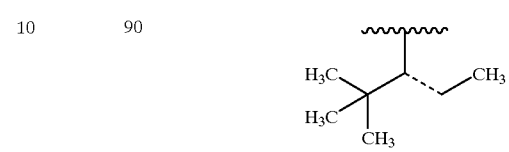 |
| 80 | 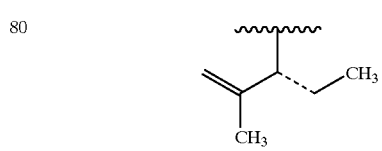 | 15 | 91 |  |
| 81 | 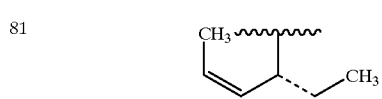 | 20 | 92 |  |
| 82 | 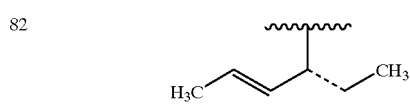 | 25 | 93 |  |
| 83 | 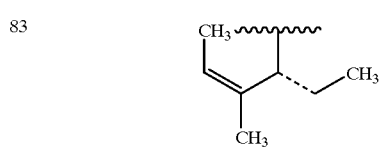 | 30 | 94 |  |
| 84 | 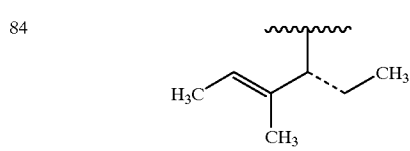 | 35 | 95 |  |
| 85 | 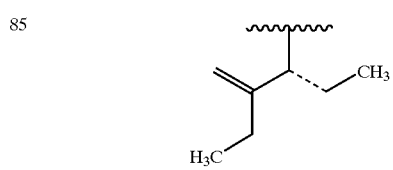 | 40 | 96 | 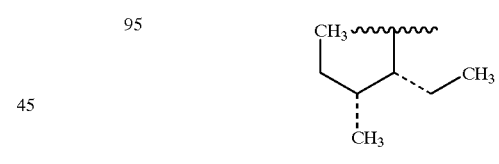 |
| 86 | 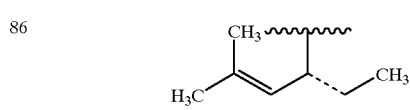 | 45 | 97 |  |
| 87 | 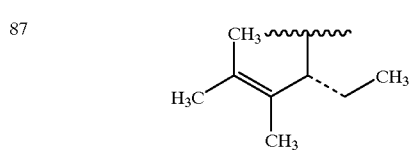 | 50 | 98 | 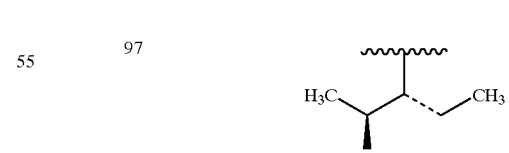 |
| 88 | 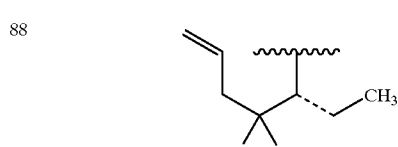 | 55 | | |

TABLE 4c-continued

TABLE 4c-continued

TABLE 4c-continued
| | | |
|---|---|---|
| 141 | 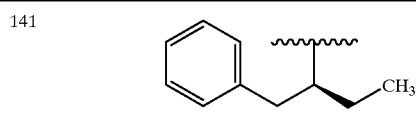 | |
| 142 | 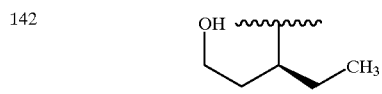 | |
| 143 | 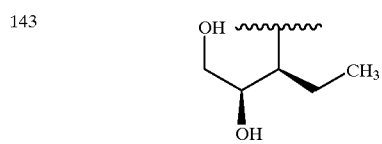 | |
| 144 | 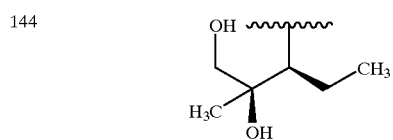 | |
| 145 | 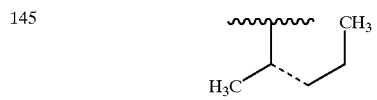 | |
| 146 | 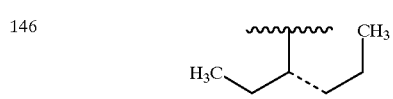 | |
| 147 | 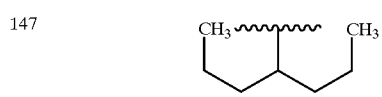 | |
| 148 | 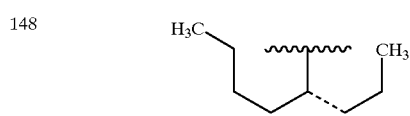 | |
| 149 | 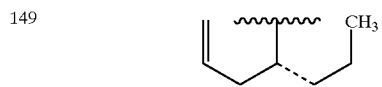 | |
| 150 | 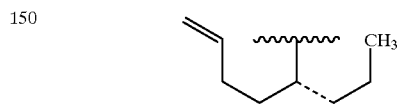 | |
| 150A | 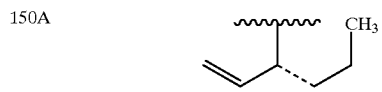 | |
| 150B | 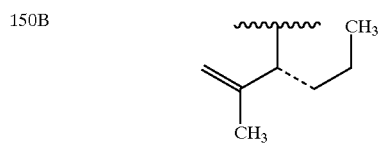 | |
| 151 | 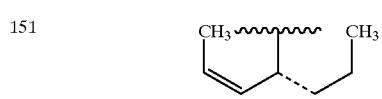 | |
TABLE 4c-continued
| | | |
|---|---|---|
| 152 | 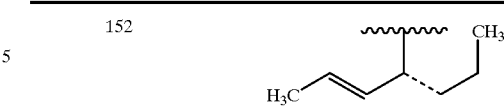 | |
| 153 | 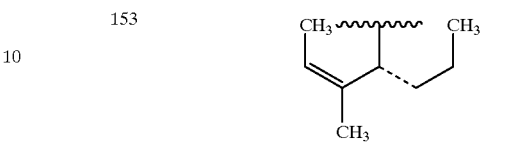 | |
| 154 | 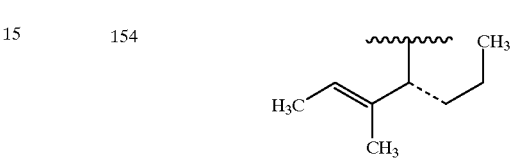 | |
| 155 |  | |
| 156 | 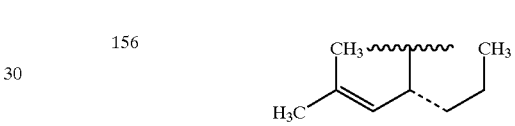 | |
| 157 | 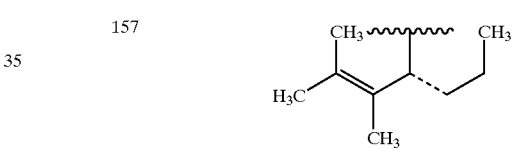 | |
| 158 | 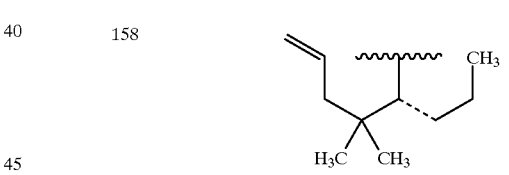 | |
| 159 | 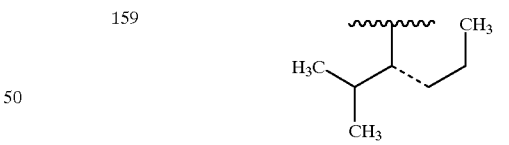 | |
| 160 | 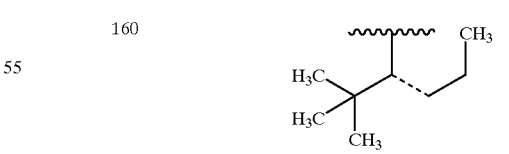 | |
| 161 | 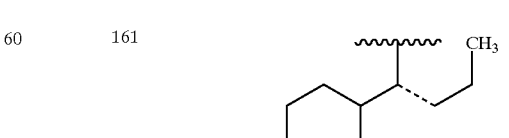 | |

TABLE 4c-continued

TABLE 4c-continued
| | | |
|---|---|---|
| 184 | 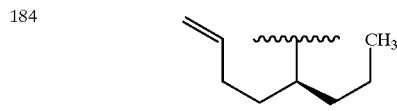 | |
| 185 | 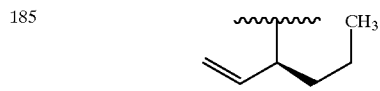 | |
| 186 | 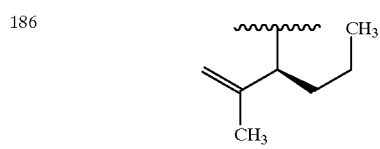 | |
| 187 | 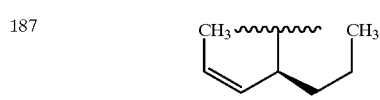 | |
| 188 | 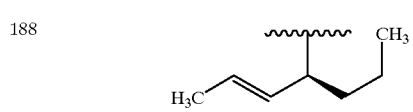 | |
| 189 | 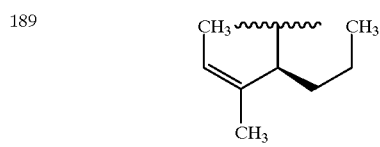 | |
| 190 | 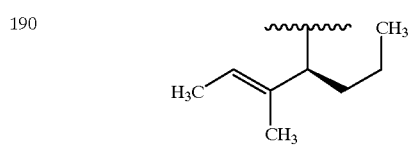 | |
| 191 | 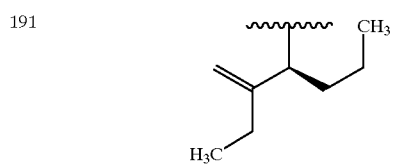 | |
| 192 | 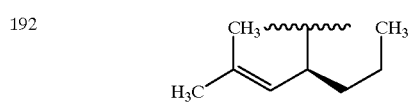 | |
| 193 | 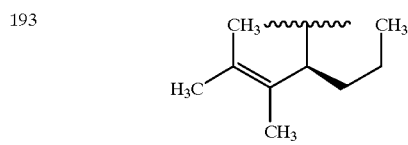 | |
| 194 | 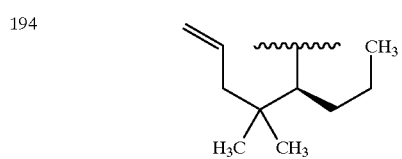 | |
TABLE 4c-continued
| | | |
|---|---|---|
| 195 | 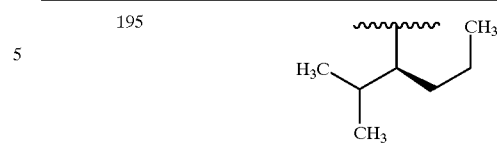 | |
| 196 | 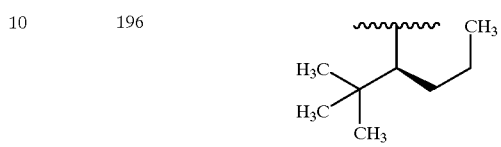 | |
| 197 | 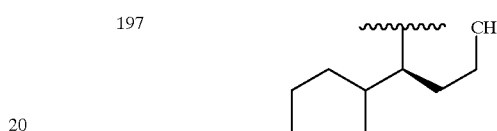 | |
| 198 | 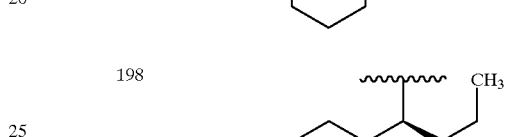 | |
| 199 |  | |
| 200 | 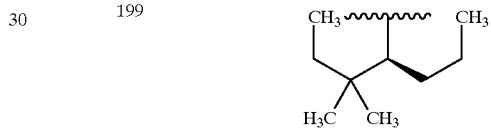 | |
| 201 | 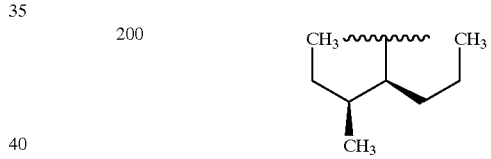 | |
| 202 | 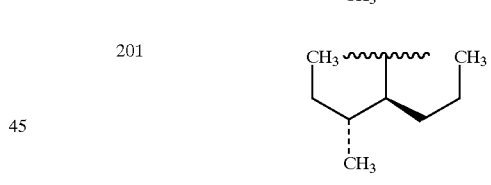 | |
| 203 |  | |
| 204 | 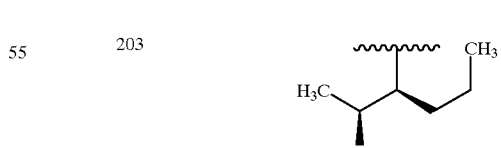 | |

TABLE 4c-continued

| | |
|---|---|
| 205 | (structure) |
| 206 | (structure) |
| 207 | (structure) |
| 208 | (structure) |
| 209 | (structure) |
| 210 | (structure) |
| 211 | (structure) |
| 212 | (structure) |
| 213 | (structure) |
| 214 | (structure) |

TABLE 4c-continued

| | |
|---|---|
| 215 | (structure) |
| 216 | (structure) |
| 217 | (structure) |
| 218 | (structure) |
| 219 | (structure) |
| 220 | (structure) |
| 221 | (structure) |
| 222 | (structure) |
| 223 | (structure) |
| 224 | (structure) |
| 225 | (structure) |
| 226 | (structure) |
| 227 | (structure) |

TABLE 4c-continued
| | | | | |
|---|---|---|---|---|
| 228 | 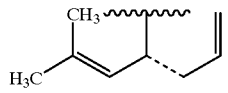 | | 238 | 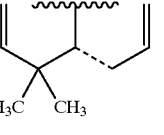 |
| 229 | 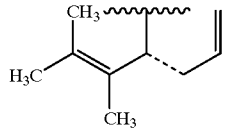 | | 239 | 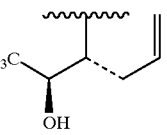 |
| 230 | 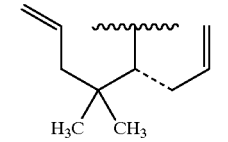 | | 240 | 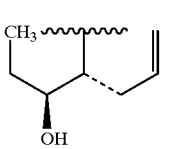 |
| 231 | 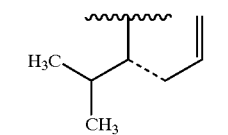 | | 241 | 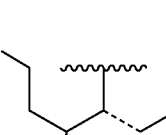 |
| 232 | 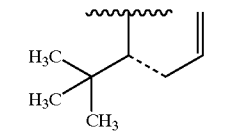 | | 242 | 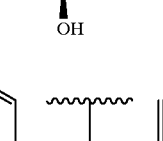 |
| 233 | 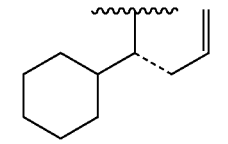 | | 243 | 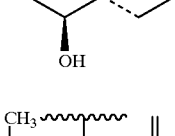 |
| 234 | 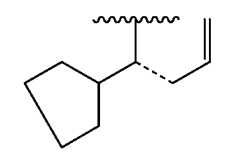 | | 244 | 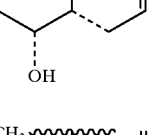 |
| 235 | 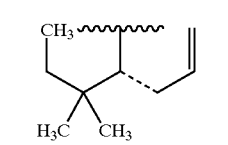 | | 245 | 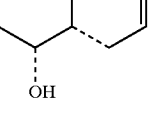 |
| 236 | 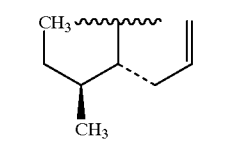 | | 246 | 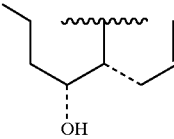 |
| 237 | 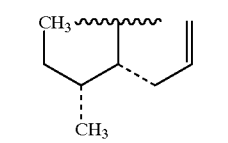 | | 247 | 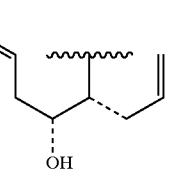 |

TABLE 4c-continued

| | |
|---|---|
| 248 | (structure: CH2OH-CH(OH)-CH(~)-CH2-CH=CH2) |
| 249 | (structure: CH2OH-CH(OH)-CH(~)-CH2-CH=CH2) |
| 250 | (structure: CH2OH-C(CH3)(OH)-CH(~)-CH2-CH=CH2) |
| 251 | (structure: CH3-CH(~)-CH2-CH=CH2) |
| 252 | (structure: CH3CH2-CH(~)-CH2-CH=CH2) |
| 253 | (structure: CH3CH2CH2-CH(~)-CH2-CH=CH2) |
| 254 | (structure: CH3CH2CH2CH2-CH(~)-CH2-CH=CH2) |
| 255 | (structure: CH2=CH-CH2-CH(~)-CH2-CH=CH2) |
| 256 | (structure: CH2=CH-CH2-CH2-CH(~)-CH2-CH=CH2) |
| 257 | (structure: CH2=CH-CH(~)-CH2-CH=CH2) |
| 258 | (structure: CH2=C(CH3)-CH(~)-CH2-CH=CH2) |
| 259 | (structure: cis CH3-CH=CH-CH(~)-CH2-CH=CH2) |
| 260 | (structure: trans CH3-CH=CH-CH(~)-CH2-CH=CH2) |

TABLE 4c-continued

| | |
|---|---|
| 261 | (structure: CH3-CH=C(CH3)-CH(~)-CH2-CH=CH2) |
| 262 | (structure: CH3CH=C(CH3)-CH(~)-CH2-CH=CH2) |
| 263 | (structure: CH2=C(CH2CH3)-CH(~)-CH2-CH=CH2) |
| 264 | (structure: (CH3)2C=CH-CH(~)-CH2-CH=CH2) |
| 265 | (structure: (CH3)2C=C(CH3)-CH(~)-CH2-CH=CH2) |
| 266 | (structure: CH2=CH-CH2-C(CH3)2-CH(~)-CH2-CH=CH2) |
| 267 | (structure: (CH3)2CH-CH(~)-CH2-CH=CH2) |
| 268 | (structure: (CH3)3C-CH(~)-CH2-CH=CH2) |
| 269 | (structure: cyclohexyl-CH(~)-CH2-CH=CH2) |
| 270 | (structure: cyclopentyl-CH(~)-CH2-CH=CH2) |

TABLE 4c-continued
| | | |
|---|---|---|
| 271 | 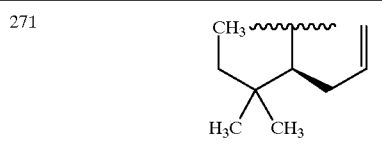 | |
| 272 | 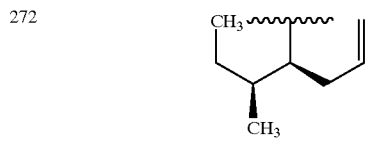 | |
| 273 | 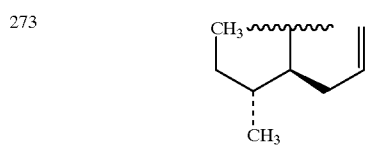 | |
| 274 | 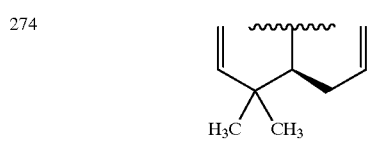 | |
| 275 | 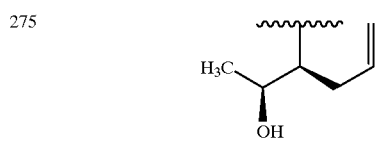 | |
| 276 | 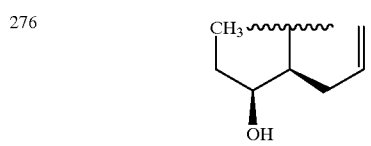 | |
| 277 | 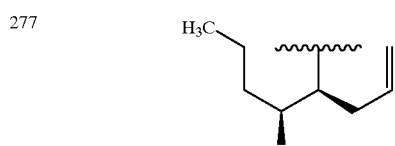 | |
| 278 | 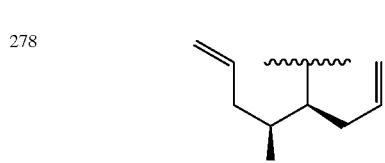 | |
| 279 | 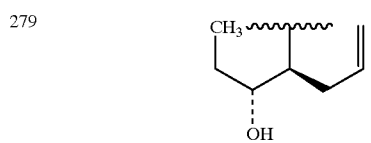 | |
| 280 | 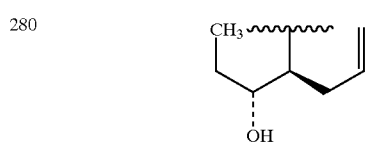 | |
TABLE 4c-continued
| | | |
|---|---|---|
| 281 | 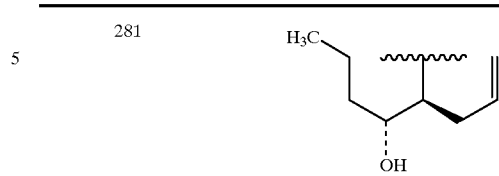 | |
| 282 | 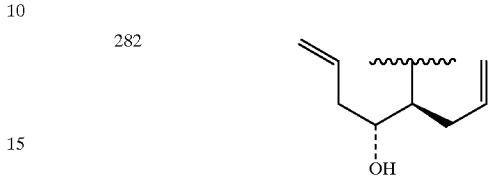 | |
| 283 | 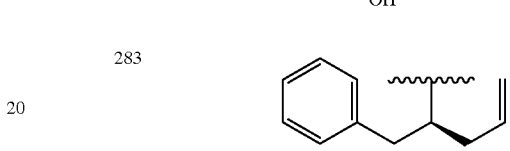 | |
| 284 |  | |
| 285 |  | |
| 286 |  | |
| 287 |  | |
| 288 |  | |
| 289 |  | |
| 290 |  | |
| 291 |  | |

TABLE 4c-continued
| | |
|---|---|
| 292 | 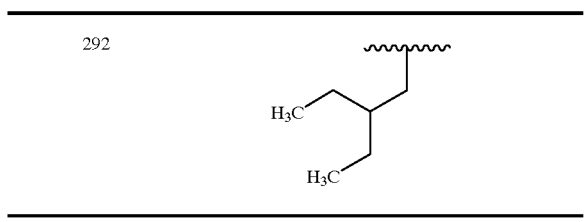 |
TABLE 4d
| | |
|---|---|
| 1 | 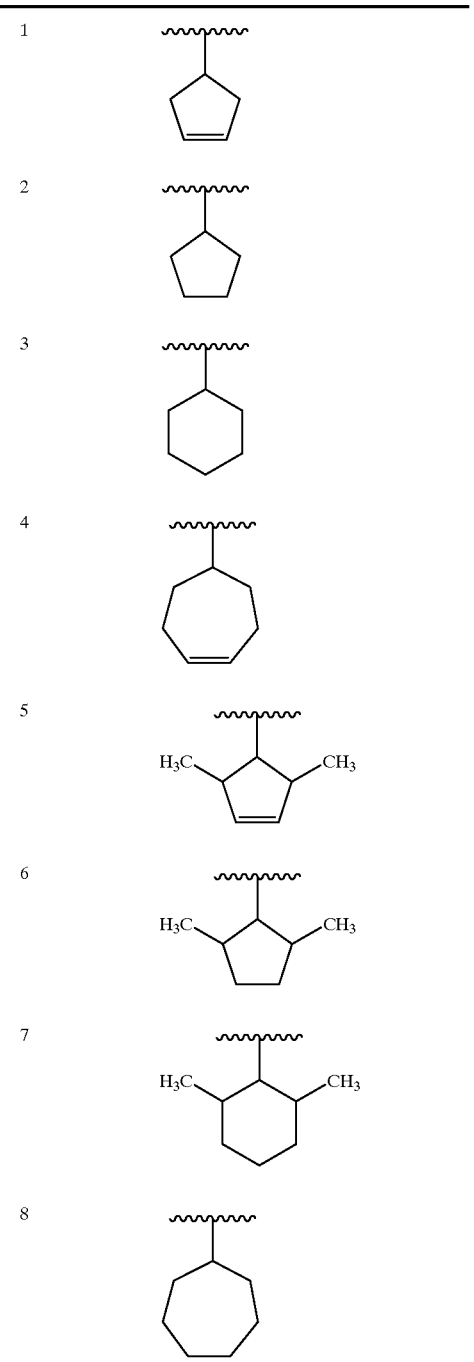 |
| 2 | |
| 3 | |
| 4 | |
| 5 | |
| 6 | |
| 7 | |
| 8 | |
TABLE 4d-continued
| | |
|---|---|
| 9 | 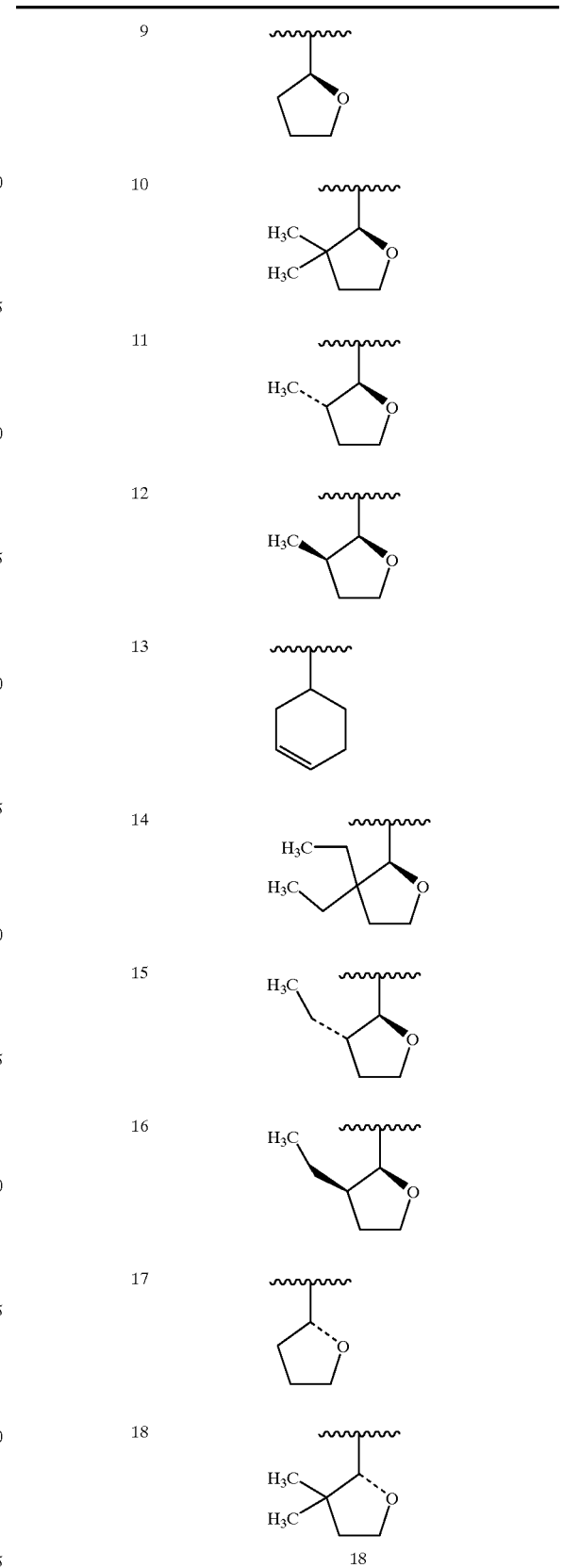 |
| 10 | |
| 11 | |
| 12 | |
| 13 | |
| 14 | |
| 15 | |
| 16 | |
| 17 | |
| 18 | |

TABLE 4d-continued
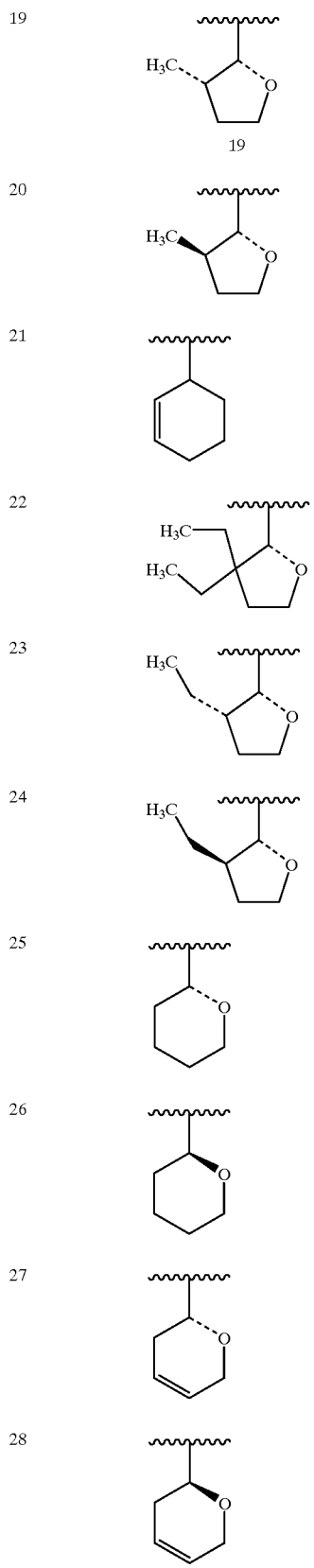
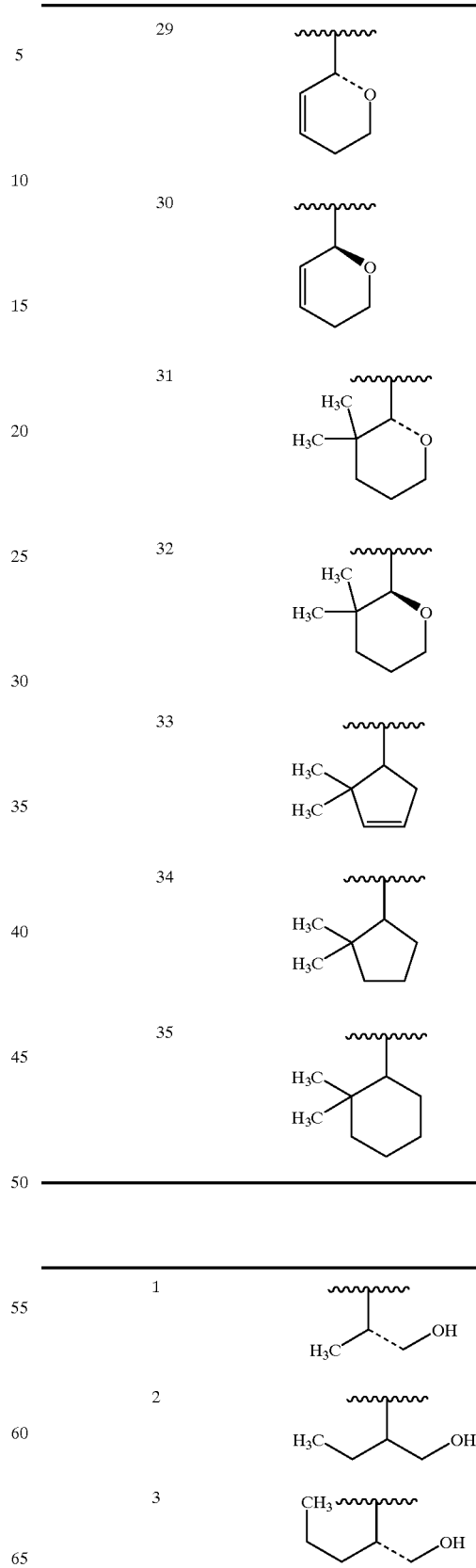

-continued
4 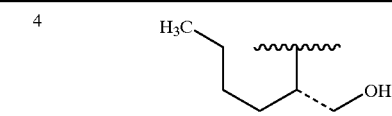
5 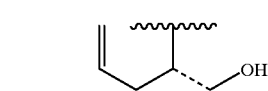
6 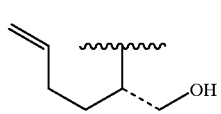
7 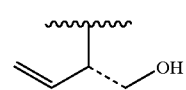
8 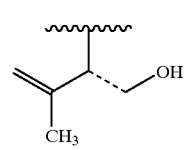
9 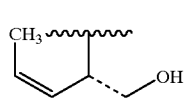
10 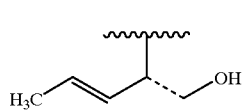
11 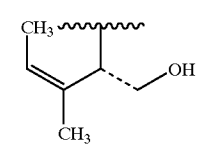
12 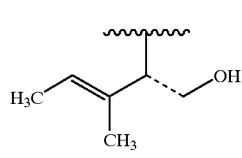
13 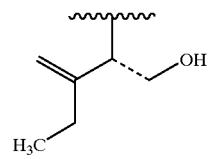
14 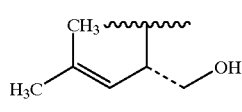
15 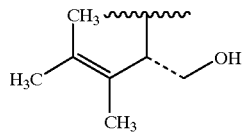
-continued
16 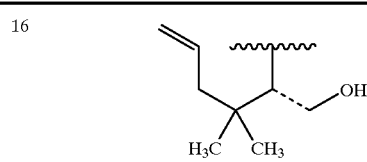
17 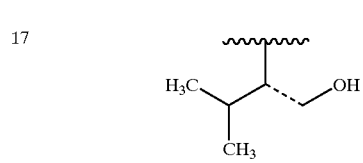
18 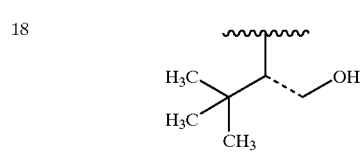
19 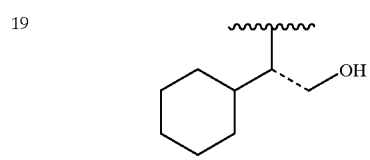
20 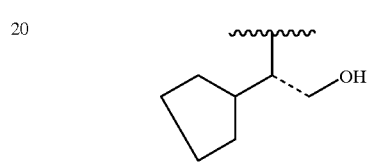
21 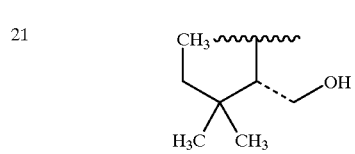
22 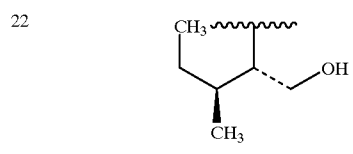
23 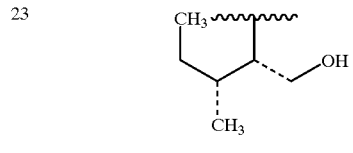
24 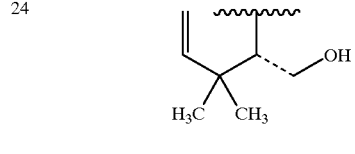
25 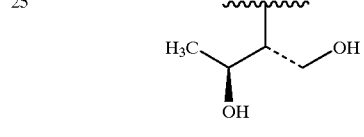

-continued
| | | |
|---|---|---|
| 26 | 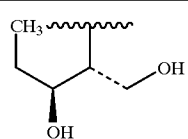 | 5 |
| 27 | 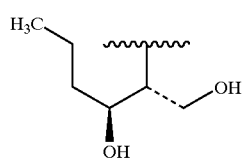 | 10 |
| 28 | 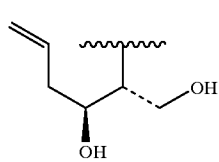 | 15 |
| 29 | 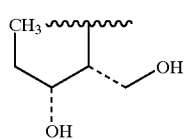 | 20 |
| 30 | 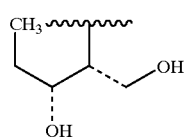 | 25 |
| 31 | 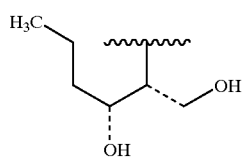 | 30 |
| 32 | 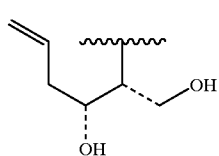 | 35 |
| 33 | 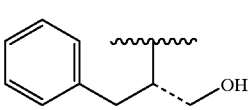 | 40 |
| 34 | 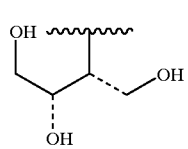 | 45 |
| 35 | 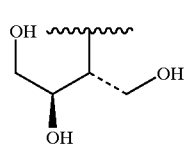 | 50 |
-continued
| | | |
|---|---|---|
| 36 | 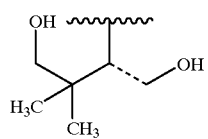 | |
| 37 | 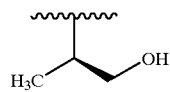 | |
| 38 | 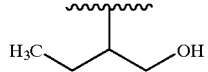 | |
| 39 | 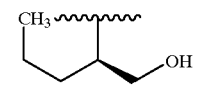 | |
| 40 | 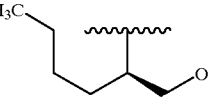 | |
| 41 | 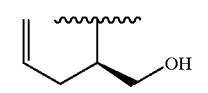 | |
| 42 | 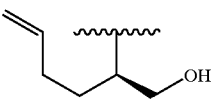 | |
| 43 | 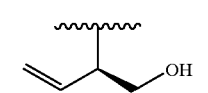 | |
| 44 | 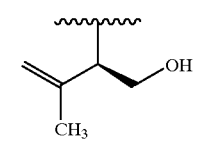 | |
| 45 | 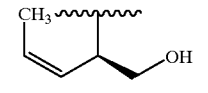 | |
| 46 | 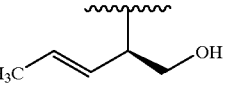 | |
| 47 | 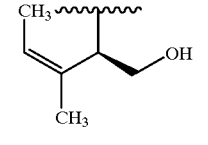 | |
| 48 | 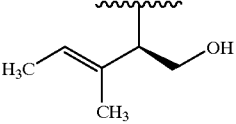 | |

| | |
|---|---|
| 49 | 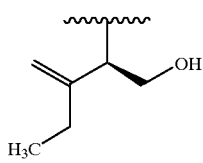 |
| 50 | 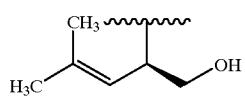 |
| 51 | 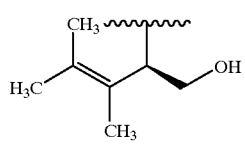 |
| 52 | 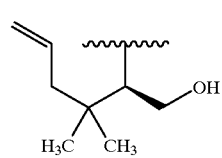 |
| 53 | 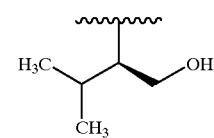 |
| 54 | 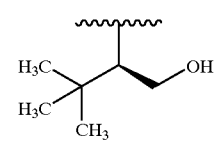 |
| 55 | 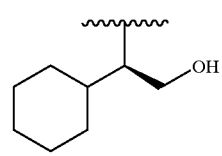 |
| 56 | 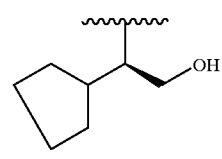 |
| 57 | 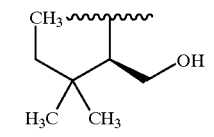 |
| 58 | 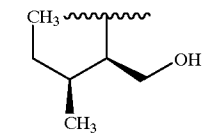 |
| | |
|---|---|
| 59 | 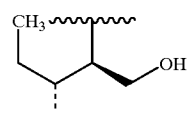 |
| 60 | 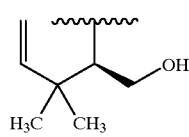 |
| 61 | 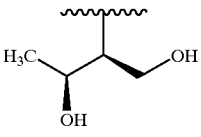 |
| 62 | 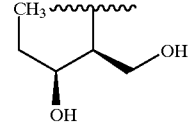 |
| 63 | 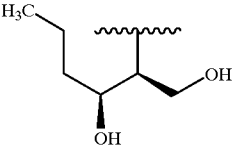 |
| 64 | 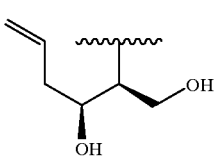 |
| 65 | 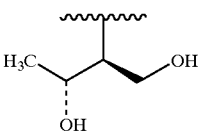 |
| 66 | 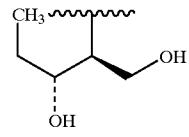 |
| 67 | 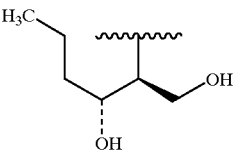 |

-continued
| | | | |
|---|---|---|---|
| 68 | 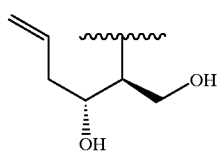 | 72 | 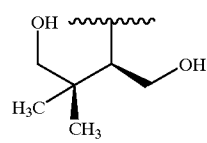 |
| 69 | 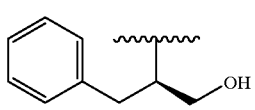 | 73 |  |
| 70 | 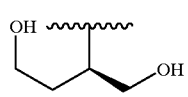 | 74 | 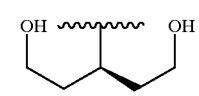 |
| 71 | 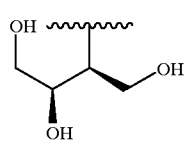 | 75 |  |
TABLE 4f
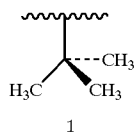
1
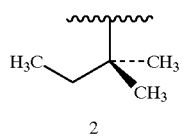
2
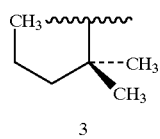
3
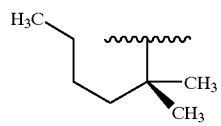
4
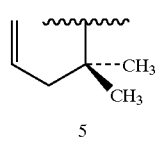
5
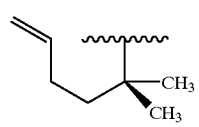
6
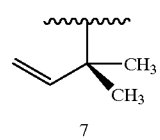
7
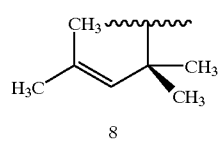
8
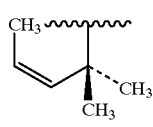
9
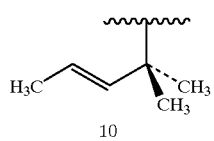
10
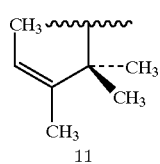
11
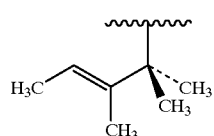
12
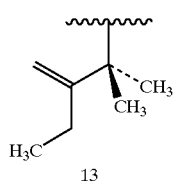
13
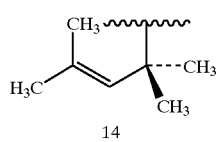
14
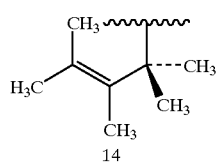
14
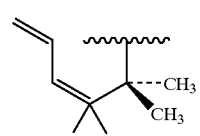
16

TABLE 4f-continued
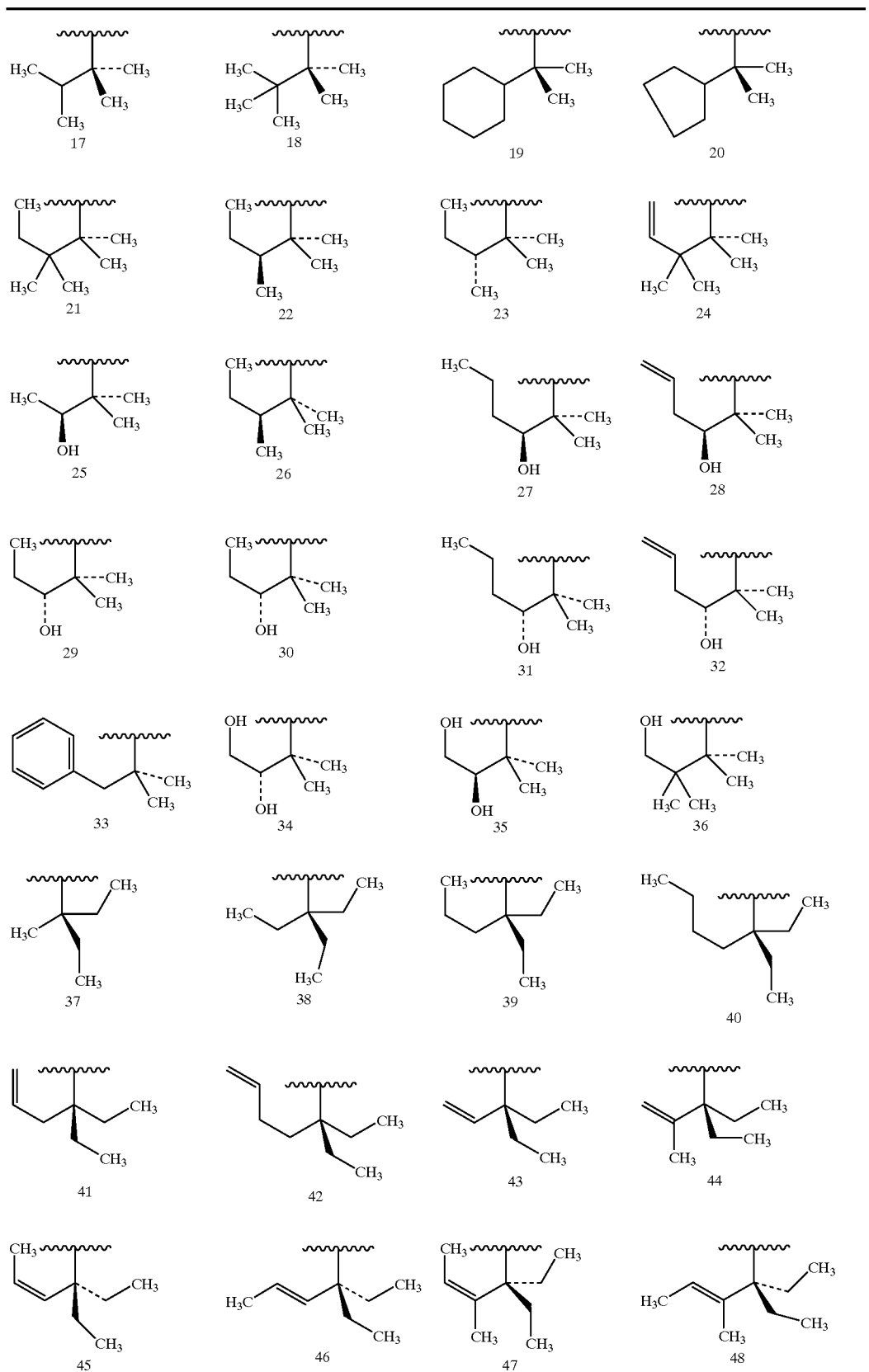

TABLE 4f-continued
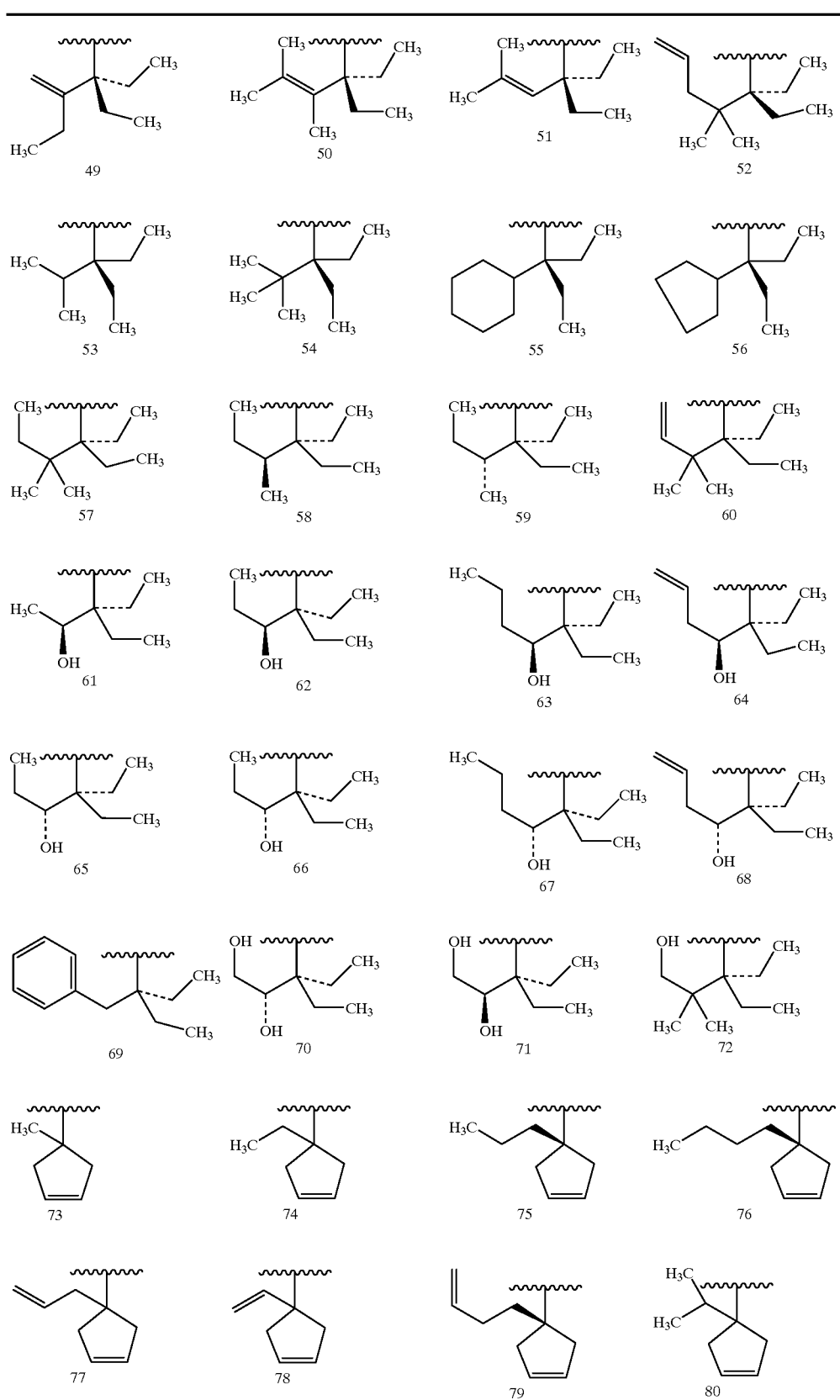

TABLE 4f-continued
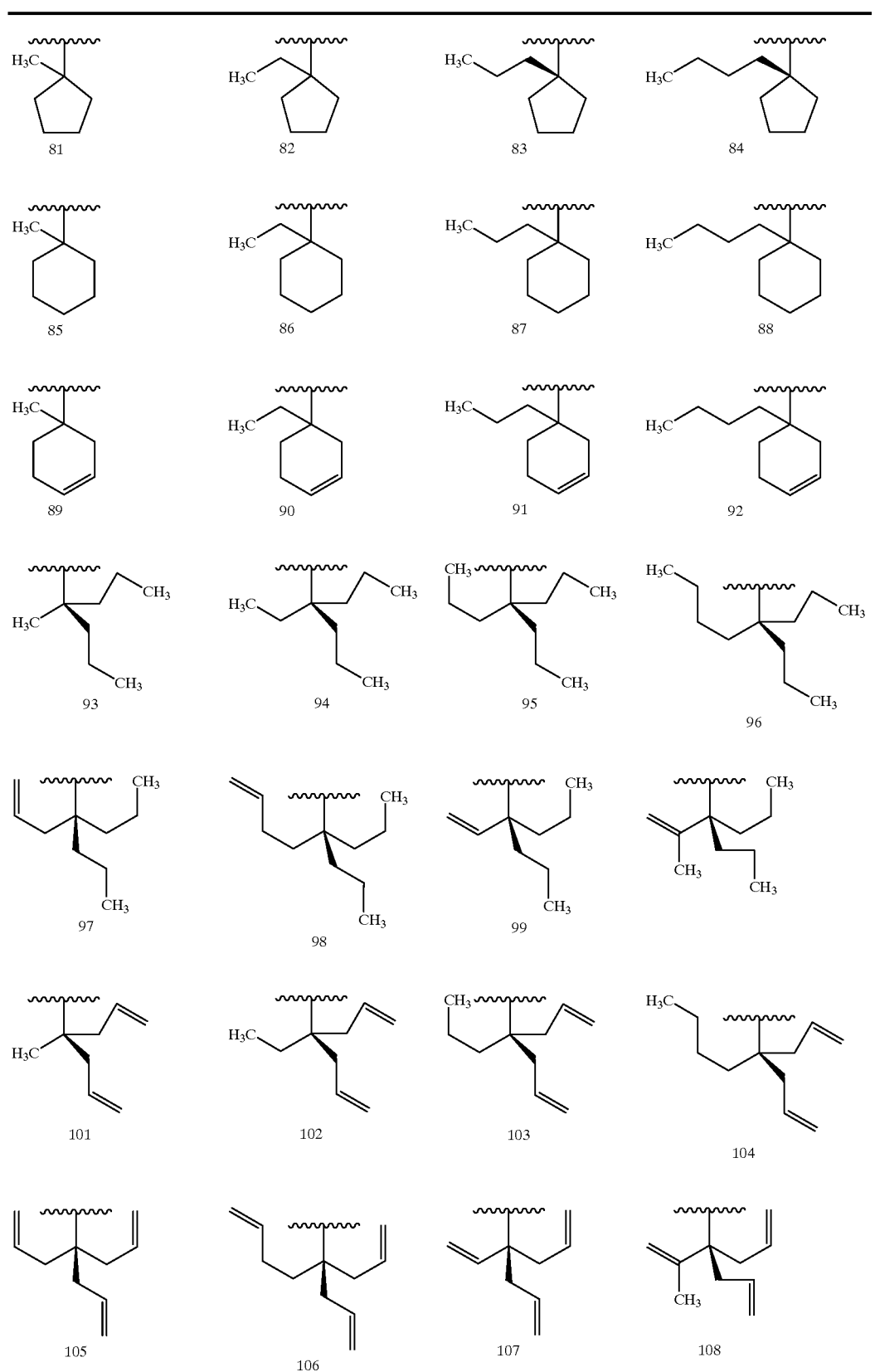

TABLE 4f-continued
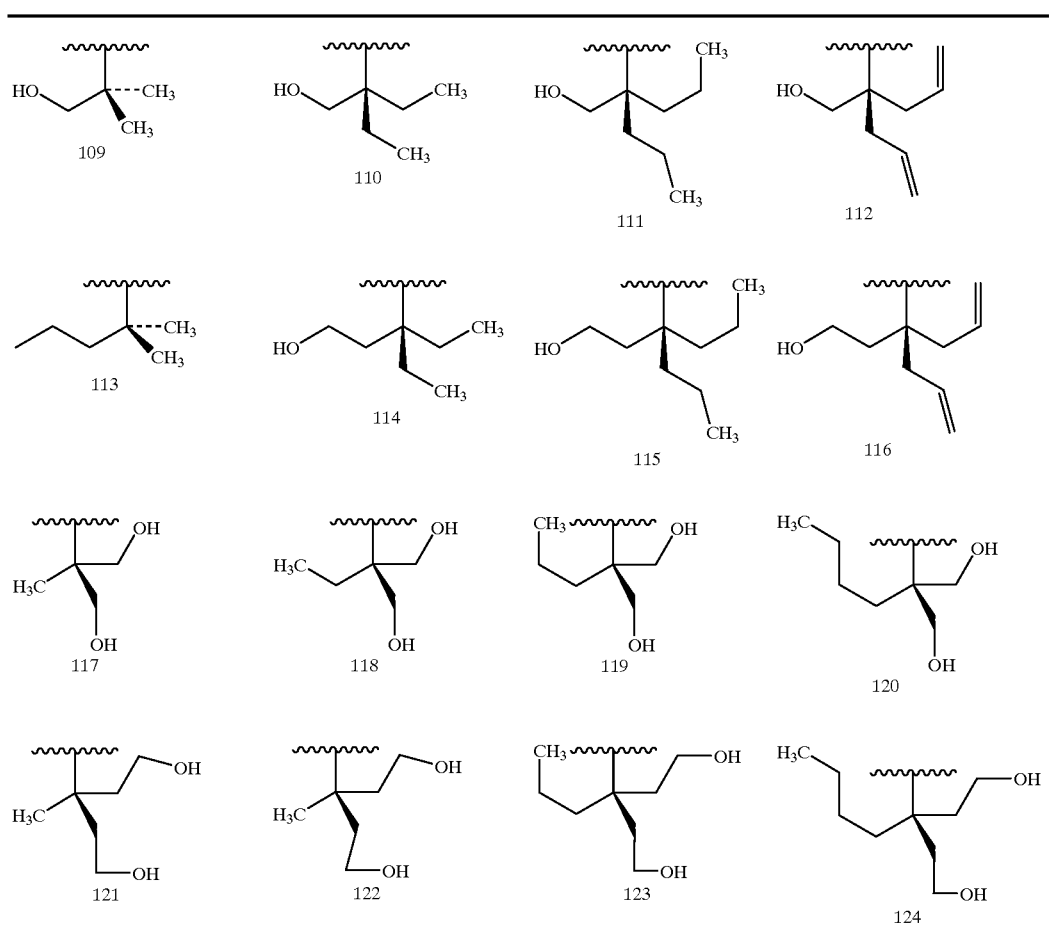
TABLE 4g
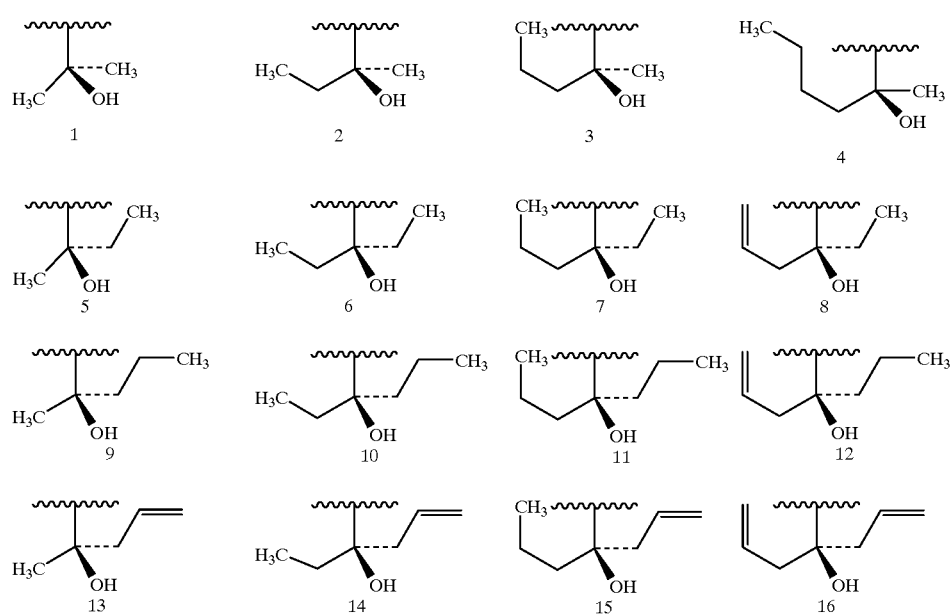

TABLE 4g-continued
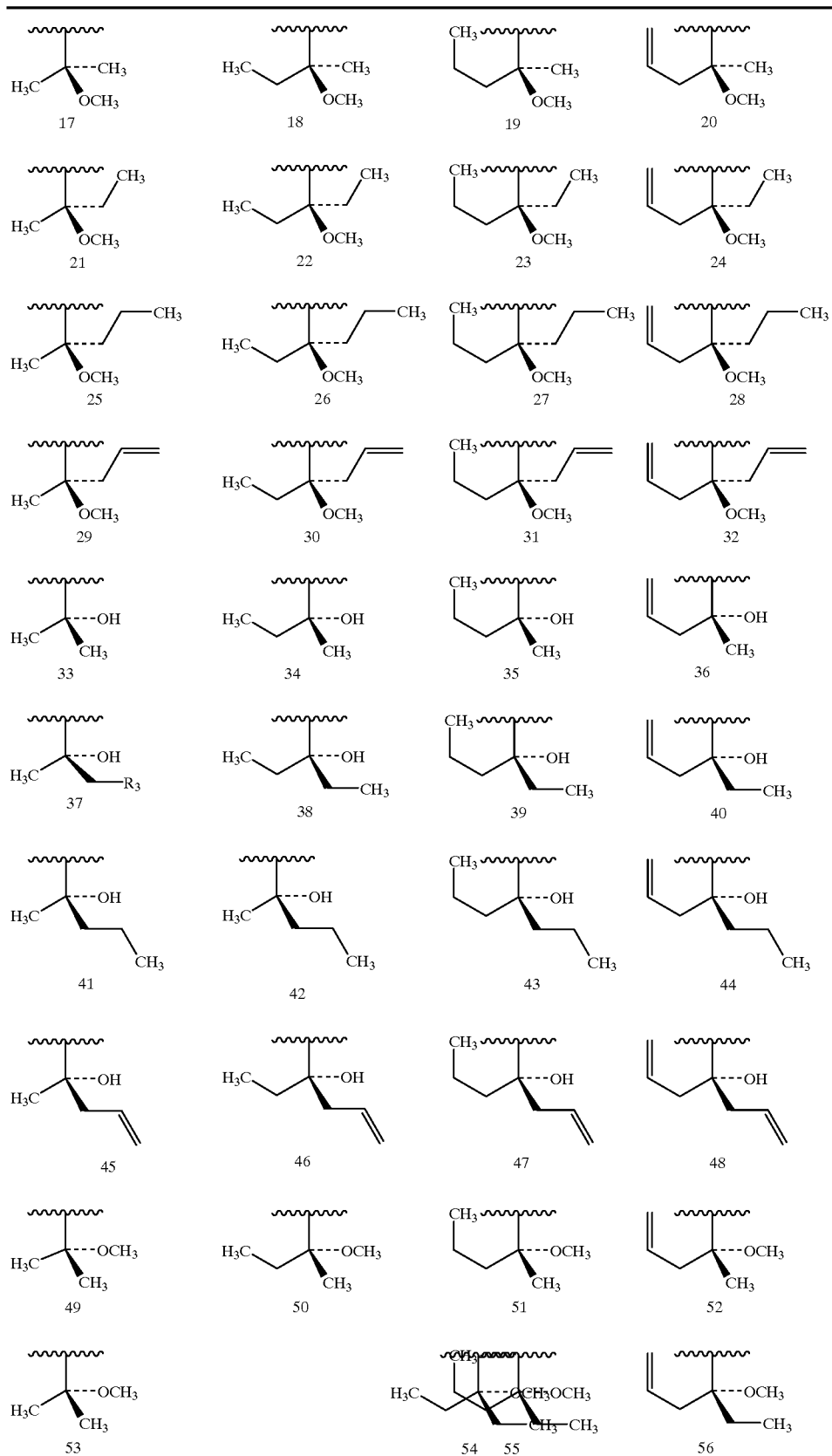

TABLE 4g-continued
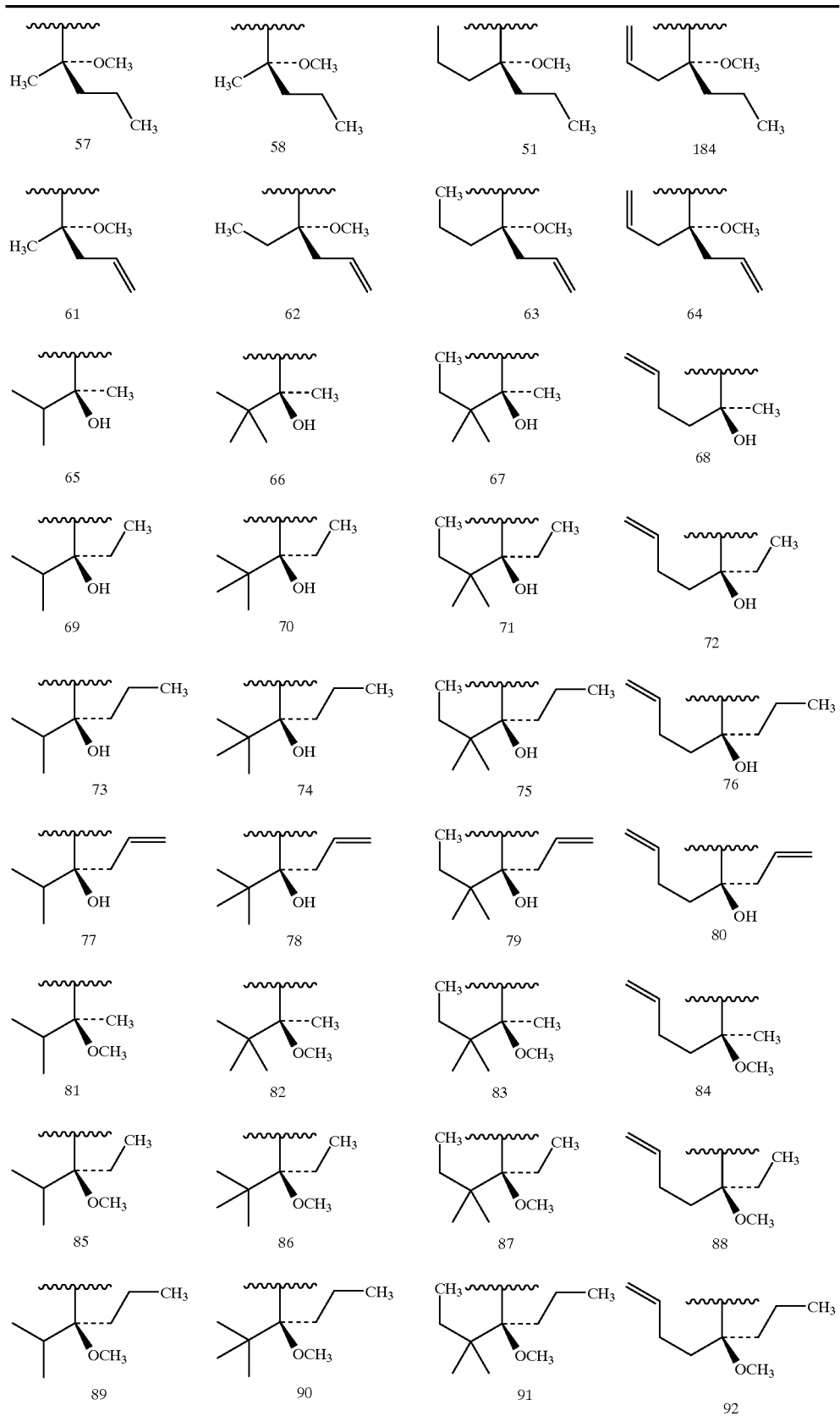

TABLE 4g-continued
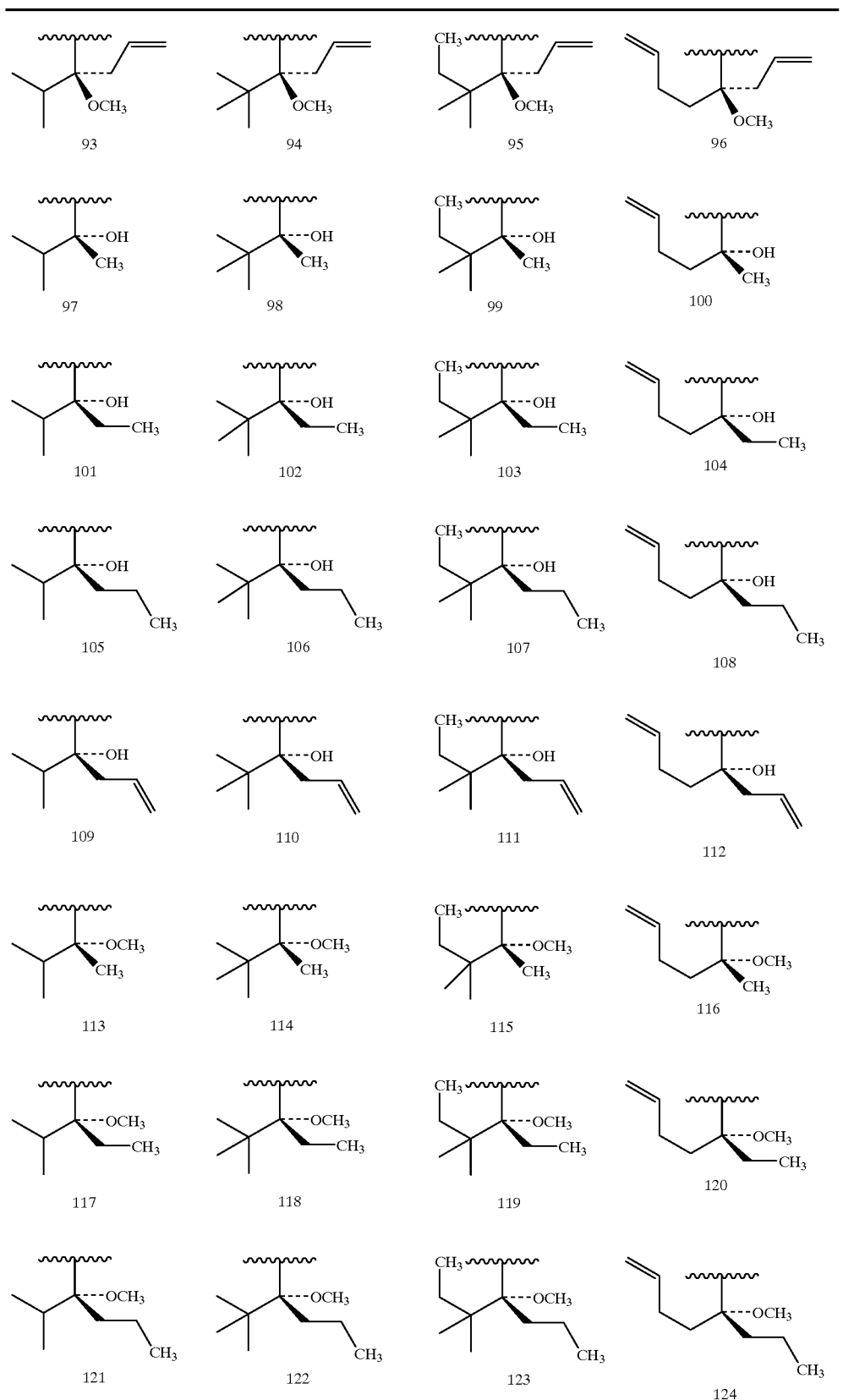

TABLE 4g-continued
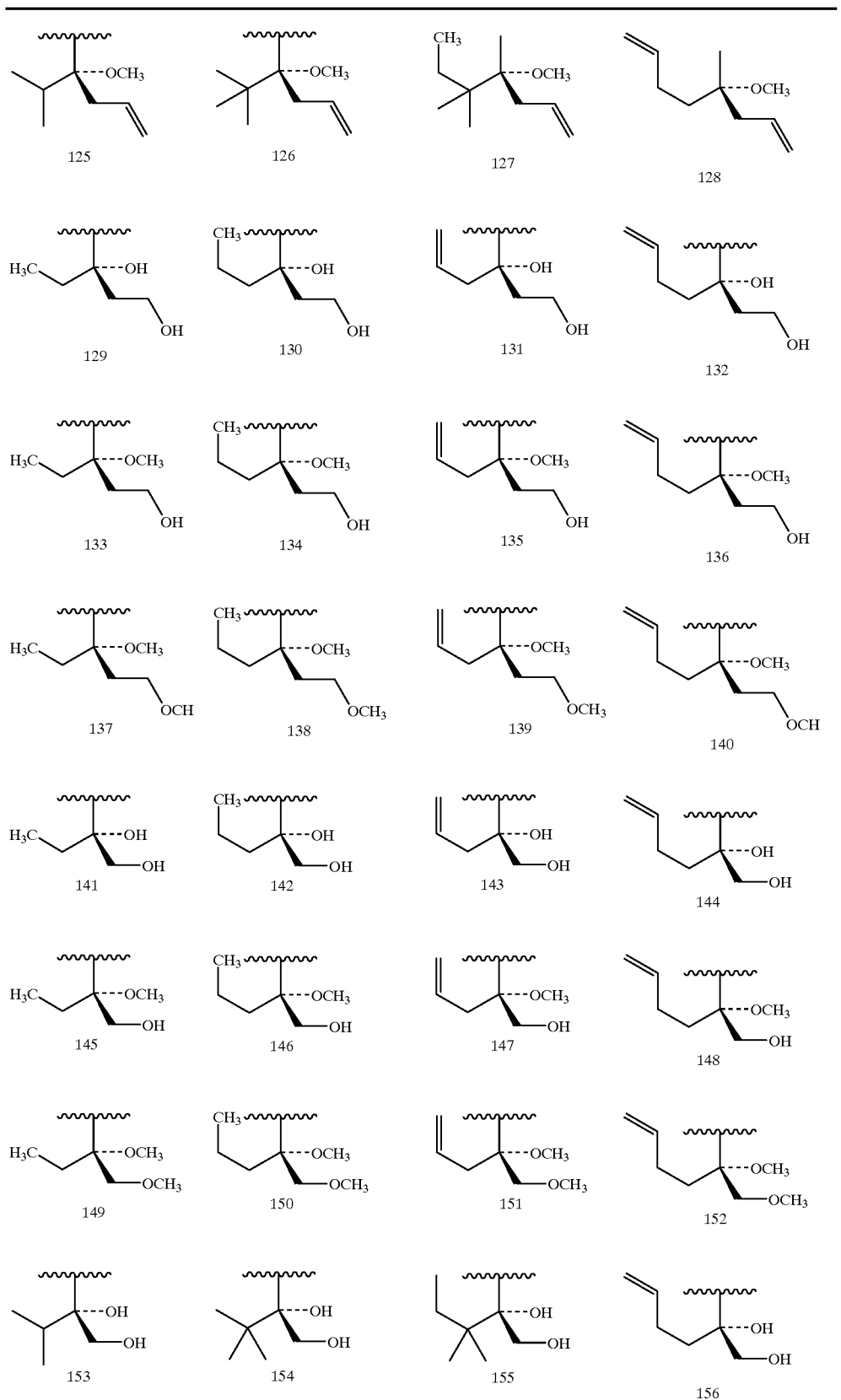

TABLE 4g-continued
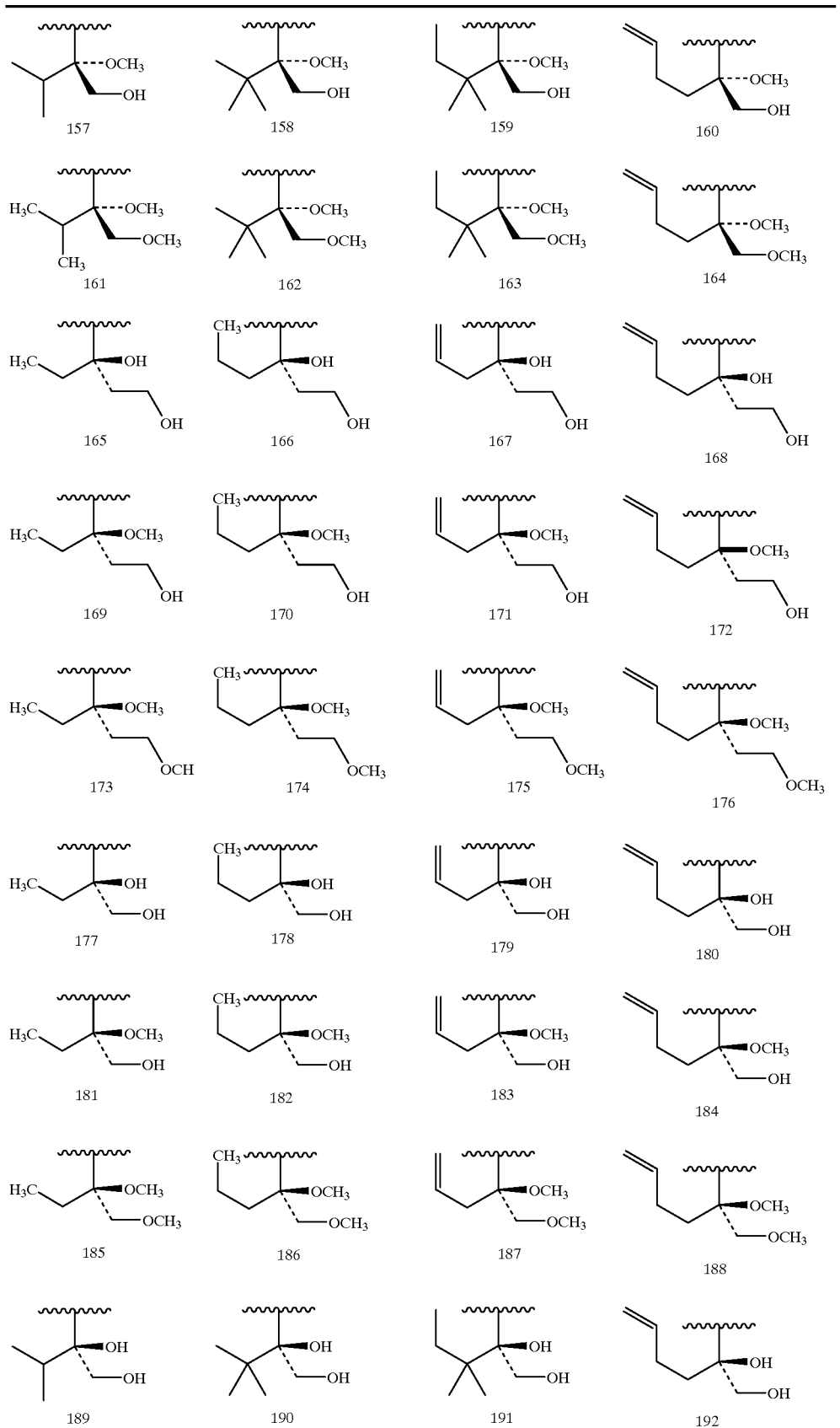

TABLE 4g-continued
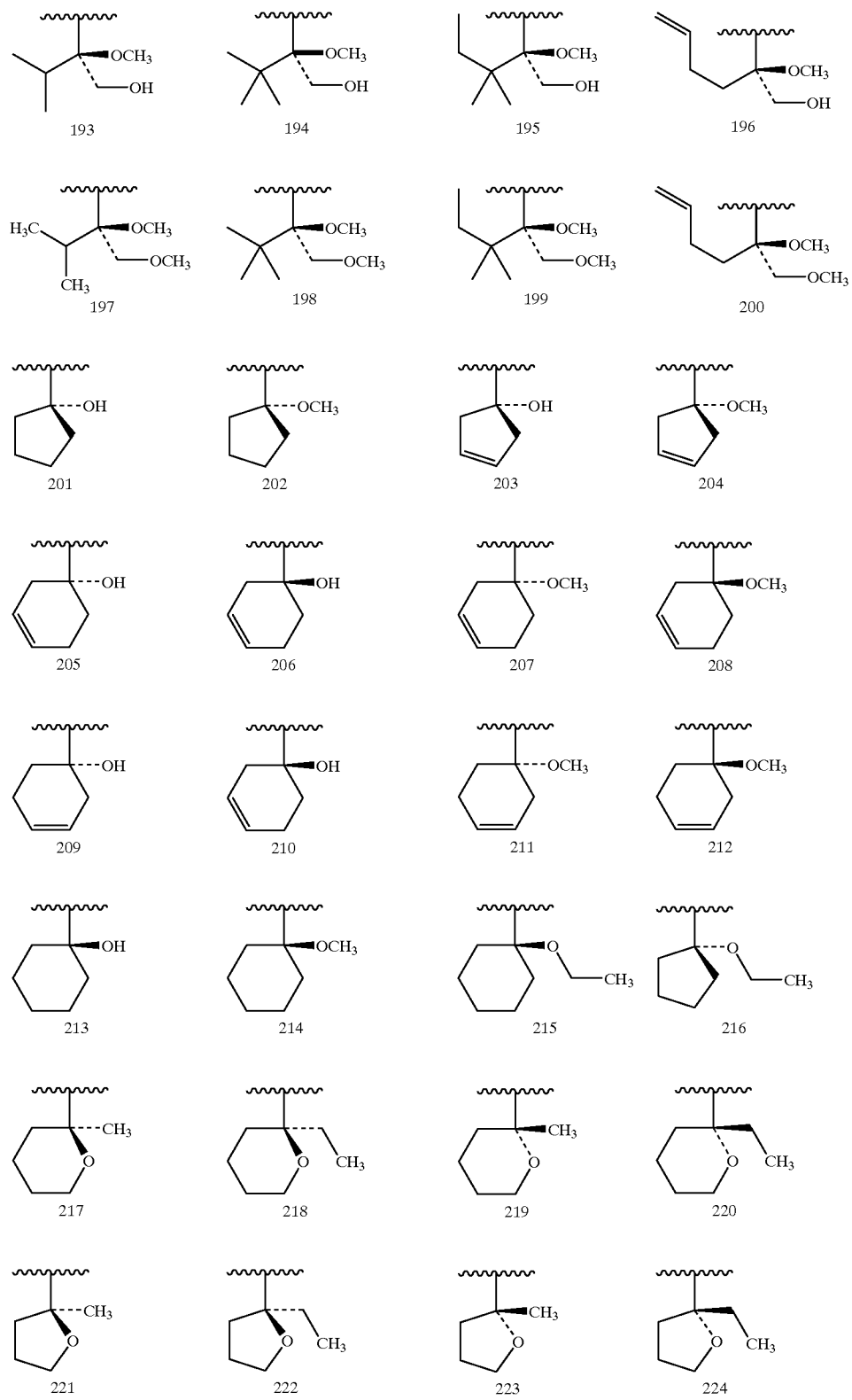

TABLE 4h

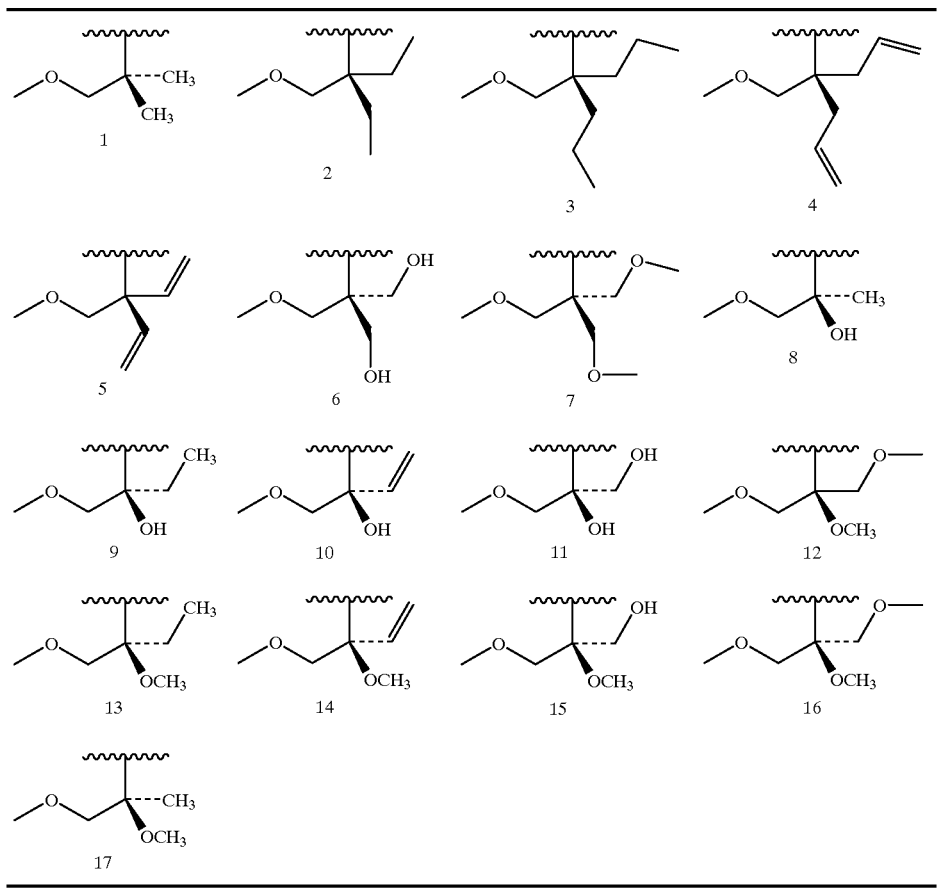

The ability of the compounds of the invention to inhibit neuraminidase in vitro can be determined according to the method described below.

Neuraminidase Inhibition Assay

Influenza virus A/N1/PR/8/34 was grown in the allantoic cavity of fertilized eggs and purified by sucrose density gradient centrifugation (Laver, W. G. (1969) in "Fundamental Techniques in Virology" (K. Habel and N. P. Salzman, eds.) pp. 92–86, Academic Press, New York). Influenza virus A/N2/Tokyo/3/67 was obtained from the tissue culture supernatents of virus grown on MDCK cells. Neuraminidase from B/Memphis/3/89 virus was prepared by digestion of the virus with TPCK-trypsin followed by centrifugation and then purification of the neuraminidase catalytic fragment using sucrose density gradient centrifugation and dialysis as described previously (Air, G. M., Laver, W. G., Luo, M., Stray, S. J., Legrone, G., and Webster, R. G. (1990) Virology 177, 578–587).

The neuraminidase inhibition assays used the neuraminidase enzymatic activity associated with the A/N1/PR/8/34 or A/N2/Tokyo/3/67 whole virus, or the B/Memphis/3/89 catalytic head fragment. The whole virus or catalytic fragment was diluted appropriately with 20 mM N-ethylmorpholine, 10 mM calcium choride, pH 7.5 buffer on the day of the experiment. Neuraminidase inhibition assays were conducted in 20 mM N-ethylmorpholine, 10 mM calcium choride, pH 7.5 buffer with 5% DMSO. Reaction mixtures included neuraminidase, inhibitor (test compound) and 20–30 $\mu$M 4-methylumbelliferyl sialic acid substrate in a total volume of 200 $\mu$L and were contained in white 96-well U-shaped plates. Typically, five to eight concentrations of inhibitor were used for each Ki value measurement. The reactions were initiated by the addition of enzyme and allowed to proceed for 30–60 minutes at room temperature. The fluorescence for each well of the plate was measured once each minute during the reaction period by a Fluoroskan II plate reader (ICN Biomedical) equipped with excitation and emission filters of 355+/−35 nm and 460+/−25 nm, respectively. The plate reader was under the control of DeltaSoft II software (Biometallics) and a Macintosh computer. If the compound exhibited linear reaction velocities during the reaction period, then the reaction velocities for the dose-response study were fit to equation 1 using a nonlinear regression program (Kaleidagraph) to determine the overall Ki value (Segel, I. H. (1975) in Enzyme Kinetics, pp. 105–106, Wiley-Interscience, New York).

$$(1-Vi/Vo)=[I]/\{[I]+Ki(1+[S]/Km)\} \qquad \text{eqn 1}$$

In equation 1, Vi and Vo represent inhibited and uninhibited reaction velocities, respectively, and Km=16–40 $\mu$M depending on the neuraminidase strain tested. For those compounds exhibiting slow-binding inhibition (Morrison, J. F. (1982) Trends Biochem. Sci. 7, 102–105), a second experiment was performed in a manner identical to the first except that neuraminidase and inhibitor were preincubated in the absence of substrate for 2 hours at room temperature prior to initiating the reactions with substrate. Data analysis for the resulting linear velocities was conducted as described above.

Equation 2 was used to measure Ki values in the sub-nanomolar range (Morrison, J. F. And Stone, S. R. (1985) *Comments Mol. Cell Biophys.* 2, 347–368).

$$V=A\{sqrt\{(Ki'+It-Et)^2+4Ki'Et\}-(Ki'+It-Et)\}] \qquad \text{eqn. 2}$$

In equation 2, V=velocity; $\alpha$=akcat[S]/2(Km+[S]); $\alpha$ is a factor to convert fluorescence units to molar concentrations; Ki'=Ki(1+[S]/Km); It=total inhibitor concentration and Et=total active concentration of neuraminidase.

The compounds of the invention inhibit influenza A neuraminidase and influenza B neuraminidase with $K_i$ values between about 0.1 nanomolar and about 500 micromolar. Preferred compounds of the invention invention inhibit influenza A neuraminidase and influenza B neuraminidase with $K_i$ values between about 0.1 nanomolar and about 3.5 micromolar.

The ability of the compounds of the invention to inhibit plaque formation in cell culture can be determined by the method described below.

Cell Culture Plague Formation Inhibition Assay

Cell Cultures: MDCK cells obtained from the American Type Culture Collection were grown in Dulbecco's Modified Eagle Medium (DMEM) high glucose (GibcoBRL) supplemented with 10% fetal calf serum (JRH Biosciences), 40 mM HEPES buffer (GibcoBRL) and antibiotics (GibcoBRL). Cells were routinely cultured in flasks or roller bottles at 37° C. and 5% $CO_2$. At confluence cells were reduced to a density of 500,000 cells in a ml using trypsin/EDTA (GibcoBRL) treatment of the monolayer followed by cell centrifugation, resuspension, and dilution into growth media. Cells were planted at a volume to surface area ratio of 1 ml over 1 $cm^2$ of growth surface.

Plaque Assay Protocol: On MDCK cell confluent 6 well plates growth media was removed and the cells were overlaid with 1.5 ml of assay media (DMEM with 1% fetal calf serum, 40 mM HEPES buffer and antibiotics) containing pre-mixed virus (influenza A/Tokyo/3/67 [H2N2]) (40 –100 plaque forming units) and 2×concentration test compound. The plates were placed on a rocker and incubated for 2 hours at room temperature. During the virus adsorption period agar overlay media was prepared. In a microwave oven 2×agarose (final concentration of 0.6% agarose) in overlay media (DMEM with 40 mM HEPES buffer) was melted and then placed in a 48° C. water bath for temperature equilibration. After the virus adsorption period was completed 1.5 ml agar over media was added and mixed with the 1.5 ml virus and test compound containing media per well.

Cultures were incubated at 35° C. for the period required for plaque development, usually several days. Plaques were fixed with 3.7% formalin in PBS for 20 minutes followed by removal of the agar overlay and staining with 0.1% crystal violet in distilled water for 15 minutes. Plaques were counted and EC 50 concentration determined from multiple concentrations of the tested compound using regression analysis.

Viral Stocks: Stocks were prepared in MDCK confluent roller bottles incubated at 37° C. in DMEM supplemented with 1% FCS, 40 mM HEPES buffer, and antibiotics. Bottles were inoculated with a multiplicity of infection of approximately 0.1 plaque forming unit for each cell. Roller bottles were harvested after the cytopathic effect of the virus was observed to be complete. Stocks were prepared from the supernatant resulting from the low speed centrifugation of the media and cell lysate. Stocks were titered and stored at −80° C.

Compounds of the invention provided plaque formation inhibition for influenza virus A/N2/Tokyo in MDCK cells with EC50 values between about 100 micromolar and about 1 nanomolar. Preferred compounds of the invention provided plaque formation inhibition for influenza virus A/N2/Tokyo in MDCK cells with EC50 values between about 1 micromolar and about 1 nanomolar.

The compounds of the invention can be tested for in vivo antiviral activity using the method described below.

In Vivo Antiviral Efficacy Method

Female BALB/c mice were placed under anesthesia (sevoflurane) and inoculated intranasally (IN) with 0.1 ml of influenza A VR-95 (Puerto Rico PR8-34) at $10^{-2}$ (diluted from frozen stock). This viral concentration consistently produced disease in mice within 5 days of inoculation. Animals were treated 4h. pre-infection and 4 h. post-infection, and periodically thereafter, with one of the following therapies: no treatment; test compound (100, 25, 6.25, 1.39 mg/kg/day BID, PO); or vehicle (sterile water BID, PO). A group of ten animals (designated as control) was inoculated with 0.9% saline. Percent survival was determined. On day five, lungs were harvested, weighed and assigned scores of 0, 1, 2, 3 or 4 based on percentage consolidation (0; 10–20; 25–50; 50–75; 75–100%, respectively). In addition, each lung pair was image analyzed to determine objective lung consolidation percentages.

The compounds of the present invention can be used in the form of salts derived from inorganic or organic acids. These salts include but are not limited to the following: acetate, trifluoroacetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, hydrobromic acid, sulfuric acid and phosphoric acid and such organic acids as oxalic acid, maleic acid, succinic acid and citric acid. Other salts include salts with alkali metals or alkaline earth metals, such as sodium, potassium, lithium, calcium or magnesium or with ammonium or $N(R^{})_4^+$ salts (where $R^{}$ is loweralkyl).

In addition, salts of the compounds of this invention with one of the naturally occurring amino acids are also contemplated.

Preferred salts of the compounds of the invention include hydrochloride, methanesulfonate, p-toluenesulfonate, sulfonate, phosphonate and isethionate.

The compounds of the formula I, IIA, IIB, IIIA or IIIB of this invention can have a substituent which is an acid group (for example, $-CO_2H$, $-SO_3H$, $-SO_2H$, $-PO_3H_2$, $-PO_2H$). Compounds of the formula I, IIA, IIB, IIIA or IIIB of this invention having a substituent which is an ester of such an acidic group are also encompassed by this invention.

Such esters may serve as prodrugs. The prodrugs of this invention are metabolized in vivo to provide the above-mentioned acidic substituent of the parental compound of formula I, IIA, IIB, IIIA or IIIB. Prodrugs may also serve to increase the solubility of these substances and/or absorption from the gastrointestinal tract. These prodrugs may also serve to increase solubility for intravenous administration of the compounds. Prodrugs may also serve to increase the hydrophobicity of the compounds. Prodrugs may also serve to increase the oral bioavailability of the compounds by increasing absorption and/or decreasing first-pass metabolism. Prodrugs may also serve to increase tissue penetration of the compounds, thereby leading to increased activity in infected tissues and/or reduced rate of clearance.

Such esters contemplated by this invention include:

- alkyl esters, especially loweralkyl esters, including, but not limited to, ethyl, n-propyl, isopropyl, n-butyl, sec-butyl, isobutyl, t-butyl, n-pentyl esters and the like;
- alkoxyalkyl esters, especially, loweralkoxyloweralkyl esters, including, but not limited to, methoxymethyl, 1-ethoxyethyl, 2-methoxyethyl, isopropoxymethyl, t-butoxymethyl esters and the like;
- alkoxyalkoxyalkyl esters, especially, alkoxyalkoxy-substituted loweralkyl esters, including, but not limited to, 2-methoxyethoxymethyl esters and the like;
- aryloxyalkyl esters, especially, aryloxy-substituted loweralkyl esters, including, but not limited to, phenoxymethyl esters and the like, wherein the aryl group is unsubstituted or substituted as previously defined herein;
- haloalkoxyalkyl esters, especially, haloalkoxy-substituted loweralkyl esters, including, but not limited to, 2,2,2-trichloroethoxymethyl esters and the like;
- alkoxycarbonylalkyl esters, especially, loweralkoxycarbonyl-substituted loweralkyl esters, including, but not limited to, methoxycarbonylmethyl esters and the like;
- cyanoalkyl esters, especially, cyano-substituted loweralkyl esters, including, but not limited to, cyanomethyl, 2-cyanoethyl esters and the like;
- thioalkoxymethyl esters, especially, lowerthioalkoxy-substituted methyl esters, including, but not limited to, methylthiomethyl, ethylthiomethyl esters and the like;
- alkylsulfonylalkyl esters, especially, loweralkylsulfonyl-substituted loweralkyl esters, including, but not limited to, 2-methanesulfonylethyl esters and the like;
- arylsulfonylalkyl esters, especially, arylsulfonyl-substituted loweralkyl esters, including, but not limited to, 2-benzenesulfonylethyl and 2-toluenesulfonylethyl esters and the like;
- acyloxyalkyl esters, especially, loweralkylacyloxy-substituted loweralkyl esters, including, but not limited to, formyloxymethyl, acetoxymethyl, pivaloyloxymethyl, acetoxyethyl, pivaloyloxyethyl esters and the like;
- cycloalkylcarbonyloxyalkyl esters including, but not limited to, cyclopentanecarbonyloxymethyl, cyclohexanecarbonyloxymethyl, cyclopentanecarbonyloxyethyl, cyclohexanecarbonyloxyethyl esters and the like;
- arylcarbonyloxyalkyl esters including, but not limited to, benzoyloxymethyl esters and the like;
- (alkoxycarbonyloxy)alkyl esters, especially, (loweralkoxycarbonyloxy)-substituted loweralkyl esters, including, but not limited to, methoxycarbonyloxymethyl, ethoxycarbonyloxymethyl, 1-(methoxycarbonyloxy)ethyl, 2-(ethoxycarbonyloxy)ethyl esters and the like;
- (cycloalkyloxycarbonyloxy)alkyl esters, especially, (cycloalkyloxycarbonyloxy)-substituted loweralkyl esters, including, but not limited to, cyclohexyloxycarbonyloxymethyl, cyclopentylomycarbonyloxyethyl, cyclohexyloxycarbonyloxypropyl esters and the like;
- oxodioxolenylmethyl esters including, but not limited to, (5-phenyl-2-oxo-1,3-dioxolen-4-yl)methyl, [5-(4-methylphenyl)-2-oxo-1,3-dioxolen-4-yl]methyl, [5-(4-methoxyphenyl)-2-oxo-1,3-dioxolen-4-yl]methyl, [5-(4-fluorophenyl)-2-oxo-1,3-dioxolen-4-yl]methyl, [5-(4-chlorophenyl)-2-oxo-1,3-dioxolen-4-yl]methyl, (2-oxo-1,3-dioxolen-4-yl)methyl, (5-methyl-2-oxo-1,3-dioxolen-4-yl)methyl, (5-ethyl-2-oxo-1,3-dioxolen-4-yl)methyl, (5-propyl-2-oxo-1,3-dioxolen-4-yl)methyl, (5-isopropyl-2-oxo-1,3-dioxolen-4-yl)methyl, (5-butyl-2-oxo-1,3-dioxolen-4-yl)methyl esters and the like;
- phthalidyl esters wherein the phenyl ring of the phthalidyl group is unsubstituted or substituted as defined previously herein, including, but not limited to, phthalidyl, dimethylphthalidyl, dimethoxyphthalidyl esters and the like;
- aryl esters including, but not limited to, phenyl, naphthyl, indanyl esters and the like;
- arylalkyl esters, especially, aryl-substitued loweralkyl esters, including, but not limited to, benzyl, phenethyl, 3-phenylpropyl, naphthylmethyl esters and the like, wherein the aryl part of the arylalkyl group is unsubstituted or substituted as previously defined herein;
- dialkylaminoalkyl esters, especially dialkylamino-substituted loweralkyl esters, including, but not limited to, 2-(N,N-dimethylamino)ethyl, 2-(N,N-diethylamino)ethyl ester and the like
- (heterocyclic)alkyl esters, especially, heterocyclic-substituted loweralkyl esters wherein the heterocycle is a nitrogen-containing heterocycle, including, but not limited to, (heterocyclic)methyl esters and the like, wherein the heterocyclic part of the (heterocyclic)alkyl group is unsubstituted or substituted as previously defined herein; and
- carboxyalkyl esters, especially, carboxy-substituted loweralkyl esters, including, but not limited to carboxymethyl esters and the like;

and the like.

Preferred prodrug esters of acid-containing compounds of the Formula I, IIA, IIB, IIIA or IIIB are loweralkyl esters, including, but not limited to, ethyl, n-propyl, isopropyl, n-butyl, sec-butyl, isobutyl, t-butyl, n-pentyl esters, 3-pentyl esters, cycloalkyl esters, cycloalkylalkyl esters and benzyl esters wherein the phenyl ring is unsubstituted or substituted as previously defined herein.

Methods for the preparation of prodrug esters of compounds of the Formula I, IIA, IIB, IIIA or IIIB are well-known in the art and include:

- reacting the acid with the corresponding halide (for example, chloride or acyl chloride) and a base (for example, triethylamine, DBU, N,N-dimethylaminopyridine and the like) in an inert solvent (for example, DMF, acetonitrile, N-methylpyrrolidone and the like);
- reacting an activated derivative of the acid (for example, an acid chloride, sulfonyl chloride, monochlorophosphonate and the like) with the corresponding alcohol or alkoxide salt; and the like.

Other examples of prodrugs of the present invention include amides derived from the substituent which is an acid group.

Such amides contemplated by this invention include:

simple amides, such as —C(O)NH$_2$ and the like;

alkylamino amides, especially, loweralkylamino amides, including, but not limited to, methylamino, ethylamino, n-propylamino, isopropylamino amides and the like;

cycloalkylamino amides, including, but not limited to, cyclopropylamino, cylcobutylamino, cyclopentylamino, cyclohexylamino amides and the like;

acylamino amides, including, but not limited to acetylamino, propionylamino, butanoylamino amides and the like;

cylcoalkylcarbonylamino amides, including, but not limited to, cyclopropylcarbonylamino, cyclobutylcarbonylamino amides and the like;

alkoxycarbonylalkylamino amides, including, but not limited to, ethoxycarbonylmethylamino, t-butyloxycarbonylmethylamino and the like;

aminoacylamino amides, including, but not limited to, aminoacetylamino amides and the like;

dialkylaminoacylamino amides, including, but not limited to, dimethylaminoacetylamino, diethylaminoacetylamino amides and the like;

(heterocyclic)acylamino amides, including, but not limited to, piperidin-1-ylacetylamino amides and the like;

amides derived from single naturally occuring L-amino acids (or from acid-protected L-amino acids, for example, esters of such amino acids and the like) or from dipeptides comprising two naturally occuring L-amino acids wherein each of the two amino acids is the same or is different (or from acid-protected dipeptides, for example, esters of such dipeptides and the like);

and the like.

Methods for preparation of prodrug amides of compounds of the invention are well-known in the art and include reacting the acid with the appropriate amine in the presence of an amide bond or peptide bond-forming coupling reagent or reacting an activated derivative of the acid with the appropriate amine and the like.

Other examples of prodrugs of the present invention include esters of hydroxyl-substituted compounds of formula I, IIA, IIB, IIIA or IIIB which have been acylated with a blocked or unblocked amino acid residue, a phosphate function, a hemisuccinate residue, an acyl residue of the formula $R^{100}C(O)$— or $R^{100}C(S)$— wherein $R^{100}$ is hydrogen, lower alkyl, haloalkyl, alkoxy, thioalkoxy, alkoxyalkyl, thioalkoxyalkyl or haloalkoxy, or an acyl residue of the formula $R^a$—$C(R^b)(R^d)$—$C(O)$— or $R^a$—$C(R^b)(R^d)$—$C(S)$— wherein $R^b$ and $R^d$ are independently selected from hydrogen or lower alkyl and $R^a$ is —$N(R^e)(R^f)$, —$OR^e$ or —$SR^e$ wherein $R^e$ and $R^f$ are independently selected from hydrogen, lower alkyl and haloalkyl, or an amino-acyl residue having the formula $R^{101}NH(CH_2)_2NHCH_2C(O)$— or $R^{101}NH(CH_2)_2OCH_2C(O)$— wherein $R^{101}$ is hydrogen, lower alkyl, (aryl)alkyl, (cycloalkyl)alkyl, acyl, benzoyl or an α-amino acyl group. The amino acid esters of particular interest are of glycine and lysine; however, other amino acid residues can also be used, including any of the naturally occuring amino acids and also including those wherein the amino acyl group is —$C(O)CH_2NR^{102}R^{103}$ wherein $R^{102}$ and $R^{103}$ are independently selected from hydrogen and lower alkyl, or the group —$NR^{102}R^{103}$, where $R^{102}$ and $R^{103}$, taken together, forms a nitrogen containing heterocyclic ring.

Other prodrugs include a hydroxyl-substituted compound of formula I, IIA, IIB, IIIA or IIIB wherein the hydroxyl group is functionalized with a substituent of the formula —$CH(R^{104})OC(O)R^{105}$ or —$CH(R^{104})OO(S)R^{105}$ wherein $R^{105}$ is lower alkyl, haloalkyl, alkoxy, thioalkoxy or haloalkoxy and $R^{104}$ is hydrogen, lower alkyl, haloalkyl, alkoxycarbonyl, aminocarbonyl, alkylaminocarbonyl or dialkylaminocarbonyl. Such prodrugs can be prepared according to the procedure of Schreiber (*Tetrahedron Lett.* 1983, 24, 2363) by ozonolysis of the corresponding methallyl ether in methanol followed by treatment with acetic anhydride.

The preparation of esters of hydroxyl-substituted compounds of formula formula I, IIA, IIB, IIIA or IIIB is carried out by reacting a hydroxyl-substituted compound of formula formula I, IIA, IIB, IIIA or IIIB, with an activated amino acyl, phosphoryl, hemisuccinyl or acyl derivative.

Prodrugs of hydroxyl-substituted-compounds of the invention can also be prepared by alkylation of the hydroxyl substituted compound of formula formula I, IIA, IIB, IIIA or IIIB, with (halo)alkyl esters, transacetalization with bis-(alkanoyl)acetals or condensation of the hydroxyl group with an activated aldehyde followed by acylation of the intermediate hemiacetal.

In preparing prodrugs it often is necessary to protect other reactive functional groups, in order to prevent unwanted side reactions. After protection of the reactive groups the desired group can be functionalized. The resulting functionalized product is then deprotected, to remove the protecting groups that were added to prevent unwanted side reactions. This will provide the desired prodrug. Suitable reaction conditions for preparing protecting groups are well known in the art. One source for reaction conditions is found in T. H. Greene and P. G. M. Wuts, *Protective Groups in Organic Synthesis*, 2nd edition, John Wiley & Sons, New York (1991).

This invention also encompasses compounds of the Formula I, IIA, IIB, IIIA or IIIB which are esters or prodrugs and which are also salts. For example, a compound of the invention can be an ester of a carboxylic acid and also an acid addition salt of an amine or nitrogen-containing substituent in the same compound.

The compounds of the present invention are useful for inhibiting neuraminidase from disease-causing microorganisms which comprise a neuraminidase. The compounds of the invention are useful (in humans, other mammals and fowl) for treating or preventing diseases caused by microorganisms which comprise a neuraminidase.

The compounds of the present invention are useful for inhibiting influenza A virus neuraminidase and influenza B virus neuraminidase, in vitro or in vivo (especially in mammals and, in particular, in humans). The compounds of the present invention are also useful for the inhibition of influenza viruses, orthomyxoviruses, and paramyxoviruses in vivo, especially the inhibition of influenza A viruses and influenza B viruses in humans and other mammals. The compounds of the present invention are also useful for the treatment of infections caused by influenza viruses, orthomyxoviruses, and paramyxoviruses in vivo, especially the human diseases caused by influenza A and influenza B viruses.

The compounds of the present invention are also useful for the prophylaxis of infections caused by influenza viruses, orthomyxoviruses, and paramyxoviruses in vivo in humans and other mammals, especially the prophylaxis of influenza A and influenza B viral infections; and, in particular, the prophylaxis of influenza A and influenza B viral infections in human subjects who are at high risk of developing other respiratory diseases concurrent with or as a consequence of influenza virus infections, or who suffer from chronic respiratory illness, such as asthma, emphysema, or cystic fibrosis.

Total daily dose administered to a human or other mammal host in single or divided doses may be in amounts, for example, from 0.001 to 300 mg/kg body weight daily and more usually 0.1 to 10 mg/kg body weight daily. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

Administration of a compound of this invention will begin before or at the time of infection or after the appearance of established symptoms and/or the confirmation of infection.

The compounds of the present invention may be administered orally, parenterally, sublingually, intranasally, by intrapulmonary administration, by inhalation or insulation as a solution, suspension or dry powder (for example, in a spray), or rectally, in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

While the compounds of the invention can be administered as the sole active pharmaceutical agent, they can also be used in combination with one or more anti-infective agents and/or other agents used to treat other acute or chronic respiratory ailments. Other agents to be administered in combination with a compound of the present invention include: an influenza vaccine; other influenza inhibitors such as, for example, amantadine, rimantadine, ribavirin, and the like; another influenza neuraminidase inhibitor, such as, for example, zanamivir or GS 4104 and the like; agents used to treat respiratory bacterial infections and bronchitis, such as, for example, erythromycin, clarithromycin, azithromycin and the like; and agents used to treat asthma, such as, for example, zileuton, albuterol (salbutamol), salmeterol, formoterol, ipratropium bromide, inhaled steroids and the like, or anti-inflammatory agents for treating asthma such as, for example, beclomethasone dipropionate, fluticasone propionate, budesonide, triamcinolone acetonide, flunisolide, cromolyn, zafirlukast, montelukast used in combination with a compound of the present invention.

When administered as a combination, the therapeutic agents can be formulated as separate compositions which are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

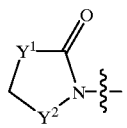

or a pharmaceutically acceptable salt, ester or prodrug thereof, wherein $R^1$ is selected from the group consisting of
(b) —$CO_2H$, (b) —$CH_2CO_2H$, (c) —$SO_3H$, (d) —$CH_2SO_3H$, (e) —$SO_2H$,
(g) —$CH_2SO_2H$, (g) —$PO_3H_2$, (h) —$CH_2PO_3H_2$, (i) —$PO_2H$, (j) —$CH_2PO_2H$, (l) tetrazolyl, (l) —CH$_2$-tetrazolyl, (m) —C(=O)—NH—S(O)$_2$—R$^{11}$, (o) —CH$_2$C(=O)—NH—S(O)$_2$—R$^{11}$, (o) —SO$_2$N(T—R$^{11}$)R$^{12}$ and (p) —CH$_2$SO$_2$N(T—R$^{11}$)R$^{12}$ wherein T is selected from the group consisting of
(i) a bond, (ii) —C(=O)—, (iii) —C(=O)O—, (iv) —C(=O)S—, (v) —C(=O)NR$^{36}$—,
(vi) —C(=S)O—, (vii) —C(=S)S—, and (viii) —C(=S)NR$^{36}$—, R$^{11}$ is selected from the group consisting of
(i) C$_1$–C$_{12}$alkyl, (ii) C$_2$–C$_{12}$ alkenyl, (iii) cycloalkyl, (iv) (cycloalkyl)alkyl,
(w) (cycloalkyl)alkenyl, (vi) cycloalkenyl, (vii) (cycloalkenyl)alkyl, (ix) (cycloalkenyl)alkenyl, (ix) aryl, (x) (aryl)alkyl,
(x) (xi) (aryl)alkenyl,
(xvii) heterocyclic, (xiii) (heterocyclic)alkyl and (xviii) (xiv) (heterocyclic)alkenyl; and R$^{12}$ and R$^{36}$ are independently selected from the group consisting of
(i) hydrogen, (ii) C$_1$–C$_{12}$ alkyl, (iii) C$_2$–C$_{12}$ alkenyl, (iv) cycloalkyl, (v) (cycloalkyl)alkyl, (vi) (cycloalkyl)alkenyl, (vii) cycloalkenyl, (viii) (cycloalkenyl)alkyl, (ix) (cycloalkenyl)alkenyl, (x) aryl, (xi) (aryl)alkyl, (xii) (aryl)alkenyl, (xiii) heterocyclic, (xiv) (heterocyclic)alkyl and (xv) (heterocyclic)alkenyl;

X is selected from the group consisting of
(a) —C(=O)—N(R*)—, (b) —N(R*)—C(=O)—, (c) —C(=S)—N(R*)—, (d) —N(R*)—C(=S)—, (e) —N(R*)—SO$_2$—, and (f) —SO$_2$—N(R*)— wherein R* is hydrogen, C$_1$–C$_3$ loweralkyl or cyclopropyl;

R$^2$ is selected from the group consisting of
(a) hydrogen, (b) C$_1$–C$_6$ alkyl, (c) C$_2$–C$_6$ alkenyl, (d) C$_3$–C$_6$ cycloalkyl, (e) C$_5$–C$_6$ cycloalkenyl, (f) halo C$_1$–C$_6$ alkyl and (g) halo C$_2$–C$_6$ alkenyl;

or R$^2$—X— is

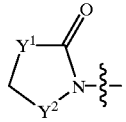

wherein
Y$^1$ is —CH$_2$—, —O—, —S— or —NH— and Y$^2$ is —C(=O)— or —C(R$^{aa}$)(R$^{bb}$)— wherein R$^{aa}$ and R$^{bb}$ are indepedently selected from the group consisting of hydrogen,
C$_1$–C$_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

R$^3$ and R$^4$ are independently selected from the group consisting of
(a) hydrogen, (b) cycloalkyl, (c) cycloalkenyl, (d) heterocyclic, (e) aryl and (f) —Z—R$^{14}$
wherein Z is
(ii) —C(R$^{37a}$)(R$^{37b}$b)—, (ii) —C(R$^{47}$)=C(R$^{48}$)—, (iii) —C≡C—, (iv) —C(=O)—, (v) —C(=S)—, (vi) —C(=NR$^{15}$)—, (vii) —C(R$^{37a}$)(OR$^{37c}$)—, (viii) —C(R$^{37a}$)(SR$^{37c}$)—, (ix) —C(R$^{37a}$)(N(R$^{37b}$)(R$^{37c}$))—, (x) —C(R$^{37a}$)(R$^{37b}$)—O—, (xi) —C(R$^{37a}$)(R$^{37b}$)—N(R$^{37c}$)—, (xii) —C(R$^{37a}$)(R$^{37b}$)—N(O)(R$^{37c}$)—, (xiii) —C(R$^{37a}$)(R$^{37b}$)—N(OH)—, (xiv) —C(R$^{37a}$)(R$^{37b}$)—S—, (xv) —C(R$^{37a}$)(R$^{37b}$)—S(O)—, (xvi) —C(R$^{37a}$)(R$^{37b}$)—S(O)$_2$—, (xviii) —C(R$^{37a}$)(R$^{37b}$)—C(=O)—, (xviii) —C(R$^{37a}$)(R$^{37b}$)—C(=S)—, (xxi) —C(R$^{37a}$)(R$^{37b}$)—C(=NR$^{15}$)—, (xx) —C(R$^{37a}$)(OR$^{37c}$)—C(=O)—, (xxi) —C(R$^{37a}$)(SR$^{37c}$)—C(=O)—, (xxi) —C(R$^{37a}$)(OR$^{37c}$)—C(=S)—, (xxiii) —C(R$^{37a}$)(SR$^{37c}$)—C(=S)—, (xxiv) —C(=O)—C(R$^{37a}$)(OR$^{37c}$)—, (xxv) —C(=O)—C(R$^{37a}$)(OR$^{37c}$)—, (xxvi) —C(=S)—C(R$^{37a}$)(OR$^{37}$c)—, (xxvii) —C(=S)—C(R$^{37a}$)(SR$^{37c}$)—, (xxviii) —C(R$^{37a}$)(OR$^{37c}$)—C(R$^{37a}$)(OR$^{37c}$)—, (xxix) —C(R$^{37a}$)(SR$^{37c}$)—C(R$^{37a}$)(OR$^{37c}$)—, (xxx) —C(R$^{37a}$)(OR$^{37c}$)—C(R$^{37a}$)(SR$^{37c}$)—, (xxxi) —C(R$^{37a}$)(SR$^{37c}$)—C(R$^{37a}$)(SR$^{37c}$)—, (xxxii) —C(=O)—C(=O)—, (xxxiii) —C(=S)—C(=S)—, (xxxiv) —C(=O)—O—, (xxxv) —C(=O)—S—, (xxxvi) —C(=S)—O—, (xxxvii) —C(=S)—S—, (xxxviii) —C(=O)—N(R$^{37a}$)—, (xxxix) —C(=S)—N(R$^{37a}$)—, (xl) —C(R$^{37a}$)(R$^{37b}$)—C(=O)—N(R$^{37a}$)—, (xli) —C(R$^{37a}$)(R$^{37b}$)—C(=S)—N(R$^{37a}$)—, (xlii) —C(R$^{37a}$)(R$^{37b}$)—C(=O)—O—, (xliii) —C(R$^{37a}$)(R$^{37b}$)—C(=O)—S—, (xliv —C(R$^{37a}$)(R$^{37b}$)—C(=S)—O—, (xlv) —C(R$^{37a}$)(R$^{37b}$)—C(=S)—S—, (xlvi) —C(R$^{37a}$)(R$^{37b}$)—N(R$^{37b}$)—C(=O)—, (xlvii) —C(R$^{37a}$)(R$^{37b}$)—N(R$^{37b}$)—C(=S)—, (xlviii) —C(R$^{37a}$)(R$^{37b}$)—O—C(=O)—, (xlix) —C(R$^{37a}$)(R$^{37b}$)—S—C(=O)—, (l) —C(R$^{37a}$)(R$^{37b}$)—O—C(=S)—, (li) —C(R$^{37a}$)(R$^{37b}$)—S—C(=S)—, (lii) —C(R$^{37a}$)(R$^{37b}$)—N(R$^{37b}$)—C(=O)—N(R$^{37a}$)—, (liii) —C(R$^{37a}$)(R$^{37b}$)—N(R$^{37b}$)—C(=S)—N(R$^{37a}$)—, (liv) —C(R$^{37a}$)(R$^{37b}$)—N(R$^{37b}$)—C(=O)—O—, (lv) —C(R$^{37a}$)(R$^{37b}$)—N(R$^{37b}$)—C(=O)—S—, (lvi) —C(R$^{37a}$)(R$^{37b}$)—N(R$^{37b}$)—C(=S)—O—, (lvii) —C(R$^{37a}$)(R$^{37b}$)—N(R$^{37b}$)—C(=S)—S—, (lviii) —C(R$^{37a}$)(R$^{37b}$)—O—C(=O)—N(R$^{37a}$)—, (lix) —C(R$^{37a}$)(R$^{37b}$)—S—C(=O)—N(R$^{37a}$)—, (lx) —C(R$^{37a}$)(R$^{37b}$)—O—C(=S)—N(R$^{37a}$)—, (lxi) —C(R$^{37a}$)(R$^{37b}$)—S—C(=S)—N(R$^{37a}$)—, (lxii) —C(R$^{37a}$)(R$^{37b}$)—O—C(=O)—O—, (lxiii) —C(R$^{37a}$)(R$^{37b}$)—S—C(=O)—O—, (lxiv) —C(R$^{37a}$)(R$^{37b}$)—O—C(=O)—S—, (lxv) —C(R$^{37a}$)(R$^{37b}$)—S—C(=O)—S—, (lxvi) —C(R$^{37a}$)(R$^{37b}$)—O—C(=S)—O—, (lxvii) —C(R$^{37a}$)(R$^{37b}$)—S—C(=S)—O—, (lxviii) —C(R$^{37a}$)(R$^{37b}$)—O—C(=S)—S—, (lxix) —C(R$^{37a}$)(R$^{37b}$)—S—C(=S)—S— or (lxx) —C(R$^{37a}$)(R$^{37b}$)—C(R$^{37a}$)(OR$^{37c}$)—;

R$^{14}$ is
(i) hydrogen, (ii) C$_1$–C$_{12}$ alkyl, (iii) haloalkyl, (iv) hydroxyalkyl, (v) thiol-substituted alkyl, (vi) R$^{37c}$O-substituted alkyl, (vii) R$^{37c}$S-substituted alkyl, (viii) aminoalkyl, (ix) (R$^{37c}$)NH-substituted alkyl, (x) (R$^{37a}$)(R$^{37c}$)N-susbstituted alkyl, (xi) R$^{37a}$O—(O=)C-substituted alkyl, (xii) R$^{37a}$S—(O=)C-substituted alkyl, (xiii) R$^{37a}$O—(S=)C-substituted alkyl, (xix) R$^{37a}$S—(S=)C-Substituted alkyl, (xx) (R$^{37a}$O)$_2$—P(=O)-substituted alkyl, (xvi) cyanoalkyl, (xxi) C$_2$–C$_{12}$ alkenyl, (xviii) haloalkenyl, (xix) C$_2$–C$_{12}$ alkynyl, (xxii) cycloalkyl, (xxi) (cycloalkyl)alkyl, (xxii) (cycloalkyl)alkenyl, (xxiv) (cycloalkyl)alkynyl, (xxiv) cycloalkenyl, (xxv) (cycloalkenyl)alkyl, (xxvii) (cycloalkenyl)alkenyl, (xxvii) (cycloalkenyl)alkynyl, (xxviii) aryl, (xxx) (aryl)alkyl, (xxx) (aryl)alkenyl, (xxxi) (aryl)alkynyl, (xxxii) heterocyclic, (xxxiii) (heterocyclic)alkyl, (xxxiv) (heterocyclic)alkenyl or (xxxv) (heterocyclic)alkynyl, with the proviso that $R^{14}$ is other than hydrogen when Z is —$C(R^{37a})(R^{37b})$—$N(R^{37b})$—$C(=O)$—O—, —$C(R^{37a})(R^{37b})$—$N(R^{37b})$—$C(=S)$—O—, —$C(R^{37a})(R^{37b})$—$N(R^{37b})$—$C(=O)$—S—, —$C(R^{37a})(R^{37b})$—$N(R^{37b})$—$C(=S)$—S—, —$C(R^{37a})(R^{37b})$—O—$C(=O)$—O—, —$C(R^{37a})(R^{37b})$—O—$C(=S)$—O—, —$C((R^{37a})(R^{37b})$—S—$C(=O)$—O—, —$C(R^{37a})(R^{37b})$—S—$C(=S)$—O—, —$C(R^{37a})(R^{37b})$—O—$C(=O)$—S—, —$C(R^{37a})(R^{37b})$—O—$C(=S)$—S—, —$C(R^{37a})(R^{37b})$—S—$C(=O)$—S— or —$C(R^{37a})(R^{37b})$—S—$C(=S)$—S—;

$R^{37a}$, $R^{37b}$, $R^{47}$, and $R^{48}$ at each occurrence are independently selected from the group consisting of
(i) hydrogen, (ii) $C_1$–$C_{12}$ alkyl, (iii) haloalkyl, (iv) hydroxyalkyl, (v) alkoxyalkyl, (vi) $C_2$–$C_{12}$ alkenyl, (vii) haloalkenyl, (viii) $C_2$–$C_{12}$ alkynyl, (ix) cycloalkyl, (x) (cycloalkyl)alkyl, (xi) (cycloalkyl)alkenyl, (xii) (cycloalkyl)alkynyl, (xiii) cycloalkenyl, (xiv) (cycloalkenyl)alkyl, (xv) (cycloalkenyl)alkenyl, (xvi) (cycloalkenyl)alkynyl, (xvii) aryl, (xviii) (aryl)alkyl, (xix) (aryl)alkenyl, (xx) (aryl)alkynyl, (xxi) heterocyclic, (xxii) (heterocyclic)alkyl, (xxiii) (heterocyclic)alkenyl and (xxiv) (heterocyclic)alkynyl;

$R^{37c}$ at each occurrence is independently selected from the group consisting of
(i) hydrogen, (ii) $C_1$–$C_{12}$ alkyl, (iii) haloalkyl, (iv) $C_2$–$C_{12}$ alkenyl, (v) haloalkenyl, (vi) $C_2$–$C_{12}$ alkynyl, (vii) cycloalkyl, (viii) (cycloalkyl)alkyl, (ix) (cycloalkyl)alkenyl, (x) (cycloalkyl)alkynyl, (xi) cycloalkenyl, (xii) (cycloalkenyl)alkyl, (xiii) (cycloalkenyl)alkenyl, (xiv) (cycloalkenyl) alkynyl, (xv) aryl, (xvi) (aryl)alkyl, (xvii) (aryl)alkenyl, (xviii) (aryl)alkynyl, (xix) heterocyclic, (xx) (heterocyclic)alkyl, (xxi) (heterocyclic)alkenyl, (xxiv) (heterocyclic)alkynyl, (xxiii) —$C(=O)$—$R^{14}$, (xxiv) —$C(=S)$—$R^{14}$, (xxv) —$S(O)_2$—$R^{14}$ and (xxvi) hydroxyalkyl;

or when Z is —$C(R^{37a})(R^{37b})$—$N(R^{37c})$—, then $N(R^{37c})$ and $R^{14}$ when taken together are an azido group;

or when Z is —$C(R^{37a})(R^{37b})$—$N(O)(R^{37c})$—, then $N(O)(R^{37c})$ and $R^{14}$ when taken together are an N-oxidized 3–7 membered heterocyclic ring having at least one N-oxidized ring nitrogen atom;

or when Z is —$C(R^{37a})(R^{37b})$—, —$C(R^{37a})(OR^{37c})$—, —$C(R^{37a})(SR^{37c})$— or —$C(R^{37a})(N(R^{37b})(R^{37c}))$—, then $R^{37a}$, $R^{14}$ and the carbon atom to which they are bonded when taken together form a cyclopentyl, cyclopentenyl, cyclohexyl or cyclohexenyl ring or then $OR^{37c}$ or $SR^{37c}$ or $N(R^{37c})$ and $R^{14}$ and the carbon atom to which they are bonded when taken together form a heterocyclic ring containing an O, S or N atom, respectively, and having from 4 to 8 ring atoms;

$R^{15}$ is selected from the group consisting of
(i) hydrogen, (ii) hydroxy, (iii) amino, (iv) $C_1$–$C_{12}$ alkyl, (v) haloalkyl, (vi) $C_2$–$C_{12}$ alkenyl, (vii) haloalkenyl, (viii) cycloalkyl, (ix) (cycloalkyl) alkyl, (x) (cycloalkyl)alkenyl, (xi) cycloalkenyl, (xii) (cycloalkenyl)alkyl, (xiii) (cycloalkenyl) alkenyl, (xiv) aryl, (xv) (aryl)alkyl, (xvi) (aryl) alkenyl, (xvii) heterocyclic, (xviii) (hetcrocyclic) alkyl and (xix) (heterocyclic)alkenyl:

or $R^3$ and $R^4$ taken together, with the atom to which they are attached, form a carbocyclic or heterocyclic ring having from 3 to 8 ring atoms;

$R^5$ is selected from the group consisting of
(a) hydrogen, (b) —$CH(R^{38})_2$, (c) —O—$R^{40}$, (d) $C_2$–$C_4$ alkynyl, (e) cyclopropyl, (f) cyclobutyl, (g) —$C(=Q^1)$—$R^{17}$, and (h) —$N(R^{19})_2$
wherein $Q^1$ is O, S, or $N(R^{18})$;
$R^{17}$ and $R^{18}$ are independently selected, at each occurrence, from the group consisting of hydrogen, methyl, and ethyl;
$R^{19}$, $R^{38}$, and $R^{40}$ are independently selected, at each occurrence, from the group consisting of
(i) hydrogen, (ii) $C_1$–$C_{12}$ alkyl, (iii) halalkyl, (iv) $C_2$–$C_{12}$ alkenyl, (v) haloalkenyl, (vi) cycloalkyl, (vii) (cycloalkyl)alkyl, (viii) (cycloalkyl)alkenyl, (ix) cylcloalkenyl, (x) (cycloakenyl)alkyl, (xi) (cycloalkenyl)alkenyl, (xii) aryl, (xiii) (aryl)alkyl, (xiv) (aryl)alkenyl, (xv) heterocyclic, (xvi) (heterocyclic)alkyl and (xvii) (heterocyclic) alkenyl;

Y is selected from the group consisting of
(a) hydrogen, (b) $C_1$–$C_5$ alkyl, (c) $C_1$–$C_5$ haloalkyl, (d) $C_2$–$C_5$ alkenyl, (e) $C_2$–$C_5$ haloalkenyl, (f) $C_2$–$C_5$ alkynyl, (g) $C_3$–$C_5$ cycloalkyl, (h) $C_3$–$C_5$ cycloalkyl-$C_1$-to-$C_3$-alkyl, (i) $C_5$ cycloalkenyl, (j) $C_5$ cycloalkenyl-$C_1$-to-$C_3$-alkyl, (k) $C_5$ cycloalkenyl-$C_2$-to-$C_3$-alkenyl, (l) —$(CHR^{39})_nOR^{20}$, (m) —$CH(OR^{20})$—$CH_2(OR^{20})$, (n) —$(CHR^{39})_nSR^{21}$, (o) —$(CHR^{39})_nCN$, (p) —$(CHR^{39})_nN_3$, (q) phenyl, (r) halo-substituted phenyl, (s) —$(CHR^{39})_nC(=Q^2)R^{22}$, (t) —$(CHR^{39})_nN(=Q^3)$, (u) —$N(O)=CHCH_3$, (v) —$(CHR^{39})_nNR^{23}R^{24}$ (w) halo and (x) a heterocyclic ring having from 3 to 6 ring atoms;
wherein n is 0, 1, or 2; $Q^2$ is O, S, $NR^{25}$ or $CHR^{26}$; and $Q^3$ is $NR^{41}$ or $CHR^{42}$;
$R^{20}$ at each occurrence is independently
(i) hydrogen, (ii) methyl, (iii) ethyl, (iv) n-propyl, (v) isopropyl, (vi) $C_1$–$C_3$ haloalkyl, (vii) vinyl, (viii) propenyl, (ix) isopropenyl, (x) allyl, (xi) $C_2$–$C_3$ haloalkenyl, (xii) amino, (xiii) —$NHCH_3$, (xiv) —$N(CH_3)_2$, (xv) —$NHCH_2CH_3$, (xvi) —$N(CH_3)(CH_2CH_3)$, (xvii) —$N(CH_2CH_3)_2$ or (xviii) —$N(=CH_2)$;
$R^{21}$ is
hydrogen, (ii) methyl, (iii) ethyl, (iv) n-propyl, (v) isopropyl, (vi) $C_1$–$C_3$ haloalkyl, (vii) vinyl, (viii) propenyl, (ix) isopropenyl, (x) allyl or (xi) $C_2$–$C_3$ haloalkenyl;
$R^{22}$ is
(i) hydrogen, (ii) methyl, (iii) ethyl, (iv) n-propyl, (v) isopropyl, (vi) hydroxy, (vii) thiol, (viii) methoxy, (ix) ethoxy, (x) n-propoxy, (xi) isopropoxy, (xii) cyclopropyloxy, (xiii) methylthio, (xiv) ethylthio, (xv) n-propylthio, (xvi) isopropylthio, (xvii) cyclopropylthio, (xviii) vinyl, (xix) propenyl, (xx) isopropenyl, (xxi) allyl, (xxii) —$N(R^{28a})(R^{28b})$, (xxv) —$CH_2R^{29}$, (xxiv) aminomethyl, (xxv) hydroxymethyl, (xxvi) thiolmethyl, (xxvii) —$NHNH_2$, (xxviii) —$N(CH_3)NH_2$ or (xxix) —$NHNH(CH_3)$;

$R^{23}$ and $R^{39}$ are independently hydrogen or methyl;

$R^{41}$ and $R^{42}$ are independently hydrogen, methyl, or ethyl;

$R^{24}$ is selected from the group consisting of
(i) hydrogen, (ii) $C_1$–$C_4$ alkyl, (iii) $C_2$–$C_4$ alkenyl, (iv) $C_2$–$C_4$ alkynyl, (v) cyclopropyl, (vi) —C(=$Q^4$)—$R^{30}$, (v) —O$R^{31}$, and (vi) —N($R^{32}$)$_2$, wherein $Q^4$ is O, S, or N($R^{33}$);

$R^{25}$ is hydrogen, hydroxy, methyl, ethyl, amino, —CN, or —NO$_2$;

$R^{26}$ group is hydrogen, methyl or ethyl;

$R^{28a}$ hydrogen, hydroxy, methyl, ethyl, amino, —NHCH$_3$, —N(CH$_3$)$_2$, methoxy, ethoxy, or —CN;

$R^{28b}$ is hydrogen, methyl or ethyl;

or $R^{28a}$, $R^{28b}$ and the nitrogen to which they are bonded taken together represent azetidinyl;

$R^{29}$ group is hydrogen, hydroxy, thiol, methyl, ethyl, amino, methoxy, ethoxy, methylthio, ethylthio, methylamino or ethylamino;

$R^{30}$ group is hydrogen, methyl, ethyl, —O$R^{34}$, —S$R^{34}$, —N($R^{35}$)$_2$, —NHOH, —NHNH$_2$, —N(CH$_3$)NH$_2$, or —N(CH$_2$CH$_3$)NH$_2$;

$R^{31}$ and $R^{32}$, at each occurrence, are independently hydrogen, methyl or ethyl;

$R^{33}$ is hydrogen, hydroxy, methyl, ethyl, amino, —CN, or —NO$_2$;

$R^{34}$ is methyl or ethyl;

$R^{35}$ is independently hydrogen, methyl or ethyl;
with the proviso that when $Q^2$ is CH$R^{26}$ then $R^{22}$ is selected from the group consisting of hydrogen, —CH$_3$, —C$_2$H$_5$, —C$_3$H$_7$, —OCH$_3$, —SCH$_3$, —O—C$_2$H$_5$, and —S—C$_2$H$_5$, and with the proviso that when $R^3$ and $R^4$ are each hydrogen, then Y is other than hydrogen;

$R^6$ and $R^7$ are independently selected from the group consisting of
(c) hydrogen, (b) $C_1$–$C_{12}$ alkyl, (c) $C_2$–$C_{12}$ alkenyl, (d) cycloalkyl, (e) (cycloalkyl)alkyl, (f) (cycloalkyl)alkenyl, (g) cycloalkenyl, (h) (cycloalkenyl)alkyl, (j) (cycloalkenyl)alkenyl, (j) aryl, (k) (aryl)alkyl, (l) (aryl)alkenyl, (m) heterocyclic, (o) (heterocyclic)alkyl and (o) (heterocyclic)alkenyl; and $R^8$, $R^9$, and $R^{10}$ are independently selected from the group consisting of
(a) hydrogen, (b) $C_1$–$C_6$ alkyl, (c) $C_2$–$C_6$ alkenyl, (d) $C_3$–$C_6$ cycloalkyl, (e) $C_3$–$C_6$ cycloalkenyl, and (f) fluorine, with the proviso that the total number of atoms, other than hydrogen, in each of $R^8$, $R^9$, and $R^{10}$, is 6 atoms or less.

2. The compound according to claim 1 having the relative stereochemistry of the formula:

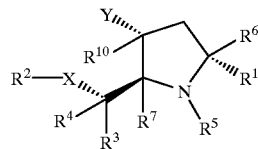

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

3. The enantiomerically enriched compound according to claim 1 having the absolute stereochemistry of the formula:

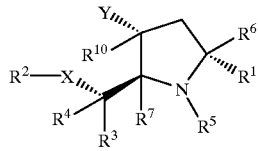

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

4. The compound according to claim 1 having the relative stereochemistry of the formula:

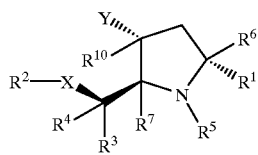

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

5. The enantiomerically enriched compound according to claim 1 having the absolute stereochemistry of the formula:

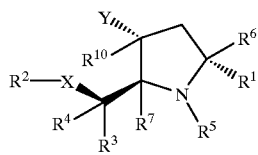

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

6. The compound according to claim 1 wherein —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

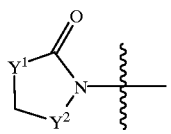

wherein
$Y^1$ is —CH$_2$—, —O—, —S— or —NH— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl, 2-hydroxyethyl, aminomethyl, 1-aminoethyl, 2-aminoethyl, thiolmethyl, 1-thiolethyl, 2-thiolethyl, methoxymethyl, N-methylaminomethyl and methylthiomethyl;

$R^3$ and $R^4$ are independently selected from hydrogen, heterocyclic and —Z—$R^{14}$ wherein Z and $R^{14}$ are defined as therein and wherein one of $R^3$ and $R^4$ is other than hydrogen;

$R^5$ is hydrogen or loweralkyl;
$R^6$ and $R^7$ are independently hydrogen or loweralkyl;
$R^8$ and $R^9$ are independently hydrogen, fluoro or loweralkyl;
$R^{10}$ is hydrogen, fluoro or loweralkyl; and
Y is $C_2$–$C_5$ alkenyl, $C_2$–$C_5$ haloalkenyl, —C(=$Q^2$) $R^{22}$, —N(=$Q^3$), —N(O)=CHCH$_3$, —NR$^{23}$R$^{24}$ or a heterocyclic ring having from 3 to 6 ring atoms, wherein $R^{22}$, $R^{23}$, $R^{24}$, $Q^2$ and $Q^3$ are as defined therein; or a pharmaceutically acceptable salt, ester or prodrug thereof.

7. The compound according to claim 6 having the relative stereochemistry of the formula:

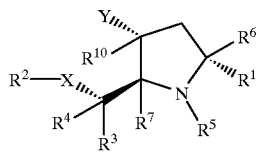

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

8. The enantiomerically enriched compound according to claim 6 having the absolute stereochemistry of the formula:

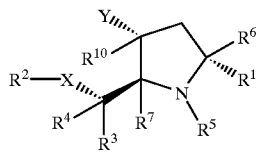

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

9. The compound according to claim 6 having the relative stereochemistry of the formula:

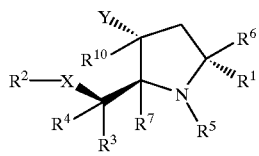

or a pharmaceutically acceptable salt, ester or prodrug thereof, wherein $R^1$, $R^2$, $R^3$, $R^4$ $R^5$, $R^6$, $R^7$, $R^{10}$, X and Y are as defined therein and wherein $R^3$ and $R^4$ are not both the same.

10. The enantiomerically enriched compound according to claim 6 having the absolute stereochemistry of the formula;

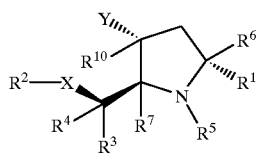

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

11. The compound according to claim 1 wherein —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_2$–$C_3$ alkenyl or —X—$R^2$ is

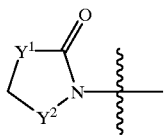

wherein
$Y^1$ is —CH$_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;
$R^3$ and $R^4$ are independently selected from hydrogen, heterocyclic and —Z—$R^{14}$ wherein Z and $R^{14}$ are defined as therein and wherein one of $R^3$ and $R^4$ is other than hydrogen;
$R^5$ is hydrogen or loweralkyl;
$R^6$ and $R^7$ are independently hydrogen or loweralkyl;
$R^8$ and $R^9$ are independently hydrogen or loweralkyl;
$R^{10}$ is hydrogen or loweralkyl; and
Y is $C_2$–$C_5$ alkenyl, $C_2$–$C_5$ haloalkenyl, —C(=$Q^2$) $R^{22}$, —N(=$Q^3$), —N(O)=CHCH$_3$, —NR$^{23}$R$^{24}$ or a heterocyclic ring having 5 ring atoms and also containing one or two double bonds, wherein $R^{22}$, $R^{23}$, $R^{24}$, $Q^2$ and $Q^3$ are defined as therein; or a pharmaceutically acceptable salt, ester or prodrug thereof.

12. The compound according to claim 11 having the relative stereochemistry of the formula:

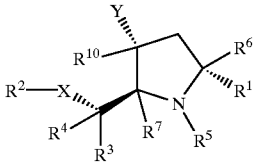

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

13. The enantiomerically enriched compound according to claim 11 having the absolute stereochemistry of the formula:

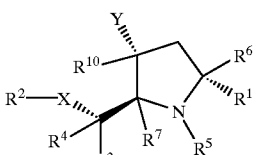

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

14. The compound according to claim 11 having the relative stereochemistry of the formula

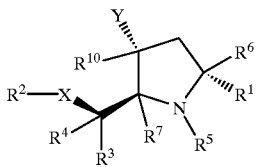

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

15. The enantiomerically enriched compound according to claim 11 having the absolute stereochemistry of the formula:

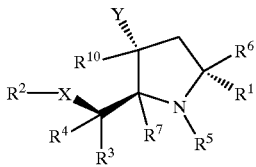

or a pharmaceutically acceptable salt, ester or prodrug thereof, wherein $R^1, R^2{}_1 R^3, R^4, R^5, R^6, R^7, R^{10}$, X and Y are as defined therein and wherein $R^3$ and $R^4$ are not both the same.

16. The compound according to claim 1 wherein —X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl, halo $C_1$–$C_3$ loweralkyl, $C_2$–$C_3$ alkenyl or halo $C_1$–$C_3$ alkenyl or —X—$R^2$ is

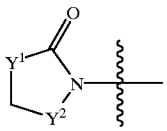

wherein $Y^1$ is —CH$_2$— and $Y^2$ is —C(=O)— or —C($R^{aa}$)($R^{bb}$)— wherein $R^{aa}$ and $R^{bb}$ are independently selected from the group consisting of hydrogen, $C_1$–$C_3$ loweralkyl, hydroxymethyl, 1-hydroxyethyl and 2-hydroxyethyl;

$R^3$ and $R^4$ are independently selected from hydrogen, heterocyclic and —Z—$R^{14}$ wherein Z and $R^{14}$ are defined as therein and wherein one of $R^3$ and $R^4$ is other than hydrogen;

$R^5$ is hydrogen or loweralkyl;

$R^6$ and $R^7$ are independently hydrogen or loweralkyl;

$R^8$ and $R^9$ are independently hydrogen or loweralkyl;

$R^{10}$ is hydrogen or loweralkyl; and

Y is $C_2$–$C_5$ alkenyl, $C_2C_5$ haloalkenyl, NH$_2$, —NHC(=NH)NH$_2$ or a heterocyclic ring having 5 ring atoms and also containing one or two double bonds; or a pharmaceutically acceptable salt, ester or prodrug thereof.

17. The compound according to claim 16 having the relative stereochemistry of the formula:

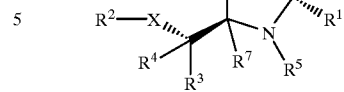

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

18. The enantiomerically enriched compound according to claim 16 having the absolute stereochemistry of the formula:

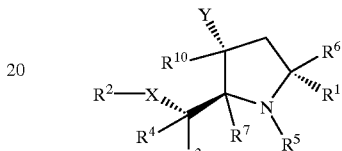

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

19. The compound according to claim 16 having the relative stereochemistry of the formula:

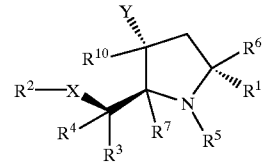

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

20. The enantiomerically enriched compound according to claim 16 having the absolute stereochemistry of the formula:

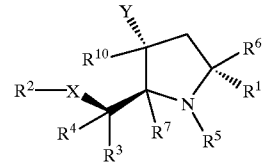

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

21. The compound according to claim 1 wherein $R^1$ is —CO$_2$H;

—X—$R^2$ is $R^2$—C(=O)—NH—, $R^2$—NH—C(=O)—, $R^2$—NH—SO$_2$— or $R^2$—SO$_2$—NH— wherein $R^2$ is $C_1$–$C_3$ loweralkyl or halo-$C_1$–$C_3$ loweralkyl;

$R^3$ and $R^4$ are independently selected from hydrogen, heterocyclic and —Z—$R^{14}$ wherein Z and $R^{14}$ are defined as therein and wherein one of R³ and R⁴ is other than hydrogen;

R⁵ is hydrogen or loweralkyl;

R⁶ and R⁷ are hydrogen independently hydrogen or loweralkyl;

R⁸ and R⁹ are hydrogen independently hydrogen or loweralkyl;

R¹⁰ is hydrogen or loweralkyl; and

Y is $C_2$–$C_5$ alkenyl, $C_2C_5$ haloalkenyl, $NH_2$, —NHC(=NH)NH₂ or a heterocyclic ring having 5 ring atoms and also containing one or two double bonds; or a pharmaceutically acceptable salt, ester or prodrug thereof.

22. The compound according to claim 21 having the relative stereochemistry of the formula:

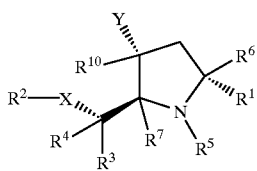

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

23. The enantiomerically enriched compound according to claim 21 having the absolute stereochemistry of the formula:

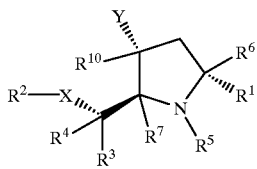

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

24. The compound according to claim 21 having the relative stereochemistry of the formula:

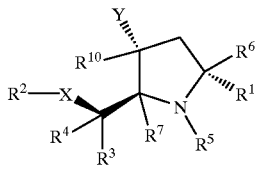

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

25. The enantiomerically enriched compound according to claim 21 having the absolute stereochemistry of the formula:

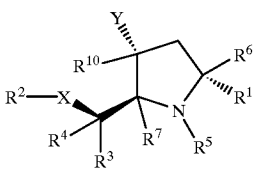

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

26. The compound according to claim 1 wherein R¹ is —CO₂H;

—X—R² is R²—C(=O)—NH—, R²—NH—C(=O)—, R²—NH—SO₂— or R²—SO₂—NH— wherein R² is $C_1$–$C_3$ loweralkyl or halo-$C_1$–$C_3$ loweralkyl;

R⁴ is hydrogen or loweralkyl and R³ is heterocyclic or —Z—R¹⁴ wherein Z and R¹⁴ are defined as therein;

R⁵ is hydrogen;

R⁶ and R⁷ are hydrogen;

R⁸ and R⁹ are hydrogen;

R¹⁰ is hydrogen; and

Y is $C_2$–$C_5$ alkenyl, $C_2$–$C_5$ haloalkenyl, NH₂, —NHC(=NH)NH₂ or a heterocyclic ring having 5 ring atoms and also containing one or two double bonds; or a pharmaceutically acceptable salt, ester or prodrug thereof.

27. The compound according to claim 26 having the relative stereochemistry of the formula;

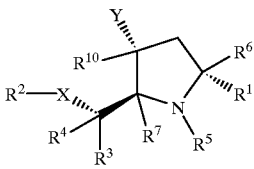

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

28. The enantiomerically enriched compound according to claim 26 having the absolute stereochemistry of the formula:

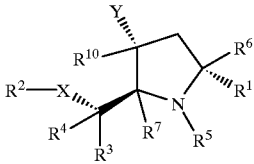

or a pharmaceutically acceptable salt, ester or prodrug thereof, wherein R¹, R², R³, R⁴, R⁵, R⁶, R⁷, R¹⁰, X and Y are as defined therein and wherein R³ and R⁴ are not both the same.

29. The compound according to claim 26 having the relative stereochemistry of the formula:

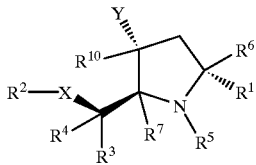

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

30. The enantiomerically enriched compound according to claim 26 having the absolute stereochemistry of the formula:

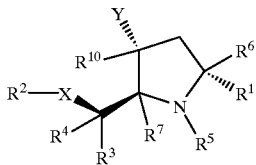

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

31. The compound according to claim 1 wherein $R^1$ is —CO$_2$H;

—Y—R$^2$ is R$^2$—C(=O)—NH—, R$^2$—NH—C(=O)—, R$^2$—NH—SO$_2$— or R$^2$—SO$_2$—NH— wherein R$^2$ is C$_1$–C$_3$ loweralkyl or halo C$_1$–C$_3$ loweralkyl;

$R^4$ is hydrogen or loweralkyl and $R^3$ is (a) heterocyclic, (b) alkyl, (d) cycloalkyl, (d) cycloalkylalkyl, (e) alkenyl, (f) alkynyl, (g) —C(=O)—R$^{14}$, (h) —C(R$^{37a}$)(OR$^{37c}$)—R$^{14}$ or (i) —C(R$^{37a}$)(R$^{37b}$)—N(O)(R$^{37c}$)R$^{14}$ wherein R$^{14}$ is (j) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) (R$^{37a}$O)—(O=)C-substituted alkyl or (xv) (R$^{37a}$O)$_2$—P(=O)-substituted alkyl;

R$^{37a}$ and R$^{37b}$ are independently selected from the group consisting of
(i) hydrogen, (ii) loweralkyl and (iii) loweralkenyl; and
R$^{37c}$ is
hydrogen, (ii) loweralkyl or (iii) loweralkenyl;

$R^5$ is hydrogen;

$R^6$ and $R^7$ are hydrogen;

$R^8$ and $R^9$ are hydrogen;

$R^{10}$ is hydrogen; and

Y is C$_2$–C$_5$ alkenyl, C$_2$–C$_5$ haloalkenyl, NH$_2$, —NHC(=NH)NH$_2$ or a heterocyclic ring having 5 ring atoms and also containing one or two double bonds; or a pharmaceutically acceptable salt, ester or prodrug thereof.

32. The compound according to claim 31 having the relative stereochemistry of the formula:

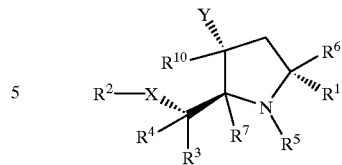

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

33. The enantiomerically enriched compound according to claim 31 having the absolute stereochemistry of the formula:

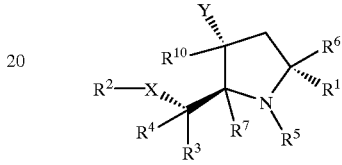

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

34. The compound according to claim 31 having the relative stereochemistry of the formula:

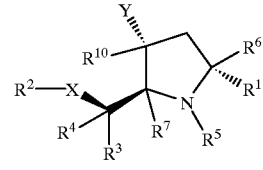

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

35. The enantiomerically enriched compound according to claim 31 having the absolute stereochemistry of the formula:

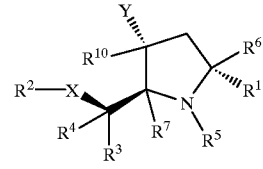

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

36. The compound according to claim 1 wherein $R^1$ is —CO$_2$H;

—X—R$^2$ is R$^2$—C(=O)—NH—, R$^2$—NH—C(=O)—, R$^2$—NH—SO$_2$— or R$^2$—SO$_2$—NH— wherein R$^2$ is C$_1$–C$_3$ loweralkyl or halo C$_1$–C$_3$ loweralkyl;

$R^4$ is hydrogen and $R^3$ is (a) heterocyclic, (b) alkyl or (c) —C(R$^{37a}$)(OR$^{37c}$)—R$^{14}$ wherein R$^{14}$ is (ii) alkyl, (ii) cycloalkyl, (iii) cycloalkylalkyl, (iv) alkenyl, (v) haloalkyl, (vi) haloalkenyl, (vii) aryl, (viii) arylalkyl, (ix) heterocyclic, (x) (heterocyclic) alkyl, (xi) hydroxyalkyl, (xii) alkoxyalkyl, (xiii) cyanoalkyl, (xiv) $(R^{37a}O)$—(O=)C-substituted alkyl or (xv) $(R^{37a}O)_2$—P(=O)-substituted alkyl;

$R^{37a}$ and $R^{37b}$ are independently selected from the group consisting of (i) hydrogen, (ii) loweralkyl and (iii) loweralkenyl; and $R^{37c}$ is hydrogen, (ii) $C_1$–$C_3$ loweralkyl or (iii) allyl;

$R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl, $C_2$–$C_5$ haloalkenyl, $NH_2$, —NHC(=NH)$NH_2$ or a heterocyclic ring having 5 ring atoms and also containing one or two double bonds; or a pharmaceutically acceptable salt, ester or prodrug thereof.

37. The compound according to claim 36 having the relative stereochemistry of the formula:

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

38. The enantiomerically enriched compound according to claim 36 having the absolute stereochemistry of the formula:

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

39. The compound according to claim 36 having the relative stereochemistry of the formula:

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

40. The enantiomerically enriched compound according to claim 36 having the absolute stereochemistry of the formula:

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

41. The compound according to claim 1 wherein $R^1$ is —$CO_2H$;

—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;

$R^4$ is hydrogen and $R^3$ is (a) heterocyclic, (b) alkyl or (c) —C($R^{37a}$)(O$R^{37c}$)—$R^{14}$ wherein $R^{14}$ is (i) loweralkyl, (ii) loweralkenyl, (iii) hydroxy-substituted loweralkyl or (iv) alkoxy-substituted loweralkyl;

$R^{37a}$ is (i) hydrogen, (ii) loweralkyl or (iii) loweralkenyl; and $R^{37c}$ is (i) hydrogen, (ii) $C_1$–$C_3$ loweralkyl or (iii) allyl;

$R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl, $C_2C_5$ haloalkenyl, $NH_2$, —NHC(=NH)$NH_2$ or a heterocyclic ring having 5 ring atoms and also containing one or two double bonds; or a pharmaceutically acceptable salt, ester or prodrug thereof.

42. The compound according to claim 41 having the relative stereochemistry of the formula:

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

43. The enantiomerically enriched compound according to claim 41 having the absolute stereochemistry of the formula:

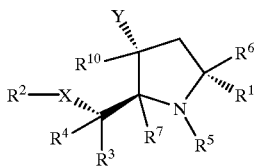

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

44. The compound according to claim 41 having the relative stereochemistry of the formula:

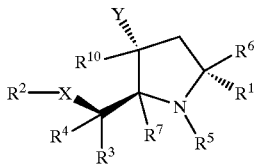

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

45. The enantiomerically enriched compound according to claim 41 having the absolute stereochemistry of the formula:

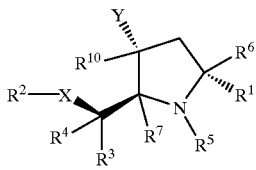

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

46. The compound according to claim 1 wherein $R^1$ is
—$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is

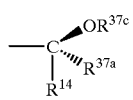

wherein
$R^{14}$ is
  loweralkyl, loweralkenyl or alkoxy-substituted loweralkyl;
$R^{37a}$ is
  loweralkyl or loweralkenyl; and
$R^{37c}$ is
  hydrogen, $C_1$–$C_3$ loweralkyl or allyl;
$R^5$ is hydrogen;
$R^6$ and $R^7$ are hydrogen;

$R^8$ and $R^9$ are hydrogen;
$R^{10}$ is hydrogen; and
Y is $C_2$–$C_5$ alkenyl, $C_2C_5$ haloalkenyl, $NH_2$, —NHC(=NH)$NH_2$ or a heterocyclic ring having 5 ring atoms and also containing one or two double bonds; or a pharmaceutically acceptable salt, ester or prodrug thereof.

47. The compound according to claim 46 having the relative stereochemistry of the formula;

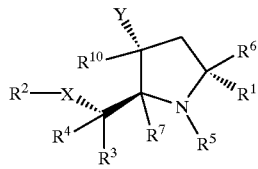

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

48. The enantiomerically enriched compound according to claim 46 having the absolute stereochemistry of the formula:

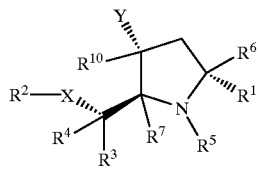

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

49. The compound according to claim 46 having the relative stereochemistry of the formula:

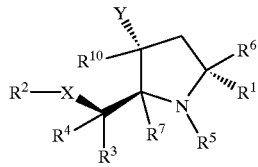

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

50. The enantiomerically enriched compound according to claim 46 having the absolute stereochemistry of the formula:

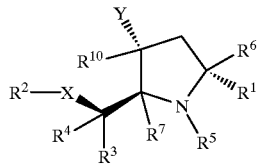

or a pharmaceutically acceptable salt, ester or prodrug thereof, wherein $R^1, R^2, R^3, R^4, R^5, R^6, R^7, R^{10}$, X and Y are as defined therein and wherein $R^3$ and $R^4$ are not both the same.

51. The compound according to claim 1 wherein $R^1$ is
—$CO_2H$;
—X—$R^2$ is $R^2$—C(=O)—NH— or $R^2$—$SO_2$—NH— wherein $R^2$ is $C_1$–$C_3$ loweralkyl or halo $C_1$–$C_3$ loweralkyl;
$R^4$ is hydrogen and $R^3$ is

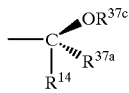

wherein $R^{14}$ is
loweralkyl, loweralkenyl or alkoxy-substituted loweralkyl;

$R^{37a}$ is
loweralkyl or loweralkenyl; and $R^{37c}$ is
hydrogen, $C_1$–$C_3$ loweralkyl or allyl;

$R^5$ is hydrogen;

$R^6$ and $R^7$ are hydrogen;

$R^8$ and $R^9$ are hydrogen;

$R^{10}$ is hydrogen; and

Y is $C_2$–$C_5$ alkenyl: or a pharmaceutically acceptable salt, ester or prodrug thereof.

52. The compound according to claim 51 having the relative stereochemistry of the formula:

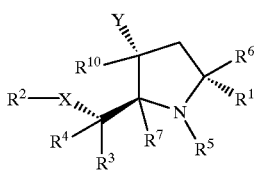

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

53. The enantiomerically enriched compound according to claim 51 having the absolute stereochemistry of the formula:

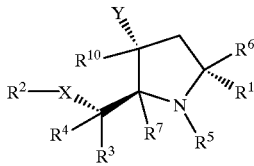

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

54. The compound according to claim 51 having the relative stereochemistry of the formula:

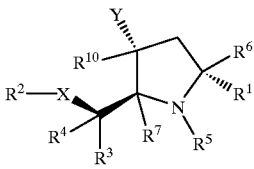

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

55. The enantiomerically enriched compound according to claim 51 having the absolute stereochemistry of the formula:

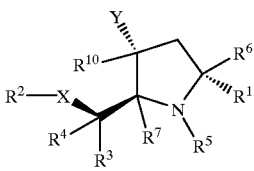

or a pharmaceutically acceptable salt, ester or prodrug thereof, wherein $R^1$, $R^2$, $R^3$, $R^4$, $R^5$, $R^6$, $R^7$, $R^{10}$, X and Y are as defined therein and wherein $R^3$ and $R^4$ are not both the same.

56. The compound according to claim 1 having the indicated relative stereochemistry selected from the group consisting of:

(±)-(2R,3S,5R,1'R)-2-(1-Acetamido-2-ethyl-2-hydroxy)butyl-3-(cis-propen-1-yl)-pyrrolidine-5-carboxylic Acid;

(±)-(2R,3S,5R,1'R,2'S)-2-(1-Acetamido-2-hydroxy-2-methyl)pentyl-3-(cis-propen-1-yl)-pyrrolidine-5-carboxylic Acid;

(±)-(2R,3S,5R,1'R,2'S)-2-(1-Acetamido-2-ethyl-2-hydroxy)pentyl-3-(cis-propen-1-yl)-pyrrolidine-5-carboxylic Acid;

(±)-(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;

(±)-(2R,3R,5R,1'R,2'R)-2-(1-Acetamido-2,3-dihydroxy)propyl-3-(cis-propen-1-yl)-pyrrolidine-5-carboxylic Acid;

(±)-(2R,3S,5R,1'R,2'S)-2-(1-Acetamido-2-hydroxy-4-vinyl)butyl-3-(cis-propen-1-yl)-pyrrolidine-5-carboxylic Acid;

(−)-(2R,3S,5R,1'S)-2-(1-Acetamido-2-hydroxy)butyl-3-(cis-propen-1-yl)-pyrrolidine-5-carboxylate Ammonium Salt;

(±)-(2R,3S,5R,1'R,2'R)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-methoxy-2-vinyl)ethyl-3-(cis-propen-1-yl)-pyrrolidine-5-carboxylic Acid;

(±)-(2R,3S,5R,1'S)-2-(1-Acetamido-2-ethyl)butyl-3-(cis-propen-1-yl)-pyrrolidine-5-carboxylic Acid;

(±)-(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;

(±)-(2R,3S,5R,1'R,2'S)-2-(1-Acetamido-2-methoxy)butyl-3-(cis-propen-1-yl)-pyrrolidine-5-carboxylic Acid;

(±)-(2R,3S,5R,1'R,2'S)-2-(1-Acetamido-2-methoxy)pentyl-3-(cis-propen-1-yl)-pyrrolidine-5-carboxylic Acid;
(±)-(2R,3R,5R,1'R,2'S)-2-(1-Acetamido-2-hydroxy)butyl-3-(pyrazol-3-yl)-pyrrolidine-5-carboxylic Acid;
(±)(2R,3S,5R,1'R,2'S)-2-(1-Aceamido-2-hydroxy)butyl-3-(cis-propen-1-yl)-pyrrolidine-5-carboxylic Acid;
(±)-(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;
(±)-(2R,3S,5R,1'R,2'S)-2-(1-Acetamido-2-methoxy-2-allyl)ethyl-3-(cis-propen-1-yl)-pyrrolidine-5-carboxylic Acid;
(±)-(2R,3S,5R,1'R,2'S,3'S)-2-(1-Acetamido-2-hydroxy-3-methyl)pentyl-3-(cis-propen-1-yl)-pyrrolidine-5-carboxylic Acid;
(±)-(2R,3S,5R,1'R,2'S)-2-(1-Acetamido-2-methoxy-4-vinyl)butyl-3-(cis-propen-1-yl)-pyrrolidine-5-carboxylic Acid;
(±)-(2R,3S,5R,1'R,2'S)-2-(1-Acetamido-2-hydroxy-3-cyano)propyl-3-(cis-propen-1-yl)-pyrrolidine-5-carboxylic Acid;
(±)-(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;
(±)-(2R,3S,5 R,1'R,2'S)-2-(1-Acetamido-2,3-dimethoxy)propyl-3-(cis-propen-1-yl)-pyrrolidine-5-carboxylic Acid;
(±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid;
(±)-(2R,3S,5R,1'R,2'S)-2-(1-Acetamido-2-ethoxy)pentyl-3-(cis-propen-1-yl)-pyrrolidine-5-carboxylic Acid;
(±)-(2R,3S,5R,1'R,2'S)-2-(1-Acetamido-2-hydroxy-3-dimethyl)butyl-3-(cis-propen-1-yl)-pyrrolidine-5-carboxylic Acid;
(±)-(2R,3S,5R,1'R,2'S)-2-(1-Acetamido-2-ethoxy-3-vinyl)propyl-3-(cis-propen-1-yl)-pyrrolidine-5-carboxylic Acid;
(±)-(2R,3S,5R,1'R,2'S)-2-(1-Acetamido-2-hydroxy-2-(propeny-2-yl))ethyl-3-(cis-propen-1-yl)-pyrrolidine-5-carboxylic Acid;
(±)-(2R,3S,5R,1'R,2'S)-2-(1-Acetamido-2-hydroxy)hexyl-3-(cis-propen-1-yl)-pyrrolidine-5-carboxylic Acid;
(±)-(2R,3S,5R,1'S)-2-(1-acetamido-3-methyl)butyl-3-(cis-propen-1-yl)-pyrrolidine-5-carboxylic Acid;
(±)-(2R,3S,5R,1'R,2'S)-2-(1-Acetamido-2-hydroxy)butyl-3-vinyl-pyrrolidine-5-carboxylic Acid;
(±)-(2R,3S,5R,1'R,2'S)-2-(1-Acetamido-2-hydroxy)pentyl-3-vinyl-pyrrolidine-5-carboxylic Acid;
(±)-(2R,3S,5R,1'R,2'R)-2-(1-Acetamido-2-hydroxyethyl-2-hydroxy)pentyl-3-(cis-propen-1-yl)-pyrrolidine-5-carboxylic Acid;
(±)-(2R,3S,5R,1'R,2'R)-2-(1-Acetamido-2-hydroxy)butyl-3-vinyl-pyrrolidine-5-carboxylic Acid;
(±)-(2R,3S,5R,1'R,2'R)-2-(1-Acetamido-2-methoxy)pentyl-3-(cis-propen-1-yl)-pyrrolidine-5-carboxylic Acid;
(±)-(2R,3S,5R,1'R,2'R)-2-(1-Acetamido-2-hydroxy)pentyl-3-vinyl-pyrrolidine-5-carboxylic Acid;
(±)-(2R,3S,5R,1'R)-2-(1-Acetamido-2-hydroxy)ethyl-3-(cis-propen-1-yl)-pyrrolidine-5-carboxylic Acid;
(±)-(2R,3S,5R,1'S)-2-(1-acetamido-3-methyl)butyl-3-(cis-2-chloro-vin-1-yl)-pyrrolidine-5-carboxylic Acid;
(±)-(2R,3R,5R,1'S)-2-(1-acetamido-3-methyl)butyl-3-(pyrazol-3-yl)-pyrrolidine-5-carboxylic Acid;
(±)-(2R,3S,5R,1'S,3'R)-2-(1-Acetamido-3-hydroxy)pentyl-3-(cis-propen-1-yl)-pyrrolidine-5-carboxylic Acid;
(±)-(2R,3R,5R,1'S)-2-(1-Acetamido-3-methyl)butyl-3-(thiazol-4-yl)-pyrrolidine-5-carboxylic Acid;
(±)-(2R,3R,5R,1'S)-1-t-Butoxycarbonyl-2-(1-acetamido-3-methyl)butyl-3-(thiazol-2-yl)-pyrrolidine-5-carboxylic Acid;
(±)-(2R,3S,5R,1'S)-2-(1-Acetamido-3-methyl)butyl-3-vinyl-pyrrolidine-5-carboxylic Acid;
(±)-(2R,3S,5R,1'S)-2-(1-acetamido-3-methyl)butyl-3-(2,2-difluoro-vin-1-yl)-pyrrolidine-5-carboxylic Acid;
(±)-(2R,3R,5R,1'S)-2-(1-acetamido-3-methyl)butyl-3-(pyrazol-3-yl)-pyrrolidine-5-carboxylic Acid;
(±)-(2R,3R,5R,1'S)-2-(1-acetamido-3-methyl)butyl-3-(isoxazol-3-yl)-pyrrolidine-5-carboxylic Acid;
(±)-(2R,3R,5R,1'S)-2-(1-acetamido-3-methyl)butyl-3-(isoxazol-5-yl)-pyrrolidine-5-carboxylic Acid;
(±)-(2R,3R,5R,1'S)-2-(1-Acetamido-3-methyl)butyl-3-(imidazol-2-yl)-pyrrolidine-5-Carboxylic Acid;
(±)-(2R,3R,5R,1'S)-2-(1-Acetamido-3-methyl)butyl-3-(imidazol-4-yl)-pyrrolidine-5-carboxylic Acid;
(±)-(2S,3R,5R,1'S)-2-(1-acetamido-3-methyl)butyl-3-amino-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;
(±)-(2R,3S,5R,1'R,2'S)-2-(1-Acetamido-2-vinyl-2-methoxy)pentyl-5-(cs-propen-1-yl)-pyrrolidine-5-carboxylic Acid;
(±)-(2R,3S,5R,1'R)-2-(1-Acetamido-2-ethyl-2-methoxy)butyl-3-(cis-propen-1-yl)-pyrrolidine-5-carboxylic Acid;
(±)-(2R,3S,5R,1'R,2'S)-2-(1-Acetamido-2-methyl-2,3-dimethoxy)propyl-3-(cis-propen-1-yl)-pyrrolidine-5-carboxylic Acid; and
(±)-(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

57. The enantiomerically enriched compound according to claim 1 having the indicated absolute stereochemistry selected from the group consisting of:
(2R,3S,5R,1'R)-2-(1-Acetamido-2-ethyl-2-hydroxy)butyl-3-(cis-propen-1-yl)-pyrrolidine-5-carboxylic Acid;
(2R,3S,5R,1'R,2')-2-(1-Acetamido-2-hydroxy-2-methyl)pentyl-3-(cis-propen-1-yl)-pyrrolidine-5-carboxylic Acid;
(2R,3S,5R,1'R,2'S)-2-(1-Acetamido-2-ethyl-2-hydroxy)pentyl-3-(cis-propen-1-yl)-pyrrolidine-5-carboxylic Acid;
(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;
(2R,3R,5R,1'R,2'R)-2-(1-Acetamido-2,3-dihydroxy)propyl-3-(cis-propen-1-yl)-pyrrolidine-5-carboxylic Acid;
(2R,3S,5R,1'R,2'S)-2-(1-Acetamido-2-hydroxy-4-vinyl)butyl-3-(cis-propen-1-yl)-pyrrolidine-5-carboxylic Acid;
(2R,3S,5R,1'S)-2-(1-Acetamido-2-hydroxy)butyl-3-(cis-propen-1-yl)-pyrrolidine-5-carboxylate Ammonium Salt;
(2R,3S,5R,1'R,2'R)-2-(1-Acetamido-2,3-dimethoxy)propyl-3-(cis-propen-1-yl)-pyrrolidine-5-carboxylic Acid;
(2R,3S,5R,1'R,2'S)-2-(1-Acetamido-2-methoxy-2-vinyl)ethyl-3-(cis-propen-1-yl)-pyrrolidine-5-carboxylic Acid;
(2R,3S,5R,1'S)-2-(1-Acetamido-2-ethyl)butyl-3-(cis-propen-1-yl)-pyrrolidine-5-carboxylic Acid;
(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;

(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;

(2R,3S,5R,1'R,2'S)-2-(1-Acetamido-2-methoxy)butyl-3-(cis-propen-1-yl)-pyrrolidine-5-carboxylic Acid;

(2R,3S,5R,1'R,2'S)-2-(1-Acetamido-2-methoxy)pentyl-3-(cis-propen-1-yl)-pyrrolidine-5-carboxylic Acid;

(2R,3R,5R,1'R,2'S)-2-(1-Acetamido-2-hydroxy)butyl-3-(pyrazol-3-yl)-pyrrolidine-5-carboxylic Acid;

(2R,3S,5R,1'R,2'S)-2-(1-Acetamido-2-hydroxy)butyl-3-(cis-propen-1-yl)-pyrrolidine-5-carboxylic Acid;

(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;

(2R,3S,5R,1'R,2'S)-2-(1-Acetamido-2-methoxy-2-allyl)ethyl-3-(cis-propen-1-yl)-pyrrolidine-5-carboxylic Acid;

(2R,3S,5R,1'R,2'S,3'S)-2-(1-Acetamido-2-hydroxy-3-methyl)pentyl-3-(cis-propen-1-yl)-pyrrolidine-5-carboxylic Acid;

(2R,3S,5R,1'R,2'S)-2-(1-Acetamido-2-methoxy-4-vinyl)butyl-3-(cis-propen-1-yl)-pyrrolidine-5-carboxylic Acid;

(2R,3S,5R,1'R,2'S)-2-(1-Acetamido-2-hydroxy-3-cyano)propyl-3-(cis-propen-1-yl)-pyrrolidine-5-carboxylic Acid;

(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;

(2R,3S,5R,1'R,2'S)-2-(1-Acetamido-2,3-dimethoxy)propyl-3-(cis-propen-1-yl)-pyrrolidine-5-carboxylic Acid;

(2R,3S,5R,1'R,2'S)-2-(1-Acetamido-2-hydroxymethyl-2-hydroxy)pentyl-3-(cis-propen-1-yl)-pyrrolidine-5-carboxylic Acid;

(2R,3S,5R,1'R,2'S)-2-(1-Acetamido-2-ethoxy)pentyl-3-(cis-propen-1-yl)-pyrrolidine-5-carboxylic Acid;

(2R,3S,5R,1'R,2'S)-2-(1-Acetamido-2-hydroxy-3-dimethyl)butyl-3-(cis-propen-1-yl)-pyrrolidine-5-carboxylic Acid;

(2R,3S,5R,1'R,2'S)-2-(1-Acetamido-2-ethoxy-3-vinyl)propyl-S-(cis-propen-1-yl)-pyrrolidine-5-carboxylic Acid;

(2R,33,5R,1'R,2'S)-2-(1-Acetamido-2-hydroxy-2-(propeny-2-yl))ethyl-3-(cis-propen-1-yl)-pyrrolidine-5-carboxylic Acid;

(2R,3S,5R,1'R,2'S)-2-(1-Acetamido-2-hydroxy)hexyl-3-(cis-propen-1-yl)-pyrrolidine-5-carboxylic Acid;

(2R,3S,5R,1'S)-2-(1-acetamido-3-methyl)butyl-3-(cis-propen-1-yl)-pyrrolidine-5-carboxylic Acid;

(2R,3S,5R,1'R,2'S)-2-(1-Acetamido-2-hydroxy)butyl-3-vinyl-pyrrolidine-5-carboxylic Acid;

(2R,3S,5R,1'R,2'S)-2-(1-Acetamido-2-hydroxy)pentyl-3-vinyl-pyrrolidine-5-carboxylic Acid;

(2R,3R,5R,1'R,2'R)-2-(1-Acetamido-2-hydroxy)pentyl-3-(cis-propen-1-yl)-pyrrolidine-5-carboxylic Acid;

(2R,3S,5R,1'R,2'R)-2-(1-Acetamido-2-hydroxy)butyl-3-vinyl-pyrrolidine-5-carboxylic Acid;

(2R,3S,5R,₁'R,2'R)-2-(1-Acetamido-2-methoxy)pentyl-3-(cis-propen-1-yl)-pyrrolidine-5-carboxylic Acid;

(2R,3S,5R,1'R,2'R)-2-(1-Acetamido-2-hydroxy)pentyl-3-vinyl-pyrrolidine-5-carboxylic Acid;

(2R,3S,5R,1'R)-2-(1-Acetamido-2-hydroxy)ethyl-3-(cis-propen-1-yl)-pyrrolidine-5-carboxylic Acid;

(2R,3S,5R,1'S)-2-(1-acetamido-3-methyl)butyl-3-(cis-2-chloro-vin-1-yl)-pyrrolidine-5-carboxylic Acid;

(2R,3R,5R,1'S)-2-(1-acetamido-3-methyl)butyl-3-(pyrazol-3-yl)-pyrrolidine-5-carboxylic Acid;

(2R,3S,5R,1'S,3'R)-2-(1-Acetamido-3-hydroxy)pentyl-3-(cis-propen-1-yl)-pyrrolidine-5-carboxylic Acid;

(2R,3R,5R,1'S)-2-(1-Acetamido-3-methyl)butyl-3-(thiazol-4-yl)-pyrrolidine-5-carboxylic Acid;

(2R,3R,5R,1'S)-1-t-Butoxycarbonyl-2-(1-acetamido-3-methyl)butyl-3-(thiazol-2-yl)-pyrrolidine-5-carboxylic Acid;

(2R,3S,5R,1'S)-2-(1-Acetamido-3-methyl)butyl-3-vinyl-pyrrolidine-5-carboxylic Acid;

(2R,3S,5R,1'S)-2-(1-acetamido-3-methyl)butyl-3-(2,2-difluoro-vin-1-yl)-pyrrolidine-5-carboxylic Acid;

(2R,3R,5R,1'S)-2-(1-acetamido-3-methyl)butyl-3-(pyrazol-3-yl)-pyrrolidine-5-carboxylic Acid;

(2R,3R,5R,1'S)-2-(1-acetamido-3-methyl)butyl-3-(isoxazol-3-yl)-pyrrolidine-5-carboxylic Acid;

(2R,3R,5R,₁'S)-2-(1-acetamido-3-methyl)butyl-3-(isoxazol-5-yl)-pyrrolidine-5-carboxylic Acid;

(2R,3R,5R,1'S)-2-(1-Acetamido-3-methyl)butyl-3-(imidazol-2-yl)-pyrrolidine-5-Carboxylic Acid;

(2R,3R,5R,1'S)-2-(1-Acetamido-3-methyl)butyl-3-(imidazol-4-yl)-pyrrolidine-5-carboxylic Acid;

(2S,3R,5R,1'S)-2-(1-acetamido-3-methyl)butyl-3-amino-pyrrolidine-5-carboxylic Acid;

(2R,3S,5R,1'R,2'S)-2-(1-Acetamido-2-methyl-2-methoxy)pentyl-3-(cis-propen-1-yl)-pyrrolidine-5-carboxylic Acid;

(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;

(2R,3S,5R,1'R,2'S)-2-(1-Acetamido-2-vinyl-2-methoxy)pentyl-3-(cis-propen-1-yl)-pyrrolidine-5-carboxylic Acid;

(2R,3S,5R,1'R)-2-(1-Acetamido-2-ethyl-2-methoxy)butyl-3-(cis-propen-1-yl)-pyrrolidine-5-carboxylic Acid;

(2R,3S,5R,1'R,2'S)-2-(1-Acetamido-2-methyl-2,3-dimethoxy)propyl-3-(cis-propen-1-yl)-pyrrolidine-5-carboxylic Acid; and (2R,3S,5R,1'R,2'S)-2-(1-Acetamido-2-methyl-2-methoxy)butyl-3-(cis-propen-1-yl)-pyrrolidine-5-carboxylic Acid;

or a pharmaceutically acceptable salt, ester or prodrug thereof.

58. The compound according to claim 1 having the indicated relative stereochemistry selected from the group consisting of:

(±)-(2R,3S,5R,1'R)-2-(1-Acetamido-2-ethyl-2-hydroxy)butyl-3-(cis-propen-1-yl)-pyrrolidine-5-carboxylic Acid;

(±)-(2R,3S,5R,1'R,2'S)-2-(1-Acetamido-2-hydroxy-2-methyl)pentyl-3-(cis-propen-1-yl)-pyrrolidine-5-carboxylic Acid;

(±)-(2R,3S,5R,1'R,2'S)-2-(1-Acetamido-2-ethyl-2-hydroxy)pentyl-3-(cis-propen-1-yl)-pyrrolidine-5-carboxylic Acid;

(±)-(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;

(±)-(2R,3R,5R,1'R,2'R)-2-(1-Acetamido-2,3-dihydroxy)propyl-3-(cis-propen-1-yl)-pyrrolidine-5-carboxylic Acid;

(±)-(2R,3S,5R,1'R,2'S)-2-(1-Acetamido-2-hydroxy-4-vinyl)butyl-3-(cis-propen-1-yl)-pyrrolidine-5-carboxylic Acid;

(−)-(2R,3S,5R,1'S)-2-(1-Acetamido-2-ethyl)butyl-3-(cis-propen-1-yl)-pyrrolidine-5-carboxylate Ammonium Salt;

(±)-(2R,3S,5R,1'R,2'R)-2-(1-Acetamido-2,3-dimethoxy)propyl-3-(cis-propen-1-yl)-pyrrolidine-5-carboxylic Acid;

(±)-(2R,3S,5R,1'R,2'S)-2-(1-Acetamido-2-methoxy-2-vinyl)ethyl-3-(cis-propen-1-yl)-pyrrolidine-5-carboxylic Acid;

(±)-(2R,3S,5R,1'S)-2-(1-Acetamido-2-ethyl)butyl-3-(cis-propen-1-yl)-pyrrolidine-5-carboxylic Acid;

(±)-(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;

(±)-(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;
(±)-(2R,3S,5R,1'R,2'S)-2-(1-Acetamido-2-methoxy)butyl-3-(cis-propen-1-yl)-pyrrolidine-5-carboxylic Acid;
(±)-(2R,3S,5R,1'R,2'S)-2-(1-Acetamido-2-methoxy)pentyl-3-(cis-propen-1-yl)-pyrrolidine-5-carboxylic Acid;
(±)-(2R,3R,5R,1'R,2'S)-2-(1-Acetamido-2-hydroxy)butyl-3-(pyrazol-3-yl)-pyrrolidine-5-carboxylic Acid;
(±)-(2R,3S,5R,1'R,2'S)-2-(1-Acetamido-2-hydroxy)butyl-3-(cis-propen-1-yl)-pyrrolidine-5-carboxylic Acid;
(±)-(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;
(±)-(2R,3S,5R,1'R,2'S)-2-(1-Acetamido-2-methoxy-2-allyl)ethyl-3-(cis-propen-1-yl)-pyrrolidine-5-carboxylic Acid;
(±)-(2R,3S,5R,1'R,2'S,3'S)-2-(1-Acetamido-2-hydroxy-3-methyl)pentyl-3-(cis-propen-1-yl)-pyrrolidine-5-carboxylic Acid;
(±)-(2R,3S,5R,1'R,2'S)-2-(1-Acetamido-2-methoxy-4-vinyl)butyl-3-(cis-propen-1-yl)-pyrrolidine-5-carboxylic Acid;
(±)-(2R,3S,5R,1'R,2'S)-2-(1-Acetamido-2-hydroxy-3-cyano)propyl-3-(cis-propen-1-yl)-pyrrolidine-5-carboxylic Acid;
(±)-(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;
(±)-(2R,3S,5R,1'R,2'S)-2-(1-Acetamido-2,3-dimethoxy)propyl-3-(cis-propen-1-yl)-pyrrolidine-5-carboxylic Acid;
(±)-(2R,3S,5R,1'R,2'S)-2-(1-Acetamido-2-hydroxymethyl-2-hydroxy)pentyl-3-(cis-propen-1-yl)-pyrrolidine-5-carboxylic Acid;
(±)-(2R,3S,5R,1'R,2'S)-2-(1-Acetamido-2-ethoxy)pentyl-3-(cis-propen-1-yl)-pyrrolidine-5-carboxylic Acid;
(±)-(2R,3S ,5R,1'R,2'S)-2-(1-Acetamido-2-hydroxy-3-dimethyl)butyl-3-(cis-propen-1-yl)-pyrrolidine-5-carboxylic Acid;
(±)-(2R,3S,5R,1'R,2'S)-2-(1-Acetamido-2-ethoxy-3-vinyl)propyl-3-(cis-propen-1-yl)-pyrrolidine-5-carboxylic Acid;
(±)-(2R,3S,5R,1'R,2'S)-2-(1-Acetamido-2-hydroxy-2-(propeny-2-yl))ethyl-3-(cis-propen-1-yl)-pyrrolidine-5-carboxylic Acid;
(±)-(2R,3S,5R,1'R,2'S)-2-(1-Acetamido-2-hydroxy)hexyl-3-(cis-propen-1-yl)-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;
(±)-(2R,3S,5R,1R,2'S)-2-(1-Acetamido-2-vinyl-2-methoxy)pentyl-3-(cis-propen-1-yl)-pyrrolidine-5-carboxylic Acid;
(±)-(2R,3S,5R,1'R)-2-(1-Acetamido-2-ethyl-2-methoxy)butyl-3-(cis-propen-1-yl)-pyrrolidine-5-carboxylic Acid;
(±)-(2R,3S,5R,1'R,2'S)-2-(1-Acetamido-2-methyl-2,3-dimethoxy)propyl-3-(cis-propen-1-yl)-pyrrolidine-5-carboxylic Acid; and
(±)-(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

59. The enantiomerically enriched compound according to claim 1 having the indicated absolute stereochemistry selected from the group consisting of:

(2R,3S,5R,1'R)-2-(1-Acetamido-2-ethyl-2-hydroxy)butyl-3-(cis-propen-1-yl)-pyrrolidine-5-carboxylic Acid;
(2R,3R,5R,1'R,2'S)-2-(1-Acetamido-2-hydroxy-2-methyl)pentyl-3-(cis-propen-1-yl)-pyrrolidine-5-carboxylic Acid;
(2R,3S,5R,1'R,2'S)-2-(1-Acetamido-2-ethyl-2-hydroxy)pentyl-3-(cis-propen-1-yl)-pyrrolidine-5-carboxylic Acid;
(2R,3S,5R,1'R,2'S)-2-(1-Acetamido-2-hydroxy)pentyl-3-(cis-propen-1-yl)-pyrrolidine-5-carboxylic Acid Trifluoroacetic Acid Salt;
(2R,3R,5R,1'R,2'R)-2-(1-Acetamido-2,3-dihydroxy)propyl-3-(cis-propen-1-yl)-pyrrolidine-5-carboxylic Acid;
(2R,3S,5R,1'R,2'S)-2-(1-Acetamido-2-hydroxy-4-vinyl)butyl-3-(cis-propen-1-yl)-pyrrolidine-5-carboxylic Acid;
(−)-(2R,3S,5R,1'R,2'S)-2-(1-Acetamido-2-ethyl)butyl-3-(cis-propen-1-yl)-pyrrolidine-5-carboxylate Ammonium Salt;
(2R,3S,5R,1'R,2'R)-2-(1-Acetamido-2,3-dimethoxy)propyl-3-(cis-propen-1-yl)-pyrrolidine-5-carboxylic Acid;
(2R,3S,5R,1'R,2'S)-2-(1-Acetamido-2-methoxy-2-vinyl)ethyl-3-(cis-propen-1-yl)-pyrrolidine-5-carboxylic Acid;
(2R,3S,5R,1'S)-2-(1-Acetamido-2-ethyl)butyl-3-(cis-propen-1-yl)-pyrrolidine-5-carboxylic Acid;
(2R,3S,5R,1'S,3'S)-2-(1-Acetamido-2-(N-isopropyl-N-methylamino-N-oxide))ethyl-3-(cis-propen-1-yl)-pyrrolidine-5-carboxylic Acid;
(2R,3S,5R,1'S,3'S)-2-(1-Acetamido-2-(N-ethyl-N-methylamino-N-oxide))ethyl-3-(cis-propen-1-yl)-pyrrolidine-5-carboxylic Acid;
(2R,3S,5R,1'R,2'S)-2-(1-Acetamido-2-methoxy)butyl-3-(cis-propen-1-yl)-pyrrolidine-5-carboxylic Acid;
(2R,3S,5R,1'R,2'S)-2-(1-Acetamido-2-methoxy)pentyl-3-(cis-propen-1-yl)-pyrrolidine-5-carboxylic Acid;
(2R,3R,5R,1'R,2'S)-2-(1-Acetamido-2-hydroxy)butyl-3-(pyrazol-3-yl)-pyrrolidine-5-carboxylic Acid;
(2R,3S,5R,1'R,2'S)-2-(1-Acetamido-2-hydroxy)butyl-3-(cis-propen-1-yl)-pyrrolidine-5-carboxylic Acid;
(2R,3S,5R,1'R,2'R)-2-(1-Acetamido-1-(3,6-dihydro-2-H-pyran-2-yl))propyl-3-(cis-propen-1-yl)-pyrrolidine-5-carboxylic Acid;
(2R,3S,5R,1'R,2'S)-2-(1-Acetamido-2-methoxy-2-allyl)ethyl-3-(cis-propen-1yl)-pyrrolidine-5-carboxylic Acid;
(2R,3S,5R,1'R,2'S,3'S)-2-(1-Acetamido-2-hydroxy-3-methyl)pentyl-3-(cis-propen-1-yl)-pyrrolidine-5-carboxylic Acid;
(2R,3S,5R,1'R,2'S)-2-(1-Acetamido-2-methoxy-4-vinyl)butyl-3-(cis-propen-1-yl)-pyrrolidine-5-carboxylic Acid;
(2R,3S,5R,1'R,2'S)-2-(1-Acetamido-2-hydroxy-3-cyano)propyl-3-(cis-propen-1-yl)-pyrrolidine-5-carboxylic Acid;
(2R,3S,5R,1'R,2'S)-2-(1-Acetamido-1-(3,6-dihydro-2-H-pyran-2-yl))methyl-3-(cis-propen-1-yl)-pyrrolidine-5-carboxylic Acid;
(2R,3S,5R,1'R,2'S)-2-(1-Acetamido-2,3-dimethoxy)propyl-3-(cis-propen-1-yl)-pyrrolidine-5-carboxylic Acid;
(2R,3S,5R,1'R,2'S)-2-(1-Acetamido-2-hydroxymethyl-2-hydroxy)pentyl-3-(cis-propen-1-yl)-pyrrolidine-5-carboxylic Acid;
(2R,3S,5R,1'R,2'S)-2-(1-Acetamido-2-ethoxy)pentyl-3-(cis-propen-1-yl)-pyrrolidine-5-carboxylic Acid;
(2R,3S,5R,1'R,2'S)-2-(1-Acetamido-2-hydroxy-3-dimethyl)butyl-3-(cis-propen-1-yl)-pyrrolidine-5-carboxylic Acid;
(2R,3S,5R,1'R,2'S)-2-(1-Acetamido-2-ethoxy-3-vinyl)propyl-3-(cis-propen-1-pyrrolidine-5-carboxylic Acid;
(2R,3S,5R,1'R,2'S)-2-(1-Acetamido-2-hydroxy-2-(propeny-2-yl))ethyl-3-(cis-propen-1-yl)-pyrrolidine-5-carboxylic Acid;

(2R,3S,5R,1'R,2'S)-2-(1-Acetamido-2-hydroxy)hexyl-3-(cis-propen-1-yl)-pyrrolidine-5-carboxylic Acid;
(2R,3S,5R,1'R,2'S)-2-(1-Acetamido-2-methyl-2-methoxy)pentyl-3-(cis-propen-1-yl)-pyrrolidine-5-carboxylic Acid;
(2R,3S,5R,1'R,2'S)-2-(1-Acetamido-2-methyl-2-methoxy)pentyl-3-(cis-propen-1-yl)-pyrrolidine-5-carboxylic Acid Ethyl Ester:
(2R,3S,5R,1'R,2'S)-2-(1-Acetamido-2-vinyl-2-methoxy)pentyl-3-(cis-propen-1-yl)-pyrrolidine-5-carboxylic Acid;
(2R,3S,5R,1'R)-2-(1-Acetamido-2-ethyl-2-methoxy)butyl-3-(cis-propen-1-yl)-pyrrolidine-5-carboxylic Acid;
(2R,3S,5R,1'R,2'S)-2-(1-Acetamido-2-methyl-2,3-dimethoxy)propyl-3-(cis-propen-1-yl)-pyrrolidine-5-carboxylic Acid; and
(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

60. The compound according to claim 1 having the indicated relative stereochemistry selected from the group consisting of:
(±)-(2R,3S,5R,1'R,2'S)-2-(1-Acetamido-2-methyl-2-methoxy)pentyl-3-(cis-propen-1-yl)-pyrrolidine-5-carboxylic Acid;
(±)-(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;
(±)-(2R,3S,5R,1'R,2'S)-2-(1-Acetamido-2-vinyl-2-methoxy)pentyl-3-(cis-propen-1-yl)-pyrrolidine-5-carboxylic Acid;
(±)-(2R,3S,5R,1'R)-2-(1-Acetamido-2-ethyl-2-methoxy)butyl-3-(cis-propen-1-yl)-pyrrolidine-5-carboxylic Acid;
(±)-(2R,3S,5R,1'R,2'S)-2-(1-Acetamido-2-methyl-2,3-dimethoxy)propyl-3-(cis-propen-1-yl)-pyrrolidine-5-carboxylic Acid; and
(±)-(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

61. The enantiomerically enriched compound according to claim 1 having the indicated absolute stereochemistry selected from the group consisting of:
(−)-(2R,3S,5R,1'R,2'S)-2-(1-Acetamido-2-methyl-2-methoxy)pentyl-3-(cis-propen-1-yl)-pyrrolidine-5-carboxylic Acid;
(−)-(2R,3S,5R,1'R,2'S)-2-(1-Acetamido-2-methyl-2-methoxy)pentyl-3-(cis-propen-1-yl)-pyrrolidine-5-carboxylic Acid Ethyl Ester;
(2R,3S,5R,1'R,2'S)-2-(1-Acetamido-2-vinyl-2-methoxy)pentyl-3-(cis-propen-1-yl)-pyrrolidine-5-carboxylic Acid;
(2R,3S,5R,1'R)-2-(1-Acetamido-2-ethyl-2-methoxy)butyl-3-(cis-propen-1-yl)-pyrrolidine-5-carboxylic Acid;
(2R,3S,5R,1'R,2'S)-2-(1-Acetamido-2-methyl-2,3-dimethoxy)propyl-3-(cis-propen-1-yl)-pyrrolidine-5-carboxylic Acid; and
(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt, ester or prodrug thereof.

62. The enantiomerically enriched esters or prodrugs of the compound according to claim 1 having the indicated absolute stereochemistry selected from the group consisting of:
(−)-(2R,3S,5R,1'R,2'S)-2-(1-Acetamido-2-methyl-2-methoxy)pentyl-3-(cis-propen-1-yl)-pyrrolidine-5-carboxylic Acid;
(2R,3S,5R,1'R,2'S)-2-(1-Acetamido-2-vinyl-2-methoxy)pentyl-3-(cis-propen-1-yl)-pyrrolidine-5-carboxylic Acid;
(2R,3S,5R,1'R)-2-(1-Acetamido-2-ethyl-2-methoxy)butyl-3-(cis-propen-1-yl)-pyrrolidine-5-carboxylic Acid;
(2R,3S,5R,1'R,2'S)-2-(1-Acetamido-2-methyl-2,3-dimethoxy)propyl-3-(cis-propen-1-yl)-pyrrolidine-5-carboxylic Acid; and
(2R,3S,5R,1'R,2'S)-2-(1-Acetamido-2-methyl-2-methoxy)butyl-3-(cis-propen-1-yl)-pyrrolidine-5-carboxylic Acid;
or a pharmaceutically acceptable salt thereof.

63. The enantiomerically enriched esters or prodrugs of the compound having the indicated absolute stereochemistry:
(−)-(2R,3S,5R,1'R,2'S)-2-(1-Acetamido-2-methyl-2-methoxy)pentyl-3-(cis-propen-1-yl)-pyrrolidine-5-carboxylic Acid;
or a pharmaceutically acceptable salt thereof.

64. A pharmaceutical composition comprising a pharmaceutical carrier and a therapeutically effective amount of a compound of claim 1.

65. A pharmaceutical composition comprising a pharmaceutical carrier and a therapeutically effective amount of a compound of claim 51.

66. A pharmaceutical composition comprising a pharmaceutical carrier and a therapeutically effective amount of a compound of claim 57.

67. A pharmaceutical composition comprising a pharmaceutical carrier and a therapeutically effective amount of a compound of claim 62.

68. A pharmaceutical composition comprising a pharmaceutical carrier and a therapeutically effective amount of a compound of claim 63.

69. A method for inhibiting neuraminidase from a disease-causing microorganism comprising administering to a human or other mammal in need thereof, a therapeutically effective amount of a compound of claim 1.

70. The method of claim 69 wherein the disease-causing microorganism is a virus.

71. The method of claim 70 wherein the virus is influenza virus.

72. A method for treating a disease caused by a microorganism which has a neuraminidase, comprising administering to a human or other mammal in need thereof, a therapeutically effective amount of a compound of claim 1.

73. The method of claim 72 wherein the disease-causing microorganism is a virus.

74. The method of claim 73 wherein the virus is influenza virus.

75. A method for preventing a disease caused by a microorganism which has a neuraminidase, comprising administering to a human or other mammal in need thereof, a therapeutically effective amount of a compound of claim 1.

76. The method of claim 75 wherein the disease-causing microorganism is a virus.

77. The method of claim 76 wherein the virus is influenza virus.

78. A method for inhibiting neuraminidase from a disease-causing microorganism comprising administering to a human or other mammal in need thereof, a therapeutically effective amount of a compound of claim 51.

79. The method of claim 78 wherein the disease-causing microorganism is a virus.

80. The method of claim 79 wherein the virus is influenza virus.

81. A method for treating a disease caused by a microorganism which has a neuraminidase, comprising administering to a human or other mammal in need thereof, a therapeutically effective amount of a compound of claim 51.

82. The method of claim 81 wherein the disease-causing microorganism is a virus.

83. The method of claim 82 wherein the virus is influenza virus.

84. A method for preventing a disease caused by a microorganism which has a neuraminidase, comprising administering to a human or other mammal in need thereof, a therapeutically effective amount of a compound of claim 51.

85. The method of claim 84 wherein the disease-causing microorganism is a virus.

86. The method of claim 85 wherein the virus is influenza virus.

87. A method for inhibiting neuraminidase from a disease-causing microorganism comprising administering to a human or other mammal in need thereof, a therapeutically effective amount of a compound of claim 57.

88. The method of claim 87 wherein the disease-causing microorganism is a virus.

89. The method of claim 88 wherein the virus is influenza virus.

90. A method for treating a disease caused by a microorganism which has a neuraminidase, comprising administering to a human or other mammal in need thereof, a therapeutically effective amount of a compound of claim 57.

91. The method of claim 90 wherein the disease-causing microorganism is a virus.

92. The method of claim 91 wherein the virus is influenza virus.

93. A method for preventing a disease caused by a microorganism which has a neuraminidase, comprising administering to a human or other mammal in need thereof, a therapeutically effective amount of a compound of claim 57.

94. The method of claim 93 wherein the disease-causing microorganism is a virus.

95. The method of claim 94 wherein the virus is influenza virus.

96. A method for inhibiting neuraminidase from a disease-causing microorganism comprising administering to a human or other mammal in need thereof, a therapeutically effective amount of a compound of claim 62.

97. The method of claim 96 wherein the disease-causing microorganism is a virus.

98. The method of claim 97 wherein the virus is influenza virus.

99. A method for treating a disease caused by a microorganism which has a neuraminidase, comprising administering to a human or other mammal in need thereof, a therapeutically effective amount of a compound of claim 62.

100. The method of claim 99 wherein the disease-causing microorganism is a virus.

101. The method of claim 100 wherein the virus is influenza virus.

102. A method for preventing a disease caused by a microorganism which has a neuraminidase, comprising administering to a human or other mammal in need thereof, a therapeutically effective amount of a compound of claim 62.

103. The method of claim 102 wherein the disease-causing microorganism is a virus.

104. The method of claim 103 wherein the virus is influenza virus.

105. A method for inhibiting neuraminidase from a disease-causing microorganism comprising administering to a human or other mammal in need thereof, a therapeutically effective amount of a compound of claim 63.

106. The method of claim 105 wherein the disease-causing microorganism is a virus.

107. The method of claim 106 wherein the virus is influenza virus.

108. A method for treating a disease caused by a microorganism which has a neuraminidase, comprising administering to a human or other mammal in need thereof, a therapeutically effective amount of a compound of claim 63.

109. The method of claim 108 wherein the disease-causing microorganism is a virus.

110. The method of claim 109 wherein the virus is influenza virus.

111. A method for preventing a disease caused by a microorganism which has a neuraminidase, comprising administering to a human or other mammal in need thereof, a therapeutically effective amount of a compound of claim 63.

112. The method of claim 111 wherein the disease-causing microorganism is a virus.

113. The method of claim 112 wherein the virus is influenza virus.

114. A compound useful forth preparation of a compound according to claim 1 and having the indicated relative stereochemistry or an enantiomerically enriched compound having the indicated absolute stereochemistry selected from the group consisting of the compound of the formula:

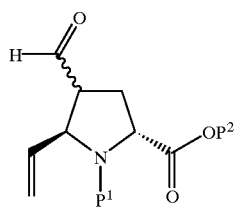

(1)

wherein $P^1$ is an N-protecting group and $P^2$ is a carboxylic acid protecting group; or a salt thereof;

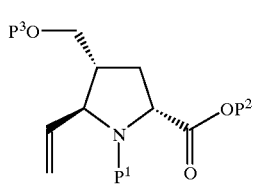

(2)

wherein $P^1$ is an N-protecting and $P^2$ is a carboxylic acid protecting and $P^3$ is hydrogen or a hydroxy protecting; or a salt thereof;

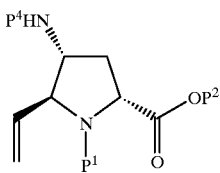

wherein $P^1$ is an N-protecting and $P^2$ is a carboxylic acid protecting and $P^4$ is hydrogen or an N-protecting; or a salt thereof;

(4)

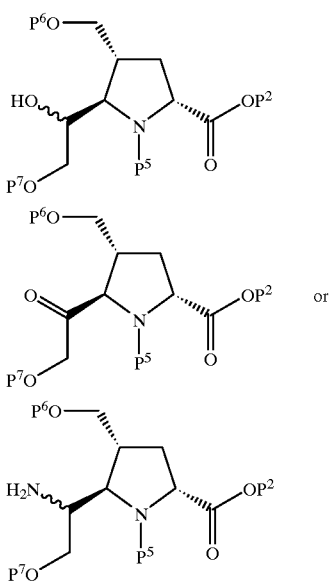

wherein $P^5$ is an N-protecting group and $P^2$ is a carboxylic acid protecting and $P^6$ is hydrogen or a hydroxy protecting group and $P^7$ is hydroxy protecting group; or a salt thereof;

(5)

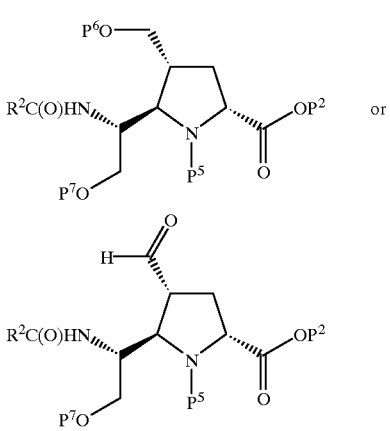

wherein $P^5$ is an N-protecting group and $P^2$ is a carboxylic acid protecting group and $P^6$ is hydrogen or a hydroxy protecting group and $P^7$ is hydroxy protecting group and $R^2$ is (a) hydrogen, (b) $C_1$–$C_6$ alkyl, (c) $C_2$–$C_6$ alkenyl, (d) $C_3$–$C_6$ cyclo-alkyl,
  (e) $C_5$–$C_6$ cycloalkenyl (f) halo $C_1$–$C_6$ alkyl or (g) halo $C_2$–$C_6$ alkenyl; or a salt thereof;

(6)

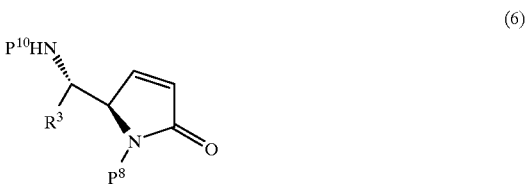

wherein $P^8$ is an N-protecting, $P^{10}$ is an N-protecting group and $R^3$ is defined as therein; or a salt thereof;

(7)

wherein $P^8$ is an N-protecting, $P^{10}$ is an N-protecting group and $R^3$ and Y are defined as therein; or a salt thereof;

(8)

wherein $P^8$ is an N-protecting, $P^{10}$ is an N-protecting group and $R^3$ and Y are defined as therein; or a salt thereof;

(9)

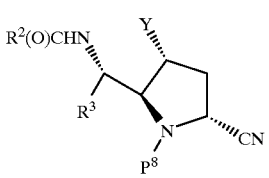

wherein $P^8$ is an N-protecting and $R^3$ and $R^2$ and Y are defined as therein; or a salt thereof;

(10)

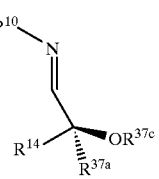

wherein $P^{10}$, $R^{14}$, $R^{37a}$ and $R^{37c}$ are as defined therein; or a salt thereof;

(11)

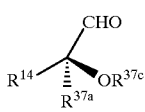

wherein $R^{14}$, $R^{37a}$ and $R^{37c}$ are as defined therein; or a salt thereof;

(12)

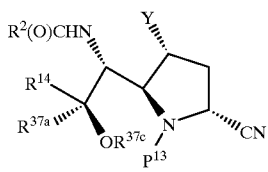

wherein $R^{14}$, $R^{37a}$ and $R^{37c}$ and $R^2$ is as defined therein and $P^{13}$ is an N-protecting group; or a salt thereof;

(13)

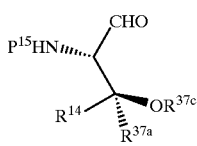

wherein $R^{14}$, $R^{37a}$ and $R^{37c}$ are as defined therein and $P^{15}$ is an N-protecting group; or a salt thereof;

(14)

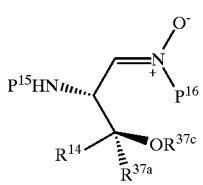

wherein $R^{14}$, $R^{37a}$, $R^{37b}$ are defined as therein and $P^{15}$ and $P^{16}$ are N-protecting groups;

(15)

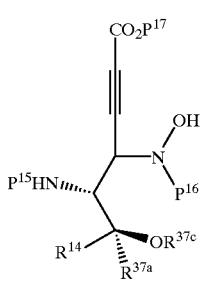

wherein $R^{14}$, $R^{37a}$, $R^{37c}$ are defined as therein $P^{15}$ and $P^{16}$ are N-protecting groups and $P^{17}$ is an acid protecting group; or a salt thereof;

(16)

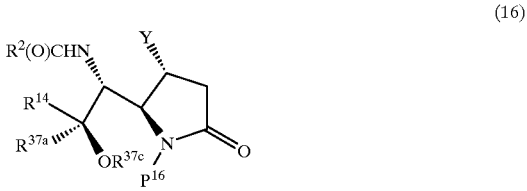

wherein $R^{14}$, $R^{37a}$, $R^{37c}$ and $R^2$ are defined as therein and $P^{16}$ is an N-protecting group; or a salt thereof; and (17)

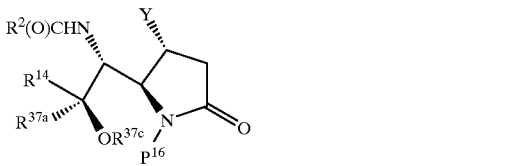

wherein $R^{14}$, $R^{37a}$, $R^{37c}$ and $R^2$ are defined as therein and $P^{16}$ is an N-protecting group; or a salt thereof.

115. A compound of the formula or a pharmaceutically acceptable salt, ester, or prodrug thereof, wherein Y is R is 
 ; and $R^3$ is

* * * * *

UNITED STATES PATENT AND TRADEMARK OFFICE
CERTIFICATE OF CORRECTION

PATENT NO.     : 6,455,571 B1                                                Page 1 of 1
DATED          : September 24, 2002
INVENTOR(S)    : Clarence J. Maring et al.

It is certified that error appears in the above-identified patent and that said Letters Patent is hereby corrected as shown below:

Column 470,
Line 9, replace "(xxi)" with -- (xxii) --.

Column 490,
Line 27, replace "pentyl-5(cs-propen-1-yl)" with -- pentyl-3-(cis-propen-1-yl) --.

Column 491,
Line 39, replace "(2R,33,5R,1'R,2'S)" with -- (2R,3S,5R,1'R,2'S) --.
Line 50, replace "(2R,3R,5R,1'R,2'R)" with -- 2R,3S,5R,1'R,2'R) --.
Line 54, replace "(2R,3R,5R, 'R,2'R)" with -- (2R,3S,5R,1'R,2'R) --.

Column 492,
Line 12, replace "(2R,3R,5R, 'S)" with -- (2R,3R,5R,1'S) --.

Column 494,
Line 51, replace the bold "H" with the italic bold -- *H* --.

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,455,571 B1  Page 1 of 1
DATED : September 24, 2002
INVENTOR(S) : Clarence J. Maring et al.

It is certified that error appears in the above-identified patent and that said Letters Patent is hereby corrected as shown below:

<u>Column 468,</u>
Line 54, replace " 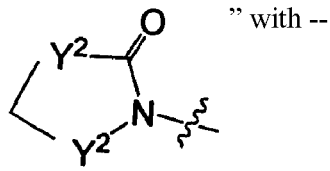 " with -- 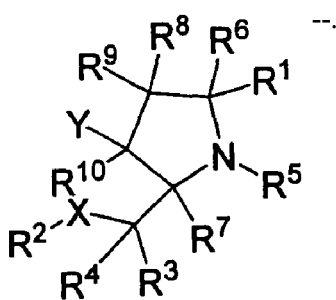 --.

Signed and Sealed this

Sixth Day of June, 2006

JON W. DUDAS
*Director of the United States Patent and Trademark Office*